United States Patent
Noel et al.

(10) Patent No.: US 10,745,674 B2
(45) Date of Patent: Aug. 18, 2020

(54) POLYKETIDE SYNTHASE VARIANTS AND USES THEREOF

(71) Applicants: SALK INSTITUTE FOR BIOLOGICAL STUDIES, La Jolla, CA (US); THE REGENTS OF THE UNIVERSITY OF CALIFORNIA, Oakland, CA (US)

(72) Inventors: Joseph Noel, La Jolla, CA (US); Kate Woods, La Jolla, CA (US); Marianne Bowman, La Jolla, CA (US); Gordon Louie, La Jolla, CA (US); Nancy Anderson Da Silva, Oakland, CA (US); Javier Pascual Cardenas, Oakland, CA (US)

(73) Assignees: SALK INSTITUTE FOR BIOLOGICAL STUDIES, La Jolla, CA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 778 days.

(21) Appl. No.: 15/123,501

(22) PCT Filed: Mar. 5, 2015

(86) PCT No.: PCT/US2015/019058
§ 371 (c)(1),
(2) Date: Sep. 2, 2016

(87) PCT Pub. No.: WO2015/134807
PCT Pub. Date: Sep. 11, 2015

(65) Prior Publication Data
US 2017/0073649 A1    Mar. 16, 2017

Related U.S. Application Data

(60) Provisional application No. 61/949,082, filed on Mar. 6, 2014.

(51) Int. Cl.
*C12N 15/52* (2006.01)
*C12N 15/09* (2006.01)
*C12N 9/10* (2006.01)
*A61K 38/00* (2006.01)

(52) U.S. Cl.
CPC .......... *C12N 9/1029* (2013.01); *C12N 15/52* (2013.01); *C12Y 203/01* (2013.01)

(58) Field of Classification Search
None
See application file for complete search history.

(56) References Cited

U.S. PATENT DOCUMENTS

| | | | |
|---|---|---|---|
| 2010/0107277 A1 | 4/2010 | Brugliera et al. | |
| 2012/0028330 A1* | 2/2012 | Yokoyama | C12N 9/93 435/183 |
| 2012/0058106 A1* | 3/2012 | Chahal | C07K 14/4748 424/130.1 |
| 2012/0096581 A1* | 4/2012 | Noel | C12N 9/00 800/278 |
| 2019/0112668 A1* | 4/2019 | Yoshimoto | C12Q 1/6837 |

OTHER PUBLICATIONS

Tang et al. (Jun. 2013) Screening for Enhanced Triacetic Acid Lactone Production by Recombinant *Escherichia coli* Expressing a Designed Triacetic Acid Lactone Reporter, J. Am. Chem. Soc., vol. 135, pp. 10099-10103.*
Mallika et al. (2011) Evolutionary Implications and Physicochemical Analyses of Selected Proteins of Type III Polyketide Synthase Family, Evolut. Bioinform., vol. 7, pp. 41-53.*
Jea et al. (2000) Structural control of polyketide formation in plant-speciёc polyketide synthases, Chem. Biol., vol. 7, pp. 919-930.*
NCBI (2018) "GenBank: RKF83271.1", pp. 1-2.*
Funa et al. (2002) Properties and Substrate Specificity of RppA, a Chalcone Synthase-related Polyketide Synthase in Streptomyces griseus, J. Biol. Chem., vol. 277, pp. 4628-4635.*
Tsang, S. et al., "Screening for enchanced triacetic acid lactone production by recombinant *Escherichia coli* expressing a designed triacetic acid lactone reporter," Journal of the American Chemical Society, 2013, vol. 135, No. 27, pp. 10099-10103, Figure 2; Tables 2-4; p. 10099-10100.
Helariutta, Y. et al., Duplication and functional divergence in the chalcone synthase gene family of Asteraceae: evolution with substrate change and catalytic simplification. Proceedings of the National Academy of Sciences of the United States of America, 1996, vol. 93, No. 17, pp. 9033-9038, p. 9033-9034; GenBank Accession Nos. X91340 and CAA62683; Figure 3; Abstract.
Funa, N. et al., "Alteration of reaction and substrate specificity of a bacterial type III polyketide synthase by site-directed mutagenesis," The Biochemical Journal, 2002, vol. 367, Pt 3, pp. 781-9, Figures 1-3; p. 782-784.
International Search Report and Written Opinion for corresponding PCT/US2015/019058, dated May 5, 2015 (12 pages).

* cited by examiner

*Primary Examiner* — Manjunath N Rao
*Assistant Examiner* — Samuel W Liu
(74) *Attorney, Agent, or Firm* — Melissa Hunter-Ensor; John L. Buchanan; Greenberg Traurig, LLP

(57) ABSTRACT

The present invention relates to methods for producing polyketide synthase variants, and for altering the activity and/or substrate specificity of putative native and variant polyketide synthases. The present invention further relates to compositions comprising said polyketide synthase variants, compounds prepared using said polyketide synthase variants, and uses of said polyketide synthase variants. In one embodiment, said polyketide synthase variant is 2-pyrone synthase.

14 Claims, 150 Drawing Sheets

Specification includes a Sequence Listing.

| FIG. 2A | FIG. 2B |

FIG. 2B
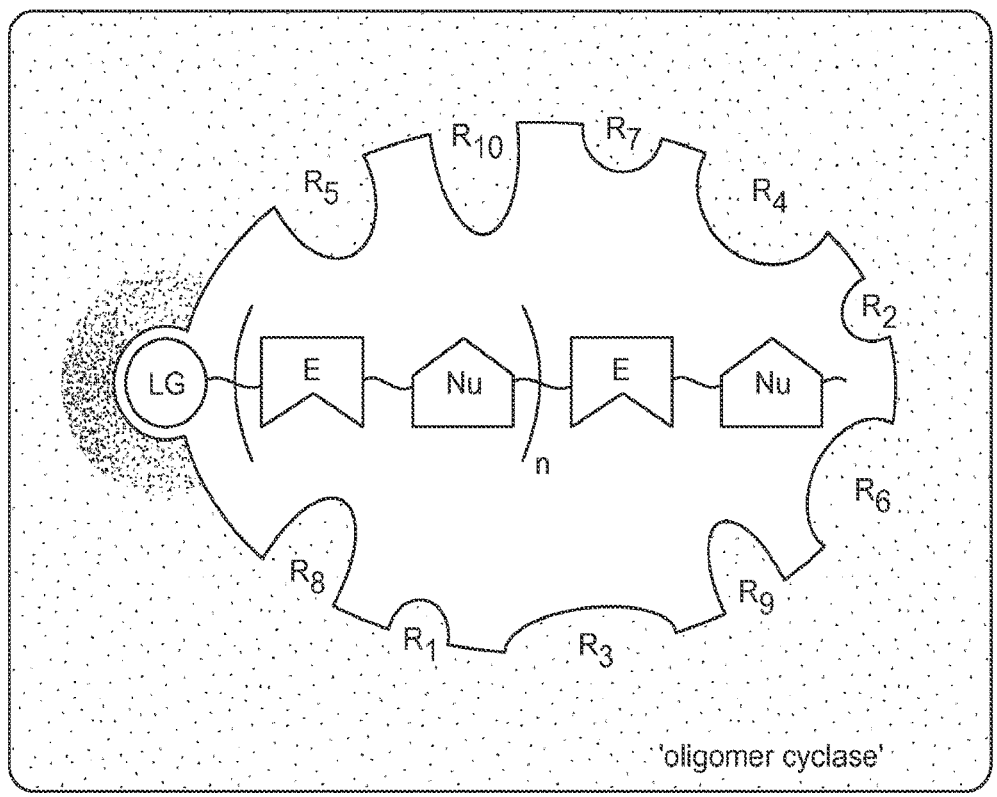
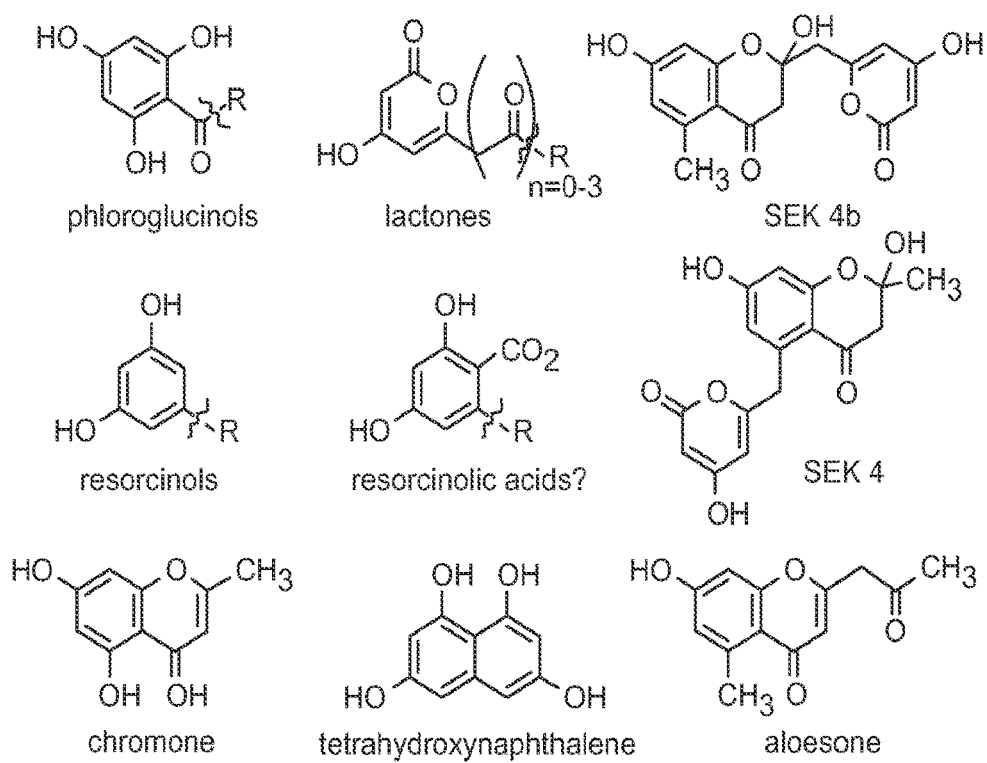
Cyclization Mechanism

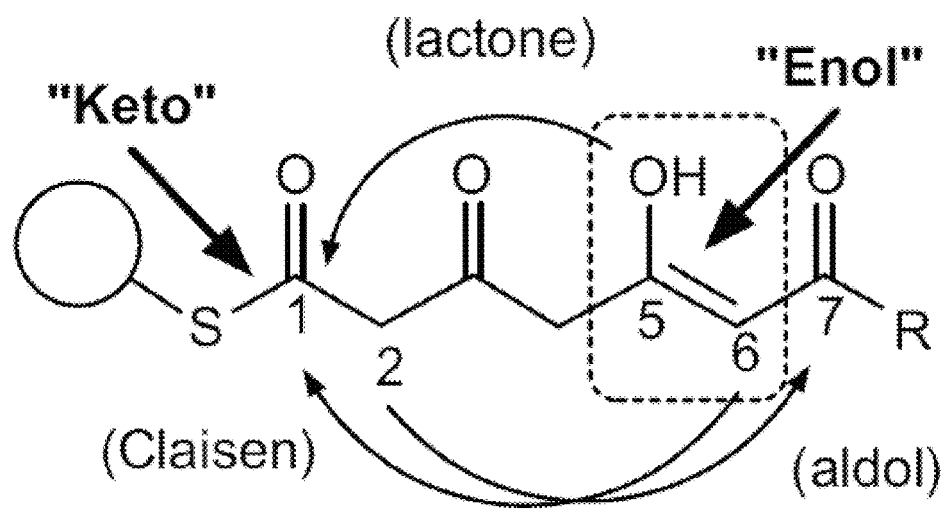
representative tetraketide intermediate
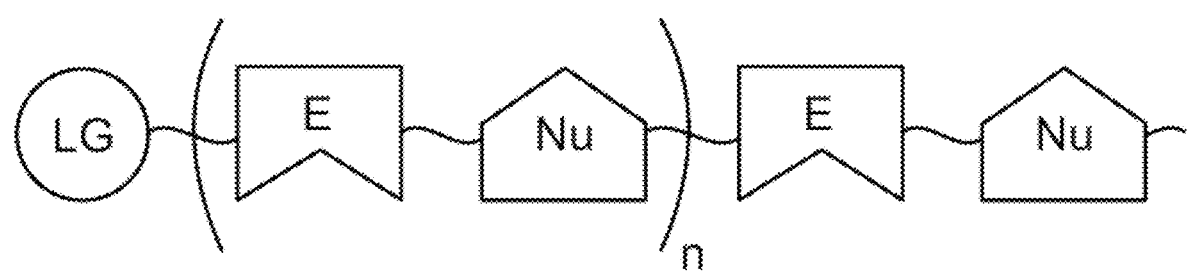
FIG. 3

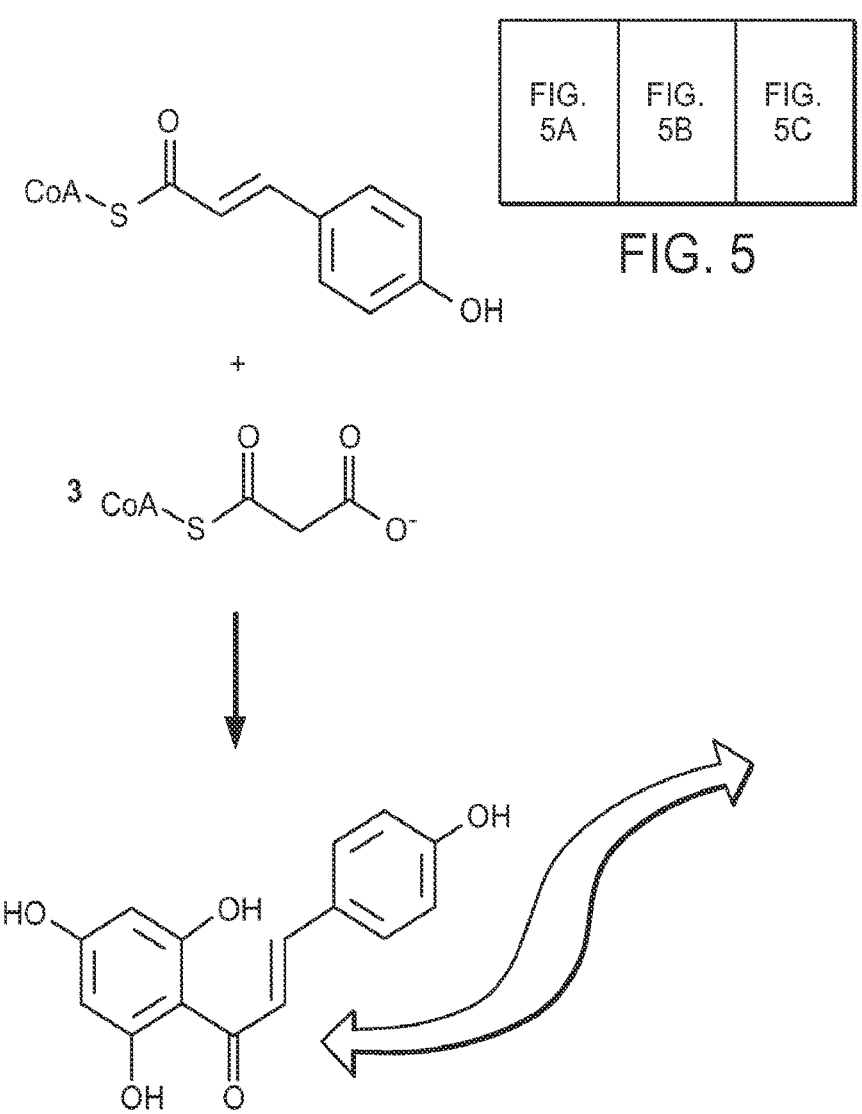
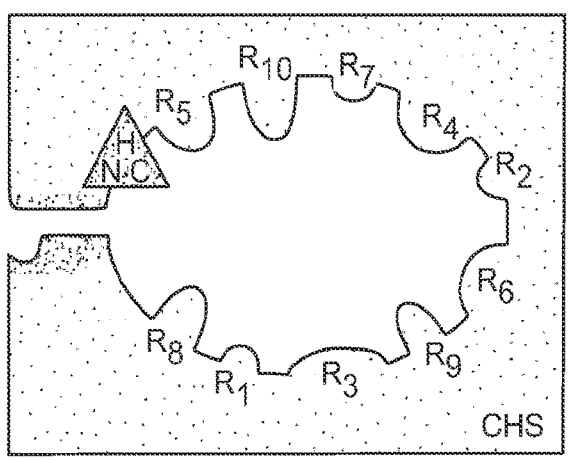
FIG. 5A 11 potential chemical intermediates and end-products identified and synthesized from TAL Pyrones are promising biorenewable platform chemicals M. Chia, T.J. Schwartz, B.H. Shanks, J.A. Dumesic, *Green Chemistry*, 14, 1850-1853, 2012

FIG. 9

```
>2-PS variant=  0: 1 Substitutions=  (wild type)
>2-PS variant=  1: 2 Substitutions=  (C169A)
>2-PS variant=  2: 3 Substitutions=  (C 35A)
>2-PS variant=  3: 1 Substitutions=  (L202F)
>2-PS variant=  4: 5 Substitutions=  (L268F)
>2-PS variant=  5: 6 Substitutions=  (L268M)
>2-PS variant=  6: 7 Substitutions=  (L202F) (L268M)
>2-PS variant=  7: 8 Substitutions=  (C 89S) (C372S)
>2-PS variant=  8: 9 Substitutions=  (C 89S) (C346A)
>2-PS variant=  9:10 Substitutions=  (C 65S) (C 89S)  (C346A) (C372S)
>2-PS variant= 10:11 Substitutions=  (C 89S) (C195S)  (C346A) (C372S)
>2-PS variant= 11:12 Substitutions=  (C 65S) (C 89S)  (C195S) (C372S)
>2-PS variant= 12:13 Substitutions=  (C 65S) (C 89S)  (C 89S)
>2-PS variant= 13:14 Substitutions=  (C 35S) (C 65S)  (C 89S) (C195S) (C372S)
(C346A) (C372S)
>2-PS variant= 14:15 Substitutions=  (C 35S) (C 65S)  (C 89S) (T137F) (C195S)
(M259L) (L261N) (C346A) (C372S)
>2-PS variant= 15:16 Substitutions=  (C 35S) (C 65S)  (C 89S) (C195S) (I201F)
(M259L) (L261N) (C346A) (C372S)
>2-PS variant= 16:17 Substitutions=  (C 35S) (C 65S)  (C 89S) (T137F) (C195S)
(M259L) (L261N) (C346A) (C372S)
>2-PS variant= 17:18 Substitutions=  (C 35S) (C 89S)  (C372S) (L202G) (C346A) (L202G)
(L268M)
>2-PS variant= 18: 3 Substitutions=  (C 35S) (C 89S)  (C372S)
>2-PS variant= 19: 4 Substitutions=  (C 35S) (C 89S)  (C346A) (C372S)
```

FIG. 9 (continued)

> 2-PS variant= 20 Substitutions= 4: (C 35S) (C 65S)
> 2-PS variant= 21 Substitutions= 5: (C 35S) (C 89S) (C 89S) (C372S)
> 2-PS variant= 22 Substitutions= 6: (C 35S) (C 65S) (C195S) (C346A)
> 2-PS variant= 23 Substitutions= 2: (C 35S) (T137F) (C 89S) (C195S) (C372S)
> 2-PS variant= 24 Substitutions= 2: (C 35S) (T137M)
> 2-PS variant= 25 Substitutions= 2: (C 35S) (M259F)
> 2-PS variant= 26 Substitutions= 2: (C 35S) (T137L)
> 2-PS variant= 27 Substitutions= 2: (C 35S) (I343F)
> 2-PS variant= 28 Substitutions= 2: (C 35S) (I343M)
> 2-PS variant= 29 Substitutions= 2: (C 35S) (I201F)
> 2-PS variant= 30 Substitutions= 2: (C 35S) (C169A)
> 2-PS variant= 31 Substitutions= 2: (C 35S) (L268M)
> 2-PS variant= 32 Substitutions= 2: (C 35S) (L202F)
> 2-PS variant= 33 Substitutions= 2: (C 35S) (I201M)
> 2-PS variant= 34 Substitutions= 2: (C 35S) (I201L)
> 2-PS variant= 35 Substitutions= 2: (C 35S) (L202M)
> 2-PS variant= 36 Substitutions= 4: (C 35S) (L202G) (M259L) (L261N)
> 2-PS variant= 37 Substitutions= 9: (C 35S) (C 65S) (C 89S) (C195S) (L202G) (M259L)
(L261N) (C346A) (C372S)
> 2-PS variant= 38 Substitutions= 2: (C 35S) (L202G)
> 2-PS variant= 39 Substitutions= 3: (C 35S) (M259L) (L261N) (L202G) (M259L)
> 2-PS variant= 40 Substitutions= 7: (C 35S) (C 65S) (C 89S) (C195S) (L202G) (M259L) (C346A)
(C372S)

FIG. 9 (continued)

> 2-PS variant= 41 Substitutions= 1: (C 35S)
> 2-PS variant= 42 Substitutions= 4: (C 35S) (T137L)
> 2-PS variant= 43 Substitutions= 5: (C 35S) (T137M)
> 2-PS variant= 44 Substitutions= 4: (C 35S) (L202F)
> 2-PS variant= 45 Substitutions= 2: (C 35S) (C372S)
> 2-PS variant= 46 Substitutions= 2: (C 35S) (C372A)
> 2-PS variant= 47 Substitutions= 2: (C 35S) (C346S)
> 2-PS variant= 48 Substitutions= 2: (C 35S) (C346A)
> 2-PS variant= 49 Substitutions= 2: (C 35S) (C195S)
> 2-PS variant= 50 Substitutions= 2: (C 35S) (C195A)
> 2-PS variant= 51 Substitutions= 2: (C 35S) (C135S)
> 2-PS variant= 52 Substitutions= 2: (C 35S) (C135A)
> 2-PS variant= 53 Substitutions= 2: (C 35S) (C 89S)
> 2-PS variant= 54 Substitutions= 2: (C 35S) (C 89A)
> 2-PS variant= 55 Substitutions= 2: (C 35S) (C 65S)
> 2-PS variant= 56 Substitutions= 2: (C 35S) (C 65A)
> 2-PS variant= 57 Substitutions= 2: (C 35S) (C169S)
> 2-PS variant= 58 Substitutions= 2: (C 35S) (N341H)
> 2-PS variant= 59 Substitutions= 2: (C 35S) (H308Q)
> 2-PS variant= 60 Substitutions= 3: (C 35S) (L202F) (L268F)
> 2-PS variant= 61 Substitutions= 3: (C 35S) (L268M) (I343M)
> 2-PS variant= 62 Substitutions= 3: (C 35S) (L202F) (L268M)

FIG. 10

\> 2-PS variant= 2  Substitutions= 1:   (C169A)

MGSYSSDDVEVIREAGRAQGLATILAIGTATPPNCVAQADYADYFRVTKSEHMVDLKEKFKRICEKTAIKKRYLALTED
YLQENPTMCEFMAPSLNARQDLVVTGVPMLGKEAAVKAIDEWGLPKSKITHLIFCTTAGVDMPGADYQLVKLLGLSPSVK
RYMLYQQ[a]AAGGTVLRLAKDLAENNKGSRVLIVCSEITAILFHGPNENHLDSLVAQALFGDGAAALIVGSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLDCGVLFGFGPMTVETVVLRSVRVTAAVAN
GN

\> 2-PS variant= 3  Substitutions= 1:   (C 35A)

MGSYSSDDVEVIREAGRAQGLATILAIGTATPPN[a]VAQADYADYFRVTKSEHMVDLKEKFKRICEKTAIKKRYLALTED
YLQENPTMCEFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIVCSEITAILFHGPNENHLDSLVAQALFGDGAAALIVGSGPHLAVERP
IFEIVSTDQTILPDTEKAMKLHLREGGLTFQLHRDVPLMVAKNIENAA

FIG. 10 (continued)

> 2-PS variant= 5 Substitutions= 1: (L268F)
MGSYSSDDVEVIREAGRAQGLATILAIGTATPPNCVAQADYADYFRVTKSEHMVDLKEKFKRICEKTAIKKRYLALTED
YLQENPTMCEFMAPSLNARQDLVTGVPMLGKEAAVKAIDEWGLPKSITHLIFCTTAGVDMPGADYQLVKLLGLSPSVK
RYMLYQQGCAAGGTVLRLAKDLAENNKGSRVLIVCSEITAILFHGPNENHLDSLVAQALFGDGAAALIVGSGPHLAVERP
IFEIVSTDQTILPDTEKAMKLHLREGG[F]TFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLDCGVLFGFGPGMTVETVVLRSVRVTAAVAN
GN > 2-PS variant= 6 Substitutions= 1: (L268M)
MGSYSSDDVEVIREAGRAQGLATILAIGTATPPNCVAQADYADYFRVTKSEHMVDLKEKFKRICEKTAIKKRYLALTED
YLQENPTMCEFMAPSLNARQDLVTGVPMLGKEAAVKAIDEWGLPKSITHLIFCTTAGVDMPGADYQLVKLLGLSPSVK
RYMLYQQGCAAGGTVLRLAKDLAENNKGSRVLIVCSEITAILFHGPNENHLDSLVAQALFGDGAAALIVGSGPHLAVERP
IFEIVSTDQTILPDTEKAMKLHLREGG[M]TFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLDCGVLFGFGPGMTVETVVLRSVRVTAAVAN
GN > 2-PS variant= 7 Substitutions= 2: (L202F) (L268M)
MGSYSSDDVEVIREAGRAQGLATILAIGTATPPNCVAQADYADYFRVTKSEHMVDLKEKFKRICEKTAIKKRYLALTED
YLQENPTMCEFMAPSLNARQDLVTGVPMLGKEAAVKAIDEWGLPKSITHLIFCTTAGVDMPGADYQLVKLLGLSPSVK
RYMLYQQGCAAGGTVLRLAKDLAENNKGSRVLIVCSEITAI[F]HGPNENHLDSLVAQALFGDGAAALIVGSGPHLAVERP
IFEIVSTDQTILPDTEKAMKLHLREGG[M]TFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLDCGVLFGFGPGMTVETVVLRSVRVTAAVAN
GN

FIG. 10 (continued)

> 2-PS variant= 2: (C 89S) (C372S)
MGSYSSDDVEVIREAGRAQGLATILAIGTATPPNCVAQADYADYFRVTKSEHMVDLKEKFKRICEKTAIKKRYLALTED
YLQENPTM[S]EFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIVCSEITAILFHGPNENHLDSLVAQALFGDGAAALIVSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLD[S]GVLFGFGPMTVETVVLRSVRVTAAVAN
GN > 2-PS variant= 3: (C 89S) (C346A) (C372S)
MGSYSSDDVEVIREAGRAQGLATILAIGTATPPNCVAQADYADYFRVTKSEHMVDLKEKFKRICEKTAIKKRYLALTED
YLQENPTM[S]EFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIVCSEITAILFHGPNENHLDSLVAQALFGDGAAALIVSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISA[A]VLFIIDEVRKRSMAEGKSTTGEGLD[S]GVLFGFGPMTVETVVLRSVRVTAAVAN
GN > 2-PS variant= 10 Substitutions: 3: (C 65S) (C 89S) (C372S)
MGSYSSDDVEVIREAGRAQGLATILAIGTATPPNCVAQADYADYFRVTKSEHMVDLKEKFKR I[S]EKTAIKKRYLALTED
YLQENPTM[S]EFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIVCSEITAILFHGPNENHLDSLVAQALFGDGAAALIVSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLD[S]GVLFGFGPMTVETVVLRSVRVTAAVAN
GN FIG. 10 (continued)

> 2-PS variant= 4:   (C 89S)   (C195S)   (C346A)   (C372S)
MGSYSSDDVEVIREAGRAQGLATILAIGTATPPNCVAQADYADYFRVTKSEHMVDLKEKFKRICEKTAIKKRYLALTED
YLQENPTM[s]EFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIV[s]SEITTAILFHGPNENHLDSLVAQALFGDGAAALIVGSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISA[a][v]LFIIDEVRKRSMAEGKSTTGEGLD[s]GVLFGFGPMTVETVVLRSVRVTAAVAN
GN > 2-PS variant= 5:   (C 65S)   (C 89S)   (C195S)   (C346A)   (C372S)
MGSYSSDDVEVIREAGRAQGLATILAIGTATPPNCVAQADYADYFRVTKSEHMVDLKEKFKR[i]EKTAIKKRYLALTED
YLQENPTM[s]EFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIV[s]SEITTAILFHGPNENHLDSLVAQALFGDGAAALIVGSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISA[a][v]LFIIDEVRKRSMAEGKSTTGEGLD[s]GVLFGFGPMTVETVVLRSVRVTAAVAN
GN > 2-PS variant= 8:   (C 35S)   (C 65S)   (C 89S)   (C195S)   (M259L)
MGSYSSDDVEVIREAGRAQGLATILAIGTATPPN[s]VAQADYADYFRVTKSEHMVDLKEKFKR[i]SEKTAIKKRYLALTED
YLQENPTM[s]EFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIV[s]SEITTAILFHGPNENHLDSLVAQALFGDGAAALIVGSGPHLAVERP
IFEIVSTDQTILPDTEKA[l]HLREGGLTFQLHRDVPLMVAKNIENAAEKALSPLGITDWNSVFWMVHPGGRAILDQVER
KLNLKEDKLRASRHVLSEYGNLISA[a][v]LFIIDEVRKRSMAEGKSTTGEGLD[s]GVLFGFGPMTVETVVLRSVRVTAAVAN
GN > 2-PS variant= 13 Substitutions=   (L261N)   (C346A)   (C372S)
MGSYSSDDVEVIREAGRAQGLATILAIGTATPPN[s]VAQADYADYFRVTKSEHMVDLKEKFKR[i]SEKTAIKKRYLALTED
YLQENPTM[s]EFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIV[s]SEITTAILFHGPNENHLDSLVAQALFGDGAAALIVGSGPHLAVERP
IFEIVSTDQTILPDTEKA[l][n]HLREGGLTFQLHRDVPLMVAKNIENAAEKALSPLGITDWNSVFWMVHPGGRAILDQVER
KLNLKEDKLRASRHVLSEYGNLISA[a][v]LFIIDEVRKRSMAEGKSTTGEGLD[s]GVLFGFGPMTVETVVLRSVRVTAAVAN
GN

FIG. 10 (continued)

> 2-PS variant= 14 Substitutions= 10: (C 35S) (C 65S) (C 89S) (T137F) (C195S) (L202G) (M259L) (C346A) (C372S) (L261N)

MGSYSSDDVEVIREAGRAQGLATILAIGTATPPNSVAQADYADYFRVTKSEHMVDLKEKFKRISEKTAIKKRYLALTED
YLQENPTMSEFMAPSLNARQDLVVTGVPMLGKEAAVKAIDEWGLPKSKITHLIFCTFAGVDMPGADYQLVKLLGLSPSVK
RYMLYQQGCAAGGTVLRLAKDLAENNKGSRVLIVSSEITAIGFHGPNENHLDSLVAQALFGDGAAALIVGSGPHLAVERP
IFEIVSTDQTILPDTEKANHLREGGLTFQLHRDVPLMVAKNIENAAEKALSPLGITDWNSVFWMVHPGGRAILDQVER
KLNLKEDKLRASRHVLSEYGNLISAAVLFIIDEVRKRSMAEGKSTTGEGLDSGVLFGFGPGMTVETVVLRSVRVTAAVAN
GN

> 2-PS variant= 15 Substitutions= 10: (C 35S) (C 65S) (C 89S) (C195S) (I201F) (L202G) (M259L) (C346A) (C372S) (L261N)

MGSYSSDDVEVIREAGRAQGLATILAIGTATPPNSVAQADYADYFRVTKSEHMVDLKEKFKRISEKTAIKKRYLALTED
YLQENPTMSEFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIVSSEITAFGFHGPNENHLDSLVAQALFGDGAAALIVGSGPHLAVERP
IFEIVSTDQTILPDTEKANHLREGGLTFQLHRDVPLMVAKNIENAAEKALSPLGITDWNSVFWMVHPGGRAILDQVER
KLNLKEDKLRASRHVLSEYGNLISAAVLFIIDEVRKRSMAEGKSTTGEGLDSGVLFGFGPGMTVETVVLRSVRVTAAVAN
GN

> 2-PS variant= 16 Substitutions= 10: (C 35S) (C 65S) (C 89S) (T137F) (C195S) (L202G) (M259L) (C346A) (C372S) (L261N)

MGSYSSDDVEVIREAGRAQGLATILAIGTATPPNSVAQADYADYFRVTKSEHMVDLKEKFKRISEKTAIKKRYLALTED
YLQENPTMSEFMAPSLNARQDLVVTGVPMLGKEAAVKAIDEWGLPKSKITHLIFCTFAGVDMPGADYQLVKLLGLSPSVK
RYMLYQQGCAAGGTVLRLAKDLAENNKGSRVLIVSSEITAIGFHGPNENHLDSLVAQALFGDGAAALIVGSGPHLAVERP
IFEIVSTDQTILPDTEKANHLREGGLTFQLHRDVPLMVAKNIENAAEKALSPLGITDWNSVFWMVHPGGRAILDQVER
KLNLKEDKLRASRHVLSEYGNLISAAVLFIIDEVRKRSMAEGKSTTGEGLDSGVLFGFGPGMTVETVVLRSVRVTAAVAN
GN

FIG. 10 (continued)

> 2-PS variant= 17 Substitutions= 10: (C 35S) (C 65S) (C 89S) (C195S)
(L202G) (M259L) (L261N) (L268M) (C346A) (C372S)
MGSYSSDDVEVIREAGRAQGLATILAIGTATPPN[S]VAQADYADYFRVTKSEHMVDLKEKFKRI[S]EKTAIKKRYLALTED
YLQENPTM[S]EFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIV[S]SEITA[A][S]FHGPNENHLDSLVAQALFGDGAAALIVGSGPHLAVERP
IFEIVSTDQTILPDTEKA[L][K]H[H]LREG[G][T]TFQLHRDVPLMVAKNIENAAEKALSPLGITDWNSVFWMVHPGGRAILDQVER
KLNLKEDKLRASRHVLSEYGNLISA[A][S][A]VLFIIDEVRKRSMAEGKSTTGEGLD[S]GVLFGFGPGMTVETVVLRSVRVTAAVAN
GN > 2-PS variant= 18 Substitutions= 3: (C 35S) (C 89S) (C372S)
MGSYSSDDVEVIREAGRAQGLATILAIGTATPPN[S]VAQADYADYFRVTKSEHMVDLKEKFKRICEKTAIKKRYLALTED
YLQENPTM[S]EFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIVCSEITAILFHGPNENHLDSLVAQALFGDGAAALIVGSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLD[S]GVLFGFGPGMTVETVVLRSVRVTAAVAN
GN > 2-PS variant= 19 Substitutions= 4: (C 35S) (C 89S) (C346A) (C372S)
MGSYSSDDVEVIREAGRAQGLATILAIGTATPPN[S]VAQADYADYFRVTKSEHMVDLKEKFKRICEKTAIKKRYLALTED
YLQENPTM[S]EFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIVCSEITAILFHGPNENHLDSLVAQALFGDGAAALIVGSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISA[A]VLFIIDEVRKRSMAEGKSTTGEGLD[S]GVLFGFGPGMTVETVVLRSVRVTAAVAN
GN

FIG. 10 (continued)

> 2-PS variant= 4:    (C 35S)    (C 65S)    (C 89S)    (C372S)
MGSYSSDDVEVIREAGRAQGLATILAIGTATPPNSVAQADYADYFRVTKSEHMVDLKEKFKRISEKTAIKKRYLALTED
YLQENPTMSEFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIVCSEITAILFHGPNENHLDSLVAQALFGDGAAALIVGSGPHLAVERP
IFEIVSTDQTILPDTEKAMKLHLREGGLTFQLHRDVPLMVAKNIENAAEKALSPLGITDWNSVFMWVHPGGRAILDQVER
KLNLIKEDKLRASRHVLSEYGNLISACVLFIIDEVRKRSMAEGKSTTGEGLDSGVLFGFGPMTVETVTVLRSVRVTAAVAN
GN > 2-PS variant= 5:    (C 35S)    (C 65S)    (C 89S)    (C195S)    (C346A)    (C372S)
MGSYSSDDVEVIREAGRAQGLATILAIGTATPPNSVAQADYADYFRVTKSEHMVDLKEKFKRICEKTAIKKRYLALTED
YLQENPTMSEFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIVSSEITAILFHGPNENHLDSLVAQALFGDGAAALIVGSGPHLAVERP
IFEIVSTDQTILPDTEKAMKLHLREGGLTFQLHRDVPLMVAKNIENAAEKALSPLGITDWNSVFMWVHPGGRAILDQVER
KLNLIKEDKLRASRHVLSEYGNLISAAVLFIIDEVRKRSMAEGKSTTGEGLDSGVLFGFGPMTVETVTVLRSVRVTAAVAN
GN > 2-PS variant= 6:    (C 35S)    (C 65S)    (C 89S)    (C195S)    (C346A)
(C372S)
MGSYSSDDVEVIREAGRAQGLATILAIGTATPPNSVAQADYADYFRVTKSEHMVDLKEKFKRISEKTAIKKRYLALTED
YLQENPTMSEFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIVSSEITAILFHGPNENHLDSLVAQALFGDGAAALIVGSGPHLAVERP
IFEIVSTDQTILPDTEKAMKLHLREGGLTFQLHRDVPLMVAKNIENAAEKALSPLGITDWNSVFMWVHPGGRAILDQVER
KLNLIKEDKLRASRHVLSEYGNLISAAVLFIIDEVRKRSMAEGKSTTGEGLDSGVLFGFGPMTVETVTVLRSVRVTAAVAN
GN

FIG. 10 (continued)

> 2-PS variant= 23 Substitutions= 2: (C 35S) (T137F)
MGSYSSDDVEVIREAGRAQGLATILAIGTATPPNS VAQADYADYFRVTKSEHMVDLKEKFKRICEKTAIKKRYLALTED
YLQENPTMCEFMAPSLNARQDLVVTGVPMLGKEAAVKAIDEWGLPKSKITHLIFCT F AGVDMPGADYQLVKLLGLSPSVK
RYMLYQQGCAAGGTVLRLAKDLAENNKGSRVLIVCSEITAILFHGPNENHLDSLVAQALFGDGAAALIVGSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLDCGVLFGFGPMTVETVVLRSVRVTAAVAN
GN > 2-PS variant= 24 Substitutions= 2: (C 35S) (T137M)
MGSYSSDDVEVIREAGRAQGLATILAIGTATPPNS VAQADYADYFRVTKSEHMVDLKEKFKRICEKTAIKKRYLALTED
YLQENPTMCEFMAPSLNARQDLVVTGVPMLGKEAAVKAIDEWGLPKSKITHLIFCT M AGVDMPGADYQLVKLLGLSPSVK
RYMLYQQGCAAGGTVLRLAKDLAENNKGSRVLIVCSEITAILFHGPNENHLDSLVAQALFGDGAAALIVGSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLDCGVLFGFGPMTVETVVLRSVRVTAAVAN
GN > 2-PS variant= 25 Substitutions= 2: (C 35S) (M259F)
MGSYSSDDVEVIREAGRAQGLATILAIGTATPPNS VAQADYADYFRVTKSEHMVDLKEKFKRICEKTAIKKRYLALTED
YLQENPTMCEFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIVCSEITAILFHGPNENHLDSLVAQALFGDGAAALIVGSGPHLAVERP
IFEIVSTDQTILPDTEKA F KLHLREGGLTFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLDCGVLFGFGPMTVETVVLRSVRVTAAVAN
GN

FIG. 10 (continued)

> 2-PS variant= 26 Substitutions= 2: (C_35S) (T137L)
MGSYSSDDVEVIREAGRAQGLATILAIGTATPPN[S]VAQADYADYFRVTKSEHMVDLKEKFKRICEKTAIKKRYLALTED
YLQENPTMCEFMAPSLNARQDLVVTGVPMLGKEAAVKAIDEWGLPKSKITHLIFCT[L]AGVDMPGADYQLVKLLGLSPSVK
RYMLYQQGCAAGGTVLRLAKDLAENNKGSRVLIVCSEITAILFHGPNENHLDSLVAQALFGDGAAALIVSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLDCGVLFGFGPGMTVETVLRSVRVTAAVAN
GN > 2-PS variant= 27 Substitutions= 2: (C_35S) (I343F)
MGSYSSDDVEVIREAGRAQGLATILAIGTATPPN[S]VAQADYADYFRVTKSEHMVDLKEKFKRICEKTAIKKRYLALTED
YLQENPTMCEFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIVCSEITAILFHGPNENHLDSLVAQALFGDGAAALIVSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNL[F]SACVLFIIDEVRKRSMAEGKSTTGEGLDCGVLFGFGPGMTVETVLRSVRVTAAVAN
GN > 2-PS variant= 28 Substitutions= 2: (C_35S) (I343M)
MGSYSSDDVEVIREAGRAQGLATILAIGTATPPN[S]VAQADYADYFRVTKSEHMVDLKEKFKRICEKTAIKKRYLALTED
YLQENPTMCEFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIVCSEITAILFHGPNENHLDSLVAQALFGDGAAALIVSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNI[M]SACVLFIIDEVRKRSMAEGKSTTGEGLDCGVLFGFGPGMTVETVLRSVRVTAAVAN
GN

FIG. 10 (continued)

> 2-PS variant= 29 Substitutions= 2:    (C_35S)   (I201F)
MGSYSSDDVEVIREAGRAQGLATILAIGTATPPNSVAQADYADYFRVTKSEHMVDLKEKFKRICEKTAIKKRYLALTED
YLQENPTMCEFMAPSLNARQDLVVTGVPMLGKEAAVKAIDEWGLPKSITHLIFCTTAGVDMPGADYQLVKLLGLSPSVK
RYMLYQQGCAAGGTVLRLAKDLAENNKGSRVLIVCSEITAFLFHGPNENHLDSLVAQALFGDGAAALIVSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLDCGVLFGFGPGMTVETVLRSVRVTAAVAN
GN > 2-PS variant= 30 Substitutions= 2:    (C_35S)   (C169A)
MGSYSSDDVEVIREAGRAQGLATILAIGTATPPNSVAQADYADYFRVTKSEHMVDLKEKFKRICEKTAIKKRYLALTED
YLQENPTMCEFMAPSLNARQDLVVTGVPMLGKEAAVKAIDEWGLPKSITHLIFCTTAGVDMPGADYQLVKLLGLSPSVK
RYMLYQQGAAAGGTVLRLAKDLAENNKGSRVLIVCSEITAILFHGPNENHLDSLVAQALFGDGAAALIVSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLDCGVLFGFGPGMTVETVLRSVRVTAAVAN
GN > 2-PS variant= 31 Substitutions= 2:    (C_35S)   (L268M)
MGSYSSDDVEVIREAGRAQGLATILAIGTATPPNSVAQADYADYFRVTKSEHMVDLKEKFKRICEKTAIKKRYLALTED
YLQENPTMCEFMAPSLNARQDLVVTGVPMLGKEAAVKAIDEWGLPKSITHLIFCTTAGVDMPGADYQLVKLLGLSPSVK
RYMLYQQGCAAGGTVLRLAKDLAENNKGSRVLIVCSEITAILFHGPNENHLDSLVAQALFGDGAAALIVSGPHLAVERP
IFEIVSTDQTILPDTEKAMKLHLREGGMTFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLDCGVLFGFGPGMTVETVLRSVRVTAAVAN
GN

FIG. 10 (continued)

```
> 2-PS variant= 32 Substitutions= 2; (C_35S) (L202F)
MGSYSSDDVEVIREAGRAQGLATILAIGTATPPNSVAQADYADYFRVTKSEHMVDLKEKFKRICEKTAIKKRYLALTED
YLQENPTMCEFMAPSLNARQDLVTGVPMLGKEAAVKAIDEWGLPKSKITHLIFCTTAGVDMPGADYQLVKLLGLSPSVK
RYMLYQQGCAAGGTVLRLAKDLAENNKGSRVLIVCSEITAFFHGPNENHLDSLVAQALFGDGAAALIVSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLDCGVLFGFGPMTVETVVLRSVRVTAAVAN
GN > 2-PS variant= 33 Substitutions= 2; (C_35S) (I201M)
MGSYSSDDVEVIREAGRAQGLATILAIGTATPPNSVAQADYADYFRVTKSEHMVDLKEKFKRICEKTAIKKRYLALTED
YLQENPTMCEFMAPSLNARQDLVTGVPMLGKEAAVKAIDEWGLPKSKITHLIFCTTAGVDMPGADYQLVKLLGLSPSVK
RYMLYQQGCAAGGTVLRLAKDLAENNKGSRVLIVCSEITAMLFHGPNENHLDSLVAQALFGDGAAALIVSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLDCGVLFGFGPMTVETVVLRSVRVTAAVAN
GN > 2-PS variant= 34 Substitutions= 2; (C_35S) (I201L)
MGSYSSDDVEVIREAGRAQGLATILAIGTATPPNSVAQADYADYFRVTKSEHMVDLKEKFKRICEKTAIKKRYLALTED
YLQENPTMCEFMAPSLNARQDLVTGVPMLGKEAAVKAIDEWGLPKSKITHLIFCTTAGVDMPGADYQLVKLLGLSPSVK
RYMLYQQGCAAGGTVLRLAKDLAENNKGSRVLIVCSEITALLFHGPNENHLDSLVAQALFGDGAAALIVSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLDCGVLFGFGPMTVETVVLRSVRVTAAVAN
GN
```

FIG. 10 (continued)

> 2-PS variant= 35 Substitutions= 2: (C 35S) (L202M)
MGSYSSDDVEVIREAGRAQGLATILAIGTATPPN[S]VAQADYADYFRVTKSEHMVDLKEKFKRICEKTAIKKRYLALTED
YLQENPTMCEFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIVCSEITAI[M]FHGPNENHLDSLVAQALFGDGAAALIVSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLDCGVLFGFGPGMTVETVVLRSVRVTAAVAN
GN > 2-PS variant= 36 Substitutions= 4: (C 35S) (L202G) (M259L) (L261N)
MGSYSSDDVEVIREAGRAQGLATILAIGTATPPN[S]VAQADYADYFRVTKSEHMVDLKEKFKRICEKTAIKKRYLALTED
YLQENPTMCEFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIVCSEITAI[G]FHGPNENHLDSLVAQALFGDGAAALIVSGPHLAVERP
IFEIVSTDQTILPDTEKA[L][N]HLREGGLTFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLDCGVLFGFGPGMTVETVVLRSVRVTAAVAN
GN > 2-PS variant= 37 Substitutions= 9: (C 35S) (C 65S) (C 89S) (C195S) (L202G)
(M259L) (L261N) (C346A) (C372S)
MGSYSSDDVEVIREAGRAQGLATILAIGTATPPN[S]VAQADYADYFRVTKSEHMVDLKEKFKRI[S]EKTAIKKRYLALTED
YLQENPTM[S]EFMAPSLNARQDLVVTGVPMLGKEAAVKAIDEWGLPKSKITHLI[S]SEITTA[G]FHGPNENHLDSLVAQALFGDGAAALIVSGPHLAVERP
RYMLYQQGCAAGGTVLRLAKDLAENNKGSRVLIV[S]SEITTA[G]FHGPNENHLDSLVAQALFGDGAAALIVSGPHLAVERP
IFEIVSTDQTILPDTEKA[L][N]HLREGGLTFQLHRDVPLMVAKNIENAAEKALSPLGITDWNSVFWMVHPGGRAILDQVER
KLNLKEDKLRASRHVLSEYGNLISA[A]VLFIIDEVRKRSMAEGKSTTGEGLD[S]GVLFGFGPGMTVETVVLRSVRVTAAVAN
GN FIG. 10 (continued)

> 2-PS variant= 38 Substitutions= 2:    (C 35S)    (L202G)
MGSYSSDDVEVIREAGRAQGLATILAIGTATPPNSVAQADYADYFRVTKSEHMVDLKEKFKRICEKTAIKKRYLALTED
YLQENPTMCEFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIVCSEITAIGFHGPNENHLDSLVAQALFGDGAAALIVGSGPHLAVERP
IFEIVSTDQTILPDTEKAMKLHLREGGLTFQLHRDVPLMVAKNIENAAEKALSPLGITDWNSVFMWVHPGGRAILDQVER
KLNLKEDKLRASRHVLSEYGNLISACVLFIIDEVRKRSMAEGKSTTGEGLDCGVLFGFGPGMTVETVVLRSVRVTAAVAN
GN > 2-PS variant= 39 Substitutions= 3:    (C 35S)    (M259L)    (L261N)
MGSYSSDDVEVIREAGRAQGLATILAIGTATPPNSVAQADYADYFRVTKSEHMVDLKEKFKRICEKTAIKKRYLALTED
YLQENPTMCEFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIVCSEITAILFHGPNENHLDSLVAQALFGDGAAALIVGSGPHLAVERP
IFEIVSTDQTILPDTEKALNHLREGGLTFQLHRDVPLMVAKNIENAAEKALSPLGITDWNSVFMWVHPGGRAILDQVER
KLNLKEDKLRASRHVLSEYGNLISACVLFIIDEVRKRSMAEGKSTTGEGLDCGVLFGFGPGMTVETVVLRSVRVTAAVAN
GN > 2-PS variant= 40 Substitutions= 7:    (C 35S)    (C 65S)    (C 89S)    (C195S)    (L202G)
(C346A)    (C372S)
MGSYSSDDVEVIREAGRAQGLATILAIGTATPPNSVAQADYADYFRVTKSEHMVDLKEKFKRISEKTAIKKRYLALTED
YLQENPTMSEFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIVSSEITAIGFHGPNENHLDSLVAQALFGDGAAALIVGSGPHLAVERP
IFEIVSTDQTILPDTEKAMKLHLREGGLTFQLHRDVPLMVAKNIENAAEKALSPLGITDWNSVFMWVHPGGRAILDQVER
KLNLKEDKLRASRHVLSEYGNLISAAVLFIIDEVRKRSMAEGKSTTGEGLISGVLFGFGPGMTVETVVLRSVRVTAAVAN
GN

FIG. 10 (continued)

> 2-PS variant= 41 Substitutions= 1: (C 35S)
MGSYSSDDVEVIREAGRAQGLATILAIGTATPPN[S]SVAQADYADYFRVTKSEHMVDLKEKFKRICEKTAIKKRYLALTED
YLQENPTMCEFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIVCSEITAILFHGPNENHLDSLVAQALFGDGAAALIVGSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLDCGVLFGFGPGMTVETVVLRSVRVTAAVAN
GN > 2-PS variant= 42 Substitutions= 4: (C 35S) (T137L) (L202F) (L268M)
MGSYSSDDVEVIREAGRAQGLATILAIGTATPPN[S]SVAQADYADYFRVTKSEHMVDLKEKFKRICEKTAIKKRYLALTED
YLQENPTMCEFMAPSLNARQDLVVTGVPMLGKEAAVKAIDEWGLPKSKITHLIFCT[L]AGVDMPGADYQLVKLLGLSPSVK
RYMLYQQGCAAGGTVLRLAKDLAENNKGSRVLIVCSEITA[F]FHGPNENHLDSLVAQALFGDGAAALIVGSGPHLAVERP
IFEIVSTDQTILPDTEKAMKLHLREGG[M]TFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLDCGVLFGFGPGMTVETVVLRSVRVTAAVAN
GN > 2-PS variant= 43 Substitutions= 5: (C 35S) (T137M) (L202F) (L268M) (I343F)
MGSYSSDDVEVIREAGRAQGLATILAIGTATPPN[S]SVAQADYADYFRVTKSEHMVDLKEKFKRICEKTAIKKRYLALTED
YLQENPTMCEFMAPSLNARQDLVVTGVPMLGKEAAVKAIDEWGLPKSKITHLIFCT[M]AGVDMPGADYQLVKLLGLSPSVK
RYMLYQQGCAAGGTVLRLAKDLAENNKGSRVLIVCSEITA[F]FHGPNENHLDSLVAQALFGDGAAALIVGSGPHLAVERP
IFEIVSTDQTILPDTEKAMKLHLREGG[M]TFQLHRDVPLMVAKNIENAAEKALSPLGITDWNSVFWMVHPGGRAILDQVER
KLNLKEDKLRASRHVLSEYGNL[F]SACVLFIIDEVRKRSMAEGKSTTGEGLDCGVLFGFGPGMTVETVVLRSVRVTAAVAN
GN

FIG. 10 (continued)

> 2-PS variant= 4: (C_35S) (L202F) (L268M) (I343F)
MGSYSSDDVEVIREAGRAQGLATILAIGTATPPN[S]VAQADYADYFRVTKSEHMVDLKEKFKRICEKTAIKKRYLALTED
YLQENPTMCEFMAPSLNARQDLVVTGVPMLGKEAAVKAIDEWGLPKSITHLIFCTTAGVDMPGADYQLVKLLGLSPSVK
RYMLYQQGCAAGGTVLRLAKDLAENNKGSRVLIVCSEITAI[F]HGPNENHLDSLVAQALFGDGAAALIVSGPHLAVERP
IFEIVSTDQTILPDTEKAMKLHLREGG[M]TFQLHRDVPLMVAKNIENAAEKALSPLGITDWNSVFWMVHPGGRAILDQVER
KLNLKEDKLRASRHVLSEYGNLI[F]SACVLFIIDEVRKRSMAEGKSTTGEGLDCGVLFGFGPMTVETVLRSVRVTAAVAN
GN > 2-PS variant= 45 Substitutions= 2: (C_35S) (C372S)
MGSYSSDDVEVIREAGRAQGLATILAIGTATPPN[S]VAQADYADYFRVTKSEHMVDLKEKFKRICEKTAIKKRYLALTED
YLQENPTMCEFMAPSLNARQDLVVTGVPMLGKEAAVKAIDEWGLPKSITHLIFCTTAGVDMPGADYQLVKLLGLSPSVK
RYMLYQQGCAAGGTVLRLAKDLAENNKGSRVLIVCSEITAILFHGPNENHLDSLVAQALFGDGAAALIVSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLD[S]GVLFGFGPMTVETVLRSVRVTAAVAN
GN > 2-PS variant= 46 Substitutions= 2: (C_35S) (C372A)
MGSYSSDDVEVIREAGRAQGLATILAIGTATPPN[S]VAQADYADYFRVTKSEHMVDLKEKFKRICEKTAIKKRYLALTED
YLQENPTMCEFMAPSLNARQDLVVTGVPMLGKEAAVKAIDEWGLPKSITHLIFCTTAGVDMPGADYQLVKLLGLSPSVK
RYMLYQQGCAAGGTVLRLAKDLAENNKGSRVLIVCSEITAILFHGPNENHLDSLVAQALFGDGAAALIVSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLD[A]GVLFGFGPMTVETVLRSVRVTAAVAN
GN

FIG. 10 (continued)

> 2-PS variant= 47 Substitutions= 2: (C_35S) (C346S)
MGSYSSDDVEVIREAGRAQGLATILAIGTATPPN[S]VAQADYADYFRVTKSEHMVDLKEKFKRICEKTAIKKRYLALTED
YLQENPTMCEFMAPSLNARQDLVTGVPMLGKEAAVKAIDEWGLPKSKITHLIFCTTAGVDMPGADYQLVKLLGLSPSVK
RYMLYQQGCAAGGTVLRLAKDLAENNKGSRVLIVCSEITAILFHGPNENHLDSLVAQALFGDGAAALIVGSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISA[S]VLFIIDEVRKRSMAEGKSTTGEGLDCGVLFGFGPGMTVETVLRSVRVTAAVAN
GN > 2-PS variant= 48 Substitutions= 2: (C_35S) (C346A)
MGSYSSDDVEVIREAGRAQGLATILAIGTATPPN[S]VAQADYADYFRVTKSEHMVDLKEKFKRICEKTAIKKRYLALTED
YLQENPTMCEFMAPSLNARQDLVTGVPMLGKEAAVKAIDEWGLPKSKITHLIFCTTAGVDMPGADYQLVKLLGLSPSVK
RYMLYQQGCAAGGTVLRLAKDLAENNKGSRVLIVCSEITAILFHGPNENHLDSLVAQALFGDGAAALIVGSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISA[A]VLFIIDEVRKRSMAEGKSTTGEGLDCGVLFGFGPGMTVETVLRSVRVTAAVAN
GN > 2-PS variant= 49 Substitutions= 2: (C_35S) (C195S)
MGSYSSDDVEVIREAGRAQGLATILAIGTATPPN[S]VAQADYADYFRVTKSEHMVDLKEKFKRICEKTAIKKRYLALTED
YLQENPTMCEFMAPSLNARQDLVTGVPMLGKEAAVKAIDEWGLPKSKITHLIFCTTAGVDMPGADYQLVKLLGLSPSVK
RYMLYQQGCAAGGTVLRLAKDLAENNKGSRVLIV[S]SEITAILFHGPNENHLDSLVAQALFGDGAAALIVGSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLDCGVLFGFGPGMTVETVLRSVRVTAAVAN
GN FIG. 10 (continued)

> 2-PS variant= 50 Substitutions= 2:   (C 35S)   (C195A)
MGSYSSDDVEVIREAGRAQGLATILAIGTATPPNSVAQADYADYFRVTKSEHMVDLKEKFKRICEKTAIKKRYLALTED
YLQENPTMCEFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIVaSEITAILFHGPNENHLDSLVAQALFGDGAAALIVSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLDCGVLFGFGPMTVETVLRSVRVTAAVAN
GN > 2-PS variant= 51 Substitutions= 2:   (C 35S)   (C135S)
MGSYSSDDVEVIREAGRAQGLATILAIGTATPPNSVAQADYADYFRVTKSEHMVDLKEKFKRICEKTAIKKRYLALTED
YLQENPTMCEFMAPSLNARQDLVVTGVPMLGKEAAVKAIDEWGLPKSKITHLIFSTTAGVDMPGADYQLVKLLGLSPSVK
RYMLYQQGCAAGGTVLRLAKDLAENNKGSRVLIVCSEITAILFHGPNENHLDSLVAQALFGDGAAALIVSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLDCGVLFGFGPMTVETVLRSVRVTAAVAN
GN > 2-PS variant= 52 Substitutions= 2:   (C 35S)   (C135A)
MGSYSSDDVEVIREAGRAQGLATILAIGTATPPNSVAQADYADYFRVTKSEHMVDLKEKFKRICEKTAIKKRYLALTED
YLQENPTMCEFMAPSLNARQDLVVTGVPMLGKEAAVKAIDEWGLPKSKITHLIFaTTAGVDMPGADYQLVKLLGLSPSVK
RYMLYQQGCAAGGTVLRLAKDLAENNKGSRVLIVCSEITAILFHGPNENHLDSLVAQALFGDGAAALIVSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLDCGVLFGFGPMTVETVLRSVRVTAAVAN
GN FIG. 10 (continued)

> 2-PS variant= 53 Substitutions= 2: (C 35S) (C 89S)
MGSYSSDDVEVIREAGRAQGLATILAIGTATPPN[S]VAQADYADYYFRVTKSEHMVDLKEKFKRICEKTAIKKRYLALTED
YLQENPTM[S]EFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIVCSEITAILFHGPNENHLDSLVAQALFGDGAAALIVGSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLDCGVLFGFGPMTVETVVLRSVRVTAAVAN
GN > 2-PS variant= 54 Substitutions= 2: (C 35S) (C 89A)
MGSYSSDDVEVIREAGRAQGLATILAIGTATPPN[S]VAQADYADYYFRVTKSEHMVDLKEKFKRICEKTAIKKRYLALTED
YLQENPTM[A]EFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIVCSEITAILFHGPNENHLDSLVAQALFGDGAAALIVGSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLDCGVLFGFGPMTVETVVLRSVRVTAAVAN
GN > 2-PS variant= 55 Substitutions= 2: (C 35S) (C 65S)
MGSYSSDDVEVIREAGRAQGLATILAIGTATPPN[S]VAQADYADYYFRVTKSEHMVDLKEKFKRI[S]EKTAIKKRYLALTED
YLQENPTMCEFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIVCSEITAILFHGPNENHLDSLVAQALFGDGAAALIVGSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLDCGVLFGFGPMTVETVVLRSVRVTAAVAN
GN

FIG. 10 (continued)

> 2-PS variant= 56 Substitutions= 2: (C_35S) (C_65A)
MGSYSSDDVEVIREAGRAQGLATILAIGTATPPN[S]VAQADYADYFRVTKSEHMVDLKEKFKR[A]EKTAIKKRYLALTED
YLQENPTMCEFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIVCSEITAILFHGPNENHLDSLVAQALFGDGAAALIVGSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLDCGVLFGFGPGMTVETVVLRSVRVTAAVAN
GN > 2-PS variant= 57 Substitutions= 2: (C_35S) (C169S)
MGSYSSDDVEVIREAGRAQGLATILAIGTATPPN[S]VAQADYADYFRVTKSEHMVDLKEKFKRICEKTAIKKRYLALTED
YLQENPTMCEFMAPSLNARQDLVVTGVPMLGKEAAVKAIDEWGLPKSKITHLIFCTTAGVDMPGADYQLVKLLGLSPSVK
RYMLYQQG[S]AAGGTVLRLAKDLAENNKGSRVLIVCSEITAILFHGPNENHLDSLVAQALFGDGAAALIVGSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLDCGVLFGFGPGMTVETVVLRSVRVTAAVAN
GN > 2-PS variant= 58 Substitutions= 2: (C_35S) (N341H)
MGSYSSDDVEVIREAGRAQGLATILAIGTATPPN[S]VAQADYADYFRVTKSEHMVDLKEKFKRICEKTAIKKRYLALTED
YLQENPTMCEFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIVCSEITAILFHGPNENHLDSLVAQALFGDGAAALIVGSGPHLAVERP
IFEIVSTDQTILPDTEKAMKLHLREGGLTFQLHRDVPLMVAKNIENAAEKALSPLGITDWNSVFWMVHPGGRAILDQVER
KLNLKEDKLRASRHVLSEYG[H]LISACVLFIIDEVRKRSMAEGKSTTGEGLDCGVLFGFGPGMTVETVVLRSVRVTAAVAN
GN

FIG. 10 (continued)

```
> 2-PS variant= 59 Substitutions= 2:    (C 35S)   (H308Q)
MGSYSSDDVEVIREAGRAQGLATILAIGTATPPNSVAQADYADYFRVTKSEHMVDLKEKFKRICEKTAIKKRYLALTED
YLQENPTMCEFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIVCSEITAILFHGPNENHLDSLVAQALFGDGAAALIVGSGPHLAVERP
IFEIVSTDQTILPDTEKAMKLHLREGGLTFQLHRDVPLMVAKNIENAAEKALSPLGITDWNSVFWMVQPGGRAILDQVER
KLNLKEDKLRASRHVLSEYGNLISACVLFIIDEVRKRSMAEGKSTTGEGLDCGVLFGFGPGMTVETVLRSVRVTAAVAN
GN > 2-PS variant= 60 Substitutions= 3:    (C 35S)   (L202F)   (L268F)
MGSYSSDDVEVIREAGRAQGLATILAIGTATPPNSVAQADYADYFRVTKSEHMVDLKEKFKRICEKTAIKKRYLALTED
YLQENPTMCEFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIVCSEITAIFFHGPNENHLDSLVAQALFGDGAAALIVGSGPHLAVERP
IFEIVSTDQTILPDTEKAMKLHLREGGFTFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLDCGVLFGFGPGMTVETVLRSVRVTAAVAN
GN > 2-PS variant= 61 Substitutions= 3:    (C 35S)   (L268M)   (I343M)
MGSYSSDDVEVIREAGRAQGLATILAIGTATPPNSVAQADYADYFRVTKSEHMVDLKEKFKRICEKTAIKKRYLALTED
YLQENPTMCEFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIVCSEITAILFHGPNENHLDSLVAQALFGDGAAALIVGSGPHLAVERP
IFEIVSTDQTILPDTEKAMKLHLREGGMTFQLHRDVPLMVAKNIENAAEKALSPLGITDWNSVFWMVHPGGRAILDQVER
KLNLKEDKLRASRHVLSEYGNLMSACVLFIIDEVRKRSMAEGKSTTGEGLDCGVLFGFGPGMTVETVLRSVRVTAAVAN
GN
```

FIG. 10 (continued)

> 2-PS variant= 62 Substitutions= 3: (C 35S) (L202F) (L268M)
MGSYSSDDVEVIREAGRAQGLATILAIGTATPPN[S]VAQADYADYFRVTKSEHMVDLKEKFKRICEKTAIKKRYLALTED
YLQENPTMCEFMAPSLNARQDLVVTGVPMLGKEAAVKAIDEWGLPKSKITHLIFCTTAGVDMPGADYQLVKLLGLSPSVK
RYMLYQQGCAAGGTVLRLAKDLAENNKGSRVLIVCSEITAI[E]FHGPNENHLDSLVAQALFGDGAAALIVGSGPHLAVERP
IFEIVSTDQTILPDTEKAMKLHLREGQ[T]TFQLHRDVPLMVAKNIENAAEKALSPLGITDWNSVFWMVHPGGRAILDQVER
KLNLKEDKLRASRHVLSEYGNLISACVLFIIDEVRKRSMAEGKSTTGEGLDCGVLFGFGPGMTVETVVLRSVRVTAAVAN
GN

FIG. 11

Amino-acid sequence alignments: 2-PS

```
         1                          .                          .                          .                          .                          .                          .         .  70
>Seq  1  MGSYSSDDVEVIREAGRAQGLATILAIGTATPPNCVAQADYADYFRVTKSEHMVDLKEKFKRICEKTAI
>Seq  2  MGSYSSDDVEVIREAGRAQGLATILAIGTATPPNCVAQADYADYFRVTKSEHMVDLKEKFKRICEKTAI
>Seq  3  MGSYSSDDVEVIREAGRAQGLATILAIGTATPPNCVAQADYADYFRVTKSEHMVDLKEKFKRICEKTAI
>Seq  4  MGSYSSDDVEVIREAGRAQGLATILAIGTATPPNaVAQADYADYFRVTKSEHMVDLKEKFKRICEKTAI
>Seq  5  MGSYSSDDVEVIREAGRAQGLATILAIGTATPPNCVAQADYADYFRVTKSEHMVDLKEKFKRICEKTAI
>Seq  6  MGSYSSDDVEVIREAGRAQGLATILAIGTATPPNCVAQADYADYFRVTKSEHMVDLKEKFKRICEKTAI
>Seq  7  MGSYSSDDVEVIREAGRAQGLATILAIGTATPPNCVAQADYADYFRVTKSEHMVDLKEKFKRICEKTAI
>Seq  8  MGSYSSDDVEVIREAGRAQGLATILAIGTATPPNCVAQADYADYFRVTKSEHMVDLKEKFKRICEKTAI
>Seq  9  MGSYSSDDVEVIREAGRAQGLATILAIGTATPPNCVAQADYADYFRVTKSEHMVDLKEKFKRICEKTAI
>Seq 10  MGSYSSDDVEVIREAGRAQGLATILAIGTATPPNCVAQADYADYFRVTKSEHMVDLKEKFKRISEKTAI
>Seq 11  MGSYSSDDVEVIREAGRAQGLATILAIGTATPPNCVAQADYADYFRVTKSEHMVDLKEKFKRISEKTAI
>Seq 12  MGSYSSDDVEVIREAGRAQGLATILAIGTATPPNCVAQADYADYFRVTKSEHMVDLKEKFKRISEKTAI
>Seq 13  MGSYSSDDVEVIREAGRAQGLATILAIGTATPPNsVAQADYADYFRVTKSEHMVDLKEKFKRISEKTAI
>Seq 14  MGSYSSDDVEVIREAGRAQGLATILAIGTATPPNsVAQADYADYFRVTKSEHMVDLKEKFKRISEKTAI
>Seq 15  MGSYSSDDVEVIREAGRAQGLATILAIGTATPPNsVAQADYADYFRVTKSEHMVDLKEKFKRISEKTAI
>Seq 16  MGSYSSDDVEVIREAGRAQGLATILAIGTATPPNsVAQADYADYFRVTKSEHMVDLKEKFKRISEKTAI
>Seq 17  MGSYSSDDVEVIREAGRAQGLATILAIGTATPPNsVAQADYADYFRVTKSEHMVDLKEKFKRISEKTAI
>Seq 18  MGSYSSDDVEVIREAGRAQGLATILAIGTATPPNsVAQADYADYFRVTKSEHMVDLKEKFKRISEKTAI
>Seq 19  MGSYSSDDVEVIREAGRAQGLATILAIGTATPPNsVAQADYADYFRVTKSEHMVDLKEKFKRISEKTAI
>Seq 20  MGSYSSDDVEVIREAGRAQGLATILAIGTATPPNsVAQADYADYFRVTKSEHMVDLKEKFKRISEKTAI
>Seq 21  MGSYSSDDVEVIREAGRAQGLATILAIGTATPPNsVAQADYADYFRVTKSEHMVDLKEKFKRISEKTAI
```

FIG. 11 (continued)

| Seq | Sequence |
|---|---|
| Seq 22 | MGSYSSDDVEVIREAGRAQGLATILAIGTATPPNSVAQADYADYYFRVTKSEHMVDLKEKFKRISEKTAI |
| Seq 23 | MGSYSSDDVEVIREAGRAQGLATILAIGTATPPNSVAQADYADYYFRVTKSEHMVDLKEKFKRICEKTAI |
| Seq 24 | MGSYSSDDVEVIREAGRAQGLATILAIGTATPPNSVAQADYADYYFRVTKSEHMVDLKEKFKRICEKTAI |
| Seq 25 | MGSYSSDDVEVIREAGRAQGLATILAIGTATPPNSVAQADYADYYFRVTKSEHMVDLKEKFKRICEKTAI |
| Seq 26 | MGSYSSDDVEVIREAGRAQGLATILAIGTATPPNSVAQADYADYYFRVTKSEHMVDLKEKFKRICEKTAI |
| Seq 27 | MGSYSSDDVEVIREAGRAQGLATILAIGTATPPNSVAQADYADYYFRVTKSEHMVDLKEKFKRICEKTAI |
| Seq 28 | MGSYSSDDVEVIREAGRAQGLATILAIGTATPPNSVAQADYADYYFRVTKSEHMVDLKEKFKRICEKTAI |
| Seq 29 | MGSYSSDDVEVIREAGRAQGLATILAIGTATPPNSVAQADYADYYFRVTKSEHMVDLKEKFKRICEKTAI |
| Seq 30 | MGSYSSDDVEVIREAGRAQGLATILAIGTATPPNSVAQADYADYYFRVTKSEHMVDLKEKFKRICEKTAI |
| Seq 31 | MGSYSSDDVEVIREAGRAQGLATILAIGTATPPNSVAQADYADYYFRVTKSEHMVDLKEKFKRICEKTAI |
| Seq 32 | MGSYSSDDVEVIREAGRAQGLATILAIGTATPPNSVAQADYADYYFRVTKSEHMVDLKEKFKRICEKTAI |
| Seq 33 | MGSYSSDDVEVIREAGRAQGLATILAIGTATPPNSVAQADYADYYFRVTKSEHMVDLKEKFKRICEKTAI |
| Seq 34 | MGSYSSDDVEVIREAGRAQGLATILAIGTATPPNSVAQADYADYYFRVTKSEHMVDLKEKFKRICEKTAI |
| Seq 35 | MGSYSSDDVEVIREAGRAQGLATILAIGTATPPNSVAQADYADYYFRVTKSEHMVDLKEKFKRICEKTAI |
| Seq 36 | MGSYSSDDVEVIREAGRAQGLATILAIGTATPPNSVAQADYADYYFRVTKSEHMVDLKEKFKRICEKTAI |
| Seq 37 | MGSYSSDDVEVIREAGRAQGLATILAIGTATPPNSVAQADYADYYFRVTKSEHMVDLKEKFKRISEKTAI |
| Seq 38 | MGSYSSDDVEVIREAGRAQGLATILAIGTATPPNSVAQADYADYYFRVTKSEHMVDLKEKFKRICEKTAI |
| Seq 39 | MGSYSSDDVEVIREAGRAQGLATILAIGTATPPNSVAQADYADYYFRVTKSEHMVDLKEKFKRICEKTAI |
| Seq 40 | MGSYSSDDVEVIREAGRAQGLATILAIGTATPPNSVAQADYADYYFRVTKSEHMVDLKEKFKRISEKTAI |
| Seq 41 | MGSYSSDDVEVIREAGRAQGLATILAIGTATPPNSVAQADYADYYFRVTKSEHMVDLKEKFKRICEKTAI |
| Seq 42 | MGSYSSDDVEVIREAGRAQGLATILAIGTATPPNSVAQADYADYYFRVTKSEHMVDLKEKFKRICEKTAI |
| Seq 43 | MGSYSSDDVEVIREAGRAQGLATILAIGTATPPNSVAQADYADYYFRVTKSEHMVDLKEKFKRICEKTAI |
| Seq 44 | MGSYSSDDVEVIREAGRAQGLATILAIGTATPPNSVAQADYADYYFRVTKSEHMVDLKEKFKRICEKTAI |
| Seq 45 | MGSYSSDDVEVIREAGRAQGLATILAIGTATPPNSVAQADYADYYFRVTKSEHMVDLKEKFKRICEKTAI |

FIG. 11 (continued)

```
>Seq 46  MGSYSSDDVEVIREAGRAQGLATILAIGTATPPNsVAQADYADYYFRVTKSEHMVDLKEKFKRICEKTAI
>Seq 47  MGSYSSDDVEVIREAGRAQGLATILAIGTATPPNsVAQADYADYYFRVTKSEHMVDLKEKFKRICEKTAI
>Seq 48  MGSYSSDDVEVIREAGRAQGLATILAIGTATPPNsVAQADYADYYFRVTKSEHMVDLKEKFKRICEKTAI
>Seq 49  MGSYSSDDVEVIREAGRAQGLATILAIGTATPPNsVAQADYADYYFRVTKSEHMVDLKEKFKRICEKTAI
>Seq 50  MGSYSSDDVEVIREAGRAQGLATILAIGTATPPNsVAQADYADYYFRVTKSEHMVDLKEKFKRICEKTAI
>Seq 51  MGSYSSDDVEVIREAGRAQGLATILAIGTATPPNsVAQADYADYYFRVTKSEHMVDLKEKFKRICEKTAI
>Seq 52  MGSYSSDDVEVIREAGRAQGLATILAIGTATPPNsVAQADYADYYFRVTKSEHMVDLKEKFKRICEKTAI
>Seq 53  MGSYSSDDVEVIREAGRAQGLATILAIGTATPPNsVAQADYADYYFRVTKSEHMVDLKEKFKRICEKTAI
>Seq 54  MGSYSSDDVEVIREAGRAQGLATILAIGTATPPNsVAQADYADYYFRVTKSEHMVDLKEKFKRICEKTAI
>Seq 55  MGSYSSDDVEVIREAGRAQGLATILAIGTATPPNsVAQADYADYYFRVTKSEHMVDLKEKFKRIsEKTAI
>Seq 56  MGSYSSDDVEVIREAGRAQGLATILAIGTATPPNsVAQADYADYYFRVTKSEHMVDLKEKFKRIaEKTAI
>Seq 57  MGSYSSDDVEVIREAGRAQGLATILAIGTATPPNsVAQADYADYYFRVTKSEHMVDLKEKFKRICEKTAI
>Seq 58  MGSYSSDDVEVIREAGRAQGLATILAIGTATPPNsVAQADYADYYFRVTKSEHMVDLKEKFKRICEKTAI
>Seq 59  MGSYSSDDVEVIREAGRAQGLATILAIGTATPPNsVAQADYADYYFRVTKSEHMVDLKEKFKRICEKTAI
>Seq 60  MGSYSSDDVEVIREAGRAQGLATILAIGTATPPNsVAQADYADYYFRVTKSEHMVDLKEKFKRICEKTAI
>Seq 61  MGSYSSDDVEVIREAGRAQGLATILAIGTATPPNsVAQADYADYYFRVTKSEHMVDLKEKFKRICEKTAI
>Seq 62  MGSYSSDDVEVIREAGRAQGLATILAIGTATPPNsVAQADYADYYFRVTKSEHMVDLKEKFKRICEKTAI 71                                                               140
>Seq 1   KKRYLALTEDYLQENPTMCEFMAPSLNARQDLVVTGVPMLGKEAAVKAIDEWGLPKSKITHLIFCTTAGV
>Seq 2   KKRYLALTEDYLQENPTMCEFMAPSLNARQDLVVTGVPMLGKEAAVKAIDEWGLPKSKITHLIFCTTAGV
>Seq 3   KKRYLALTEDYLQENPTMCEFMAPSLNARQDLVVTGVPMLGKEAAVKAIDEWGLPKSKITHLIFCTTAGV
>Seq 4   KKRYLALTEDYLQENPTMCEFMAPSLNARQDLVVTGVPMLGKEAAVKAIDEWGLPKSKITHLIFCTTAGV
>Seq 5   KKRYLALTEDYLQENPTMCEFMAPSLNARQDLVVTGVPMLGKEAAVKAIDEWGLPKSKITHLIFCTTAGV
```

FIG. 11 (continued)

```
Seq ~ 6  KKRYLALTEDYLQENPTMCEFMAPSLNARQDLVVTGVPMLGKEAAVKAIDEWGLPKSKITHLIFCTTAGV
Seq ~ 7  KKRYLALTEDYLQENPTMCEFMAPSLNARQDLVVTGVPMLGKEAAVKAIDEWGLPKSKITHLIFCTTAGV
Seq ~ 8  KKRYLALTEDYLQENPTMsEFMAPSLNARQDLVVTGVPMLGKEAAVKAIDEWGLPKSKITHLIFCTTAGV
Seq ~ 9  KKRYLALTEDYLQENPTMsEFMAPSLNARQDLVVTGVPMLGKEAAVKAIDEWGLPKSKITHLIFCTTAGV
Seq ~ 10 KKRYLALTEDYLQENPTMsEFMAPSLNARQDLVVTGVPMLGKEAAVKAIDEWGLPKSKITHLIFCTTAGV
Seq ~ 11 KKRYLALTEDYLQENPTMsEFMAPSLNARQDLVVTGVPMLGKEAAVKAIDEWGLPKSKITHLIFCTTAGV
Seq ~ 12 KKRYLALTEDYLQENPTMsEFMAPSLNARQDLVVTGVPMLGKEAAVKAIDEWGLPKSKITHLIFCTTAGV
Seq ~ 13 KKRYLALTEDYLQENPTMsEFMAPSLNARQDLVVTGVPMLGKEAAVKAIDEWGLPKSKITHLIFCTfAGV
Seq ~ 14 KKRYLALTEDYLQENPTMsEFMAPSLNARQDLVVTGVPMLGKEAAVKAIDEWGLPKSKITHLIFCTfAGV
Seq ~ 15 KKRYLALTEDYLQENPTMsEFMAPSLNARQDLVVTGVPMLGKEAAVKAIDEWGLPKSKITHLIFCTTAGV
Seq ~ 16 KKRYLALTEDYLQENPTMsEFMAPSLNARQDLVVTGVPMLGKEAAVKAIDEWGLPKSKITHLIFCTfAGV
Seq ~ 17 KKRYLALTEDYLQENPTMsEFMAPSLNARQDLVVTGVPMLGKEAAVKAIDEWGLPKSKITHLIFCTfAGV
Seq ~ 18 KKRYLALTEDYLQENPTMsEFMAPSLNARQDLVVTGVPMLGKEAAVKAIDEWGLPKSKITHLIFCTTAGV
Seq ~ 19 KKRYLALTEDYLQENPTMsEFMAPSLNARQDLVVTGVPMLGKEAAVKAIDEWGLPKSKITHLIFCTTAGV
Seq ~ 20 KKRYLALTEDYLQENPTMsEFMAPSLNARQDLVVTGVPMLGKEAAVKAIDEWGLPKSKITHLIFCTTAGV
Seq ~ 21 KKRYLALTEDYLQENPTMsEFMAPSLNARQDLVVTGVPMLGKEAAVKAIDEWGLPKSKITHLIFCTTAGV
Seq ~ 22 KKRYLALTEDYLQENPTMsEFMAPSLNARQDLVVTGVPMLGKEAAVKAIDEWGLPKSKITHLIFCTTAGV
Seq ~ 23 KKRYLALTEDYLQENPTMCEFMAPSLNARQDLVVTGVPMLGKEAAVKAIDEWGLPKSKITHLIFCTTAGV
Seq ~ 24 KKRYLALTEDYLQENPTMCEFMAPSLNARQDLVVTGVPMLGKEAAVKAIDEWGLPKSKITHLIFCTmAGV
Seq ~ 25 KKRYLALTEDYLQENPTMCEFMAPSLNARQDLVVTGVPMLGKEAAVKAIDEWGLPKSKITHLIFCTTAGV
Seq ~ 26 KKRYLALTEDYLQENPTMCEFMAPSLNARQDLVVTGVPMLGKEAAVKAIDEWGLPKSKITHLIFCTTAGV
Seq ~ 27 KKRYLALTEDYLQENPTMCEFMAPSLNARQDLVVTGVPMLGKEAAVKAIDEWGLPKSKITHLIFCTlAGV
Seq ~ 28 KKRYLALTEDYLQENPTMCEFMAPSLNARQDLVVTGVPMLGKEAAVKAIDEWGLPKSKITHLIFCTTAGV
Seq ~ 29 KKRYLALTEDYLQENPTMCEFMAPSLNARQDLVVTGVPMLGKEAAVKAIDEWGLPKSKITHLIFCTTAGV
```

FIG. 11 (continued)

```
Seq 30  KKRYLALTEDYLQENPTMCEFMAPSLNARQDLVVTGVPMLGKEAAVKAIDEWGLPKSKITHLIFCTTAGV
Seq 31  KKRYLALTEDYLQENPTMCEFMAPSLNARQDLVVTGVPMLGKEAAVKAIDEWGLPKSKITHLIFCTTAGV
Seq 32  KKRYLALTEDYLQENPTMCEFMAPSLNARQDLVVTGVPMLGKEAAVKAIDEWGLPKSKITHLIFCTTAGV
Seq 33  KKRYLALTEDYLQENPTMCEFMAPSLNARQDLVVTGVPMLGKEAAVKAIDEWGLPKSKITHLIFCTTAGV
Seq 34  KKRYLALTEDYLQENPTMCEFMAPSLNARQDLVVTGVPMLGKEAAVKAIDEWGLPKSKITHLIFCTTAGV
Seq 35  KKRYLALTEDYLQENPTMCEFMAPSLNARQDLVVTGVPMLGKEAAVKAIDEWGLPKSKITHLIFCTTAGV
Seq 36  KKRYLALTEDYLQENPTMCEFMAPSLNARQDLVVTGVPMLGKEAAVKAIDEWGLPKSKITHLIFCTTAGV
Seq 37  KKRYLALTEDYLQENPTMsEFMAPSLNARQDLVVTGVPMLGKEAAVKAIDEWGLPKSKITHLIFCTTAGV
Seq 38  KKRYLALTEDYLQENPTMCEFMAPSLNARQDLVVTGVPMLGKEAAVKAIDEWGLPKSKITHLIFCTTAGV
Seq 39  KKRYLALTEDYLQENPTMsEFMAPSLNARQDLVVTGVPMLGKEAAVKAIDEWGLPKSKITHLIFCTIAGV
Seq 40  KKRYLALTEDYLQENPTMCEFMAPSLNARQDLVVTGVPMLGKEAAVKAIDEWGLPKSKITHLIFCTTAGV
Seq 41  KKRYLALTEDYLQENPTMCEFMAPSLNARQDLVVTGVPMLGKEAAVKAIDEWGLPKSKITHLIFCTTAGV
Seq 42  KKRYLALTEDYLQENPTMCEFMAPSLNARQDLVVTGVPMLGKEAAVKAIDEWGLPKSKITHLIFCTmAGV
Seq 43  KKRYLALTEDYLQENPTMCEFMAPSLNARQDLVVTGVPMLGKEAAVKAIDEWGLPKSKITHLIFCTTAGV
Seq 44  KKRYLALTEDYLQENPTMCEFMAPSLNARQDLVVTGVPMLGKEAAVKAIDEWGLPKSKITHLIFCTTAGV
Seq 45  KKRYLALTEDYLQENPTMCEFMAPSLNARQDLVVTGVPMLGKEAAVKAIDEWGLPKSKITHLIFCTTAGV
Seq 46  KKRYLALTEDYLQENPTMCEFMAPSLNARQDLVVTGVPMLGKEAAVKAIDEWGLPKSKITHLIFCTTAGV
Seq 47  KKRYLALTEDYLQENPTMCEFMAPSLNARQDLVVTGVPMLGKEAAVKAIDEWGLPKSKITHLIFCTTAGV
Seq 48  KKRYLALTEDYLQENPTMCEFMAPSLNARQDLVVTGVPMLGKEAAVKAIDEWGLPKSKITHLIFCTTAGV
Seq 49  KKRYLALTEDYLQENPTMCEFMAPSLNARQDLVVTGVPMLGKEAAVKAIDEWGLPKSKITHLIFCTTAGV
Seq 50  KKRYLALTEDYLQENPTMCEFMAPSLNARQDLVVTGVPMLGKEAAVKAIDEWGLPKSKITHLIFCTTAGV
Seq 51  KKRYLALTEDYLQENPTMCEFMAPSLNARQDLVVTGVPMLGKEAAVKAIDEWGLPKSKITHLIFsTTAGV
Seq 52  KKRYLALTEDYLQENPTMCEFMAPSLNARQDLVVTGVPMLGKEAAVKAIDEWGLPKSKITHLIFaTTAGV
Seq 53  KKRYLALTEDYLQENPTMsEFMAPSLNARQDLVVTGVPMLGKEAAVKAIDEWGLPKSKITHLIFCTTAGV
```

FIG. 11 (continued)

```
              54  KKRYLALTEDYLQENPTMaEFMAPSLNARQDLVVTGVPMLGKEAAVKAIDEWGLPKSKITHLIFCTTAGV
              55  KKRYLALTEDYLQENPTMCEFMAPSLNARQDLVVTGVPMLGKEAAVKAIDEWGLPKSKITHLIFCTTAGV
              56  KKRYLALTEDYLQENPTMCEFMAPSLNARQDLVVTGVPMLGKEAAVKAIDEWGLPKSKITHLIFCTTAGV
              57  KKRYLALTEDYLQENPTMCEFMAPSLNARQDLVVTGVPMLGKEAAVKAIDEWGLPKSKITHLIFCTTAGV
              58  KKRYLALTEDYLQENPTMCEFMAPSLNARQDLVVTGVPMLGKEAAVKAIDEWGLPKSKITHLIFCTTAGV
              59  KKRYLALTEDYLQENPTMCEFMAPSLNARQDLVVTGVPMLGKEAAVKAIDEWGLPKSKITHLIFCTTAGV
              60  KKRYLALTEDYLQENPTMCEFMAPSLNARQDLVVTGVPMLGKEAAVKAIDEWGLPKSKITHLIFCTTAGV
              61  KKRYLALTEDYLQENPTMCEFMAPSLNARQDLVVTGVPMLGKEAAVKAIDEWGLPKSKITHLIFCTTAGV
              62  KKRYLALTEDYLQENPTMCEFMAPSLNARQDLVVTGVPMLGKEAAVKAIDEWGLPKSKITHLIFCTTAGV

141                                            .                       210
^ Seq         1   DMPGADYQLVKLLGLSPSVKRYMLYQQGCAAGGTVLRLAKDLAENNKGSRVLIVCSEITTAILFHGPNENH
^ Seq         2   DMPGADYQLVKLLGLSPSVKRYMLYQQGCAAGGTVLRLAKDLAENNKGSRVLIVCSEITTAILFHGPNENH
^ Seq         3   DMPGADYQLVKLLGLSPSVKRYMLYQQGCAAGGTVLRLAKDLAENNKGSRVLIVCSEITTAIfFHGPNENH
^ Seq         4   DMPGADYQLVKLLGLSPSVKRYMLYQQGCAAGGTVLRLAKDLAENNKGSRVLIVCSEITTAILFHGPNENH
^ Seq         5   DMPGADYQLVKLLGLSPSVKRYMLYQQGCAAGGTVLRLAKDLAENNKGSRVLIVCSEITTAILFHGPNENH
^ Seq         6   DMPGADYQLVKLLGLSPSVKRYMLYQQGCAAGGTVLRLAKDLAENNKGSRVLIVCSEITTAILFHGPNENH
^ Seq         7   DMPGADYQLVKLLGLSPSVKRYMLYQQGCAaAGGTVLRLAKDLAENNKGSRVLIVCSEITTAILFHGPNENH
^ Seq         8   DMPGADYQLVKLLGLSPSVKRYMLYQQGCAAGGTVLRLAKDLAENNKGSRVLIVCSEITTAILFHGPNENH
^ Seq         9   DMPGADYQLVKLLGLSPSVKRYMLYQQGCAAGGTVLRLAKDLAENNKGSRVLIVCSEITTAILFHGPNENH
^ Seq        10   DMPGADYQLVKLLGLSPSVKRYMLYQQGCAAGGTVLRLAKDLAENNKGSRVLIVCSEITTAILFHGPNENH
^ Seq        11   DMPGADYQLVKLLGLSPSVKRYMLYQQGCAAGGTVLRLAKDLAENNKGSRVLIVsSEITAILFHGPNENH
^ Seq        12   DMPGADYQLVKLLGLSPSVKRYMLYQQGCAAGGTVLRLAKDLAENNKGSRVLIVsSEITAILFHGPNENH
^ Seq        13   DMPGADYQLVKLLGLSPSVKRYMLYQQGCAAGGTVLRLAKDLAENNKGSRVLIVsSEITAILFHGPNENH
```

FIG. 11 (continued)

```
Seq > 14  DMPGADYQLVKLLLGLSPSVKRYMLYQQGCAAGGTVLRLAKDLAENNKGSRVLIVsSEITAIgFHGPNENH
Seq > 15  DMPGADYQLVKLLLGLSPSVKRYMLYQQGCAAGGTVLRLAKDLAENNKGSRVLIVsSEITAfgFHGPNENH
Seq > 16  DMPGADYQLVKLLLGLSPSVKRYMLYQQGCAAGGTVLRLAKDLAENNKGSRVLIVsSEITAIgFHGPNENH
Seq > 17  DMPGADYQLVKLLLGLSPSVKRYMLYQQGCAAGGTVLRLAKDLAENNKGSRVLIVsSEITAIgFHGPNENH
Seq > 18  DMPGADYQLVKLLLGLSPSVKRYMLYQQGCAAGGTVLRLAKDLAENNKGSRVLIVCSEITAILFHGPNENH
Seq > 19  DMPGADYQLVKLLLGLSPSVKRYMLYQQGCAAGGTVLRLAKDLAENNKGSRVLIVCSEITAILFHGPNENH
Seq > 20  DMPGADYQLVKLLLGLSPSVKRYMLYQQGCAAGGTVLRLAKDLAENNKGSRVLIVCSEITAILFHGPNENH
Seq > 21  DMPGADYQLVKLLLGLSPSVKRYMLYQQGCAAGGTVLRLAKDLAENNKGSRVLIVsSEITAILFHGPNENH
Seq > 22  DMPGADYQLVKLLLGLSPSVKRYMLYQQGCAAGGTVLRLAKDLAENNKGSRVLIVsSEITAILFHGPNENH
Seq > 23  DMPGADYQLVKLLLGLSPSVKRYMLYQQGCAAGGTVLRLAKDLAENNKGSRVLIVCSEITAILFHGPNENH
Seq > 24  DMPGADYQLVKLLLGLSPSVKRYMLYQQGCAAGGTVLRLAKDLAENNKGSRVLIVCSEITAILFHGPNENH
Seq > 25  DMPGADYQLVKLLLGLSPSVKRYMLYQQGCAAGGTVLRLAKDLAENNKGSRVLIVCSEITAILFHGPNENH
Seq > 26  DMPGADYQLVKLLLGLSPSVKRYMLYQQGCAAGGTVLRLAKDLAENNKGSRVLIVCSEITAILFHGPNENH
Seq > 27  DMPGADYQLVKLLLGLSPSVKRYMLYQQGCAAGGTVLRLAKDLAENNKGSRVLIVCSEITAILFHGPNENH
Seq > 28  DMPGADYQLVKLLLGLSPSVKRYMLYQQGCAAGGTVLRLAKDLAENNKGSRVLIVCSEITAILFHGPNENH
Seq > 29  DMPGADYQLVKLLLGLSPSVKRYMLYQQGCAAGGaAAGGTVLRLAKDLAENNKGSRVLIVCSEITAILFHGPNENH
Seq > 30  DMPGADYQLVKLLLGLSPSVKRYMLYQQGCAAGGTVLRLAKDLAENNKGSRVLIVCSEITAfLFHGPNENH
Seq > 31  DMPGADYQLVKLLLGLSPSVKRYMLYQQGCAAGGTVLRLAKDLAENNKGSRVLIVCSEITAILFHGPNENH
Seq > 32  DMPGADYQLVKLLLGLSPSVKRYMLYQQGCAAGGTVLRLAKDLAENNKGSRVLIVCSEITAILFHGPNENH
Seq > 33  DMPGADYQLVKLLLGLSPSVKRYMLYQQGCAAGGTVLRLAKDLAENNKGSRVLIVCSEITAmLFHGPNENH
Seq > 34  DMPGADYQLVKLLLGLSPSVKRYMLYQQGCAAGGTVLRLAKDLAENNKGSRVLIVCSEITAILFHGPNENH
Seq > 35  DMPGADYQLVKLLLGLSPSVKRYMLYQQGCAAGGTVLRLAKDLAENNKGSRVLIVCSEITAImFHGPNENH
Seq > 36  DMPGADYQLVKLLLGLSPSVKRYMLYQQGCAAGGTVLRLAKDLAENNKGSRVLIVCSEITAIgFHGPNENH
Seq > 37  DMPGADYQLVKLLLGLSPSVKRYMLYQQGCAAGGTVLRLAKDLAENNKGSRVLIVsSEITAIgFHGPNENH
```

FIG. 11 (continued)

```
Seq 38  DMPGADYQLVKLLLGLSPSVKRYMLYQQGCAAGGTVLRLAKDLAENNKGSRVLIVCSEITTAIgFHGPNENH
Seq 39  DMPGADYQLVKLLLGLSPSVKRYMLYQQGCAAGGTVLRLAKDLAENNKGSRVLIVCSEITTAILFHGPNENH
Seq 40  DMPGADYQLVKLLLGLSPSVKRYMLYQQGCAAGGTVLRLAKDLAENNKGSRVLIVCSEITTAILFHGPNENH
Seq 41  DMPGADYQLVKLLLGLSPSVKRYMLYQQGCAAGGTVLRLAKDLAENNKGSRVLIVsSEITTAIgFHGPNENH
Seq 42  DMPGADYQLVKLLLGLSPSVKRYMLYQQGCAAGGTVLRLAKDLAENNKGSRVLIVCSEITTAILFHGPNENH
Seq 43  DMPGADYQLVKLLLGLSPSVKRYMLYQQGCAAGGTVLRLAKDLAENNKGSRVLIVCSEITTAILFHGPNENH
Seq 44  DMPGADYQLVKLLLGLSPSVKRYMLYQQGCAAGGTVLRLAKDLAENNKGSRVLIVCSEITTAIfFHGPNENH
Seq 45  DMPGADYQLVKLLLGLSPSVKRYMLYQQGCAAGGTVLRLAKDLAENNKGSRVLIVCSEITTAIfFHGPNENH
Seq 46  DMPGADYQLVKLLLGLSPSVKRYMLYQQGCAAGGTVLRLAKDLAENNKGSRVLIVCSEITTAIfFHGPNENH
Seq 47  DMPGADYQLVKLLLGLSPSVKRYMLYQQGCAAGGTVLRLAKDLAENNKGSRVLIVCSEITTAILFHGPNENH
Seq 48  DMPGADYQLVKLLLGLSPSVKRYMLYQQGCAAGGTVLRLAKDLAENNKGSRVLIVCSEITTAILFHGPNENH
Seq 49  DMPGADYQLVKLLLGLSPSVKRYMLYQQGCAAGGTVLRLAKDLAENNKGSRVLIVsSEITTAILFHGPNENH
Seq 50  DMPGADYQLVKLLLGLSPSVKRYMLYQQGCAAGGTVLRLAKDLAENNKGSRVLIVCSEITTAILFHGPNENH
Seq 51  DMPGADYQLVKLLLGLSPSVKRYMLYQQGCAAGGTVLRLAKDLAENNKGSRVLIVCSEITTAILFHGPNENH
Seq 52  DMPGADYQLVKLLLGLSPSVKRYMLYQQGCAAGGTVLRLAKDLAENNKGSRVLIVCSEITTAILFHGPNENH
Seq 53  DMPGADYQLVKLLLGLSPSVKRYMLYQQGCAAGGTVLRLAKDLAENNKGSRVLIVaSEITTAILFHGPNENH
Seq 54  DMPGADYQLVKLLLGLSPSVKRYMLYQQGCAAGGTVLRLAKDLAENNKGSRVLIVCSEITTAILFHGPNENH
Seq 55  DMPGADYQLVKLLLGLSPSVKRYMLYQQGCAAGGTVLRLAKDLAENNKGSRVLIVCSEITTAILFHGPNENH
Seq 56  DMPGADYQLVKLLLGLSPSVKRYMLYQQGsAAGGTVLRLAKDLAENNKGSRVLIVCSEITTAILFHGPNENH
Seq 57  DMPGADYQLVKLLLGLSPSVKRYMLYQQGCAAGGTVLRLAKDLAENNKGSRVLIVCSEITTAILFHGPNENH
Seq 58  DMPGADYQLVKLLLGLSPSVKRYMLYQQGCAAGGTVLRLAKDLAENNKGSRVLIVCSEITTAILFHGPNENH
Seq 59  DMPGADYQLVKLLLGLSPSVKRYMLYQQGCAAGGTVLRLAKDLAENNKGSRVLIVCSEITTAILFHGPNENH
Seq 60  DMPGADYQLVKLLLGLSPSVKRYMLYQQGCAAGGTVLRLAKDLAENNKGSRVLIVCSEITTAIfFHGPNENH
Seq 61  DMPGADYQLVKLLLGLSPSVKRYMLYQQGCAAGGTVLRLAKDLAENNKGSRVLIVCSEITTAILFHGPNENH
```

FIG. 11 (continued)

```
>Seq    62  DMPGADYQLVKLLGLSPSVKRYMLYQQGCAAGGTVLRLAKDLAENNKGSRVLIVCSEITAIFFHGPNENH 211                                                                    280
>Seq  1     LDSLVAQALFGDGAAALIVGSGPHLAVERPIFEIVSTDQTILPDTEKAMKLHLREGGLTFQLHRDVPLMV
>Seq  2     LDSLVAQALFGDGAAALIVGSGPHLAVERPIFEIVSTDQTILPDTEKAMKLHLREGGLTFQLHRDVPLMV
>Seq  3     LDSLVAQALFGDGAAALIVGSGPHLAVERPIFEIVSTDQTILPDTEKAMKLHLREGGLTFQLHRDVPLMV
>Seq  4     LDSLVAQALFGDGAAALIVGSGPHLAVERPIFEIVSTDQTILPDTEKAMKLHLREGGLTFQLHRDVPLMV
>Seq  5     LDSLVAQALFGDGAAALIVGSGPHLAVERPIFEIVSTDQTILPDTEKAMKLHLREGGfTFQLHRDVPLMV
>Seq  6     LDSLVAQALFGDGAAALIVGSGPHLAVERPIFEIVSTDQTILPDTEKAMKLHLREGGmTFQLHRDVPLMV
>Seq  7     LDSLVAQALFGDGAAALIVGSGPHLAVERPIFEIVSTDQTILPDTEKAMKLHLREGGmTFQLHRDVPLMV
>Seq  8     LDSLVAQALFGDGAAALIVGSGPHLAVERPIFEIVSTDQTILPDTEKAMKLHLREGGLTFQLHRDVPLMV
>Seq  9     LDSLVAQALFGDGAAALIVGSGPHLAVERPIFEIVSTDQTILPDTEKAMKLHLREGGLTFQLHRDVPLMV
>Seq 10     LDSLVAQALFGDGAAALIVGSGPHLAVERPIFEIVSTDQTILPDTEKAMKLHLREGGLTFQLHRDVPLMV
>Seq 11     LDSLVAQALFGDGAAALIVGSGPHLAVERPIFEIVSTDQTILPDTEKAMKLHLREGGLTFQLHRDVPLMV
>Seq 12     LDSLVAQALFGDGAAALIVGSGPHLAVERPIFEIVSTDQTILPDTEKAlKnHLREGGLTFQLHRDVPLMV
>Seq 13     LDSLVAQALFGDGAAALIVGSGPHLAVERPIFEIVSTDQTILPDTEKAlKnHLREGGLTFQLHRDVPLMV
>Seq 14     LDSLVAQALFGDGAAALIVGSGPHLAVERPIFEIVSTDQTILPDTEKAlKnHLREGGLTFQLHRDVPLMV
>Seq 15     LDSLVAQALFGDGAAALIVGSGPHLAVERPIFEIVSTDQTILPDTEKAlKnHLREGGLTFQLHRDVPLMV
>Seq 16     LDSLVAQALFGDGAAALIVGSGPHLAVERPIFEIVSTDQTILPDTEKAlKnHLREGGmTFQLHRDVPLMV
>Seq 17     LDSLVAQALFGDGAAALIVGSGPHLAVERPIFEIVSTDQTILPDTEKAlKnHLREGGLTFQLHRDVPLMV
>Seq 18     LDSLVAQALFGDGAAALIVGSGPHLAVERPIFEIVSTDQTILPDTEKAMKLHLREGGLTFQLHRDVPLMV
>Seq 19     LDSLVAQALFGDGAAALIVGSGPHLAVERPIFEIVSTDQTILPDTEKAMKLHLREGGLTFQLHRDVPLMV
>Seq 20     LDSLVAQALFGDGAAALIVGSGPHLAVERPIFEIVSTDQTILPDTEKAMKLHLREGGLTFQLHRDVPLMV
>Seq 21     LDSLVAQALFGDGAAALIVGSGPHLAVERPIFEIVSTDQTILPDTEKAMKLHLREGGLTFQLHRDVPLMV
```

FIG. 11 (continued)

| Seq | Sequence |
|---|---|
| Seq 22 | LDSLVAQALFGDGAAALIVGSGPHLAVERPIFEIVSTDQTILPDTEKAMKLHLREGGLTFQLHRDVPLMV |
| Seq 23 | LDSLVAQALFGDGAAALIVGSGPHLAVERPIFEIVSTDQTILPDTEKAMKLHLREGGLTFQLHRDVPLMV |
| Seq 24 | LDSLVAQALFGDGAAALIVGSGPHLAVERPIFEIVSTDQTILPDTEKAMKLHLREGGLTFQLHRDVPLMV |
| Seq 25 | LDSLVAQALFGDGAAALIVGSGPHLAVERPIFEIVSTDQTILPDTEKAfKLHLREGGLTFQLHRDVPLMV |
| Seq 26 | LDSLVAQALFGDGAAALIVGSGPHLAVERPIFEIVSTDQTILPDTEKAMKLHLREGGLTFQLHRDVPLMV |
| Seq 27 | LDSLVAQALFGDGAAALIVGSGPHLAVERPIFEIVSTDQTILPDTEKAMKLHLREGGLTFQLHRDVPLMV |
| Seq 28 | LDSLVAQALFGDGAAALIVGSGPHLAVERPIFEIVSTDQTILPDTEKAMKLHLREGGLTFQLHRDVPLMV |
| Seq 29 | LDSLVAQALFGDGAAALIVGSGPHLAVERPIFEIVSTDQTILPDTEKAMKLHLREGGLTFQLHRDVPLMV |
| Seq 30 | LDSLVAQALFGDGAAALIVGSGPHLAVERPIFEIVSTDQTILPDTEKAMKLHLREGGLTFQLHRDVPLMV |
| Seq 31 | LDSLVAQALFGDGAAALIVGSGPHLAVERPIFEIVSTDQTILPDTEKAMKLHLREGGLTFQLHRDVPLMV |
| Seq 32 | LDSLVAQALFGDGAAALIVGSGPHLAVERPIFEIVSTDQTILPDTEKAMKLHLREGGmTFQLHRDVPLMV |
| Seq 33 | LDSLVAQALFGDGAAALIVGSGPHLAVERPIFEIVSTDQTILPDTEKAMKLHLREGGLTFQLHRDVPLMV |
| Seq 34 | LDSLVAQALFGDGAAALIVGSGPHLAVERPIFEIVSTDQTILPDTEKAMKLHLREGGLTFQLHRDVPLMV |
| Seq 35 | LDSLVAQALFGDGAAALIVGSGPHLAVERPIFEIVSTDQTILPDTEKAMKLHLREGGLTFQLHRDVPLMV |
| Seq 36 | LDSLVAQALFGDGAAALIVGSGPHLAVERPIFEIVSTDQTILPDTEKAlKnHLREGGLTFQLHRDVPLMV |
| Seq 37 | LDSLVAQALFGDGAAALIVGSGPHLAVERPIFEIVSTDQTILPDTEKAlKnHLREGGLTFQLHRDVPLMV |
| Seq 38 | LDSLVAQALFGDGAAALIVGSGPHLAVERPIFEIVSTDQTILPDTEKAMKLHLREGGLTFQLHRDVPLMV |
| Seq 39 | LDSLVAQALFGDGAAALIVGSGPHLAVERPIFEIVSTDQTILPDTEKAMKLHLREGGLTFQLHRDVPLMV |
| Seq 40 | LDSLVAQALFGDGAAALIVGSGPHLAVERPIFEIVSTDQTILPDTEKAMKLHLREGGLTFQLHRDVPLMV |
| Seq 41 | LDSLVAQALFGDGAAALIVGSGPHLAVERPIFEIVSTDQTILPDTEKAMKLHLREGGLTFQLHRDVPLMV |
| Seq 42 | LDSLVAQALFGDGAAALIVGSGPHLAVERPIFEIVSTDQTILPDTEKAMKLHLREGmTFQLHRDVPLMV |
| Seq 43 | LDSLVAQALFGDGAAALIVGSGPHLAVERPIFEIVSTDQTILPDTEKAMKLHLREGmTFQLHRDVPLMV |
| Seq 44 | LDSLVAQALFGDGAAALIVGSGPHLAVERPIFEIVSTDQTILPDTEKAMKLHLREGmTFQLHRDVPLMV |
| Seq 45 | LDSLVAQALFGDGAAALIVGSGPHLAVERPIFEIVSTDQTILPDTEKAMKLHLREGGLTFQLHRDVPLMV |

FIG. 11 (continued)

```
           46  LDSLVAQALFGDGAAALIVGSGPHLAVERPIFEIVSTDQTILPDTEKAMKLHLREGGLTFQLHRDVPLMV
> Seq      47  LDSLVAQALFGDGAAALIVGSGPHLAVERPIFEIVSTDQTILPDTEKAMKLHLREGGLTFQLHRDVPLMV
> Seq      48  LDSLVAQALFGDGAAALIVGSGPHLAVERPIFEIVSTDQTILPDTEKAMKLHLREGGLTFQLHRDVPLMV
> Seq      49  LDSLVAQALFGDGAAALIVGSGPHLAVERPIFEIVSTDQTILPDTEKAMKLHLREGGLTFQLHRDVPLMV
> Seq      50  LDSLVAQALFGDGAAALIVGSGPHLAVERPIFEIVSTDQTILPDTEKAMKLHLREGGLTFQLHRDVPLMV
> Seq      51  LDSLVAQALFGDGAAALIVGSGPHLAVERPIFEIVSTDQTILPDTEKAMKLHLREGGLTFQLHRDVPLMV
> Seq      52  LDSLVAQALFGDGAAALIVGSGPHLAVERPIFEIVSTDQTILPDTEKAMKLHLREGGLTFQLHRDVPLMV
> Seq      53  LDSLVAQALFGDGAAALIVGSGPHLAVERPIFEIVSTDQTILPDTEKAMKLHLREGGLTFQLHRDVPLMV
> Seq      54  LDSLVAQALFGDGAAALIVGSGPHLAVERPIFEIVSTDQTILPDTEKAMKLHLREGGLTFQLHRDVPLMV
> Seq      55  LDSLVAQALFGDGAAALIVGSGPHLAVERPIFEIVSTDQTILPDTEKAMKLHLREGGLTFQLHRDVPLMV
> Seq      56  LDSLVAQALFGDGAAALIVGSGPHLAVERPIFEIVSTDQTILPDTEKAMKLHLREGGLTFQLHRDVPLMV
> Seq      57  LDSLVAQALFGDGAAALIVGSGPHLAVERPIFEIVSTDQTILPDTEKAMKLHLREGGLTFQLHRDVPLMV
> Seq      58  LDSLVAQALFGDGAAALIVGSGPHLAVERPIFEIVSTDQTILPDTEKAMKLHLREGGLTFQLHRDVPLMV
> Seq      59  LDSLVAQALFGDGAAALIVGSGPHLAVERPIFEIVSTDQTILPDTEKAMKLHLREGGLTFQLHRDVPLMV
> Seq      60  LDSLVAQALFGDGAAALIVGSGPHLAVERPIFEIVSTDQTILPDTEKAMKLHLREGGfTFQLHRDVPLMV
> Seq      61  LDSLVAQALFGDGAAALIVGSGPHLAVERPIFEIVSTDQTILPDTEKAMKLHLREGGmTFQLHRDVPLMV
> Seq      62  LDSLVAQALFGDGAAALIVGSGPHLAVERPIFEIVSTDQTILPDTEKAMKLHLREGGmTFQLHRDVPLMV

281                       .               .               .               350
> Seq      1   AKNIENAAEKALSPLGITDWNSVFWMVHPGGRAILDQVERKLNLKEDKLRASRHVLSEYGNLISACVLFI
> Seq      2   AKNIENAAEKALSPLGITDWNSVFWMVHPGGRAILDQVERKLNLKEDKLRASRHVLSEYGNLISACVLFI
> Seq      3   AKNIENAAEKALSPLGITDWNSVFWMVHPGGRAILDQVERKLNLKEDKLRASRHVLSEYGNLISACVLFI
> Seq      4   AKNIENAAEKALSPLGITDWNSVFWMVHPGGRAILDQVERKLNLKEDKLRASRHVLSEYGNLISACVLFI
> Seq      5   AKNIENAAEKALSPLGITDWNSVFWMVHPGGRAILDQVERKLNLKEDKLRASRHVLSEYGNLISACVLFI
```

FIG. 11 (continued)

Seq 6  AKNIENAAEKALSPLGITDWNSVFWMVHPGGRAILDQVERKLNLKEDKLRASRHVLSEYGNLISACVLFI
Seq 7  AKNIENAAEKALSPLGITDWNSVFWMVHPGGRAILDQVERKLNLKEDKLRASRHVLSEYGNLISACVLFI
Seq 8  AKNIENAAEKALSPLGITDWNSVFWMVHPGGRAILDQVERKLNLKEDKLRASRHVLSEYGNLISACVLFI
Seq 9  AKNIENAAEKALSPLGITDWNSVFWMVHPGGRAILDQVERKLNLKEDKLRASRHVLSEYGNLISAaVLFI
Seq 10 AKNIENAAEKALSPLGITDWNSVFWMVHPGGRAILDQVERKLNLKEDKLRASRHVLSEYGNLISAaVLFI
Seq 11 AKNIENAAEKALSPLGITDWNSVFWMVHPGGRAILDQVERKLNLKEDKLRASRHVLSEYGNLISAaVLFI
Seq 12 AKNIENAAEKALSPLGITDWNSVFWMVHPGGRAILDQVERKLNLKEDKLRASRHVLSEYGNLISAaVLFI
Seq 13 AKNIENAAEKALSPLGITDWNSVFWMVHPGGRAILDQVERKLNLKEDKLRASRHVLSEYGNLISAaVLFI
Seq 14 AKNIENAAEKALSPLGITDWNSVFWMVHPGGRAILDQVERKLNLKEDKLRASRHVLSEYGNLISAaVLFI
Seq 15 AKNIENAAEKALSPLGITDWNSVFWMVHPGGRAILDQVERKLNLKEDKLRASRHVLSEYGNLISAaVLFI
Seq 16 AKNIENAAEKALSPLGITDWNSVFWMVHPGGRAILDQVERKLNLKEDKLRASRHVLSEYGNLISAaVLFI
Seq 17 AKNIENAAEKALSPLGITDWNSVFWMVHPGGRAILDQVERKLNLKEDKLRASRHVLSEYGNLISAaVLFI
Seq 18 AKNIENAAEKALSPLGITDWNSVFWMVHPGGRAILDQVERKLNLKEDKLRASRHVLSEYGNLISACVLFI
Seq 19 AKNIENAAEKALSPLGITDWNSVFWMVHPGGRAILDQVERKLNLKEDKLRASRHVLSEYGNLISAaVLFI
Seq 20 AKNIENAAEKALSPLGITDWNSVFWMVHPGGRAILDQVERKLNLKEDKLRASRHVLSEYGNLISAaVLFI
Seq 21 AKNIENAAEKALSPLGITDWNSVFWMVHPGGRAILDQVERKLNLKEDKLRASRHVLSEYGNLISAaVLFI
Seq 22 AKNIENAAEKALSPLGITDWNSVFWMVHPGGRAILDQVERKLNLKEDKLRASRHVLSEYGNLISAaVLFI
Seq 23 AKNIENAAEKALSPLGITDWNSVFWMVHPGGRAILDQVERKLNLKEDKLRASRHVLSEYGNLISAaVLFI
Seq 24 AKNIENAAEKALSPLGITDWNSVFWMVHPGGRAILDQVERKLNLKEDKLRASRHVLSEYGNLISAaVLFI
Seq 25 AKNIENAAEKALSPLGITDWNSVFWMVHPGGRAILDQVERKLNLKEDKLRASRHVLSEYGNLISAaVLFI
Seq 26 AKNIENAAEKALSPLGITDWNSVFWMVHPGGRAILDQVERKLNLKEDKLRASRHVLSEYGNLISAaVLFI
Seq 27 AKNIENAAEKALSPLGITDWNSVFWMVHPGGRAILDQVERKLNLKEDKLRASRHVLSEYGNLfSACVLFI
Seq 28 AKNIENAAEKALSPLGITDWNSVFWMVHPGGRAILDQVERKLNLKEDKLRASRHVLSEYGNLmSACVLFI
Seq 29 AKNIENAAEKALSPLGITDWNSVFWMVHPGGRAILDQVERKLNLKEDKLRASRHVLSEYGNLISACVLFI

FIG. 11 (continued)

```
> Seq 30  AKNIENAAEKALSPLGITDWNSVFWMVHPGGRAILDQVERKLNLKEDKLRASRHVLSEYGNLISACVLFI
> Seq 31  AKNIENAAEKALSPLGITDWNSVFWMVHPGGRAILDQVERKLNLKEDKLRASRHVLSEYGNLISACVLFI
> Seq 32  AKNIENAAEKALSPLGITDWNSVFWMVHPGGRAILDQVERKLNLKEDKLRASRHVLSEYGNLISACVLFI
> Seq 33  AKNIENAAEKALSPLGITDWNSVFWMVHPGGRAILDQVERKLNLKEDKLRASRHVLSEYGNLISACVLFI
> Seq 34  AKNIENAAEKALSPLGITDWNSVFWMVHPGGRAILDQVERKLNLKEDKLRASRHVLSEYGNLISACVLFI
> Seq 35  AKNIENAAEKALSPLGITDWNSVFWMVHPGGRAILDQVERKLNLKEDKLRASRHVLSEYGNLISACVLFI
> Seq 36  AKNIENAAEKALSPLGITDWNSVFWMVHPGGRAILDQVERKLNLKEDKLRASRHVLSEYGNLISACVLFI
> Seq 37  AKNIENAAEKALSPLGITDWNSVFWMVHPGGRAILDQVERKLNLKEDKLRASRHVLSEYGNLISAaVLFI
> Seq 38  AKNIENAAEKALSPLGITDWNSVFWMVHPGGRAILDQVERKLNLKEDKLRASRHVLSEYGNLISACVLFI
> Seq 39  AKNIENAAEKALSPLGITDWNSVFWMVHPGGRAILDQVERKLNLKEDKLRASRHVLSEYGNLISACVLFI
> Seq 40  AKNIENAAEKALSPLGITDWNSVFWMVHPGGRAILDQVERKLNLKEDKLRASRHVLSEYGNLISACVLFI
> Seq 41  AKNIENAAEKALSPLGITDWNSVFWMVHPGGRAILDQVERKLNLKEDKLRASRHVLSEYGNLISACVLFI
> Seq 42  AKNIENAAEKALSPLGITDWNSVFWMVHPGGRAILDQVERKLNLKEDKLRASRHVLSEYGNLfSACVLFI
> Seq 43  AKNIENAAEKALSPLGITDWNSVFWMVHPGGRAILDQVERKLNLKEDKLRASRHVLSEYGNLfSACVLFI
> Seq 44  AKNIENAAEKALSPLGITDWNSVFWMVHPGGRAILDQVERKLNLKEDKLRASRHVLSEYGNLISACVLFI
> Seq 45  AKNIENAAEKALSPLGITDWNSVFWMVHPGGRAILDQVERKLNLKEDKLRASRHVLSEYGNLISACVLFI
> Seq 46  AKNIENAAEKALSPLGITDWNSVFWMVHPGGRAILDQVERKLNLKEDKLRASRHVLSEYGNLISAsVLFI
> Seq 47  AKNIENAAEKALSPLGITDWNSVFWMVHPGGRAILDQVERKLNLKEDKLRASRHVLSEYGNLISAaVLFI
> Seq 48  AKNIENAAEKALSPLGITDWNSVFWMVHPGGRAILDQVERKLNLKEDKLRASRHVLSEYGNLISACVLFI
> Seq 49  AKNIENAAEKALSPLGITDWNSVFWMVHPGGRAILDQVERKLNLKEDKLRASRHVLSEYGNLISACVLFI
> Seq 50  AKNIENAAEKALSPLGITDWNSVFWMVHPGGRAILDQVERKLNLKEDKLRASRHVLSEYGNLISACVLFI
> Seq 51  AKNIENAAEKALSPLGITDWNSVFWMVHPGGRAILDQVERKLNLKEDKLRASRHVLSEYGNLISAaVLFI
> Seq 52  AKNIENAAEKALSPLGITDWNSVFWMVHPGGRAILDQVERKLNLKEDKLRASRHVLSEYGNLISACVLFI
> Seq 53  AKNIENAAEKALSPLGITDWNSVFWMVHPGGRAILDQVERKLNLKEDKLRASRHVLSEYGNLISACVLFI
```

FIG. 11 (continued)

```
       402
       .
>Seq 54 AKNIENAAEKALSPLGITDWNSVFWMVHPGGRAILDQVERKLNLKEDKLRASRHVLSEYGNLISACVLFI
>Seq 55 AKNIENAAEKALSPLGITDWNSVFWMVHPGGRAILDQVERKLNLKEDKLRASRHVLSEYGNLISACVLFI
>Seq 56 AKNIENAAEKALSPLGITDWNSVFWMVHPGGRAILDQVERKLNLKEDKLRASRHVLSEYGNLISACVLFI
>Seq 57 AKNIENAAEKALSPLGITDWNSVFWMVHPGGRAILDQVERKLNLKEDKLRASRHVLSEYGNLISACVLFI
>Seq 58 AKNIENAAEKALSPLGITDWNSVFWMVHPGGRAILDQVERKLNLKEDKLRASRHVLSEYGNLISACVLFI
>Seq 59 AKNIENAAEKALSPLGITDWNSVFWMVqPGGRAILDQVERKLNLKEDKLRASRHVLSEYGNLISACVLFI
>Seq 60 AKNIENAAEKALSPLGITDWNSVFWMVHPGGRAILDQVERKLNLKEDKLRASRHVLSEYGhLISACVLFI
>Seq 61 AKNIENAAEKALSPLGITDWNSVFWMVHPGGRAILDQVERKLNLKEDKLRASRHVLSEYGNLmSACVLFI
>Seq 62 AKNIENAAEKALSPLGITDWNSVFWMVHPGGRAILDQVERKLNLKEDKLRASRHVLSEYGNLISACVLFI 351                                                              402
         .         .         .         .         .         .         .
>Seq  1 IDEVRKRSMAEGKSTTGEGLDCGVLFGFGPMTVETVVLRSVRVTAAVANGN
>Seq  2 IDEVRKRSMAEGKSTTGEGLDCGVLFGFGPMTVETVVLRSVRVTAAVANGN
>Seq  3 IDEVRKRSMAEGKSTTGEGLDCGVLFGFGPMTVETVVLRSVRVTAAVANGN
>Seq  4 IDEVRKRSMAEGKSTTGEGLDCGVLFGFGPMTVETVVLRSVRVTAAVANGN
>Seq  5 IDEVRKRSMAEGKSTTGEGLDCGVLFGFGPMTVETVVLRSVRVTAAVANGN
>Seq  6 IDEVRKRSMAEGKSTTGEGLDCGVLFGFGPMTVETVVLRSVRVTAAVANGN
>Seq  7 IDEVRKRSMAEGKSTTGEGLDCGVLFGFGPMTVETVVLRSVRVTAAVANGN
>Seq  8 IDEVRKRSMAEGKSTTGEGLDSGVLFGFGPMTVETVVLRSVRVTAAVANGN
>Seq  9 IDEVRKRSMAEGKSTTGEGLDSGVLFGFGPMTVETVVLRSVRVTAAVANGN
>Seq 10 IDEVRKRSMAEGKSTTGEGLDSGVLFGFGPMTVETVVLRSVRVTAAVANGN
>Seq 11 IDEVRKRSMAEGKSTTGEGLDSGVLFGFGPMTVETVVLRSVRVTAAVANGN
>Seq 12 IDEVRKRSMAEGKSTTGEGLDsGVLFGFGPMTVETVVLRSVRVTAAVANGN
>Seq 13 IDEVRKRSMAEGKSTTGEGLDSGVLFGFGPMTVETVVLRSVRVTAAVANGN
```

FIG. 11 (continued)

| | | |
|---|---|---|
| Seq 14 | IDEVRKRSMAEGKSTTGEGLDSGVLFGFGPGMTVETVVLRSVRVTAAVANGN |
| Seq 15 | IDEVRKRSMAEGKSTTGEGLDSGVLFGFGPGMTVETVVLRSVRVTAAVANGN |
| Seq 16 | IDEVRKRSMAEGKSTTGEGLDSGVLFGFGPGMTVETVVLRSVRVTAAVANGN |
| Seq 17 | IDEVRKRSMAEGKSTTGEGLDSGVLFGFGPGMTVETVVLRSVRVTAAVANGN |
| Seq 18 | IDEVRKRSMAEGKSTTGEGLDSGVLFGFGPGMTVETVVLRSVRVTAAVANGN |
| Seq 19 | IDEVRKRSMAEGKSTTGEGLDSGVLFGFGPGMTVETVVLRSVRVTAAVANGN |
| Seq 20 | IDEVRKRSMAEGKSTTGEGLDSGVLFGFGPGMTVETVVLRSVRVTAAVANGN |
| Seq 21 | IDEVRKRSMAEGKSTTGEGLDSGVLFGFGPGMTVETVVLRSVRVTAAVANGN |
| Seq 22 | IDEVRKRSMAEGKSTTGEGLDSGVLFGFGPGMTVETVVLRSVRVTAAVANGN |
| Seq 23 | IDEVRKRSMAEGKSTTGEGLDCGVLFGFGPGMTVETVVLRSVRVTAAVANGN |
| Seq 24 | IDEVRKRSMAEGKSTTGEGLDCGVLFGFGPGMTVETVVLRSVRVTAAVANGN |
| Seq 25 | IDEVRKRSMAEGKSTTGEGLDCGVLFGFGPGMTVETVVLRSVRVTAAVANGN |
| Seq 26 | IDEVRKRSMAEGKSTTGEGLDCGVLFGFGPGMTVETVVLRSVRVTAAVANGN |
| Seq 27 | IDEVRKRSMAEGKSTTGEGLDCGVLFGFGPGMTVETVVLRSVRVTAAVANGN |
| Seq 28 | IDEVRKRSMAEGKSTTGEGLDCGVLFGFGPGMTVETVVLRSVRVTAAVANGN |
| Seq 29 | IDEVRKRSMAEGKSTTGEGLDCGVLFGFGPGMTVETVVLRSVRVTAAVANGN |
| Seq 30 | IDEVRKRSMAEGKSTTGEGLDCGVLFGFGPGMTVETVVLRSVRVTAAVANGN |
| Seq 31 | IDEVRKRSMAEGKSTTGEGLDCGVLFGFGPGMTVETVVLRSVRVTAAVANGN |
| Seq 32 | IDEVRKRSMAEGKSTTGEGLDCGVLFGFGPGMTVETVVLRSVRVTAAVANGN |
| Seq 33 | IDEVRKRSMAEGKSTTGEGLDCGVLFGFGPGMTVETVVLRSVRVTAAVANGN |
| Seq 34 | IDEVRKRSMAEGKSTTGEGLDCGVLFGFGPGMTVETVVLRSVRVTAAVANGN |
| Seq 35 | IDEVRKRSMAEGKSTTGEGLDCGVLFGFGPGMTVETVVLRSVRVTAAVANGN |
| Seq 36 | IDEVRKRSMAEGKSTTGEGLDCGVLFGFGPGMTVETVVLRSVRVTAAVANGN |
| Seq 37 | IDEVRKRSMAEGKSTTGEGLDSGVLFGFGPGMTVETVVLRSVRVTAAVANGN |

FIG. 11 (continued)

| | | |
|---|---|---|
| Seq 38 | IDEVRKRSMAEGKSTTGEGLDCGVLFGFGPGMTVETVVLRSVRVTAAVANGN |
| Seq 39 | IDEVRKRSMAEGKSTTGEGLDCGVLFGFGPGMTVETVVLRSVRVTAAVANGN |
| Seq 40 | IDEVRKRSMAEGKSTTGEGLDsGVLFGFGPGMTVETVVLRSVRVTAAVANGN |
| Seq 41 | IDEVRKRSMAEGKSTTGEGLDCGVLFGFGPGMTVETVVLRSVRVTAAVANGN |
| Seq 42 | IDEVRKRSMAEGKSTTGEGLDCGVLFGFGPGMTVETVVLRSVRVTAAVANGN |
| Seq 43 | IDEVRKRSMAEGKSTTGEGLDCGVLFGFGPGMTVETVVLRSVRVTAAVANGN |
| Seq 44 | IDEVRKRSMAEGKSTTGEGLDCGVLFGFGPGMTVETVVLRSVRVTAAVANGN |
| Seq 45 | IDEVRKRSMAEGKSTTGEGLDCGVLFGFGPGMTVETVVLRSVRVTAAVANGN |
| Seq 46 | IDEVRKRSMAEGKSTTGEGLDsGVLFGFGPGMTVETVVLRSVRVTAAVANGN |
| Seq 47 | IDEVRKRSMAEGKSTTGEGLDaGVLFGFGPGMTVETVVLRSVRVTAAVANGN |
| Seq 48 | IDEVRKRSMAEGKSTTGEGLDCGVLFGFGPGMTVETVVLRSVRVTAAVANGN |
| Seq 49 | IDEVRKRSMAEGKSTTGEGLDCGVLFGFGPGMTVETVVLRSVRVTAAVANGN |
| Seq 50 | IDEVRKRSMAEGKSTTGEGLDCGVLFGFGPGMTVETVVLRSVRVTAAVANGN |
| Seq 51 | IDEVRKRSMAEGKSTTGEGLDCGVLFGFGPGMTVETVVLRSVRVTAAVANGN |
| Seq 52 | IDEVRKRSMAEGKSTTGEGLDCGVLFGFGPGMTVETVVLRSVRVTAAVANGN |
| Seq 53 | IDEVRKRSMAEGKSTTGEGLDCGVLFGFGPGMTVETVVLRSVRVTAAVANGN |
| Seq 54 | IDEVRKRSMAEGKSTTGEGLDCGVLFGFGPGMTVETVVLRSVRVTAAVANGN |
| Seq 55 | IDEVRKRSMAEGKSTTGEGLDCGVLFGFGPGMTVETVVLRSVRVTAAVANGN |
| Seq 56 | IDEVRKRSMAEGKSTTGEGLDCGVLFGFGPGMTVETVVLRSVRVTAAVANGN |
| Seq 57 | IDEVRKRSMAEGKSTTGEGLDCGVLFGFGPGMTVETVVLRSVRVTAAVANGN |
| Seq 58 | IDEVRKRSMAEGKSTTGEGLDCGVLFGFGPGMTVETVVLRSVRVTAAVANGN |
| Seq 59 | IDEVRKRSMAEGKSTTGEGLDCGVLFGFGPGMTVETVVLRSVRVTAAVANGN |
| Seq 60 | IDEVRKRSMAEGKSTTGEGLDCGVLFGFGPGMTVETVVLRSVRVTAAVANGN |
| Seq 61 | IDEVRKRSMAEGKSTTGEGLDCGVLFGFGPGMTVETVVLRSVRVTAAVANGN |
| Seq 62 | IDEVRKRSMAEGKSTTGEGLDCGVLFGFGPGMTVETVVLRSVRVTAAVANGN |

FIG. 12

> 2-PS variant= 2 Substitutions= 1: (C169A)

ATGGGATCTTACTCCATCCGATGATGTGGAGGTGATTCGTGAGGCCGGGACGGGCACAAGGTTTAGCCACGATTCTTGCCAT
TGGCACTGCTACTCCCTCCCAATTGCGTCGCTCAAGCTGATTATGCAGACTATTATTTCGTGTCACTAAGAGCGAACATA
TGGTTGATCTTAAAGAGAACCCAACAATGTGAGTTCATGGAGTTCATGAGAAACGATACCTAGCGCCTCACCGAAGAC
TATCGCAAGAACCCAACAATGTGTGAGTTCATGGAGTTCAAGGCTCCATCCTTAAACGCTCGACAAGACCTAGTGGTCACCGGCGT
CCCAATGCTTGGCAAGAGCCAGTCAAGAGCCGCAGTCAAGAGCCGCAGAACATCAACTCGTCAAATCCCAGATCACCCACCTCATCT
TCTGCACCACGCTGGCGTTGACATGCCCGGTTGCTGACTATCAACTCGTCAAATCCCTGGTCTCTCCCCTTCAGTCAAA
CGCTATATGTTGTACCAACAGGGAgctGCCGCCGGCACAGTCCTCCGGCTAGCCAAGGACCTTGCTGAAAACAACAA
GGGCTCACGAGTCCTTATCGTCGTCCGAGATCACTGCTATCTTATTCCATGGACCCAATGAGAACCACCTTGACTCAC
TCGTCGCTCAAGCTTTATTCGGAGACGAGCTCAAACAATCTTGCCGGACACTGAAGTTACACTTGCCCTAGAACGGCCA
ATATTCGAGATCGTGTCAGTTGCAATAGAGATGTACCCCTTTTCTGGAGGTCGCAAAGAACACATAGAGAACAGCCGGAGAAAGCCGTTGTCTC
GTTGACGTTTCAGTTGCAATAGAGATGTACCCCCTTTTCTGGAGGTCGCAAAGAACACATAGAGAACAGCCGGAGAAAGCCGTTGTCTC
CACTAGGGATAACTGATTGGAACTCAGTTGGAACTAAGTTAAGGGAAGAGATCTATGGCGAAGAGTACAACCGGTGAAGGTTTGGATTGCGGTG
AAACTAAACCTTAAGCTACGAGGTGACCAGGCATGTGGCAAGGAAGAGTACAACCGGTGAAGGTTTGGATTGCGGTG
GTTGTTCATCATTGACCGAGTTTGGACCCGGGTATGGACTCTGTTGTTCTTCCGTCCGCGTTACTGCTGCCGGTTGCCAAT
TTTTGTTTTGGATTTGGAGACCCGGGTATGGACTCTGTTGTTCTTCCGTCCGCGTTACTGCTGCCGGTTGCCAAT
GGAAACTGA > 2-PS variant= 3 Substitutions= 1: (C 35A)

ATGGGATCTTACTCCATCCGATGATGTGGAGGTGATTCGTGAGGCCGGGACGGGCACAAGGTTTAGCCACGATTCTTGCCAT
TGGCACTGCTACTCCCTCCCAATgccGTCGCTCAAGCTGATTATGCAGACTATTATTTCGTGTCACTAAGAGCGAACATA
TGGTTGATCTTAAAGAGAACCCAACAATTTAAACGCATTTGTGAGAAACGATAAAGAACGATACCTAGCCCTCACCGAAGAC
TATCTGCAAGAACCCAACAATGTGTGAGTTCATGGAGTTCAAGGCTCCATCCTTAAACGCTCGACAAGACCTAGTGGTCACCGGCGT
CCCAATGCTTGGCAAGAGCCAGTCAAGGCCGCAGTCAAGGCCGCCAGTCTAAACGACTACCAAAATCACCCACCTCATCT

FIG. 12 (continued)

```
TCTGCACCACCGGCTGGCGTTGACATGCCCGGTGCTGACTATCAACTCGTCAAACTCCTTGGTCTCTCCCTTCAGTCAAA
CGCTATATGTTGTACAACAGGGATGTGCCGGCTCCTCCGGCTAGCCAAGGACCCTTGGCCAAGACCACCTTGAAAACAACAA
GGGCTCACGAGTCCTTATCGTCTGCTCCGAGATCACTGCTATCTTATTCCATGGACCCAATGAGAACCACCTTGACTCAC
TCGTCGCTCAAGCTTGATCCGGAGACGAGCTGATCAAACAATCTTGCCGGACACTGAAGCAGGCAATGAAGTTACACTTGGCCTTGAAGCGGAGGG
ATATTCGAGATCGTGTCAACTGCTGCATAGATGTACCCTTCAGTTTCTGGAATCTCAGTTCTCGAACCTGAAACCTGATTGGCACCAGGTGGAGCGA
GTTGACGTTTCAGTTGCATAGATGTACCCTTCAGTTTCTGGAATGGCTCGAGCCATATTGGACCAGGTGGAGCGA
CACTAGGGATAAACCTAAAGGAACTGATTGGAACTCAGTTAAGGAAGATAAGTTAAGGCGTGGCCCCTGTGGGCCTAGCGCTTGTGT
AAACTAAACCTAAAGCAGAGTGACCAGGTGAAGATCTATGGCGAAGAGTACAACCGGTGAAGGGTTTGGATTGCGGGTG
GTTGTTCATCATTGACCGGGTATGACTCTGTTGAGACTCTGTTCTTCGGTAGCGCTTTACTGCCGGTTGCCAAT
TTTGTTTGGATTGACCGGGTATGACTCTGTTGAGACTGTTCTTGGAACTGA
GGAAACTGA

> 2-PS variant= 4 Substitutions= 1: (L202F)
ATGGGATCTTACTCATCCGATGATGTGAGGTCGTGAGGCCGGACGGGCACAAGGTTTAGCCACGATTCTTGCCAT
TGGCACTGCTACTCCTCCCAATTGCGTCGCTCAAGCTGATTATGCAGACTATTTCGTGTCACTAAGAGCGAACATA
TGGTTGATCTTAAAGAGAATTTAAACGCATTGTGTAGAAACAGCGATAAAGAAACAGAACGTCCACCGAAGAC
TATCTGCAAGAGACTTGGGCAGAAGAGCCGCAGTCAAGCTCAGTGTGAGTTCATGGCCAGAACCTAGTGGTCACCGGCGT
CCCAATGCTTGGCAAGAGCCGCAGTCAAGCGCGACTATCAACCGGTGCTGACTATCAACAGTCCGGAGAATCACCACCTCATCT
TCTGCACCACCGGCTGGCGTTGACATGGAGGATGCCGGTGACTATCAACTCGTCAAACTCCTTGGTCTCTCCCTTCAGTCAAA
CGCTATATGTTGTACAACAGGGATGTGCCGGCTCCTCCGGCTAGCCAAGGACCACGATTGAAAACAACAA
GGGCTCACGAGTCCTTATCGTCTGCTCCGAGATCACTGCTATCTTATTCCATGGACCCAATGAGAACCACCTTGACTCAC
TCGTCGCTCAAGCTTGATCCGGAGACGAGCTGATCAAACAATCTTGCCGGACACTGAAGTTACACTTGGCCGCCA
ATATTCGAGATCGTGTCAACTGCTGCATAGATGTACCCTTCAGTTTCTGGAATGGCTCGAGCCATATTGGACCAGGTGGAGCGA
GTTGACGTTTCAGTTGCATAGATGTACCCTTCAGTTTCTGGAATGGCGGAGAAGACATAGAGAACAGCAGCGGAGAAGCGTTGTCTC
```

FIG. 12 (continued)

```
CACTAGGGATAACTGATTGGAACTCAGTTTTCTGGATGGTGCACCCAGTGGTCGAGCCATATTGGACCAGGTGGAGCGA
AAACTAAACCTAAGGAAGATAAGTTAAGGGCTAGCAGGCATGTGCTTAGTGAAACGGAACCGTGATTAGCGCTTGTGT
GTTGTTCATCATTGACGAGGTGAGGAAGAGATCTATGGCGAAGGAAGAGTACAACCGGTGAAGGTTTGGATTGCGGTG
TTTGTTTGGATTTGGACCGGGTATGACTGTTGAGACTGTTCTTGCGTAGCTGTTCTTCGCGGTTACTGCTGCGGTTGCCAAT
GGAAACTGA

> 2-PS variant= 5 Substitutions= 1: (L268F)
ATGGGGATCTTACTCAGTCCATCGGATGATGTGGAGGTGATTCGTGAGGCCACAAGGTTTAGCCACGATTCTTGCCAT
TGGCACTGCTACTCCTCCCACTTGCGTCGCTCAAGCTGATTATGCAGACTATTATTTCGTGTCACTAAGAGCGAACATA
TGGTTGATCTTAAAGAGAGAATTTAAACGCATTTGTGAGAAAACAGCGATAAAGAAAACGATACCTAGCCCTCACCGAAGAC
TATCTGCAAGAGAACCAACAATGTGTAGTTGGATGGTTCATGGAGTTCAAGGGACTCGACAAAATCCAAGATCACCACCTCATCT
CCCAATGCTTGGCAAAGAAGCCCAGTCAAGGCCATTGACACTATCAACTCCTCAAACTCCCTTGGTCTCTCCCCTTCAGTCAAA
TCTGCACCACCGGTGGGCGGTTGTACCAACAGGGATGTGCCCGGCACACTCCTCCGGCTAGCCAAGGACCTTGCTGAAAACAACAA
CGCTATATGTTGTACCAACAGGGATGTGCTCGCTGCCGAGATCACTCGTGCAGCACTCACTGGACCCAATGAAGTTACACTTGACTCAC
GGGCTCACCAGTCCTTATCGTGCCGAGACGGAGCTGCAGCACTCACTGGACCCAATGAAGTTACACTTGGCCGTAGAACGGCCA
TCGTC GCTCAAGCTTTATTGGAGACGGAGCTGCAGCACTCACTGTGGGGTTCAGGCCATGAAGGCAATGAAGTTACACTTGAGAGAGGAGG
ATATTCGAGATCGTGTCAACTGTCAACTAGAGATGTACCCTTGATGGTCGCAAAGAACATAGAGAACGCAGCGGAGAAAGCGTTGTCTC
gtcACGTTTCAGTTGCATAGAGATGTACCCTTGATGGTCGCAAAGAACATAGAGAACGCAGCGGAGAAAGCGTTGTCTC
CACTAGGGATAACTGATTGGAACTCAGTTTTCTGGATGGTGCACCCAGTGGTCGAGCCATATTGGACCAGGTGGAGCGA
AAACTAAACCTAAGGAAGATAAGTTAAGGGCTAGCAGGCATGTGAATACGGAACCGGTGATTAGCGCTTGTGT
GTTGTTCATCATTGACGAGGTGAGGAAGAGATCTATGGCGAAGGAAGAGTACAACCGGTGAAGGTTTGGATTGCGGTG
TTTGTTTGGATTTGGACCGGGTATGACTGTTGAGACTGTTCTTGCGTAGCTGTTCTTCGCGGTTACTGCTGCGGTTGCCAAT
GGAAACTGA
```

FIG. 12 (continued)

```
> 2-PS variant= 6 Substitutions=  1:    (L268M)
ATGGGATCTTACTCATCCGATGATGTGGAGGTGATTCGTGAGGCCGGACGGGCACAAGGTTTAGCCACGATTCTTGCCAT
TGGCACTGCTACTCCTCCCAATTGCGTCGCTCAAGCTGATTATGCAGACTATTATTTCGTGTCACTAAGAGCGAACATA
TGGTTGATCTTAAAGAGAACCCAACAGAAAATTTAAACGCATTTGTGAGAAACAGCGATAACGATATACCTCACCGAAGAC
TATCTGCAAGAGAACCCAACAGTGTGAGTTCATGGAGTTCATGGAGCTCCATCCCTTAAACGCTCGACAAGACCTAGTGGTCACCGGCGT
CCCAATGCTTGGCAAGAACCAAGAAGCCAGTCAAGGCCATTGATGAATCAACTCGTCAAACTCCTTGGTCTCTCCCTTCAGTCAAA
TCTGCACCACCGCTGGCCGTTGACACAGGGATGCGCCGGCACACCTCAGGACCCTAGCCCAAGGACCCTAGCCAAGGACCCTTGAAAACAACAA
CGCTCTATATGTGTACAACAGGGATGCGCTCTCCGAGATCGCTGCTATCTTATTCCATGGAAGAACCAATGAGAACCACCTTGACTCAC
GGGCTCACGAGTCCTTATCGCTGCTCGAGATCGCTGCTATCTTATTCCATGGAAGAACCAATGAGAACCACCTTGACTCAC
TCGTCGCTCAAGCTTTATTCCGGACGGATCAAACAATCTTGCCGACACTGAAGGCCAATGAAGTTACACTTGAGAGAGGAGG
ATATTCGAGATCGTGTCAACTGATCAGAGATCCTTGAAGGAACCAATGAAGTTACACTTGAGAGAGGAGG
|Gatg|ACGTTTCAGTTGCATAGAGATGCTTGGAACTCAGTTTTCTGGATGGTGCAGCCAGGTGGTCGAGCCAATATTGGACCAGGTGGAGCGA
CACTAGGGATAACTGATTGGAAGATAAGTTAAGGCATGTCTTAGTGAAGAAGAGTACAACCGGTGAAGGTTTGGAGTTGGCGGTG
AAACTAAAACCTTAAGGAAGATAAGTTAAGGCATGTCTTAGTGAAGAAGAGTACAACCGGTGAAGGTTTGGAGTTGGCGGTG
GTTGTTCATCATTGACGAGGTTGGAGAGATCTATGGAAGACTGTTGAAGACCTGTTACTGCTGCCGGTTGCCAAT
TTTTGTTGTTTGGATTTGGACCGGGGTATGACTGATTTGTTCTTCTTCCGTCCGTTACTGCTGCCGGTTGCCAAT
GGAAACTGA > 2-PS variant= 7 Substitutions=  2:    (L202F) (L268M)
ATGGGATCTTACTCATCCGATGATGTGGAGGTGATTCGTGAGGCCGGACGGGCACAAGGTTTAGCCACGATTCTTGCCAT
TGGCACTGCTACTCCTCCCAATTGCGTCGCTCAAGCTGATTATGCAGACTATTATTTCGTGTCACTAAGAGCGAACATA
TGGTTGATCTTAAAGAGAACCCAACAGAAAATTTAAACGCATTTGTGAGAAACAGCGATAACGATATACCTCACCGAAGAC
TATCTGCAAGAGAACCCAACAGTGTGAGTTCATGGAGCTCCATCCTTAAACGCTCGACAAGACCTAGTGGTCACCGGCGT
CCCAATGCTTGGCAAGAACCAAGAAGCCAGTCAAGGCCAGTCTGATGAATGGGACTACCAAAATCCAAGATCACCCACCTCATCT
```

FIG. 12 (continued)

```
TCTGCACCACCGCTGGCGTTGACATGCCCGGTGCTGACTATCAACTCGTCAAACTCCTTGGTCTCTCCCCTTCAGTCAAA
CGCTATATGTTGTACCAACAGGATGTGCCGCGGCACACTGTCTGCTCCGAGATCACTGCTATCtcTTCCATGACCCAAGAACCACCTTGACTCAC
GGGCTCACGAGTCCTTATCGTGTCTGCTTCGGAGACGAGCAAACAATCTTGTGGGTTCAGGGTTCACTTGGCCGTTGAGAGAGGAGG
TCGTCGCTCAAGTTTATTCGGAGACGAGCAAACAATCTTGTGGGTTCAGGGTTCACTTGGCCGTTGAGAGAGGAGG
ATATTCGAGATCGTGTCAACTGATCAAATGTACCCTTGATGTGCAAGAACATAGAGAAACGGCCATATTGGAAACCGTGAAGCGTTGTCTC
GatgACGTTTCAGTTGCATAGAGATGTACCCTTGATGTGCAAGAACATAGAGAAACGGCCATATTGGAAACCGTGAAGCGTTGTCTC
CACTAGGATAAACTTAAGGAAGATAAGTTAAGGCTAGCAGGAAGATCTATGGAGACTGTTGAGACTGTTGAGACTGCGTGCGAAGGTTTGATTGCGCTTGTGT
AAACTAAACCTAAGGAAGATAAGTTAAGGCTAGCAGGAAGATCTATGGAGACTGTTGAGACGATACAACCGTGAAGTTTGCTGCTGCCGTGT
GTTGTTCATCATTGACGAGGATTGGACCGGGTATGTTGAGACTGTTGTTCTTCGTAGCGTCCGGTTACTGCGTGCGCAAT
TTTTGGATTGACACCGGGTATGTTGAGACTGTTGTTCTTCGTAGCGTCCGGTTACTGCGTGCGCAAT
GGAAACTGA > 2-PS variant=   8 Substitutions=  2:    ( C 89S)     (C372S)
ATGGATCTTACTGCTACTCCTCCAATTGCGTCGCTCAAGCTGATTATGCAGACTGATTATTTCGTGTCACTAAGAGCGAACATA
TGGTTGATCTTAAAGAGAATTTAAACGCATTGTGAGAAAACAGCGATAAAGAAACAGCGATAAAGAAACATACCCTCACCGAAGAC
TATCTGCAAGAGCTTCATGGCTCCATCTTAAACGCTCGACAAGACCTAGTGGTCACCACCTCATCT
CCCAATGCTTGGCAAAGAACCCAAAGAAGAGCAGTGCGACTACAAATCCAAGATCAAGATCTCTCCCCTTCAGTCAAA
TCTGCACTGGTACAACAGGATGTCGCTCCGAGATCGTGCTCGACAAATCCAAGATCAAGATCTCTCCCTTGCTGAAAACAA
CGCTATATGTTGTACAACAGGATGTCGCTCCGAGATCACTGCTATCTTACCATGACCCTAGCAAGGACCTTGCTGAAAACAA
GGGCTCACGAGTCCTTATCGTGTCTGCTTCGGAGAGCAGCAAACAATCTTGTGGGTTCAGGGTTCACTTGGCCGTAGAGAGGAGG
TCGTCGCTCAAGTTTATTCGGAGACGAGCAAACAATCTTGTGGGTTCAGGGTTCACTTGGCCGTAGAGAGGAGG
ATATTCGAGTTTCAGTTGCATGATCGTGTCAACTGATCAAATGTACCCTTGATGTGCCGGACACTGAAGTTACACTGCCGAAGAGGAGG
GTTGACGTTTCAGTTGCATAGATGTACCGGTCGCAAGAATGTGCCGAAGGTCGCAAGAACATAGAGAACGCAGCGAGAAAGCGTTGTCTC
```

FIG. 12 (continued)

CACTAGGGATAACTGATTGGAACTCAGTTTTCTGGATGGTGCACCCAGGTGGTCGAGCCATATTGGACCAGGTGGAGCGA
AAACTAAACCTTAAGGAAGATAAGTTAAGGGCTAGCAGGCATGTGCTTAGTGAATACGGAAACCGTGATTAGCGCTTGTGT
GTTGTTCATCATTGACGAGGTGAGGAAGAGATCTATGGCGAAGGAAGAGTACAACCGGTGACTGTTCGCGTACTGCGGTTGATTtcgGGTG
TTTTGTTTGGATTTGGACCGGGTATGACTGTTGAGACTGTTCTTGTTCTTCGTAGCGTCCGCGTTACTGCTGCGGTTGCCAAT
GGAAACTGA > 2-PS variant= 9 Substitutions= 3: (C 89S) (C346A) (C372S)

ATGGGAGATCTTACTCACTCCTCCATCGATGATGTGTGAGGTGATTCGTGAGGCCGGTGAGCCCACGATTCTTGCCAT
TGGCACTGCTACTCCTCCCCCAATTGCGTCGCTCAAGCTGATTATGCAGACTATATTCGTGTCACTAAGAGCGAACATA
TGGTTGATCTTAAAGAGAACATTAAACGCATTTGTGAGAAAACAGCGATAAAGAAACAGATACCCTCACCGAAGAC
TATCTGCAAGAGAACCCAACAATgtcGAGTTCATGGCTCCATCTTAAACGCTCGACAAGACCTAGTGGTCACCGCGT
CCCAATGCTTGGCAAAGAACGCCAGTGCCAGTCAAGCCATTGATGAATGGGACTACCAAATCCAAAATCCTTGTCTCTCCCTTCAGTCAAA
TCTGCACCACCGCTGTTGACATGGGATGTGCCGCCGGAGATCACTGCTATCTTATTCATGGACCCAAGAACCACTTGACTCAC
CGCTATATGTTGTACCAACAGGATGTCCTTATCGTGCTCCGAGATCACTGCTATCTTATTGTGGTTCAGGCCGTAGAGACGGCCA
GGGCTCAAGAGTCGTGCTCAAGCTTTATTCGGAGACTGATCAACTGATCAAGCACTGTCATTGTGGGTTCAGGCCAATGAAGTTACACTTGAGAGAGGAGG
TCGTCGCAAGCTTTATTCGGAGATCGTCAACTGATCAGATAGATGTACCCCTTGATGGTGCAAAGACACATAGAGAACAGCGGGAGAAAGCGGTTGTCTC
ATATTCGAGATCGTGTCAGTTGCATAGAGATGTACCCCTTGATGGTGCAAAGACACATAGAGAACAGCGGAGAAAGCGGTTGTCTC
CACTGAGAACCTTAAGGAAGATAAGTTAAGGGCTAGCAGGCATGTGCTTAGTGAATACGGAAACCGTGATTAGCGcTgtcGGTG
GTTGTTCATCATTGACGAGGTGAGGAAGAGATCTATGGCGAAGGAAGAGTACAACCGGTGACTGTTCGCGTACTGCGGTTGATTtcgGGTG
TTTTGTTTGGATTTGGACCGGGTATGACTGTTGAGACTGTTCTTGTTCTTCGTAGCGTCCGCGTTACTGCTGCGGTTGCCAAT
GGAAACTGA

FIG. 12 (continued)

> 2-PS variant= 10 Substitutions= 3: (C 65S) (C 89S) (C372S)
ATGGGATCTTACTCATCGATGATGATTCGTGAGGCCGACGGGCACAAGGTTTAGCCACGATTCTTGCCAT
TGGCACTGCTACTCCTCCCATGCGTTCGCTCAAGCTGATTATGCAGACTATTTTCGTGTCACTAAGAGCGAACATA
TGGTTGATCTTAAAGAGAACCAGAAATTTAAACGCATT[tct]GAGAAAACAGCGATAAAGAAACGATACCCTCACCGAAGAC
TATCTGCAAGAGAACCAACAATG[tct]GAGTTCATGGCTCCATCCTTAAACGCTCGACAGACCTAGTGGTCACCGGCGT
CCCAATGCTTGGCAAGAGAGCCGCAGTCAAGGCCATTGATGAATCAACTCGTCAAACTCCTTGGTCTCTCCCCTTCAGTCAAA
TCTGCACCACCGCTGTTGTACAAGAGGATGCTGCAAGGCCACATCTTGGGTCCGTGCTACTGCCAAGCCCGTAGAACGGCCA
CGCTATATGTTGTCAAGAGATCCTTATCGTCTCTCCGAGATCACTTGCTATCTTATTCCATGGAGATCATGAACAACTTGACTCAC
GGGCTCACGAGTCCTTATCGTCTGCTCCGAGATCACTGCAGCAGTGCTAGACGAGCAATGAAGAACCATAGAACCACCTTGACTCAC
TCGTCGCTCAAGCTGTTATTCGGACGACGAGTCAATCTTGCCGGACACTGAAGTTACACTTGAGAGAGGAGG
ATATTCGAGATCGTGTCAACTGATCAAACATCCCTTGATGGTGTGCAAGAACATAGAACCAGGTGGTCGAGCCCATATTGAAACCTGATTAGCGCTTGTGT
GTTGTTCATCATTGACGAGGTGAGGAGAACTCAGTTTTCTGGAACGATAAGTTAAGGCGAAGAGATCTATGACTGTTGTCACCAGCTACAACCGGTGAAGGTTTGGAT[tcc]GGTG
CACTAGGGATAACTGATTGGAACTCAGTTTTCTGGAACGATAAGTTAAGGCGAAGAGATCTATGACTGTTGTCACCGTTCCGCGTTACTGCTGCGGTTGCCAAT
AAACTAAACCTTAAGACGAGGTGAGGAGAACTCAGTTTTCTGGAACGATAAGTTAAGGCGAAGAGATCTATGACTGTTGTT
GTTGTTCATCATTGACGAGGTGAGGAGAACTCAGTTTTCTGGAACGATAAGTTAAGGCGAAGAGATCTATGAC
TTTTGTTTGGATTTGGACCGGTTGGACCGGTCCGCGTTACTGCTGCGGTTGCCAAT
GGAAACTGA > 2-PS variant= 11 Substitutions= 4: (C 89S) (C195S) (C346A) (C372S)
ATGGGATCTTACTCATCGATGATGATTCGTGAGGTGGAGGTTTAGCCACGATTCTTGCCAT
TGGCACTGCTACTCCTCCCATGCGTTCGCTCAAGCTGATTATGCAGACTATTTTCGTGTCACTAAGAGCGAACATA
TGGTTGATCTTAAAGAGAACCAGAAATTTAAACGCATTTGTGAGAAAACAGCGATAAAGAAACGATACCCTCACCGAAGAC
TATCTGCAAGAGAACCAACAATG[tct]GAGTTCATGGCTTCCATCCTTAAACGCTCGACAAGACCTAGTGGTCACCGGCGT
CCCAATGCTTGGCAAGTCCAGTCAAGGCCGCAGTCAAGAGCCGCAGTACCACCAAAATCCAAGATCACCACCTCATCT

FIG. 12 (continued)

```
TCTGCACCACGCCTGGCGTTGACATGCCCCGGTGCTGACTATCAACTCGTCAAACTCCTTGGTCTCTCCCCTTCAGTCAAA
CGCTATATGTTGTACCAACAGGGATGTGCCGCCGGCACAGTCCTCCGGCTAGCCAAGGACCCTTGCTGAAAACAACAA
GGGCTCACGAGTCCTTATCGTCtccTCCGAGATCACTGCTGTCTTATTCCATGGAACCCAATGAGAACCACCTTGACTCAC
TCGTCGCTCAAGCTTTATTCGGAGACGGAGCTGCAGCACTCAAACAATCTTGCCGGTCACTGGGCGTACACTTGAGAGAGGGGAGG
ATATTCGAGATCGTCGTCAACTGATCGATCAGAGATGTACCCTTGTGGGCAAGGCAATAGAACGCAGCCATATTGGACCGGTTGTCTC
GTTGACGTTTCAGTTGCATAGAGATGTACCCTTTTTCTGGAACTCAGTTGCTCGCAACCAGTGGTCGAGCCATATTGGACCAGGTGGAGCGA
CACTAGGGATAACTGATTGGAACTAAGTTAAGGGCTAGCAGGCATGTGCTTAGTGAATACGAAACCTGATTAGCGCTgctGT
AAACTAAACCTTAAGGAAGATAAGTTAAGGGCTAGCAGGCATGTGCTTAGTGAATACGAAACCTGTGAAGGTTTGGATtccGGTG
GTTGTTCATCATTGACGAGGTGAGGAAGAGAATCTATGGCGGAAGAGTACAACCGTGAAGGTTTGGATtccGGTG
TTTTGTTTTGGATTTGGACCCGGTATGACTGTTGAGACTGTTGTTCTTCGTAGCGTCCGCGTTACTGCTGCCGTTGCCAAT
GGAAACTGA > 2-PS variant= 12 Substitutions= 5: (C 65S) (C 89S) (C195S) (C346A) (C372S)
ATGGGATCTTACTACTCCATCCGATGATGTGCGTTGAGGCTCGTGAGGCGCCACAAGGTTTAGCCACGATTCTTGCCAT
TGGCACTGCTACTCCTCCCAATTGCGTCGCTCAAGCTGATTATGCAGACTGAATAAAGAAGCTCACTAGAGGAACATA
TGGTTGATCTTAAAGAGAACAGCGATAAACATGCtctGAGTTCATGGCTCAAGGCCAGTCAAGGACCTAGTGGTCACCGGCGT
TATCGCAAGATGCTTTGGCAAAGAACCACATCATGATGAAGCTCCAAAATCCAAGATCACCACCTCATCT
CCCAATGCTTGGCAAAGAACCAACGACTGCCGAGTCAAGGCGACTACCAAAATCCAAGATCACCACCTCATCT
TCTGCACCACGCCTGGCGTTGACATGCCCCGGTGCTGACTATCAACTCGTCAAACTCCTTGGTCTCTCCCCTTCAGTCAAA
CGCTATATGTTGTACCAACAGGGATGTGCCGCCGGCACAGTCCTCCGGCTAGCCAAGGACCCTTGCTGAAAACAACAA
GGGCTCACGAGTCCTTATCGTCtccTCCGAGATCACTGCTGTCTTATTCCATGGAACCCAATGAGAACCACCTTGACTCAC
TCGTCGCTCAAGCTTTATTCGGAGACGGAGCTGCAGCACTCAAACAATCTTGCCGGTCACTGGGCGTACACTTGAGAGAGGGGAGG
ATATTCGAGATCGTGTCAACTGATCGATCAGAGATGTACCCTTGTGGGCAAGGCAATAGAACGCAGCCATATTGGACCGGTTGTCTC
GTTGACGTTTCAGTTGCATAGAGATGTACCCTTTTTCTGGAACTCAGTTGCTCGCAACCAGTGGTCGAGCCATATTGGACCAGGTGGAGCGA
```

FIG. 12 (continued)

CACTAGGGATAACTGATTGGAACTCAGTTTTCTGGATGGTGTGCACCCAGGTGGTCGAGCCATATTGGACCAGGTGGAGCGA
AAACTAAACCTTAAGGAAGATAAGTTAAGGGCAGGCATGTGCTTAGTGAATACGGAAACCGTGAATACGGATTAGCGCT[gt]
GTTGTTCATCATTGACGAGGTGAGGAAGAGAGATCTATGGCGAAGAGTACAACCGTGAAGGTTTGGA[tcc]GGTG
TTTTGTTTGGATTTGGACCGGGTATGACTGTTGAGACTGTTCTTGCTGCCGTTACTGCGTTGCCAAT
GGAAACTGA >2-PS variant= 13 Substitutions= 8:    (C 35S)    (C 65S)    (C 89S)    (C195S)
(M259L)  (L261N)  (C346A)  (C372S)
ATGGGATCTTACTCATCCGATGATGATGTGAGGCCGGACGGGTGATTCGTGAGGCCGACAAGGTTTAGCCACGATTCTTGCCAT
TGGCACTGCTACTGCCCTCCCCAATt[cg]GTCGCTCAAGCTCGATTATGCAGATCAGAGATCATTATTTTCGTGTCACTAAGAGCGAACATA
TGGTTGATCTTAAAGAGAATTTAAACGCATT[ct]GAGTTCATGAGCCTCCATCCTTAAAACGCTCGACAAACGATAAAGAAAACGATAAATCCAAGATCACCACCCTCATCT
TATCTGCAAGAGAACCAAACCCAGTCGAACAATG[tct]GAGTTCATGGCCAGTCAAGGCCAGTCAAGGCCAGTCAAGCCGCAGTCAGATGCGCAGTATGGGGACTACAACTCGTCAAAATCCTTGGTCTCTCCCTTCAGTCAAA
CCCAATGCTTGGCAAAGAAGCCGCAGTCAAGGCCAGTTGACATGCTGACTATCATCGTCAAACTCGTCTCCGGCTAGCCAAGACCTTGCTGAAACAACAA
TCTGCACCACCGCTGGTGTACCAACAGGGATGTGCCGCCGAGATCATGGACCAATGTCAGGCCCCACTTGGGCCGTAGACGGCCA
CGCTATATGTTGTACCAACAGGGGATGTGCCGCCGAGATCATGGACCAATGTCAGGCCACTTGCCCGTAGAACGGCCA
GGGCTCACGAGTCCTTATGCGTG[tcc]CCGAGATCAGGAGCTGCAGCACTCAGGCTTCAGGCCCTCACTTGGCCGTAGAACGGCCA
TCGTCGCTCAAGCTTTATTCGGAGACGGAGCTGCAGCACTCAGGCTTCAGGCGCACT[gaa]CACTTGAGAGAGGAGG
ATATTCGAGATCGTCAGTTGCATAGAGATGTACCCTGATGGTCGCAAAGAACATAGAGAACCAGCCAGCAGCAGCGGTTGTCTC
GTTGACGTTTCAGTTGCATAGAGATGTACCCTGATGGTCGCAAAGAACATAGAGAACCAGCCAGCAGCAGCGGTTGTCTC
CACTAGGGATAACTGATTGGAACTCAGTTTTCTGGAACTAGTAAGGGCTAGCAGGCATGTGAATACGGAAGCCGTGGAGCGA
AAACTAAACCTTAAGGAAGATAAGTTAAGGGCAAGAGATAATACGGAAACCGTGAATACGGATTAGCGCT[gt]GGTG
GTTGTTCATCATTGACGAGGTGAGGAAGAGAGATCTATGGCGAAGAGTACAACCGTGAAGGTTTGGA[tcc]GGTG
TTTTGTTTGGATTTGGACCGGGTATGACTGTTGAGACTGTTCTTGCTGCCGTTACTGCGTTGCCAAT
GGAAACTGA

FIG. 12 (continued)

```
> 2-PS variant= 14 Substitutions= 10:     (C 35S)   (C 65S)    (C 89S)    (T137F)
  (C195S)   (L202G)   (M259L)   (L261N)   (C346A)   (C372S)
ATGGGATCTTACTCATCCGATGATGTGGAGGTGATTCGTGAGGCCGAGCGGCACAAGGTTTAGCCACGATTCTTGCCAT
TGGCACTGCTACTCCCTCCCAATtcgGTCGCTCAAGCTGATTATGCAGAGATCGATAAAACAGCGATATAATTTTCGTGTCACTAAGAGCGAACATA
TGGTTGATCTTAAAGAGAAATTTAAACGCATTtctGAGAAACAGCTGATAAAGAACGATACCTAGCCCTCACCGAAGAC
TATCTCGAAGAGATCTTGGCAAAGAGACCCAACAGtctGAGTTCAAGGCTCCATTGATGAATCCAAGATCACCACCTCATCT
CCCAATGCTTGGCAAAGAGCCAGTCAAGGCCATTGATGAATCAACTCGTTGGCTCTCCCCTTCAGTCAAA
TCTGCACGttcgGCTGGCTTGTACCAACAGGATGTGCCGCCGGACACAGTCGTATCGtccTCCGAGATCGCTGACTCAC
CGCTATATGTTGTACCAAGAGTCCTTATTCGGAGACGGATCAAACAATCGTACCCCTGAGACTCGCAGAAACCATTAGCGCCA
GGGCTCACGAGTCCTTATTCGGAGACGGATCAAACAATCGTACCCCTGAGACTCGCAGAAACCTTGACTCAC
CGTCGCTCAAGCTTTATTGGGGATCCCGAGATCTGCAGCAGGCACTGgtTTCCATGCTCAGGGGTTCAGCCCTACTGAGAAGGCACTTGagaacCACTTGAGAGAGGAGG
ATATTCGACGTTTCAGTCGTCAAATAACTGATAGAGATAAGTTGAAACATAGAGAAACGCAGCAGCCATATTGGACCAGGTGGAGCGA
GTTGTTCATCATTGACGAGGTGAGCGGTATGACTCAGTTGTTCTTCGTAGCCGCGTTACTCCGTTGCCAAT
TTTTGTTTGGATTTGGACCGGTTAAGGAACGAGAGGGTATGACTCAGTTGTTCTTCGTAGCCGCGTTACTCCGTTGCCAAT
GGAAACTGA > 2-PS variant= 15 Substitutions= 10:     (C 35S)   (C 65S)    (C 89S)    (C195S)
  (I201F)   (L202G)   (M259L)   (L261N)   (C346A)   (C372S)
ATGGGATCTTACTCATCCGATGATGTGGAGGTGATTCGTGAGGCCGAGCGGCACAAGGTTTAGCCACGATTCTTGCCAT
TGGCACTGCTACTCCCTCCCAATtccGTCGCTCAAGCTGATTATGCAGAGATCGATAAAACAGCGATATAATTTTCGTGTCACTAAGAGCGAACATA
TGGTTGATCTTAAAGAGAAATTTAAACGCATTtctGAGAAACAGCTGATAAAGAACGATACCTAGCCCTCACCGAAGAC
```

FIG. 12 (continued)

```
TATCTGCAAGAGAACCCAACAATGtctGAGTTCATGGCTCCATCCTTAAACGCTCGACAAGACCTAGTGGTCACCGGCGT
CCCAATGCTTGGCAAGAAAGCCGCAGTCAAGGCCATTGATGAATGCTACCAAGATCAACTCCTTGGTCTCTCCCCTTCAGTCAAA
TCTGCACCACCGCTGGCGTTGACATGGAAGGATGCCGGGCCCAGTCGTTGACTATCAACTCGTCAAACTCCTTGGTCAAACTTGCTGAAAACAA
CGCTATATGTTGTACCAACAAGGATCCTTATCGTGtccTCCGAGATCACTGCTTTCCATGGACCCAATGAGAACCACCTTGACTCAC
GGGCTCACGAGTCCTCAAGCTTTATTCGGAGAGCTGCAGCCATTGTGGGTTCAGGCCCTCATTGGCCGTAGAACGGCCA
TCGTCGCTCAAGATCGTGTCAACTGATCAACAATCTTGCCGGACACTGAGAAGGCACTTGAGAGAGGAGG
ATATTCGAGATCGTGTCAGTTGCATAGAGATGTACCCCTTGATGGTCGCAAAGAACGCAGGAGAAAGCGTTGTCTC
GTTGACGTTTCAGTTGCATAGAGATGTACCCCTTGATGGTCGCAAAGAACGCAGGAGAAAGCGTTGTCTC
CACTAGGGATAACTGATTGGAACTCAGTTTTCTGGAACTGAAATACGGAAACCGTGATTAGCGCTgtGGTG
AAACTAAACCTTAAGGAAGATAAGTTAAGGAAGAGTACAACCGTGAAGGTTTGAAGTTTGAATtccGGTTGCCAAT
GTTGTTCATCATTGACGAGGTGAGGAAGATCTATGGCGGAAGGAAGAGTACAACCGTGTACTCGCCGGTTGCCAAT
TTTTGTTTGGATTTGGACCGGGTACTGAGACTGTTGAGTACTGTTCTTCGTAGCGTGAGCGCGGTTTGCTGCGCCAAT
GGAAACTGA >2-PS variant= 16 Substitutions= 10: (C 35S) (C 65S) (T137F)
(C195S) (L202G) (M259L) (L261N) (C346A) (C372S)
ATGGGATCTTACTGCTCATCGATGATGTGAGGTGATTCGTGAGGCCGAACGGCACAAGGTTTAGCCACGATTCTTGCCAT
TGGCACTGCTACTCCTCCCAATtccGTCGCTCAAGCTGATTATGCAGAGACTATTATTTCGTGTAAGAGCGAACATA
TGGTTGATCTTAAAGAAATTTAAACGCATtctGAGAAAACAGCGATACCTAGCCCTCACCGAAGAC
TATCTGCAAGAGAACCCAACAATGtctGAGTTCATGGCTCCATCCTTAAACGCTCGACAAGACCTAGTGGTCACCGGCGT
CCCAATGCTTGGCAAGAAAGCCGCAGTCAAGGCCATTGATGAATGCTACCAAGATCAACTCCTTGGTCTCTCCCCTTCAGTCAAA
TCTGCACCtcTGCTGGCGTTGACATGGAAGGATGCCGGGCCCAGTCGTTGACTATCAACTCGTCAAACTCCTTGGTCAAACAACAA
GGGCTCACGAGTCCTTATCGTGtccTCCGAGATCACTGCTATcgaTTCCATGGACCCAATGAGAACCACCTTGACTCAC
```

FIG. 12 (continued)

```
TCGTCGCTCAAGCTTTATTCGGAGACGGAGCTGCAGCACTCATTGTGGGTTCAGGCCCTCACTTGGCGTAGAACGGCCA
ATATTCGAGATCGTGTCAGTTGCATAGAGATCGATTGGAGCAACTGAAAGAACATAGAGAACGGAGCCATATATTGGACCGGAGAAGCGTTGTCTC
GTTGACGTTTCAGTTGCATAGAGATCGATTGGAGCAACTGAAAGAACATAGAGAACGGCAGCCATATATTGGACCGGAGAAGCGTTGTCTC
CACTAGGGATAACTAAACCTTAAGGAAGATAAGTTAAGGGCTAGCAGGCATGTGCTTAGTGAATACGAAACCTGATTAGCGCT[gc]GGTG
AAACTAAAACCTTAAGGAAGATAAGTTAAGGGCTAGCAGGCATGTGCTTAGTGAATACGAAACCTGATTAGCGCT[gc]GGTG
GTTGTTCATCATTGACGAGGTGAGGAAGAGATCTATGGCGAAGGAAGAGTACAACCGTGTTCCGCTTACTGCGGTTGCCAAT
TTTTGTTTGATTTGGACCGGGTATGACTGTTGAGACTGTTCTTGTTCTTCGTAGCGTTCCGGTTGCTGCGGTTGCCAAT
GGAAACTGA

>2-PS variant= 17 Substitutions= 10: ( C 35S)  ( C 65S)  ( C 89S)  (C195S)  (L202G)
(M259L)  (L261N)  (L268M)  (C346A)  (C372S)
ATGGGATCTTACTCATCCGATGATGTCGATTCGTGAGGCCGACGGGCAAGGTTTAGCCACGATTCTTGCCAT
TGGCACTGCTACTCCCTCCCCAAT[tcc]GTCGCTCAAGCTGATTATGCAGACTATATTTCGTGTCACTAAGAGCGAACATA
TGGTTGATCTTAAAGAGAACAGCGATATAAAGAACGATACCTAGCCCCTCACCGAAGAC
TATCTGCAAGAGAACCAACATG[tct]GAGTTCATGGCCATTGATGAATCAACTCGTCAAACTCCTTGTCTCCTTCAGTCAA
CCCAATGCTTGGCAAGAACCCGCAGTGCCAGTCATGCCCGGTTGACATCCGTCAACTCGTCAAACTCCTTGTCTCCTTCAGTCAA
TCTGCACCACGGCTGGTACCAACAGGATGTGCCGCGCGCGATATCGAGAACCTTGACTCAC
CGCTATATGTTGATCCTTATCGTC[tct]CCGAGATCACTGTC[gga]TTCCATGGGTTCAGGCCAC TTGCCGGAGAACAATAGAGAACGGCCA
GGGCTCACGAGTCCTTATCGTC[tct]CCGAGATCACTGTC[gga]TTCCATGGGTTCAGGCCAC TTGCCGGAGAACAATAGAGAACGGCCA
TCGTCGCTCAAGCTTTATTCGGAGATCGATCAACAATCTTGCCGGATGGTCGCAGCCATATATTGGACCGGAGAAGCGTTGTCTC
ATATTCGAGATCGTGTCAGTTGCATAGATCGATTGGAGCAACTGAAAGAACATAGAGAACGGCAGCCATATATTGGACCGGAGAAGCGTTGTCTC
Ga[tg]ACGTTTCAGTTGCATAGATCGATTGGAGCAACTCAAATGTACCCGTGCACCCCAGTTTTTCGGATGGTCGCAGCCATGTGCT
CACTAGGGATAACTAAACCTTAAGGAAGATAAGTTAAGGGCTAGCAGGCATGTGCTTAGTGAATACGAAACCTGATTAGCGCT[gc]GGT
AAACTAAAACCTTAAGGAAGATAAGTTAAGGGCTAGCAGGCATGTGCTTAGTGAATACGAAACCTGATTAGCGCT[gc]GGT
```

FIG. 12 (continued)

```
GTTGTTCATCATTGACGAGGTGAGGAAGAGATCTATGGCGAAGGGAAGAGTACAACCGGTGAAGTTTGGA tcgGGTG
TTTGTTGGATTTGACCGGGTATGACTGTTGAGACTGTTCTTGTTCGTAGCGTCCGCGTTACTGCTGCCGGTTGCCAAT
GGAAACTGA > 2-PS variant= 3 Substitutions= 18     (C 35S)   (C 89S)   (C372S)
ATGGGATCTTACTCATCCGATGAGGTGATTCGTGAGGCCGGACAAGGTTTAGCCACGATTCTTGCCAT
TGGCACTGCTACTCCCTCCCAATtccGTCGCTCAAGCTGATTATGCAGACTATTATTTCGTGTCATAAGAGGAACATA
TGGTTGATCTTAAAGAGAATTTAAACGGCATTGTGAGAGAAACAGCGATAAAGAAACGCTCACCCTAGCCCTCACCGAAGAC
TATCTGCAAGAGAACCCAACAATG tct GAGTTCATGGCTCCATCCTTAAACGCTCGACAAGATCCATCAACCCTCATCT
CCCAATGCTTGGCAAGAAGCCGGTTGACTGTCAAGGCCATTGATGAATGAATCTCGTCAAACTCGTCAAAACCTCGTCTCCTTGGTCTCTCCCCTCAGTCAAA
TCTGCACCACCGCTGGCTTGTGTACAAGCCGGATGCCGTTGACATGGCCCGGTTGAACAGGATGCGTTGACTCGTCGTAAGACCTCGTCAAAGGACCTTGTCCAATCAA
CGCTATATGTGTTGTACAAGCCCTATCGTCTGCTCCGAGATCAGTCGCTATCTTATTCGATGGACCCCCAATGAGAACCACCTTGACTCAC
GGGCTCACGAGTCCTTAGTCCAAGCTTTATTCGGACGAGCTCATTCTTCGGTGGTTCAGCCCCTCACTTGGCCATGGCCATGGCCA
TCGTCGCTCAAGCTTTATTCGGACGAGCTCATTCTTCGGTGGTTCAGCCCCTCACTTGGCCATGGGCATAGAGAAGCCAGGCCA
ATATTCGAGATCGTGTCAACTGACATCAAAACAATCTTGCCGGACAATGAAGTTACACTTGAGAGAGGAGG
GTTGACGTTTCAGTTGCATAGATCGTCAAATGAAATCGGAGAAAAGCGTTGTCTC
CACTAGGGATAACTGATTGGAACTCAGTTTTCTGCACCCAGGTGGTGCACCCAGGTGGTGCAGCCATATTGGAAACCTGATTAGGCGTGAGCGA
AAACTAAAACCTTAAGACGAGGTGATTCAGTGAGAAGAGATCTATGCGGAAGAGTACAACCGGTGAAGTTTGGAtcgGGTG
GTTGTTCATCATTGACGAGGTGATTTGGAGACTGTTGAGACTGTTCTTGTTCGTAGCGTCCGCGTTACTGCTGCCGGTTGCCAAT
TTTGTTGGATTTGGA
GGAAACTGA > 2-PS variant= 4 Substitutions= 19     (C 35S)   (C 89S)  (C346A)  (C372S)
ATGGGATCTTACTCATCCGATGATGTGGAGGTGATTCGTGAGGCCGACGGGCACAAGGTTTAGCCACGATTCTTGCCAT
```

FIG. 12 (continued)

```
TGGCACTGCTACTCCTCCCAATtcgGTCGCTCAAGCTGATTATGCAGACTATTATTTCGTGTCACTAAGAGCGAACATA
TGGTTGATCTTAAAGAGAACCCAACAATTTAAACGCATTGTGAGAAACAGCGATAAAGAAACGATACCTAGCCCTCACCGAAGAC
TATCTGCAAGAGAACCAACAATGtctGAGTTCATGGCTCCATCCTTAAACGCTGACAAGACCTAGTGGTCACCGGCGT
CCAATTCGATGCAAGAGAACGCAGTCAAGGCCATTGATGAATCAACTCGTCAAATCCTTGGTCTCTCCCTTCAGTCAAA
TCTGCACCACCGGCTGTTGTACCAGGATGTGCTCTGCTATCGTCTTATTCCAGAACTCGTCCCAAGACCACCTTGACTCAC
CGGCTCACGAGTCCTTATCGTCTCCGAGATCGTCGCTCTGCTATCCATTGTGGGTTGCACACTGCAAGGCCAATGAGAACCACTTGGCCGTAGAACGGCCA
TCGTCGCTCAAGCTTTATTCGGAGACGAGCAATCAAATCTTCCCGACACTGAGAAGGCAATGAAGTTACACTTGAGAGAGGAGG
ATATTCGAGATCGTCAACTGAACATAGAGATGTCCCAGGTGGTTGCACCAGGCCATGTGTCTGAATACGGAGAAGTTGAACCAGGTGTCTC
GTTGTTCAGTTGCATAGAGATGTCCCTGCTTCTGGAATGGTTGCAGGAGATCTATGGGAAGAGTACAACCGGTGAAGTTGGATtcgGGGTG
CACTAGGGATAACCTAAGCAAGAGCGAGGTGAGAGAGGATAAGTTAAGGGAAGAGATCTATGGGAAGAGTACAACCGGTGAAGTTGGATtcgGGTG
AAACTAAACCTTAAGCAAGAGCGAGGTGAGAGAGGATAAGTTAAGGGAAGAGATCTATGGGATGTTGAGACTGTTGAGAGCGA
GTTGTTCATCATTGACGAAGAGACGAGCGAGGTGAGAGAGGATAAGTTAAGGGAAGAGATCTATGGGATGTTGAGACTGTTGAGAGCGA
TTTTGTTTGGATTTGGACCGGGTATGATGATGATGAGACTGTTGAGACTGTTGAGACTGTTGAGACTGTTGCGGTTGCCAAT
GGAAACTGA >2-PS variant= 20 Substitutions= 4:   (C 35S)   (C 65S)   (C 89S)   (C372S)
ATGGGATCTTACTCCTCCATCCATCCCAATtcgGTGAGGTGATGTGGAGGCCGAGGTTCGTGTGACTTAGCCACGATTCTTGCCAT
TGGCACTGCTACTCCTCCCAATtcgGTGAGGTGATGTGGAGGCCGAGGTTCGTGTGACTATTGCAGACTTAGCGAACATA
TGGTTGATCTTAAAGAGAACCCAACAATTTAAACGCATTGTGAGAAACAGCGATAAAGAAACGATACCTAGCCCTCACCGAAGAC
TATCTGCAAGAGAACCAACAATGtctGAGTTCATGGCTCCATCCTTAAACGCTGACAAGACCTAGTGGTCACCGGCGT
CCAATTCGATGCAAGAGAACGCAGTCAAGGCCATTGATGAATCAACTCGTCAAATCCTTGGTCTCTCCCTTCAGTCAAA
TCTGCACCACCGGCTGTTGTACCAGGATGTGCTCTGCTATCGTCTTATTCCAGAACTCGTCCCAAGACCACCTTGACTCAC
CGCTATATGTTGTACCAACAGGATGTGCTCTGCTATCGTCTTATTCCAGAACTCGTCCCAAGACCACCTTGACTCAC
```

FIG. 12 (continued)

```
GGGCTCACGAGTCCTTATCGTCTGCTCCGAGATCACTGCTATCTTATTCCATGGACCCAATGAGAACCACCTTGACTCAC
TCGCTCGCTCAAGCTTTATTCGGAGAGCAGCTGCAGCACTGTCAGCCCTCACTTGTGGGTTCAGGCCTCCGTAGAACGGCCA
ATATTCGAGATCGTGTCAACTGATCAAACAATCTTGCCGGACACTGAAGTTACACTTGAGAGAGGAGG
GTTGACGCGTTTCAGTTGCATAGAGATGTATCACCCTTGCAAAGACTGTCGCAAAGAACGCGGAGAAAGCGGTTGTCTC
CACTAGGGATAACTGATTGGAACTCAGTTTTCTGGAACTGGTGCACCGTGTGTCAGCCATGTTGCCACCAGTGGACCGA
AAACTAAACCTTAAGGAAGATAAGTTAAGGGCTAGCAGAGATCATGGCGAAGAGTACAACCGGTGAAGGTTTGGATtcgGGTG
GTTGTTCATCATTGACGAGGAGCCGGGTTGGACCGGGTATGACTGTTGTTCTTCGTAGCGGTTACTCCGCGTTGCCAAT
TTTTGATTTGGATTTTGGATTTTGGATTTGGAAATGA
GAAACTGA >2-PS variant= 21 Substitutions= 5: (C 35S) (C 89S) (C195S) (C346A) (C372S)
ATGGGATCTTACTCATCCGATGATGTGAGGCCGGACGGTCGTGAGGCCACAAGGTTTAGCCACGATTCTTGCCAT
TGGCACTGCTACTCCTCCCAATtccGTCGCTCAAGCTGATTATGCAGACTATATTTCGTGTCACTAAGAGCGAACATA
TGGTTGATCTTAAAGAGAATTTAAACGCATTGTGAGAAACAGCGATAAAGAAACGATAAACGATCTAGCCCTCACCGAAGAC
TATCTGCAAGAGAAGCGCCCAACAGCAATGtctGAGTTCATGGCCATTGATGAATGGGACTCGTCAAATCCTTGGTCTCTCCCTTCAGTCAA
CCCAATGCTTGGCAAAGAACGCGCAGTCATGCCGGTTGACATCGTCCGTGAACAGGATGCTCAAACTCCTCCGCCAAATGAACCACCTCATCT
CGCACCACCGTGTACAACAGGATGCTCAAACTCCTCCGTCCGACCAATGAACCACCTTCAGTCAA
CGTCATATGTTGTACAACAGGATGCTCAACAGGATGtctCCGAGACGGACGGAACAATGAACCACCTTGACTCAC
GGGCTCGCTCAAGCTTTATTCGGAGAGCAGCTGATCAAACAATCTTGCCGGACACTGAAGTTACACTTGCGTAGAACGGCCA
TCGTCGCTCAAGCTTTCAGTTGCATAGAGATCAAACAATCTTGCCGGACACTGAAGTTACACTTGAGAGAAGCGGTTGTCTC
GTTGACGTTTCAGTTGCATAGAGATGTGTGCACGGTCGCGCCATGAGAACATGAGACGCAGCCATATGAGAAAGCGGTTGTCTC
CACTAGGGATAACTGATTGGAACTCAGTTTAAGGGCTAGCCATGGTGAATACGAAACCTGATTAGCGCT
AAACTAAACCTTAAGGAAGATAAGTTAAGGGCTAGCCATGGTGAATACGAAACCTGATTAGCGCTgctGT
```

FIG. 12 (continued)

GTTGTTCATCATTGACGAGGTGAGGAAGAGATCTATGGCGAAGGGAAGAGTACAACCGGTGAAGGTTTGGAT`tc`GGTG
TTTTGTTTGGATTTGGACCGGGTATGACTGTTGAGACTGTTCTTCGTAGCGTCCGGCGTTACTGCTGCGGTTGCCAAT
GGAAACTGA

> 2-PS variant= 22 Substitutions= 6: (C 35S) (C 65S) (C 89S) (C195S) (C346A) (C372S)

ATGGGATCTTACTCATCCGATGAGTGTGGAGGTGATTCGTGAGGCCGGACGGGCACAAGGTTTAGCCACGATTCTTGCCAT
TGGCACTGCTACTCCTCCCAAT`tc`GTCGCTCAAGCTGATTATGCAGACTATTATTTTCGTGTCACTAAGAGCGAACATA
TGGTTGATCTTAAAGAGAACCCAGAAATTTAAACGCATT`tct`GAGTTCATGGCTCCATCCTTAAACGCTGACAAGACGATACCTAGCCCTCACCGGCGT
TATCTGCAAGATGCTTGGCAAAGAACCCAGTCAAGGCCAGTCAAGGGACTACCAAAATCGTCAAACTCCTTGGTCTCCTCCCCTTCAGTCAAA
CCCAATGCTTGGCAAAGAACCCAGTCAAGGCCAGTCAAGGGACTACCAAAATCGTCAAACTCCTTGGTCTCCTCCCCTTCAGTCAAA
TCTGCACCACCGGCTGGCGTTGACAAGGGATGTGCCGGCGGTTGACAAGGGATGTGCCGGCGGATCACTGCTATTCTTATTCGTGGGTTCAGGCCCTCACTTGGCCGTAGACGGCCA
CGCTATATGTTGTCAACAGGATCCCTTATCGT`tct`CCCGAGATCACTGCTATTCTTATTCGTGGGTTCAGGCCCTCACTTGGCCGTAGACGGCCA
GGGCTCACGAGTCGTCAAGCTTTATTCGGACGAACTGATCAAACAATCTTGCCGACACTGAGAAGCCAATGAGTTACACTTGAGAGAGGAGG
TCGTCGCTCAAGCTTTATTCGGACGAACTGATCAAACAATCTTGCCGACACTGAGAAGCCAATGAGTTACACTTGAGAGAGGAGG
ATATTCGAGATCGTGTCAATAGAGATGTACCCTTGCTGATGGTCGCAAAGAACATAGAGCCAGCGGAGAAAGCGTTGTCTC
GTTGACGTTTCAGTTGCATAGAGATGTACCCTTGCTGATGGTCGCAAAGAACATAGAGCCAGCGGAGAAAGCGTTGTCTC
CACTAGGATAACCTTAAGGAAGATAAGTTAAGGCTAGCAGGCATGTGCTTAGTGAATACGGAAAACCTGTTGAATACGGAAAACCTGTTGAACCGGTGAAGGTTTGATTAGCGCT`tgt`GGTG
AAACTAAAACCTTAAGGAAGATAAGTTAAGGCTAGCAGGCATGTGCTTAGTGAATACGGAAAACCTGTTGAATACGGAAAACCTGTTGAACCGGTGAAGGTTTGATTAGCGCT`tgt`GGTG
GTTGTTCATCATTGACGGGTATGACTGTTCTTCGTAGCGTCCGCGTTACTGCTGCGGTTGCCAAT
TTTTGTTTGGATTTGGACCGGGTATGACTGTTGAGACTGTTCTTCGTAGCGTCCGCGTTACTGCTGCGGTTGCCAAT
GGAAACTGA

FIG. 12 (continued)

> 2-PS variant= 23 Substitutions= 2: (C 35S) (T137F)
ATGGGATCTTACTCTCATCGATGATGTGAGGTGATTCGTGAGGCCGAAGGTTTAGCCACGATTCTTGCCAT
TGGCACTGCTACTCCCTCCCAAT tcc GTCGCTCAAGCTGATTATGCAGACTATTATTTCGTGTCACTAAGAGCGAACATA
TGGTTTGATCTTAAAGAGAACCCAACATTGTTAAACGCATTGTGAGAAAACAGGATATAAAGAACGATAAAGAACGCCTCACCGAAGAC
TATCTGCAAGAGAACCCAACAATTGTGTAAACGCTCCATCCTTAAACGCTCGACAAGACCTAGCCCTCACCGGCGT
CCCAATGCTTGGCAAGAGCCGCAGTCAGCCGACTACCAAATCCAAGATCACCCACCCTCAGTCAAA
TCTGCACCT tg GCTGGCGTTGACATGCCCGTTGACATCAACTCGTCAAACTCCTTGGTCTCTCCCTTGAAAACAACAA
CGCTATATGTTGTACCAGTCGTCTGCTCCGAGATCACTGCTATCTTATTCCATGGACCCAGTAGCGTCCGGCCAATGAGAACCCTTGACTCAC
GGGCTCACGAGTCCTTATCGTCTGCTCCGAGATCACTGCAGCGAGCTCCTCACTTGTGTCTTGGGTTCAGGCAATGAAGTTACACTTGAGAGAGGAGG
TCGTCGCTCAAGCTTTATTCGGACACGCATCAAACAATCTTGCCGGACACTGAAGGCAATGAGAGAACATAGAGAAACCAGGTGGTCGAGCCAATGGACCCAGTGGAGCGA
ATATTCGAGATCGTGTCAACTGCATAGAGATGTCTTGTTGAGACTGTTGTTCTTCGTAGCGTTCCGCGTTACTGCGTCCGGGTTGCTGCGGGTGCCCAAT
GTTGACGTTTCAGTTCAGTTGCTTGATGATAACCCCTTTCAGTTCTGGAACTCAGTTGGAAACTCAGTTGGGATAACCTTGAAGGTTTTGGGATTGCGGTGGATTGCGGTG
CACTAGGGATAAACCTTAAGAACTGATTGGAAGATAAGTTAAGGAAGATAAGTTAAGGGAAGAGTAACAACCGGTGAATACGAACCGTGAACGTTATATCGAAGGTTTGAAGGTTTTGGATTGCGGTG
AAACTAAACCTTAAGAACTGATTGGAAGATAAGTTAAGGAAGATCTATGGCGAAGGAAGAGTAACAACCGGTGAATACGAAACCGTGAACGTTATATTCGAAGGTTTGAAGGTTTTGGATTGCGGTG
GTTGTTCATTCATTGACGAGGTGAGAAGATCTATGGCGAAGGAAGAGTTCTTCTTCGTAGCGTTCCGCGTTACTGCGTCCGGGTTGCTGCGGGTTGCCCAAT
TTTGTTGTTGGATTGATTGGATTGGAAACTGA
GGAAACTGA > 2-PS variant= 24 Substitutions= 2: (C 35S) (T137M)
ATGGGATCTTACTCTCATCGATGATGTGAGGTGATTCGTGAGGCCGAAGGTTTAGCCACGATTCTTGCCAT
TGGCACTGCTACTCCCTCCCAAT tcg GTCGCTCAAGCTGATTATGCAGACTATTATTTCGTGTCACTAAGAGCGAACATA
TGGTTTGATCTTAAAGAGAACCCAACATTGTTAAACGCATTGTGAGAAAACAGGATATAAAGAACGATAAAGAACGCCTCACCGAAGAC
TATCTGCAAGAGAACCCAACAATTGTGTAAACGCTCCATCCTTAAACGCTCGACAAGACCTAGCCCTCACCGGCGT
CCCAATGCTTGGCAAGAGCCGCAGTCAGCCGACTACCAAATCCAAGATCACCCACCCTCATCT

FIG. 12 (continued)

```
TCTGCACCatgGCTGGCGTTGACATGCCGGTGCTGACTATCAACTCGTCAAACTCCTTGGTCTCTCCCCTTCAGTCAAA
CGCTATATGTTGTACCAACAGGATGTGCCGCCGGGCACACTGCTGCTCTGCCCGAGATCGTCGTCTGCTCCCGAGATCTGCCCGAGATCCCAATGAGACCCTTGACTCAC
GGGCTCACGAGTCCCTTATCGTCGTCTGCTCCCGAGATCGTCGTCTGCTCCCGAGATCGTCGTCTGCTCCCGAGATCGTCGTCTGCTCCCGAGATCGTCGTCTGCTCCCGAGATCGTCAC
TCGTCGCTCAAGCTTGTGTCAACGGAGACGGAGAGCTGCAGCACTGCAGCGAGCGCAATCTTGCCGACACTGTTGCCGACACTGTTGCCGACACTGGCCGTAGAACGGCCA
ATATTCGAGATCGTCGTCAGTTGCATAGAGATGTACCCTTGATGGTGCAAGAACATAGAGAACCAGCAGCGGAGAACCAGCGGGAGAACCAGCAGCGGAGAGGGAGG
GTTGACGTTTCAGTTTGCATAGAGATGTACCCTTGATGGTGCAAGAACATAGAGAACCAGCAGCGGAGAACCAGCGGGAGAACCAGCAGCGGAGAGGGAGAGCGTTGTCTC
CACTGGGATAACCTTAAGGAAGATAAGTTAAGGGCATGGTAGCAGGCATATTGGAACCGTGAATACGGAACCTGAATTAGCGCTTGTGT
AAACTAAACCTTAAGGAAGATAAGTTAAGGGCATGGTAGCAGGCATATTGGAACCGTGAATACGGAACCTGAAGTTTGGATTGCGGTG
GTTGTTCATCATTGACGAGGTGAGGAGATCTATGGACCGGGTATGTTGAGACTGTTGTTCTTCGTAGCGTCCGGCGTTACTGCGCGTTGCCAAT
TTTTGTTGATTTGGATTGTTGAGACCGGGTATGTTGAGACTGTTGTTCTTCGTAGCGTCCGGCGTTACTGCGCGTTGCCAAT
GGAAACTGA > 2-PS variant= 25 Substitutions= 2: (C 35S) (M259F)
ATGGGATCTTACTGACTCATCGATGATGTGAGGTGATTCGTGAGGCCGGACGGAGTTTAGCCACGGCACAAGTTTAGCCACGATTCTTGCCAT
TGGCACTGCTACTCTGCTGCCAATtcgGTCGCTCAAGCTGATTATGCAGACTATTATTTTCGTGTCACTAAGAGCGAACATA
TGGTTGATCTTAAAGAGAACCAGCAGCGGAGAGCATTTGTGAGAAGAAACAGCAGCCTTGTGAGAAGAAACAGCAGATACCCTCCACCGAAGAC
TATCTGCAAGACGTCGCAACAGTGTGTGAGTTCATGGCTCCATCTGAGTTCATGGCTCCATCTTAAACGCTCGACAAGACCTAGTGGTCACCGGCGT
CCCAATGCTTGGCAAGAACCGCAAAGAAGCCGTTGCGAAGAAATCCAAGAATCCAAAATCCTTGGTCTCCTCCCTTCAGTCAAA
TCTGCCACCACCTTACCAACAGGATGTGCCGCCGGGCACACTGCTAGCAAGGACCCTTGAAAACAACAA
CGGCTCACGAGTCCCTTATCGTCGCTCCGAGATCAGCTGATTATGCAGACCCTGAAAACAGCCCTGAAGACCCTTGACTCAC
TCGTCGCTCAAGCTTGTGTCAACGAGACGGAGAGCTGCAGCACTGCAGCGAGCGCAATCTTGCCGACACTGTTGCCGACACTGGCCGTAGAACGGCCA
ATATTCGAGATCGTCGTCAACTGCAGCAACATCAAACAATCTTGCCGACACTGAGAAGGCAttAAGTTACACTTGAGAGAGGAGG
GTTGACGTTTCAGTTGCATAGAGATGTACCCTTGATGGTGCAAGAACATAGAGAACCAGCCGGAGAAAGCGTTGTCTC
```

FIG. 12 (continued)

```
CACTAGGGATAACTGATTGGAACTCAGTTTTCTGGATGGTGCACCCAGGTGGTCGAGCCATATTGGACCAGGTGGAGCGA
AAACTAAACCTTAAGGAAGATAAGTTAAGGGCCATGTGCTCTTAGTGAATACGGAAACCTGATTAGGCGCTTGTGT
GTTGTTCATCATTGACGAGGTGAGGAAGATCTATGGCCGAAGGAAGAGTACAACCGGTGAAGGTTTGGATTGCGGTG
TTTTGTTTGGATTTGGACCGGGTATGACTGTTGAGACTGTTCTTCGTAGCGTTACTGCTGCGGTTGCCAAT
GGAAACTGA

> 2-PS variant= 26 Substitutions=    2:   (C 35S)    (T137L)
ATGGGAGATCTTACTCATCGATGATGGAGTGATTCGTGCTCAAGCTGATTATGCAGACTATTATTTCGTGTCACTAAGAGCAACATA
TGGCACTGCTACTCCTCCCAATtcgGTCGCTCAAGCTGATTATGCAGACTATTATTTCGTGTCACTAAGAGCAACATA
TGGTTGATCTTAAAGAGAACAATTTAAACGCATTGTGAGCTGTCATGGTCAGTGTGAGCTTAAACGATACCTAGCCCTCACCGAAGAC
TATCTGCAAGAGAACCCAACAAGAGCCGCAGTGAAGGCCATTGATGAATGGGACTACCAAAATCCAAGATCACCACCTCATCT
CCCAATGCTTGGCAAAGACGGCAAAGACCGCAGTCAAGGCCATTGATGAATGGGACTACCAAAATCCAAGATCACCACCTCATCT
TCTGCACGctgGCTGTTGACATGGACCCGGTTGCTGACATCAACTCGTCAAGGACCTTCTCCCCTTCAGTCAAA
CGCTATATGTTGTACAACAGGATGTGCCGCCGAGATCATGGGACTATATCTTATTGTGGGTTCAGCCCAATGAGAACCACCTGACTCAC
GGGCTCACGAGTCCTTACGTCTCGAGATCGTGCTCGAGGGACTATATCTTATTGTGGGTTCAGCCCAATGAGAACCACCTGACTCAC
TCGTCGCTCAAGCTTTATTGGAGACGGACAATCTTGCCGGACACTGCCAAATGAAGTTACACTTGAGAGAGGAGG
ATATTCGAGATCGTCAGTTGCATAGAGATGTACCCTGATGGTCGCAAGACATAGACAGCCAGCTGGAGAAAGCGGTTGTCTC
GTTGACGTTTCAGTTGCATAGAGATGTACCCTGATGGTCGCAAGACATAGACAGCCAGCTGGAGAAAGCGGTTGTCTC
CACTAGGATAACCTTAAGGAAGATAACTGAGGAAGTTAAGGGCCATGAATACGGAAACCTGATTAGGCGCTTGTGT
AAACTAAACCTTAAGGAAGATAACTGAGGAAGTTAAGGGCCATGAATACGGAAACCTGATTAGGCGCTTGTGT
GTTGTTCATCATTGACGAGGTGAGGAAGATCTATGGCCGAAGGAAGAGTACAACCGGTCGAAGGTTTGGATTGCGGTG
TTTTGTTTGGATTTGGACCGGGTATGACTGTTGAGACTGTTCTTGTTCTTCGTAGCGTTACTGCTGCGGTTGCCAAT
GGAAACTGA
```

FIG. 12 (continued)

> 2-PS variant= 27 Substitutions= 2; (C 35S) (I343F)

```
ATGGGATCTTACTCATCCGATGATGTGAGGTGATTCGTGAGGCCGACGGGCACAAGGTTTAGCCACGATTCTTGCCAT
TGGCACTGCTACTCCTCCCCAATtccGTCGCTCAAGCTGATTATGCAGACTATTATTTCGTGTCACTAAGAGCGAACATA
TGGTTGATCTTAAAGAGAACCCAACAATTAAAGCTGTGAGAAAACAGCGATAAAGAAAACGATACCTACCCTCACGGAGAC
TATCTGCAAGAGAACCCAACAATTAAAGCTGTGAGTTCATGGCTCCATCCTTAAACGCTCGACAGAGACCTTGGTCACGGCGT
CCCAATGCTTGGCAAGAAGCCAGTCAAGGCGACTCAAGATGTGAGTTCATGGCTCCATCCTTAAACGATCACCCACCCTCATCT
TCTGCACCACCGCTGCGTTGACATGCCCGGTTGACATGCCCCGGCGTTGACAAGGATGCCGCCGCGGCGTTGACAAGGATGTGC
CGCTATATGTTGTCAACAGGATCCTTATCGTCTGCTCCGAGATCACTGCTATCTTATTCGAGAACGACCACCTTGACTCAC
GGGCTCACGAGTCCTTATCGTCTGCTCCGAGATCACTGCTATCTTATTCGGGTTGAGAAGGCAATGAGAGAACAACAA
TCGTCGCTCAAGCTTTATTCGGAGACGACTCAACGAATCAACCCTTTGATGGTCAGGCATGTGCGAGCCATATTGGACCAGGTGCAG
ATATTCGAGATCGTGTCAACTGATCAAATCTTGCCGGACACTGAAGTTACACTTGAGAGAGGAGG
GTTGACGTTTCAGTTGCATAGAGATGAACAAGATAGCCACCCAGGTGTGCCAGCAATGTGGGAAGCCATATTGGAGCCATATTCGT
GTTGTTCATCATTCAGTTGCATAGAGATGATAGCCTCGGTGTGCCAGCGCAATATCCTATGGCGAAGATCTATGGGCGAAGGTTTTGAGGTTA
CACTAGGGATAAGGATCCATGCGAGAGATTAGTTAAGGCATGCTATGATGAATGCGAAGAACTACAAAAGCCGTCGTGAATTGGAAGGTTTG
GTTGTTCATCATTCAGTTGCATCATCGACGAGCATCGAGGAGTTCATCGTGACACTGAGCTCTGGAGATTCATGTTCTTCGTAGCGTCCGCCGTTACTGCCGGTTGCCAAT
TTTGTTGGATTTGGACCGGGTTATGACTGTGAGATCAACCTCCAAGGCAAAATCTTGGCGAGCCACCTCGCGAGACCACCACCACCCCCCCCCCATGGGAAACTGA
GGAAACTGA
```

> 2-PS variant= 28 Substitutions= 2; (C 35S) (I343M)

```
ATGGGATCTTACTCATCCGATGATGTGAGGTGATTCGTGAGGCCGACGGGCACAAGGTTTAGCCACGATTCTTGCCAT
TGGCACTGCTACTCCTCCCCAATtcgGTCGCTCAAGCTGATTATGCAGACTATTATTTCGTGTCACTAAGAGCGAACATA
TGGTTGATCTTAAAGAGAACCCAACAATTAAAGCTGTGAGAAAACAGCGATAAAGAAAACGATACCTACCCTCACGGAGAC
TATCTGCAAGAGAACCCAACAATTAAAGCTGTGAGTTCATGGCTCCATCCTTAAACGCTCGACAGAGACCTAGTGGTCACGGCGT
CCCAATGCTTGGCAAGAAGCCAGTCAAGGCCGCAGTCTTGACATGCCCCGGCGTTGACATGCCCCGGCGTTGACAAGGATGTGC
```

FIG. 12 (continued)

```
TCTGCACCACGCCTGGCGGTTGACATGCCGGTGCTGACTATCAACTCGTCAAACTCCTTGGTCTCTCCCCTTCAGTCAAA
CGCTATATGTTGTACCAACAGGATGTGCCGGCGGGCGTGCTCCGGCTAGCCAAGACCCTTGCTGAAAACAACAA
GGGCTCACGAGTCCTTATCGTCTGCTCCGAGATCACTGGCTATCTTATTCGTGGGTTCAGGCCCTCACTTGACTCAC
TCGTCGCTCAAGTTTATTCGGAGACGGCACTGTCAACTGATCAAACAATCTTGCCGGACAAGGCAATGAAGTTACACTTGACTTGCCGTAGAACGGCCA
ATATTCGAGATCGTGTCAGTTGCAACTGATCAAACAATCTTGCCGGACAACTGAAGTTACACTTGAGAGAGGAGG
GTTGACGTTTCAGTTGCATAGAGATGTACCCTTTGATGGTCGCAAAGAACATAGAACGCAGCCATATTGGAACCAGGTGGAGCGA
CACTAGGGATAACTGATTGGAACTCAGTTTTCTGGAACTCAGTGCTTAGTGAATACGAACCTGAAGGGCTTGTGT
AAACTAAACCTTAAGGAAGATAAGTTAAGGCTAGCAACAGATCTATGGCGGAAGAGTACAACCGGTGACTGCTGCCGGTTGCCAAT
GTTGTTCATCATTGACGAGGTGAGGAAGAGATCTATGGCGGAAGAGTACAACCGGTCCGCGGTTACTGCTGCCGGTTGCCAAT
TTTTGTTGTTGGATTTGGACCGGTTATGACTGGAAACTGA
GGAAACTGA

> 2-PS variant= 29 Substitutions= 2:    (C 35S)    (I201F)
ATGGGATCTTACTCATCCGATGTGAGGTGATTGCAGGCCGGCAAGGTTTAGCCACGATTCTTGCCAT
TGGCACTGCTACTCCCTCCCAAT[tcc]GTCGCTCAAGCTGATTATGCAGACTATATTTTCGTGTCACTAAGAGCGAACATA
TGGTTGATCTTAAAGAGAACCAAGATTTAAACGAAGCTGTGAGAAACAGGCGATAAAGAACCTCCACCGAGAC
TATCTGCAAGAGAACCAACATGTGTAGCTCCATCGTAGAGTTCATGGGGACTCAAGACCTAGTGGTCACCGGCGT
CCCATGCTTGGCAATGCCGCAGTGCAGTCAAGCGTTCGACATTGACTATCAACTCGTCAAAATCACCACCTCATCT
TCTGCACCACGCCTGGCGGTTGCAACAGGATGTGCTCCGGCGCCAATGTCCGGCCAAGACCCTTGCTGAAAACAA
CGGCTCACGAGTCCTTATCGTCTGCTCCGAGATCACTGCAGCGATCACTGGCTATCTTATTGAGAACCTTGACTCAC
TCGTCGCTCAAGTTTATTCGGAGACGCACTCGTGCAGTTCATTTGTCCGGACACTGAAGTTACACTTGGCCGGCCA
ATATTCGAGATCGTGTCAACTGATCAAACAATCTTGCCGGACACTGAAGTTACACTTGAGAGAGGAGG
GTTGACGTTTCAGTTGCATAGAGATGTACCCTTTGATGGTCGCAAAGAACATAGAACGCAGCGGAGAAAGCGTTGTCTC
```

FIG. 12 (continued)

CACTAGGGATAACTGATTGGAACTCAGTTTTCTGGATGGTGCACCCAGGTGGTCGAGCCAGTGGTGGAGCGA
AAACTAAACCTTAAGGAAGATAAGTTAAGGGCTAGGCCATGTGCTTAGTGGAAACCTGATTAGCGCTTGT
GTTGTTCATCATTGGATTTGACGAGGTGAGGAAGAGTACAACCGGTGAAGGTTGAAGGTTTGGATTGCGGTG
TTTTGTTTGGATTTGGACCGGGTATGACTGTTGAGGACTGTTCTTCGTAGCGTTCCGCGTTACTGCGTTGCCAAT
GGAAACTGA

> 2-PS variant= 30 Substitutions= 2:  (C 35S)  (C169A)

ATGGGATCTTACTCATCCGATGATGTGAGGTGATTCGTGAGGCCGGACCACAAGGTTTAGCCACGATTCTTGCCAT
TGGCACTGTACTCCTCCCAATtccGTCGCTCAAGCTGATTATGCAGACTATTATTTCGTGTCACTAAGAGCGAACATA
TGGTTGATCTTAAAGAGAACCATTTAAACGCATTTGTGAGAAAACAGCGATAAAGAACGATACCTAGCCCTCACCGAAGAC
TATCTGCAAGAACCAACAATGTGTGAGTCATGCTCCATCCTTAAACGCTCGACAGACCTAGTGGTCACCGCGT
CCCAATGCTTGGCAAAGAACCGCAGTCAAGGCCATTGATGAATGGGACTACCAAAATCCAAAGATCACCACCTCATCT
TCTGCACCACCGCTGGCGTTGACATGCCCGGTTGACTATCAACTCCTCCGGCTAGCCAAGGACCTTGAAAACAACAA
CGCTATAGTTGTACCAACAGGAGgctGCCGAGATCGTCTCCGAGACGGAGCGAATGAAGTTACACTTGAGAGAGGAGG
GGGCTCAAGAGTCCTTATCCCTTATTCCATGAGGTTGCTGCACTGCAGGGTTGCAGCCAATAGACGAGGAACACTCAC
TCGTCGCTCAAGCTTTATTCGGACGGAGCGTCAGCCACTCATTGTCGGTTCAGGCCTACTGGCCGTAGAACGGCCA
ATATTCGAGATCGTCAACTGATCAAACAATCTTGCCGGACACTGAAGGCAATGAAGTTACACTTGAGAGAGGAGG
GTTGACGTTTCAGTTGCATAGAGATGTCAGTTGTGAGGACTGCAAAGACATAGCAGCGGAGAAAGCCGGTGTCTC
CACTAGGGATAACCTTAAGGAAGATAAGTTAAGGGCTAGGCCATGTGCTTAGTGGAAACCTGATTAGCGCGGA
AAACTAAACCTTAAGGAAGATAAGTTAAGGGCTAGGCCATGTGCTTAGTGGAAACCTGATTAGCGCTTGT
GTTGTTCATCATTGGATTTGACGAGGTGAGGAAGAGTACAACCGGTGAAGGTTGAAGGTTTGGATTGCGGTG
TTTTGTTTGGATTTGGACCGGGTATGACTGTTGAGACTGTTGTTCTTCGTAGCGTTCCGCGTTACTGCGTTGCCAAT
GGAAACTGA

FIG. 12 (continued)

> 2-PS variant= 31 Substitutions= 2;    (C 35S)    (L268M)
ATGGGATCTTACTCATCCATGATGTGAGTTCGTGAGGCCGACAAGGTTTAGCCACGATTCTTGCCAT
TGGCACTGCTACTCCCTCCCAATtcgGTCGCTCAAGCTGATTATGCAGAGACTATTATTTTCGTGTCACTAAGAGGAACATA
TGGTTGATCTTAAAGAGAACCAACAATTTAAACGATAAACAGCGATAAAGAAAACGATACCTAGCCCTCACCGAAGAC
TATCTGCAAGAGAACCAACAATGTGTGAGTTCATGGCTCCATCCTTAAACGCTCGACAAGACCTAGTGGTCACCGGCGT
CCCAATGCTTGGCAAGAAGCCGTTGACAATGTGCTGACTATCAACTCGTCAAATCCAAGATCACCACCCTCAGTCAAA
TCTGCACCACCGCTGGCGTTGTACAACAGGATGTGCCGTTGACAATGTGCCGCACCTGGTGTCTCCCCTTGTGAAAACAACAA
CGCTATATGTTGTACAACAGGATGTGCCGCTTGACATGCCCGTAGCCAAGGACCTTGCTGAAAACAACCTTGACTCAC
GGGCTCACGAGTCCTTATCGTCGTCCCGAGATCACTGCTATCTTATTCCATGGATTCAGGGTTCATGGCCAAATGAGAACGGCCA
TCGTCGCTCAAGCTTTATTCGGAAGATCATCGCTGATGGTTCGCCAAACAATCTTGAGAGAAGCAATGAAGTTACACTTGAGAGAGGAGG
ATATTCGAGATCGTGTCAGTTGCATAGAGATCAAAATGTACCCTTTGATGGTTTCTGAACTGAGCCCATATTGGACCAGGTGGAGCGA
gatACGTTTCAGTTGCATAGAGATCAAAATGTACCCCTTTGATGGTTTCTGAACTGAGCCCATATTGGACCAGGTGGAGCGA
CACTAGGGATAAACTGATTGGAACTCAGTTCTGAACTGAGATAAGTTAAGGAAGAAGTACAACCGGTTCCGCTTACTGCTGCGGTTGCCAAT
AAACTAAACCTTAAGGAAGATAAGTTAAGGAAGAAGAGTACAACCGGTTCCGCTTACTGCTGCGGTTGCCAAT
GTTGTTCATTCATTGACGAGGTGAGGAAGAGATCTATGCGAAGGAGAGTACAACCGGTTGAAGTTTGGATTGCGGTG
TTTTGTTTGGATTTGGATTTGGACCGGTATGACTGTTCTTCGTAGCCGTCCGCTTGTCCGTTGTCCGTTTACTGCTGCGGTTGCCAAT
GGAAACTGA > 2-PS variant= 32 Substitutions= 2;    (C 35S)    (L202F)
ATGGGATCTTACTCATCCATGATGTGAGTTCGTGAGGCCGACAAGGTTTAGCCACGATTCTTGCCAT
TGGCACTGCTACTCCCTCCCAATtcgGTCGCTCAAGCTGATTATGCAGAGACTATTATTTTCGTGTCACTAAGAGGAACATA
TGGTTGATCTTAAAGAGAACCAACAATTTAAACGATAAACAGCGATAAAGAAAACGATACCTAGCCCTCACCGAAGAC
TATCTGCAAGAGAACCAACAATGTGTGAGTTCATGGCTCCATCCTTAAACGCTCGACAAGACCTAGTGGTCACCGGCGT
CCCAATGCTTGGCAAGAAGCCGCAGTCAACGCCGCAGTCAAGGCCTACCAAATCCAAGATCACCCACCCTCATCT

FIG. 12 (continued)

```
TCTGCACCACGCCTGGCGTTGACATGCCCGGTGCTGACTATCAACTCGTCAAACTCCTTGTCTCTCCCTTCAGTCAAA
CGCTATATGTTGTACAACAGGATGTGCCGCCCAAGACCTTGCAAGACCTTGCAAAACAACAA
GGGCTCACAGAGTCCTTATCGTCTCCGAGATCACTGTATCTTCCATGACCCAATGAGAACCACCTTGACTCAC
CGTCGCTCAAGCTTTATTGGAGACGAGCTCAGCACTGTGGGTTCAGCCCTCACTGTGGCCTAGAACGGCCA
ATATTCGAGATCGTGTCAACTGACAAACAATCTTCCGGACACTGAAGAAGCAATGAAGTTACACTTGAGAGAGGAGG
GTTGACGTTTCAGTTGCATAGATGTACCCTTGATGGTCGCAAAGAACATAGAACGCGAGAAAGCGTTGTCTC
CACTAGGGATAACTTAAGCTGATTGGAACTCAGTTTTCTGAAGGGCATGGTGCACCCAGGTGCTGAATACGGAAGCGA
AAACTAAACCTTAAGGAAGATAAGTTAAGGCTGAAATCTATGGCGAAGAAGAGTACAACCGTGAAGTTTGATTGCGGTG
GTTGTTCATCATTGACGAGGTGAGAGGTGACCGCTGTTCAGGACTGTTGAGACTGTTGAGACGTTCTGCGGTTGCCAAT
TTTTGTTTGGATTTGGACCGGGTATGCTGTTGAGACTGTTGAGACGTCCGGCGTTACTGCCGTTGCCAAT
GGAAACTGA

> 2-PS variant= 33 Substitutions= 2:  (C 35S) (I201M)
ATGGGATCTTACTGCTCATCGTCCCATGATGGGTGAGGTCGTGAGGCCGGAAGGTTTAGCCACAAGGTTCCACGATTCTTGCCAT
TGGCACTGCTACTCCCTCCCAATtcgGTCGCTCAAGCTGATTGCAGACTATTATTTTCGTGTCACTAAGAGCGAACATA
TGGTTGATCTTAAAGAGAATTAAAGCATTGTGTAAAACAGCCGATAACGAAGAAACGCTCACCTAGCCCTCACCGAAGAC
TATCTGCAAGAGAACCCAACAGTGTCAGTTCATGGCTCAAGCCTCAAGACCTAGTGGTCACCACCTCATCT
CCCAATGCTTGGCAGAAGACCGCAGTGCTTGACATGCCCGGTGCTGACTATCAACTCGTCAAAATCCTTGGTCTCCCCTTCAGTCAAA
TCTGCACCACGCCTGGCGTTGACATGCCCGGTGCTGACTATCAACTCGTCAAAATCCTTGGTCTCCCCTTCAGTCAAA
CGCTATATGTTGTACAACAGGATGTGCCGCCCAAGACCTTGCAAAGACCTTGCTGAAAACAACAA
GGGCTCACGAGTCCTTATCGTCTCCGAGATCACTGCTtTATTCCATGGTTCAGCCCTCACTGTGGTCAGGCCCA
TCGTCGCTCAAGCTTTATTCGGAGACGAGCTCAGCACTGTGCCGGACACTGAAGAAGCAATGAAGTTACACTTGAGAGAGGAGG
ATATTCGAGATCGTGTCAACTGATCAACAATCTTGCCGGACACTGAAGAAGCAATGAAGTTACACTTGAGAGAGGAGG
GTTGACGTTTCAGTTGCATAGATGTACCCTTGATGGTCGCAAAGAACATAGAGAACGCGAGGAGAAAGCGTTGTCTC
```

FIG. 12 (continued)

```
CACTAGGGATAACTGATTGGAACTCAGTTTTCTGGATGGTGCACCCAGGTGGTCGAGCCATATTGGACCAGGTGGAGCGA
AAACTAAACCTTAAGGAAGATAAGTTAAGGGCTAGCAGGCATGTGCTTAGTGAAGAGTACGGAAACCTGATTAGCGCTTGTGT
GTTGTTCATCATTGACGAGGTGAGGAAGAGATCTATGGCGGAAGGAAGAGTACAACCGGTGAAGGTTTGGATTGCGGTG
TTTGTTTGGATTTGGACTCGGTTGGACTCTTGTTGTTCTTCCGTAGCGTCGTTACTCTGCCGTTGCCAAT
GGAAACTGA

> 2-PS variant= 34 Substitutions= 2:      (C 35S)    (I201L)
ATGGGACTTTACTGCTACTCCTCCCAAT[tcg]GTCGCTCAAGCTGATTATGCAGACTATTATTTCGTGTCACTAAGAGCGAACATA
TGGCACTGCTACTCCTCCCAATCCGGTCGCTCAAGCTGATTATGCAGACTATTATTTCGTGTCACTAAGAGCGAACATA
TGGTTGATCTTAAAGAGAATTTAAACGCATTTGTGAGAAACAGCGATAAAGAAACGATATACCTAGCCCTCACCGAAGAC
TATCTGCAAGAGAACCCAACAATGTGTGAGTTCATGGCTCAAATCCTTAAACGCTCGACAAGACTCAGTGGTCACCGGCGT
CCCAATGCTTGGCAAAGAACGCAGTCAAGCAGCCATTGATGAATGGGACTACCAAATCCAAGATCACCACCTCATCT
TCTGCACCACGCTGGCGTTGACACAGGATGTGCCGCCGGATGCTCTCCGAGATCACTGCT[tg]TATTCCATGACTGAGAACCACCTTGACTCAC
CGCTATATGTTGTACACAGGATGTGCCGCCGGATGCTCTCCGAGATCACTGCTGTTATTCCATGACTGAGAACCACCTTGACTCAC
GGGCTCACGAGTCCTTATCGTCTCCGAGATCACTGCTGTATTCCATGACTGAGAACCACCTTGACTCAC
TCGTCGCTCAAGCTTTATTCGGAGGAGCTTGAGGACTCATTGTGGGTTCAGCGCCATTCAGCGCAATGAAGTTACACTTGAGAGAGGGAGG
ATATTCGAGATCGTGTCAATCGTCAGTTGCATAGAGATGTCAAAACTTCAAACAATACCCTTTTTCTGGAAGGAAGAGGGAGAGAACATAGCGGAGAACATAGGGGAGAAAGCGTTGTCTC
GTTGACGTTTCAGTTGCATAGAGATGTCAGTTGGAACTGAATGTGTGCAAAGACACACTGGTGTTATGGTGCAGCCATGGTCAGGTGAGCGA
CACTAGGGATAACCTTAAGGAAGATAAGTTAAGGGCTAGCAGGCATGTTAGTGAATACGGAAACCTGATTAGCGCTTGTGT
GTTGTTCATCATTGACGAGGTGAGGAAGAGATCTATGGCGGAAGGAAGAGTACAACCGGTGAAGGTTTGGATTGCGGTG
TTTGTTTGGATTTGGACTCGGTTGGACTCTGTTGTTCTTCCGTAGCGTCGTTACTCTGCCGTTGCCAAT
GGAAACTGA
```

FIG. 12 (continued)

> 2-PS variant= 35 Substitutions= 2: (C 35S) (L202M)
ATGGGATCTTACTCATCATCGATGATGTGAGGTGATTCGTGAGGCCGGACGGGCACAAGGTTTAGCCACGATTCTTGCCAT
TGGCACTGCTACTCCTCCCAATtcgGTCGCTCAAGCTGATTATGCAGACTATATTTTCGTGTCACTAAGAGCGAACATA
TGGTTGATCTTAAAGAGAACCAACAATTTAAACGCATTTGTGAGAAAACAGCGATAAAGAAACGCTCACCGAAGAC
TATCTCGAAGAACCAACAATGTGTGAGTTCATGGCTCCATCCTTAAACGCTCGACAGAACCTAGTGGTCACCGGCGT
CCCAATGCTTGGCAAAGAAGCCGCAGTCAAGACCGTTGACATGCCGGTGCTGACTATCAACTCGTCAAATCCTTGGTCTCTCCCCTTCAGTCAAA
TCTGCACCACCGCTGCCGTTGACACAGGATGTGCCGCGGTTGACATGCCGGTGCTGACTATCAACTCGTCAAATCCTTGGTCTCTCCCCTTGAAAACAACAA
CGCTATATGTTGTACCAACAGGATGTGCTCCGAGATCACTGCTATGGACCAAGACCCAATGAGAACCACCTTGACTCAC
GGGCTCACGAGTCCCTTATCGTCTGCTCCGAGATCACTGCTATGgtgTTCCATGGGGTTGCCGTTGGGCCGTAGAACGGCCA
TCGTCGCTCAAGCTTTATTCGGAACGGCAGTCCATTGTGGGTCGCTGGAGACACTGCTACTTGGCCGTAGAACGGCCA
ATATTCGAGATCGTGTCAACTGCATCAAACAATCTTGCCGGACACTGAAGTTACACTTGAGAGAGGAGG
GTTGACGTTTCAGTTGCATAGATAGAAGATGTCAACCCTTGATGGTCGCAAAGAACATAGAGAACGCAGCGCCATATTGGACCAGGTGGAGCGA
CACTAGGGGATAACCTTAAGGAAGAGATAAGTTAAGGCGAAGATCTATGGCGGAAGAGTACAACCGGTGAATACGGCCATATTGGACCAGGTGGAGCGA
AAACTAAAACCTTAAGGAAGAGATAAGTTAAGGCGAAGATCTATGGCGGAAGAGTACAACCGGTGAATACGGCCGAAGGTTTTGATTGCGGTG
TTTGTTCATCATTGACGGGTATGACTGTTGAGACTGTTCTTGTTCTTCGTAGCGTCCGCCGTTACTCCGCTGCTGCCGGTTGCCAAT
GGAAACTGA > 2-PS variant= 36 Substitutions= 4: (C 35S) (L202G) (M259L) (L261N)
ATGGGATCTTACTCATCATCGATGATGTGAGGTGATTCGTGAGGCCGGACGGGCACAAGGTTTAGCCACGATTCTTGCCAT
TGGCACTGCTACTCCTCCCAATtccGTCGCTCAAGCTGATTATGCAGACTATATTTTCGTGTCACTAAGAGCGAACATA
TGGTTGATCTTAAAGAGAACCAACAATTTAAACGCATTTGTGAGAAAACAGCGATAAAGAAACGCTCACCGAAGAC
TATCTCGAAGAACCAACAATGTGTGAGTTCATGGCTCCATCCTTAAACGCTCGACAGACCTAGTGGTCACCGGCGT
CCCAATGCTTGGCAAAGAAGCCGCAGTCAAGGCCGTACTACCAAGATCAAAATCCAAGACCACCTCATCT FIG. 12 (continued)

```
TCTGCACCACCGGCTGGCGTTGACATGCCCGGTGCTGACTATCAACTCGTCAAACTCCTTGGTCTCTCCCCTTCAGTCAAA
CGCTATATGTTGTACCAACAGGGATGTGCCGCCGGATCACTCGTCTCCGAGATCACTCGTGCTATGgaTTCCATGGACCCCCAATGAGAACCACCTTGACTCAC
GGGCTCACGAGTCCTTAGCTTTATTCGGACGGACTGCAGCACTCATTGTCCGGACACTCATTGGGTTCAGGCCGTAGAACGGCCA
TCGTCGCTCAAGCTTTATTCGGACGGACTGCAGCACTCATTGTCCGGACACTGCCGGACACTTGCCGGACACTGCTG
ATATTCGAGATCGTGTCAACTGATCAAACAATCTTGCCGGACAAGAAGCAcTGaaCACTTGAGAGAGGAGG
GTTGACGTTCAGTGCATAGAGATGTACCCTTGATGGTGCAAAGATGTGCACCAGGTGGTGCGAGAACGCAGCCATATGGGAAGCGTTGTCTC
CACTAGGGATAACTGATTGGAACTCAGTTTTCTGGGAACTTAAGGGCTGGTGCGAATCTAGTAATACGAACCCGGTGAAGGCCAGTGGACCGA
AAACTAAACCTTAAGGATAATAAGTTAAGGCTGAAGAGAATCTATGCGGAAGGAAGAGTACAACCGGTGAAGGTTTGATTGCGGTG
GTTGTTCATCATTGACGAGGTGAGAGACTGTGAGACTGTTGAGACGGGTATGACCGGGTATGACTGTTGAGACGTCCGCGTTACTGCTGCGGTTGCCAAT
TTTGTTTGGATTGGACCGGGTATGACTGTTGAGACGTCCGCGTTACTGCTGCGGTTGCCAAT
GGAAACTGA

> 2-PS variant= 37 Substitutions= 9:      (C 35S)     (C 65S)     (C 89S)     (C195S)     (L202G)
(M259L)   (L261N)   (C346A)    (C372S)
ATGGGATCTTACTCATCCGATGATGTGGAGGTGATTCGTGAGGCGATTAGCCACAAGGTTTAGCCACGATTCTTGCCAT
TGGCACTGCTACTCCTCCCAATtcgGTCGCTCAAGCTGATTATGCAGATCTGATTCGTGTCACTAAGAGCGAACATA
TGGTTGATCTTAAAGAGAAGAACCCAAGAAATTTAAACGCATTtctGAGAAAACAGCAGCGATAACGATACCCTCACCGAAGAC
TATCTGCAAGAGAACCAAGAACCCAACAATGtctGAGTTCATGGACTCCATCTTAAACGCTCGACAAGACTAGTGGTCACCGGCGT
CCCAATGCTTGGCGAAGAACCCGAGTCAGTGCCGCCCGGTGACTATCAACTCGTCCAAAATCCAAGATCACCACCTCATCT
TCTGCACCACCGGCTGGCGTTGACATGCCCGGTGCTGACTATCAACTCGTCCTTGGTCTCTCCCTTGTCTCTCCCCTTCAGTCAAA
CGCTATATGTTGTACCAACAGGGATGTGCCGCCGGATCCTCCGGCCAAGGACCCTTGCTGAACACCACCTTGACTCAC
GGGCTCACGAGTCCTTAGCTTTATTCGGACGGACTGCAGCACTCATTGTCCGGACACTGCCGGACACTGAACGGCCA
TCGTCGCTCAAGCTTTATTCGGACGGACTGCAGCACTCATTGTCCGGACACTGCCGGACACTTGGCCGTAGAACGGCCA
ATATTCGAGATCGTGTCAACTGATCAAACAATCTTGCCGGACAAGAAGCAcTGaaCACTTGAGAGAGGAGG
```

FIG. 12 (continued)

GTTGACGTTTCAGTTGCATAGAGATGTACCCTTGATGGTCGCAAAGAACATAGAGAAGCGAGCGGAGAAAGCGTTGTCTC
CACTAGGGATAACTGATTGGAACTCAGTTTCTGAAGTCCACCCAGTGGTCGATGGTGCGAGCCATATTGGACCAGTGGAGCGA
AAACTAAACCTTAAGGAGAAGATAAGTTAAGGCCATGTGCTTAGTGCATACGGAAACCTGATTAGCGCTgctgt
GTTGTTCATCATTGACGAGGTGAGGAAGAGATCTATGGCGAAGGAGTACAACCGTTGAAGGTTTGGATtcGgGTG
TTTTGTTTGGATTTGGACCGGTATGACTGTTGTTCTTCGTAGCGTTCCGCGTTACTGCTGCGGTTGCCAAT
GGAAACTGA > 2-PS variant= 38 Substitutions= 2: (C 35S) (L202G)
ATGGGATCTTACTCATCCGATGATGTGAGGTGATTCGTGAGGCCGGACAAGTTTAGCCACGATTCTTGCCAT
TGGCACTGCTACTCCCTCCCCAATtcgGTCGCTCAAGCTGATTATGCAGACTATTATTTTCGTGTCACAAGAGCGAACATA
TGGTTGATCTTAAAGAGAATCAGCATTGTGAGAAAACAGCGATAAAGAAACGATACCTAGCCCTCACCGAAGAC
TATCTGCAAGAGAACCAACAATGTGCTCAGTTGTGAGTTCTGAGTTCTGACAAGCTCAGTAGCACCCCCTCATCT
CCCAATGCTTGGCAAAGAACCGCAGTCAAGGCGACTCAAGGGGACTACTCGTCAAAATCCAAGATCACCACCCCTTCATCT
TCTGCACCACGGCTGGCGTTGACAACAGGATGTGCCGCGGGGATGTCCTCCCGGCTAGCCAAGGACCTTGCTGAAAACAACAA
CGCTATATGTTGTACCAACAGAGTCTCGTGCTCCCGAGATCACTGCTATCGgaTTCCATGACCCATTGTGGGGTTCAGGCCCTCACTTGTGGGGTTCAGG
GGGCTCACGAGTCCTTATCGTCGCTCAAGCTTTATTCGGAGAACGGATCAAACAATCTTGCCGACACTTGAGAACCACCTTGACTCAC
TCGTCGCTCAAGCTTTATTCGGAGAACGGATCAAACAATCTTGCCGACACTTGAGAACCACCTTGACTCAC
ATATTCGAGACGTTCAGTCGTCAGTTGCATAGAGATGTACCCTTGTTTCTGGAACATAGAGAACCAGCGTGCAGCTTGTCTC
GTTGACGTTTCAGTCGTTGCATAGAGATGTACCCTTGTTTCTGGAACATAGAGAACCAGCGTGCAGCTTGTCTC
CACTAGGGATAAACCTGATTGGCATAGAGATAACTGAACTCAGTTTTCTGGAACATACGGAAACCTGATTAGCGCTTGTGT
AAACTAAACCTTAAGGAGAAGATAAGTTAAGGGCTAGCAGCCATGTGAATGCGAAACCGTTGATTAGCGCTTGTGT
GTTGTTCATCATTGACGAGGTGAGGAAGAGATCTATGGGGAAGAAGTACAACCGTTGAAGGTTTGATTGCGGTG
TTTTGTTTGGATTTGGACCGGTATGACTGTTGTTCTTCGTAGCGTTCCGCGTTACTGCTGCGGTTGCCAAT
GGAAACTGA

FIG. 12 (continued)

> 2-PS variant= 39 Substitutions= 3: (C 35S) (M259L) (L261N)
ATGGGATCTTACTCATCGATGATGTGAGGTGATTCGTGAGGCCGACGGGCACAAGGTTTAGCCACGATTCTTGCCAT
TGGCACTGCTACTCCTCCCAATtcgGTCGCTCAAGCTGATTATGCAGACTATTATTTTCGTGTCACTAAGAGGAACATA
TGGTTGATCTTAAAGAGAACCAACAATTAAACGCTCCATCCTTAAACGATCAAGACCTAGTGGTCACGGCGT
TATCTGCAAGAGAACCCAACAATGTGTGAGTTCATGGCTCCATCCTTAAACGATCAAGACCTAGTGGTCACGGCGT
CCCAATGCTTGGCAAGAGCCCGGTTCAACAGGATGCCGGTTGACTATCGTCAAACTCGTCAAACTCCTTGGTCTCTCCCCTTCAGTCAAA
TCTGCACCACCCGCTGGTTACCAACGGATGCTGCTCCGAGATCACTGCTATCTTATTCGTCAAACTCCTTGGTCTCTCCCCTTCAGTCAAA
CGGCTCACGAGTCCTTATCGTCTGCTCCGAGATCACTGCTATCTTATTCAGGACCCAATGTCAGGGCCCGGTTAAGAACCTTGACTCAC
TCGTCGCTCAAGCTTTATTCGGACACTGACGCCCCTCACTTGGCCGTAGAACGGCCA
ATATTCGAGATCGTGTCAACTGATCAAACAATCTTGCCGGACACTGAAGGCACTTGAGAAGGCACTTGAGAGAGAGGAGG
GTTGACGTTTCAGTTGCATAGAGATGTACCCCTTGATGGTCGCAAAGAACGAGACGCGGAGAAAGCGTTGTCTC
CACTAGGATAACTGATTGGAACTCAGTTTCTGGATGGTGCAGCCATATTGGACCAGGTGGAGCGA
AAACTAAACCTTAAGGAAGATAAGTTAAGGGCATATGGCGAAGAGAGTACAACCGGTGAAGGTTTGAAGGTTTGGATTGCGGTG
GTTGTTCATCATTGACGAGGTGAGGAGGTGAGGAAGAGATCTATGGACTCTTGAGACTGTTGTTCTTCGTAGCGTCCGGTTACTGCTGCGGTTGCCAAT
TTTTGTTTGGATTTGACTGTTGAGACTGTTGAGACTGTTGAGACTGTTGAGACTGA
GGAAACTGA > 2-PS variant= 40 Substitutions= 7: (C 35S) (C 65S) (C 89S) (C195S)
(L202G) (C346A) (C372S)
ATGGGATCTTACTCATCGATGATGTGAGGTGATTCGTGAGGCCGACGGGCACAAGGTTTAGCCACGATTCTTGCCAT
TGGCACTGCTACTCCTCCCAATtcgGTCGCTCAAGCTGATTATGCAGACTATTATTTTCGTGTCACTAAGAGGAACATA
TGGTTGATCTTAAAGAGAACCAACAATTAAACGCAATtctGAGAAAACAGCGATAAAGAAACGATACCTAGCCCTCACCGAAGAC
TATCTGCAAGAGAACCCAACAATGTtctGAGTTCATGGCTCCATCCTTAAACGATCAAGACCTAGTGGTCACGGCGT

FIG. 12 (continued)

```
CCCAATGCTTGGCAAAGAAGCCCAGTCAAGGCCCATTGATGAATGGGGACTACCAAAATCCAAGATCACCCCTCATCT
TCTGCCACCGCTGGCGTTGACATGCCCGTTGACTGACTATCAACTCGTCAAACTCCTTGGTCTCTCCCTTCAGTCAAA
CGCTATATGTTGTACCAACAGGATGTGCCGCGGCACACTGTCCGCAAGACCTTAGCCACACCTTGCTGAAACAACAA
GGGCTCACGAGTCCCTTATCGTGtcTCCGAGATCACTGCTATGggaTTCCATGGACCAATGAGAACCACCTTGACTCAC
TCGTCGCTCAAGCTTTATTCGAGAGCTGTTCAGCCTCATTGTGGGTTGAGAACACTGAAGTTACACTTGGCCGTAGAACGGCCA
ATATTCGAGATCGTGTCAACTGTCAAATCAAACATAGAAACAATCTTGCCGACACTGAAGAAGTACACCCTGAGAGAGGAG
GTTGACGTTTCAGTTGCATAGAATGTACCCCTGTTTTCTGGAACTCAGTTAAGGGCTAGAACTAAGAGAAGCGTGTCTC
CACTAGGGATAAACCTTAAGGAAGATAAGTTGGAACTCAGTTAAGGGCTAGAAGATCTATGGCGGAAGAGTACAACCGTGGTGGAGCGA
AAACTAAACTGATCATTGACGAGGTGAGAGAATGAGAGATCTATGGCGGAAGAGTACAACCGTGTTCTTGTTCCTAGCGTTCTGCGTTGCCAAT
GTTGTTCATCATTGACGAGGTGAGAGAATGACCGGGTATGATGTTGAGACTGTTGTTCTTGTTCCTAGCGTTCTGCGTTGCCAAT
TTTTGTTGGATTTGGAATTGGAATCAATGCTATTTTCGTCCTATGCTGACGCGTTAGCGCTtcGGTTG
GGAAACTGA
```

> 2-PS variant= 41 Substitutions= 1:     (C 35S)

```
ATGGGATCTTACTCATCCATCGATGATGATCGATGGAGGTGATTCGTGAGGCCGAACAAGGTTTAGCCACGATTCTTGCCAT
TGGCACTGCTACTCCTCCCAATtcgGTCGCTCAAGCTGATTATGCAGACTGATTATTTCGTGTCACTAAGAGCGAACATA
TGGTTGATCTTAAAGAGAACAGCGATAAAGAAACAGCGATAAACGCTTAAACGATACCCTCACCGAAGAC
TATCTGCAAGAGTCCCTTATCGTGTGAGTTCATGGCCATTGATGAATCAAGCTACCAAAATCCTTGGTCTCTCCCTTCAGTCAAA
CCCAAGCTTGGCAAAGAAGCCCAGTCAAGGCCCATTGATGACTACCAAGACCTCGTAAACTCCTTCCCCTTCAGTCAAA
TCTGCCACCGCTGGCGTTGACATGTCCCGTGACTGACTATCAACTCGTCAAACTCCTTGGTCTCTCCCTTCAGTCAAA
CGCTATATGTTGTACCAACAGGATGTGCCGCGGCACACTGCTATCTTTATTCCATGGGTTCAGCGCTCACTGAACCTTAC
TCGTCGCTCAAGCTTTATTCGAGACGGACACTCATTGCAGCACTCATTGTGGGTTGAGCACGCTAGGCCGTAGAACGGCCA
ATATTCGAGATCGTCAACTGATCAAACAATCTTGCCGACACTGAAGTTACACTTGAGAGAGG
```

FIG. 12 (continued)

GTTGACGTTTCAGTTGCATAGAGATGTACCCTTGATGGTGCAAAGAACATAGAGAACGCAGCGGAGAAAGCGTTGTCTC
CACTAGGATAACTGATTGGAACTCAGTTTTCTGGATGGTGCACCCAGGCCATATTGGAGCCAGGTGAGCGA
AAACTAAACCTTAAGGAAGATAAGTTAAGGCATGCTAGCAGGCATGTGCTTAGTAGAGAAACTGATTAGCGCTTGTGT
GTTGTTCATCATTGACGAGGTGAGGAAGAGATCTATGGCGAAGAGTACACCGGTGAAGTTTGGATTGCGGTG
TTTTGTTTGGATTTGGACCGGGTATGACTGTTGTTCTTCGTTACTGCGTTCCGCGTTACTGCTGCGGTTGCCAAT
GGAAACTGA

> 2-PS variant= 42 Substitutions=  4:   (C 35S)   (T137L)   (L202F)   (L268M)
ATGGGATCTTACTGCTCATCCGATGATGTCGATGATCGTGAGGCGTGATTCGTGAGGCCACAAGGTTTAGCCACGATTCTTGCCAT
TGGCACTGCTACTGCCTCCCCAAT[tc]GTCGCTCAAGCTGATTATGCAGAGACTATTATTTTCGTGTCACTAAGAGGAACATA
TGGTTGATCTTAAAGAGAACAGCCCATTTGTGAGAAACAGCGATAAAGAAAACGATACCTAGCCCTCACCGAAGAC
TATCTGCAAGAGAACCCAACAGTGTGTAGCCTCCATCCTTAAACGCTCGACAAAATCCAAGATCACCCACCTCATCT
CCCAATGCTTGGCAAAGAAGCCGCAGTCAAGGCGACTACCAAACTCGTCATCAACTCCTTGGTCTCTCCCTTCAGTCAAA
TCTGCACC[ctg]GCTGGCGTTGACAACAGGATGTGCCCCGGCCACAGTCCTCCGGCTAGCCAAGGACCTTGCTGAAAACAACAA
CGCTATATGTTGTACAACAGTCCTTATCGTCTGCTCCGAGATCACTGCTATC[ttc]TTCCATGGAACACCTCACTCAC
GGGCTCACGAGTCCTTAAGTTTATTCGGAGACGGAGCTGCACTGCAGCACTGCAGCCTCCCACTTGGCCGTAGAACGGCCA
TCGTCGCTCAAGCTTTAAGCTTCAGTTTCGGAACTACGAAGGCAATGAAGTTACACTTGACTTGAGAGAGGAGG
ATATTCGAGATCGTCAACTGCATAGAGATGTACCCCTTGATGGTCGCAAAGAACGCAGCGGAGAAAGCGTTGTCTC
G[atg]ACGTTTCAGTTGCATAGAGATGTTGGAACTCAGTTTTCTGGATGGTGCACCCAGGTGCTGGAGAGCGA
CACTAGGGATAACTGATTGGAACTCAGTTTTCTGGATGGTGCACCCAGGTGGTGGAGAGCGA
AAACTAAACCTTAAGGAAGATAAGTTAAGGGCATGCTAGCAGGCATGTGAATAACCCGATTAGCGCTTGTGT
GTTGTTCATCATTGACGAGGTGAGGAAGAGATCTATGGCGAAGGAAGAGTACAACCGGTGAAGTTTGGATTGCGGTG
TTTTGTTTGGATTTGGACCGGGTATGACTGTTGTTCTTCGTTACTGCGTTCCGCGTTACTGCTGCGGTTGCCAAT
GGAAACTGA

FIG. 12 (continued)

> 2-PS variant= 43 Substitutions= 5: (C 35S) (T137M) (L202F) (L268M) (I343F)
ATGGGATCTTACTCATCATCCGATGATGTGGAGGTGATTCGTGAGGCCGACGGGCACAAGGTTTAGCCACGATTCTTGCCAT
TGGCACTGCTACTCCTCCCCAAT[tcg]GTCGCTCAAGCTGATTATGCAGACTGATTATTTCGTGTCACTAAGAGCGAACATA
TGGTTGATCTGCTACTTAAAGAGAACCCAACATTGTGAGTTCATGCGATCATTGTGAGAAAACAGCGATAAAGAAACGATCAAGAC
TATCTGCAAGAGAACCCAACATGTGTAGCTTCATGCGTGTAGTTCATGGCTCAGGTCCATCCTTAAACGCTCGACAAGACCTAGTGGTCACCGGCGT
CCCAATGCTTGGCAAAGAACCGCAGTCATGCCCGTGACATGAATCAACTCGTCAAACTCCTTGGCTCTCCCCTTCAGTCAAA
TCTGCACC[atg]GCTGGCGTTGACATGGAACAGGATGTCGTCTGCTCAACAGAGCCGCACAGTCCTCCGGCTCAAGGACCCTTGCTGAAAACAACAA
CGCTATATATGTTGTACCAAGAGTCCTTATCGTCTGCTCCGAGATCACTGTGCTAT[ttc]TCCATGCCAAGAACCACCTTGACTCAC
GGGCTCGCTCAAGCTTTATTCGGAGACGAGCTGCACTCCATTGTGCCGGACACTAGAAGGCAATGAGAACGCAGCCCCCTCACTTGCCGTAGAACGGCCA
TCGTGCGCTCAAGCTTTATTCGGAGACGAGCTGCACTCCATTGTGCCGGACACTAGAAGGCAATGAGAACGCAGCCCGGGAGAAAAGCGTTGTCTC
ATATTCGAGATCGTGTCAATAGAGATGTACCCTGATGGTTCTCGGAACTCAGTTTCTTCAGTTGCATAGAGATGTACCCTGATGGTTCTCGGAACTCAGTTTCTTCAGT[Gat]ACGTTTCAGTTGCATAGAGATGTACCCTGATGGTTCTCGGAACTCAGTTTCTTCA
AAACTAAACTTAAGGAAGATAAGTTAAGGGCTAGCAGGCATGTGCTTAGTGAAGGAAGATACAACCGTGAAGGTTTGGATTGCGGTG
GTGTTTGTTTGTTGATTTGGACCGGGTATGACTGTTGAGACTGTTGTTCTTCGTAGCGTCCGCGTTACTGCTGCGGTTGCCAAT
TTTGTTGTTGATTTGGACCGGGTATGACTGTTGAGACTGTTGTTCTTCGTAGCGTCCGCGTTACTGCTGCGGTTGCCAAT
GGAAACTGA > 2-PS variant= 44 Substitutions= 4: (C 35S) (L202F) (L268M) (I343F)
ATGGGATCTTACTCATCATCCGATGATGTGGAGGTGATTCGTGAGGCCGACGGGCACAAGGTTTAGCCACGATTCTTGCCAT
TGGCACTGCTACTCCTCCCCAAT[cg]GTCGCTCAAGCTGATTATGCAGACTGATTATTTCGTGTCACTAAGAGCGAACATA
TGGTTGATCTTAAAGAGAACCCAACATTGTGAGTTCATGCGATAAAGAAACAGCGATAAAGAAACGATCAAGAC
TATCTGCAAGAGAACCCAACATGTGAGTTCATGCGTTCATGGCTGCTGACATTCTTAAACGCTCGACAAGACCTAGTGGTCACCGGCGT FIG. 12 (continued)

```
CCCAATGCTTGGCAAAGAAGCGCAGTCAAGGCCATTGATGAATGGGACTACCAAATCCAAGATCACCCACCTCATCT
TCTGCACCACCGCTGGCGTTGACATGCCGGTTGACTATCAACTCGTCACTTCCTTGGTCTCTCCCCTTCAGTCAAA
CGCTATATGTTGTACAACAGGATGTGCCGCCGGCACAGTCCCCGGCTAGCCACCTTGCTGAAAACAACAA
GGGCTCACGAGTCCTTATCGTCTGCTCCGAGATCAACGACCACTGCTATCTtcTTCCATGGAACATGAGAACCTTGACTCAC
TCGTCGCTCAAGCTTTATTCGGAGACGGAGCTGCAGCCACTGTGGGTTCAGGCCCTCACTTGGCCGTAGAGAGGCCA
ATATTCGAGATCGTGTCAACTGATCAAACAATTCTGCCGGACACTGAAGTAAGTTACACTTGAGAGAAGCGTTGTCTC
GatgACGTTTCAGTTGCATAGAGATGTACCCTTGATGGTCGCAAAGAACATAGAGGTCGAGCCATATTGCACCGAGCGA
CACTAGGGATAAACCTTAAGGAACTCAGTTGGAACTCAGTTTCTGAAGGCTAGCCAGGCATGTGAATACGAAAACCTGtttAGCGCTTGTGT
AAACTAAACCTTAAGGAGATAAGTTAAGGCGTGAGGATCTATGCGAAGGACATGGTTGCAACCGGTGAAGGTTTGATTGCCGTG
GTTGTTCATCATTGGATTGGACCGGGTATGACTGTTGTTCTTGTTCCGTAGCGTCCGCGTTACTGCTGCCGGTTGCCAAT
TTTTGTTTGGATTTGGATTTGGACCGGGTATGACTGTTGTTCTTGTTCCGTAGCGTCCGCGTTACTGCTGCCGGTTGCCAAT
GGAAACTGA > 2-PS variant= 45 Substitutions= 2:      (C 35S)      (C372S)
ATGGGATCTTACTCATCCGATGATGTGGAGGTCGATTCGTGAGGCCGACGGCACAAGGTTTAGCCACAAGGTTTAGCCACGATTCTTGCCAT
TGGCACTGCTACTCCCTCCCAATtcgGTCGCTCAAGCTGATTATGCAGACTACTATTATTTCGTGTCACTAAGAGCGAACACATA
TGGTTGATCTTAAAGAGAACCAGCATTGTGAGAACAGCGATAAAGAAACGATACCCTAGCCCCTCACCGAAGAC
TATCTGCAAGACCAACAGTGTGTAAGCGCTCCATCCTTAAACGCTCCTTAAACGCTCCTTAAACAGCGATAAAGAAACGATACCTAGTGGTCACCGGCGT
CCCAATGCTTGGCAAAGAAGCCGCAGTCAAGGCCATTGATGAATGGGACTATCAACTCCTTGGTCTCTCCCCTTCAGTCAAA
TCTGCACCACGCTGGCGTTGTACCAACAGGGATGTCTCGCCGGAGATCACTGCTATCTTATTCCATGGACCTTGAAAACAACAA
CGGCTCACGAGTCCTATCGTCTGCTCCGAGATCAACGACCACTGCTATCTTATTCCATGGGTTCAGGCCCTGAGAACGGCCA
TCGTCGCTCAAGCTTTATTCGGAGACGGAGCTGCAGCCACTGTGGGTTCAGGCCCTCACTTGGCCGTAGAACGGCCA
ATATTCGAGATCGTGTCAACTGATCAAACAATCTTGCCGGACACTGAAGTTACACTTGAGAGAGGAGG
```

FIG. 12 (continued)

```
GTTGAGCGTTTCAGTTGCATAGAGATGTACCCTTGATGGTGCAAAGAACATAGAGAACGCAGGGAGAAAGCGTTGTCTC
CACTAGGATAACTGATTGGAACTCAGTTTTCTGGATGGTGCACCCAGGTGGTCGAGCCGCATATTGGACCAGGTGGAGCGA
AAACTAAACCTTAAGGAAGATAAGTTAAGGGCTAGCAGGCATGTGCTTAGTGCTTGAAATACGGAAACCTGATTAGCGCTTGTGT
GTTGTTCATCATTGACGAGAGTGAGGAAGAGATCTATGGCGAAGGAGTACAACCGGTGAAGGTTTGGAT[tcg]GGTG
TTTTGTTTGGATTTGGACCGGGTATGACTGTTGAGACTGTTCTTGTTCTTGCCGTTCCGCGTTACTGCTGCCGGTTGCCAAT
GGAAACTGA > 2-PS variant= 46 Substitutions=  2:     (C 35S)   (C372A)
ATGGGATCTGCTACTCTCATCCGATGATGTGGAGGTGATTCGTGAGGCCGGACGGTGATTGAGCCACAAGGTTTAGCCACGATTCTTGCCAT
TGGCACTGCTACTCCTCCCCAAT[tcg]GTCGCTCAAGCTGATTATGCAGACTATTATTTTCGTGTCACTAAGAGCGAACATA
TGGTTGATCTTAAAGAGAATTTAAACGCATTGTGAGAAACAGCGATAAAGAAACGCTCACCGGATACCCTCACCGAAGAC
TATCTGCAAATGCTTGGCAAGAGAAGCGCAGTCAAGGCACTACCTCAAACTCGTCAAATCCTTGGTCTCTCCCCTCAGTCAAA
CCCAATGCTTGGCAAAGAGAAGCGCAGTCAAGGCACTACCCTCAAACTCGTCAAATCCTTGGTCTCTCCCCTCAGTCAAA
TCTGCACCACGCTGGCGTTGACAACAGGGATGTGCCGCCCGAGATCACTGCTATCGTCTGCCGAGACCACCTCCGACCTCAC
CGCTATATGTTGTACCAAGCTCCTTATCGTTATTCGGAGACGGAGCTGCAGCACTGTCAGGCCCTCACTGTGGGTTCAGGCCCGTAGAACGGCCA
GGGCTCACGAGTCCTTAGCTTTATTCGGAGACGGAGCTGCAGCACTGTCAGGCCCTCACTGTGGGTTCAGGCCCGTAGAACGGCCA
TCGTCGCTCAAGCTTATTCGGAGACGGAGCTGCAGCACTGTCAGGCCCTCACTGTGGGTTCAGGCCCGTAGAACGGCCA
ATATTCGAGATCGTCAGTTGCATAGAGATGTACCCTTGATGGTCGCAAAGAACATAGAGAACGCAGCGGTGGAGAAAGCGTTGTCTC
GTTGACGTTTCAGTTGCATAGAGATGTACCCTTGATGGTCGCAAAGAACATAGAGAACGCAGCGGTGGAGAAAGCGTTGTCTC
CACTAGGATAACTGATTGGAACTCAGTTTTCTGGATGGTGCACCCAGGTGGTCGAGCCGCATATTGGACCAGGTGGAGCGA
AAACTAAACCTTAAGGAAGATAAGTTAAGGGCTAGCAGGCATGTGCTTAGTGAATACGGAAACCTGATTAGCGCTTGTGT
GTTGTTCATCATTGACGAGAGTGAGGAAGAGATCTATGGCGAAGGAGTACAACCGGTGAAGGTTTGGAT[gcg]GGTG
TTTTGTTTGGATTTGGACCGGGTATGACTGTTGTTCTTGTTCTTGCCGTTACTGCTGCCGGTTGCCAAT
GGAAACTGA
```

FIG. 12 (continued)

> 2-PS variant= 47 Substitutions= 2:   (C 35S)   (C346S)
ATGGGATCTTACTCATCGATGATGTGAGGTGATTCGTGAGGCCGGCACAAGGTTTAGCCACGATTCTTGCCAT
TGGCACTGCTACTCCTCCCAATtcgGTCGCTCAAGCTGATTATGCAGACTATTATTTCGTGTCACTAAGAGCGAACATA
TGGTTGATCTTAAAGAGAACCAACATGTTAAACGCATTTGTGAGAAAACAGAAGAATACCTAGCGCCCTCACCGAAGAC
TATCTGCAAGACAAGCCCAAAGAAGCCATCCTTAAACGCTCCATCCTGAGTTCATGAGTCTGACAAGACCTAGTGGTCACCGGCGT
CCCAATGCTTGGCAAGAGAACCAAAGAAGCCGTTGAGTGTGAGTTCATGAGTTCAAGGCCTAGTCACAGACCTAGTGGTCACCCTCATCT
TCTGCACCACCGCTGGCGTTGACATGTCCCGGTGCTGACTATCACTCGTCAAACTCGTTGGTCTCTCCCCTTCAGTCAAA
CGCTATATGTTGTACAACAGGATGTGCTCTGCTGCCGCGATGCACTCACTGCTATCGTCTCCGAGATCAACTGAGAACAACAA
GGGCTCACGAGTCCTTATCGTCTCCGAGATCAACTGCTATCACTCGTCTCCGAGATGAGAACCACCTTGACTCAC
TCGTCGCTCAAGCTTGTTATTCGGAACGGAGCTGCAAAACAATCTTGCCGGAACGGCAATGAGAAGGCAATGAGAAGCGCCAGTGAACGGCCA
ATATTCGAGATCGTGTCAACTGAGACAATCTTGCCGGAACGGCAATGAGAAGGCAATAGAGAACATAGAAGTTACACTTGAGAGAAGCGTTGTCTC
GTTGACGTTTCAGTTCAGTTGCATAGAGAGATGACTCAGTTGGAACTAAGTTAAAGGCAGGCCAGGGAAACCTGGTGAATACGGAAACCTGAACGGCGA
CACTAGGGATAACCTTAAGGAGAAGATAAGTTAAAGGCAGGCCAGGGAATGCCGGTGAAGGTTTGATTGCGGTG
AAACTAAACTGATCATTGACGAGGTGAGGAAGATCTATGGCGGGAAGAAGAGTACAACCGGTGAAGGTTTGATTGCGGTG
GTTGTTCATCATTGACGAGGTGAGGAAGATCTATGGCGGGAAGAAGAGTACAACCGGTGAAGGTTTGATTGCGGTG
TTTGTTTGGATTTGATTTGGATTTGAGACTGTTGAGACTGTGAGATGACTGTGTTGTCTTCTTCCGTAGCGTCCGCGTTACTGCTGCGCGGTTGCCAAT
GGAAACTGA > 2-PS variant= 48 Substitutions= 2:   (C 35S)   (C346A)
ATGGGATCTTACTCATCGATGATGTGAGGTGATTCGTGAGGCCGGCACAAGGTTTAGCCACGATTCTTGCCAT
TGGCACTGCTACTCCTCCCAATtcgGTCGCTCAAGCTGATTATGCAGACTATTATTTCGTGTCACTAAGAGCGAACATA
TGGTTGATCTTAAAGAGAACCAACATGTTAAACGCATTTGTGAGAAAACAGAAGAATACCTAGCGCCCTCACCGAAGAC
TATCTGCAAGACAAGCCCAAAGAAGCCATCCTTAAACGCTCCATCCTGAGTTCATGAGTCTGACAAGACCTAGTGGTCACCGGCGT
CCCAATGCTTGGCAAGAGAACCAAAGAAGCCGTTGAGTGTGAGTTCATGAGTTCAAGGCCTAGTCACAGACCTAGTGGTCACCCTCATCT

FIG. 12 (continued)

```
TCTGCACCACCGCTGGCGTTGACATGCCGGTGCTGACTATCAACTCCTTGGTCTCTCCCCTTCAGTCAAA
CGCTATATGTTGTACCAACAGGATGTGCCGCGGCCAAGTCCTCCGGCCAAGGACCTTGTGAAAACAACAA
GGGCTCACAGAGTCCTTATCGTCTGCTCCGAGATCACTGTCTATCTTATTCCATGAGAACCACCTTGACTCAC
TCGTCGCTCAAGCTTTATTCGGACGAGCACTGATCAAACAATCTGCCGGACACTGAAGTTACACTTGAGAACGGCCA
ATATTCGAGAGATCGTGTCAACTGATGCATAGAGATGTACCCTTGCCGCAAACAATCTGAGAACGAAGTTACACTTGAGAGAGGAGG
GTTGACGTTTCAGTGTCATTGGAACTGATTGGAAGATAACTCAGTTTCTGATTTTTCTGATGGTCGCAAAACGGGCCATATTGGACCAGGTGAGCGA
CACTAGGGATAAACCTTAAGGAAGATAAGTTAAGGCTATTGATGAATACCGGTGAATACCGGTGAAGGTTTGGATTGCGGTG
AAACTAAAACCTTAAGGAAGATAAGTTAAGGCTAGTTAAGGAAGATCTATGGCGGAAGAGTACAACCGGTGAAGGTTTGGATTGCGGTG
GTTGTTCATCATTGACGAGGTGAGGAAGATCTATGGCGGAAGAGTACAACCGGTAGCGTCCGGTTACTGCTGCCGGTTGCCAAT
TTTTGTTTGGATTTGGACCGGGTATGACTGTTGAGACTGTTGAGACTGATTACTGCAGTCGTCCGGTTACTGCTGCCGGTTGCCAAT
GGAAACTGA

>2-PS variant= 49 Substitutions=  2:   (C 35S)   (C195S)
ATGGGAGATCTTACTCATCGATGATGTGAGGTGATTCGTGAGGCCGGACGGCCAAGGTTTAGCCACGATTCTTGCCAT
TGGCACTGCTACTCCCTCCCAAT[tcg]GTCCGCTCAAGCTGATTATGCCAGACTATTATTTTCGTGTCACTAAGAGGAACATA
TGGTTGATCTTAAAGAGAATTAAACGCCATTGTGAGTTCAGGAACAGAACGATACCTCAGCCCTCGAAGAC
TATCTGCAAGAGATGTGTGAGTTCATGGCTCAAGGCCAGTTCATGATGAATCAACTCGTCAAACTCCTTGGTCTCTCCCTTCAGTCAAA
CCCAATGCTTGGCAAAGAGCCGCAGTCAAGGCCGACTACCAAATCAACCTCGTCAAACTCCTTGGTCTCTCCCTTCAGTCAAA
TCTGCACCACCGGCGTTGACATGCCGGTGCTGACTATCAACAGTCCTCCGGCCAAGGACCTTGAAAAACAACAA
CGCTATATGTTGTACCAACAGGATGTGCCGCGGCCGATGTGCCGCCGGATCACTGTCTATCTTATTCCATGAGAACCACCTTGACTCAC
GGGCTCACGAGTCCTTATCGTCG[tcc]CCGAGATCACTGTCAGCACTGCTATCTTATTGTGGGTTCAGGCGTAGAACGGCCA
TCGTCGCAAGTTTATTCGGACGAGCACTGATCAAACAATCTTGCCGGACACTGAAGTTACACTTGGCCGTAGAACGGCCA
ATATTCGAGATCGTGTCAACTGATCAAACATAGAGATGTACCCTTGATGTCGCAAAGAACATAGAACGGCCA
GTTGACGTTTCAGTTGCATAGATGTACCCTTGATGTCGCAAGAACATAGAGAACGCGCCAGCGAGGAGG
```

FIG. 12 (continued)

CACTAGGGATAACTGATTGGAACTCAGTTTTCTGGATGGTGCACCCAGGTGGTCGAGCCATATTGGACCAGGTGGAGCGA
AAACTAAACCTTAAGGAAGATAAGTTAAGGCTAGTGCTTAGTGAAACCTGAAACCTGATTAGCGCTTGTGT
GTTGTTCATCATTGACGAGGTGAGGAAGAGATCTATGGCGGAAGAGTACAACCGGTGAAGGTTTGGATTGCGGTG
TTTTGTTTGGATTTGGACCGGGTATGACTGTTCTTCGTAGCTGCCGTTACTGCGGTTGCCAAT
GGAAACTGA

> 2-PS variant= 50 Substitutions= 2; (C 35S) (C195A)
ATGGGATCTTACTGCTCATCGATGATGTGAGGTGATTCGTGAGGCCACAAGTTTAGCCACGATTCTTGCCAT
TGGCACTGCTACTCCCTCCCAATtccGTCGCTCAAGCTGATTATGCAGACTATTATTTCGTGTCACTAAGAGCGAACATA
TGGTTGATCTTAAAGAGAATTAAACGCATTGTGAGAAGCGATAAAGAAACGATAAAGAAACGATACCGAAGAC
TATCTGCAAGACAACCCAACATGTGAGTTCATGGCCAGTCAAGGCCATTGATGAATCGTCGACAAGACCTAAAAACGCTCGACAAGACCTCAGACTAGTGGTCACGGCGT
CCCAATGCTTGGCAAAGAAGCCGCAGTCAAGGCCATTGATGAATCGTCGACAAGACCTCAAAATCCAAGATCACCCTCATCT
TCTGCCACCACCGGCTGTGTACCAACAGGCATGCCGCCGGAGATCACTGCTATCTCCGGACCACTGAAACAACAA
CGCTATATGTTGTCAACAGGCATGCCGCCGGAGATCACTGCTATCTCATTGTGGGTTCAGGCCCCTCACTTGCCCGTAGAACGGCCA
GGGCTCACGAGTCCTTATCGTGccTCCGAGATCACTGCTATCTCATTGTGGGTTCAGGCCCCTCACTTGCCCGTAGAACGGCCA
TCGTCGCTCAAGCTTTATTCGGAGAACAATCAAACAATCTTGCCGGACACTGTCAAAGAACATAGAGAACGCAGCAGGTTGTCTC
ATATTCGAGATCGTCAGTTGCATAGAGATGTACCCCTTGATGGTCGCAAAGAACATAGAGAACGCAGCAGGTTGTCTC
GTTGACGTTTCAGTTGCATAGAGATGTACCCCTTGATGGTCGCAAAGAACATAGAGAACGCAGCAGGTTGTCTC
CACTAGGGATAACCTTAAGGAACTCAGTTTTCTGGATGGTCTAGTGCTTAGTGAATACGGAACCTGAAGGTTTGTGT
AAACTAAACCTTAAGGAAGATAAGTTAAGGCTAGTGCTTAGTGCTTAGTGAAGGTACAACCGGTGAAGGTTTGTGT
GTTGTTCATCATTGACGAGGTGAGGAAGAGATCTATGGCGGAAGAGTACAACCGGTGAAGGTTTGGATTGCGGTG
TTTTGTTTGGATTTGGACCGGGTATGACTGTTGTTCTTCGTAGCTGCCGTTACTGCTGCCGGTTGCCAAT
GGAAACTGA

FIG. 12 (continued)

> 2-PS variant= 51 Substitutions= 2:      (C 35S)    (C135S)
ATGGGATCTTACTCTCATCGATGATGTGAGGTGATTCGTGAGGCCGGACGGCACAAGGTTTAGCCACGATTCTTGCCAT
TGGCACTGCTACTCCTCCCAAT[tcc]GTCGCTCAAGCTGATTATGCAGACTATTATTTTCGTGTCACTAAGAGCGAACATA
TGGTTGATCTTAAAGAGAACCCAACAAATTTAAACGCATTGTGAGATACCCATCAGCCCTCACCGAAGAC
TATCTGCAAGAGAACCCAACAAATTTAAACGCATTGTGAGTTCATGGCTCCATCCTTAAACGCTCGACAAGACCTAGTGGTCACCGCGT
CCCAATGCTTGGCAAGAAGCCGCAGTTGACATGCCGGTTGACAAGCCAAGAAGCCGTTGACATATCAACTCGTCAAATCTCCTTGTCTCTCCCTTCAGTCAAA
CGCTATATGTTGTCAACAGGATGTCGCTCCCGAGATCACTGCCTTATTCCATGAACTCGTAGGCCTTATGGTTCACTCAC
GGGCTCACGAGTCCTTATTCGTCTGCCTCGAGATCACTGCTCTATTCCATGAACTCGTAGGCAATGAAGTTACACTTGAGGCCA
TCGTCGCTCAAGCTGATGCGTGTCAACTGAACAATCTTGCCGGACACTGAAGGCAATGAAGTTACACTTGAGAGAGGAGG
ATATTCGAGATCGTGTCAACTGAACAATCTTGCCGGACACTGAAGGTCGAGCCATATTGGACCAGGTGAGCGA
GTTGACGTTTCATTCAGTTGCATAGATGTACCAGTTTTCTGAACTAAGTTAAGGCGAAGATCTATGGCGGAAGAGTACAACCGTGAAGGTTTGATTAGCGCTTGTGT
CACTAGGGATAACTGATTGGAACGATGAACCTAAGGCGAAGATCTATGGCGAAGAGTACAACCGGTTGAAGGTTTGATTAGCGCTTGTGT
AAACTAAACCTTAAGCAAGATGAACCTAAGGCGAAGATCTATGGCGAAGAGTACAACCGGTCCGGCGTTACTGCTGCGGTTGCCAAT
GTTGTTCATCATTGACGAGGTGAGGAGGTATGACTGTTGAGACTTCTTCGTAGCGTCCGGCGTTACTGCTGCGGTTGCCAAT
TTTTGTTTGGATTTGAGACCGGTGAGGTATGACTGTTGAGACTTCTTCGTAGCGTCCGGCGTTACTGCTGCGGTTGCCAAT
GGAAACTGA > 2-PS variant= 52 Substitutions= 2:      (C 35S)    (C135A)
ATGGGATCTTACTCTCATCGATGATGTGAGGTGATTCGTGAGGCCGGACGGCACAAGGTTTAGCCACGATTCTTGCCAT
TGGCACTGCTACTCCTCCCAAT[tcc]GTCGCTCAAGCTGATTATGCAGACTATTATTTTCGTGTCACTAAGAGCGAACATA
TGGTTGATCTTAAAGAGAAATTTAAACAACAGCGATAAAGAACGATACCCATCAGCCCTCACCGAAGAC
TATCTGCAAGAGAACCAACAAATGTGTCAGTTCATGGCTCCATCCTTAAACGCTCGACAAGACCTAGTGGTCACCGGCGT
CCCAATGCTTGGCAAGAAGCCGCAGTCAAGGCCGTTGACATGCCGGACTACCAAAATCCAAGATCACCCACCTCATCT

FIG. 12 (continued)

```
TGgcgACCACCGCTGGCGTTGACATGCCGGTGCTGACTATCAACTCGTCTCCCCTTGGTCTCTCCCCTTCAGTCAAA
CGCTATATGTTGTACCAACAGGATGTGCCGCGGCACAGTGCTCCTCCGGCACTATTCTTCTTATTCCATGAGAACCTTGCTGAAAACAACAA
GGGCTCACGAGTCCTTATCGTCTGCTCGCTCACTGCTATCTTCTTATTCCATGAGAACCTTGACTCAC
TCGTCGCTCAAGCTTTATTCGGAGACGGAGCTTCAGGCCTCACTTGGGTTCAGGCCCTCACTTGGCGTAGAACGGCCA
ATATTCGAGATCGTCAGTTGCAACTGATCAAACAATCTTGCCGGACTGAAGTTACACTTGAGAGAGGAGG
GTTGACGTTTCAGTTGCATAGAGATGTACCCTTGATGGTCGCAAAGAACATAGAGAACGCAGCGGAGACCAGGTGTCTC
CACTGGGATAACTGATTGGAAGAGATAAGTTAAGGGCTAGCAGGCATGTGCTTAGTGAATACGGAAACCTGATTAGCGCTTGTGT
AAACTAAACCTTAATGAGAAGATAAGTTAAGGGCTAGCAGGCATGTGCTTAGTGAATACGGAAACCTGATTAGCGCTTGTGT
GTTGTTCATCATTGACGGAACGGTTGGACCGGGTATGACTGTTGAGACTGTTCTTGTTCTTCGTAGCGTCCGCGTTACTGCTGCGGTTGCCAAT
TTTTGTTTGGATTTGGACCGGGTATGACTGTTGAGACTGTTCTTGTTCTTCGTAGCGTCCGCGTTACTGCTGCGGTTGCCAAT
GGAAACTGA > 2-PS variant= 53 Substitutions= 2: (C 35S) (C 89S)
ATGGGATCTTACTCATCCGATGATGTGGAGGTGATTCGTGAGGCGGACGGCCACAAGGTTTAGCCACATTCTTGCCAT
TGGCACTGCTACTCCCTCCCAATtcgGTCGCTCAAGCTGATTATGCAGACTATTATTTCGTGTCACTAAGAGGAACATA
TGGTTGATCTTAAAGAGAATTTAAACGCATTGTGAGAAACAGCGATAACCTAGCCCTCACCGAAGAC
TATCTGCAAGAGACCCAACAATGAGTTCATGGCCATCCCTTAAACGCTCGACAAGACCTAGTGGTCATCCGGCGT
CCCAATGCTTGGCAAAGAACCGCAGTCAAGGCCATTGATGAATGGGACTACCAAATCCAAGATCACCCACCTCATCT
TCTGCACCACCGCTGGCGTTGACAACAGGGATGTGCCGCGGATATCAACTCGTCCCCTTGGTCTCTCCCCTTCAGTCAAA
CGCTATATGTTGTACCAACAGGATGTGCCGGCGATATCAACTCGTCCCCTTGGTCTCTCCCCTTCAGTCAAA
GGGCTCACGAGTCCTTATCGTCTGCTCCGAGATCACTGCTGCAGCACTGATCACAGAGAACCTTGACTCAC
TCGTCGCTCAAGCTTTATTCGGAGACGGAGCTGCAGCACTGCTGCAGCACTGCAGAACCTTGACTCAC
ATATTCGAGATCGTCGTCAACTGATCAAACAATCTTGCCGGACAAGAAGTTACACTTGAGAGAGGAGG
```

FIG. 12 (continued)

```
GTTGACGTTTCAGTTGCATAGAGATGTACCCTTGATGGTCGCAAAGAACATAGAGAACGCAGCGGAGAAAGCGTTGTCTC
CACTAGGATAACTGATTGGAACTCAGTTTTCTGGATGGTGAGCCAGTGGTCGAGCCCATATTGGAGCCTGGTGGAGCGA
AAACTAAACCTTAAGGAAGATAAGTTAAGGGCTAGCAGGCATGTGCTTAGTGAATACGGAAACCTGATTACGCTTGTGT
GTTGTTCATCATTGACGAGGTGAGGAGGTGGCGGAAGAGATCTATGGCGAAGAGTACAACCGGTGAAGGTTTGAAGGTG
TTTGTTTGGATTTGGACCGGGTATGACTGTTGAGACTGTTCTTCCGTAGCGTCCCGGTTACTGCTGCGGTTGCCAAT
GGAAACTGA

> 2-PS variant= 54 Substitutions= 2:    (C 35S)    (C 89A)
ATGGGATCTTACTCATCCATCGATGATGTGGAGGTTGATTCGTGAGGCCACGGTTTAGCCACAAGGTTTAGCCACGATTCTTGCCAT
TGGCACTGCTACTCCTCCCAATtcGTCGCTCAAGCTCATTATGCAGACTATTATTTTCGTGTCAAGAGGAACATA
TGGTTGATCTTAAAGAGAATTAAACGCATTTGTGAGAAAACAGCGATAAAGAACGATACCTAGCCCTCACCGAAGAC
TATCTCGCAAGATGCTTCATGGCTCCATCCTTAAACGCTCGACAAAATCCAAGATCACCCACCCTCATCT
CCCAATGCTTGGCAAAGAAGCCGCAGTCAAGGCCATTGATGAATGGGACTACCAAATCGTCCCCCCTTCAGTCAAA
TCTGCACCACCGCTGGCGTTGACATGTGCCGCCGAGATCGTCTGCCTCCGAGACGGATGTGCCGCCAAGCCAATGAGAACAACCTTGACTCAC
CGCTATATGTTGTACCAACAGGATGTGCCGCCGAGATCGTCTGCCTCCGAGACGGAGCTGCAGCTGCACACTGGTAAGCGGCCA
GGGCTCACGAGTCCTTATCGTCCGGAGACGGAGCTGCAGCTGCACACTCTTGCCGGACAATCTTGCCGGACAATGAGAACCACCTTGACTCAC
TCGTCGCTCAAGCTTTATTCGGAGACTAAGCTTATTCCCGGAGTCAATGAGAACTGTGGGTCAGCTGCAGGCGACACTGTGTTCCGGCCA
ATATTCGAGATCGTGCAGTGCAAACAATCTTGCCGGAGTCGCAAAGATAGAGAACCAGGGTCGTGCACCAGGCGTTGTCTC
GTTGACGTTTCAGTTGCATAGAGATGTACCCTTGACGGTCGCAAAGATAGAGAACGCAGCAGGGAGAAAGCGTTGTCTC
CACTAGGATAACTGATTGGAACTCAGTTTTAAGGAAGATAAGTTAAGGGCTAGCAGGCATGTGCTTAGTGAAGATCGCAGTGGTCAGGTGGAGCGA
AAACTAAACCTTAAGGAAGATAAGTTAAGGGCTAGCAGGCATGTGCTTAGTGAAGAAGAGTACAACCGGTGAAGGTTTGAAGCGCTTGTGT
GTTGTTCATCATTGACGAGGTGAGGAGGTGGCAAGATCTATGCGGAAGAGTACAACCGGTGAAGGTTTGAAGCGCTTGTGT
TTTGTTTGGATTTGGACCGGGTATGACTGTTGAGACTGTTCTTGTTCTTCCGTAGCGTCCGCGTTACTGCTGCCGGTTGCCAAT
GGAAACTGA
```

FIG. 12 (continued)

> 2-PS variant= 55 Substitutions= 2: (C 35S) (C 65S)
ATGGGATCTTACTCATCCATCGATGATCGTGAGGTGAGGTCGCTCAAGCCGAACGGTTTAGCCACGATTCTTGCCAT
TGGCACTGCTACTCCTCCCAATtcgGTCGCTCAAGCTGATTATGCAGACTATTATTTCGTGTCACTAAGAGCGAACATA
TGGTTGATCTTAAAGAGAATTAAACGCATTtctGAGAAAACAGCGATAAAGAAACGATACCTAGCCCTCACCGAAGAC
TATCTGCAAGAGAACCCAACAATGTGTGAGTTCATGGCTCAAGCCTAGTGGAAATCCAAGATCACCCACCCTCATCT
CCCAATGCTTGGCAAAGAGCCAGTGCTTGACATGGGGACTACCAAAATCCTTGGTCTCTCCCCTTCAGTCAAA
TCTGCACCACCGCTGGCTTGACAACAGGATGTCCGCGGTTGACTATCAACTCGTCAAACTCCTTGTCTCCCCTTCAGTCAAA
CGCTATATGTTGTACCAAGACCGGGGGATGCGGCCCGAGATCACTCGCTATCTTATTCCATGGTGTTCAGGCCCA
GGGCTCAAGCGAGTCCTTATCGTCGTCCGAGATCACTCGCTATCTTATTCCATGGTGTTCAGGCCAATGAGACCTT
TCGTCGCTCAAGCTTTATTCGGAGATCTCAACTGATAGACGATCCCCTTGAAGTTACACTTGAGAGGAAGGTTGTCTC
ATATTCGAGATCGTGTCAGTTGCATGACGGAACTCAGTTGGAAGTTACACTGAAGATCCGGAGAAAGCGTTGTCTC
GTTGACGTTTCAGTTGCATGATCAAACGATGAAATGCGCCCATATTGGACCGTGATTAGCGCTTGTGT
CACTAGGGATAAACTGATGGAACTCAGTTGGAAGATAAGTTAAGGGAAGAGATCTATGGCGGAAGAGTACAACCGTGAAGGTTGATTGCGGTG
AAACTAAACCTAAGGAAGATAAGTTAAGGGAAGAGATCTATGGCGGAAGAGTACAACCGTGAAGGTTGATTGCGGTG
GTTGTTCATCATTGACGCGTTTGGACCGGGTATGACTGAGACTGTTCTTCGTAGCGTCGCGTTACTGCTGCGGTTGCCAAT
TTTGTTTGGATTTGGACCGGGTATGACTGAGACTGTTCTTCGTAGCGTCGCGTTACTGCTGCGGTTGCCAAT
GGAAACTGA > 2-PS variant= 56 Substitutions= 2: (C 35S) (C 65A)
ATGGGATCTTACTCATCCATCGATGATCGTGAGGTGAGGTCGCTCAAGCCGAACGGTTTAGCCACGATTCTTGCCAT
TGGCACTGCTACTCCTCCCAATtcgGTCGCTCAAGCTGATTATGCAGACTATTATTTCGTGTCACTAAGAGCGAACATA
TGGTTGATCTTAAAGAGAATTAAACGCATTgctGAGAAAACAGCGATAAAGAAACGATACCTAGCCCTCACCGAAGAC
TATCTGCAAGAGAACCCAACAATGTGTGAGTTCATGGCTCAAGCCTAGTGGTCACCGGCGT
CCCAATGCTTGGCAAAGAGCCAGTGCTTGACATGGGGACTACCAAAATCAAGATCACCCACCCTCATCT FIG. 12 (continued)

TCTGCACCACCGGCTGGCGTTGACATGCCCGGTGCTGACTATCAACTCGTCTCCCTTCAGTCAAA
CGCTATATGTTGTACCAACAGGATGTGCCGGCGCACACAGTCCCTAAGGACCTTGTGAAAACAA
GGGCTCACGAGTCCTTATCGTCTGCTCCGAGATCACTGCTATCTTATTCCATGAGAACCACCTTGACTCAC
TCGTCGCTCAAGCTTTATTGGAGACGGAGCTTCAGCACTGTGGGTCAGCCCTCACTTGGCCGTAGAACGGCCA
ATATTGAGATCGTGTCAACATGATCAAACAATCTTCCGGACGAAGAAGTTACACTTGAGAGAGGAGG
GTTGACGTTTCAGTTGCATAGAGATGTACCCTTGATGGTCGCAAAGAACATAGACGCGGAGAAAGCGTTGTCTC
CACTAGGGATAACTGATTGGAACTCAGTTCTCGATGGTGCTGCCAGTGCGAGCCATATTGGAGCCAGGTGAGCGA
AAACTAAACCTTAAGGAAGATAAGTTAAGGCATGCTAGCAGGAAGATCTATGCCGAAGAGTACAACCGGTGAAGTTTGGATTAGCGCTTGT
GTTGTTCATCATTGACGAGGTGAGGAAGAATCTATGGCCGGGTATGACTGTTGTTCTTCGTAGCGCCGGTTACTGCCGGTTGCCAAT
TTTTGTTTGGATTTGGACCGGGTATGACTGTTGAGACTGTTGAGACTGTTCCTTTCTTCCGCCGTTACTGCCGGTTGCCAAT
GGAAACTGA

>2-PS variant= 57 Substitutions= 2:     (C 35S)    (C169S)
ATGGGATCTTACTGCTACTCCCATCCGATGATGTGGAGGTGATTCGTGAGGCCGGACGGGCACCAAGGTTTAGCCACGATTCTTGCCAT
TGGCCACTGCTACTCCCCAATtcgGTCCGCTCAAGCTGATTATGCCAGACTATTATTTTTCGTGTCACTAAGAGCGAACATA
TGGTTGATCTTAAAGAGAATTAAACGCAGCCATTGTGAGAAACAGCGATAAAGAAACGATACCTAGCCCTCACCGAAGAC
TATCTGCAAGAGAATGTGCAGCTTCATGAGTTGTAGAGTTCATGGCTCCATCCTTAAACGCTCGACAAGACTACCAAATCACCACCTCATCT
CCCAATGCTTGGCAAGAAGCCAGTCAGCCGTTGACATGCCCGGTTGCTGACTATCAAACTCGTCAAACTCCTTGGTCTCTCCCTTCAGTCAAA
TCTGCACCACCGGCTGGCGTTGACATGCCCGGTTGCTGACTATCAAACTCGTCAAACTCCTTGGTCTCTCCCTTCAGTCAAA
CGCTATATGTTGTAGTCAACAGGGAtctGCCCGGCGCACATGTGCCCGGCGCACCAGTTGCCAAGGACCTTGAAAAACAA
GGGCTCACGAGTCCTTATCGTCTGCTCCGAGATCACTGCTATCTTATTCCATGAGAACCACCTTGACTCAC
TCGTCGCTCAAGCTTTATTGGAGACGGAGCTTCAGCACTGTGGGTCAGCCCTCACTTGGCCGTAGAACGGCCA
ATATTCGAGATCGTGTCAACTGATCAAACAATCTTGCCGGACGAAGCAATGAAGTTACACTTGAGAGAGGAGG
GTTGACGTTTCAGTTGCATAGAGATGTACCCTTGATGGTCGCAAAGAACATAGAACGCGGAGAAAGCGTTGTCTC

FIG. 12 (continued)

```
CACTAGGGATAACTGATTGGAACTCAGTTTTCTGGATGGTGCACCCAGGTGGTCGAGCCATATTGGACCAGGTGGAGCGA
AAACTAAACCTTAAGGAAGATAAGTTAAGGCTAGCAGGTGTGCTTAGTGCTTAGTGAAACCTGATTAGCGCTTGTGT
GTTGTTCATCATTGACGAGGTGACGGTTGGACGGGAAGAGATCTATGGCGAAGGAGAGTACAACCGGTGAAGGTTTGGATTGCGGTG
TTTTGTTTGGATTTGGACCGGTTGGGACTGTTCTTCGTTACTGCTGCGGTTGCCAAT
GGAAACTGA

> 2-PS variant= 58 Substitutions= 2:   (C 35S)   (N341H)
ATGGGATCTTACTACTCCTCCCAATtcgGTCGCTGCTCAAGCTGATGATGTGATTCGTGAGGCCACGATTCTTGCCAT
TGGCACTGCTACTCCTCCCAATtcgGTCGCTCAAGCTGATTATGCAGACTATTATTTCGTGTCACTAAGAGCGAACATA
TGGTTGATCTTAAAGAGAATTTAAACGCATTTGTGAGAAAACGATAAAGAAAACGATATACCCTCACCGAAGAC
TATCTGCAAGAACCCAACAATGTGTGAGTTCATGGCTCCATCTTAAACGCTCGACAAGACCTAGTGGTCACCGCGT
CCCAATGCTTGGCAAGAACGCAGTCAAGGCCATTGATGAATCAAGATCCAAATCCAAGATCACCACCTCATCT
TCTGCACCACCTGGCGTTGACAAGGATGCCCCGGTGCTGACATCGTCAAGCCCGTATCAACTCGTCAAGGACCTTCAGTCAAA
GCTATATGTTGTACCAACGATGTCGCTCCGAGATCGTCTTATCGCTATCTTATTCCATGGACCCAATGCCAAGAACCCATGGGTTCAGCAATAGAAGTACACTTGAGAAGCCA
GGGCTCACGAGTCCTTATCGTCTCCGAGATCGGAGCGGACACTGCTCACTCCATTGGGTTCAGCAATAGAAGTACACTTGAGAGAAGGAGG
TCGTCGCTCAAGCTTTATTGGAACTGTCAACTGATCAAACAATCTTGCCGGACTGAGAACTACTGAACTGGAGAGAAGTTGTCTC
ATATTGAGAGTCGTCAGTGCATAGAGATGTTCAGTTGGAAGATAAGTGCTTAGTACGAcacCTGATTAGCGCTTGTGT
GTTGACGTTTCAGTGCATAGAGATGTTCAGTTGGAAGATAAGTTAAGGCTAGCAGGTGTGCTTAGTGCTTAGTGAGCGA
CACTAGGGATAACTGATTGGAACTCAGTTTTCTGGATGGTGCACCCAGGTGGTCGAGCCATATTGGACCAGGTGGAGCGA
AAACTAAACCTTAAGGAAGATAAGTTAAGGCTAGCAGGTGTGCTTAGTGCTTAGTGAAACCTGATTAGCGCTTGTGT
GTTGTTCATCATTGACGAGGTGACGGTTGGACGGGAAGAGATCTATGGCGAAGGAGAGTACAACCGGTGAAGGTTGCGGTG
TTTTGTTTGGATTTGGACCGGTTGGGACTGTTCTTCGTTACTGCTGCGGTTGCCAAT
GGAAACTGA
```

FIG. 12 (continued)

> 2-PS variant= 59 Substitutions= 2: (C 35S) (H308Q)
ATGGATCTTACTCATCGATGATGGAGGTGATTCGTGAGGCCACAAGGTTTAGCCACGATTCTTGCCAT
TGGCACTGCTACTCCTCCCAATcgGTCGCTCAAGCTGATTATGCAGACTATATTTTCGTGTCACTAAGAGCGAACATA
TGGTTGATCTTAAAGAGAACCAACAGCCATTGTGAGAAAACAGATACCTAGCCCTCACCGAAGAC
TATCTGCAAGAGAACCCAACAATGTGAGTTCATGGCTCAAACGCTCGACAAGACCTAGTGGTCACCGCGT
CCCAATGCTTGGCAAAGAAGCCGTTGACAGGCCATTGATGAATGGGACTACCAAAATCCAAGATCACCACCTCATCT
TCTGCACCACCGCTGGTACCAACAGGGATGCCCCTCCAAACTCGTCAAATCTCTTGGTCTCTCCCCTTCAGTCAAA
CGCTATATGTTGTACCAGTCCTTATCGTCTGCTCCGAGATCACTGCTCCCGGCTAGCCATGGACCCCATTGAACCACCTTGACTCAC
GGGCTCACGAGTCCTTATCGTCTGCTCCGAGATCACTGCTCTCCCGAGATCAGTCTATCTTATTCCATGGGTTCAGGCCAATGAGAACCATGAGAACCATGAGAACAACATAGAGAACACCGGAGAAAGCCTTGTCTC
TCGTCGCTCAAGCTTCCGGATAAACGCATTTCCGGAGAACTGAACGGCCAATGTGGGTTCAGGCCCATATTGCGAGCTGGTCGAGCCAGGTGGAACGGCCA
ATATTCGAGATCGTGTCAGTTGCATAGAGATCAAAACAATCTTGCCGGACACTGAAGGCAATGAGAAGGTACACTTGAGAGAAGGAGG
GTTGACGTTTCAGTTGCATAGAGATCAAAACAATCTACCCCTTGATGGTCGCAAAGACATAGAGAACACCGGAGAAAGCCTTGTCTC
CACTAGGGATAAACCTGATTGGAACTCAGTTTCTCTGGAATGGTGCTAGTGAAGGGAAGAGAGTACAACCGGTGAAGGTTTGGATTGCGGTG
AAACTAAAACCTTAAGGAAGAGATAAGTTAAGGCATGAGAACGAGTACAACCGGTGAAGGTTTGGATTGCGGTG
GTTGTTCATCATTGACGAGTTGGACCGGGTATGACTGTTGTGTTCTTCGTAGCGTCCGGTTACTCGCCGGTTGCCAAT
TTTTGTTTGGATTTGAGACCGGGTATGACTGTTGTGTTCTTCGTAGCGTCCGGTTACTCGCCGGTTGCCAAT
GGAAACTGA > 2-PS variant= 60 Substitutions= 3: (C 35S) (L202F) (L268F)
ATGGATCTTACTCATCGATGATGGAGGTGATTCGTGAGGCCACAAGGTTTAGCCACGATTCTTGCCAT
TGGCACTGCTACTCCTCCCAATcgGTCGCTCAAGCTGATTATGCAGACTATATTTTCGTGTCACTAAGAGCGAACATA
TGGTTGATCTTAAAGAGAACCAACAGCCATTGTGAGAAAACAGATACCTAGCCCTCACCGAAGAC
TATCTGCAAGAGAACCCAACAATGTGAGTTCATGGCTCAAACGCTCGACAAGACCTAGTGGTCACCGCGT
CCCAATGCTTGGCAAAGAAGCCGTTGACAGGCCATTGATGAATGGGACTACCAAAATCCAAGATCACCACCTCATCT

FIG. 12 (continued)

```
TCTGCACCACCGCTGGCGTTGCGGTGCTGACTATCAACTCGTCGACTATCAACTCCTTGGTCTCTCCCTTCAGTCAAA
CGCTATATGTTGTCAACAGGATGTGCCCGGCCACAGTCCTCCCGGCACCTTGCTGAAGGACCTTGAAAACAACAA
GGGCTCACGAGTCCTTATCGTCTGCTCCGAGATCACTGCTATG TTCCATGGACCCAATGAGAACCACCTTGACTCAC
TCGTCGCTCAAGCTTTATTCGGACGACTGCCACTCATTGTGGGTTCAGGCCCTCACTTGGCCGTAGAACGGCCA
ATATTCGAGATCGTGTCAACTGATCAAACAATCTTGCCGGACACTGAAGTTACACTTGAGAGAAAGCGTTGTCTC
G t ACGTTTCAGTTGCATAGAGATGTACCCCTTGATGGTCGCAAAGAACCAGCTGGTGCACCTGATGGTGAGCCGA
CACTAGGATAAACTGATTGGAACTCAGTTTTCTGGAACTCAGTGCTTAGTGAATACCAACCGTGAAGTTTGATTGCCGTG
AAACTAAACCTAAGGAAGATAAGTTAAGGCTAGCAGGAAGATCTATGGCGGAAGGAGTACAACCGTGAAGTTTGATTGCCGTG
GTTGTTCATCATTGACGAGTGAGGATATGACTGTTGAATGGGGTATGACTGTTGTTCTTCGTAGCGTTACTGCGGTTGCCAAT
TTTGTTTGGGATTTGGACCGGGTACGGGTATGACTGTTGTTCTTCGTAGCCTAGCGTTACTGCGGTTGCCAAT
GGAAACTGA

>2-PS variant= 61 Substitutions= 3:  (C 35S)   (L268M)    (I343M)
ATGGGATCTTACTGTCATCGATGATGATTCGTGAGGCCGGTGATTCGTGAGGCCACAAGTTTAGCCACGATTCTTGCCAT
TGGCACTGTACTCCTCCCAAT cc GTCGCTCAAGCTGATTATGCAGACTATTATTTCGTGTCACTAAGAGCGAACATA
TGGTTGATCTTAAAGAGAACCCAACAGTGTTAAACGCATTGTGAGTTCATGGCCATTGACAAGACTAGTGGTCACCGGCGT
TATCTGCAAGATGCTTGGCAAAGAGCGCAGTGCCATTGATGAATGGCTAGCAAATCCAAGATCACCACCTCATCT
CCCAATGCTTGGCAAAGAGCGCAGTGCCATTGATGAATGGCTAGCAAATCCAAGATCACCACCTCATCT
CACCACCAGTTGTACAACCGTTGGACAGGATGTGCCCGGCCACAGTCCTCAAACTCGTCTCCCCTTCAGTCAAA
CGCTATATGTTGTCAACAGGATGTGCCCGGCCACAGTCCTCAAACTCGTCTCCCCTTCAGTCAAA
GGGCTCACGAGTCCTTATCGTCTGCTCCGAGATCACTGCTATTCCATGGACCCAATGAGAACCACCTTGACTCAC
TCGTCGCTCAAGCTTTATTCGGACGACTGCCACTCATTGTGGGTTCAGGCCCTCACTTGGCCGTAGAACGGCCA
ATATTCGAGATCGTGTCAACTGATCAAACAATCTTGCCGGACACTGAAGTTACACTTGAGAGAAAGCGTTGTCTC
G atg ACGTTTCAGTTGCATAGAGATGTACCCCTTGATGGTCGCAAAGAACCAGCTGGTGCACCTGATGGTGAGCCGA
```

FIG. 12 (continued)

```
CACTAGGGATAACCTTAAGTTAAGGAAGATAAGTGAACTCAGTTTTCTGGATGGTGCACCCAGGTGGTGTCGAGCCATATTGGACCAGGTGGAGCGA
AAACTAAACCTTAAGCAAGATAAGTTAAGGGCTAGCAGGCATGTGCTTAGTGAATACGAACCTGAGCGCTTGTGT
GTTGTTCATCATTGACGAGGTGAGAGAGATGAGGAAGAGATACCGTGAGAGTACAACCGTGAAGGTTTGATTGCGGTG
TTTTGTTTGGATTTGGATTTGGACCGGTTACGCGGGTATGACTGTTGAGACTGTTGTTCTTCGTAGCGTCCGCGGTTACTGCGCGGTTGCCAAT
GGAAACTGA

>2-PS variant= 62 Substitutions=  3:    (C 35S)    (L202F)    (L268M)
ATGGGAAGATCTTACTCATCATCCGATGATGATTCGTGAGGCCGAGCGCAAGGTTTAGCCACGATTCTTGCCAT
TGGCACTGCTACTCCCCCAATtcgGTCGCTCAAGCTGATTATGCAGACTATTATTTCGTGTCACTAAGAGCGAACATA
TGGTTGATCTTAAAGAGAATTAAACGCATTTGTGAGAAAACAGCGATAAAGAAACGATACCCTCACCGAAGAC
TATCTGCAAGAGACCAACAATGTGTGAGTTCATGGCTCCATCTTAAACGCTCGACAAGACCTAGTGGTCACGGCGT
CCCAATGCTTGGCAAAGAACCGCAGTCAAGGCCATTGATGAATCAACTCGTCAAAATCCTTGGTCTCTCCCCTTCAGTCAAA
TCTGCACCACCGGTCTGGCGTTGACATGCCGGTTGCTGACAAGGATGTGCTCGTCCGAGATCACTGCTATCtTcGTTGCCAAGGACCACCTTGACTCAC
GGGCTCACGAGTCCTTATCGTCTGCCGAGATCACTGCTATCtTcTTCCATGGACCCAATGAGTTACACTTGAGAGAGGAGG
TCGTCGCTCAAGCTTTATTCGGAGAGATCTGTCAACTGAACATAGAACCAGCGACCAGGTGGACCGA
ATATTCGAGATCGTGTCAGTTGCATAGAGATTGGAACTGAGAACTGATAGAAGATGTACAGTTACACTTGAGAGAGGAGG
gatgACGTTTCAGTTGCATAGAGATTGGAACTGATGGTGCACCCAGGTGGTGCTTAGTGAATACGAACCTGAGCGCTTGTGT
CACTAGGGATAACCTTAAGCAAGATAAGTTAAGGGCTAGCAGGCATGTGCTTAGTGAATACGAACCTGAGCGCTTGTGT
AAACTAAACCTTAAGTTAAGGAAGATAAGTGAACTCAGTTTTCTGGATGGTGCACCCAGGTGGTGCTTAGTGAATACGAACCTGAGCGCTTGTGT
GTTGTTCATCATTGACGAGGTGAGAGAGATGAGGAAGAGATACCGTGAGAGTACAACCGTGAAGGTTTGATTGCGGTG
TTTTGTTTGGATTTGGATTTGGACCGGTTACGCGGGTATGACTGTTGAGACTGTTGTTCTTCGTAGCGTCCGCGGTTACTGCGCGGTTGCCAAT
GGAAACTGA
```

FIG. 13

Nucleotide sequence alignments: 2-PS

```
                 1                                                                          70
> Seq  1   ATGGGATCTTACTTCATCTCATCCGATGATGATGTGATTCGTGAGGTGAGGCCGGACGGGCACAAGGTTTAGCCACGA
> Seq  2   ATGGGATCTTACTTCATCTCATCCGATGATGATGTGATTCGTGAGGTGAGGCCGGACGGGCACAAGGTTTAGCCACGA
> Seq  3   ATGGGATCTTACTTCATCTCATCCGATGATGATGTGATTCGTGAGGTGAGGCCGGACGGGCACAAGGTTTAGCCACGA
> Seq  4   ATGGGATCTTACTTCATCTCATCCGATGATGATGTGATTCGTGAGGTGAGGCCGGACGGGCACAAGGTTTAGCCACGA
> Seq  5   ATGGGATCTTACTTCATCTCATCCGATGATGATGTGATTCGTGAGGTGAGGCCGGACGGGCACAAGGTTTAGCCACGA
> Seq  6   ATGGGATCTTACTTCATCTCATCCGATGATGATGTGATTCGTGAGGTGAGGCCGGACGGGCACAAGGTTTAGCCACGA
> Seq  7   ATGGGATCTTACTTCATCTCATCCGATGATGATGTGATTCGTGAGGTGAGGCCGGACGGGCACAAGGTTTAGCCACGA
> Seq  8   ATGGGATCTTACTTCATCTCATCCGATGATGATGTGATTCGTGAGGTGAGGCCGGACGGGCACAAGGTTTAGCCACGA
> Seq  9   ATGGGATCTTACTTCATCTCATCCGATGATGATGTGATTCGTGAGGTGAGGCCGGACGGGCACAAGGTTTAGCCACGA
> Seq 10   ATGGGATCTTACTTCATCTCATCCGATGATGATGTGATTCGTGAGGTGAGGCCGGACGGGCACAAGGTTTAGCCACGA
> Seq 11   ATGGGATCTTACTTCATCTCATCCGATGATGATGTGATTCGTGAGGTGAGGCCGGACGGGCACAAGGTTTAGCCACGA
> Seq 12   ATGGGATCTTACTTCATCTCATCCGATGATGATGTGATTCGTGAGGTGAGGCCGGACGGGCACAAGGTTTAGCCACGA
> Seq 13   ATGGGATCTTACTTCATCTCATCCGATGATGATGTGATTCGTGAGGTGAGGCCGGACGGGCACAAGGTTTAGCCACGA
> Seq 14   ATGGGATCTTACTTCATCTCATCCGATGATGATGTGATTCGTGAGGTGAGGCCGGACGGGCACAAGGTTTAGCCACGA
> Seq 15   ATGGGATCTTACTTCATCTCATCCGATGATGATGTGATTCGTGAGGTGAGGCCGGACGGGCACAAGGTTTAGCCACGA
> Seq 16   ATGGGATCTTACTTCATCTCATCCGATGATGATGTGATTCGTGAGGTGAGGCCGGACGGGCACAAGGTTTAGCCACGA
> Seq 17   ATGGGATCTTACTTCATCTCATCCGATGATGATGTGATTCGTGAGGTGAGGCCGGACGGGCACAAGGTTTAGCCACGA
> Seq 18   ATGGGATCTTACTTCATCTCATCCGATGATGATGTGATTCGTGAGGTGAGGCCGGACGGGCACAAGGTTTAGCCACGA
> Seq 19   ATGGGATCTTACTTCATCTCATCCGATGATGATGTGATTCGTGAGGTGAGGCCGGACGGGCACAAGGTTTAGCCACGA
> Seq 20   ATGGGATCTTACTTCATCTCATCCGATGATGATGTGATTCGTGAGGTGAGGCCGGACGGGCACAAGGTTTAGCCACGA
> Seq 21   ATGGGATCTTACTTCATCTCATCCGATGATGATGTGATTCGTGAGGTGAGGCCGGACGGGCACAAGGTTTAGCCACGA
```

| | | |
|---|---|---|
| Seq 46 | ATGGGATCTTACTTCATCCGATGATGTGGAGGTGATTCGTGAGGCCCGGACGGGCACAAGGTTTAGCCACGA | |
| Seq 47 | ATGGGATCTTACTTCATCCGATGATGTGGAGGTGATTCGTGAGGCCCGGACGGGCACAAGGTTTAGCCACGA | |
| Seq 48 | ATGGGATCTTACTTCATCCGATGATGTGGAGGTGATTCGTGAGGCCCGGACGGGCACAAGGTTTAGCCACGA | |
| Seq 49 | ATGGGATCTTACTTCATCCGATGATGTGGAGGTGATTCGTGAGGCCCGGACGGGCACAAGGTTTAGCCACGA | |
| Seq 50 | ATGGGATCTTACTTCATCCGATGATGTGGAGGTGATTCGTGAGGCCCGGACGGGCACAAGGTTTAGCCACGA | |
| Seq 51 | ATGGGATCTTACTTCATCCGATGATGTGGAGGTGATTCGTGAGGCCCGGACGGGCACAAGGTTTAGCCACGA | |
| Seq 52 | ATGGGATCTTACTTCATCCGATGATGTGGAGGTGATTCGTGAGGCCCGGACGGGCACAAGGTTTAGCCACGA | |
| Seq 53 | ATGGGATCTTACTTCATCCGATGATGTGGAGGTGATTCGTGAGGCCCGGACGGGCACAAGGTTTAGCCACGA | |
| Seq 54 | ATGGGATCTTACTTCATCCGATGATGTGGAGGTGATTCGTGAGGCCCGGACGGGCACAAGGTTTAGCCACGA | |
| Seq 55 | ATGGGATCTTACTTCATCCGATGATGTGGAGGTGATTCGTGAGGCCCGGACGGGCACAAGGTTTAGCCACGA | |
| Seq 56 | ATGGGATCTTACTTCATCCGATGATGTGGAGGTGATTCGTGAGGCCCGGACGGGCACAAGGTTTAGCCACGA | |
| Seq 57 | ATGGGATCTTACTTCATCCGATGATGTGGAGGTGATTCGTGAGGCCCGGACGGGCACAAGGTTTAGCCACGA | |
| Seq 58 | ATGGGATCTTACTTCATCCGATGATGTGGAGGTGATTCGTGAGGCCCGGACGGGCACAAGGTTTAGCCACGA | |
| Seq 59 | ATGGGATCTTACTTCATCCGATGATGTGGAGGTGATTCGTGAGGCCCGGACGGGCACAAGGTTTAGCCACGA | |
| Seq 60 | ATGGGATCTTACTTCATCCGATGATGTGGAGGTGATTCGTGAGGCCCGGACGGGCACAAGGTTTAGCCACGA | |
| Seq 61 | ATGGGATCTTACTTCATCCGATGATGTGGAGGTGATTCGTGAGGCCCGGACGGGCACAAGGTTTAGCCACGA | |
| Seq 62 | ATGGGATCTTACTTCATCCGATGATGATGTGGAGGTGATTCGTGAGGCCCGGACGGGCACAAGGTTTAGCCACGA | |

| | 71 | 140 |
|---|---|---|
| Seq 1 | TTCTTGCCATTGGCACTGCTACTCCTCCCAATTGCGTCGCTCAAGCTGATTATGCAGACTATTATTTTCG | |
| Seq 2 | TTCTTGCCATTGGCACTGCTACTCCTCCCAATTGCGTCGCTCAAGCTGATTATGCAGACTATTATTTTCG | |
| Seq 3 | TTCTTGCCATTGGCACTGCTACTCCTCCCAATTGCCGTCGCTCAAGCTGATTATGCAGACTATTATTTTCG | |
| Seq 4 | TTCTTGCCATTGGCACTGCTACTCCTCCCAATgccGTCGCTCAAGCTGATTATGCAGACTATTATTTTCG | |
| Seq 5 | TTCTTGCCATTGGCACTGCTACTCCTCCCAATTGCGTCGCTCAAGCTGATTATGCAGACTATTATTTTCG | |

FIG. 13 (continued)

```
Seq > 6   TTCTTGCCATTGGCACTGCTACTCCTCCCAATTGCGTCGCTCAAGCTGATTATGCAGACTATTATTTTCG
Seq > 7   TTCTTGCCATTGGCACTGCTACTCCTCCCAATTGCGTCGCTCAAGCTGATTATGCAGACTATTATTTTCG
Seq > 8   TTCTTGCCATTGGCACTGCTACTCCTCCCAATTGCGTCGCTCAAGCTGATTATGCAGACTATTATTTTCG
Seq > 9   TTCTTGCCATTGGCACTGCTACTCCTCCCAATTGCGTCGCTCAAGCTGATTATGCAGACTATTATTTTCG
Seq > 10  TTCTTGCCATTGGCACTGCTACTCCTCCCAATTGCGTCGCTCAAGCTGATTATGCAGACTATTATTTTCG
Seq > 11  TTCTTGCCATTGGCACTGCTACTCCTCCCAATTGCGTCGCTCAAGCTGATTATGCAGACTATTATTTTCG
Seq > 12  TTCTTGCCATTGGCACTGCTACTCCTCCCAATTGCGTCGCTCAAGCTGATTATGCAGACTATTATTTTCG
Seq > 13  TTCTTGCCATTGGCACTGCTACTCCTCCCAATTGCGTCGCTCAAGCTGATTATGCAGACTATTATTTTCG
Seq > 14  TTCTTGCCATTGGCACTGCTACTCCTCCCAATtCCGTCGCTCAAGCTGATTATGCAGACTATTATTTTCG
Seq > 15  TTCTTGCCATTGGCACTGCTACTCCTCCCAATtCCGTCGCTCAAGCTGATTATGCAGACTATTATTTTCG
Seq > 16  TTCTTGCCATTGGCACTGCTACTCCTCCCAATtCCGTCGCTCAAGCTGATTATGCAGACTATTATTTTCG
Seq > 17  TTCTTGCCATTGGCACTGCTACTCCTCCCAATtCCGTCGCTCAAGCTGATTATGCAGACTATTATTTTCG
Seq > 18  TTCTTGCCATTGGCACTGCTACTCCTCCCAATtCCGTCGCTCAAGCTGATTATGCAGACTATTATTTTCG
Seq > 19  TTCTTGCCATTGGCACTGCTACTCCTCCCAATtCCGTCGCTCAAGCTGATTATGCAGACTATTATTTTCG
Seq > 20  TTCTTGCCATTGGCACTGCTACTCCTCCCAATtCCGTCGCTCAAGCTGATTATGCAGACTATTATTTTCG
Seq > 21  TTCTTGCCATTGGCACTGCTACTCCTCCCAATtCCGTCGCTCAAGCTGATTATGCAGACTATTATTTTCG
Seq > 22  TTCTTGCCATTGGCACTGCTACTCCTCCCAATtCCGTCGCTCAAGCTGATTATGCAGACTATTATTTTCG
Seq > 23  TTCTTGCCATTGGCACTGCTACTCCTCCCAATtCCGTCGCTCAAGCTGATTATGCAGACTATTATTTTCG
Seq > 24  TTCTTGCCATTGGCACTGCTACTCCTCCCAATtCCGTCGCTCAAGCTGATTATGCAGACTATTATTTTCG
Seq > 25  TTCTTGCCATTGGCACTGCTACTCCTCCCAATtCCGTCGCTCAAGCTGATTATGCAGACTATTATTTTCG
Seq > 26  TTCTTGCCATTGGCACTGCTACTCCTCCCAATtCCGTCGCTCAAGCTGATTATGCAGACTATTATTTTCG
Seq > 27  TTCTTGCCATTGGCACTGCTACTCCTCCCAATtCCGTCGCTCAAGCTGATTATGCAGACTATTATTTTCG
Seq > 28  TTCTTGCCATTGGCACTGCTACTCCTCCCAATtCCGTCGCTCAAGCTGATTATGCAGACTATTATTTTCG
Seq > 29  TTCTTGCCATTGGCACTGCTACTCCTCCCAATtCCGTCGCTCAAGCTGATTATGCAGACTATTATTTTCG
```

FIG. 13 (continued)

| | |
|---|---|
| Seq 30 | TTCTTGCCATTGGCACTGCTACTCCTCCCAATtccGTCGCTCAAGCTGATTATGCAGACTATTATTTTCG |
| Seq 31 | TTCTTGCCATTGGCACTGCTACTCCTCCCAATtccGTCGCTCAAGCTGATTATGCAGACTATTATTTTCG |
| Seq 32 | TTCTTGCCATTGGCACTGCTACTCCTCCCAATtccGTCGCTCAAGCTGATTATGCAGACTATTATTTTCG |
| Seq 33 | TTCTTGCCATTGGCACTGCTACTCCTCCCAATtccGTCGCTCAAGCTGATTATGCAGACTATTATTTTCG |
| Seq 34 | TTCTTGCCATTGGCACTGCTACTCCTCCCAATtccGTCGCTCAAGCTGATTATGCAGACTATTATTTTCG |
| Seq 35 | TTCTTGCCATTGGCACTGCTACTCCTCCCAATtccGTCGCTCAAGCTGATTATGCAGACTATTATTTTCG |
| Seq 36 | TTCTTGCCATTGGCACTGCTACTCCTCCCAATtccGTCGCTCAAGCTGATTATGCAGACTATTATTTTCG |
| Seq 37 | TTCTTGCCATTGGCACTGCTACTCCTCCCAATtccGTCGCTCAAGCTGATTATGCAGACTATTATTTTCG |
| Seq 38 | TTCTTGCCATTGGCACTGCTACTCCTCCCAATtccGTCGCTCAAGCTGATTATGCAGACTATTATTTTCG |
| Seq 39 | TTCTTGCCATTGGCACTGCTACTCCTCCCAATtccGTCGCTCAAGCTGATTATGCAGACTATTATTTTCG |
| Seq 40 | TTCTTGCCATTGGCACTGCTACTCCTCCCAATtccGTCGCTCAAGCTGATTATGCAGACTATTATTTTCG |
| Seq 41 | TTCTTGCCATTGGCACTGCTACTCCTCCCAATtccGTCGCTCAAGCTGATTATGCAGACTATTATTTTCG |
| Seq 42 | TTCTTGCCATTGGCACTGCTACTCCTCCCAATtccGTCGCTCAAGCTGATTATGCAGACTATTATTTTCG |
| Seq 43 | TTCTTGCCATTGGCACTGCTACTCCTCCCAATtccGTCGCTCAAGCTGATTATGCAGACTATTATTTTCG |
| Seq 44 | TTCTTGCCATTGGCACTGCTACTCCTCCCAATtccGTCGCTCAAGCTGATTATGCAGACTATTATTTTCG |
| Seq 45 | TTCTTGCCATTGGCACTGCTACTCCTCCCAATtccGTCGCTCAAGCTGATTATGCAGACTATTATTTTCG |
| Seq 46 | TTCTTGCCATTGGCACTGCTACTCCTCCCAATtccGTCGCTCAAGCTGATTATGCAGACTATTATTTTCG |
| Seq 47 | TTCTTGCCATTGGCACTGCTACTCCTCCCAATtccGTCGCTCAAGCTGATTATGCAGACTATTATTTTCG |
| Seq 48 | TTCTTGCCATTGGCACTGCTACTCCTCCCAATtccGTCGCTCAAGCTGATTATGCAGACTATTATTTTCG |
| Seq 49 | TTCTTGCCATTGGCACTGCTACTCCTCCCAATtccGTCGCTCAAGCTGATTATGCAGACTATTATTTTCG |
| Seq 50 | TTCTTGCCATTGGCACTGCTACTCCTCCCAATtccGTCGCTCAAGCTGATTATGCAGACTATTATTTTCG |
| Seq 51 | TTCTTGCCATTGGCACTGCTACTCCTCCCAATtccGTCGCTCAAGCTGATTATGCAGACTATTATTTTCG |
| Seq 52 | TTCTTGCCATTGGCACTGCTACTCCTCCCAATtccGTCGCTCAAGCTGATTATGCAGACTATTATTTTCG |
| Seq 53 | TTCTTGCCATTGGCACTGCTACTCCTCCCAATtccGTCGCTCAAGCTGATTATGCAGACTATTATTTTCG |

FIG. 13 (continued)

```
       54 TTCTTGCCATTGGCACTGCTACTCCTCCCAATtccGTCGCTCAAGCTGATTATGCAGACTATTATTTTCG
       55 TTCTTGCCATTGGCACTGCTACTCCTCCCAATtccGTCGCTCAAGCTGATTATGCAGACTATTATTTTCG
       56 TTCTTGCCATTGGCACTGCTACTCCTCCCAATtccGTCGCTCAAGCTGATTATGCAGACTATTATTTTCG
       57 TTCTTGCCATTGGCACTGCTACTCCTCCCAATtccGTCGCTCAAGCTGATTATGCAGACTATTATTTTCG
       58 TTCTTGCCATTGGCACTGCTACTCCTCCCAATtccGTCGCTCAAGCTGATTATGCAGACTATTATTTTCG
       59 TTCTTGCCATTGGCACTGCTACTCCTCCCAATtccGTCGCTCAAGCTGATTATGCAGACTATTATTTTCG
       60 TTCTTGCCATTGGCACTGCTACTCCTCCCAATtccGTCGCTCAAGCTGATTATGCAGACTATTATTTTCG
       61 TTCTTGCCATTGGCACTGCTACTCCTCCCAATtccGTCGCTCAAGCTGATTATGCAGACTATTATTTTCG
       62 TTCTTGCCATTGGCACTGCTACTCCTCCCAATtccGTCGCTCAAGCTGATTATGCAGACTATTATTTTCG 141                                                                    210
        1 TGTCACTAAGAGCGAACATATGGTTGATCTTAAAGAGAAATTTAAACGCATTTGTGAGAAAACAGCGATA
        2 TGTCACTAAGAGCGAACATATGGTTGATCTTAAAGAGAAATTTAAACGCATTTGTGAGAAAACAGCGATA
        3 TGTCACTAAGAGCGAACATATGGTTGATCTTAAAGAGAAATTTAAACGCATTTGTGAGAAAACAGCGATA
        4 TGTCACTAAGAGCGAACATATGGTTGATCTTAAAGAGAAATTTAAACGCATTTGTGAGAAAACAGCGATA
        5 TGTCACTAAGAGCGAACATATGGTTGATCTTAAAGAGAAATTTAAACGCATTTGTGAGAAAACAGCGATA
        6 TGTCACTAAGAGCGAACATATGGTTGATCTTAAAGAGAAATTTAAACGCATTTGTGAGAAAACAGCGATA
        7 TGTCACTAAGAGCGAACATATGGTTGATCTTAAAGAGAAATTTAAACGCATTTGTGAGAAAACAGCGATA
        8 TGTCACTAAGAGCGAACATATGGTTGATCTTAAAGAGAAATTTAAACGCATTTGTGAGAAAACAGCGATA
        9 TGTCACTAAGAGCGAACATATGGTTGATCTTAAAGAGAAATTTAAACGCATTTGTGAGAAAACAGCGATA
       10 TGTCACTAAGAGCGAACATATGGTTGATCTTAAAGAGAAATTTAAACGCATTtctGAGAAAACAGCGATA
       11 TGTCACTAAGAGCGAACATATGGTTGATCTTAAAGAGAAATTTAAACGCATTtctGAGAAAACAGCGATA
       12 TGTCACTAAGAGCGAACATATGGTTGATCTTAAAGAGAAATTTAAACGCATTtctGAGAAAACAGCGATA
       13 TGTCACTAAGAGCGAACATATGGTTGATCTTAAAGAGAAATTTAAACGCATTtctGAGAAAACAGCGATA
```

FIG. 13 (continued)

```
> Seq 14  TGTCACTAAGAGCGAACATATGGTTGATCTTAAAGAGAAATTTAAACGCATTtctGAGAAAACAGCGATA
> Seq 15  TGTCACTAAGAGCGAACATATGGTTGATCTTAAAGAGAAATTTAAACGCATTtctGAGAAAACAGCGATA
> Seq 16  TGTCACTAAGAGCGAACATATGGTTGATCTTAAAGAGAAATTTAAACGCATTtctGAGAAAACAGCGATA
> Seq 17  TGTCACTAAGAGCGAACATATGGTTGATCTTAAAGAGAAATTTAAACGCATTtctGAGAAAACAGCGATA
> Seq 18  TGTCACTAAGAGCGAACATATGGTTGATCTTAAAGAGAAATTTAAACGCATTtctGAGAAAACAGCGATA
> Seq 19  TGTCACTAAGAGCGAACATATGGTTGATCTTAAAGAGAAATTTAAACGCATTTGTGAGAAAACAGCGATA
> Seq 20  TGTCACTAAGAGCGAACATATGGTTGATCTTAAAGAGAAATTTAAACGCATTTGTGAGAAAACAGCGATA
> Seq 21  TGTCACTAAGAGCGAACATATGGTTGATCTTAAAGAGAAATTTAAACGCATTtctGAGAAAACAGCGATA
> Seq 22  TGTCACTAAGAGCGAACATATGGTTGATCTTAAAGAGAAATTTAAACGCATTTGTGAGAAAACAGCGATA
> Seq 23  TGTCACTAAGAGCGAACATATGGTTGATCTTAAAGAGAAATTTAAACGCATTtctGAGAAAACAGCGATA
> Seq 24  TGTCACTAAGAGCGAACATATGGTTGATCTTAAAGAGAAATTTAAACGCATTTGTGAGAAAACAGCGATA
> Seq 25  TGTCACTAAGAGCGAACATATGGTTGATCTTAAAGAGAAATTTAAACGCATTTGTGAGAAAACAGCGATA
> Seq 26  TGTCACTAAGAGCGAACATATGGTTGATCTTAAAGAGAAATTTAAACGCATTTGTGAGAAAACAGCGATA
> Seq 27  TGTCACTAAGAGCGAACATATGGTTGATCTTAAAGAGAAATTTAAACGCATTTGTGAGAAAACAGCGATA
> Seq 28  TGTCACTAAGAGCGAACATATGGTTGATCTTAAAGAGAAATTTAAACGCATTTGTGAGAAAACAGCGATA
> Seq 29  TGTCACTAAGAGCGAACATATGGTTGATCTTAAAGAGAAATTTAAACGCATTTGTGAGAAAACAGCGATA
> Seq 30  TGTCACTAAGAGCGAACATATGGTTGATCTTAAAGAGAAATTTAAACGCATTTGTGAGAAAACAGCGATA
> Seq 31  TGTCACTAAGAGCGAACATATGGTTGATCTTAAAGAGAAATTTAAACGCATTTGTGAGAAAACAGCGATA
> Seq 32  TGTCACTAAGAGCGAACATATGGTTGATCTTAAAGAGAAATTTAAACGCATTTGTGAGAAAACAGCGATA
> Seq 33  TGTCACTAAGAGCGAACATATGGTTGATCTTAAAGAGAAATTTAAACGCATTTGTGAGAAAACAGCGATA
> Seq 34  TGTCACTAAGAGCGAACATATGGTTGATCTTAAAGAGAAATTTAAACGCATTTGTGAGAAAACAGCGATA
> Seq 35  TGTCACTAAGAGCGAACATATGGTTGATCTTAAAGAGAAATTTAAACGCATTTGTGAGAAAACAGCGATA
> Seq 36  TGTCACTAAGAGCGAACATATGGTTGATCTTAAAGAGAAATTTAAACGCATTTGTGAGAAAACAGCGATA
> Seq 37  TGTCACTAAGAGCGAACATATGGTTGATCTTAAAGAGAAATTTAAACGCATTtctGAGAAAACAGCGATA
```

FIG. 13 (continued)

| | |
|---|---|
| >Seq 38 | TGTCACTAAGAGCGAACATATGGTTGATCTTAAAGAGAAATTTAAACGCATTTGTGAGAAAACAGCGATA |
| >Seq 39 | TGTCACTAAGAGCGAACATATGGTTGATCTTAAAGAGAAATTTAAACGCATTTGTGAGAAAACAGCGATA |
| >Seq 40 | TGTCACTAAGAGCGAACATATGGTTGATCTTAAAGAGAAATTTAAACGCATTtctGAGAAAACAGCGATA |
| >Seq 41 | TGTCACTAAGAGCGAACATATGGTTGATCTTAAAGAGAAATTTAAACGCATTTGTGAGAAAACAGCGATA |
| >Seq 42 | TGTCACTAAGAGCGAACATATGGTTGATCTTAAAGAGAAATTTAAACGCATTTGTGAGAAAACAGCGATA |
| >Seq 43 | TGTCACTAAGAGCGAACATATGGTTGATCTTAAAGAGAAATTTAAACGCATTTGTGAGAAAACAGCGATA |
| >Seq 44 | TGTCACTAAGAGCGAACATATGGTTGATCTTAAAGAGAAATTTAAACGCATTTGTGAGAAAACAGCGATA |
| >Seq 45 | TGTCACTAAGAGCGAACATATGGTTGATCTTAAAGAGAAATTTAAACGCATTTGTGAGAAAACAGCGATA |
| >Seq 46 | TGTCACTAAGAGCGAACATATGGTTGATCTTAAAGAGAAATTTAAACGCATTTGTGAGAAAACAGCGATA |
| >Seq 47 | TGTCACTAAGAGCGAACATATGGTTGATCTTAAAGAGAAATTTAAACGCATTTGTGAGAAAACAGCGATA |
| >Seq 48 | TGTCACTAAGAGCGAACATATGGTTGATCTTAAAGAGAAATTTAAACGCATTTGTGAGAAAACAGCGATA |
| >Seq 49 | TGTCACTAAGAGCGAACATATGGTTGATCTTAAAGAGAAATTTAAACGCATTTGTGAGAAAACAGCGATA |
| >Seq 50 | TGTCACTAAGAGCGAACATATGGTTGATCTTAAAGAGAAATTTAAACGCATTTGTGAGAAAACAGCGATA |
| >Seq 51 | TGTCACTAAGAGCGAACATATGGTTGATCTTAAAGAGAAATTTAAACGCATTTGTGAGAAAACAGCGATA |
| >Seq 52 | TGTCACTAAGAGCGAACATATGGTTGATCTTAAAGAGAAATTTAAACGCATTTGTGAGAAAACAGCGATA |
| >Seq 53 | TGTCACTAAGAGCGAACATATGGTTGATCTTAAAGAGAAATTTAAACGCATTTGTGAGAAAACAGCGATA |
| >Seq 54 | TGTCACTAAGAGCGAACATATGGTTGATCTTAAAGAGAAATTTAAACGCATTTGTGAGAAAACAGCGATA |
| >Seq 55 | TGTCACTAAGAGCGAACATATGGTTGATCTTAAAGAGAAATTTAAACGCATTtctGAGAAAACAGCGATA |
| >Seq 56 | TGTCACTAAGAGCGAACATATGGTTGATCTTAAAGAGAAATTTAAACGCATTgctGAGAAAACAGCGATA |
| >Seq 57 | TGTCACTAAGAGCGAACATATGGTTGATCTTAAAGAGAAATTTAAACGCATTTGTGAGAAAACAGCGATA |
| >Seq 58 | TGTCACTAAGAGCGAACATATGGTTGATCTTAAAGAGAAATTTAAACGCATTTGTGAGAAAACAGCGATA |
| >Seq 59 | TGTCACTAAGAGCGAACATATGGTTGATCTTAAAGAGAAATTTAAACGCATTTGTGAGAAAACAGCGATA |
| >Seq 60 | TGTCACTAAGAGCGAACATATGGTTGATCTTAAAGAGAAATTTAAACGCATTTGTGAGAAAACAGCGATA |
| >Seq 61 | TGTCACTAAGAGCGAACATATGGTTGATCTTAAAGAGAAATTTAAACGCATTTGTGAGAAAACAGCGATA |

FIG. 13 (continued)

```
> Seq  62  TGTCACTAAGAGCGAACATATGGTTGATCTTAAAGAGAAATTTAAACGCATTTGTGAGAAACAGCGATA
            211                     .                    .                    .                280
> Seq   1  AAGAAACGATACCTAGCCCTCACCGAAGAGACTATCTGCAAGAGAAACCCAACAATGTGAGTTCATGGCTC
> Seq   2  AAGAAACGATACCTAGCCCTCACCGAAGAGACTATCTGCAAGAGAAACCCAACAATGTGAGTTCATGGCTC
> Seq   3  AAGAAACGATACCTAGCCCTCACCGAAGAGACTATCTGCAAGAGAAACCCAACAATGTGAGTTCATGGCTC
> Seq   4  AAGAAACGATACCTAGCCCTCACCGAAGAGACTATCTGCAAGAGAAACCCAACAATGTGAGTTCATGGCTC
> Seq   5  AAGAAACGATACCTAGCCCTCACCGAAGAGACTATCTGCAAGAGAAACCCAACAATGTGAGTTCATGGCTC
> Seq   6  AAGAAACGATACCTAGCCCTCACCGAAGAGACTATCTGCAAGAGAAACCCAACAATGTGAGTTCATGGCTC
> Seq   7  AAGAAACGATACCTAGCCCTCACCGAAGAGACTATCTGCAAGAGAAACCCAACAATGTGAGTTCATGGCTC
> Seq   8  AAGAAACGATACCTAGCCCTCACCGAAGAGACTATCTGCAAGAGAAACCCAACAATGTGAGTTCATGGCTC
> Seq   9  AAGAAACGATACCTAGCCCTCACCGAAGAGACTATCTGCAAGAGAAACCCAACAATGTGAGTTCATGGCTC
> Seq  10  AAGAAACGATACCTAGCCCTCACCGAAGAGACTATCTGCAAGAGAAACCCAACAATGtctGAGTTCATGGCTC
> Seq  11  AAGAAACGATACCTAGCCCTCACCGAAGAGACTATCTGCAAGAGAAACCCAACAATGtctGAGTTCATGGCTC
> Seq  12  AAGAAACGATACCTAGCCCTCACCGAAGAGACTATCTGCAAGAGAAACCCAACAATGtctGAGTTCATGGCTC
> Seq  13  AAGAAACGATACCTAGCCCTCACCGAAGAGACTATCTGCAAGAGAAACCCAACAATGtctGAGTTCATGGCTC
> Seq  14  AAGAAACGATACCTAGCCCTCACCGAAGAGACTATCTGCAAGAGAAACCCAACAATGtctGAGTTCATGGCTC
> Seq  15  AAGAAACGATACCTAGCCCTCACCGAAGAGACTATCTGCAAGAGAAACCCAACAATGtctGAGTTCATGGCTC
> Seq  16  AAGAAACGATACCTAGCCCTCACCGAAGAGACTATCTGCAAGAGAAACCCAACAATGtctGAGTTCATGGCTC
> Seq  17  AAGAAACGATACCTAGCCCTCACCGAAGAGACTATCTGCAAGAGAAACCCAACAATGtctGAGTTCATGGCTC
> Seq  18  AAGAAACGATACCTAGCCCTCACCGAAGAGACTATCTGCAAGAGAAACCCAACAATGtctGAGTTCATGGCTC
> Seq  19  AAGAAACGATACCTAGCCCTCACCGAAGAGACTATCTGCAAGAGAAACCCAACAATGtctGAGTTCATGGCTC
> Seq  20  AAGAAACGATACCTAGCCCTCACCGAAGAGACTATCTGCAAGAGAAACCCAACAATGtctGAGTTCATGGCTC
> Seq  21  AAGAAACGATACCTAGCCCTCACCGAAGAGACTATCTGCAAGAGAAACCCAACAATGtctGAGTTCATGGCTC
```

FIG. 13 (continued)

| Seq | Sequence |
|---|---|
| Seq 22 | AAGAAACGATACCTAGCCCTCACCGAAGACTATCTGCAAGAGAACCCAACAATGtctGAGTTCATGGCTC |
| Seq 23 | AAGAAACGATACCTAGCCCTCACCGAAGACTATCTGCAAGAGAACCCAACAATGTGAGTTCATGGCTC |
| Seq 24 | AAGAAACGATACCTAGCCCTCACCGAAGACTATCTGCAAGAGAACCCAACAATGTGAGTTCATGGCTC |
| Seq 25 | AAGAAACGATACCTAGCCCTCACCGAAGACTATCTGCAAGAGAACCCAACAATGTGAGTTCATGGCTC |
| Seq 26 | AAGAAACGATACCTAGCCCTCACCGAAGACTATCTGCAAGAGAACCCAACAATGTGAGTTCATGGCTC |
| Seq 27 | AAGAAACGATACCTAGCCCTCACCGAAGACTATCTGCAAGAGAACCCAACAATGTGAGTTCATGGCTC |
| Seq 28 | AAGAAACGATACCTAGCCCTCACCGAAGACTATCTGCAAGAGAACCCAACAATGTGAGTTCATGGCTC |
| Seq 29 | AAGAAACGATACCTAGCCCTCACCGAAGACTATCTGCAAGAGAACCCAACAATGTGAGTTCATGGCTC |
| Seq 30 | AAGAAACGATACCTAGCCCTCACCGAAGACTATCTGCAAGAGAACCCAACAATGTGAGTTCATGGCTC |
| Seq 31 | AAGAAACGATACCTAGCCCTCACCGAAGACTATCTGCAAGAGAACCCAACAATGTGAGTTCATGGCTC |
| Seq 32 | AAGAAACGATACCTAGCCCTCACCGAAGACTATCTGCAAGAGAACCCAACAATGTGAGTTCATGGCTC |
| Seq 33 | AAGAAACGATACCTAGCCCTCACCGAAGACTATCTGCAAGAGAACCCAACAATGTGAGTTCATGGCTC |
| Seq 34 | AAGAAACGATACCTAGCCCTCACCGAAGACTATCTGCAAGAGAACCCAACAATGTGAGTTCATGGCTC |
| Seq 35 | AAGAAACGATACCTAGCCCTCACCGAAGACTATCTGCAAGAGAACCCAACAATGTGAGTTCATGGCTC |
| Seq 36 | AAGAAACGATACCTAGCCCTCACCGAAGACTATCTGCAAGAGAACCCAACAATGTGAGTTCATGGCTC |
| Seq 37 | AAGAAACGATACCTAGCCCTCACCGAAGACTATCTGCAAGAGAACCCAACAATGtctGAGTTCATGGCTC |
| Seq 38 | AAGAAACGATACCTAGCCCTCACCGAAGACTATCTGCAAGAGAACCCAACAATGTGAGTTCATGGCTC |
| Seq 39 | AAGAAACGATACCTAGCCCTCACCGAAGACTATCTGCAAGAGAACCCAACAATGTGAGTTCATGGCTC |
| Seq 40 | AAGAAACGATACCTAGCCCTCACCGAAGACTATCTGCAAGAGAACCCAACAATGtctGAGTTCATGGCTC |
| Seq 41 | AAGAAACGATACCTAGCCCTCACCGAAGACTATCTGCAAGAGAACCCAACAATGTGAGTTCATGGCTC |
| Seq 42 | AAGAAACGATACCTAGCCCTCACCGAAGACTATCTGCAAGAGAACCCAACAATGTGAGTTCATGGCTC |
| Seq 43 | AAGAAACGATACCTAGCCCTCACCGAAGACTATCTGCAAGAGAACCCAACAATGTGAGTTCATGGCTC |
| Seq 44 | AAGAAACGATACCTAGCCCTCACCGAAGACTATCTGCAAGAGAACCCAACAATGTGAGTTCATGGCTC |
| Seq 45 | AAGAAACGATACCTAGCCCTCACCGAAGACTATCTGCAAGAGAACCCAACAATGTGAGTTCATGGCTC |

FIG. 13 (continued)

```
> Seq 46 AAGAAACGATACCTAGCCCTCACCGAAGACTATCTGCAAGAGAACCCAACAATGTGAGTTCATGGCTC
> Seq 47 AAGAAACGATACCTAGCCCTCACCGAAGACTATCTGCAAGAGAACCCAACAATGTGAGTTCATGGCTC
> Seq 48 AAGAAACGATACCTAGCCCTCACCGAAGACTATCTGCAAGAGAACCCAACAATGTGAGTTCATGGCTC
> Seq 49 AAGAAACGATACCTAGCCCTCACCGAAGACTATCTGCAAGAGAACCCAACAATGTGAGTTCATGGCTC
> Seq 50 AAGAAACGATACCTAGCCCTCACCGAAGACTATCTGCAAGAGAACCCAACAATGTGAGTTCATGGCTC
> Seq 51 AAGAAACGATACCTAGCCCTCACCGAAGACTATCTGCAAGAGAACCCAACAATGTGAGTTCATGGCTC
> Seq 52 AAGAAACGATACCTAGCCCTCACCGAAGACTATCTGCAAGAGAACCCAACAATGTGAGTTCATGGCTC
> Seq 53 AAGAAACGATACCTAGCCCTCACCGAAGACTATCTGCAAGAGAACCCAACAATGTGAGTTCATGGCTC
> Seq 54 AAGAAACGATACCTAGCCCTCACCGAAGACTATCTGCAAGAGAACCCAACAATGtctGAGTTCATGGCTC
> Seq 55 AAGAAACGATACCTAGCCCTCACCGAAGACTATCTGCAAGAGAACCCAACAATGgctGAGTTCATGGCTC
> Seq 56 AAGAAACGATACCTAGCCCTCACCGAAGACTATCTGCAAGAGAACCCAACAATGTGTGAGTTCATGGCTC
> Seq 57 AAGAAACGATACCTAGCCCTCACCGAAGACTATCTGCAAGAGAACCCAACAATGTGTGAGTTCATGGCTC
> Seq 58 AAGAAACGATACCTAGCCCTCACCGAAGACTATCTGCAAGAGAACCCAACAATGTGTGAGTTCATGGCTC
> Seq 59 AAGAAACGATACCTAGCCCTCACCGAAGACTATCTGCAAGAGAACCCAACAATGTGTGAGTTCATGGCTC
> Seq 60 AAGAAACGATACCTAGCCCTCACCGAAGACTATCTGCAAGAGAACCCAACAATGTGTGAGTTCATGGCTC
> Seq 61 AAGAAACGATACCTAGCCCTCACCGAAGACTATCTGCAAGAGAACCCAACAATGTGTGAGTTCATGGCTC
> Seq 62 AAGAAACGATACCTAGCCCTCACCGAAGACTATCTGCAAGAGAACCCAACAATGTGTGAGTTCATGGCTC 281                                                              350
> Seq 1 CATCCTTAAACGCTCGACAAGACCTAGTGGTCACCGGCGTCCCAATGCTTGCAAAGAAGCCGCAGTCAA
> Seq 2 CATCCTTAAACGCTCGACAAGACCTAGTGGTCACCGGCGTCCCAATGCTTGCAAAGAAGCCGCAGTCAA
> Seq 3 CATCCTTAAACGCTCGACAAGACCTAGTGGTCACCGGCGTCCCAATGCTTGCAAAGAAGCCGCAGTCAA
> Seq 4 CATCCTTAAACGCTCGACAAGACCTAGTGGTCACCGGCGTCCCAATGCTTGCAAAGAAGCCGCAGTCAA
> Seq 5 CATCCTTAAACGCTCGACAAGACCTAGTGGTCACCGGCGTCCCAATGCTTGCAAAGAAGCCGCAGTCAA
```

FIG. 13 (continued)

| | |
|---|---|
| Seq 6 | CATCCTTAAACGCTCGACAAGACCTAGTGGTCACCGGCGTCCCAATGCTTGGCAAAGAAGCCGCAGTCAA |
| Seq 7 | CATCCTTAAACGCTCGACAAGACCTAGTGGTCACCGGCGTCCCAATGCTTGGCAAAGAAGCCGCAGTCAA |
| Seq 8 | CATCCTTAAACGCTCGACAAGACCTAGTGGTCACCGGCGTCCCAATGCTTGGCAAAGAAGCCGCAGTCAA |
| Seq 9 | CATCCTTAAACGCTCGACAAGACCTAGTGGTCACCGGCGTCCCAATGCTTGGCAAAGAAGCCGCAGTCAA |
| Seq 10 | CATCCTTAAACGCTCGACAAGACCTAGTGGTCACCGGCGTCCCAATGCTTGGCAAAGAAGCCGCAGTCAA |
| Seq 11 | CATCCTTAAACGCTCGACAAGACCTAGTGGTCACCGGCGTCCCAATGCTTGGCAAAGAAGCCGCAGTCAA |
| Seq 12 | CATCCTTAAACGCTCGACAAGACCTAGTGGTCACCGGCGTCCCAATGCTTGGCAAAGAAGCCGCAGTCAA |
| Seq 13 | CATCCTTAAACGCTCGACAAGACCTAGTGGTCACCGGCGTCCCAATGCTTGGCAAAGAAGCCGCAGTCAA |
| Seq 14 | CATCCTTAAACGCTCGACAAGACCTAGTGGTCACCGGCGTCCCAATGCTTGGCAAAGAAGCCGCAGTCAA |
| Seq 15 | CATCCTTAAACGCTCGACAAGACCTAGTGGTCACCGGCGTCCCAATGCTTGGCAAAGAAGCCGCAGTCAA |
| Seq 16 | CATCCTTAAACGCTCGACAAGACCTAGTGGTCACCGGCGTCCCAATGCTTGGCAAAGAAGCCGCAGTCAA |
| Seq 17 | CATCCTTAAACGCTCGACAAGACCTAGTGGTCACCGGCGTCCCAATGCTTGGCAAAGAAGCCGCAGTCAA |
| Seq 18 | CATCCTTAAACGCTCGACAAGACCTAGTGGTCACCGGCGTCCCAATGCTTGGCAAAGAAGCCGCAGTCAA |
| Seq 19 | CATCCTTAAACGCTCGACAAGACCTAGTGGTCACCGGCGTCCCAATGCTTGGCAAAGAAGCCGCAGTCAA |
| Seq 20 | CATCCTTAAACGCTCGACAAGACCTAGTGGTCACCGGCGTCCCAATGCTTGGCAAAGAAGCCGCAGTCAA |
| Seq 21 | CATCCTTAAACGCTCGACAAGACCTAGTGGTCACCGGCGTCCCAATGCTTGGCAAAGAAGCCGCAGTCAA |
| Seq 22 | CATCCTTAAACGCTCGACAAGACCTAGTGGTCACCGGCGTCCCAATGCTTGGCAAAGAAGCCGCAGTCAA |
| Seq 23 | CATCCTTAAACGCTCGACAAGACCTAGTGGTCACCGGCGTCCCAATGCTTGGCAAAGAAGCCGCAGTCAA |
| Seq 24 | CATCCTTAAACGCTCGACAAGACCTAGTGGTCACCGGCGTCCCAATGCTTGGCAAAGAAGCCGCAGTCAA |
| Seq 25 | CATCCTTAAACGCTCGACAAGACCTAGTGGTCACCGGCGTCCCAATGCTTGGCAAAGAAGCCGCAGTCAA |
| Seq 26 | CATCCTTAAACGCTCGACAAGACCTAGTGGTCACCGGCGTCCCAATGCTTGGCAAAGAAGCCGCAGTCAA |
| Seq 27 | CATCCTTAAACGCTCGACAAGACCTAGTGGTCACCGGCGTCCCAATGCTTGGCAAAGAAGCCGCAGTCAA |
| Seq 28 | CATCCTTAAACGCTCGACAAGACCTAGTGGTCACCGGCGTCCCAATGCTTGGCAAAGAAGCCGCAGTCAA |
| Seq 29 | CATCCTTAAACGCTCGACAAGACCTAGTGGTCACCGGCGTCCCAATGCTTGGCAAAGAAGCCGCAGTCAA |

FIG. 13 (continued)

| | | |
|---|---|---|
| Seq 30 | CATCCTTAAACGCTCGACAAGACCTAGTGGTCACCGGCGTCCCAATGCTTGGCAAAGAAGCCGCAGTCAA |
| Seq 31 | CATCCTTAAACGCTCGACAAGACCTAGTGGTCACCGGCGTCCCAATGCTTGGCAAAGAAGCCGCAGTCAA |
| Seq 32 | CATCCTTAAACGCTCGACAAGACCTAGTGGTCACCGGCGTCCCAATGCTTGGCAAAGAAGCCGCAGTCAA |
| Seq 33 | CATCCTTAAACGCTCGACAAGACCTAGTGGTCACCGGCGTCCCAATGCTTGGCAAAGAAGCCGCAGTCAA |
| Seq 34 | CATCCTTAAACGCTCGACAAGACCTAGTGGTCACCGGCGTCCCAATGCTTGGCAAAGAAGCCGCAGTCAA |
| Seq 35 | CATCCTTAAACGCTCGACAAGACCTAGTGGTCACCGGCGTCCCAATGCTTGGCAAAGAAGCCGCAGTCAA |
| Seq 36 | CATCCTTAAACGCTCGACAAGACCTAGTGGTCACCGGCGTCCCAATGCTTGGCAAAGAAGCCGCAGTCAA |
| Seq 37 | CATCCTTAAACGCTCGACAAGACCTAGTGGTCACCGGCGTCCCAATGCTTGGCAAAGAAGCCGCAGTCAA |
| Seq 38 | CATCCTTAAACGCTCGACAAGACCTAGTGGTCACCGGCGTCCCAATGCTTGGCAAAGAAGCCGCAGTCAA |
| Seq 39 | CATCCTTAAACGCTCGACAAGACCTAGTGGTCACCGGCGTCCCAATGCTTGGCAAAGAAGCCGCAGTCAA |
| Seq 40 | CATCCTTAAACGCTCGACAAGACCTAGTGGTCACCGGCGTCCCAATGCTTGGCAAAGAAGCCGCAGTCAA |
| Seq 41 | CATCCTTAAACGCTCGACAAGACCTAGTGGTCACCGGCGTCCCAATGCTTGGCAAAGAAGCCGCAGTCAA |
| Seq 42 | CATCCTTAAACGCTCGACAAGACCTAGTGGTCACCGGCGTCCCAATGCTTGGCAAAGAAGCCGCAGTCAA |
| Seq 43 | CATCCTTAAACGCTCGACAAGACCTAGTGGTCACCGGCGTCCCAATGCTTGGCAAAGAAGCCGCAGTCAA |
| Seq 44 | CATCCTTAAACGCTCGACAAGACCTAGTGGTCACCGGCGTCCCAATGCTTGGCAAAGAAGCCGCAGTCAA |
| Seq 45 | CATCCTTAAACGCTCGACAAGACCTAGTGGTCACCGGCGTCCCAATGCTTGGCAAAGAAGCCGCAGTCAA |
| Seq 46 | CATCCTTAAACGCTCGACAAGACCTAGTGGTCACCGGCGTCCCAATGCTTGGCAAAGAAGCCGCAGTCAA |
| Seq 47 | CATCCTTAAACGCTCGACAAGACCTAGTGGTCACCGGCGTCCCAATGCTTGGCAAAGAAGCCGCAGTCAA |
| Seq 48 | CATCCTTAAACGCTCGACAAGACCTAGTGGTCACCGGCGTCCCAATGCTTGGCAAAGAAGCCGCAGTCAA |
| Seq 49 | CATCCTTAAACGCTCGACAAGACCTAGTGGTCACCGGCGTCCCAATGCTTGGCAAAGAAGCCGCAGTCAA |
| Seq 50 | CATCCTTAAACGCTCGACAAGACCTAGTGGTCACCGGCGTCCCAATGCTTGGCAAAGAAGCCGCAGTCAA |
| Seq 51 | CATCCTTAAACGCTCGACAAGACCTAGTGGTCACCGGCGTCCCAATGCTTGGCAAAGAAGCCGCAGTCAA |
| Seq 52 | CATCCTTAAACGCTCGACAAGACCTAGTGGTCACCGGCGTCCCAATGCTTGGCAAAGAAGCCGCAGTCAA |
| Seq 53 | CATCCTTAAACGCTCGACAAGACCTAGTGGTCACCGGCGTCCCAATGCTTGGCAAAGAAGCCGCAGTCAA |

FIG. 13 (continued)

```
     54 CATCCTTAAACGCTCGACAAGACCTAGTGGTCACCGGCGTCCCAATGCTTGGCAAAGAAGCCCAGTCAA
     55 CATCCTTAAACGCTCGACAAGACCTAGTGGTCACCGGCGTCCCAATGCTTGGCAAAGAAGCCCAGTCAA
     56 CATCCTTAAACGCTCGACAAGACCTAGTGGTCACCGGCGTCCCAATGCTTGGCAAAGAAGCCCAGTCAA
     57 CATCCTTAAACGCTCGACAAGACCTAGTGGTCACCGGCGTCCCAATGCTTGGCAAAGAAGCCCAGTCAA
     58 CATCCTTAAACGCTCGACAAGACCTAGTGGTCACCGGCGTCCCAATGCTTGGCAAAGAAGCCCAGTCAA
     59 CATCCTTAAACGCTCGACAAGACCTAGTGGTCACCGGCGTCCCAATGCTTGGCAAAGAAGCCCAGTCAA
     60 CATCCTTAAACGCTCGACAAGACCTAGTGGTCACCGGCGTCCCAATGCTTGGCAAAGAAGCCCAGTCAA
     61 CATCCTTAAACGCTCGACAAGACCTAGTGGTCACCGGCGTCCCAATGCTTGGCAAAGAAGCCCAGTCAA
     62 CATCCTTAAACGCTCGACAAGACCTAGTGGTCACCGGCGTCCCAATGCTTGGCAAAGAAGCCCAGTCAA 351                                                                420
      1 GGCCATTGATGATGAATGGGGACTACCAAGATCACCCAAAATCCAAGATCACCCACCTCACCGCTGGCGTT
      2 GGCCATTGATGATGAATGGGGACTACCAAGATCACCCAAAATCCAAGATCACCCACCTCACCGCTGGCGTT
      3 GGCCATTGATGATGAATGGGGACTACCAAGATCACCCAAAATCCAAGATCACCCACCTCACCGCTGGCGTT
      4 GGCCATTGATGATGAATGGGGACTACCAAGATCACCCAAAATCCAAGATCACCCACCTCACCGCTGGCGTT
      5 GGCCATTGATGATGAATGGGGACTACCAAGATCACCCAAAATCCAAGATCACCCACCTCACCGCTGGCGTT
      6 GGCCATTGATGATGAATGGGGACTACCAAGATCACCCAAAATCCAAGATCACCCACCTCACCGCTGGCGTT
      7 GGCCATTGATGATGAATGGGGACTACCAAGATCACCCAAAATCCAAGATCACCCACCTCACCGCTGGCGTT
      8 GGCCATTGATGATGAATGGGGACTACCAAGATCACCCAAAATCCAAGATCACCCACCTCACCGCTGGCGTT
      9 GGCCATTGATGATGAATGGGGACTACCAAGATCACCCAAAATCCAAGATCACCCACCTCACCGCTGGCGTT
     10 GGCCATTGATGATGAATGGGGACTACCAAGATCACCCAAAATCCAAGATCACCCACCTCACCGCTGGCGTT
     11 GGCCATTGATGATGAATGGGGACTACCAAGATCACCCAAAATCCAAGATCACCCACCTCACCGCTGGCGTT
     12 GGCCATTGATGATGAATGGGGACTACCAAGATCACCCAAAATCCAAGATCACCCACCTCACCGCTGGCGTT
     13 GGCCATTGATGATGAATGGGGACTACCAAGATCACCCAAAATCCAAGATCACCCACCTCACCGCTGGCGTT
```

FIG. 13 (continued)

| Seq | Sequence |
|---|---|
| Seq 14 | GGCCATTGATGAATGGGGACTACCAAAAATCCAAGATCACCCACCTCATCTTTCTGCACCttcGCTGGCGTT |
| Seq 15 | GGCCATTGATGAATGGGGACTACCAAAAATCCAAGATCACCCACCTCATCTTTCTGCACCGCGCTGGCGTT |
| Seq 16 | GGCCATTGATGAATGGGGACTACCAAAAATCCAAGATCACCCACCTCATCTTTCTGCACCGCGCTGGCGTT |
| Seq 17 | GGCCATTGATGAATGGGGACTACCAAAAATCCAAGATCACCCACCTCATCTTTCTGCACCttcGCTGGCGTT |
| Seq 18 | GGCCATTGATGAATGGGGACTACCAAAAATCCAAGATCACCCACCTCATCTTTCTGCACCGCGCTGGCGTT |
| Seq 19 | GGCCATTGATGAATGGGGACTACCAAAAATCCAAGATCACCCACCTCATCTTTCTGCACCGCGCTGGCGTT |
| Seq 20 | GGCCATTGATGAATGGGGACTACCAAAAATCCAAGATCACCCACCTCATCTTTCTGCACCGCGCTGGCGTT |
| Seq 21 | GGCCATTGATGAATGGGGACTACCAAAAATCCAAGATCACCCACCTCATCTTTCTGCACCGCGCTGGCGTT |
| Seq 22 | GGCCATTGATGAATGGGGACTACCAAAAATCCAAGATCACCCACCTCATCTTTCTGCACCGCGCTGGCGTT |
| Seq 23 | GGCCATTGATGAATGGGGACTACCAAAAATCCAAGATCACCCACCTCATCTTTCTGCACCGCGCTGGCGTT |
| Seq 24 | GGCCATTGATGAATGGGGACTACCAAAAATCCAAGATCACCCACCTCATCTTTCTGCACCttGCTGGCGTT |
| Seq 25 | GGCCATTGATGAATGGGGACTACCAAAAATCCAAGATCACCCACCTCATCTTTCTGCACCatgGCTGGCGTT |
| Seq 26 | GGCCATTGATGAATGGGGACTACCAAAAATCCAAGATCACCCACCTCATCTTTCTGCACCctcGCTGGCGTT |
| Seq 27 | GGCCATTGATGAATGGGGACTACCAAAAATCCAAGATCACCCACCTCATCTTTCTGCACCGCGCTGGCGTT |
| Seq 28 | GGCCATTGATGAATGGGGACTACCAAAAATCCAAGATCACCCACCTCATCTTTCTGCACCGCGCTGGCGTT |
| Seq 29 | GGCCATTGATGAATGGGGACTACCAAAAATCCAAGATCACCCACCTCATCTTTCTGCACCGCGCTGGCGTT |
| Seq 30 | GGCCATTGATGAATGGGGACTACCAAAAATCCAAGATCACCCACCTCATCTTTCTGCACCGCGCTGGCGTT |
| Seq 31 | GGCCATTGATGAATGGGGACTACCAAAAATCCAAGATCACCCACCTCATCTTTCTGCACCGCGCTGGCGTT |
| Seq 32 | GGCCATTGATGAATGGGGACTACCAAAAATCCAAGATCACCCACCTCATCTTTCTGCACCGCGCTGGCGTT |
| Seq 33 | GGCCATTGATGAATGGGGACTACCAAAAATCCAAGATCACCCACCTCATCTTTCTGCACCGCGCTGGCGTT |
| Seq 34 | GGCCATTGATGAATGGGGACTACCAAAAATCCAAGATCACCCACCTCATCTTTCTGCACCGCGCTGGCGTT |
| Seq 35 | GGCCATTGATGAATGGGGACTACCAAAAATCCAAGATCACCCACCTCATCTTTCTGCACCGCGCTGGCGTT |
| Seq 36 | GGCCATTGATGAATGGGGACTACCAAAAATCCAAGATCACCCACCTCATCTTTCTGCACCGCGCTGGCGTT |
| Seq 37 | GGCCATTGATGAATGGGGACTACCAAAAATCCAAGATCACCCACCTCATCTTTCTGCACCGCGCTGGCGTT |

FIG. 13 (continued)

| Seq | Sequence |
|---|---|
| > Seq 38 | GGCCATTGATGAATGGGGACTACCAAGATCACCCACCTCATCTTTCTGCACCACCGCTGGCGTT |
| > Seq 39 | GGCCATTGATGAATGGGGACTACCAAAATCACCCACCTCATCTTTCTGCACCACCGCTGGCGTT |
| > Seq 40 | GGCCATTGATGAATGGGGACTACCAAAATCACCCACCTCATCTTTCTGCACCACCGCTGGCGTT |
| > Seq 41 | GGCCATTGATGAATGGGGACTACCAAAATCACCCACCTCATCTTTCTGCACCACCGCTGGCGTT |
| > Seq 42 | GGCCATTGATGAATGGGGACTACCAAAATCACCCACCTCATCTTTCTGCACCctcGCTGGCGTT |
| > Seq 43 | GGCCATTGATGAATGGGGACTACCAAAATCACCCACCTCATCTTTCTGCACCatgGCTGGCGTT |
| > Seq 44 | GGCCATTGATGAATGGGGACTACCAAAATCACCCACCTCATCTTTCTGCACCACCGCTGGCGTT |
| > Seq 45 | GGCCATTGATGAATGGGGACTACCAAAATCACCCACCTCATCTTTCTGCACCACCGCTGGCGTT |
| > Seq 46 | GGCCATTGATGAATGGGGACTACCAAAATCACCCACCTCATCTTTCTGCACCACCGCTGGCGTT |
| > Seq 47 | GGCCATTGATGAATGGGGACTACCAAAATCACCCACCTCATCTTTCTGCACCACCGCTGGCGTT |
| > Seq 48 | GGCCATTGATGAATGGGGACTACCAAAATCACCCACCTCATCTTTCTGCACCACCGCTGGCGTT |
| > Seq 49 | GGCCATTGATGAATGGGGACTACCAAAATCACCCACCTCATCTTTCTGCACCACCGCTGGCGTT |
| > Seq 50 | GGCCATTGATGAATGGGGACTACCAAAATCACCCACCTCATCTTTCTGCACCACCGCTGGCGTT |
| > Seq 51 | GGCCATTGATGAATGGGGACTACCAAAATCACCCACCTCATCTTTCTtcACCACCGCTGGCGTT |
| > Seq 52 | GGCCATTGATGAATGGGGACTACCAAAATCACCCACCTCATCTTTCTTgcgCCACCGCTGGCGTT |
| > Seq 53 | GGCCATTGATGAATGGGGACTACCAAAATCACCCACCTCATCTTTCTGCACCACCGCTGGCGTT |
| > Seq 54 | GGCCATTGATGAATGGGGACTACCAAAATCACCCACCTCATCTTTCTGCACCACCGCTGGCGTT |
| > Seq 55 | GGCCATTGATGAATGGGGACTACCAAAATCACCCACCTCATCTTTCTGCACCACCGCTGGCGTT |
| > Seq 56 | GGCCATTGATGAATGGGGACTACCAAAATCACCCACCTCATCTTTCTGCACCACCGCTGGCGTT |
| > Seq 57 | GGCCATTGATGAATGGGGACTACCAAAATCACCCACCTCATCTTTCTGCACCACCGCTGGCGTT |
| > Seq 58 | GGCCATTGATGAATGGGGACTACCAAAATCACCCACCTCATCTTTCTGCACCACCGCTGGCGTT |
| > Seq 59 | GGCCATTGATGAATGGGGACTACCAAAATCACCCACCTCATCTTTCTGCACCACCGCTGGCGTT |
| > Seq 60 | GGCCATTGATGAATGGGGACTACCAAAATCACCCACCTCATCTTTCTGCACCACCGCTGGCGTT |
| > Seq 61 | GGCCATTGATGAATGGGGACTACCAAAATCACCCACCTCATCTTTCTGCACCACCGCTGGCGTT |

FIG. 13 (continued)

```
> Seq  62  GGCCATTGATGATGAATGGGACTACCAAAATCCAAGATCACCCACCTCATCTTCTGCACCACCGCTGGCGTT 421                                                                    490
> Seq   1  GACATGCCCGGTGCTGACTATCAACTCGTCAAACTCGTCAAACTCCTTGGTCTCTCCCCTTCAGTCAAACGCTATATGT
> Seq   2  GACATGCCCGGTGCTGACTATCAACTCGTCAAACTCGTCAAACTCCTTGGTCTCTCCCCTTCAGTCAAACGCTATATGT
> Seq   3  GACATGCCCGGTGCTGACTATCAACTCGTCAAACTCGTCAAACTCCTTGGTCTCTCCCCTTCAGTCAAACGCTATATGT
> Seq   4  GACATGCCCGGTGCTGACTATCAACTCGTCAAACTCGTCAAACTCCTTGGTCTCTCCCCTTCAGTCAAACGCTATATGT
> Seq   5  GACATGCCCGGTGCTGACTATCAACTCGTCAAACTCGTCAAACTCCTTGGTCTCTCCCCTTCAGTCAAACGCTATATGT
> Seq   6  GACATGCCCGGTGCTGACTATCAACTCGTCAAACTCGTCAAACTCCTTGGTCTCTCCCCTTCAGTCAAACGCTATATGT
> Seq   7  GACATGCCCGGTGCTGACTATCAACTCGTCAAACTCGTCAAACTCCTTGGTCTCTCCCCTTCAGTCAAACGCTATATGT
> Seq   8  GACATGCCCGGTGCTGACTATCAACTCGTCAAACTCGTCAAACTCCTTGGTCTCTCCCCTTCAGTCAAACGCTATATGT
> Seq   9  GACATGCCCGGTGCTGACTATCAACTCGTCAAACTCGTCAAACTCCTTGGTCTCTCCCCTTCAGTCAAACGCTATATGT
> Seq  10  GACATGCCCGGTGCTGACTATCAACTCGTCAAACTCGTCAAACTCCTTGGTCTCTCCCCTTCAGTCAAACGCTATATGT
> Seq  11  GACATGCCCGGTGCTGACTATCAACTCGTCAAACTCGTCAAACTCCTTGGTCTCTCCCCTTCAGTCAAACGCTATATGT
> Seq  12  GACATGCCCGGTGCTGACTATCAACTCGTCAAACTCGTCAAACTCCTTGGTCTCTCCCCTTCAGTCAAACGCTATATGT
> Seq  13  GACATGCCCGGTGCTGACTATCAACTCGTCAAACTCGTCAAACTCCTTGGTCTCTCCCCTTCAGTCAAACGCTATATGT
> Seq  14  GACATGCCCGGTGCTGACTATCAACTCGTCAAACTCGTCAAACTCCTTGGTCTCTCCCCTTCAGTCAAACGCTATATGT
> Seq  15  GACATGCCCGGTGCTGACTATCAACTCGTCAAACTCGTCAAACTCCTTGGTCTCTCCCCTTCAGTCAAACGCTATATGT
> Seq  16  GACATGCCCGGTGCTGACTATCAACTCGTCAAACTCGTCAAACTCCTTGGTCTCTCCCCTTCAGTCAAACGCTATATGT
> Seq  17  GACATGCCCGGTGCTGACTATCAACTCGTCAAACTCGTCAAACTCCTTGGTCTCTCCCCTTCAGTCAAACGCTATATGT
> Seq  18  GACATGCCCGGTGCTGACTATCAACTCGTCAAACTCGTCAAACTCCTTGGTCTCTCCCCTTCAGTCAAACGCTATATGT
> Seq  19  GACATGCCCGGTGCTGACTATCAACTCGTCAAACTCGTCAAACTCCTTGGTCTCTCCCCTTCAGTCAAACGCTATATGT
> Seq  20  GACATGCCCGGTGCTGACTATCAACTCGTCAAACTCGTCAAACTCCTTGGTCTCTCCCCTTCAGTCAAACGCTATATGT
> Seq  21  GACATGCCCGGTGCTGACTATCAACTCGTCAAACTCGTCAAACTCCTTGGTCTCTCCCCTTCAGTCAAACGCTATATGT
```

FIG. 13 (continued)

```
> Seq 22  GACATGCCCGGTGCTGACTATCAAACTCGTCGTCAAACTCCTTGGTCTCTCCCTTCAGTCAAACGCTATATGT
> Seq 23  GACATGCCCGGTGCTGACTATCAAACTCGTCGTCAAACTCCTTGGTCTCTCCCTTCAGTCAAACGCTATATGT
> Seq 24  GACATGCCCGGTGCTGACTATCAAACTCGTCGTCAAACTCCTTGGTCTCTCCCTTCAGTCAAACGCTATATGT
> Seq 25  GACATGCCCGGTGCTGACTATCAAACTCGTCGTCAAACTCCTTGGTCTCTCCCTTCAGTCAAACGCTATATGT
> Seq 26  GACATGCCCGGTGCTGACTATCAAACTCGTCGTCAAACTCCTTGGTCTCTCCCTTCAGTCAAACGCTATATGT
> Seq 27  GACATGCCCGGTGCTGACTATCAAACTCGTCGTCAAACTCCTTGGTCTCTCCCTTCAGTCAAACGCTATATGT
> Seq 28  GACATGCCCGGTGCTGACTATCAAACTCGTCGTCAAACTCCTTGGTCTCTCCCTTCAGTCAAACGCTATATGT
> Seq 29  GACATGCCCGGTGCTGACTATCAAACTCGTCGTCAAACTCCTTGGTCTCTCCCTTCAGTCAAACGCTATATGT
> Seq 30  GACATGCCCGGTGCTGACTATCAAACTCGTCGTCAAACTCCTTGGTCTCTCCCTTCAGTCAAACGCTATATGT
> Seq 31  GACATGCCCGGTGCTGACTATCAAACTCGTCGTCAAACTCCTTGGTCTCTCCCTTCAGTCAAACGCTATATGT
> Seq 32  GACATGCCCGGTGCTGACTATCAAACTCGTCGTCAAACTCCTTGGTCTCTCCCTTCAGTCAAACGCTATATGT
> Seq 33  GACATGCCCGGTGCTGACTATCAAACTCGTCGTCAAACTCCTTGGTCTCTCCCTTCAGTCAAACGCTATATGT
> Seq 34  GACATGCCCGGTGCTGACTATCAAACTCGTCGTCAAACTCCTTGGTCTCTCCCTTCAGTCAAACGCTATATGT
> Seq 35  GACATGCCCGGTGCTGACTATCAAACTCGTCGTCAAACTCCTTGGTCTCTCCCTTCAGTCAAACGCTATATGT
> Seq 36  GACATGCCCGGTGCTGACTATCAAACTCGTCGTCAAACTCCTTGGTCTCTCCCTTCAGTCAAACGCTATATGT
> Seq 37  GACATGCCCGGTGCTGACTATCAAACTCGTCGTCAAACTCCTTGGTCTCTCCCTTCAGTCAAACGCTATATGT
> Seq 38  GACATGCCCGGTGCTGACTATCAAACTCGTCGTCAAACTCCTTGGTCTCTCCCTTCAGTCAAACGCTATATGT
> Seq 39  GACATGCCCGGTGCTGACTATCAAACTCGTCGTCAAACTCCTTGGTCTCTCCCTTCAGTCAAACGCTATATGT
> Seq 40  GACATGCCCGGTGCTGACTATCAAACTCGTCGTCAAACTCCTTGGTCTCTCCCTTCAGTCAAACGCTATATGT
> Seq 41  GACATGCCCGGTGCTGACTATCAAACTCGTCGTCAAACTCCTTGGTCTCTCCCTTCAGTCAAACGCTATATGT
> Seq 42  GACATGCCCGGTGCTGACTATCAAACTCGTCGTCAAACTCCTTGGTCTCTCCCTTCAGTCAAACGCTATATGT
> Seq 43  GACATGCCCGGTGCTGACTATCAAACTCGTCGTCAAACTCCTTGGTCTCTCCCTTCAGTCAAACGCTATATGT
> Seq 44  GACATGCCCGGTGCTGACTATCAAACTCGTCGTCAAACTCCTTGGTCTCTCCCTTCAGTCAAACGCTATATGT
> Seq 45  GACATGCCCGGTGCTGACTATCAAACTCGTCGTCAAACTCCTTGGTCTCTCCCTTCAGTCAAACGCTATATGT
```

FIG. 13 (continued)

```
     46 GACATGCCCGGTGCTGACTATCAAACTCGTCAAACTCCTTGGTCTCTCCCTTCAGTCAAACGCTATATGT
     47 GACATGCCCGGTGCTGACTATCAAACTCGTCAAACTCCTTGGTCTCTCCCTTCAGTCAAACGCTATATGT
     48 GACATGCCCGGTGCTGACTATCAAACTCGTCAAACTCCTTGGTCTCTCCCTTCAGTCAAACGCTATATGT
     49 GACATGCCCGGTGCTGACTATCAAACTCGTCAAACTCCTTGGTCTCTCCCTTCAGTCAAACGCTATATGT
     50 GACATGCCCGGTGCTGACTATCAAACTCGTCAAACTCCTTGGTCTCTCCCTTCAGTCAAACGCTATATGT
     51 GACATGCCCGGTGCTGACTATCAAACTCGTCAAACTCCTTGGTCTCTCCCTTCAGTCAAACGCTATATGT
     52 GACATGCCCGGTGCTGACTATCAAACTCGTCAAACTCCTTGGTCTCTCCCTTCAGTCAAACGCTATATGT
     53 GACATGCCCGGTGCTGACTATCAAACTCGTCAAACTCCTTGGTCTCTCCCTTCAGTCAAACGCTATATGT
     54 GACATGCCCGGTGCTGACTATCAAACTCGTCAAACTCCTTGGTCTCTCCCTTCAGTCAAACGCTATATGT
     55 GACATGCCCGGTGCTGACTATCAAACTCGTCAAACTCCTTGGTCTCTCCCTTCAGTCAAACGCTATATGT
     56 GACATGCCCGGTGCTGACTATCAAACTCGTCAAACTCCTTGGTCTCTCCCTTCAGTCAAACGCTATATGT
     57 GACATGCCCGGTGCTGACTATCAAACTCGTCAAACTCCTTGGTCTCTCCCTTCAGTCAAACGCTATATGT
     58 GACATGCCCGGTGCTGACTATCAAACTCGTCAAACTCCTTGGTCTCTCCCTTCAGTCAAACGCTATATGT
     59 GACATGCCCGGTGCTGACTATCAAACTCGTCAAACTCCTTGGTCTCTCCCTTCAGTCAAACGCTATATGT
     60 GACATGCCCGGTGCTGACTATCAAACTCGTCAAACTCCTTGGTCTCTCCCTTCAGTCAAACGCTATATGT
     61 GACATGCCCGGTGCTGACTATCAAACTCGTCAAACTCCTTGGTCTCTCCCTTCAGTCAAACGCTATATGT
     62 GACATGCCCGGTGCTGACTATCAAACTCGTCAAACTCCTTGGTCTCTCCCTTCAGTCAAACGCTATATGT 491                                                                  560
      1 TGTACCAACAGGGATGTGCCGGCCGGGCACAGTCCTCCGGCTAGCCAAGGACTTGCTGAAAACAACAA
      2 TGTACCAACAGGGATGTGCCGGCCGGGCACAGTCCTCCGGCTAGCCAAGGACTTGCTGAAAACAACAA
      3 TGTACCAACAGGGAgctGCCGGCCGGGCACAGTCCTCCGGCTAGCCAAGGACTTGCTGAAAACAACAA
      4 TGTACCAACAGGGATGTGCCGGCCGGGCACAGTCCTCCGGCTAGCCAAGGACTTGCTGAAAACAACAA
      5 TGTACCAACAGGGATGTGCCGGCCGGGCACAGTCCTCCGGCTAGCCAAGGACTTGCTGAAAACAACAA
```

FIG. 13 (continued)

| Seq | Sequence |
|---|---|
| Seq v 6 | TGTACCAACAGGGATGTGCCGGCGGCACAGTCCTCCGGCTAGCCAAGGACCTTGCTGAAAAACAACAA |
| Seq v 7 | TGTACCAACAGGGATGTGCCGGCGGCACAGTCCTCCGGCTAGCCAAGGACCTTGCTGAAAAACAACAA |
| Seq v 8 | TGTACCAACAGGGATGTGCCGGCGGCACAGTCCTCCGGCTAGCCAAGGACCTTGCTGAAAAACAACAA |
| Seq v 9 | TGTACCAACAGGGATGTGCCGCCGGCACAGTCCTCCGGCTAGCCAAGGACCTTGCTGAAAAACAACAA |
| Seq v 10 | TGTACCAACAGGGATGTGCCGCCGGCACAGTCCTCCGGCTAGCCAAGGACCTTGCTGAAAAACAACAA |
| Seq v 11 | TGTACCAACAGGGATGTGCCGCCGGCACAGTCCTCCGGCTAGCCAAGGACCTTGCTGAAAAACAACAA |
| Seq v 12 | TGTACCAACAGGGATGTGCCGCCGGCACAGTCCTCCGGCTAGCCAAGGACCTTGCTGAAAAACAACAA |
| Seq v 13 | TGTACCAACAGGGATGTGCCGCCGGCACAGTCCTCCGGCTAGCCAAGGACCTTGCTGAAAAACAACAA |
| Seq v 14 | TGTACCAACAGGGATGTGCCGCCGGCACAGTCCTCCGGCTAGCCAAGGACCTTGCTGAAAAACAACAA |
| Seq v 15 | TGTACCAACAGGGATGTGCCGCCGGCACAGTCCTCCGGCTAGCCAAGGACCTTGCTGAAAAACAACAA |
| Seq v 16 | TGTACCAACAGGGATGTGCCGCCGGCACAGTCCTCCGGCTAGCCAAGGACCTTGCTGAAAAACAACAA |
| Seq v 17 | TGTACCAACAGGGATGTGCCGCCGGCACAGTCCTCCGGCTAGCCAAGGACCTTGCTGAAAAACAACAA |
| Seq v 18 | TGTACCAACAGGGATGTGCCGCCGGCACAGTCCTCCGGCTAGCCAAGGACCTTGCTGAAAAACAACAA |
| Seq v 19 | TGTACCAACAGGGATGTGCCGCCGGCACAGTCCTCCGGCTAGCCAAGGACCTTGCTGAAAAACAACAA |
| Seq v 20 | TGTACCAACAGGGATGTGCCGCCGGCACAGTCCTCCGGCTAGCCAAGGACCTTGCTGAAAAACAACAA |
| Seq v 21 | TGTACCAACAGGGATGTGCCGCCGGCACAGTCCTCCGGCTAGCCAAGGACCTTGCTGAAAAACAACAA |
| Seq v 22 | TGTACCAACAGGGATGTGCCGCCGGCACAGTCCTCCGGCTAGCCAAGGACCTTGCTGAAAAACAACAA |
| Seq v 23 | TGTACCAACAGGGATGTGCCGCCGGCACAGTCCTCCGGCTAGCCAAGGACCTTGCTGAAAAACAACAA |
| Seq v 24 | TGTACCAACAGGGATGTGCCGCCGGCACAGTCCTCCGGCTAGCCAAGGACCTTGCTGAAAAACAACAA |
| Seq v 25 | TGTACCAACAGGGATGTGCCGCCGGCACAGTCCTCCGGCTAGCCAAGGACCTTGCTGAAAAACAACAA |
| Seq v 26 | TGTACCAACAGGGATGTGCCGCCGGCACAGTCCTCCGGCTAGCCAAGGACCTTGCTGAAAAACAACAA |
| Seq v 27 | TGTACCAACAGGGATGTGCCGCCGGCACAGTCCTCCGGCTAGCCAAGGACCTTGCTGAAAAACAACAA |
| Seq v 28 | TGTACCAACAGGGATGTGCCGCCGGCACAGTCCTCCGGCTAGCCAAGGACCTTGCTGAAAAACAACAA |
| Seq v 29 | TGTACCAACAGGGATGTGCCGCCGGCACAGTCCTCCGGCTAGCCAAGGACCTTGCTGAAAAACAACAA |

FIG. 13 (continued)

| Seq 30 | TGTACCAACAGGGAgctGCCGCCGGCACAGTCCTCCGGCTAGCCAAGGACCTTGCTGAAAACAACAA |
| Seq 31 | TGTACCAACAGGGATGTGCCGCCGGCACAGTCCTCCGGCTAGCCAAGGACCTTGCTGAAAACAACAA |
| Seq 32 | TGTACCAACAGGGATGTGCCGCCGGCACAGTCCTCCGGCTAGCCAAGGACCTTGCTGAAAACAACAA |
| Seq 33 | TGTACCAACAGGGATGTGCCGCCGGCACAGTCCTCCGGCTAGCCAAGGACCTTGCTGAAAACAACAA |
| Seq 34 | TGTACCAACAGGGATGTGCCGCCGGCACAGTCCTCCGGCTAGCCAAGGACCTTGCTGAAAACAACAA |
| Seq 35 | TGTACCAACAGGGATGTGCCGCCGGCACAGTCCTCCGGCTAGCCAAGGACCTTGCTGAAAACAACAA |
| Seq 36 | TGTACCAACAGGGATGTGCCGCCGGCACAGTCCTCCGGCTAGCCAAGGACCTTGCTGAAAACAACAA |
| Seq 37 | TGTACCAACAGGGATGTGCCGCCGGCACAGTCCTCCGGCTAGCCAAGGACCTTGCTGAAAACAACAA |
| Seq 38 | TGTACCAACAGGGATGTGCCGCCGGCACAGTCCTCCGGCTAGCCAAGGACCTTGCTGAAAACAACAA |
| Seq 39 | TGTACCAACAGGGATGTGCCGCCGGCACAGTCCTCCGGCTAGCCAAGGACCTTGCTGAAAACAACAA |
| Seq 40 | TGTACCAACAGGGATGTGCCGCCGGCACAGTCCTCCGGCTAGCCAAGGACCTTGCTGAAAACAACAA |
| Seq 41 | TGTACCAACAGGGATGTGCCGCCGGCACAGTCCTCCGGCTAGCCAAGGACCTTGCTGAAAACAACAA |
| Seq 42 | TGTACCAACAGGGATGTGCCGCCGGCACAGTCCTCCGGCTAGCCAAGGACCTTGCTGAAAACAACAA |
| Seq 43 | TGTACCAACAGGGATGTGCCGCCGGCACAGTCCTCCGGCTAGCCAAGGACCTTGCTGAAAACAACAA |
| Seq 44 | TGTACCAACAGGGATGTGCCGCCGGCACAGTCCTCCGGCTAGCCAAGGACCTTGCTGAAAACAACAA |
| Seq 45 | TGTACCAACAGGGATGTGCCGCCGGCACAGTCCTCCGGCTAGCCAAGGACCTTGCTGAAAACAACAA |
| Seq 46 | TGTACCAACAGGGATGTGCCGCCGGCACAGTCCTCCGGCTAGCCAAGGACCTTGCTGAAAACAACAA |
| Seq 47 | TGTACCAACAGGGATGTGCCGCCGGCACAGTCCTCCGGCTAGCCAAGGACCTTGCTGAAAACAACAA |
| Seq 48 | TGTACCAACAGGGATGTGCCGCCGGCACAGTCCTCCGGCTAGCCAAGGACCTTGCTGAAAACAACAA |
| Seq 49 | TGTACCAACAGGGATGTGCCGCCGGCACAGTCCTCCGGCTAGCCAAGGACCTTGCTGAAAACAACAA |
| Seq 50 | TGTACCAACAGGGATGTGCCGCCGGCACAGTCCTCCGGCTAGCCAAGGACCTTGCTGAAAACAACAA |
| Seq 51 | TGTACCAACAGGGATGTGCCGCCGGCACAGTCCTCCGGCTAGCCAAGGACCTTGCTGAAAACAACAA |
| Seq 52 | TGTACCAACAGGGATGTGCCGCCGGCACAGTCCTCCGGCTAGCCAAGGACCTTGCTGAAAACAACAA |
| Seq 53 | TGTACCAACAGGGATGTGCCGCCGGCACAGTCCTCCGGCTAGCCAAGGACCTTGCTGAAAACAACAA |

FIG. 13 (continued)

```
     TGTACCAACAGGGATGTGCCGCCGGCGGCACAGTCCTCCCGGCTAGCCAAGGACCTTGCTGAAAACAACAA
Seq 54 TGTACCAACAGGGATGTGCCGCCGGCGGCACAGTCCTCCCGGCTAGCCAAGGACCTTGCTGAAAACAACAA
Seq 55 TGTACCAACAGGGATGTGCCGCCGGCGGCACAGTCCTCCCGGCTAGCCAAGGACCTTGCTGAAAACAACAA
Seq 56 TGTACCAACAGGGATGTGCCGCCGGCGGCACAGTCCTCCCGGCTAGCCAAGGACCTTGCTGAAAACAACAA
Seq 57 TGTACCAACAGGGATctGCCGCCGGCGGCACAGTCCTCCCGGCTAGCCAAGGACCTTGCTGAAAACAACAA
Seq 58 TGTACCAACAGGGATGTGCCGCCGGCGGCACAGTCCTCCCGGCTAGCCAAGGACCTTGCTGAAAACAACAA
Seq 59 TGTACCAACAGGGATGTGCCGCCGGCGGCACAGTCCTCCCGGCTAGCCAAGGACCTTGCTGAAAACAACAA
Seq 60 TGTACCAACAGGGATGTGCCGCCGGCGGCACAGTCCTCCCGGCTAGCCAAGGACCTTGCTGAAAACAACAA
Seq 61 TGTACCAACAGGGATGTGCCGCCGGCGGCACAGTCCTCCCGGCTAGCCAAGGACCTTGCTGAAAACAACAA
Seq 62 TGTACCAACAGGGATGTGCCGCCGGCGGCACAGTCCTCCCGGCTAGCCAAGGACCTTGCTGAAAACAACAA 561                                                              630
Seq 1  GGGCTCACGAGTCCTTATCGTCTGCTCCGAGATCACTGCTATCTTATTCCATGGACCCAATGAGAACCAC
Seq 2  GGGCTCACGAGTCCTTATCGTCTGCTCCGAGATCACTGCTATCTTATTCCATGGACCCAATGAGAACCAC
Seq 3  GGGCTCACGAGTCCTTATCGTCTGCTCCGAGATCACTGCTATCTTATTCCATGGACCCAATGAGAACCAC
Seq 4  GGGCTCACGAGTCCTTATCGTCTGCTCCGAGATCACTGCTATCttcTTCCATGGACCCAATGAGAACCAC
Seq 5  GGGCTCACGAGTCCTTATCGTCTGCTCCGAGATCACTGCTATCTTATTCCATGGACCCAATGAGAACCAC
Seq 6  GGGCTCACGAGTCCTTATCGTCTGCTCCGAGATCACTGCTATCTTATTCCATGGACCCAATGAGAACCAC
Seq 7  GGGCTCACGAGTCCTTATCGTCTGCTCCGAGATCACTGCTATCtcTTCCATGGACCCAATGAGAACCAC
Seq 8  GGGCTCACGAGTCCTTATCGTCTGCTCCGAGATCACTGCTATCTTATTCCATGGACCCAATGAGAACCAC
Seq 9  GGGCTCACGAGTCCTTATCGTCTGCTCCGAGATCACTGCTATCTTATTCCATGGACCCAATGAGAACCAC
Seq 10 GGGCTCACGAGTCCTTATCGTCTGCTCCGAGATCACTGCTATCTTATTCCATGGACCCAATGAGAACCAC
Seq 11 GGGCTCACGAGTCCTTATCGTCTGCtcCTCCGAGATCACTGCTATCTTATTCCATGGACCCAATGAGAACCAC
Seq 12 GGGCTCACGAGTCCTTATCGTCTGCtcCTCCGAGATCACTGCTATCTTATTCCATGGACCCAATGAGAACCAC
Seq 13 GGGCTCACGAGTCCTTATCGTCTGCtccTCCGAGATCACTGCTATCTTATTCCATGGACCCAATGAGAACCAC
```

FIG. 13 (continued)

| | | |
|---|---|---|
| Seq 14 | GGGCTCACGAGTCCTTATCGTCtccTCCGAGATCACTGCTATCGgaTTCCATGGACCCAATGAGAACCAC |
| Seq 15 | GGGCTCACGAGTCCTTATCGTCtccTCCGAGATCACTGCTGCTtcggaTTCCATGGACCCAATGAGAACCAC |
| Seq 16 | GGGCTCACGAGTCCTTATCGTCtccTCCGAGATCACTGCTATCGgaTTCCATGGACCCAATGAGAACCAC |
| Seq 17 | GGGCTCACGAGTCCTTATCGTCtccTCCGAGATCACTGCTATCGgaTTCCATGGACCCAATGAGAACCAC |
| Seq 18 | GGGCTCACGAGTCCTTATCGTCGCTCCGAGATCACTGCTATCTTATTCCATGGACCCAATGAGAACCAC |
| Seq 19 | GGGCTCACGAGTCCTTATCGTCGCTGCTCCGAGATCACTGCTATCTTATTCCATGGACCCAATGAGAACCAC |
| Seq 20 | GGGCTCACGAGTCCTTATCGTCGCTGCTCCGAGATCACTGCTATCTTATTCCATGGACCCAATGAGAACCAC |
| Seq 21 | GGGCTCACGAGTCCTTATCGTCGCTGCTCCGAGATCACTGCTATCTTATTCCATGGACCCAATGAGAACCAC |
| Seq 22 | GGGCTCACGAGTCCTTATCGTCtccTCCGAGATCACTGCTATCTTATTCCATGGACCCAATGAGAACCAC |
| Seq 23 | GGGCTCACGAGTCCTTATCGTCtccTCCGAGATCACTGCTATCTTATTCCATGGACCCAATGAGAACCAC |
| Seq 24 | GGGCTCACGAGTCCTTATCGTCGCTGCTCCGAGATCACTGCTATCTTATTCCATGGACCCAATGAGAACCAC |
| Seq 25 | GGGCTCACGAGTCCTTATCGTCGCTGCTCCGAGATCACTGCTATCTTATTCCATGGACCCAATGAGAACCAC |
| Seq 26 | GGGCTCACGAGTCCTTATCGTCGCTGCTCCGAGATCACTGCTATCTTATTCCATGGACCCAATGAGAACCAC |
| Seq 27 | GGGCTCACGAGTCCTTATCGTCGCTGCTCCGAGATCACTGCTATCTTATTCCATGGACCCAATGAGAACCAC |
| Seq 28 | GGGCTCACGAGTCCTTATCGTCGCTGCTCCGAGATCACTGCTATCTTATTCCATGGACCCAATGAGAACCAC |
| Seq 29 | GGGCTCACGAGTCCTTATCGTCGCTGCTCCGAGATCACTGCTGCTtcCTTATTCCATGGACCCAATGAGAACCAC |
| Seq 30 | GGGCTCACGAGTCCTTATCGTCGCTGCTCCGAGATCACTGCTATCTTATTCCATGGACCCAATGAGAACCAC |
| Seq 31 | GGGCTCACGAGTCCTTATCGTCGCTGCTCCGAGATCACTGCTATCtccTTCCATGGACCCAATGAGAACCAC |
| Seq 32 | GGGCTCACGAGTCCTTATCGTCGCTGCTCCGAGATCACTGCTATCTatgTTATTCCATGGACCCAATGAGAACCAC |
| Seq 33 | GGGCTCACGAGTCCTTATCGTCGCTGCTCCGAGATCACTGCTGCTttgTTATTCCATGGACCCAATGAGAACCAC |
| Seq 34 | GGGCTCACGAGTCCTTATCGTCGCTGCTCCGAGATCACTGCTATCatgTTCCATGGACCCAATGAGAACCAC |
| Seq 35 | GGGCTCACGAGTCCTTATCGTCGCTGCTCCGAGATCACTGCTATCgtTCCATGGACCCAATGAGAACCAC |
| Seq 36 | GGGCTCACGAGTCCTTATCGTCGCTGCTCCGAGATCACTGCTATCGgaTTCCATGGACCCAATGAGAACCAC |
| Seq 37 | GGGCTCACGAGTCCTTATCGTCtccTCCGAGATCACTGCTATCGgaTTCCATGGACCCAATGAGAACCAC |

FIG. 13 (continued)

```
>Seq 38  GGGCTCACGAGTCCTTATCGTCTGCTCCGAGATCACTGCTATCGTATCGgaTTCCATGGACCCAATGAGAACCAC
>Seq 39  GGGCTCACGAGTCCTTATCGTCTGCTCCGAGATCACTGCTATCGTATCGgaTTCCATGGACCCAATGAGAACCAC
>Seq 40  GGGCTCACGAGTCCTTATCGTCtcCTCCGAGATCACTGCTATCGTATCGgaTTCCATGGACCCAATGAGAACCAC
>Seq 41  GGGCTCACGAGTCCTTATCGTCTGCTCCGAGATCACTGCTATCttcTTCCATGGACCCAATGAGAACCAC
>Seq 42  GGGCTCACGAGTCCTTATCGTCTGCTCCGAGATCACTGCTATCttcTTCCATGGACCCAATGAGAACCAC
>Seq 43  GGGCTCACGAGTCCTTATCGTCTGCTCCGAGATCACTGCTATCttcTTCCATGGACCCAATGAGAACCAC
>Seq 44  GGGCTCACGAGTCCTTATCGTCTGCTCCGAGATCACTGCTATCttcTTCCATGGACCCAATGAGAACCAC
>Seq 45  GGGCTCACGAGTCCTTATCGTCTGCTCCGAGATCACTGCTATCTTATTCCATGGACCCAATGAGAACCAC
>Seq 46  GGGCTCACGAGTCCTTATCGTCTGCTCCGAGATCACTGCTATCTTATTCCATGGACCCAATGAGAACCAC
>Seq 47  GGGCTCACGAGTCCTTATCGTCTGCTCCGAGATCACTGCTATCTTATTCCATGGACCCAATGAGAACCAC
>Seq 48  GGGCTCACGAGTCCTTATCGTCtcCTCCGAGATCACTGCTATCTTATTCCATGGACCCAATGAGAACCAC
>Seq 49  GGGCTCACGAGTCCTTATCGTCTGCgccTCCGAGATCACTGCTATCTTATTCCATGGACCCAATGAGAACCAC
>Seq 50  GGGCTCACGAGTCCTTATCGTCTGCTCCGAGATCACTGCTATCTTATTCCATGGACCCAATGAGAACCAC
>Seq 51  GGGCTCACGAGTCCTTATCGTCTGCTCCGAGATCACTGCTATCTTATTCCATGGACCCAATGAGAACCAC
>Seq 52  GGGCTCACGAGTCCTTATCGTCTGCTCCGAGATCACTGCTATCTTATTCCATGGACCCAATGAGAACCAC
>Seq 53  GGGCTCACGAGTCCTTATCGTCTGCTCCGAGATCACTGCTATCTTATTCCATGGACCCAATGAGAACCAC
>Seq 54  GGGCTCACGAGTCCTTATCGTCTGCTCCGAGATCACTGCTATCTTATTCCATGGACCCAATGAGAACCAC
>Seq 55  GGGCTCACGAGTCCTTATCGTCTGCTCCGAGATCACTGCTATCTTATTCCATGGACCCAATGAGAACCAC
>Seq 56  GGGCTCACGAGTCCTTATCGTCTGCTCCGAGATCACTGCTATCTTATTCCATGGACCCAATGAGAACCAC
>Seq 57  GGGCTCACGAGTCCTTATCGTCTGCTCCGAGATCACTGCTATCTTATTCCATGGACCCAATGAGAACCAC
>Seq 58  GGGCTCACGAGTCCTTATCGTCTGCTCCGAGATCACTGCTATCTTATTCCATGGACCCAATGAGAACCAC
>Seq 59  GGGCTCACGAGTCCTTATCGTCTGCTCCGAGATCACTGCTATCttcTTATTCCATGGACCCAATGAGAACCAC
>Seq 60  GGGCTCACGAGTCCTTATCGTCTGCTCCGAGATCACTGCTATCTTATTCCATGGACCCAATGAGAACCAC
>Seq 61  GGGCTCACGAGTCCTTATCGTCTGCTCCGAGATCACTGCTATCTTATTCCATGGACCCAATGAGAACCAC
```

FIG. 13 (continued)

```
> Seq    62  GGGCTCAGGAGTCCTTATCGTCTGCTCCGAGATCACTGCTATCttcTTCCATGGACCCAATGAGAACCAC
                                                                                            700
> Seq     1  CTTGACTCACTCGTCGCTCGCTCAAGCTTTATTCGGAGAGACGGAGCTGCAGCACTCATTGTGGGTTCAGGCCCTC
> Seq     2  CTTGACTCACTCGTCGCTCGCTCAAGCTTTATTCGGAGAGACGGAGCTGCAGCACTCATTGTGGGTTCAGGCCCTC
> Seq     3  CTTGACTCACTCGTCGCTCGCTCAAGCTTTATTCGGAGAGACGGAGCTGCAGCACTCATTGTGGGTTCAGGCCCTC
> Seq     4  CTTGACTCACTCGTCGCTCGCTCAAGCTTTATTCGGAGAGACGGAGCTGCAGCACTCATTGTGGGTTCAGGCCCTC
> Seq     5  CTTGACTCACTCGTCGCTCGCTCAAGCTTTATTCGGAGAGACGGAGCTGCAGCACTCATTGTGGGTTCAGGCCCTC
> Seq     6  CTTGACTCACTCGTCGCTCGCTCAAGCTTTATTCGGAGAGACGGAGCTGCAGCACTCATTGTGGGTTCAGGCCCTC
> Seq     7  CTTGACTCACTCGTCGCTCGCTCAAGCTTTATTCGGAGAGACGGAGCTGCAGCACTCATTGTGGGTTCAGGCCCTC
> Seq     8  CTTGACTCACTCGTCGCTCGCTCAAGCTTTATTCGGAGAGACGGAGCTGCAGCACTCATTGTGGGTTCAGGCCCTC
> Seq     9  CTTGACTCACTCGTCGCTCGCTCAAGCTTTATTCGGAGAGACGGAGCTGCAGCACTCATTGTGGGTTCAGGCCCTC
> Seq    10  CTTGACTCACTCGTCGCTCGCTCAAGCTTTATTCGGAGAGACGGAGCTGCAGCACTCATTGTGGGTTCAGGCCCTC
> Seq    11  CTTGACTCACTCGTCGCTCGCTCAAGCTTTATTCGGAGAGACGGAGCTGCAGCACTCATTGTGGGTTCAGGCCCTC
> Seq    12  CTTGACTCACTCGTCGCTCGCTCAAGCTTTATTCGGAGAGACGGAGCTGCAGCACTCATTGTGGGTTCAGGCCCTC
> Seq    13  CTTGACTCACTCGTCGCTCGCTCAAGCTTTATTCGGAGAGACGGAGCTGCAGCACTCATTGTGGGTTCAGGCCCTC
> Seq    14  CTTGACTCACTCGTCGCTCGCTCAAGCTTTATTCGGAGAGACGGAGCTGCAGCACTCATTGTGGGTTCAGGCCCTC
> Seq    15  CTTGACTCACTCGTCGCTCGCTCAAGCTTTATTCGGAGAGACGGAGCTGCAGCACTCATTGTGGGTTCAGGCCCTC
> Seq    16  CTTGACTCACTCGTCGCTCGCTCAAGCTTTATTCGGAGAGACGGAGCTGCAGCACTCATTGTGGGTTCAGGCCCTC
> Seq    17  CTTGACTCACTCGTCGCTCGCTCAAGCTTTATTCGGAGAGACGGAGCTGCAGCACTCATTGTGGGTTCAGGCCCTC
> Seq    18  CTTGACTCACTCGTCGCTCGCTCAAGCTTTATTCGGAGAGACGGAGCTGCAGCACTCATTGTGGGTTCAGGCCCTC
> Seq    19  CTTGACTCACTCGTCGCTCGCTCAAGCTTTATTCGGAGAGACGGAGCTGCAGCACTCATTGTGGGTTCAGGCCCTC
> Seq    20  CTTGACTCACTCGTCGCTCGCTCAAGCTTTATTCGGAGAGACGGAGCTGCAGCACTCATTGTGGGTTCAGGCCCTC
> Seq    21  CTTGACTCACTCGTCGCTCGCTCAAGCTTTATTCGGAGAGACGGAGCTGCAGCACTCATTGTGGGTTCAGGCCCTC
```

FIG. 13 (continued)

| | | |
|---|---|---|
| Seq 22 | CTTGACTCACTCGTCGCTCGCTCAAGCTTTTATTCGGAGACGGACGAGCTGCAGCACTCATTGTGGGTTCAGGCCCTC |
| Seq 23 | CTTGACTCACTCGTCGCTCGCTCAAGCTTTTATTCGGAGACGGACGAGCTGCAGCACTCATTGTGGGTTCAGGCCCTC |
| Seq 24 | CTTGACTCACTCGTCGCTCGCTCAAGCTTTTATTCGGAGACGGACGAGCTGCAGCACTCATTGTGGGTTCAGGCCCTC |
| Seq 25 | CTTGACTCACTCGTCGCTCGCTCAAGCTTTTATTCGGAGACGGACGAGCTGCAGCACTCATTGTGGGTTCAGGCCCTC |
| Seq 26 | CTTGACTCACTCGTCGCTCGCTCAAGCTTTTATTCGGAGACGGACGAGCTGCAGCACTCATTGTGGGTTCAGGCCCTC |
| Seq 27 | CTTGACTCACTCGTCGCTCGCTCAAGCTTTTATTCGGAGACGGACGAGCTGCAGCACTCATTGTGGGTTCAGGCCCTC |
| Seq 28 | CTTGACTCACTCGTCGCTCGCTCAAGCTTTTATTCGGAGACGGACGAGCTGCAGCACTCATTGTGGGTTCAGGCCCTC |
| Seq 29 | CTTGACTCACTCGTCGCTCGCTCAAGCTTTTATTCGGAGACGGACGAGCTGCAGCACTCATTGTGGGTTCAGGCCCTC |
| Seq 30 | CTTGACTCACTCGTCGCTCGCTCAAGCTTTTATTCGGAGACGGACGAGCTGCAGCACTCATTGTGGGTTCAGGCCCTC |
| Seq 31 | CTTGACTCACTCGTCGCTCGCTCAAGCTTTTATTCGGAGACGGACGAGCTGCAGCACTCATTGTGGGTTCAGGCCCTC |
| Seq 32 | CTTGACTCACTCGTCGCTCGCTCAAGCTTTTATTCGGAGACGGACGAGCTGCAGCACTCATTGTGGGTTCAGGCCCTC |
| Seq 33 | CTTGACTCACTCGTCGCTCGCTCAAGCTTTTATTCGGAGACGGACGAGCTGCAGCACTCATTGTGGGTTCAGGCCCTC |
| Seq 34 | CTTGACTCACTCGTCGCTCGCTCAAGCTTTTATTCGGAGACGGACGAGCTGCAGCACTCATTGTGGGTTCAGGCCCTC |
| Seq 35 | CTTGACTCACTCGTCGCTCGCTCAAGCTTTTATTCGGAGACGGACGAGCTGCAGCACTCATTGTGGGTTCAGGCCCTC |
| Seq 36 | CTTGACTCACTCGTCGCTCGCTCAAGCTTTTATTCGGAGACGGACGAGCTGCAGCACTCATTGTGGGTTCAGGCCCTC |
| Seq 37 | CTTGACTCACTCGTCGCTCGCTCAAGCTTTTATTCGGAGACGGACGAGCTGCAGCACTCATTGTGGGTTCAGGCCCTC |
| Seq 38 | CTTGACTCACTCGTCGCTCGCTCAAGCTTTTATTCGGAGACGGACGAGCTGCAGCACTCATTGTGGGTTCAGGCCCTC |
| Seq 39 | CTTGACTCACTCGTCGCTCGCTCAAGCTTTTATTCGGAGACGGACGAGCTGCAGCACTCATTGTGGGTTCAGGCCCTC |
| Seq 40 | CTTGACTCACTCGTCGCTCGCTCAAGCTTTTATTCGGAGACGGACGAGCTGCAGCACTCATTGTGGGTTCAGGCCCTC |
| Seq 41 | CTTGACTCACTCGTCGCTCGCTCAAGCTTTTATTCGGAGACGGACGAGCTGCAGCACTCATTGTGGGTTCAGGCCCTC |
| Seq 42 | CTTGACTCACTCGTCGCTCGCTCAAGCTTTTATTCGGAGACGGACGAGCTGCAGCACTCATTGTGGGTTCAGGCCCTC |
| Seq 43 | CTTGACTCACTCGTCGCTCGCTCAAGCTTTTATTCGGAGACGGACGAGCTGCAGCACTCATTGTGGGTTCAGGCCCTC |
| Seq 44 | CTTGACTCACTCGTCGCTCGCTCAAGCTTTTATTCGGAGACGGACGAGCTGCAGCACTCATTGTGGGTTCAGGCCCTC |
| Seq 45 | CTTGACTCACTCGTCGCTCGCTCAAGCTTTTATTCGGAGACGGACGAGCTGCAGCACTCATTGTGGGTTCAGGCCCTC |

FIG. 13 (continued)

```
        CTTGACTCACTCGTCGCTCAAGCTTTATTCGGAGACGGAGCTGCAGCACTCATTGTGGGTTCAGGCCCTC
Seq 46  CTTGACTCACTCGTCGCTCAAGCTTTATTCGGAGACGGAGCTGCAGCACTCATTGTGGGTTCAGGCCCTC
Seq 47  CTTGACTCACTCGTCGCTCAAGCTTTATTCGGAGACGGAGCTGCAGCACTCATTGTGGGTTCAGGCCCTC
Seq 48  CTTGACTCACTCGTCGCTCAAGCTTTATTCGGAGACGGAGCTGCAGCACTCATTGTGGGTTCAGGCCCTC
Seq 49  CTTGACTCACTCGTCGCTCAAGCTTTATTCGGAGACGGAGCTGCAGCACTCATTGTGGGTTCAGGCCCTC
Seq 50  CTTGACTCACTCGTCGCTCAAGCTTTATTCGGAGACGGAGCTGCAGCACTCATTGTGGGTTCAGGCCCTC
Seq 51  CTTGACTCACTCGTCGCTCAAGCTTTATTCGGAGACGGAGCTGCAGCACTCATTGTGGGTTCAGGCCCTC
Seq 52  CTTGACTCACTCGTCGCTCAAGCTTTATTCGGAGACGGAGCTGCAGCACTCATTGTGGGTTCAGGCCCTC
Seq 53  CTTGACTCACTCGTCGCTCAAGCTTTATTCGGAGACGGAGCTGCAGCACTCATTGTGGGTTCAGGCCCTC
Seq 54  CTTGACTCACTCGTCGCTCAAGCTTTATTCGGAGACGGAGCTGCAGCACTCATTGTGGGTTCAGGCCCTC
Seq 55  CTTGACTCACTCGTCGCTCAAGCTTTATTCGGAGACGGAGCTGCAGCACTCATTGTGGGTTCAGGCCCTC
Seq 56  CTTGACTCACTCGTCGCTCAAGCTTTATTCGGAGACGGAGCTGCAGCACTCATTGTGGGTTCAGGCCCTC
Seq 57  CTTGACTCACTCGTCGCTCAAGCTTTATTCGGAGACGGAGCTGCAGCACTCATTGTGGGTTCAGGCCCTC
Seq 58  CTTGACTCACTCGTCGCTCAAGCTTTATTCGGAGACGGAGCTGCAGCACTCATTGTGGGTTCAGGCCCTC
Seq 59  CTTGACTCACTCGTCGTCCAAGCTTTATTCGGAGACGGAGCTGCAGCACTCATTGTGGGTTCAGGCCCTC
Seq 60  CTTGACTCACTCGTCGCTCAAGCTTTATTCGGAGACGGAGCTGCAGCACTCATTGTGGGTTCAGGCCCTC
Seq 61  CTTGACTCACTCGTCGCTCAAGCTTTATTCGGAGACGGAGCTGCAGCACTCATTGTGGGTTCAGGCCCTC
Seq 62  CTTGACTCACTCGTCGCTCAAGCTTTATTCGGAGACGGAGCTGCAGCACTCATTGTGGGTTCAGGCCCTC 701                                                              770
Seq 1   ACTTGGCCGTAGAACGGCCAATATTCGAGATCGTGTCAACTGATCAAACAATCTTGCCGGACACTGAGAA
Seq 2   ACTTGGCCGTAGAACGGCCAATATTCGAGATCGTGTCAACTGATCAAACAATCTTGCCGGACACTGAGAA
Seq 3   ACTTGGCCGTAGAACGGCCAATATTCGAGATCGTGTCAACTGATCAAACAATCTTGCCGGACACTGAGAA
Seq 4   ACTTGGCCGTAGAACGGCCAATATTCGAGATCGTGTCAACTGATCAAACAATCTTGCCGGACACTGAGAA
Seq 5   ACTTGGCCGTAGAACGGCCAATATTCGAGATCGTGTCAACTGATCAAACAATCTTGCCGGACACTGAGAA
```

FIG. 13 (continued)

| | | |
|---|---|---|
| Seq > 6 | ACTTGGCCGTAGAACGGCCAATATTCGAGATCGTGTCAACTGATCAAACAATCTTGCCGGACACTGAGAA |
| Seq > 7 | ACTTGGCCGTAGAACGGCCAATATTCGAGATCGTGTCAACTGATCAAACAATCTTGCCGGACACTGAGAA |
| Seq > 8 | ACTTGGCCGTAGAACGGCCAATATTCGAGATCGTGTCAACTGATCAAACAATCTTGCCGGACACTGAGAA |
| Seq > 9 | ACTTGGCCGTAGAACGGCCAATATTCGAGATCGTGTCAACTGATCAAACAATCTTGCCGGACACTGAGAA |
| Seq > 10 | ACTTGGCCGTAGAACGGCCAATATTCGAGATCGTGTCAACTGATCAAACAATCTTGCCGGACACTGAGAA |
| Seq > 11 | ACTTGGCCGTAGAACGGCCAATATTCGAGATCGTGTCAACTGATCAAACAATCTTGCCGGACACTGAGAA |
| Seq > 12 | ACTTGGCCGTAGAACGGCCAATATTCGAGATCGTGTCAACTGATCAAACAATCTTGCCGGACACTGAGAA |
| Seq > 13 | ACTTGGCCGTAGAACGGCCAATATTCGAGATCGTGTCAACTGATCAAACAATCTTGCCGGACACTGAGAA |
| Seq > 14 | ACTTGGCCGTAGAACGGCCAATATTCGAGATCGTGTCAACTGATCAAACAATCTTGCCGGACACTGAGAA |
| Seq > 15 | ACTTGGCCGTAGAACGGCCAATATTCGAGATCGTGTCAACTGATCAAACAATCTTGCCGGACACTGAGAA |
| Seq > 16 | ACTTGGCCGTAGAACGGCCAATATTCGAGATCGTGTCAACTGATCAAACAATCTTGCCGGACACTGAGAA |
| Seq > 17 | ACTTGGCCGTAGAACGGCCAATATTCGAGATCGTGTCAACTGATCAAACAATCTTGCCGGACACTGAGAA |
| Seq > 18 | ACTTGGCCGTAGAACGGCCAATATTCGAGATCGTGTCAACTGATCAAACAATCTTGCCGGACACTGAGAA |
| Seq > 19 | ACTTGGCCGTAGAACGGCCAATATTCGAGATCGTGTCAACTGATCAAACAATCTTGCCGGACACTGAGAA |
| Seq > 20 | ACTTGGCCGTAGAACGGCCAATATTCGAGATCGTGTCAACTGATCAAACAATCTTGCCGGACACTGAGAA |
| Seq > 21 | ACTTGGCCGTAGAACGGCCAATATTCGAGATCGTGTCAACTGATCAAACAATCTTGCCGGACACTGAGAA |
| Seq > 22 | ACTTGGCCGTAGAACGGCCAATATTCGAGATCGTGTCAACTGATCAAACAATCTTGCCGGACACTGAGAA |
| Seq > 23 | ACTTGGCCGTAGAACGGCCAATATTCGAGATCGTGTCAACTGATCAAACAATCTTGCCGGACACTGAGAA |
| Seq > 24 | ACTTGGCCGTAGAACGGCCAATATTCGAGATCGTGTCAACTGATCAAACAATCTTGCCGGACACTGAGAA |
| Seq > 25 | ACTTGGCCGTAGAACGGCCAATATTCGAGATCGTGTCAACTGATCAAACAATCTTGCCGGACACTGAGAA |
| Seq > 26 | ACTTGGCCGTAGAACGGCCAATATTCGAGATCGTGTCAACTGATCAAACAATCTTGCCGGACACTGAGAA |
| Seq > 27 | ACTTGGCCGTAGAACGGCCAATATTCGAGATCGTGTCAACTGATCAAACAATCTTGCCGGACACTGAGAA |
| Seq > 28 | ACTTGGCCGTAGAACGGCCAATATTCGAGATCGTGTCAACTGATCAAACAATCTTGCCGGACACTGAGAA |
| Seq > 29 | ACTTGGCCGTAGAACGGCCAATATTCGAGATCGTGTCAACTGATCAAACAATCTTGCCGGACACTGAGAA |

FIG. 13 (continued)

| | | |
|---|---|---|
| > Seq 30 | ACTTGGCCCGTAGAACGGCCAATATTCGAGATCGTGTCAACTGATCAAACAATCTTGCCGGACACTGAGAA |
| > Seq 31 | ACTTGGCCCGTAGAACGGCCAATATTCGAGATCGTGTCAACTGATCAAACAATCTTGCCGGACACTGAGAA |
| > Seq 32 | ACTTGGCCCGTAGAACGGCCAATATTCGAGATCGTGTCAACTGATCAAACAATCTTGCCGGACACTGAGAA |
| > Seq 33 | ACTTGGCCCGTAGAACGGCCAATATTCGAGATCGTGTCAACTGATCAAACAATCTTGCCGGACACTGAGAA |
| > Seq 34 | ACTTGGCCCGTAGAACGGCCAATATTCGAGATCGTGTCAACTGATCAAACAATCTTGCCGGACACTGAGAA |
| > Seq 35 | ACTTGGCCCGTAGAACGGCCAATATTCGAGATCGTGTCAACTGATCAAACAATCTTGCCGGACACTGAGAA |
| > Seq 36 | ACTTGGCCCGTAGAACGGCCAATATTCGAGATCGTGTCAACTGATCAAACAATCTTGCCGGACACTGAGAA |
| > Seq 37 | ACTTGGCCCGTAGAACGGCCAATATTCGAGATCGTGTCAACTGATCAAACAATCTTGCCGGACACTGAGAA |
| > Seq 38 | ACTTGGCCCGTAGAACGGCCAATATTCGAGATCGTGTCAACTGATCAAACAATCTTGCCGGACACTGAGAA |
| > Seq 39 | ACTTGGCCCGTAGAACGGCCAATATTCGAGATCGTGTCAACTGATCAAACAATCTTGCCGGACACTGAGAA |
| > Seq 40 | ACTTGGCCCGTAGAACGGCCAATATTCGAGATCGTGTCAACTGATCAAACAATCTTGCCGGACACTGAGAA |
| > Seq 41 | ACTTGGCCCGTAGAACGGCCAATATTCGAGATCGTGTCAACTGATCAAACAATCTTGCCGGACACTGAGAA |
| > Seq 42 | ACTTGGCCCGTAGAACGGCCAATATTCGAGATCGTGTCAACTGATCAAACAATCTTGCCGGACACTGAGAA |
| > Seq 43 | ACTTGGCCCGTAGAACGGCCAATATTCGAGATCGTGTCAACTGATCAAACAATCTTGCCGGACACTGAGAA |
| > Seq 44 | ACTTGGCCCGTAGAACGGCCAATATTCGAGATCGTGTCAACTGATCAAACAATCTTGCCGGACACTGAGAA |
| > Seq 45 | ACTTGGCCCGTAGAACGGCCAATATTCGAGATCGTGTCAACTGATCAAACAATCTTGCCGGACACTGAGAA |
| > Seq 46 | ACTTGGCCCGTAGAACGGCCAATATTCGAGATCGTGTCAACTGATCAAACAATCTTGCCGGACACTGAGAA |
| > Seq 47 | ACTTGGCCCGTAGAACGGCCAATATTCGAGATCGTGTCAACTGATCAAACAATCTTGCCGGACACTGAGAA |
| > Seq 48 | ACTTGGCCCGTAGAACGGCCAATATTCGAGATCGTGTCAACTGATCAAACAATCTTGCCGGACACTGAGAA |
| > Seq 49 | ACTTGGCCCGTAGAACGGCCAATATTCGAGATCGTGTCAACTGATCAAACAATCTTGCCGGACACTGAGAA |
| > Seq 50 | ACTTGGCCCGTAGAACGGCCAATATTCGAGATCGTGTCAACTGATCAAACAATCTTGCCGGACACTGAGAA |
| > Seq 51 | ACTTGGCCCGTAGAACGGCCAATATTCGAGATCGTGTCAACTGATCAAACAATCTTGCCGGACACTGAGAA |
| > Seq 52 | ACTTGGCCCGTAGAACGGCCAATATTCGAGATCGTGTCAACTGATCAAACAATCTTGCCGGACACTGAGAA |
| > Seq 53 | ACTTGGCCCGTAGAACGGCCAATATTCGAGATCGTGTCAACTGATCAAACAATCTTGCCGGACACTGAGAA |

FIG. 13 (continued)

```
    ACTTGGCCGTAGAACGGCCAATATTCGAGATCGTGTCAACTGATCAAACAATCTTGCCGACACTGAGAA
>Seq 54 ACTTGGCCGTAGAACGGCCAATATTCGAGATCGTGTCAACTGATCAAACAATCTTGCCGACACTGAGAA
>Seq 55 ACTTGGCCGTAGAACGGCCAATATTCGAGATCGTGTCAACTGATCAAACAATCTTGCCGACACTGAGAA
>Seq 56 ACTTGGCCGTAGAACGGCCAATATTCGAGATCGTGTCAACTGATCAAACAATCTTGCCGACACTGAGAA
>Seq 57 ACTTGGCCGTAGAACGGCCAATATTCGAGATCGTGTCAACTGATCAAACAATCTTGCCGACACTGAGAA
>Seq 58 ACTTGGCCGTAGAACGGCCAATATTCGAGATCGTGTCAACTGATCAAACAATCTTGCCGACACTGAGAA
>Seq 59 ACTTGGCCGTAGAACGGCCAATATTCGAGATCGTGTCAACTGATCAAACAATCTTGCCGACACTGAGAA
>Seq 60 ACTTGGCCGTAGAACGGCCAATATTCGAGATCGTGTCAACTGATCAAACAATCTTGCCGACACTGAGAA
>Seq 61 ACTTGGCCGTAGAACGGCCAATATTCGAGATCGTGTCAACTGATCAAACAATCTTGCCGACACTGAGAA
>Seq 62 ACTTGGCCGTAGAACGGCCAATATTCGAGATCGTGTCAACTGATCAAACAATCTTGCCGACACTGAGAA 771                                                              840
>Seq 1  GGCAATGAAGTTACACTTGAGAGAGGGAGGGTTGACGTTTCAGTTGCATAGAGATGTACCCTTGATGGTC
>Seq 2  GGCAATGAAGTTACACTTGAGAGAGGGAGGGTTGACGTTTCAGTTGCATAGAGATGTACCCTTGATGGTC
>Seq 3  GGCAATGAAGTTACACTTGAGAGAGGGAGGGTTGACGTTTCAGTTGCATAGAGATGTACCCTTGATGGTC
>Seq 4  GGCAATGAAGTTACACTTGAGAGAGGGAGGGTTGACGTTTCAGTTGCATAGAGATGTACCCTTGATGGTC
>Seq 5  GGCAATGAAGTTACACTTGAGAGAGGGAGGGttCACGTTTCAGTTGCATAGAGATGTACCCTTGATGGTC
>Seq 6  GGCAATGAAGTTACACTTGAGAGAGGGAGGGatgACGTTTCAGTTGCATAGAGATGTACCCTTGATGGTC
>Seq 7  GGCAATGAAGTTACACTTGAGAGAGGGAGGGatgACGTTTCAGTTGCATAGAGATGTACCCTTGATGGTC
>Seq 8  GGCAATGAAGTTACACTTGAGAGAGGGAGGGTTGACGTTTCAGTTGCATAGAGATGTACCCTTGATGGTC
>Seq 9  GGCAATGAAGTTACACTTGAGAGAGGGAGGGTTGACGTTTCAGTTGCATAGAGATGTACCCTTGATGGTC
>Seq 10 GGCAATGAAGTTACACTTGAGAGAGGGAGGGTTGACGTTTCAGTTGCATAGAGATGTACCCTTGATGGTC
>Seq 11 GGCAATGAAGTTACACTTGAGAGAGGGAGGGTTGACGTTTCAGTTGCATAGAGATGTACCCTTGATGGTC
>Seq 12 GGCAATGAAGTTACACTTGAGAGAGGGAGGGTTGACGTTTCAGTTGCATAGAGATGTACCCTTGATGGTC
>Seq 13 GGCActgAAGaaCACTTGAGAGAGGGAGGGTTGACGTTTCAGTTGCATAGAGATGTACCCTTGATGGTC
```

FIG. 13 (continued)

```
Seq 14  GGCActgAAGaacCACTTGAGAGAGGGAGGGGTTGACGTTTCAGTTGCATAGAGATGTACCCTTGATGGTC
Seq 15  GGCActgAAGaacCACTTGAGAGAGGGAGGGGTTGACGTTTCAGTTGCATAGAGATGTACCCTTGATGGTC
Seq 16  GGCActgAAGaacCACTTGAGAGAGGGAGGGGTTGACGTTTCAGTTGCATAGAGATGTACCCTTGATGGTC
Seq 17  GGCActgAAGaacCACTTGAGAGAGGGAGGGGatgACGTTTCAGTTGCATAGAGATGTACCCTTGATGGTC
Seq 18  GGCAATGAAGTTACACTTGAGAGAGGGAGGGGTTGACGTTTCAGTTGCATAGAGATGTACCCTTGATGGTC
Seq 19  GGCAATGAAGTTACACTTGAGAGAGGGAGGGGTTGACGTTTCAGTTGCATAGAGATGTACCCTTGATGGTC
Seq 20  GGCAATGAAGTTACACTTGAGAGAGGGAGGGGTTGACGTTTCAGTTGCATAGAGATGTACCCTTGATGGTC
Seq 21  GGCAATGAAGTTACACTTGAGAGAGGGAGGGGTTGACGTTTCAGTTGCATAGAGATGTACCCTTGATGGTC
Seq 22  GGCAATGAAGTTACACTTGAGAGAGGGAGGGGTTGACGTTTCAGTTGCATAGAGATGTACCCTTGATGGTC
Seq 23  GGCAATGAAGTTACACTTGAGAGAGGGAGGGGTTGACGTTTCAGTTGCATAGAGATGTACCCTTGATGGTC
Seq 24  GGCAATGAAGTTACACTTGAGAGAGGGAGGGGTTGACGTTTCAGTTGCATAGAGATGTACCCTTGATGGTC
Seq 25  GGCAttAAGTTACACTTGAGAGAGGGAGGGGTTGACGTTTCAGTTGCATAGAGATGTACCCTTGATGGTC
Seq 26  GGCAATGAAGTTACACTTGAGAGAGGGAGGGGTTGACGTTTCAGTTGCATAGAGATGTACCCTTGATGGTC
Seq 27  GGCAATGAAGTTACACTTGAGAGAGGGAGGGGTTGACGTTTCAGTTGCATAGAGATGTACCCTTGATGGTC
Seq 28  GGCAATGAAGTTACACTTGAGAGAGGGAGGGGTTGACGTTTCAGTTGCATAGAGATGTACCCTTGATGGTC
Seq 29  GGCAATGAAGTTACACTTGAGAGAGGGAGGGGTTGACGTTTCAGTTGCATAGAGATGTACCCTTGATGGTC
Seq 30  GGCAATGAAGTTACACTTGAGAGAGGGAGGGGatgACGTTTCAGTTGCATAGAGATGTACCCTTGATGGTC
Seq 31  GGCAATGAAGTTACACTTGAGAGAGGGAGGGGTTGACGTTTCAGTTGCATAGAGATGTACCCTTGATGGTC
Seq 32  GGCAATGAAGTTACACTTGAGAGAGGGAGGGGTTGACGTTTCAGTTGCATAGAGATGTACCCTTGATGGTC
Seq 33  GGCAATGAAGTTACACTTGAGAGAGGGAGGGGTTGACGTTTCAGTTGCATAGAGATGTACCCTTGATGGTC
Seq 34  GGCAATGAAGTTACACTTGAGAGAGGGAGGGGTTGACGTTTCAGTTGCATAGAGATGTACCCTTGATGGTC
Seq 35  GGCAATGAAGTTACACTTGAGAGAGGGAGGGGTTGACGTTTCAGTTGCATAGAGATGTACCCTTGATGGTC
Seq 36  GGCActgAAGaacCACTTGAGAGAGGGAGGGGTTGACGTTTCAGTTGCATAGAGATGTACCCTTGATGGTC
Seq 37  GGCActgAAGaacCACTTGAGAGAGGGAGGGGTTGACGTTTCAGTTGCATAGAGATGTACCCTTGATGGTC
```

FIG. 13 (continued)

Seq 38 GGCAATGAAGTTACACTTGAGAGAGGGAGGGTTGACGTTTCAGTTGCATAGAGATGTACCCTTGATGGTC
Seq 39 GGCActgAAGaaCCACTTGAGAGAGGGAGGGTTGACGTTTCAGTTGCATAGAGATGTACCCTTGATGGTC
Seq 40 GGCAATGAAGTTACACTTGAGAGAGGGAGGGTTGACGTTTCAGTTGCATAGAGATGTACCCTTGATGGTC
Seq 41 GGCAATGAAGTTACACTTGAGAGAGGGAGGGTTGACGTTTCAGTTGCATAGAGATGTACCCTTGATGGTC
Seq 42 GGCAATGAAGTTACACTTGAGAGAGGGAGGGatgACGTTTCAGTTGCATAGAGATGTACCCTTGATGGTC
Seq 43 GGCAATGAAGTTACACTTGAGAGAGGGAGGGatgACGTTTCAGTTGCATAGAGATGTACCCTTGATGGTC
Seq 44 GGCAATGAAGTTACACTTGAGAGAGGGAGGGatgACGTTTCAGTTGCATAGAGATGTACCCTTGATGGTC
Seq 45 GGCAATGAAGTTACACTTGAGAGAGGGAGGGatgACGTTTCAGTTGCATAGAGATGTACCCTTGATGGTC
Seq 46 GGCAATGAAGTTACACTTGAGAGAGGGAGGGTTGACGTTTCAGTTGCATAGAGATGTACCCTTGATGGTC
Seq 47 GGCAATGAAGTTACACTTGAGAGAGGGAGGGTTGACGTTTCAGTTGCATAGAGATGTACCCTTGATGGTC
Seq 48 GGCAATGAAGTTACACTTGAGAGAGGGAGGGTTGACGTTTCAGTTGCATAGAGATGTACCCTTGATGGTC
Seq 49 GGCAATGAAGTTACACTTGAGAGAGGGAGGGTTGACGTTTCAGTTGCATAGAGATGTACCCTTGATGGTC
Seq 50 GGCAATGAAGTTACACTTGAGAGAGGGAGGGTTGACGTTTCAGTTGCATAGAGATGTACCCTTGATGGTC
Seq 51 GGCAATGAAGTTACACTTGAGAGAGGGAGGGTTGACGTTTCAGTTGCATAGAGATGTACCCTTGATGGTC
Seq 52 GGCAATGAAGTTACACTTGAGAGAGGGAGGGTTGACGTTTCAGTTGCATAGAGATGTACCCTTGATGGTC
Seq 53 GGCAATGAAGTTACACTTGAGAGAGGGAGGGTTGACGTTTCAGTTGCATAGAGATGTACCCTTGATGGTC
Seq 54 GGCAATGAAGTTACACTTGAGAGAGGGAGGGTTGACGTTTCAGTTGCATAGAGATGTACCCTTGATGGTC
Seq 55 GGCAATGAAGTTACACTTGAGAGAGGGAGGGTTGACGTTTCAGTTGCATAGAGATGTACCCTTGATGGTC
Seq 56 GGCAATGAAGTTACACTTGAGAGAGGGAGGGTTGACGTTTCAGTTGCATAGAGATGTACCCTTGATGGTC
Seq 57 GGCAATGAAGTTACACTTGAGAGAGGGAGGGTTGACGTTTCAGTTGCATAGAGATGTACCCTTGATGGTC
Seq 58 GGCAATGAAGTTACACTTGAGAGAGGGAGGGTTGACGTTTCAGTTGCATAGAGATGTACCCTTGATGGTC
Seq 59 GGCAATGAAGTTACACTTGAGAGAGGGAGGGTTGACGTTTCAGTTGCATAGAGATGTACCCTTGATGGTC
Seq 60 GGCAATGAAGTTACACTTGAGAGAGGGAGGGttcACGTTTCAGTTGCATAGAGATGTACCCTTGATGGTC
Seq 61 GGCAATGAAGTTACACTTGAGAGAGGGAGGGatgACGTTTCAGTTGCATAGAGATGTACCCTTGATGGTC FIG. 13 (continued)

```
> Seq 62  GGCAATGAAGTTACACTTGAGAGAGGGAGGGatgACGTTTCAGTTGCATAGAGATGTACCCTTGATGGTC
                                                                            910
         841                                                                  .
> Seq  1  GCAAAGAACATAGAGAACGCAGCCGGAGAAAGCGTTGTCTCCACTAGGGATAACTGATTGGAACTCAGTTT
> Seq  2  GCAAAGAACATAGAGAACGCAGCCGGAGAAAGCGTTGTCTCCACTAGGGATAACTGATTGGAACTCAGTTT
> Seq  3  GCAAAGAACATAGAGAACGCAGCCGGAGAAAGCGTTGTCTCCACTAGGGATAACTGATTGGAACTCAGTTT
> Seq  4  GCAAAGAACATAGAGAACGCAGCCGGAGAAAGCGTTGTCTCCACTAGGGATAACTGATTGGAACTCAGTTT
> Seq  5  GCAAAGAACATAGAGAACGCAGCCGGAGAAAGCGTTGTCTCCACTAGGGATAACTGATTGGAACTCAGTTT
> Seq  6  GCAAAGAACATAGAGAACGCAGCCGGAGAAAGCGTTGTCTCCACTAGGGATAACTGATTGGAACTCAGTTT
> Seq  7  GCAAAGAACATAGAGAACGCAGCCGGAGAAAGCGTTGTCTCCACTAGGGATAACTGATTGGAACTCAGTTT
> Seq  8  GCAAAGAACATAGAGAACGCAGCCGGAGAAAGCGTTGTCTCCACTAGGGATAACTGATTGGAACTCAGTTT
> Seq  9  GCAAAGAACATAGAGAACGCAGCCGGAGAAAGCGTTGTCTCCACTAGGGATAACTGATTGGAACTCAGTTT
> Seq 10  GCAAAGAACATAGAGAACGCAGCCGGAGAAAGCGTTGTCTCCACTAGGGATAACTGATTGGAACTCAGTTT
> Seq 11  GCAAAGAACATAGAGAACGCAGCCGGAGAAAGCGTTGTCTCCACTAGGGATAACTGATTGGAACTCAGTTT
> Seq 12  GCAAAGAACATAGAGAACGCAGCCGGAGAAAGCGTTGTCTCCACTAGGGATAACTGATTGGAACTCAGTTT
> Seq 13  GCAAAGAACATAGAGAACGCAGCCGGAGAAAGCGTTGTCTCCACTAGGGATAACTGATTGGAACTCAGTTT
> Seq 14  GCAAAGAACATAGAGAACGCAGCCGGAGAAAGCGTTGTCTCCACTAGGGATAACTGATTGGAACTCAGTTT
> Seq 15  GCAAAGAACATAGAGAACGCAGCCGGAGAAAGCGTTGTCTCCACTAGGGATAACTGATTGGAACTCAGTTT
> Seq 16  GCAAAGAACATAGAGAACGCAGCCGGAGAAAGCGTTGTCTCCACTAGGGATAACTGATTGGAACTCAGTTT
> Seq 17  GCAAAGAACATAGAGAACGCAGCCGGAGAAAGCGTTGTCTCCACTAGGGATAACTGATTGGAACTCAGTTT
> Seq 18  GCAAAGAACATAGAGAACGCAGCCGGAGAAAGCGTTGTCTCCACTAGGGATAACTGATTGGAACTCAGTTT
> Seq 19  GCAAAGAACATAGAGAACGCAGCCGGAGAAAGCGTTGTCTCCACTAGGGATAACTGATTGGAACTCAGTTT
> Seq 20  GCAAAGAACATAGAGAACGCAGCCGGAGAAAGCGTTGTCTCCACTAGGGATAACTGATTGGAACTCAGTTT
> Seq 21  GCAAAGAACATAGAGAACGCAGCCGGAGAAAGCGTTGTCTCCACTAGGGATAACTGATTGGAACTCAGTTT
```

FIG. 13 (continued)

| | | |
|---|---|---|
| > Seq 22 | GCAAAGAACATAGAGAACGCAGCGGAGAAAGCGTTGTCTCCACTAGGGATAACTGATTGGAACTCAGTTT |
| > Seq 23 | GCAAAGAACATAGAGAACGCAGCGGAGAAAGCGTTGTCTCCACTAGGGATAACTGATTGGAACTCAGTTT |
| > Seq 24 | GCAAAGAACATAGAGAACGCAGCGGAGAAAGCGTTGTCTCCACTAGGGATAACTGATTGGAACTCAGTTT |
| > Seq 25 | GCAAAGAACATAGAGAACGCAGCGGAGAAAGCGTTGTCTCCACTAGGGATAACTGATTGGAACTCAGTTT |
| > Seq 26 | GCAAAGAACATAGAGAACGCAGCGGAGAAAGCGTTGTCTCCACTAGGGATAACTGATTGGAACTCAGTTT |
| > Seq 27 | GCAAAGAACATAGAGAACGCAGCGGAGAAAGCGTTGTCTCCACTAGGGATAACTGATTGGAACTCAGTTT |
| > Seq 28 | GCAAAGAACATAGAGAACGCAGCGGAGAAAGCGTTGTCTCCACTAGGGATAACTGATTGGAACTCAGTTT |
| > Seq 29 | GCAAAGAACATAGAGAACGCAGCGGAGAAAGCGTTGTCTCCACTAGGGATAACTGATTGGAACTCAGTTT |
| > Seq 30 | GCAAAGAACATAGAGAACGCAGCGGAGAAAGCGTTGTCTCCACTAGGGATAACTGATTGGAACTCAGTTT |
| > Seq 31 | GCAAAGAACATAGAGAACGCAGCGGAGAAAGCGTTGTCTCCACTAGGGATAACTGATTGGAACTCAGTTT |
| > Seq 32 | GCAAAGAACATAGAGAACGCAGCGGAGAAAGCGTTGTCTCCACTAGGGATAACTGATTGGAACTCAGTTT |
| > Seq 33 | GCAAAGAACATAGAGAACGCAGCGGAGAAAGCGTTGTCTCCACTAGGGATAACTGATTGGAACTCAGTTT |
| > Seq 34 | GCAAAGAACATAGAGAACGCAGCGGAGAAAGCGTTGTCTCCACTAGGGATAACTGATTGGAACTCAGTTT |
| > Seq 35 | GCAAAGAACATAGAGAACGCAGCGGAGAAAGCGTTGTCTCCACTAGGGATAACTGATTGGAACTCAGTTT |
| > Seq 36 | GCAAAGAACATAGAGAACGCAGCGGAGAAAGCGTTGTCTCCACTAGGGATAACTGATTGGAACTCAGTTT |
| > Seq 37 | GCAAAGAACATAGAGAACGCAGCGGAGAAAGCGTTGTCTCCACTAGGGATAACTGATTGGAACTCAGTTT |
| > Seq 38 | GCAAAGAACATAGAGAACGCAGCGGAGAAAGCGTTGTCTCCACTAGGGATAACTGATTGGAACTCAGTTT |
| > Seq 39 | GCAAAGAACATAGAGAACGCAGCGGAGAAAGCGTTGTCTCCACTAGGGATAACTGATTGGAACTCAGTTT |
| > Seq 40 | GCAAAGAACATAGAGAACGCAGCGGAGAAAGCGTTGTCTCCACTAGGGATAACTGATTGGAACTCAGTTT |
| > Seq 41 | GCAAAGAACATAGAGAACGCAGCGGAGAAAGCGTTGTCTCCACTAGGGATAACTGATTGGAACTCAGTTT |
| > Seq 42 | GCAAAGAACATAGAGAACGCAGCGGAGAAAGCGTTGTCTCCACTAGGGATAACTGATTGGAACTCAGTTT |
| > Seq 43 | GCAAAGAACATAGAGAACGCAGCGGAGAAAGCGTTGTCTCCACTAGGGATAACTGATTGGAACTCAGTTT |
| > Seq 44 | GCAAAGAACATAGAGAACGCAGCGGAGAAAGCGTTGTCTCCACTAGGGATAACTGATTGGAACTCAGTTT |
| > Seq 45 | GCAAAGAACATAGAGAACGCAGCGGAGAAAGCGTTGTCTCCACTAGGGATAACTGATTGGAACTCAGTTT |

| | | |
|---|---|---|
| Seq 6 | TCTGGATGGTGCACCCAGGTGGTCGAGCCATATATTGGACCAGGTGGAGCGAAAACTAAACCTTAAGGAAGA |
| Seq 7 | TCTGGATGGTGCACCCAGGTGGTCGAGCCATATATTGGACCAGGTGGAGCGAAAACTAAACCTTAAGGAAGA |
| Seq 8 | TCTGGATGGTGCACCCAGGTGGTCGAGCCATATATTGGACCAGGTGGAGCGAAAACTAAACCTTAAGGAAGA |
| Seq 9 | TCTGGATGGTGCACCCAGGTGGTCGAGCCATATATTGGACCAGGTGGAGCGAAAACTAAACCTTAAGGAAGA |
| Seq 10 | TCTGGATGGTGCACCCAGGTGGTCGAGCCATATATTGGACCAGGTGGAGCGAAAACTAAACCTTAAGGAAGA |
| Seq 11 | TCTGGATGGTGCACCCAGGTGGTCGAGCCATATATTGGACCAGGTGGAGCGAAAACTAAACCTTAAGGAAGA |
| Seq 12 | TCTGGATGGTGCACCCAGGTGGTCGAGCCATATATTGGACCAGGTGGAGCGAAAACTAAACCTTAAGGAAGA |
| Seq 13 | TCTGGATGGTGCACCCAGGTGGTCGAGCCATATATTGGACCAGGTGGAGCGAAAACTAAACCTTAAGGAAGA |
| Seq 14 | TCTGGATGGTGCACCCAGGTGGTCGAGCCATATATTGGACCAGGTGGAGCGAAAACTAAACCTTAAGGAAGA |
| Seq 15 | TCTGGATGGTGCACCCAGGTGGTCGAGCCATATATTGGACCAGGTGGAGCGAAAACTAAACCTTAAGGAAGA |
| Seq 16 | TCTGGATGGTGCACCCAGGTGGTCGAGCCATATATTGGACCAGGTGGAGCGAAAACTAAACCTTAAGGAAGA |
| Seq 17 | TCTGGATGGTGCACCCAGGTGGTCGAGCCATATATTGGACCAGGTGGAGCGAAAACTAAACCTTAAGGAAGA |
| Seq 18 | TCTGGATGGTGCACCCAGGTGGTCGAGCCATATATTGGACCAGGTGGAGCGAAAACTAAACCTTAAGGAAGA |
| Seq 19 | TCTGGATGGTGCACCCAGGTGGTCGAGCCATATATTGGACCAGGTGGAGCGAAAACTAAACCTTAAGGAAGA |
| Seq 20 | TCTGGATGGTGCACCCAGGTGGTCGAGCCATATATTGGACCAGGTGGAGCGAAAACTAAACCTTAAGGAAGA |
| Seq 21 | TCTGGATGGTGCACCCAGGTGGTCGAGCCATATATTGGACCAGGTGGAGCGAAAACTAAACCTTAAGGAAGA |
| Seq 22 | TCTGGATGGTGCACCCAGGTGGTCGAGCCATATATTGGACCAGGTGGAGCGAAAACTAAACCTTAAGGAAGA |
| Seq 23 | TCTGGATGGTGCACCCAGGTGGTCGAGCCATATATTGGACCAGGTGGAGCGAAAACTAAACCTTAAGGAAGA |
| Seq 24 | TCTGGATGGTGCACCCAGGTGGTCGAGCCATATATTGGACCAGGTGGAGCGAAAACTAAACCTTAAGGAAGA |
| Seq 25 | TCTGGATGGTGCACCCAGGTGGTCGAGCCATATATTGGACCAGGTGGAGCGAAAACTAAACCTTAAGGAAGA |
| Seq 26 | TCTGGATGGTGCACCCAGGTGGTCGAGCCATATATTGGACCAGGTGGAGCGAAAACTAAACCTTAAGGAAGA |
| Seq 27 | TCTGGATGGTGCACCCAGGTGGTCGAGCCATATATTGGACCAGGTGGAGCGAAAACTAAACCTTAAGGAAGA |
| Seq 28 | TCTGGATGGTGCACCCAGGTGGTCGAGCCATATATTGGACCAGGTGGAGCGAAAACTAAACCTTAAGGAAGA |
| Seq 29 | TCTGGATGGTGCACCCAGGTGGTCGAGCCATATATTGGACCAGGTGGAGCGAAAACTAAACCTTAAGGAAGA |

FIG. 13 (continued)

| | |
|---|---|
| Seq 30 | TCTGGATGGTGCACCCAGGTGGTCGAGCCATATTGGACCAGGTGGAGCGAAAACTAAACCTTAAGGAAGA |
| Seq 31 | TCTGGATGGTGCACCCAGGTGGTCGAGCCATATTGGACCAGGTGGAGCGAAAACTAAACCTTAAGGAAGA |
| Seq 32 | TCTGGATGGTGCACCCAGGTGGTCGAGCCATATTGGACCAGGTGGAGCGAAAACTAAACCTTAAGGAAGA |
| Seq 33 | TCTGGATGGTGCACCCAGGTGGTCGAGCCATATTGGACCAGGTGGAGCGAAAACTAAACCTTAAGGAAGA |
| Seq 34 | TCTGGATGGTGCACCCAGGTGGTCGAGCCATATTGGACCAGGTGGAGCGAAAACTAAACCTTAAGGAAGA |
| Seq 35 | TCTGGATGGTGCACCCAGGTGGTCGAGCCATATTGGACCAGGTGGAGCGAAAACTAAACCTTAAGGAAGA |
| Seq 36 | TCTGGATGGTGCACCCAGGTGGTCGAGCCATATTGGACCAGGTGGAGCGAAAACTAAACCTTAAGGAAGA |
| Seq 37 | TCTGGATGGTGCACCCAGGTGGTCGAGCCATATTGGACCAGGTGGAGCGAAAACTAAACCTTAAGGAAGA |
| Seq 38 | TCTGGATGGTGCACCCAGGTGGTCGAGCCATATTGGACCAGGTGGAGCGAAAACTAAACCTTAAGGAAGA |
| Seq 39 | TCTGGATGGTGCACCCAGGTGGTCGAGCCATATTGGACCAGGTGGAGCGAAAACTAAACCTTAAGGAAGA |
| Seq 40 | TCTGGATGGTGCACCCAGGTGGTCGAGCCATATTGGACCAGGTGGAGCGAAAACTAAACCTTAAGGAAGA |
| Seq 41 | TCTGGATGGTGCACCCAGGTGGTCGAGCCATATTGGACCAGGTGGAGCGAAAACTAAACCTTAAGGAAGA |
| Seq 42 | TCTGGATGGTGCACCCAGGTGGTCGAGCCATATTGGACCAGGTGGAGCGAAAACTAAACCTTAAGGAAGA |
| Seq 43 | TCTGGATGGTGCACCCAGGTGGTCGAGCCATATTGGACCAGGTGGAGCGAAAACTAAACCTTAAGGAAGA |
| Seq 44 | TCTGGATGGTGCACCCAGGTGGTCGAGCCATATTGGACCAGGTGGAGCGAAAACTAAACCTTAAGGAAGA |
| Seq 45 | TCTGGATGGTGCACCCAGGTGGTCGAGCCATATTGGACCAGGTGGAGCGAAAACTAAACCTTAAGGAAGA |
| Seq 46 | TCTGGATGGTGCACCCAGGTGGTCGAGCCATATTGGACCAGGTGGAGCGAAAACTAAACCTTAAGGAAGA |
| Seq 47 | TCTGGATGGTGCACCCAGGTGGTCGAGCCATATTGGACCAGGTGGAGCGAAAACTAAACCTTAAGGAAGA |
| Seq 48 | TCTGGATGGTGCACCCAGGTGGTCGAGCCATATTGGACCAGGTGGAGCGAAAACTAAACCTTAAGGAAGA |
| Seq 49 | TCTGGATGGTGCACCCAGGTGGTCGAGCCATATTGGACCAGGTGGAGCGAAAACTAAACCTTAAGGAAGA |
| Seq 50 | TCTGGATGGTGCACCCAGGTGGTCGAGCCATATTGGACCAGGTGGAGCGAAAACTAAACCTTAAGGAAGA |
| Seq 51 | TCTGGATGGTGCACCCAGGTGGTCGAGCCATATTGGACCAGGTGGAGCGAAAACTAAACCTTAAGGAAGA |
| Seq 52 | TCTGGATGGTGCACCCAGGTGGTCGAGCCATATTGGACCAGGTGGAGCGAAAACTAAACCTTAAGGAAGA |
| Seq 53 | TCTGGATGGTGCACCCAGGTGGTCGAGCCATATTGGACCAGGTGGAGCGAAAACTAAACCTTAAGGAAGA |

FIG. 13 (continued)

```
Seq 54  TCTGGATGGTGCACCCAGGTGGTCGAGCCATATTGGACCAGGTGGAGCGGAAAACTAAACCTTAAGGAAGA
Seq 55  TCTGGATGGTGCACCCAGGTGGTCGAGCCATATTGGACCAGGTGGAGCGGAAAACTAAACCTTAAGGAAGA
Seq 56  TCTGGATGGTGCACCCAGGTGGTCGAGCCATATTGGACCAGGTGGAGCGGAAAACTAAACCTTAAGGAAGA
Seq 57  TCTGGATGGTGCACCCAGGTGGTCGAGCCATATTGGACCAGGTGGAGCGGAAAACTAAACCTTAAGGAAGA
Seq 58  TCTGGATGGTGCACCCAGGTGGTCGAGCCATATTGGACCAGGTGGAGCGGAAAACTAAACCTTAAGGAAGA
Seq 59  TCTGGATGGTGCcagCCAGGTGGTCGAGCCATATTGGACCAGGTGGAGCGGAAAACTAAACCTTAAGGAAGA
Seq 60  TCTGGATGGTGCACCCAGGTGGTCGAGCCATATTGGACCAGGTGGAGCGGAAAACTAAACCTTAAGGAAGA
Seq 61  TCTGGATGGTGCACCCAGGTGGTCGAGCCATATTGGACCAGGTGGAGCGGAAAACTAAACCTTAAGGAAGA
Seq 62  TCTGGATGGTGCACCCAGGTGGTCGAGCCATATTGGACCAGGTGGAGCGGAAAACTAAACCTTAAGGAAGA 1050
981
Seq 1   TAAGTTAAGGGCTAGCAGGCATGTGCTTAGTGAATACGGAAACCTGATTAGCGCTTGTGTTGTTCATC
Seq 2   TAAGTTAAGGGCTAGCAGGCATGTGCTTAGTGAATACGGAAACCTGATTAGCGCTTGTGTTGTTCATC
Seq 3   TAAGTTAAGGGCTAGCAGGCATGTGCTTAGTGAATACGGAAACCTGATTAGCGCTTGTGTTGTTCATC
Seq 4   TAAGTTAAGGGCTAGCAGGCATGTGCTTAGTGAATACGGAAACCTGATTAGCGCTTGTGTTGTTCATC
Seq 5   TAAGTTAAGGGCTAGCAGGCATGTGCTTAGTGAATACGGAAACCTGATTAGCGCTTGTGTTGTTCATC
Seq 6   TAAGTTAAGGGCTAGCAGGCATGTGCTTAGTGAATACGGAAACCTGATTAGCGCTTGTGTTGTTCATC
Seq 7   TAAGTTAAGGGCTAGCAGGCATGTGCTTAGTGAATACGGAAACCTGATTAGCGCTTGTGTTGTTCATC
Seq 8   TAAGTTAAGGGCTAGCAGGCATGTGCTTAGTGAATACGGAAACCTGATTAGCGCTTGTGTTGTTCATC
Seq 9   TAAGTTAAGGGCTAGCAGGCATGTGCTTAGTGAATACGGAAACCTGATTAGCGCTTGctGTGTTGTTCATC
Seq 10  TAAGTTAAGGGCTAGCAGGCATGTGCTTAGTGAATACGGAAACCTGATTAGCGCTTGTGTTGTTCATC
Seq 11  TAAGTTAAGGGCTAGCAGGCATGTGCTTAGTGAATACGGAAACCTGATTAGCGCTTGctGTGTTGTTCATC
Seq 12  TAAGTTAAGGGCTAGCAGGCATGTGCTTAGTGAATACGGAAACCTGATTAGCGCTTGctGTGTTGTTCATC
Seq 13  TAAGTTAAGGGCTAGCAGGCATGTGCTTAGTGAATACGGAAACCTGATTAGCGCTTGTGTTGTTCATC
```

FIG. 13 (continued)

```
>Seq 14  TAAGTTAAGGGCTAGCAGGCATGTGCTTAGTGAATACGGAAACCTGATTAGCGCTgctGTGTTGTTCATC
>Seq 15  TAAGTTAAGGGCTAGCAGGCATGTGCTTAGTGAATACGGAAACCTGATTAGCGCTgctGTGTTGTTCATC
>Seq 16  TAAGTTAAGGGCTAGCAGGCATGTGCTTAGTGAATACGGAAACCTGATTAGCGCTgctGTGTTGTTCATC
>Seq 17  TAAGTTAAGGGCTAGCAGGCATGTGCTTAGTGAATACGGAAACCTGATTAGCGCTgctGTGTTGTTCATC
>Seq 18  TAAGTTAAGGGCTAGCAGGCATGTGCTTAGTGAATACGGAAACCTGATTAGCGCTgctGTGTTGTTCATC
>Seq 19  TAAGTTAAGGGCTAGCAGGCATGTGCTTAGTGAATACGGAAACCTGATTAGCGCTgctGTGTTGTTCATC
>Seq 20  TAAGTTAAGGGCTAGCAGGCATGTGCTTAGTGAATACGGAAACCTGATTAGCGCTgctGTGTTGTTCATC
>Seq 21  TAAGTTAAGGGCTAGCAGGCATGTGCTTAGTGAATACGGAAACCTGATTAGCGCTgctGTGTTGTTCATC
>Seq 22  TAAGTTAAGGGCTAGCAGGCATGTGCTTAGTGAATACGGAAACCTGATTAGCGCTgctGTGTTGTTCATC
>Seq 23  TAAGTTAAGGGCTAGCAGGCATGTGCTTAGTGAATACGGAAACCTGATTAGCGCTgctGTGTTGTTCATC
>Seq 24  TAAGTTAAGGGCTAGCAGGCATGTGCTTAGTGAATACGGAAACCTGATTAGCGCTgctGTGTTGTTCATC
>Seq 25  TAAGTTAAGGGCTAGCAGGCATGTGCTTAGTGAATACGGAAACCTGATTAGCGCTgctGTGTTGTTCATC
>Seq 26  TAAGTTAAGGGCTAGCAGGCATGTGCTTAGTGAATACGGAAACCTGATTAGCGCTgctGTGTTGTTCATC
>Seq 27  TAAGTTAAGGGCTAGCAGGCATGTGCTTAGTGAATACGGAAACCTGtttAGCGCTGTTGTGTTGTTCATC
>Seq 28  TAAGTTAAGGGCTAGCAGGCATGTGCTTAGTGAATACGGAAACCTGatgAGCGCTGCTGTGTTGTTCATC
>Seq 29  TAAGTTAAGGGCTAGCAGGCATGTGCTTAGTGAATACGGAAACCTGATTAGCGCTGCTGTGTTGTTCATC
>Seq 30  TAAGTTAAGGGCTAGCAGGCATGTGCTTAGTGAATACGGAAACCTGATTAGCGCTGCTGTGTTGTTCATC
>Seq 31  TAAGTTAAGGGCTAGCAGGCATGTGCTTAGTGAATACGGAAACCTGATTAGCGCTGCTGTGTTGTTCATC
>Seq 32  TAAGTTAAGGGCTAGCAGGCATGTGCTTAGTGAATACGGAAACCTGATTAGCGCTGCTGTGTTGTTCATC
>Seq 33  TAAGTTAAGGGCTAGCAGGCATGTGCTTAGTGAATACGGAAACCTGATTAGCGCTGCTGTGTTGTTCATC
>Seq 34  TAAGTTAAGGGCTAGCAGGCATGTGCTTAGTGAATACGGAAACCTGATTAGCGCTGCTGTGTTGTTCATC
>Seq 35  TAAGTTAAGGGCTAGCAGGCATGTGCTTAGTGAATACGGAAACCTGATTAGCGCTGCTGTGTTGTTCATC
>Seq 36  TAAGTTAAGGGCTAGCAGGCATGTGCTTAGTGAATACGGAAACCTGATTAGCGCTGCTGTGTTGTTCATC
>Seq 37  TAAGTTAAGGGCTAGCAGGCATGTGCTTAGTGAATACGGAAACCTGATTAGCGCTgctGTGTTGTTCATC
```

FIG. 13 (continued)

| | |
|---|---|
| Seq 38 | TAAGTTAAGGGCTAGCAGGCATGTGCTTAGTGAATACGGAAACCTGATTAGCGCTTGTGTGTTGTTCATC |
| Seq 39 | TAAGTTAAGGGCTAGCAGGCATGTGCTTAGTGAATACGGAAACCTGATTAGCGCTTGTGTGTTGTTCATC |
| Seq 40 | TAAGTTAAGGGCTAGCAGGCATGTGCTTAGTGAATACGGAAACCTGATTAGCGCTgCTGTGTGTTGTTCATC |
| Seq 41 | TAAGTTAAGGGCTAGCAGGCATGTGCTTAGTGAATACGGAAACCTGATTAGCGCTTGTGTGTTGTTCATC |
| Seq 42 | TAAGTTAAGGGCTAGCAGGCATGTGCTTAGTGAATACGGAAACCTGATTAGCGCTTGTGTGTTGTTCATC |
| Seq 43 | TAAGTTAAGGGCTAGCAGGCATGTGCTTAGTGAATACGGAAACCTGttAGCGCTTGTGTGTTGTTCATC |
| Seq 44 | TAAGTTAAGGGCTAGCAGGCATGTGCTTAGTGAATACGGAAACCTGtttAGCGCTTGTGTGTTGTTCATC |
| Seq 45 | TAAGTTAAGGGCTAGCAGGCATGTGCTTAGTGAATACGGAAACCTGATTAGCGCTTGTGTGTTGTTCATC |
| Seq 46 | TAAGTTAAGGGCTAGCAGGCATGTGCTTAGTGAATACGGAAACCTGATTAGCGCTTGTGTGTTGTTCATC |
| Seq 47 | TAAGTTAAGGGCTAGCAGGCATGTGCTTAGTGAATACGGAAACCTGATTAGCGCTtctGTGTGTTGTTCATC |
| Seq 48 | TAAGTTAAGGGCTAGCAGGCATGTGCTTAGTGAATACGGAAACCTGATTAGCGCTgctGTGTGTTGTTCATC |
| Seq 49 | TAAGTTAAGGGCTAGCAGGCATGTGCTTAGTGAATACGGAAACCTGATTAGCGCTTGTGTGTTGTTCATC |
| Seq 50 | TAAGTTAAGGGCTAGCAGGCATGTGCTTAGTGAATACGGAAACCTGATTAGCGCTTGTGTGTTGTTCATC |
| Seq 51 | TAAGTTAAGGGCTAGCAGGCATGTGCTTAGTGAATACGGAAACCTGATTAGCGCTTGTGTGTTGTTCATC |
| Seq 52 | TAAGTTAAGGGCTAGCAGGCATGTGCTTAGTGAATACGGAAACCTGATTAGCGCTTGTGTGTTGTTCATC |
| Seq 53 | TAAGTTAAGGGCTAGCAGGCATGTGCTTAGTGAATACGGAAACCTGATTAGCGCTTGTGTGTTGTTCATC |
| Seq 54 | TAAGTTAAGGGCTAGCAGGCATGTGCTTAGTGAATACGGAAACCTGATTAGCGCTTGTGTGTTGTTCATC |
| Seq 55 | TAAGTTAAGGGCTAGCAGGCATGTGCTTAGTGAATACGGAAACCTGATTAGCGCTTGTGTGTTGTTCATC |
| Seq 56 | TAAGTTAAGGGCTAGCAGGCATGTGCTTAGTGAATACGGAAACCTGATTAGCGCTTGTGTGTTGTTCATC |
| Seq 57 | TAAGTTAAGGGCTAGCAGGCATGTGCTTAGTGAATACGGAAACCTGATTAGCGCTTGTGTGTTGTTCATC |
| Seq 58 | TAAGTTAAGGGCTAGCAGGCATGTGCTTAGTGAATACGGAcaCCTGATTAGCGCTTGTGTGTTGTTCATC |
| Seq 59 | TAAGTTAAGGGCTAGCAGGCATGTGCTTAGTGAATACGGAAACCTGATTAGCGCTTGTGTGTTGTTCATC |
| Seq 60 | TAAGTTAAGGGCTAGCAGGCATGTGCTTAGTGAATACGGAAACCTGATTAGCGCTTGTGTGTTGTTCATC |
| Seq 61 | TAAGTTAAGGGCTAGCAGGCATGTGCTTAGTGAATACGGAAACCTGatgAGCGCTTGTGTGTTGTTCATC |

FIG. 13 (continued)

```
> Seq 62   TAAGTTAAGGGCTAGCAGGCATGTGCTTAGTGAATACGGAAACCTGATTAGCGCTTGTGTTGTTCATC
           1051                                                                    1120
                 .         .         .         .         .         .         .
> Seq  1   ATTGACGAGGTGAGGAAGAGATCTATGGCGGAAGGGAAGAGTACAACCGGTGAAGGTTTGGATTGCGGTG
> Seq  2   ATTGACGAGGTGAGGAAGAGATCTATGGCGGAAGGGAAGAGTACAACCGGTGAAGGTTTGGATTGCGGTG
> Seq  3   ATTGACGAGGTGAGGAAGAGATCTATGGCGGAAGGGAAGAGTACAACCGGTGAAGGTTTGGATTGCGGTG
> Seq  4   ATTGACGAGGTGAGGAAGAGATCTATGGCGGAAGGGAAGAGTACAACCGGTGAAGGTTTGGATTGCGGTG
> Seq  5   ATTGACGAGGTGAGGAAGAGATCTATGGCGGAAGGGAAGAGTACAACCGGTGAAGGTTTGGATTGCGGTG
> Seq  6   ATTGACGAGGTGAGGAAGAGATCTATGGCGGAAGGGAAGAGTACAACCGGTGAAGGTTTGGATTGCGGTG
> Seq  7   ATTGACGAGGTGAGGAAGAGATCTATGGCGGAAGGGAAGAGTACAACCGGTGAAGGTTTGGATTGCGGTG
> Seq  8   ATTGACGAGGTGAGGAAGAGATCTATGGCGGAAGGGAAGAGTACAACCGGTGAAGGTTTGGATTGCGGTG
> Seq  9   ATTGACGAGGTGAGGAAGAGATCTATGGCGGAAGGGAAGAGTACAACCGGTGAAGGTTTGGATtCCGGTG
> Seq 10   ATTGACGAGGTGAGGAAGAGATCTATGGCGGAAGGGAAGAGTACAACCGGTGAAGGTTTGGATtCCGGTG
> Seq 11   ATTGACGAGGTGAGGAAGAGATCTATGGCGGAAGGGAAGAGTACAACCGGTGAAGGTTTGGATtCCGGTG
> Seq 12   ATTGACGAGGTGAGGAAGAGATCTATGGCGGAAGGGAAGAGTACAACCGGTGAAGGTTTGGATtCCGGTG
> Seq 13   ATTGACGAGGTGAGGAAGAGATCTATGGCGGAAGGGAAGAGTACAACCGGTGAAGGTTTGGATtCCGGTG
> Seq 14   ATTGACGAGGTGAGGAAGAGATCTATGGCGGAAGGGAAGAGTACAACCGGTGAAGGTTTGGATtCCGGTG
> Seq 15   ATTGACGAGGTGAGGAAGAGATCTATGGCGGAAGGGAAGAGTACAACCGGTGAAGGTTTGGATtCCGGTG
> Seq 16   ATTGACGAGGTGAGGAAGAGATCTATGGCGGAAGGGAAGAGTACAACCGGTGAAGGTTTGGATtCCGGTG
> Seq 17   ATTGACGAGGTGAGGAAGAGATCTATGGCGGAAGGGAAGAGTACAACCGGTGAAGGTTTGGATtCCGGTG
> Seq 18   ATTGACGAGGTGAGGAAGAGATCTATGGCGGAAGGGAAGAGTACAACCGGTGAAGGTTTGGATtCCGGTG
> Seq 19   ATTGACGAGGTGAGGAAGAGATCTATGGCGGAAGGGAAGAGTACAACCGGTGAAGGTTTGGATtCCGGTG
> Seq 20   ATTGACGAGGTGAGGAAGAGATCTATGGCGGAAGGGAAGAGTACAACCGGTGAAGGTTTGGATtCCGGTG
> Seq 21   ATTGACGAGGTGAGGAAGAGATCTATGGCGGAAGGGAAGAGTACAACCGGTGAAGGTTTGGATtCCGGTG
```

FIG. 13 (continued)

| | |
|---|---|
| Seq 22 | ATTGACGAGGTGAGGAAGAGATCTATGGCGGAAGGGAAGAGTACAACCGGTGAAGGTGAAGGTTTGGATtccGGTG |
| Seq 23 | ATTGACGAGGTGAGGAAGAGATCTATGGCGGAAGGGAAGAGTACAACCGGTGAAGGTGAAGGTTTGGATTGCGGTG |
| Seq 24 | ATTGACGAGGTGAGGAAGAGATCTATGGCGGAAGGGAAGAGTACAACCGGTGAAGGTGAAGGTTTGGATTGCGGTG |
| Seq 25 | ATTGACGAGGTGAGGAAGAGATCTATGGCGGAAGGGAAGAGTACAACCGGTGAAGGTGAAGGTTTGGATTGCGGTG |
| Seq 26 | ATTGACGAGGTGAGGAAGAGATCTATGGCGGAAGGGAAGAGTACAACCGGTGAAGGTGAAGGTTTGGATTGCGGTG |
| Seq 27 | ATTGACGAGGTGAGGAAGAGATCTATGGCGGAAGGGAAGAGTACAACCGGTGAAGGTGAAGGTTTGGATTGCGGTG |
| Seq 28 | ATTGACGAGGTGAGGAAGAGATCTATGGCGGAAGGGAAGAGTACAACCGGTGAAGGTGAAGGTTTGGATTGCGGTG |
| Seq 29 | ATTGACGAGGTGAGGAAGAGATCTATGGCGGAAGGGAAGAGTACAACCGGTGAAGGTGAAGGTTTGGATTGCGGTG |
| Seq 30 | ATTGACCAGGTGAGGAAGAGATCTATGGCGGAAGGGAAGAGTACAACCGGTGAAGGTGAAGGTTTGGATTGCGGTG |
| Seq 31 | ATTGACGAGGTGAGGAAGAGATCTATGGCGGAAGGGAAGAGTACAACCGGTGAAGGTGAAGGTTTGGATTGCGGTG |
| Seq 32 | ATTGACGAGGTGAGGAAGAGATCTATGGCGGAAGGGAAGAGTACAACCGGTGAAGGTGAAGGTTTGGATTGCGGTG |
| Seq 33 | ATTGACGAGGTGAGGAAGAGATCTATGGCGGAAGGGAAGAGTACAACCGGTGAAGGTGAAGGTTTGGATTGCGGTG |
| Seq 34 | ATTGACGAGGTGAGGAAGAGATCTATGGCGGAAGGGAAGAGTACAACCGGTGAAGGTGAAGGTTTGGATTGCGGTG |
| Seq 35 | ATTGACGAGGTGAGGAAGAGATCTATGGCGGAAGGGAAGAGTACAACCGGTGAAGGTGAAGGTTTGGATTGCGGTG |
| Seq 36 | ATTGACGAGGTGAGGAAGAGATCTATGGCGGAAGGGAAGAGTACAACCGGTGAAGGTGAAGGTTTGGATTGCGGTG |
| Seq 37 | ATTGACGAGGTGAGGAAGAGATCTATGGCGGAAGGGAAGAGTACAACCGGTGAAGGTGAAGGTTTGGATtccGGTG |
| Seq 38 | ATTGACGAGGTGAGGAAGAGATCTATGGCGGAAGGGAAGAGTACAACCGGTGAAGGTGAAGGTTTGGATTGCGGTG |
| Seq 39 | ATTGACGAGGTGAGGAAGAGATCTATGGCGGAAGGGAAGAGTACAACCGGTGAAGGTGAAGGTTTGGATTGCGGTG |
| Seq 40 | ATTGACGAGGTGAGGAAGAGATCTATGGCGGAAGGGAAGAGTACAACCGGTGAAGGTGAAGGTTTGGATTGCGGTG |
| Seq 41 | ATTGACGAGGTGAGGAAGAGATCTATGGCGGAAGGGAAGAGTACAACCGGTGAAGGTGAAGGTTTGGATTGCGGTG |
| Seq 42 | ATTGACGAGGTGAGGAAGAGATCTATGGCGGAAGGGAAGAGTACAACCGGTGAAGGTGAAGGTTTGGATTGCGGTG |
| Seq 43 | ATTGACGAGGTGAGGAAGAGATCTATGGCGGAAGGGAAGAGTACAACCGGTGAAGGTGAAGGTTTGGATTGCGGTG |
| Seq 44 | ATTGACGAGGTGAGGAAGAGATCTATGGCGGAAGGGAAGAGTACAACCGGTGAAGGTGAAGGTTTGGATTGCGGTG |
| Seq 45 | ATTGACGAGGTGAGGAAGAGATCTATGGCGGAAGGGAAGAGTACAACCGGTGAAGGTGAAGGTTTGGATtccGGTG |

FIG. 13 (continued)

```
      46 ATTGACGAGGTGAGGAGAAGAGATCTATGGCGGAAGGGAAGAGTACAACCGGTGAAGGTTTGGATgccGGTG
      47 ATTGACGAGGTGAGGAGAAGAGATCTATGGCGGAAGGGAAGAGTACAACCGGTGAAGGTTTGGATTGCGGTG
      48 ATTGACGAGGTGAGGAGAAGAGATCTATGGCGGAAGGGAAGAGTACAACCGGTGAAGGTTTGGATTGCGGTG
      49 ATTGACGAGGTGAGGAGAAGAGATCTATGGCGGAAGGGAAGAGTACAACCGGTGAAGGTTTGGATTGCGGTG
      50 ATTGACGAGGTGAGGAGAAGAGATCTATGGCGGAAGGGAAGAGTACAACCGGTGAAGGTTTGGATTGCGGTG
      51 ATTGACGAGGTGAGGAGAAGAGATCTATGGCGGAAGGGAAGAGTACAACCGGTGAAGGTTTGGATTGCGGTG
      52 ATTGACGAGGTGAGGAGAAGAGATCTATGGCGGAAGGGAAGAGTACAACCGGTGAAGGTTTGGATTGCGGTG
      53 ATTGACGAGGTGAGGAGAAGAGATCTATGGCGGAAGGGAAGAGTACAACCGGTGAAGGTTTGGATTGCGGTG
      54 ATTGACGAGGTGAGGAGAAGAGATCTATGGCGGAAGGGAAGAGTACAACCGGTGAAGGTTTGGATTGCGGTG
      55 ATTGACGAGGTGAGGAGAAGAGATCTATGGCGGAAGGGAAGAGTACAACCGGTGAAGGTTTGGATTGCGGTG
      56 ATTGACGAGGTGAGGAGAAGAGATCTATGGCGGAAGGGAAGAGTACAACCGGTGAAGGTTTGGATTGCGGTG
      57 ATTGACGAGGTGAGGAGAAGAGATCTATGGCGGAAGGGAAGAGTACAACCGGTGAAGGTTTGGATTGCGGTG
      58 ATTGACGAGGTGAGGAGAAGAGATCTATGGCGGAAGGGAAGAGTACAACCGGTGAAGGTTTGGATTGCGGTG
      59 ATTGACGAGGTGAGGAGAAGAGATCTATGGCGGAAGGGAAGAGTACAACCGGTGAAGGTTTGGATTGCGGTG
      60 ATTGACGAGGTGAGGAGAAGAGATCTATGGCGGAAGGGAAGAGTACAACCGGTGAAGGTTTGGATTGCGGTG
      61 ATTGACGAGGTGAGGAGAAGAGATCTATGGCGGAAGGGAAGAGTACAACCGGTGAAGGTTTGGATTGCGGTG
      62 ATTGACGAGGTGAGGAGAAGAGATCTATGGCGGAAGGGAAGAGTACAACCGGTGAAGGTTTGGATTGCGGTG 1121                                                                    1190
       1 TTTTGTTTTGGATTTGGACCGGTATGACTGTTGAGACTGTTGTTCTTCGTAGCGTCCGCGTTACTGCTGC
       2 TTTTGTTTTGGATTTGGACCGGTATGACTGTTGAGACTGTTGTTCTTCGTAGCGTCCGCGTTACTGCTGC
       3 TTTTGTTTTGGATTTGGACCGGTATGACTGTTGAGACTGTTGTTCTTCGTAGCGTCCGCGTTACTGCTGC
       4 TTTTGTTTTGGATTTGGACCGGTATGACTGTTGAGACTGTTGTTCTTCGTAGCGTCCGCGTTACTGCTGC
       5 TTTTGTTTTGGATTTGGACCGGTATGACTGTTGAGACTGTTGTTCTTCGTAGCGTCCGCGTTACTGCTGC
```

FIG. 13 (continued)

```
>Seq 6   TTTTGTTTGGATTTGGACCGGGTATGACTGTTGAGACTGTTGTTCTTCGTAGCGTCCGCGTTACTGCTGC
>Seq 7   TTTTGTTTGGATTTGGACCGGGTATGACTGTTGAGACTGTTGTTCTTCGTAGCGTCCGCGTTACTGCTGC
>Seq 8   TTTTGTTTGGATTTGGACCGGGTATGACTGTTGAGACTGTTGTTCTTCGTAGCGTCCGCGTTACTGCTGC
>Seq 9   TTTTGTTTGGATTTGGACCGGGTATGACTGTTGAGACTGTTGTTCTTCGTAGCGTCCGCGTTACTGCTGC
>Seq 10  TTTTGTTTGGATTTGGACCGGGTATGACTGTTGAGACTGTTGTTCTTCGTAGCGTCCGCGTTACTGCTGC
>Seq 11  TTTTGTTTGGATTTGGACCGGGTATGACTGTTGAGACTGTTGTTCTTCGTAGCGTCCGCGTTACTGCTGC
>Seq 12  TTTTGTTTGGATTTGGACCGGGTATGACTGTTGAGACTGTTGTTCTTCGTAGCGTCCGCGTTACTGCTGC
>Seq 13  TTTTGTTTGGATTTGGACCGGGTATGACTGTTGAGACTGTTGTTCTTCGTAGCGTCCGCGTTACTGCTGC
>Seq 14  TTTTGTTTGGATTTGGACCGGGTATGACTGTTGAGACTGTTGTTCTTCGTAGCGTCCGCGTTACTGCTGC
>Seq 15  TTTTGTTTGGATTTGGACCGGGTATGACTGTTGAGACTGTTGTTCTTCGTAGCGTCCGCGTTACTGCTGC
>Seq 16  TTTTGTTTGGATTTGGACCGGGTATGACTGTTGAGACTGTTGTTCTTCGTAGCGTCCGCGTTACTGCTGC
>Seq 17  TTTTGTTTGGATTTGGACCGGGTATGACTGTTGAGACTGTTGTTCTTCGTAGCGTCCGCGTTACTGCTGC
>Seq 18  TTTTGTTTGGATTTGGACCGGGTATGACTGTTGAGACTGTTGTTCTTCGTAGCGTCCGCGTTACTGCTGC
>Seq 19  TTTTGTTTGGATTTGGACCGGGTATGACTGTTGAGACTGTTGTTCTTCGTAGCGTCCGCGTTACTGCTGC
>Seq 20  TTTTGTTTGGATTTGGACCGGGTATGACTGTTGAGACTGTTGTTCTTCGTAGCGTCCGCGTTACTGCTGC
>Seq 21  TTTTGTTTGGATTTGGACCGGGTATGACTGTTGAGACTGTTGTTCTTCGTAGCGTCCGCGTTACTGCTGC
>Seq 22  TTTTGTTTGGATTTGGACCGGGTATGACTGTTGAGACTGTTGTTCTTCGTAGCGTCCGCGTTACTGCTGC
>Seq 23  TTTTGTTTGGATTTGGACCGGGTATGACTGTTGAGACTGTTGTTCTTCGTAGCGTCCGCGTTACTGCTGC
>Seq 24  TTTTGTTTGGATTTGGACCGGGTATGACTGTTGAGACTGTTGTTCTTCGTAGCGTCCGCGTTACTGCTGC
>Seq 25  TTTTGTTTGGATTTGGACCGGGTATGACTGTTGAGACTGTTGTTCTTCGTAGCGTCCGCGTTACTGCTGC
>Seq 26  TTTTGTTTGGATTTGGACCGGGTATGACTGTTGAGACTGTTGTTCTTCGTAGCGTCCGCGTTACTGCTGC
>Seq 27  TTTTGTTTGGATTTGGACCGGGTATGACTGTTGAGACTGTTGTTCTTCGTAGCGTCCGCGTTACTGCTGC
>Seq 28  TTTTGTTTGGATTTGGACCGGGTATGACTGTTGAGACTGTTGTTCTTCGTAGCGTCCGCGTTACTGCTGC
>Seq 29  TTTTGTTTGGATTTGGACCGGGTATGACTGTTGAGACTGTTGTTCTTCGTAGCGTCCGCGTTACTGCTGC
```

FIG. 13 (continued)

| Seq | Sequence |
|---|---|
| > Seq 30 | TTTTGTTTGGATTTGGACCGGGTATGACTGTTGAGACTGTTGTTCTTCGTAGCGTCCGCGTTACTGCTGC |
| > Seq 31 | TTTTGTTTGGATTTGGACCGGGTATGACTGTTGAGACTGTTGTTCTTCGTAGCGTCCGCGTTACTGCTGC |
| > Seq 32 | TTTTGTTTGGATTTGGACCGGGTATGACTGTTGAGACTGTTGTTCTTCGTAGCGTCCGCGTTACTGCTGC |
| > Seq 33 | TTTTGTTTGGATTTGGACCGGGTATGACTGTTGAGACTGTTGTTCTTCGTAGCGTCCGCGTTACTGCTGC |
| > Seq 34 | TTTTGTTTGGATTTGGACCGGGTATGACTGTTGAGACTGTTGTTCTTCGTAGCGTCCGCGTTACTGCTGC |
| > Seq 35 | TTTTGTTTGGATTTGGACCGGGTATGACTGTTGAGACTGTTGTTCTTCGTAGCGTCCGCGTTACTGCTGC |
| > Seq 36 | TTTTGTTTGGATTTGGACCGGGTATGACTGTTGAGACTGTTGTTCTTCGTAGCGTCCGCGTTACTGCTGC |
| > Seq 37 | TTTTGTTTGGATTTGGACCGGGTATGACTGTTGAGACTGTTGTTCTTCGTAGCGTCCGCGTTACTGCTGC |
| > Seq 38 | TTTTGTTTGGATTTGGACCGGGTATGACTGTTGAGACTGTTGTTCTTCGTAGCGTCCGCGTTACTGCTGC |
| > Seq 39 | TTTTGTTTGGATTTGGACCGGGTATGACTGTTGAGACTGTTGTTCTTCGTAGCGTCCGCGTTACTGCTGC |
| > Seq 40 | TTTTGTTTGGATTTGGACCGGGTATGACTGTTGAGACTGTTGTTCTTCGTAGCGTCCGCGTTACTGCTGC |
| > Seq 41 | TTTTGTTTGGATTTGGACCGGGTATGACTGTTGAGACTGTTGTTCTTCGTAGCGTCCGCGTTACTGCTGC |
| > Seq 42 | TTTTGTTTGGATTTGGACCGGGTATGACTGTTGAGACTGTTGTTCTTCGTAGCGTCCGCGTTACTGCTGC |
| > Seq 43 | TTTTGTTTGGATTTGGACCGGGTATGACTGTTGAGACTGTTGTTCTTCGTAGCGTCCGCGTTACTGCTGC |
| > Seq 44 | TTTTGTTTGGATTTGGACCGGGTATGACTGTTGAGACTGTTGTTCTTCGTAGCGTCCGCGTTACTGCTGC |
| > Seq 45 | TTTTGTTTGGATTTGGACCGGGTATGACTGTTGAGACTGTTGTTCTTCGTAGCGTCCGCGTTACTGCTGC |
| > Seq 46 | TTTTGTTTGGATTTGGACCGGGTATGACTGTTGAGACTGTTGTTCTTCGTAGCGTCCGCGTTACTGCTGC |
| > Seq 47 | TTTTGTTTGGATTTGGACCGGGTATGACTGTTGAGACTGTTGTTCTTCGTAGCGTCCGCGTTACTGCTGC |
| > Seq 48 | TTTTGTTTGGATTTGGACCGGGTATGACTGTTGAGACTGTTGTTCTTCGTAGCGTCCGCGTTACTGCTGC |
| > Seq 49 | TTTTGTTTGGATTTGGACCGGGTATGACTGTTGAGACTGTTGTTCTTCGTAGCGTCCGCGTTACTGCTGC |
| > Seq 50 | TTTTGTTTGGATTTGGACCGGGTATGACTGTTGAGACTGTTGTTCTTCGTAGCGTCCGCGTTACTGCTGC |
| > Seq 51 | TTTTGTTTGGATTTGGACCGGGTATGACTGTTGAGACTGTTGTTCTTCGTAGCGTCCGCGTTACTGCTGC |
| > Seq 52 | TTTTGTTTGGATTTGGACCGGGTATGACTGTTGAGACTGTTGTTCTTCGTAGCGTCCGCGTTACTGCTGC |
| > Seq 53 | TTTTGTTTGGATTTGGACCGGGTATGACTGTTGAGACTGTTGTTCTTCGTAGCGTCCGCGTTACTGCTGC |

FIG. 13 (continued)

```
>Seq 54 TTTTGTTTTGGATTTGGACCGGGTATGACTGTTGAGACTGTTGTTCTTCGTAGCGTCCGCGTTACTGCTGC
>Seq 55 TTTTGTTTTGGATTTGGACCGGGTATGACTGTTGAGACTGTTGTTCTTCGTAGCGTCCGCGTTACTGCTGC
>Seq 56 TTTTGTTTTGGATTTGGACCGGGTATGACTGTTGAGACTGTTGTTCTTCGTAGCGTCCGCGTTACTGCTGC
>Seq 57 TTTTGTTTTGGATTTGGACCGGGTATGACTGTTGAGACTGTTGTTCTTCGTAGCGTCCGCGTTACTGCTGC
>Seq 58 TTTTGTTTTGGATTTGGACCGGGTATGACTGTTGAGACTGTTGTTCTTCGTAGCGTCCGCGTTACTGCTGC
>Seq 59 TTTTGTTTTGGATTTGGACCGGGTATGACTGTTGAGACTGTTGTTCTTCGTAGCGTCCGCGTTACTGCTGC
>Seq 60 TTTTGTTTTGGATTTGGACCGGGTATGACTGTTGAGACTGTTGTTCTTCGTAGCGTCCGCGTTACTGCTGC
>Seq 61 TTTTGTTTTGGATTTGGACCGGGTATGACTGTTGAGACTGTTGTTCTTCGTAGCGTCCGCGTTACTGCTGC
>Seq 62 TTTTGTTTTGGATTTGGACCGGGTATGACTGTTGAGACTGTTGTTCTTCGTAGCGTCCGCGTTACTGCTGC 1191                        1209
>Seq 1  GGTTGCCAATGGAAAACTGA
>Seq 2  GGTTGCCAATGGAAAACTGA
>Seq 3  GGTTGCCAATGGAAAACTGA
>Seq 4  GGTTGCCAATGGAAAACTGA
>Seq 5  GGTTGCCAATGGAAAACTGA
>Seq 6  GGTTGCCAATGGAAAACTGA
>Seq 7  GGTTGCCAATGGAAAACTGA
>Seq 8  GGTTGCCAATGGAAAACTGA
>Seq 9  GGTTGCCAATGGAAAACTGA
>Seq 10 GGTTGCCAATGGAAAACTGA
>Seq 11 GGTTGCCAATGGAAAACTGA
>Seq 12 GGTTGCCAATGGAAAACTGA
>Seq 13 GGTTGCCAATGGAAAACTGA
```

FIG. 13 (continued)

> Seq 14 GGTTGCCAATGGAAACTGA
> Seq 15 GGTTGCCAATGGAAACTGA
> Seq 16 GGTTGCCAATGGAAACTGA
> Seq 17 GGTTGCCAATGGAAACTGA
> Seq 18 GGTTGCCAATGGAAACTGA
> Seq 19 GGTTGCCAATGGAAACTGA
> Seq 20 GGTTGCCAATGGAAACTGA
> Seq 21 GGTTGCCAATGGAAACTGA
> Seq 22 GGTTGCCAATGGAAACTGA
> Seq 23 GGTTGCCAATGGAAACTGA
> Seq 24 GGTTGCCAATGGAAACTGA
> Seq 25 GGTTGCCAATGGAAACTGA
> Seq 26 GGTTGCCAATGGAAACTGA
> Seq 27 GGTTGCCAATGGAAACTGA
> Seq 28 GGTTGCCAATGGAAACTGA
> Seq 29 GGTTGCCAATGGAAACTGA
> Seq 30 GGTTGCCAATGGAAACTGA
> Seq 31 GGTTGCCAATGGAAACTGA
> Seq 32 GGTTGCCAATGGAAACTGA
> Seq 33 GGTTGCCAATGGAAACTGA
> Seq 34 GGTTGCCAATGGAAACTGA
> Seq 35 GGTTGCCAATGGAAACTGA
> Seq 36 GGTTGCCAATGGAAACTGA
> Seq 37 GGTTGCCAATGGAAACTGA

FIG. 13 (continued)

> Seq 38 GGTTGCCAATGGAAACTGA
> Seq 39 GGTTGCCAATGGAAACTGA
> Seq 40 GGTTGCCAATGGAAACTGA
> Seq 41 GGTTGCCAATGGAAACTGA
> Seq 42 GGTTGCCAATGGAAACTGA
> Seq 43 GGTTGCCAATGGAAACTGA
> Seq 44 GGTTGCCAATGGAAACTGA
> Seq 45 GGTTGCCAATGGAAACTGA
> Seq 46 GGTTGCCAATGGAAACTGA
> Seq 47 GGTTGCCAATGGAAACTGA
> Seq 48 GGTTGCCAATGGAAACTGA
> Seq 49 GGTTGCCAATGGAAACTGA
> Seq 50 GGTTGCCAATGGAAACTGA
> Seq 51 GGTTGCCAATGGAAACTGA
> Seq 52 GGTTGCCAATGGAAACTGA
> Seq 53 GGTTGCCAATGGAAACTGA
> Seq 54 GGTTGCCAATGGAAACTGA
> Seq 55 GGTTGCCAATGGAAACTGA
> Seq 56 GGTTGCCAATGGAAACTGA
> Seq 57 GGTTGCCAATGGAAACTGA
> Seq 58 GGTTGCCAATGGAAACTGA
> Seq 59 GGTTGCCAATGGAAACTGA
> Seq 60 GGTTGCCAATGGAAACTGA
> Seq 61 GGTTGCCAATGGAAACTGA
> Seq 62 GGTTGCCAATGGAAACTGA

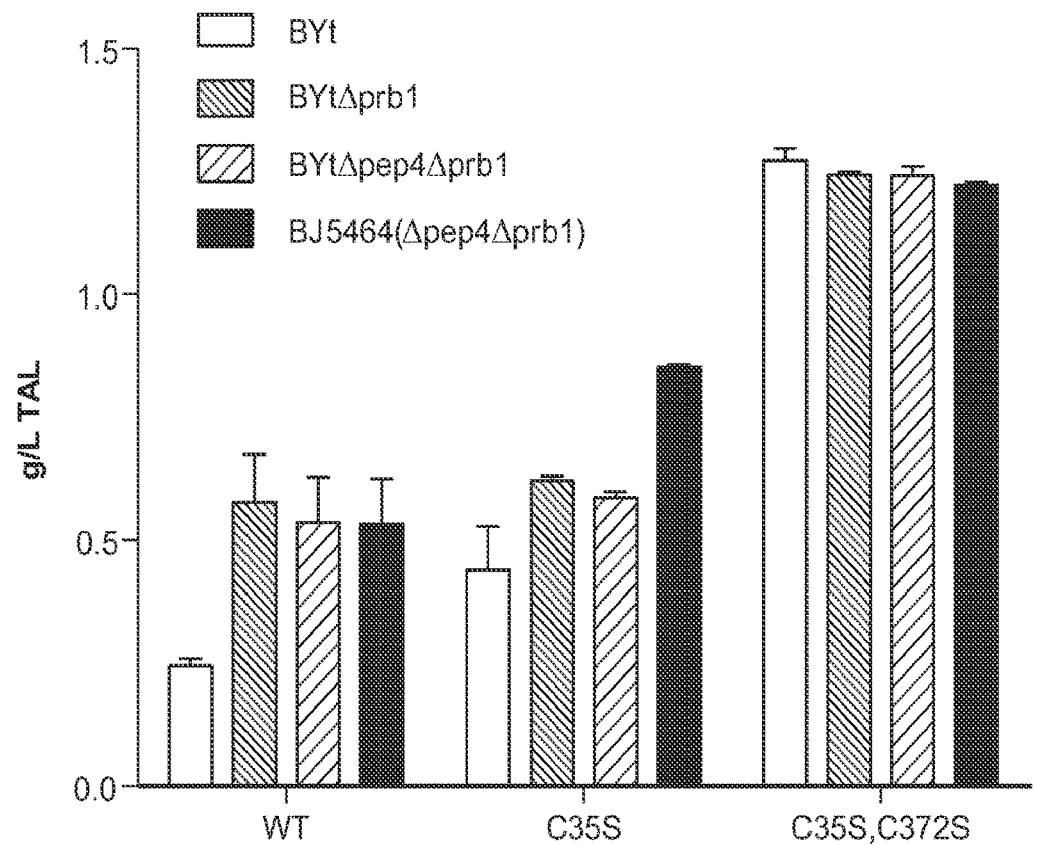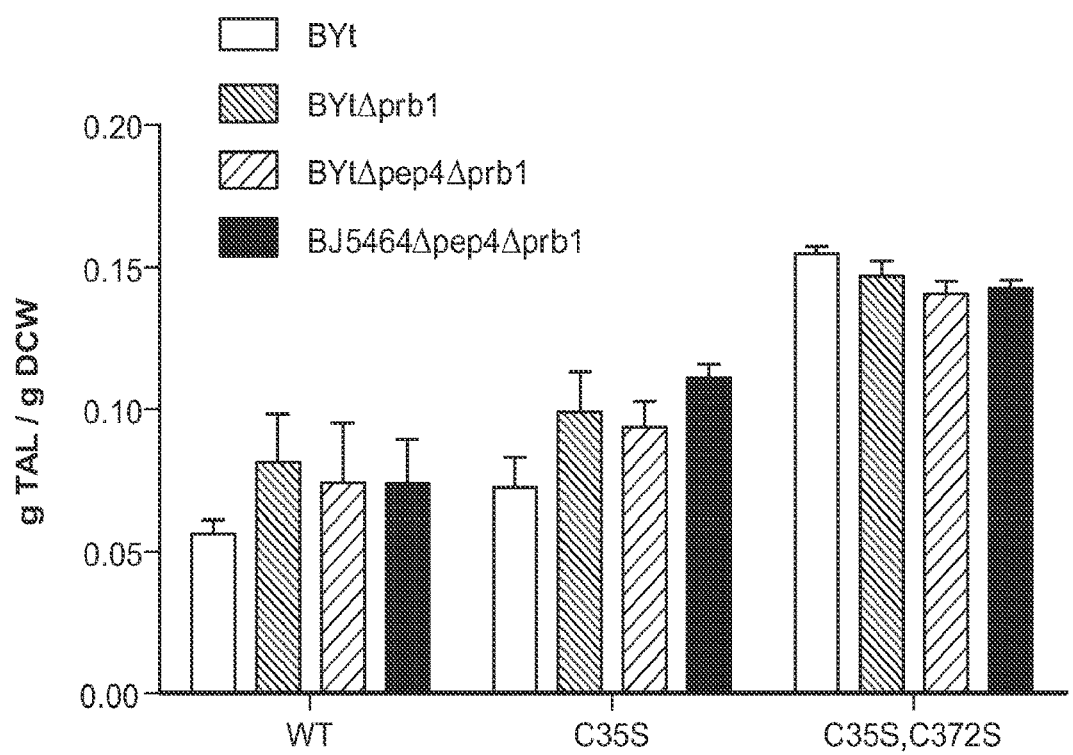
FIG. 18

POLYKETIDE SYNTHASE VARIANTS AND USES THEREOF

CROSS REFERENCE TO RELATED APPLICATIONS

This application is the U.S. national phase application, pursuant to 35 U.S.C. § 371, of PCT international application Ser. No.: PCT/US2015/019058, filed Mar. 5, 2015, designating the United States and published in English, which claims benefit of U.S. Provisional Application Ser. No. 61/949,082, filed Mar. 6, 2014, the entire contents of which are incorporated herein by reference.

STATEMENT OF RIGHTS TO INVENTIONS MADE UNDER FEDERALLY SPONSORED RESEARCH

This invention was made with government support under Grant Nos. EEC-0813570 and MCB-0645794 awarded by the National Science Foundation. The government has certain rights in the invention.

SEQUENCE LISTING

The instant application contains a Sequence Listing which has been submitted electronically in ASCII format and is hereby incorporated by reference in its entirety. Said ASCII copy, created on Mar. 5, 2015, is named 365550.1003WO1_SL.txt and is 335,357 bytes in size.

BACKGROUND

There has been great interest in utilizing either naturally occurring enzymes or engineered enzymes to prepare commercially useful chemical compounds. 2-Pyrone (also termed 2PY) is an attractive target for large-scale commercial production because it serves as a starting material for the synthesis of at least three distinct commodity chemicals. Through chemical catalysis, 2-Pyrone can be converted to sorbic acid, a preservative used widely in dairy-based foods. Moreover, further chemical modification yields the enone, 3-pentene-2-one, which is useful for chemical synthesis, and the diene 1,3-pentadiene, which is useful as a plasticizer. Additionally, 2-pyrone itself may be used as a food additive, as a phytochemical or as part of a phytochemical mix.

2-Pyrone synthase (also termed 2-PS) catalyzes the synthesis of 2-Pyrone using acetyl-CoA as one of the starting materials. 2-Pyrone synthase or other 2-Polyketide synthase variants having altered capabilities could expand the enzymatic toolbox available for rational enzyme-based chemical synthesis. More specifically, the discovery of 2-polyketide synthase variants is required to provide novel non-native enzymes having new synthetic capabilities and/or enhanced enzymatic activity.

SUMMARY OF THE INVENTION

As described below, the present invention provides polyketide synthase variants having altered enzymatic activity, host cells (e.g., yeast, plant, algae, bacterial, mammalian, insect) comprising such variants and in vitro and in vivo methods of using such enzymes for the production of desired chemical compounds, including polyketide, pyrone and lactone products.

In one aspect, the invention provides an isolated nucleic acid molecule encoding a polyketide synthase variant having an altered amino acid residue corresponding to amino acid positions C35, T137, I201, L202, L268, C65, C89, C195, C346; and/or C372 of 2-pyrone synthase.

In another aspect, the invention provides a vector containing the isolated nucleic acid molecule of any aspect described herein.

In still another aspect, the invention provides a cell containing the isolated nucleic acid molecule and/or vector of any aspect described herein.

In yet another aspect, the invention provides a plant containing the isolated nucleic acid molecule and/or vector of any aspect described herein. In various embodiments, the nucleic acid molecule is expressed in a glandular tricone.

In one aspect, the invention provides an isolated polyketide synthase polypeptide having an altered amino acid residue corresponding to amino acid positions C35, T137, I201, L202, L268, C65, C89, C195, C346; and/or C372 of 2-pyrone synthase.

In another aspect, the invention provides a method of increasing the activity of a polyketide synthase, the method involving introducing an altered amino acid residue at a position corresponding to C35, T137, I201, L202, L268, C65, C89, C195, C346; and/or C372 of 2-pyrone synthase.

In another aspect, the invention provides an isolated nucleic acid molecule encoding a polyketide synthase variant comprising an altered amino acid residue corresponding to amino acid positions C35, C65, C89, C135, C195, C346, C372, T137, I201, L202, and/or L268 of 2-pyrone synthase. In various embodiments, the altered amino acid residue is any one or more of C35S, C65S, C89S, C135S, C195S, C346A, C372S, L202F, L268F, L268M, and T137F. In particular embodiments, the altered amino acid residue is any one or more of C35S, C65S, C89S, C135S, C195S, C346A, C372S, L202F, L268F, L268M, and T137F. In one embodiment, the encoded polyketide synthase variant comprises C35S and C372S (also denoted as "C35SC372S" herein).

In another aspect, the invention features an isolated polyketide synthase polypeptide comprising an altered amino acid residue corresponding to amino acid positions C35, C65, C89, C135, C195, C346, C372, T137, I201, L202, and/or L268 of 2-pyrone synthase. In particular embodiments, the altered amino acid residue is any one or more of C35S, C65S, C89S, C135S, C195S, C346A, C372S, T137F, L202F, L268F, and L268M. In one embodiment, the polyketide synthase polypeptide comprises C35S and C372S, termed "C35SC372S" herein.

In another aspect, the invention features a method of increasing the activity of a polyketide synthase, the method comprising introducing an altered amino acid residue at a position corresponding to C35, C65, C89, C135, C195, C346, C372, T137, I201, L202, and/or L268 of 2-pyrone synthase. In one embodiment, the altered amino acid residue is selected from the group consisting of C35S, C65S, C89S, C135S, C195S, C346A, C372S, T137F, L202F, L268F, and L268M.

In still another aspect, the invention provides a method of preparing a cyclic compound, or a salt, solvate or derivative thereof, the method involving contacting the isolated polyketide synthase of any aspect delineated herein with a substrate of formula (I), or a salt, solvate or derivative thereof:

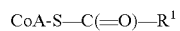

$$\text{CoA-S—C(=O)—R}^1 \qquad (I),$$

where the cyclic compound is selected from the group consisting of:

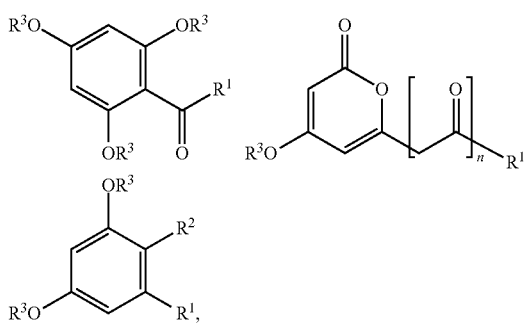

where:

R¹ is selected from the group consisting of $C_1$-$C_{20}$ alkyl, $C_1$-$C_{20}$ cycloalkyl, aryl-($C_1$-$C_{20}$ alkyl), carboxy-($C_1$-$C_{20}$ alkyl), aryl, heterocyclyl, heteroaryl, aryl-CH═CH—, heterocyclyl-CH═CH— and heteroaryl-CH═CH—, R² is selected from the group consisting of H, carboxy, C(═O)O($C_1$-$C_6$)alkyl, cyano, —C(═O)NH₂, —C(═O)NH($C_1$-$C_6$)alkyl, and —C(═O)N(($C_1$-$C_6$)alkyl)₂;

each occurrence of R³ is independently selected from the group consisting of H, $C_1$-$C_{20}$ alkyl, aryl-($C_1$-$C_{20}$ alkyl), $C_1$-$C_{20}$ acyl, aroyl, and heteroaroyl; and, n is 0, 1, 2 or 3;

where each alkyl, cycloalkyl, aryl, heterocyclyl or heteroaryl group is independently optionally substituted with at least one substituent selected from the group consisting of F, Cl, Br, I, hydroxy, alkoxy, amino, nitro, monoalkylamino, dialkylamino, carboxy, C(═O)O($C_1$-$C_6$)alkyl, trifluoromethyl, cyano, —C(═O)NH₂, —C(═O)NH($C_1$-$C_6$)alkyl, —C(═O)N(($C_1$-$C_6$)alkyl)₂, —SO₂NH₂, and —C(═NH)NH₂.

In various embodiments, R¹ is $C_1$-$C_{20}$ alkyl, carboxy-($C_1$-$C_{20}$ alkyl), aryl, heteroaryl, aryl-CH═CH—, or heteroaryl-CH═CH—. In particular embodiments, R¹ is $C_1$-$C_{20}$ alkyl, carboxy-($C_1$-$C_{20}$ alkyl), aryl, or aryl-CH═CH—. In various embodiments, each occurrence of aryl comprises phenyl.

In still another aspect, the invention provides a method of preparing a polyketide using a cell containing the isolated nucleic acid molecule and/or vector of any aspect described herein.

In another aspect, the invention provides a kit containing an isolated polyketide synthase, a nucleic acid molecule, a vector or a cell of any aspect described herein.

In various embodiments of any of the aspects delineated herein, the polyketide synthase variant is 2-pyrone synthase. In various embodiments the altered amino acid residue is selected from the group consisting of C35S, C65S, C89S, C195S, C346A, C372S, L202F, and L268M.

In particular embodiments, the altered amino acid residue is C35S. In certain embodiments, the polyketide synthase variant has a combination of altered amino acid residues that is C35S, T137F; C35S, T137L; C35S, I201F; C35S, I201L; C35S, L202F; C35S, L202M; C35S, L268F; C35S, L268M; C35S; C35S, C65S; C35S, C89S; C35S, C195S; C35S, C346A; C35S, C372A; C35S, C372S; C35S, C89S, C372S; C35S, C65S, C89S, C372S; C35S, C89S, C195S, C346A, C372S; and C35S, C65S, C89S, C195S, C346A, or C372S. In specific embodiments, the polyketide synthase polypeptide has a combination of altered amino acid residues that is C35S, C65S, C89S, C195S, C346A, C372S, L202F, and L268M.

In various embodiments of any of the aspects delineated herein, the activity and/or stability of the polyketide synthase is increased relative to a reference polypeptide (e.g., wild-type 2-pyrone synthase). In particular embodiments the $k_{cat}$ of the polyketide synthase is increased and/or $K_m$ of the synthase is decreased relative to a wild-type 2-pyrone synthase polypeptide. In various embodiments, the activity of the polyketide synthase involves production of a compound that is one or more of a pyrone, a chromone, a triacetic lactone, a polyhydroxynaphthalene, a phloroglucinol, a resorcinol, a resorcinol acid, SEK 4, SEK4b, and aloesone, including combinations thereof. In a particular embodiment, the lactone is triacetic lactone.

In various embodiments of any of the aspects delineated herein, the cell is a yeast, plant, algae, bacterial, mammalian, or insect cell. In various embodiments, the variant polyketide synthase is expressed in a yeast, plant, bacteria, mammal, or insect cell. In various embodiments, the cell is in vitro or in vivo.

Other aspects, embodiments, advantages, and features of the present invention will become apparent from the following specification.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "polyketide synthase (PS) polypeptide" is meant a polypeptide or fragment thereof having at least about 85% amino acid identity to UniProt Accession No. P48391 and having polyketide synthase activity. Polyketide synthase activity includes, but is not limited to, Claisen condensing carbon-carbon bond formation, aldol condensing carbon-carbon bond formation, lactonizing carbon-oxygen bonding formation, decarboxylation and/or (thio)ester cleavage. In other embodiments, a polyketide synthase polypeptide has at least about 85%, 90, 95, 96, 97, 98, 99, or 100% identity to a wild-type polyketide synthase polypeptide. Accordingly, the term polyketide synthase polypeptide encompasses polyketide synthase variants. Sequences useful in the methods of the invention are provided at FIGS. 9-13.

Polyketide synthases include any one of a family of enzymes that catalyze the formation of polyketide compounds. Polyketide synthases are generally homodimers, with each monomer being enzymatically active. An exemplary polyketide synthase is the *Gerbera hybrida* 2-pyrone synthase (2-PS) (also termed Gh2PS), which amino acid sequence is shown below.

(SEQ ID NO: 1)
1   mgsyssddve vireagraqg latilaigta tppncvaqad yadyyfrvtk sehmvdlkek

```
 61  fkricektai kkrylalted ylqenptmce fmapslnarq dlvvtgvpml gkeaavkaid
121  ewglpkskit hlifcttagv dmpgadyqlv kllglspsvk rymlyqqgca aggtvlrlak
181  dlaennkgsr vlivcseita ilfhgpnenh ldslvaqalf gdgaaalivg sgphlaverp
241  ifeivstdqt ilpdtekamk lhlreggltf qlhrdvplmv aknienaaek alsplgitdw
301  nsvfwmvhpg graildqver klnlkedklr asrhvlseyg nlisacvlfi idevrkrsma
361  egksttgegl dcgvlfgfgp gmtvetvvlr svrvtaavan gn
```

By "polyketide synthase (PS) nucleic acid molecule" is meant a polynucleotide encoding a polyketide synthase polypeptide or fragment thereof. An exemplary PS nucleic acid molecule sequence is provided under NCBI Accession No. Z38097, and is shown below, with the protein-encoding region spanning bases 163 to 1371 in bold.

```
                                                         (SEQ ID NO: 2)
   1  aaaaggccta ctcaagcctt gaaattctct tttcttttct tttcattccc ttccctcaaa
  61  ttataaactt acctttctgt ttctttcaaa gaatttagct gcctcaaacg aagatcttca
 121  tatctcattt gttaggatat acaaacatca atctcgagta aaatgggatc ttactcatcc
 181  gatgatgtgg aggtgattcg tgaggccgga cgggcacaag gtttagccac gattcttgcc
 241  attggcactg ctactcctcc caattgcgtc gctcaagctg attatgcaga ctattatttt
 301  cgtgtcacta agagcgaaca tatggttgat cttaaagaga aatttaaacg catttgtgag
 361  aaaacagcga taaagaaacg atacctagcc ctcaccgaag actatctgca agagaaccca
 421  acaatgtgtg agttcatggc tccatcctta aacgctcgac aagacctagt ggtcaccggc
 481  gtcccaatgc ttggcaaaga agccgcagtc aaggccattg atgaatgggg actaccaaaa
 541  tccaagatca cccactcat cttctgcacc accgctggcg ttgacatgcc cggtgctgac
 601  tatcaactcg tcaaactcct tggtctctcc ccttcagtca aacgctatat gttgtaccaa
 661  cagggatgtg ccgccggcgg cacagtcctc cggctagcca aggaccttgc tgaaaacaac
 721  aagggctcac gagtccttat cgtctgctcc gagatcactg ctatcttatt ccatggaccc
 781  aatgagaacc accttgactc actcgtcgct caagctttat cggagacgg agctgcagca
 841  ctcattgtgg gttcaggccc tcacttggcc gtagaacggc caatattcga gatcgtgtca
 901  actgatcaaa caatcttgcc ggacactgag aaggcaatga agttacactt gagagaggga
 961  gggttgacgt tcagttgca tagagatgta cccttgatgg tcgcaaagaa catagagaac
1021  gcagcggaga aagcgttgtc tccactaggg ataactgatt ggaactcagt tttctggatg
1081  gtgcacccag gtggtcgagc catattggac caggtggagc gaaaactaaa ccttaaggaa
1141  gataagttaa gggctagcag gcatgtgctt agtgaatacg gaaacctgat tagcgcttgt
1201  gtgttgttca tcattgacga ggtgaggaag agatctatgc cggaagggaa gagtacaacc
1261  ggtgaaggtt tggattgcgg tgtttttgttt ggatttggac cgggtatgac tgttgagact
1321  gttgttcttc gtagcgtccg cgttactgct gcggttgcca atgaaactg atcactgttg
1381  tttgcaaaat attacttttt actacggtat gtttccttgt ttatgagttt gtcattcacc
1441  tatgataata gggtctgtat ttttcttgtt tatgatttta ttttctcaaa gatgatgtaa
1501  gttggcaatt aaataaagat tgttttttcct atgaataata taagattaca ttttc
```

As used herein, the term "substrate" refers to a Coenzyme-A (CoA) thioester that acts as an enzymatic substrate for a wild-type polyketide synthase or a polyketide synthase variant contemplated within the invention. In certain embodiments, a substrate comprises acetyl-CoA, malonyl-CoA, coumaroyl-CoA, hexamoyl-CoA, a synthetic CoA thioester, ACP or NAC thioesters and the like. In certain embodiments, the term "substrate" refers to CoA thioesters found in natural systems, as well as CoA thioesters that are chemically synthesized and not found in natural systems.

As used herein the term "pyrone" refers to a class of cyclic chemical compounds having the molecular formula $C_5H_4O_2$ and comprising an unsaturated six membered ring comprising one oxygen atom and a ketone functional group. Two isomers denoted as 2-pyrone (2PY) and 4-pyrone (4-PY) are exemplified herein. As used herein, the term "pyrone" also refers to a compound comprising a 2-pyrone moiety or a 4-pyrone moiety, and derivatives thereof.

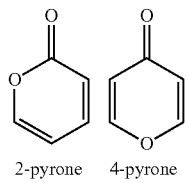

2-pyrone    4-pyrone

By "complex" is meant a chemical association of two or more molecules. Complexes may include a network of weak electrostatic bonds that maintain the association of the molecules. Other types of interactions, such as covalent bond, ionic bond, hydrogen bond, hydrophobic interaction, or van der Waals interactions, may be present instead of or in addition to electrostatic bonds between members of a complex.

By "specifically binds" is meant a compound or antibody that recognizes and binds a polypeptide of the invention, but which does not substantially recognize and bind other molecules in a sample.

By "computer modeling" is meant the application of a computational program to determine one or more of the following: the location and binding proximity of a ligand to a binding moiety, the occupied space of a bound ligand, the amount of complementary contact surface between a binding moiety and a ligand, the deformation energy of binding of a given ligand to a binding moiety, and some estimate of hydrogen bonding strength, van der Waals interaction, hydrophobic interaction, and/or electrostatic interaction energies between ligand and binding moiety. Computer modeling can also provide comparisons between the features of a model system and a candidate compound. For example, a computer modeling experiment can compare a pharmacophore model of the invention with a candidate compound to assess the fit of the candidate compound with the model. Examples of techniques useful in the above evaluations include: quantum mechanics, molecular mechanics, molecular dynamics, Monte Carlo sampling, systematic searches and distance geometry methods. Further descriptions of computer modeling programs are provided elsewhere herein.

As used herein, "molecular replacement" refers to generating a preliminary model of a polyketide synthase whose structural coordinates are unknown, by orienting and positioning a molecule whose structural coordinates are known within the unit cell of the unknown crystal so as best to account for the observed diffraction pattern of the unknown crystal. Phases can then be calculated from this model and combined with the observed amplitudes to give an approximate Fourier synthesis of the structure whose coordinates are unknown. This in turn can be subject to any of the several forms of refinement to provide a final, accurate structure of the unknown crystal (Lattman, E., 1985, in Methods in Enzymology, 11 5.55-77; Rossmann, M G., ed., "The Molecular Replacement Method" 1972, Int, Sci. Rev. Ser., No. 13, Gordon & Breach, New York). Using structure coordinates of the polyketide synthase provided herein (see e.g., PDB Accession Numbers) molecular replacement maybe used to determine the structural coordinates of a crystalline mutant, homolog, or a different crystal form of polyketide synthase.

By "decreases" is meant a negative alteration of at least 10%, 25%, 50%, 75%, or 100%.

By "increase" is meant a positive alteration of at least 10%, 25%, 50%, 75%, or 100%. In one embodiment, the presence of a mutation increases the activity of an enzyme of the invention by at least about 5%, 10%, 15%, 20%, 25%, or 50%.

The term "detect" refers to identifying the presence, absence, level, or concentration of an analyte.

By "foreign" or "heterologous" is meant a gene encoding a protein whose exact amino acid sequence is not normally found in the host cell. Exemplary host cells include yeast, plant, algae, bacterial, mammalian, and insect cells.

By "fragment" is meant a portion of a polypeptide or nucleic acid molecule. This portion contains at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

As used herein, "-carbon" refers to the chiral carbon atom found in an amino acid residue. Typically, four substituents will be covalently bound to said -carbon including an amine group, a carboxylic acid group, a hydrogen atom, and an R-group.

As used herein, "R-group" refers to the substituent attached to the -carbon of an amino acid residue. An R-group is an important determinant of the overall chemical character of an amino acid. There are twenty natural R-groups found in proteins, which make up the twenty naturally occurring amino acids.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). In one embodiment, such a sequence is at least 60%, 80%, 85%, 90%, 95% or even 100% identical at the amino acid level or nucleic acid to the sequence used for comparison (e.g., wild-type reference sequence).

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{"3}$ and $e^{"100}$ indicating a closely related sequence.

As used herein, "active site" refers to a site in a synthase defined by amino acid residues that interact with substrate and facilitate a biosynthetic reaction that allows one or more products to be produced. Active site amino acids for 2-pyrone synthase include L202 and L268. The three-dimensional space position of an -carbon at the active site of a synthase and of R-groups associated therewith can be determined using techniques such as three-dimensional modeling, X-ray crystallography, and/or techniques associated therewith. Active sites can be specified by a set of amino acid residues. Other residues can play a role in substrate specificity and enzyme activity by modulating size, shape, charge, and the like of the active site. In addition, residues external to the active site may also modulate the specificity and/or activity of the enzyme.

As used herein, "hydrophilic amino acid" and "hydrophilic R-group" includes any naturally occurring or unnatural amino acid that is relatively soluble in water and/or has high affinity for water. Examples of naturally occurring hydrophilic amino acids include serine, threonine, tyrosine, asparagine, glutamine, cysteine, and the like.

As used herein, "hydrophobic amino acid" and "hydrophobic R-group" includes any naturally occurring or unnatural amino acid that is relatively insoluble in water and/or has low affinity for water. Examples of naturally occurring hydrophobic amino acids are alanine, leucine, isoleucine, valine, proline, phenylalanine, tryptophan, methionine, and the like.

As used herein, "naturally occurring amino acid" and "naturally occurring R-group" includes L-isomers of the twenty amino acids naturally occurring in proteins. Naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine, and lysine. Unless specially indicated, all amino acids referred to in this application are in the L-form.

As used herein, "negatively charged amino acid" and "negatively charged R-group" includes any naturally occurring or unnatural amino acid having a side chain which is negatively charged under normal physiological conditions. Examples of negatively charged, naturally occurring amino acids include aspartic acid, glutamic acid, and the like.

As used herein, "positively charged amino acid" and "positively charged R-group" includes any naturally occurring or unnatural amino acid having a side chain which is positively charged under normal physiological conditions. Examples of positively charged, naturally occurring amino acids include arginine, lysine, histidine, and the like.

As used herein, "unnatural amino acid" and "unnatural R-group" includes amino acids that are not naturally found in proteins. Examples of unnatural amino acids included herein are racemic mixtures of selenocysteine and selenomethionme. In addition, unnatural amino acids include the D- or L-forms of, for example, nor-leucine, para-nitrophenylalanine, homophenylalanine, para-fluorophenylalanine, 3-amino-2-benzylpropionic acid, homoarginines, D-phenylalanine, and the like. Unnatural amino acids and peptides including such amino acids are described in U.S. Pat. Nos. 6,566,330 and 6,555,522.

By "variant" as is meant a polynucleotide or polypeptide sequence that differs from a wild-type or reference sequence by one or more nucleotides or one or more amino acids. Exemplary 2-pyrone synthase variants include those having an amino acid change at any one or more of T137, I201, L202, L268, C35, C65, C89, C195, C346, and C372.

In one embodiment, exemplary 2-pyrone synthase variants include the following combinations of the following amino acid substitutions: C35S, T137F; C35S, T137L; C35S, I201F; C35S, I201L; C35S, L202F; C35S, L202M; C35S, L268F; C35S, L268M; C35S; C35S, C65S; C35S, C89S; C35S, C195S; C35S, C346A; C35S, C372A; C35S, C372S; C35S, C89S, C372S; C35S, C65S, C89S, C372S; C35S, C89S, C195S, C346A, C372; and C35S, C65S, C89S, C195S, C346A, and C372S.

In another embodiment, the enzyme comprises at least C35S, C65S, C89S, C195S, C346A, and C372S. This background might be useful for generating active site variants.

As used herein, "isolated" refers to a molecule that is substantially free of other elements present in its natural environment. For instance, an isolated protein is substantially free of cellular material or other proteins from the cell or tissue source from which it is derived. The term "isolated" also refers to preparations where the isolated protein is sufficiently pure to be administered as a pharmaceutical composition, or at least 70-80% (w/w) pure, more preferably, at least 80-90% (w/w) pure, even more preferably, 90-95% pure; and, most preferably, at least 95%, 96%, 97%, 98%, 99%, or 100% (w/w) pure.

As used herein, "native" or "native polypeptide" refers to proteins that occur or are produced in nature (e.g., wild-type 2-pyrone synthase).

As used herein, "mutant" or "mutated polypeptide" refers to a polypeptide containing amino acid residues that have been substituted or modified with respect to a wild type polypeptide (e.g., polyketone synthase).

By a "substantially pure polypeptide" is meant a polypeptide (e.g., a pyrone synthase) which has been separated from components which naturally accompany it or accompany it in vitro. Typically, the polypeptide is substantially pure when it is at least 60%, by weight, free from the proteins and naturally-occurring organic molecules with which it is naturally associated. In one embodiment, the preparation is at least about 75%, 85%, 90%, 95%, or 99%, by weight, pure. A substantially pure synthase polypeptide may be obtained, for example, by extraction from a natural source; by expression of a recombinant nucleic acid encoding an synthase polypeptide; or by chemically synthesizing the protein. Purity can be measured by any appropriate method (e.g., column chromatography, polyacrylamide gel electrophoresis, or by HPLC analysis).

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

By "reference" is meant a standard or control condition.

A "reference sequence" is a defined sequence used as a basis for sequence comparison.

As used herein, "space group" refers to the arrangement of symmetry elements within a crystal.

As used herein, "structure coordinates" refers to Cartesian coordinates (x, y, and z positions) derived from mathematical equations involving Fourier synthesis as determined from patterns obtained via diffraction of a monochromatic beam of X-rays by the atoms (scattering centers) of a polyketide synthase molecule in crystal form. Diffraction data are used to calculate electron density maps of repeating protein units in the crystal (unit cell). Electron density maps are used to establish the positions of individual atoms within a crystal's unit cell. The term "crystal structure coordinates" refers to mathematical coordinates derived from mathematical equations related to the patterns obtained on diffraction of a monochromatic beam of X-rays by the atoms (scattering centers) of a synthase polypeptide (e.g., a chalcone synthase protein molecule) in crystal form. The diffraction data are used to calculate an electron density map of the repeating unit of the crystal. The electron density maps are used to establish the positions of the individual atoms within the unit cell of the crystal. The crystal structure coordinates of a synthase can be obtained from crystals and can also be obtained by means of computational analysis.

By "three-dimensional model" is meant a three-dimensional representation of a molecule's structure. Computer modeling may be used to generate such a model in conjunction with structural data. These data could include x-ray crystallographic data, nuclear magnetic resonance data, electron microscopy data, or any other source of experimental or theoretical data useful for generating a model of a molecule or complex of molecules.

By "unit cell" is meant the fundamental repeating unit of a crystal.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 g/ml denatured salmon sperm DNA (ssDNA). In a most preferred embodiment, hybridization will occur at 42° C. in 250 mM NaCl, 25 mM trisodium citrate, 1% SDS, 50% formamide, and 200 g/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS.

Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

As used herein, the term "alkyl," by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$) alkyl, such as, but not limited to, ethyl, methyl, isopropyl, isobutyl, n-pentyl, n-hexyl and cyclopropylmethyl.

As used herein, the term "cycloalkyl," by itself or as part of another substituent means, unless otherwise stated, a cyclic chain hydrocarbon having the number of carbon atoms designated (i.e., $C_3$-$C_6$ means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Most preferred is ($C_3$-$C_6$)cycloalkyl, such as, but not limited to, cyclopropyl, cyclobutyl, cyclopentyl and cyclohexyl.

As used herein, the term "substituted alkyl," "substituted cycloalkyl," "substituted alkenyl" or "substituted alkynyl" means alkyl, cycloalkyl, alkenyl or alkynyl, as defined above, substituted by one, two or three substituents selected from the group consisting of halogen, —OH, alkoxy, tetrahydro-2-H-pyranyl, —$NH_2$, —$N(CH_3)_2$, (1-methyl-imidazol-2-yl), pyridin-2-yl, pyridin-3-yl, pyridin-4-yl, —C(=O) OH, trifluoromethyl, —C≡N, —C(=O)O($C_1$-$C_4$)alkyl, —C(=O)$NH_2$, —C(=O)NH($C_1$-$C_4$)alkyl, —C(=O)N ((C$_1$-C$_4$)alkyl)$_2$, —SO$_2$NH$_2$, —C(=NH)NH$_2$, and —NO$_2$, preferably containing one or two substituents selected from halogen, —OH, alkoxy, —NH$_2$, trifluoromethyl, —N(CH$_3$)$_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

As used herein in a chemical context, the term "substituted" means that an atom or group of atoms has replaced hydrogen as the substituent attached to another group.

For a cyclic group, the term "substituted" as applied to the ring(s) of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of C$_{1-6}$ alkyl, —OH, C$_{1-6}$ alkoxy, halo, amino, acetamido and nitro. As used herein, where a substituent is an alkyl or alkoxy group, the carbon chain may be branched, straight or cyclic, with straight being preferred.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Any compounds, compositions, or methods provided herein can be combined with one or more of any of the other compositions and methods provided herein.

Unless specifically stated or obvious from context, as used herein, the term "or" is understood to be inclusive. Unless specifically stated or obvious from context, as used herein, the terms "a", "an", and "the" are understood to be singular or plural. Thus, for example, reference to "an amino acid substitution" includes reference to more than one amino acid substitution.

The term "including" is used herein to mean, and is used interchangeably with, the phrase "including but not limited to."

As used herein, the terms "comprises," "comprising," "containing," "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

Other features and advantages of the invention will be apparent from the following description of the desirable embodiments thereof, and from the claims.

BRIEF DESCRIPTION OF THE DRAWINGS

FIG. 1A shows variants bearing amino-acid substitutions at sites within the enzyme's active site. FIG. 1B shows variants bearing amino-acid substitutions at sites external to the enzyme's active site. For each variant, the amino-acid substitution(s) with respect to the wild-type (WT) 2-PS sequence is(are) indicated. For the measurement of triacetic lactone titers, yeast strains were cultured in selective SDC(A) medium (1% dextrose, 0.67% yeast nitrogen base, 0.5% Bacto casamino acids, 0.5% ammonium sulfate and 100 mg/L adenine), aliquots of the cultures were measured turbidimetrically for cell density and then centrifuged to pellet cell material, and TAL in the supernatant was quantitated by HPLC analysis with separation by reversed-phase chromatography on a C18 column.

FIG. 3 provides a schematic depiction of an intermediate of polyketide biosynthesis highlighting reactive chemical groups. FIG. 3 shows tautomeric states and atomic proximity modulate bond formation; repetitive and flexible linear oligomers; and activating Leaving Groups (chemical handles). Bottom of figure: a type-III PKS enzyme catalyzes iterative chain extension via decarboxylative condensations with malonyl-CoA to generate a repetitive and flexible linear oligomer carried on a catalytic cysteine. Top of figure: within the extended polyketide intermediate, the carbonyl groups of the individual building-blocks can undergo ketoenol tautomerization (dashed box), and these tautomeric states and reactive-group proximity dictate intramolecular covalent-bond formation with consequent cyclization of the polyketide oligomer. In some embodiments, the activation barrier is raised to alter polyketide intermediate activity.

FIG. 8 depicts chemical conversions of the starting reagent triacetic acid lactone that generate exemplary intermediates or end-products useful, for example, in chemical syntheses.

FIG. 9 is a non-limiting list of 2-pyrone synthase variants, including the number of amino acid substitutions in each one relative to the wild-type amino acid sequence and the specific amino acid substitution identified by position.

FIG. 10 is a list of amino acid sequences (SEQ ID NOs 3-63, respectively, in order of appearance) of the 2-pyrone synthase variants.

FIG. 11 is an alignment of the amino acid sequences (SEQ ID NOs 1 and 3-63, respectively, in order of appearance) of the 2-pyrone synthase variants.

FIG. 12 is a list of nucleic acid sequences (SEQ ID NOs 64-124, respectively, in order of appearance) of the 2-pyrone synthase variants.

Figure 13:
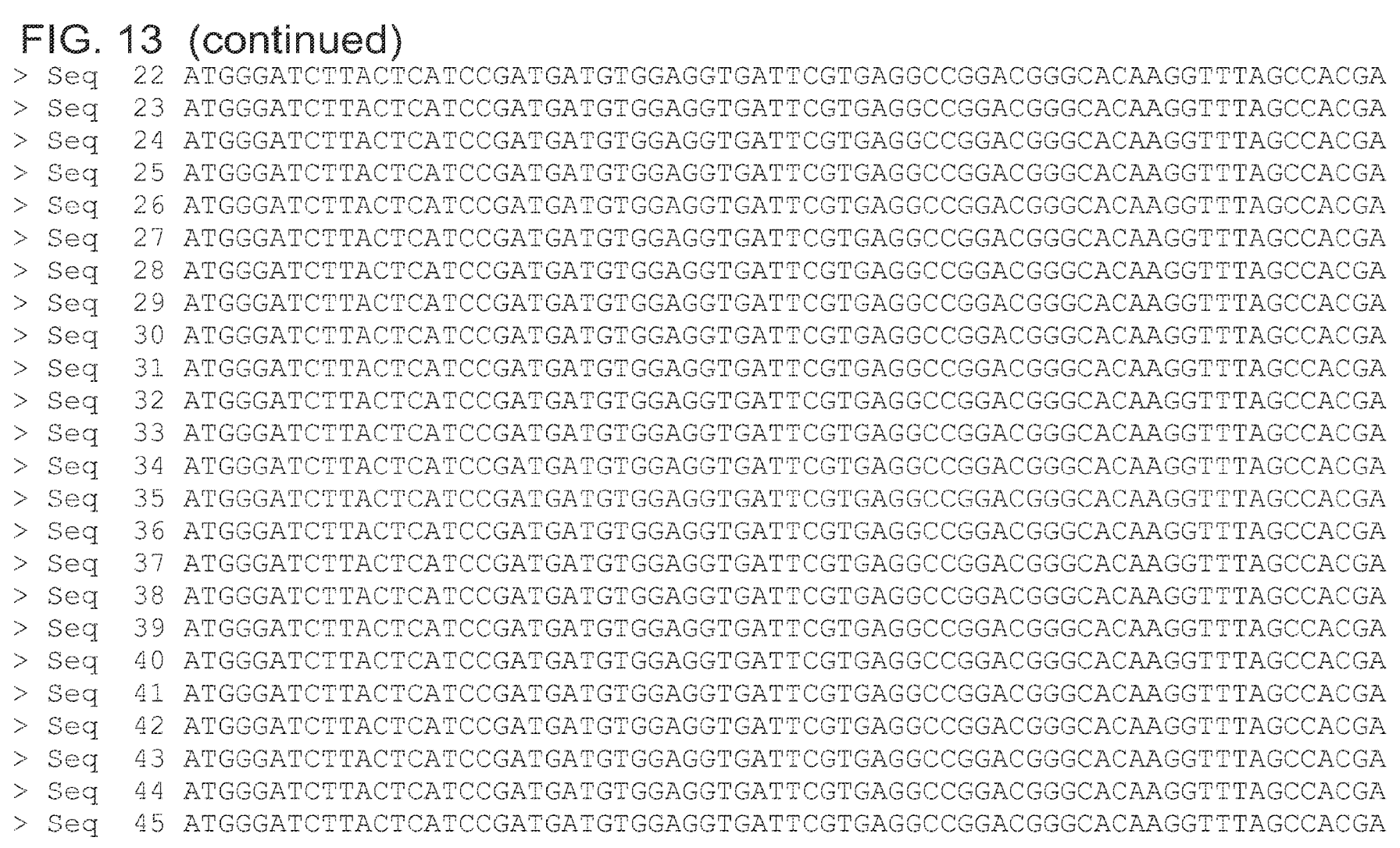

FIG. 13 is an alignment of the nucleic acid sequences (SEQ ID NOs 125 and 64-124, respectively, in order of appearance) of the 2-pyrone synthase variants FIG. 14 includes a graph and a table. The graph compares triacetic lactone (TAL) titers (g/L) for 2-pyrone synthase (2-PS) variants C35A, C35S, L268F, and C35SL268F relative to the wildtype G. hybrida 2-pyrone synthase (WT). Bars represent mean values±one standard deviation (n=6 independent experiments).

FIG. 18 provides two graphs. The graph at the top of FIG. 18 compares triacetic lactone (TAL) levels (g/L TAL) for strain BYt and protease-knockout strains (BYtΔprb1, BYtΔpep4Δprb1 and BJ5464(Δpep4Δprb1) with wild-type 2-Pyrone synthase (WT) or variants C35S or C35SC372S). The graph at the bottom of FIG. 18 compares g TAL/g (DCW), i.e., dry cell weight) for strain BYt and protease-knockout strains (BYtΔprb1, BYtΔpep4Δprb1 and BJ5464 (Δpep4Δprb1) with wild-type 2-Pyrone synthase (WT) or variants (C35S or C35SC372S). Bars represent mean values±with one standard deviation (n=6 biological replicates).

DETAILED DESCRIPTION OF THE INVENTION

As described below, the present invention provides polyketide synthase variants having altered enzymatic activity, host cells (e.g., yeast, plant, algae, bacterial, mammalian, insect) comprising such variants and in vitro and in vivo methods of using such enzymes for the production of desired chemical compounds, including polyketide, pyrone and lactone products.

The invention is based, at least in part, on the discovery of 2-pyrone synthase variants having increased enzyme activity. More specifically, as reported in detail below, the invention provides polyketide synthase variants having increased triacetic acid lactone production relative to a wild-type polyketide synthase enzyme. Such enzymes are useful, for example, for enhancing the enzymatic synthesis of polyketide, pyrone and lactone products relative to wild-type enzyme.

Accordingly, the invention provides polyketide synthase variants proteins having increased enzyme activity, polynucleotides encoding the polyketide synthase variants, host cells (e.g., yeast, algae, plant, bacterial, mammalian, insect) comprising such polynucleotides), and methods of using these host cells for the production of desired compounds (e.g., polyketide, pyrone and lactone products).

Polyketide Synthases

Figures 2, 2A:
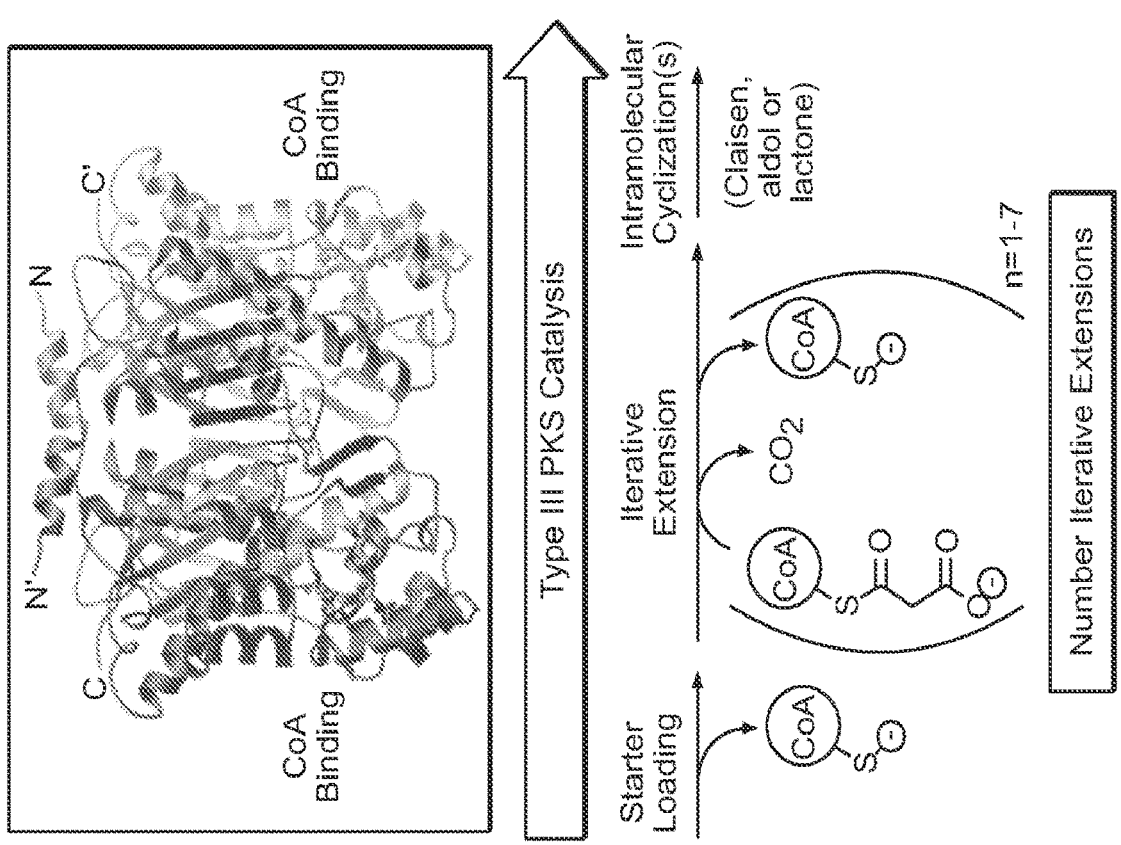
FIG. 2 provides a schematic overview of polyketide biosynthesis highlighting the potential for the generation of a large number of biologically useful cyclic compounds. Diversity in the final polyketide products (examples are shown at the lower right) can originate from variation in the starter molecular-group (lower left box: shown are acetyl, octanoyl, malonyl, methyl-anthraniloyl, isopentanoyl, and coumaroyl); the identity and sequence variant of the type-III polyketide-synthase enzyme (represented by the ribbon diagram of a PKS homodimer); the number of iterations of chain extension; and the mechanism of cyclization (which is governed sterically by the shape of the enzyme's active-site cavity, as represented pictorially at the top right).

Polyketides are a class of compounds that includes a broad range of antibiotics, immunosuppressants and anticancer agents. Polyketides encompass molecules with extremely rich bioactivities, including antibiotics (e.g., tetracyclines and erythromycin), anti-cancer agents (e.g., daunomycin), immunosuppressants (e.g., FK506 and rapamycin), and veterinary products (e.g., monensin). Many polyketides (produced by polyketide synthases) are valuable as therapeutic agents. Polyketide synthases are multifunctional enzymes that catalyze the biosynthesis of a variety of carbon chains differing in length and patterns of functionality and cyclization (FIG. 2).

In particular, the compound 2-pyrone is an attractive target for large-scale commercial production because it serves as a starting material for the synthesis of a variety of commodity chemicals. Through chemical catalysis, 2-pyrone can be converted to sorbic acid, a preservative used widely in dairy-based foods. Moreover, further chemical modification yields the enone, 3-pentene-2-one, which is useful for chemical synthesis, and the diene, 1,3-pentadiene, which is useful as a plasticizer. In addition, 2-pyrone itself may be of value as a food additive, as a phytochemical, or as part of a phytochemical mix.

2-Pyrone synthase (also termed 2-PS) is used to catalyze the synthesis of 2-pyrone. As described herein, the enzyme-engineering methods described herein with 2-pyrone synthase constitute a generally useful approach that can be applied to virtually any 2-pyrone synthase-type (type-III polyketide synthase) enzyme for enhancing overall small molecule production in a yeast metabolic-engineering host or other suitable hosts. Atomic resolution x-ray crystal structures were found to be important in the rational engineering of the enzyme to accept a variety of CoA-thioester starter molecules, the number of decarboxylative acetyl additions and the termination chemistry used to offload useful products (Claisen and aldol condensations and lactonization) (FIG. 3). Moreover, the molecular structure of 2-pyrone synthase is useful for characterizing variants that greatly improve in vivo stability and production through the replacement of key Cys residues that are either externally exposed to the bulk solvent or buried. Replacing Cys residues defined by the x-ray structures with non-oxidizable amino acids has the potential to increase productivity of the polyketide synthase enzymes in vitro and in vivo, which is useful for biocatalysis and bioengineering. Thus, the effects of particular Cys residues was determined by creating and characterizing such variants in 2-pyrone synthase.

A 2-pyrone synthase polypeptide of the invention encompasses wild-type polyketides (e.g., a $G.$ $hybrida$ 2-pyrone synthase amino acid sequence), or 2-pyrone synthase variants having one or more mutations (e.g., those described in FIG. 10 or otherwise delineated herein) relative to the wild-type sequence. Mutations include deletions and additions of amino acid residues, and substitutions of one amino acid residue for another. Exemplary substitutions include: C35S (where Cys at position 35 of a wild type 2-pyrone synthase is changed to Ser), I343F, I343M, I201M, L202F, L268M, T137F, T137L, I201F, I201L, L202F, L202M, L268F, L268M, C35A, C65A, C346S, C135A, C65S, C89S, C195S, C346A, C372A, C372S mutants, variants and conservative substitutions thereof comprising L- or D-amino acids and include modified sequences, such as glycoproteins.

Accordingly, the polypeptides of the invention encompass naturally occurring proteins, as well as those which are recombinantly or synthetically synthesized. Polypeptide or protein fragments are also encompassed by the invention. Fragments can have the same or substantially the same amino acid sequence as the naturally occurring protein. In general, polypeptides of the invention include peptides, or full-length proteins, that contain substitutions, deletions, or insertions into the protein backbone, that would still have an approximately 70%, 80%, 85%, 90%, 95% or even 100% sequence identity to the original protein over the corresponding portion.

A conservative variation denotes the replacement of an amino acid residue by a biologically similar residue. Examples of conservative variations include the substitution of one hydrophobic residue, such as isoleucine, valine, leucine or methionine, for another hydrophobic residue, or the substitution of one polar residue for another polar residue, such as the substitution of arginine for lysine, glutamic for aspartic acids, or glutamine for asparagine. Other illustrative examples of conservative substitutions include the following: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucme or methionine; serine to threonine; threonine to serine; tryptophan to tyrosine; tyrosine to tryptophan or phenylalanine; and valine to isoleucine or leucine.

The present invention encompasses sequence alterations that increase stability or enhance solubility.

Nucleic Acids, Cloning and Expression Systems

The present disclosure further provides isolated nucleic acids encoding the disclosed polyketide synthases, and active fragments thereof. The nucleic acids may comprise DNA or RNA and may be wholly or partially synthetic or recombinant. Reference to a nucleotide sequence as set out herein encompasses a DNA molecule with the specified sequence, and encompasses a RNA molecule with the specified sequence in which U is substituted for T, unless context requires otherwise.

The present disclosure also provides constructs in the form of plasmids, vectors, phagemids, transcription or expression cassettes that comprise at least one nucleic acid encoding a polyketide synthase or a fragment thereof, disclosed herein.

The disclosure further provides a host cell that comprises one or more constructs as above.

Also provided are methods of making the encoded products. The method comprises expressing the encoded product from the encoding nucleic acid. Expression may be achieved by culturing under appropriate conditions recombinant host cells containing the nucleic acid. Following production by expression a polyketide synthase may be isolated and/or purified using any suitable technique, then used as appropriate.

Polyketide synthases, active fragments, and encoding nucleic acid molecules and vectors may be isolated and/or purified from their natural environment, in substantially pure or homogeneous form, or, in the case of nucleic acid, free or substantially free of nucleic acid or genes of origin other than the sequence encoding a polypeptide with the required function.

Systems for cloning and expression of a polypeptide in a variety of different host cells are well known in the art. For cells suitable for producing antibodies, see Gene Expression Systems, Academic Press, eds. Fernandez et al., 1999. Briefly, suitable host cells include, but are not limited to yeast, plant, algae, bacterial, mammalian, and insect cells. Mammalian cell lines available in the art for expression of a heterologous polypeptide include Chinese hamster ovary cells, HeLa cells, baby hamster kidney cells, NS0 mouse myeloma cells, and many others. A common bacterial host is E. coli. Any protein expression system compatible with the invention may be used to produce the disclosed antibodies. Suitable expression systems include transgenic animals described in Gene Expression Systems, Academic Press, eds. Fernandez et al., 1999.

Suitable vectors can be chosen or constructed, so that they contain appropriate regulatory sequences, including promoter sequences, terminator sequences, polyadenylation sequences, enhancer sequences, marker genes and other sequences as appropriate. Vectors may be plasmids or viral, e.g., phage, or phagemid, as appropriate. For further details see, for example, Sambrook et al., Molecular Cloning: A Laboratory Manual, 2nd ed., Cold Spring Harbor Laboratory Press, 1989. Many known techniques and protocols for manipulation of nucleic acid, for example, in preparation of nucleic acid constructs, mutagenesis, sequencing, introduction of DNA into cells and gene expression, and analysis of proteins, are described in detail in Current Protocols in Molecular Biology, 2nd Edition, eds. Ausubel et al., John Wiley & Sons, 1992.

A further aspect of the disclosure provides a host cell comprising a nucleic acid as disclosed here. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g., vaccinia or, for insect cells, baculovirus. For bacterial cells, suitable techniques may include calcium chloride transformation, electroporation and transfection using bacteriophage. The introduction of the nucleic acid into the cells may be followed by causing or allowing expression from the nucleic acid, e.g., by culturing host cells under conditions for expression of the gene.

A wide variety of host cells are available for expressing polyketide synthase mutants of the present invention. Such host cells include, for example, yeast, plant, algae, bacterial, mammalian, and insect cells.

Once a synthase of the present invention is expressed, the protein obtained therefrom can be purified so that structural analysis, modeling, and/or biochemical analysis can be performed, as exemplified herein. The nature of the protein obtained can be dependent on the expression system used. For example, genes, when expressed in mammalian or other eukaryotic cells, may contain latent signal sequences that may result in glycosylation, phosphorylation, or other post-translational modifications, which may or may not alter function. Therefore, a preferred embodiment of the present invention is the expression of mutant synthase genes in E. coli cells. Once said proteins are expressed, they can be easily purified using techniques common to the person having ordinary skill in the art of protein biochemistry, such as, for example, techniques described in Colligan et al, (1997) Current Protocols in Protein Science, Chanda, V. B., d., John Wiley & Sons, Inc., which is incorporated by reference herein. Such techniques often include the use of cation-exchange or anion-exchange chromatography, gel filtration-size exclusion chromatography, and the like. Another technique that may be commonly used is affinity chromatography. Affinity chromatography can include the use of antibodies, substrate analogs, or histidine residues (His-tag technology).

Expression of 2-Pyrone Synthase in Plants

Plants (including isolated plant cells) may be modified to express a 2-pyrone synthase variant (e.g., a variant comprising one or more mutations described herein). A transgenic plant, or population of such plants, expressing a 2-pyrone synthase variant transgene (e.g., a 2-pyrone synthase variant polypeptide or 2-pyrone synthase variant nucleic acid molecule) are useful in the methods of the invention. If desired, a plant expressing a 2-pyrone synthase variant of the invention includes one or more other transgenes.

In one embodiment, a 2-pyrone synthase variant nucleic acid molecule is expressed by a stably-transfected plant cell line, a transiently-transfected plant cell line, or by a transgenic plant. A number of vectors suitable for stable or extrachromosomal transfection of plant cells or for the establishment of transgenic plants are available to the public; such vectors are described in Pouwels et al. (supra), Weissbach and Weissbach (supra), and Gelvin et al. (supra). Methods for constructing such cell lines are described in, e. g., Weissbach and Weissbach (supra), and Gelvin et all. (supra).

Typically, plant expression vectors include (1) a cloned plant gene under the transcriptional control of 5' and 3' regulatory sequences and (2) a dominant selectable marker. Such plant expression vectors may also contain, if desired, a promoter regulatory region (for example, one conferring inducible or constitutive, pathogen- or wound-induced, environmentally- or developmentally-regulated, or cell- or tissue-specific expression), a transcription initiation start site, a ribosome binding site, an RNA processing signal, a transcription termination site, and/or a polyadenylation signal. In one embodiment, a 2-pyrone synthase variant polypeptide is expressed, for example, in the glandular tricone tissue of a plant.

If desired, a 2-Pyrone synthase variant of the invention is modified to enhance expression in a desired plant or plant cell. In one embodiment, a non-coding flanking is subjected to mutagenesis. In one embodiment, a 2-pyrone synthase variant DNA sequence of the invention may, if desired, be combined with other DNA sequences in a variety of ways. A 2-Pyrone synthase DNA sequence of the invention may be employed with all or part of the gene sequences normally associated with a 2-Pyrone synthase protein. In its component parts, a DNA sequence encoding an 2-Pyrone synthase protein is combined in a DNA construct having a transcription initiation control region capable of promoting transcription and translation in a host cell.

In general, the constructs will involve regulatory regions functional in plants which provide for modified production of a 2-Pyrone synthase protein as discussed herein. The open reading frame coding for the 2-Pyrone synthase protein or functional fragment thereof will be joined at its 5' end to a transcription initiation regulatory region. Numerous transcription initiation regions are available which provide for constitutive or inducible regulation. For applications where developmental, cell, tissue, hormonal, or environmental expression is desired, appropriate 5' upstream non-coding regions are obtained from other genes, for example, from genes regulated during meristem development, seed development, embryo development, or leaf development.

Regulatory transcript termination regions may also be provided in DNA constructs of this invention as well. Transcript termination regions may be provided by the DNA sequence encoding a 2-Pyrone synthase protein or any convenient transcription termination region derived from a different gene source. In various embodiments, the transcript termination region will contain at least 1-3 kb of sequence 3' to the structural gene from which the termination region is derived. Plant expression constructs having a 2-Pyrone synthase gene as the DNA sequence of interest for expression may be employed with a wide variety of plant life, particularly plant life involved in the production of storage reserves (for example, those involving carbon and nitrogen metabolism). Such genetically-engineered plants are useful for a variety of industrial and agricultural applications. Importantly, this invention is applicable to dicotyledons and monocotyledons, and will be readily applicable to any new or improved transformation or regeneration method.

The expression constructs include at least one promoter operably linked to at least one 2-Pyrone synthase gene. An example of a useful plant promoter according to the invention is a caulimovirus promoter, for example, a cauliflower mosaic virus (CaMV) promoter. These promoters confer high levels of expression in most plant tissues, and the activity of these promoters is not dependent on virally encoded proteins. CaMV is a source for both the 35S and 19S promoters.

Examples of plant expression constructs using these promoters are found in Fraley et al., U.S. Pat. No. 5,352,605. In most tissues of transgenic plants, the CaMV 35S promoter is a strong promoter (see, e.g., Odell et al., Nature 313:810, 1985). The CaMV promoter is also highly active in monocots (see, e.g., Dekeyser et al., Plant Cell 2: 591, 1990; Terada and Shimamoto, Mol. Gen. t Genet. 220: 389, 1990). Moreover, activity of this promoter can be further increased (i. e., between 2-10 fold) by duplication of the CaMV 35S promoter (see e.g., Kay et al., Science 236: 1299, 1987; Ow et al., Proc. Natl. Acad. Sci., U.S.A. 84:4870, 1987; and Fang et al., Plant Cell 1: 141, 1989, and McPherson and Kay, U.S. Pat. No. 5,378,142). Other useful plant promoters include, without limitation, the nopaline synthase (NOS) promoter (An et al., Plant Physiol. 88: 547, 1988 and Rodgers and Fraley, U.S. Pat. No. 5,034,322), the octopine synthase promoter (Fromm et al., Plant Cell 1: 977, 1989), figwort mosaic virus (FMV) promoter (Rodgers, U.S. Pat. No. 5,378,619), and the rice actin promoter (Wu and McElroy, WO91/09948). Exemplary monocot promoters include, without limitation, *commelina* yellow mottle virus promoter, sugar cane badna virus promoter, ricetungrobacilliform virus promoter, maize streak virus element, and wheat dwarf virus promoter.

For certain applications, it may be desirable to produce the 2-Pyrone synthase gene product in an appropriate tissue, such as glandular tricone tissue, at an appropriate level, or at an appropriate developmental time. For this purpose, there are an assortment of gene promoters, each with its own distinct characteristics embodied in its regulatory sequences, shown to be regulated in response to inducible signals such as the environment, hormones, and/or developmental cues. These include, without limitation, gene promoters that are responsible for heat-regulated gene expression (see, e.g., Callis et al., Plant Physiol. 88: 965, 1988; Takahashi and Komeda, Mol. Gen. Genet. 219: 365, 1989; and Takahashi et al. Plant J. 2: 751, 1992), light-regulated gene expression (e.g., the pea rbcS-3A described by Kuhlemeier et al., Plant Cell 1: 471, 1989; the maizerbcS promoter described by Schaffner and Sheen, Plant Cell 3: 997, 1991; the chlorophyll a/b-binding protein gene found in pea described by Simpson et al., EMBO J. 4: 2723, 1985; the Arabssu promoter; or the rice rbs promoter), hormone-regulated gene expression (for example, the abscisic acid (ABA) responsive sequences from the Em gene of wheat described by Marcotte et al., Plant Cell 1: 969, 1989; the ABA-inducible HVA1 and HVA22, and rd29A promoters described for barley and *Arabidopsis* by Straub et al., Plant Cell 6: 617, 1994 and Shen et al., Plant Cell 7: 295, 1995, organ-specific gene expression (for example, of the tuber-specific storage protein gene described by Roshal et al., EMBOJ. 6:1155, 1987; the 23-kDa zein gene from maize described by Schernthaner et al., EMBO J. 7: 1249, 1988; or the French bean B-phaseolin gene described by Bustos et al., Plant Cell 1: 839, 1989.

Plant expression vectors may also optionally include RNA processing signals, e.g., introns, which have been shown to be important for efficient RNA synthesis and accumulation (Callis et al., Genes and Dev. 1: 1183, 1987). The location of the RNA splice sequences can dramatically influence the level of transgene expression in plants. In view of this fact, an intron may be positioned upstream or downstream of an 2-Pyrone synthase polypeptide-encoding sequence in the transgene to modulate levels of gene expression.

In addition to the aforementioned 5' regulatory control sequences, the expression vectors may also include regulatory control regions which are generally present in the 3' regions of plant genes (Thornburg et al., Proc. Natl. Acad. Sci. U.S.A. 84:744, 1987; An et al., Plant Cell 1: 115, 1989). For example, the 3' terminator region may be included in the expression vector to increase stability of the mRNA. One such terminator region may be derived from the PI-11 terminator region of potato. In addition, other commonly used terminators are derived from the octopine or nopaline synthase signals. The plant expression vector also typically contains a dominant selectable marker gene used to identify those cells that have become transformed. Useful selectable genes for plant systems include genes encoding antibiotic resistance genes, for example, those encoding resistance to hygromycin, kanamycin, bleomycin, G418, streptomycin, or spectinomycin. Genes required for photosynthesis may also be used as selectable markers in photosynthetic-deficient strains. Finally, genes encoding herbicide resistance may be used as selectable markers; useful herbicide resistance genes include the bar gene encoding the enzyme phosphinothricin acetyltransferase and conferring resistance to the broad spectrum herbicide Basta (Frankfurt, Germany).

Efficient use of selectable markers is facilitated by a determination of the susceptibility of a plant cell to a particular selectable agent and a determination of the concentration of this agent which effectively kills most, if not all, of the transformed cells. Some useful concentrations of antibiotics for tobacco transformation include, e.g., 75-100 µg/mL (kanamycin), 20-50 µg/mL (hygromycin), or 5-10 µg/mL (bleomycin). A useful strategy for selection of transformants for herbicide resistance is described, e.g., by Vasil et al., supra. In addition, if desired, the plant expression construct may contain a modified or fully-synthetic structural 2-Pyrone synthase coding sequence that has been changed to enhance the performance of the gene in plants. Methods for constructing such a modified or synthetic gene are described in Fischoff and Perlak, U.S. Pat. No. 5,500,365. It should be readily apparent to one skilled in the art of molecular biology, especially in the field of plant molecular biology, that the level of gene expression is dependent, not only on the combination of promoters, RNA processing signals, and terminator elements, but also on how these elements are used to increase the levels of selectable marker gene expression.

Plant Transformation

Upon construction of the plant expression vector, several standard methods are available for introduction of the vector into a plant host, thereby generating a transgenic plant. These methods include (1) *Agrobacterium*-mediated transformation (*A. tumefaciens* or *A. rhiizogenes*) (see, e. g., Lichtenstein and Fuller In: Genetic Engineering, vol 6, PWJ Rigby, ed, London, Academic Press, 1987; and Lichtenstein, C. P., and Draper, J, In: DNA Cloning, Vol II, D. M. Glover, ed, Oxford, IRI Press, 1985)), (2) the particle delivery system (see, e.g., Gordon-Kamm et al., Plant Cell 2: 603 (1990); or BioRad Technical Bulletin 1687, supra), (3) microinjection protocols (see, e. g., Green et al., supra), (4) polyethylene glycol (PEG) procedures (see, e. g., Draper et al., Plant Cell Physiol. 23: 451, 1982; or e.g., Zhang and Wu, Theor. Appl. Genet. 76: 835, 1988), (5) liposome-mediated DNA uptake (see, e. g., Freeman al., Plant Cell Physiol. 25: 1353, 1984), (6) electroporation protocols (see, e.g., Gelvin et al., supra; Dekeyser et al., supra; Fromm et al., Nature 319: 791, 1986; Sheen Plant Cell 2: 1027, 1990; or Jang and Sheen Plant Cell 6: 1665, 1994), and (7) the vortexing method (see, e. g., Kindle supra).

The method of transformation is not critical to the invention. Any method which provides for efficient transformation may be employed. As newer methods are available to transform crops or other host cells, they may be directly applied. Suitable plants for use in the practice of the invention include, but are not limited to, artemesia, sugar cane, wheat, rice, maize, sugar beet, potato, barley, manioc, sweet potato, soybean, sorghum, cassava, banana, grape, oats, solanaceus plants (e.g., tomato), millet, coconut, orange, rye, cabbage, apple, watermelon, canola, cotton, carrot, garlic, onion, pepper, strawberry, yam, peanut, onion, bean, pea, mango, citrus plants, walnuts, and sunflower.

The following is an example outlining one particular technique, an *Agrobacterium*-mediated plant transformation. By this technique, the general process for manipulating genes to be transferred into the genome of plant cells is carried out in two phases. First, cloning and DNA modification steps are carried out in *E. coli*, and the plasmid containing the gene construct of interest is transferred by conjugation or electroporation into *Agrobacterium*. Second, the resulting *Agrobacterium* strain is used to transform plant cells. Thus, for the generalized plant expression vector, the plasmid contains an origin of replication that allows it to replicate in *Agrobacterium* and a high copy number origin of replication functional in *E. coli*. This permits facile production and testing of transgenes in *E. coli* prior to transfer to *Agrobacterium* for subsequent introduction into plants. Resistance genes can be carried on the vector, one for selection in bacteria, for example, streptomycin, and another that will function in plants, for example, a gene encoding kanamycin resistance or herbicide resistance. Also present on the vector are restriction endonuclease sites for the addition of one or more transgenes and directional T-DNA border sequences which, when recognized by the transfer functions of *Agrobacterium*, delimit the DNA region that will be transferred to the plant.

In another example, plant cells may be transformed by shooting into the cell tungsten microprojectiles on which cloned DNA is precipitated. In the Biolistic Apparatus (Bio-Rad) used for the shooting, a gunpowder charge (22 caliber Power Piston Tool Charge) or an air-driven blast drives a plastic macroprojectile through a gun barrel. An aliquot of a suspension of tungsten particles on which DNA has been precipitated is placed on the front of the plastic macroprojectile. The latter is fired at an acrylic stopping plate that has a hole through it that is too small for the macroprojectile to pass through. As a result, the plastic macroprojectile smashes against the stopping plate, and the tungsten microprojectiles continue toward their target through the hole in the plate. For the instant invention the target can be any plant cell, tissue, seed, or embryo. The DNA introduced into the cell on the microprojectiles becomes integrated into either the nucleus or the chloroplast. In general, transfer and expression of transgenes in plant cells are now routine for one skilled in the art, and have become major tools to carry out gene expression studies in plants and to produce improved plant varieties of agricultural or commercial interest.

Transgenic Plant Regeneration

Plant cells transformed with a plant expression vector can be regenerated, for example, from single cells, callus tissue, or leaf discs according to standard plant tissue culture techniques. It is well known in the art that various cells, tissues, and organs from almost any plant can be successfully cultured to regenerate an entire plant; such techniques are described, e.g., in Vasil supra; Green et al., supra; Weissbach and Weissbach, supra; and Gelvin et al., supra. In one particular example, a cloned 2-Pyrone synthase polypeptide expression construct under the control of the 35SCaMV promoter and the nopaline synthase terminator and carrying a selectable marker (for example, kanamycin resistance) is transformed into *Agrobacterium*. Transformation of leaf discs, with vector-containing *Agrobacterium* is carried out as described by Horsch et al. (Science 227: 1229, 1985). Putative transformants are selected after a few weeks (for example, 3 to 5 weeks) on plant tissue culture media containing kanamycin (e. g. 100 Lg/nlL). Kanamycin-resistant shoots are then placed on plant tissue culture media without hormones for root initiation. Kanamycin resistant plants are then selected for greenhouse growth. If desired, seeds from self-fertilized transgenic plants can then be sowed in a soil-less medium and grown in a greenhouse. Kanamycin-resistant progeny are selected by sowing surfaced sterilized seeds on hormone-free kanamycin-containing media.

Analysis for the integration of the transgene is accomplished by standard techniques (see, for example, Ausubel et al. supra; Gelvin et al. supra). Transgenic plants expressing the selectable marker are then screened for transmission of the transgene DNA by standard immunoblot and DNA detection techniques. Each positive transgenic plant and its transgenic progeny are unique in comparison to other transgenic plants established with the same transgene. Integration of the transgene DNA into the plant genomic DNA is in most cases random, and the site of integration can profoundly affect the levels and the tissue and developmental patterns of transgene expression. Consequently, a number of transgenic lines are usually screened for each transgene to identify and select plants with the most appropriate expression profiles. Transgenic Plant Lines are Evaluated for Levels of Transgene Expression.

Pyrone synthase variant expression at the RNA level is determined initially to identify and quantitate expression-positive plants. Standard techniques for RNA analysis are employed for transgenic plants expressing 2-Pyrone synthase nucleic acids. Such techniques include PCR amplification assays using oligonucleotide primers designed to amplify only transgene RNA templates and solution hybridization assays using transgene-specific probes (see, e.g., Ausubel et al., supra). Those RNA-positive plants that encode a 2-Pyrone synthase protein are then analyzed for protein expression by Western immunoblot analysis using 2-Pyrone synthase specific antibodies (see, e.g., Ausubel et al., supra). In addition, in situ hybridization and immunocytochemistry according to standard protocols can be done using transgene-specific nucleotide probes and antibodies, respectively, to localize sites of expression within transgenic tissue.

Yeast Cells and Expression

In one embodiment, 2-pyrone synthase variants having increased activity are expressed in yeast cells. Exemplary species include *Kluyverei lactis, Schizosaccharomyces pombe, Ustilaqo maydis,* and *Saccharomyces cerevisiae*. Other yeast which can be used in practicing the invention include, but are not limited to, *Neurospora crassa, Aspergillus niger, Aspergillus nidulans, Pichia pastoris, Candida tropicalis,* and *Hansenula polymorpha*. The term "yeast", as used herein, includes not only yeast in a strictly taxonomic sense, i.e., unicellular organisms, but also yeast-like multicellular fungi or filamentous fungi.

If desired, the yeast strain is subjected to genetic selection. Such methods are known in the art. In one embodiment, nutritional selection is used. For example, yeast strains that are auxotrophic for histidine (HIS 3) are known, see Struhl and Hill, (1987) Mol. Cell. Biol., 7:104; Fasullo and Davis, Mol. Cell. Biol., (1988) 8:4370), and the HIS3 (imidazoleglycerol phosphate dehydratase) gene has been used as a selective marker in yeast. See Sikorski and Heiter, (1989) Genetics, 122:19; Struhl, et al., P.N.A.S. (1979) 76:1035; and, for FUS1-HIS3 fusions, see Stevenson, et al., (1992) Genes Dev., 6:1293.

In certain embodiments, the host yeast cell can be modified in other ways. For example, it may be desirable to inactivate, such as by mutation or deletion, an endogenous yeast polypeptide. In general, it will be desirable that an expression vector be capable of replication in a host cell. Heterologous DNA may be integrated into the host genome, and thereafter replicated as a part of the chromosomal DNA, or it may be DNA which replicates autonomously, as in the case of a plasmid. In the latter case, the vector will include an origin of replication which is functional in the host. In the case of an integrating vector, the vector may include sequences which facilitate integration, e.g., sequences homologous to host sequences, or encoding integrases.

Appropriate cloning and expression vectors for use with bacterial, fungal, plant, insect, yeast, and mammalian cellular hosts are known in the art, and are described in, for example, Powels et al. (Cloning Vectors: A Laboratory Manual, Elsevier, N.Y., 1985). A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in Experimental Manipulation of Gene Expression, ed. M. Inouye Academic Press, p. 83, incorporated by reference herein). These vectors can replicate in *E. coli* due to the presence of the pBR322 ori, and in *S. cerevisiae* due to the replication determinant of the yeast 2 micron plasmid.

In addition, drug resistance markers such as ampicillin can be used. Suitable promoters for function in yeast include the promoters for metallothionein, 3-phosphoglycerate kinase (Hitzeman et al., J. Biol. Chem. 255, 2073 (1980) or other glycolytic enzymes (Hess et al., J. Adv. Enzyme Req. 7, 149 (1968); and Holland et al. Biochemistry 17, 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phospho-glucose isomerase, and glucokinase. Suitable vectors and promoters for use in yeast expression are further described in R. Hitzeman et al., EPO Pub. No. 73,657.

Mutagenesis and Expression of Biomolecules of Interest

Various types of cloning and mutagenesis methods can be used with the methods herein, e.g., to produce and/or isolate polyketide synthases and/or to further modify/mutate the polypeptides (e.g., polyketide synthases) provided herein.

In some embodiments, isolated nucleic acids, polypeptides and/or viruses can be further mutated. Mutagenesis methods include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA and the like. Additional suitable mutagenesis methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the methods herein. In some embodiments, mutagenesis can be guided by known information of the naturally occurring molecule or altered or mutated naturally occurring molecule, e.g., sequence, sequence comparisons, physical properties, crystal structure or the like.

Oligonucleotides for use in mutagenesis are typically synthesized chemically according to the solid phase phosphoramidite triester method described by Beaucage and Caruthers, Tetrahedron Letts 22(20):1859-1862, (1981) using an automated synthesizer, as described in Needham-VanDevanter et al., Nucleic Acids Res, 12:6159-6168 (1984). In addition, essentially any nucleic acid can be custom or standard ordered from any of a variety of commercial sources. Similarly, peptides and antibodies can be custom ordered from any of a variety of sources.

Also provided herein are host cells and organisms comprising a polyketide synthase or other polypeptide and/or nucleic acid provided herein or such polyketide synthase or other sequences within various vectors such as viruses, plasmids in plasmid rescue systems, and the like. Host cells can be transformed, transduced or transfected with the vectors provided herein, which can be, for example, a cloning vector or an expression vector. The vector can be, for example, in the form of a plasmid, a bacterium, a virus, a naked polynucleotide, or a conjugated polynucleotide. The vectors can be introduced into cells and/or microorganisms by standard methods including electroporation (see, From et al., Proc Natl Acad Sci USA 82, 5824 (1985)), infection by viral vectors, high velocity ballistic penetration by small particles with the nucleic acid either within the matrix of small beads or particles, or on the surface (Klein et al., Nature 327, 70-73 (1987)).

Several well-known methods of introducing target nucleic acids into bacterial cells are available, any of which can be used with the methods herein. These include, for example, fusion of the recipient cells with bacterial protoplasts containing the DNA, electroporation, projectile bombardment, and infection with viral vectors, and the like. Bacterial cells can be used to amplify the number of plasmids containing DNA constructs. The bacteria are grown to log phase and the plasmids within the bacteria can be isolated by a variety of methods known in the art. In addition, a plethora of kits are commercially available for the purification of plasmids from bacteria, (see, e.g., EasyPrep™, FlexiPrep™, both from Pharmacia Biotech; StrataClean™, from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or both. See, Giliman & Smith, Gene 8:81 (1979); Roberts, et al., Nature, 328:731 (1987); Schneider, B., et al., Protein Expr Purif 6435:10 (1995); Ausubel, Sambrook, Berger (all supra). A catalogue of bacteria and bacteriophages useful for cloning is provided, e.g., by the ATCC, e.g., The ATCC Catalogue of Bacteria and Bacteriophage (1992) Gherna et al. (eds.) published by the ATCC. Additional basic procedures for sequencing, cloning and other aspects of molecular biology and underlying theoretical considerations are known in the art.

According to the present invention, nucleic acid sequences encoding a mutated polyketide synthase can be produced by the methods described herein, or any alternative methods available to the skilled artisan. In designing the nucleic acid sequence of interest, it maybe desirable to reengineer said gene for improved expression in a particular expression system. For example, it has been shown that many bacterially derived genes do not express well in yeast systems, in some cases, yeast-derived genes do not express well in bacteria. This phenomenon may be due to the non-optimal G+C content and/or A+T content of said gene relative to the expression system being used. Thus, one goal in the design of genes is to generate nucleic acid sequences that have a G+C content that affords mRNA stability and translation accuracy for a particular expression system.

Due to the redundancy of the genetic code (i.e., many amino acids are specified by more than one codon), evolution of the genomes of different organisms or classes of organisms has resulted in differential usage of redundant codons. This "codon bias" is reflected in the mean base composition of protein coding regions. For example, organisms with relatively low G+C contents utilize codons having A or T in the third position of redundant codons, whereas those having higher G+C contents utilize codons having G or C in the third position.

Therefore, in reengineering genes for expression, one may wish to determine the codon bias of the organism in which the gene is to be expressed. Looking at the usage of the codons as determined for genes of a particular organism deposited in GenBank can provide this information. After determining the bias thereof, the new gene sequence can be analyzed for restriction enzyme sites as well as other sites that could affect transcription such as exon intron junctions, polyA addition signals, or RNA polymerase termination signals.

Once expressed, mutants of the present invention may be purified for characterization by any of several different properties. In some embodiments, such mutants may have altered active site surface charges of one or more charge units. In addition, said mutants may have altered substrate specificity or product capability relative to a non-mutated polyketide synthase. In other embodiments, such mutants may have altered stability.

Compounds and Methods of Making Same

The present invention includes methods of preparing compounds using the synthases and substrates contemplated within the invention. The present invention further includes compounds that are prepared using the synthases and substrates contemplated within the invention. The invention further includes derivatives of compounds that are prepared using the synthases and substrates contemplated within the invention, such as, but not limited to, partially or fully alkylated, or partially or fully acylated derivatives thereof.

The preparation of a compound contemplated within the invention includes the step of contacting a substrate contemplated within the invention with a synthase contemplated within the invention, wherein the synthase catalyzes reaction of the substrate. In certain embodiments, the substrate comprises acetyl-CoA. In other embodiments, the substrate comprises acetoacetyl-CoA, malonyl-CoA, or coumaryl-CoA. In yet other embodiments, the substrate comprises a compound of formula (I), or a salt, solvate or derivative thereof:

$$\text{CoA-S—C(=O)—R}^1 \qquad (I),$$

wherein in (I) $R^1$ is selected from the group consisting of $C_1$-$C_{20}$ alkyl, $C_1$-$C_{20}$ cycloalkyl, aryl-($C_1$-$C_{20}$ alkyl), carboxy-($C_1$-$C_{20}$ alkyl), aryl, heterocyclyl, heteroaryl, aryl-CH=CH—, heterocyclyl-CH=CH—, and heteroaryl-CH=CH—, wherein each alkyl, cycloalkyl, aryl, heterocyclyl or heteroaryl group is independently optionally substituted with at least one substituent selected from the group consisting of F, Cl, Br, I, hydroxy, alkoxy, amino, nitro, monoalkylamino, dialkylamino, carboxy, C(=O)O ($C_1$-$C_6$)alkyl, trifluoromethyl, cyano, —C(=O)NH$_2$, —C(=O)NH($C_1$-$C_6$)alkyl, —C(=O)N(($C_1$-$C_6$) alkyl)$_2$, —SO$_2$NH$_2$, and —C(=NH)NH$_2$. In certain embodiments, $R^1$ is selected from the group consisting of $C_1$-$C_{20}$ alkyl, carboxy-($C_1$-$C_{20}$ alkyl), aryl, heteroaryl, aryl-CH=CH— and heteroaryl-CH=CH—. In certain embodiments, the alkyl, cycloalkyl, aryl or heteroaryl group is optionally substituted with at least one substituent selected from the group consisting of F, Cl, Br, I, hydroxy, alkoxy, amino, nitro, monoalkylamino, dialkylamino, carboxy, C(=O)O($C_1$-$C_6$)alkyl, trifluoromethyl, cyano, —C(═O)NH$_2$, —C(═O)NH(C$_1$-C$_6$)alkyl, —C(═O)N((C$_1$-C$_6$)alkyl)$_2$, —SO$_2$NH$_2$, and —C(═NH)NH$_2$. In certain embodiments, the aryl group is phenyl. In certain embodiments, the heteroaryl group is pyridyl.

The substrate comprising the compound of formula (I) may be prepared using methods known to those skilled in the art, such as but not limited to acylation of CoA using the appropriate acylating agent under conditions known to those skilled in the art.

Upon contacting the substrate and the synthase contemplated within the invention, the substrate undergoes a chemical reaction that is catalyzed by the synthase. In certain embodiments, the product of the synthase-catalyzed substrate reaction is a compound contemplated within the invention. In other embodiments, the product of the synthase-catalyzed substrate reaction is further derivatized, and the resulting derivatization product is a compound contemplated within the invention. The derivatization of any compound may be performed using chemical methods (i.e., reacting the product of the synthase-catalyzed substrate reaction with one or more chemical reagents, either simultaneously or in sequence), enzymatic methods (i.e., contacting the product of the synthase-catalyzed substrate reaction with one or more enzymes, such as but not limited to other synthases, chalcones and the like, either simultaneously or in sequence), and/or a combination of chemical methods and biochemical methods.

The product of the synthase-catalyzed substrate reaction and/or the resulting product from the derivatization of the product of the synthase-catalyzed substrate reaction may be isolated using methods known to those skilled in the art, such as but not limited to chromatography, liquid-liquid or liquid-solid extraction, precipitation, evaporation and/or sublimation.

The invention contemplates compounds generated using the naturally occurring or mutant synthases of the invention. In certain embodiments, the compounds contemplated within the invention comprise a cyclic compound, or a salt, solvate or derivative thereof, selected from the group consisting of:

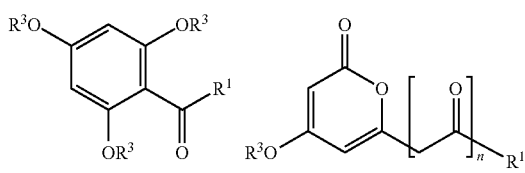

-continued

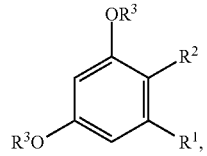

wherein:
R$^1$ is selected from the group consisting of C$_1$-C$_{20}$ alkyl, C$_1$-C$_{20}$ cycloalkyl, aryl-(C$_1$-C$_{20}$ alkyl), carboxy-(C$_1$-C$_{20}$ alkyl), aryl, heterocyclyl, heteroaryl, aryl-CH═CH—, heterocyclyl-CH═CH— and heteroaryl-CH═CH—,
R$^2$ is selected from the group consisting of H, carboxy, C(═O)O(C$_1$-C$_6$)alkyl, cyano, —C(═O)NH$_2$, —C(═O)NH(C$_1$-C$_6$)alkyl, and —C(═O)N((C$_1$-C$_6$)alkyl)$_2$;
each occurrence of R$^3$ is independently selected from the group consisting of H, C$_1$-C$_{20}$ alkyl, aryl-(C$_1$-C$_{20}$ alkyl), C$_1$-C$_{20}$ acyl, aroyl, and heteroaroyl; and,
n is 0, 1, 2 or 3;
wherein each alkyl, cycloalkyl, aryl, heterocyclyl or heteroaryl group is independently optionally substituted with at least one substituent selected from the group consisting of F, Cl, Br, I, hydroxy, alkoxy, amino, nitro, monoalkylamino, dialkylamino, carboxy, C(═O)O(C$_1$-C$_6$)alkyl, trifluoromethyl, cyano, —C(═O)NH$_2$, —C(═O)NH(C$_1$-C$_6$)alkyl, —C(═O)N((C$_1$-C$_6$)alkyl)$_2$, —SO$_2$NH$_2$, and —C(═NH)NH$_2$.

In certain embodiments, the compound obtained by contacting a compound of formula (I) with a synthase contemplated within the invention may be further derivatized by, such as but not limited to, partial or total alkylation, or partial or total acylation. Any chemical products of such derivatization reactions are also compounds contemplated within the invention.

In certain embodiments, the compound obtained by contacting acetyl-CoA or any known acylated CoA derivative with a synthase contemplated within the invention may be further derivatized by, such as but not limited to, partial or total alkylation, or partial or total acylation; any products of such derivatization reactions are also compounds contemplated within the invention.

In certain embodiments, the compounds of the invention may be further derivatized using known procedures known in the art, and any products obtained by such derivatization reactions are also compounds contemplated within the present invention. In a non-limiting example, all compounds illustrated in the following scheme are compounds contemplated within the present invention.

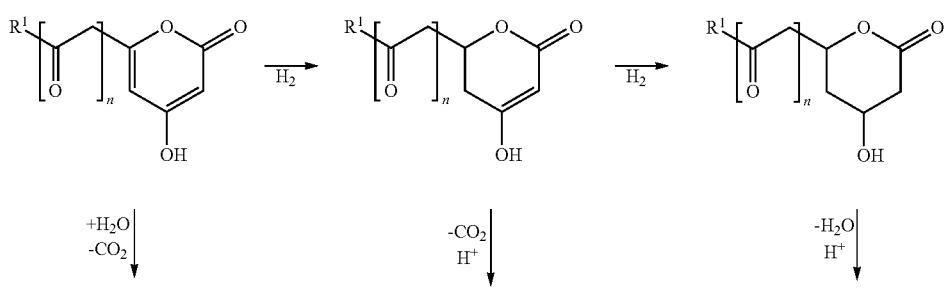

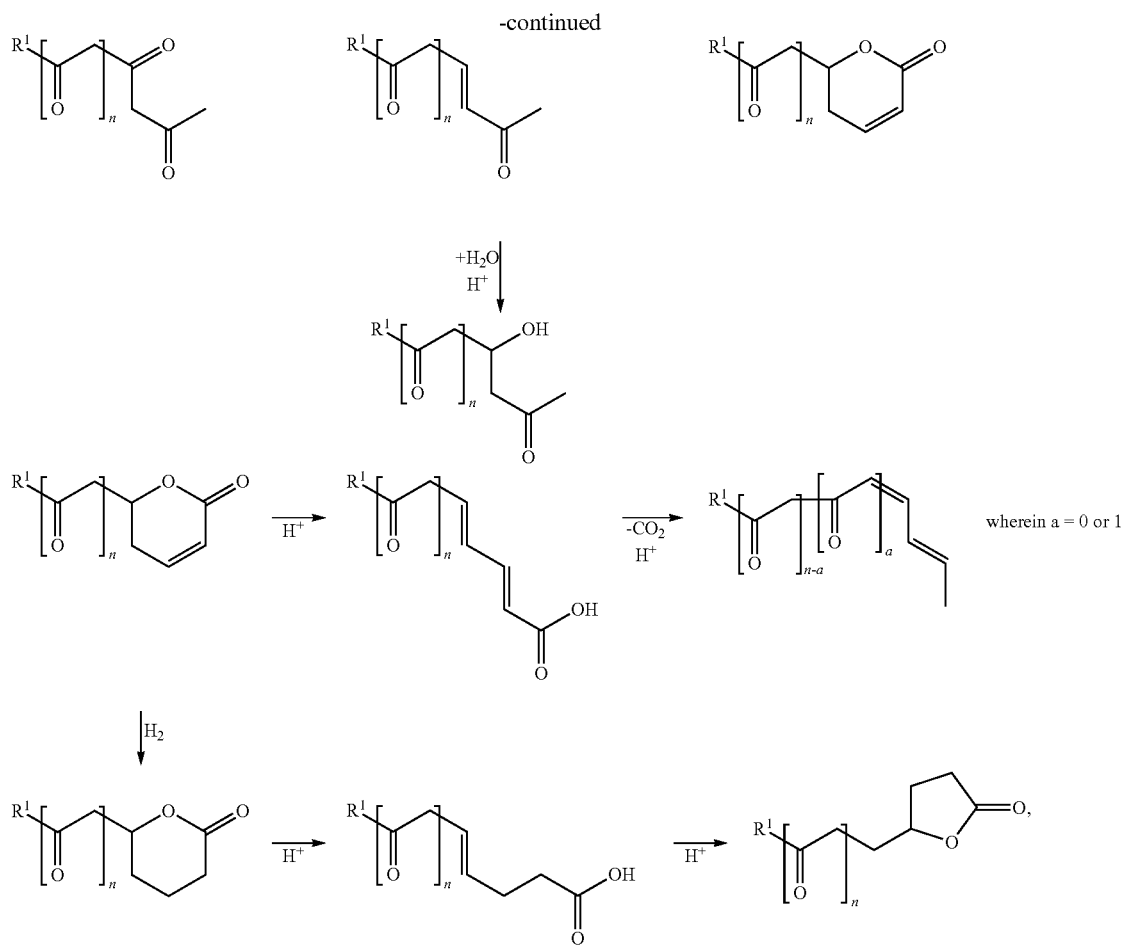

wherein $R^1$ is selected from the group consisting of $C_1$-$C_{20}$ alkyl, $C_1$-$C_{20}$ cycloalkyl, aryl-($C_1$-$C_{20}$ alkyl), carboxy-($C_1$-$C_{20}$ alkyl), aryl, heterocyclyl, heteroaryl, aryl-CH=CH—, heterocyclyl-CH=CH— and heteroaryl-CH=CH—, wherein each alkyl, cycloalkyl, aryl, heterocyclyl or heteroaryl group is independently optionally substituted with at least one substituent selected from the group consisting of F, Cl, Br, I, hydroxy, alkoxy, amino, nitro, monoalkylamino, dialkylamino, carboxy, C(=O)O($C_1$-$C_6$)alkyl, trifluoromethyl, cyano, —C(=O)NH$_2$, —C(=O)NH($C_1$-$C_6$)alkyl, —C(=O)N(($C_1$-$C_6$)alkyl)$_2$, —SO$_2$NH$_2$, and —C(=NH)NH$_2$.

In certain embodiments, at least one functional group of the compound of the invention is protected with an appropriate protective group before the compound of the invention is further derivatized, as to avoid premature reaction of the at least one functional group being protected. The protective groups that are useful within the invention are well-known to those skilled in the art, and are determined in view of the functional group reactivity and the derivatization conditions used. In certain embodiments, the functional groups of the compounds of the invention are not protected with a protective group before the compound of the invention is further derivatized. In the event that derivatization has the effect of modifying any functional group(s) of the compounds of the invention, the resulting modified products are also compounds of the present invention.

The compounds of the present invention may be formulated as pharmaceutically acceptable compositions, wherein the compositions further comprise at least one pharmaceutically acceptable carrier.

Structural and Computational Methods

The three-dimensional structures of polyketide synthase proteins have been determined. In the present study, new structures of 2-pyrone synthase were obtained. The invention encompasses specific three-dimensional space coordinates of at least fourteen -carbon atoms defined for the active site. R-groups attached to said -carbons are defined such that mutants can be made by changing at least one R-group found in the synthase active site. Such mutants may have unique and useful properties within the present invention.

One aspect of the invention resides in obtaining crystals of the polyketide synthase polypeptide, of sufficient quality to determine the three dimensional (tertiary) structure of the protein by X-ray diffraction methods. The knowledge obtained concerning the three-dimensional structure of chalcone synthase can be used in the determination of the three-dimensional structure of other synthase polypeptides in the polyketide synthesis pathway. The structural coordinates of a polyketide synthase can be used to develop new polyketide synthesis enzymes or synthase inhibitors using various computer modeling protocols. Based on the structural coordinates of a polyketide synthase polypeptide (e.g., the three-dimensional protein structure), novel polyketide synthases can be engineered. In addition, small molecules that mimic or interact with a synthase molecule functional domain can be designed and synthesized to modulate chalcone synthase, pyrone synthase, and other polyketide synthase biological functions, as well as the biological functions of other polyketide synthases.

Accordingly, in one embodiment, the invention provides a method of "rational" enzyme or drug design. Another approach to "rational" enzyme or drug design is based on a lead compound discovered using high throughput screening. This lead compound can be further modified in order to optimize its binding and/or developability properties, based on a crystal structure of the binding regions of the molecule in question. Accordingly, another aspect of the invention is to provide related protein sequences or materials that are a starting material in the rational design of new synthases or drugs, which can then lead to the synthesis of new polyketides or the rational modification of the polyketide synthesis pathway.

The present invention relates to crystallized polyketide synthases and mutants thereof, from which the position of specific -carbon atoms and R-groups associated therewith comprising the active site can be determined in three-dimensional space. The invention also relates to structural coordinates of said polyketide synthases, the use of said structural coordinates to develop structural information related to polyketide synthase homologues, mutants, and the like, and to crystal forms of such synthases.

Furthermore, the invention, as disclosed herein, provides a method whereby said -carbon structural coordinates determined for atoms comprising the active site of said synthase can be used to design synthases wherein R-groups associated with active site -carbon atoms are different from the R-groups found in native 2-pyrone synthase, e.g., variant synthases. In addition, the invention provides for production of variant polyketide synthases based on the structural information of synthases and for use of said mutant synthases to make a variety of polyketide-based compounds using a variety of substrates (as described in PCT Application No. PCT/US00/20674, filed Jul. 27, 2000, incorporated by reference in its entirety herein). The present invention also provides methods of producing novel mutant polyketide synthases by comparing the crystal structures of two different polyketide synthases and identifying residues to be mutated, deleted or added.

Crystal structures are preferably obtained at a resolution of about 1.56 Å to about 3 Å for a polyketide synthase in the presence and in the absence of bound substrate or substrate analog. Coordinates for a polyketide synthase in the absence of a substrate bound in the active site have been deposited at the Protein Data Bank, accession number 1QLV. Those skilled in the art understand that a set of structure coordinates determined by X-ray crystallography is not without standard error.

In one embodiment, the active site may be altered to vary the activity of a polyketide synthase. An appropriate combination of R-groups, linked to active site -carbons, can facilitate the formation of one or more desired reaction products. The combination of R-groups selected for use in a synthase can be any combination other than the ordered arrangements of R-groups found in known native isolated polyketide synthases. Typically, R-groups found on active site -carbons are those found in naturally occurring amino acids, in some embodiments, however, R-groups other than those found in naturally occurring amino acids can be used.

The present invention permits the use of molecular design techniques to design, select, and synthesize mutant polyketide synthases that use the same substrates as the native synthases but yet produce different and/or novel polyketide compounds. Mutant proteins of the present invention, and nucleic acids encoding the same, can be designed by genetic manipulation based on structural information about polyketide synthases. For example, one or more R-groups associated with the active site -carbon atoms of 2-pyrone synthase can be changed by altering the nucleotide sequence of the corresponding 2-pyrone synthase gene, thus making one or more variant polyketide synthases. Such genetic manipulations can be guided by structural information concerning the R-groups found in the active site -carbons when substrate is bound to the protein upon crystallization. Alternatively, mutant polyketide synthases can be prepared by standard protocols for polypeptide synthesis, as is well known in the art.

Furthermore, structural coordinates may be used to determine the structure of the crystalline form of other proteins with significant amino acid or structural homology to any functional domain of a synthase. One method that may be employed for such purpose is molecular replacement. In this method, the unknown crystal structure, whether it is another crystal form of a synthase, a synthase having a mutated active site, or the crystal of another protein with significant sequence and/or structural identity to a polyketide synthase, may be determined using a set of coordinates. This method provides sufficient structural information for the unknown crystal more efficiently than attempting to determine such information ab initio. In addition, this method can be used to determine whether or not a given polyketide synthase in question falls within the scope of this invention. Furthermore, polyketide synthases and variants thereof may be crystallized in the presence or absence of substrates and substrate analogs. The crystal structures of a series of complexes may then be solved by molecular replacement and compared to that of the wild-type to assist in determination of suitable replacements for R-groups within the active site, thus making synthase mutants according to the present invention.

All variants of the present inventions maybe modeled using previously obtained structural information without necessarily having to crystallize and solve the structure for each and every mutant. For example, one skilled in the art may use one of several specialized computer programs to assist in the process of designing synthases having mutated active sites relative to the wild-type. Examples of such programs include: GRID (Goodford, 1985, J. Mod. Chem.: 2S: 849-857), MCSS (Miranker and Karplus, 1991, Proteins: Structure, Function and Genetics, 11:29-34); AUTODOCK (Goodsell and Olsen, 1990, Proteins. Structure, Fumtion, and Genetics, 8:195-202); and DOCK (Kuntz et al, 1982, J. Mol Biol: 161:269-288), and the like. In addition, specific computer programs are also available to evaluate specific substrate-active site interactions and the deformation energies and electrostatic interactions resulting therefrom. MODELLER is a computer program often used for homology or comparative modeling of the three-dimensional structure of a protein (A. Saii & T. L. Blundell. J Mol. Biol 234:779-815, 1993). A sequence to be modeled is aligned with one or more known related structures and the MODELLER program is used to calculate a full-atom model, based on optimum satisfaction of spatial restraints. Such restraints can include, inter alia, homologous structures, site-directed mutagenesis, fluorescence spectroscopy results, NMR experiment results, or atom-atom potentials of mean force.

The present invention enables polyketide synthase mutants to be made and the crystal structure thereof to be solved. Moreover, by virtue of the present invention, the location of the active site and the interface of substrate therewith permit the identification of desirable R-groups for mutagenesis.

The three-dimensional coordinates of the polyketide synthase may be used to predict the activity and or substrate specificity of a protein whose primary amino acid sequence suggests that it may have polyketide synthase activity. The family of 2-pyrone synthase-related enzymes is defined, in part, by the presence of four highly conserved amino acid residues, Cys164, Phe215, His303, and Asn336.

In addition, the structural coordinates and three-dimensional models disclosed herein can be used to design or identify polyketide synthase inhibitors. Using the modeling techniques disclosed herein, potential inhibitor structures can be modeled with the polyketide synthase active site and those that appear to interact therewith can subsequently be tested in activity assays in the presence of substrate.

Methods of using crystal structure data to design binding agents or substrates are known in the art. Thus, the crystal structure data provided herein can be used in the design of new or improved inhibitors, substrates or binding agents. For example, the synthase polypeptide coordinates can be superimposed onto available coordinates of other similar enzymes to identify modifications in the active sites of the enzymes, thus allowing the novel enzyme products or the modulation of polyketide synthesis. Alternatively, the synthase polypeptide coordinates can be superimposed onto available coordinates of other similar enzymes which have substrates or inhibitors bound to them to give an approximation of the way these and related substrates or inhibitors might bind to a synthase. Alternatively, computer programs employed in the practice of rational drug design can be used to identify compounds that reproduce interaction characteristics similar to those found between a synthase polypeptide and a cocrystalized substrate. Furthermore, detailed knowledge of the nature of binding site interactions allows for the modification of compounds to alter or improve developability parameters, such as but not limited to solubility, pharmacokinetics and the like, without affecting binding activity.

Widely available are computer programs capable of carrying out the activities necessary to design agents using the crystal structure information provided herein. Examples include, but are not limited to, the following computer programs: Catalyst Databases™—an information retrieval program accessing chemical databases such as BioByte Master File, Derwent WDI and ACD; Catalyst HYPO™—generates models of compounds and hypotheses to explain variations of activity with the structure of drug candidates; Ludi™—fits molecules into the active site of a protein by identifying and matching complementary polar and hydrophobic groups; Leapfrog™—"grows" new ligands using a genetic algorithm with parameters under the control of the user.

In addition, various general purpose machines may be used with programs written in accordance with the teachings herein, or it may be more convenient to construct more specialized apparatus to perform the operations. However, preferably the embodiment is implemented in one or more computer programs executing on programmable systems each comprising at least one processor, at least one data storage system (including volatile and non-volatile memory and or storage elements), at least one input device, and at least one output device. The program is executed on the processor to perform the functions described herein.

Each such program may be implemented in any desired computer language (including machine, assembly, high level procedural, object oriented programming languages, or the like) to communicate with a computer system. In any case, the language may be a compiled or interpreted language. The computer program will typically be stored on a storage media or device (e.g., ROM, CD-ROM, or magnetic or optical media) readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

Embodiments of the invention include systems (e.g., internet based systems), particularly computer systems which store and manipulate coordinate and sequence information. As used herein, "a computer system" refers to the hardware components, software components, and data storage components used to analyze coordinate and sequence information. The computer system typically includes a processor for processing, accessing and manipulating the sequence data. The processor can be any well-known type of central processing unit, such as, for example, the Pentium in from Intel Corporation, or similar processor from Sun, Motorola, Compaq, AMD or International Business Machines.

One approach enabled by this invention is to use the structure coordinates to design new enzymes capable of synthesizing novel and known polyketides. For example, polyketide synthases (PKSs) generate molecular diversity in their products by utilizing different starter molecules and by varying the final size of the polyketide chain. The structural coordinates allow the elucidation of the nature by which PKSs achieve starter molecule selectivity and control polyketide chain length. For example, by comparing the structure of chalcone synthase that yields a tetraketide product to 2-pyrone synthases that form a triketide product of the invention, it was demonstrated that 2-pyrone synthase maintains a smaller initiation/elongation cavity. Accordingly, generation of a chalcone synthase mutant with an active site sterically analogous to 2-pyrone synthase results in the synthesis of a polyketide product of a different size. The subject invention allows for the strategic development and biosynthesis of more diverse polyketides and demonstrates a structural basis for control of polyketide chain length in other PKSs. In addition, the structural coordinates allow for the development of substrates or binding agents that bind to the polypeptide and alter the physical properties of the compounds in different ways, e.g., solubility.

In another embodiment, one approach is to computationally screen small molecule databases for chemical entities or compounds that can bind in whole, or in part, to a polyketide synthase polypeptide or fragment thereof. In this screening, the quality of fit of such entities or compounds to the binding site may be judged either by shape complementarity or by estimated interaction energy. Meng, E. C. et al., J. Comp. Chem., 13:505-524 (1992).

The design of substrates, compounds or binding agents that bind to or inhibit a polyketide synthase polypeptide according to the invention generally involves consideration of two factors. First, the substrate, compound or binding agent must be capable of physically and structurally associating with a polyketide synthase molecule. Non-covalent molecular interactions important in the association of a polyketide synthase with a substrate include hydrogen bonding, van der Waals and hydrophobic interactions, and the like.

Second, the substrate, compound or binding agent must be able to assume a conformation that allows it to associate with a polyketide synthase molecule. Although certain portions of the substrate, compound or binding agent will not directly participate in this association, those portions may still influence the overall conformation of the molecule. This, in turn, may have a significant impact on potency. Such conformational requirements include the overall three-dimensional structure and orientation of the chemical entity or compound in relation to all or a portion of the binding site, e.g., active site or accessory binding site of a polyketide synthase (e.g., a 2-pyrone synthase polypeptide), or the spacing between functional groups of a substrate or compound comprising several chemical entities that directly interact with a polyketide synthase.

The potential binding effect of a substrate or chemical compound on a polyketide synthase, or the activity that a newly synthesized or mutated polyketide synthase might have on a known substrate, may be analyzed prior to its actual synthesis and testing by the use of computer modeling techniques. For example, if the theoretical structure of the given substrate or compound suggests insufficient interaction and association between it and a polyketide synthase, synthesis and testing of the compound may be obviated. However, if computer modeling indicates a strong interaction, the molecule may then be tested for its ability to bind to, initiate catalysis or elongation of a polyketide by a polyketide synthase. Methods of assaying for polyketide synthase activity are known in the art (as identified and discussed herein). Methods for assaying the effect of a newly created polyketide synthase or a potential substrate or binding agent can be performed in the presence of a known binding agent or polyketide synthase. For example, the effect of the potential binding agent can be assayed by measuring the ability of the potential binding agent to compete with a known substrate.

Specialized computer programs may also assist in the process of selecting fragments or chemical entities. These include:
1. GRID (Goodford, P. J., "A Computational Procedure for Determining Energetically Favorable Binding Sites on Biologically Important Macromolecules", J. Med. Chem., 28:849-857 (1985)). GRID is available from Oxford University, Oxford, UK.
2. MCSS (Miranker, A. and M. Karplus, "Functionality Maps of Binding Sites: A Multiple Copy Simultaneous Search Method." Proteins: Structure. Function and Genetics, 11:29-34 (1991)). MCSS is available from Molecular Simulations, Burlington, Mass.
3. AUTODOCK (Goodsell, D. S. and A. J. Olsen, "Automated Docking of Substrates to Proteins by Simulated Annealing", Proteins: Structure. Function, and Genetics, 8:195-202 (1990)). AUTODOCK is available from Scripps Research Institute, La Jolla, Calif.
4. DOCK (Kuntz, I. D. et al., "A Geometric Approach to Macromolecule-Ligand Interactions", J. Mol. Biol, 161: 269-288 (1982)). DOCK is available from University of California, San Francisco, Calif.

Once suitable substrates, chemical entities or fragments have been selected, they can be assembled into a single polypeptide, compound or binding agent (e.g., an inhibitor). Assembly may be performed by visual inspection of the relationship of the fragments to each other on the three-dimensional image displayed on a computer screen in relation to the structure coordinates of the molecules. This would be followed by manual model building using software such as Quanta or Sybyl.

Useful programs to aid one of skill in the art in connecting the individual chemical entities or fragments include:
1. CAVEAT (Bartlett, P. A. et al., "CAVEAT: A Program to Facilitate the Structure-Derived Design of Biologically Active Molecules". In "Molecular Recognition in Chemical and Biological Problems", Special Pub., Royal Chem. Soc, 78, pp. 182-196 (1989)). CAVEAT is available from the University of California, Berkeley, Calif.
2. 3D Database systems such as MACCS-3D (MDL Information Systems, San Leandro, Calif.). This area is reviewed in Martin, Y. C, "3D Database Searching in Drug Design", J Med. Chem., 35:2145-2154 (1992)).
3. HOOK (available from Molecular Simulations, Burlington, Mass.).

In addition to the method of building or identifying novel enzymes or a polyketide synthase substrate or binding agent in a stepwise fashion, one fragment or chemical entity at a time as described above, substrates, inhibitors or other polyketide synthase interactions may be designed as a whole or "de novo" using either an empty active site or optionally including some portion(s) of known substrates, binding agents or inhibitors. These methods include:
1. LUDI (Bohm, H.-L, "The Computer Program LUDI: A New Method for the De Novo Design of Enzyme Inhibitors", J Comp. Aid. Molec. Design, 6:61-78 (1992)). LUDI is available from Biosym Technologies, San Diego, Calif.
2. LEGEND (Mshibata, Y. and A. Itai, Tetrahedron, 47:8985 (1991)). LEGEND is available from Molecular Simulations, Burlington, Mass.
3. LeapFrog (available from Tripos Associates, St. Louis, Mo.).

Other molecular modeling techniques may also be employed in accordance with this invention. See, e.g., Cohen, N. C. et al., "Molecular Modeling Software and Methods for Medicinal Chemistry", J. Med. Chem., 33:883-894 (1990). See also, Navia, M. A. and M. A. Murcko, "The Use of Structural Information in Drug Design", Current Opinions in Structural Biology, 2:202-210 (1992).

Kits

In various embodiments, the invention provides kits comprising a polyketide synthase variant having altered enzymatic activity and/or a host cell (e.g., yeast, plant, algae, bacterial, mammalian, insect) comprising such a variant. Such kits are useful in in vitro and in vivo methods for the production of desired chemical compounds, including polyketide, pyrone and lactone products.

In some embodiments, the kit provides a sterile container comprising a composition of the invention; such containers can be boxes, ampoules, bottles, vials, tubes, bags, pouches, blister-packs, or other suitable container forms known in the art. Such containers can be made of plastic, glass, laminated paper, metal foil, or other materials suitable for holding reagents. If desired a polypeptide of the invention is provided together with instructions for pyrone production. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the compositions of the invention, and are not intended to limit the scope of what the inventors regard as their invention.

EXAMPLES

Example 1. Cloning, Expression, and Purification of 2-Pyrone Synthase Enzymes

*Gerbera hybrida* 2-Pyrone synthase (Gh2PS) was subcloned into the pHIS8 expression vector, derived from pET28a(+) (Jez et al., 2000a). For protein expression, Gh2PS/pHIS8-transformed *E. coli* BL21(DE3) cells were incubated with shaking at 37° C. in Terrific-broth medium containing 50 μg/ml kanamycin until the OD(600 nm) reached ~1.0, and then induced with 0.5 mM isopropyl 1-thio-galactopyranoside (IPTG), grown at 18° C. overnight, and finally harvested by centrifugation at 8,000×g. Cell pellets were resuspended in lysis buffer A [TNB, 20 mM imidazole, 10% (v/v) glycerol, 1% (v/v) Tween-20, and 10 mM-mercaptoethanol (-ME); TNB is 50 mM Tris-HCl (pH 8.0), 500 mM NaCl] supplemented with 4 mM benzamidine, 1 mM PMSF, 2 μg/ml leupeptin, and 0.5 mg/ml lysozyme. Following cell lysis by sonication and centrifugation at 100,000×g, the cleared cell lysate was passed over a $Ni^{2+}$-NTA column (Qiagen, Valencia, Calif.) equilibrated in lysis buffer A, which was then washed with 10 bed volumes of wash buffer (TNB, 20 mM imidazole, 10 mM-ME). His-tagged protein was eluted with 10 bed volumes of elution buffer (TNB, 250 mM imidazole, 10 mM-ME), and the N-terminal His-tag was cleaved by thrombin digestion during a 24-hour dialysis against digestion buffer (TNB, 10 mM-ME) at 4° C. Cleaved protein was isolated by running the dialyzed sample over another $Ni^{2+}$-NTA column equilibrated in digestion buffer to remove the His-containing peptide and any un-cleaved protein, followed by a benzamidine sepharose chromatography to remove thrombin. A Superdex200 or S75 gel-filtration column (Amersham) equilibrated in TNB with 2 mM DTT was utilized to isolate homogeneous protein, which was finally dialyzed against storage buffer [100 mM NaCl, 50 mM Tris-HCl (pH 8.0), 2 mM DTT)], and prior to concentration to 10-20 mg/ml and for storage at −80° C. Site-directed mutants 2-Pyrone synthase were generated in the Gh2PS/pHIS8 expression vector, using the QuikChange strategy (Stratagene). The mutant proteins were expressed and purified as described above for the native protein.

Example 2. Crystallization, X-Ray Diffraction Data Collection, and Structure Determination Crystals of wild-type and mutant Gh2PS were grown by vapor diffusion at 4° C. in hanging drops, which consisted of 1 μl protein in storage buffer mixed with 1 μl crystallization reservoir [1.7 M ammonium sulfate, 7.5% (v/v) glycerol, 100 mM sodium succinate (pH 5.5), and 4 mM DTT]. Seeding was used to improve the quality and size of the crystals, which grew to 0.3×0.2×0.2 mm.

Prior to freezing in liquid nitrogen, crystals of Gh2PS were soaked for 3 minutes in cryoprotectant [crystallization reservoir supplemented with 17% (v/v) ethylene glycol]. X-ray diffraction data were collected on ADSC Q315 CCD detectors at beamlines 8.2.1 and 8.2.2 of the Advanced Light Source, Lawrence Berkeley National Laboratory.

Diffraction data were indexed, integrated, and scaled with MOSFLM (Battye et al., 2011) and SCALA (Evans, 2006). Gh2PS crystallized in one of two distinct forms: space group $P3_121$ with unit-cell dimensions a=b=83 Å and c=242 Å and two monomers in the asymmetric unit; or space group $P3_221$ with unit-cell dimensions a=b=83 Å and c=120 Å and one monomer in the asymmetric unit.

The structures of Gh2PS proteins were determined for the $P3_121$ crystal form from refinements initiated directly with the previously published Gh2PS homodimeric structure (PDB entry 1EE0; Jez et al., 2000b); or for the $P3_221$ crystal form through molecular-replacement (MR) analysis with the Molrep program (Vagin and Teplyakov, 2010) and a starting search model consisting of one monomer of PDB entry 1EE0. Further structural refinements utilized the Phenix suite of programs (Adams et al., 2010) programs. Coot (Emsley and Cowtan, 2004) was used for graphical map inspection and manual rebuilding of atomic models.

Example 3. In Vivo Production Using 2-Pyrone Synthase Variants

Figure 4:
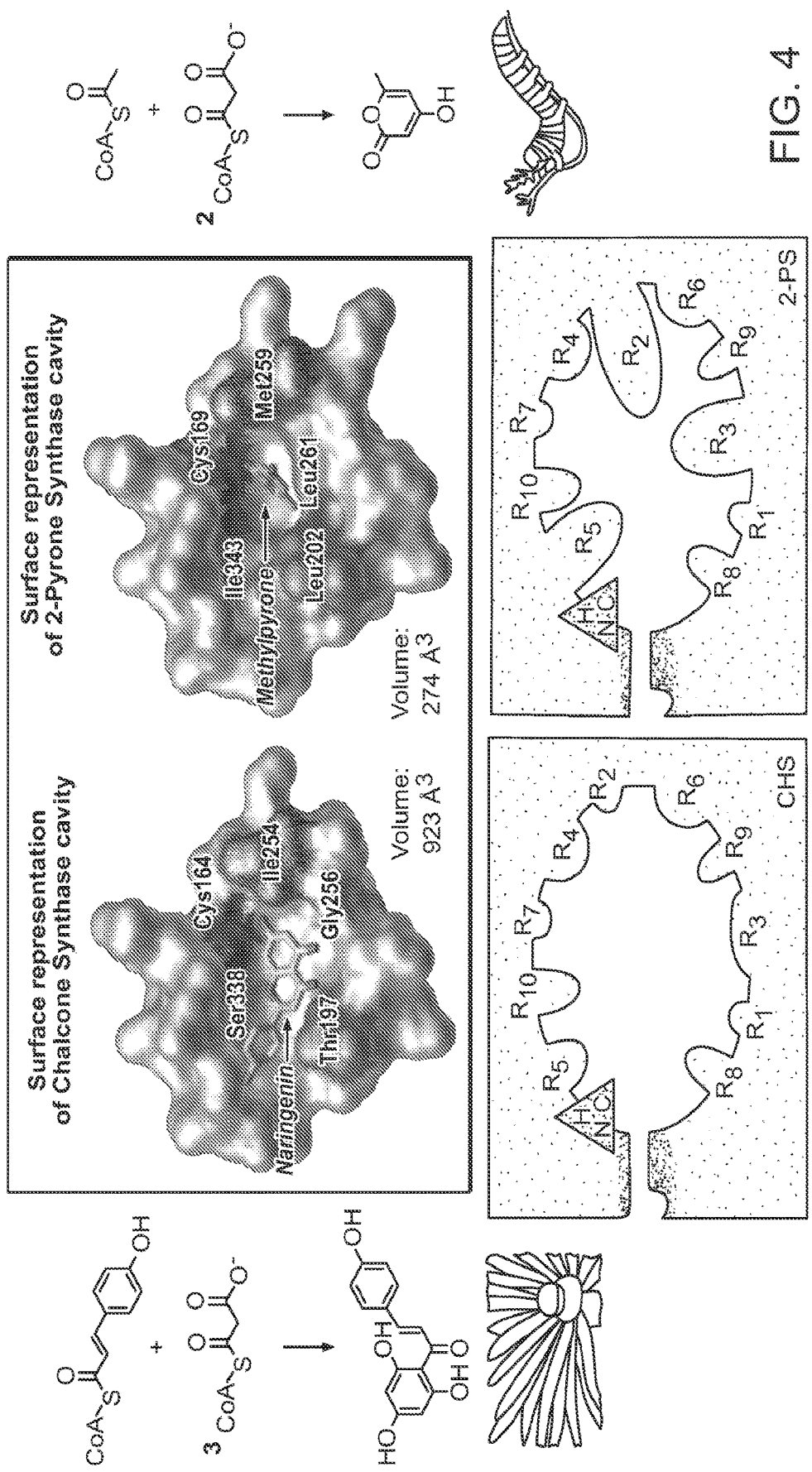
FIG. 4 depicts catalyzed reactions and active-site cavity structures of two polyketide-synthase enzymes, chalcone synthase (left) and 2-pyrone synthase (right). The top panels show molecular surface representations of the enzymes bound to their respective substrates (the CHS/naringenin complex derives from a crystal structure, which guided in part the modeling of methylpyrone into the 2-PS structure). (Phe 220 and Phe 270 in 2-PS, and Phe 215 and Phe 265 in CHS were removed for clarity in these depictions.) Highlighted in color on each molecular surface are the catalytic cysteine residue (red), three residues at which targeted amino-acid substitutions confer 2-PS-like activity on CHS (green), and a site at which amino-acid substitution has no effect on these enzymes' product specificity (blue). The bottom panels show schematic representations of the active-site cavities of the two enzymes, highlighting the surrounding R-groups that sterically define the volume of each active-site cavity.
Figure 5B:
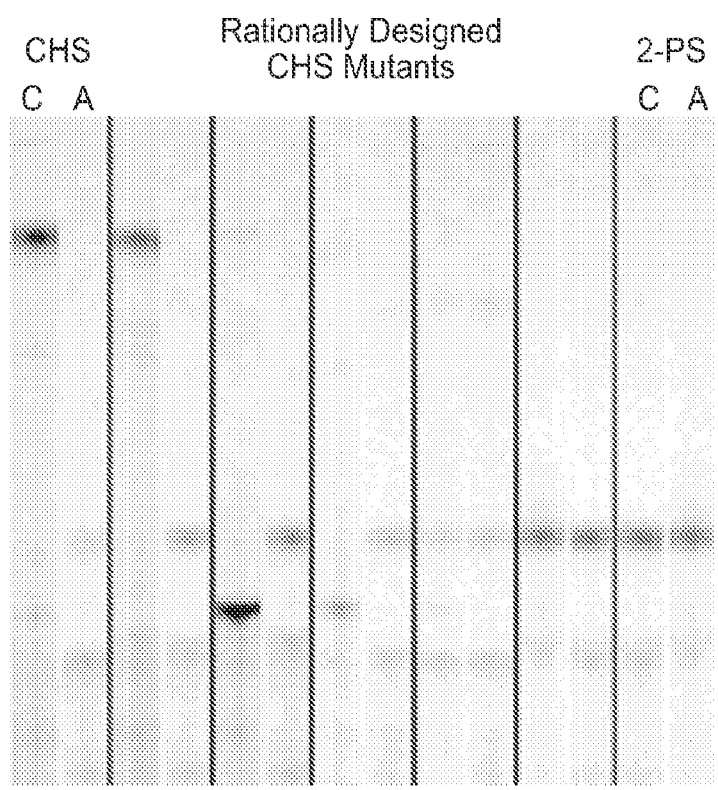
FIG. 5 depicts steric engineering to alter the substrate specificity of chalcone synthase from coumaryl CoA to acetyl CoA. The radiogram shows thin-layer chromatographic analyses of the reaction products generated by CHS or 2-PS enzymes with the substrates radiolabeled malonyl-CoA and either p-coumaroyl-CoA (C) or acetyl-CoA (A) as the starter molecule: leftmost lane, wild-type CHS; rightmost lane, wild-type 2-PS; middle lanes, several CHS variants bearing amino-acid substitution(s) at sites as described in FIG. 4. The mobilities of naringenin (formed from the spontaneous cyclization of chalcone) and methylpyrone are indicated by blue and red (respectively) arrows. The variant chalcone-synthases that have been sterically engineered to accept acetyl CoA catalyze only two chain extensions and thereby produce triacetic acid lactone.
Figure 5C:
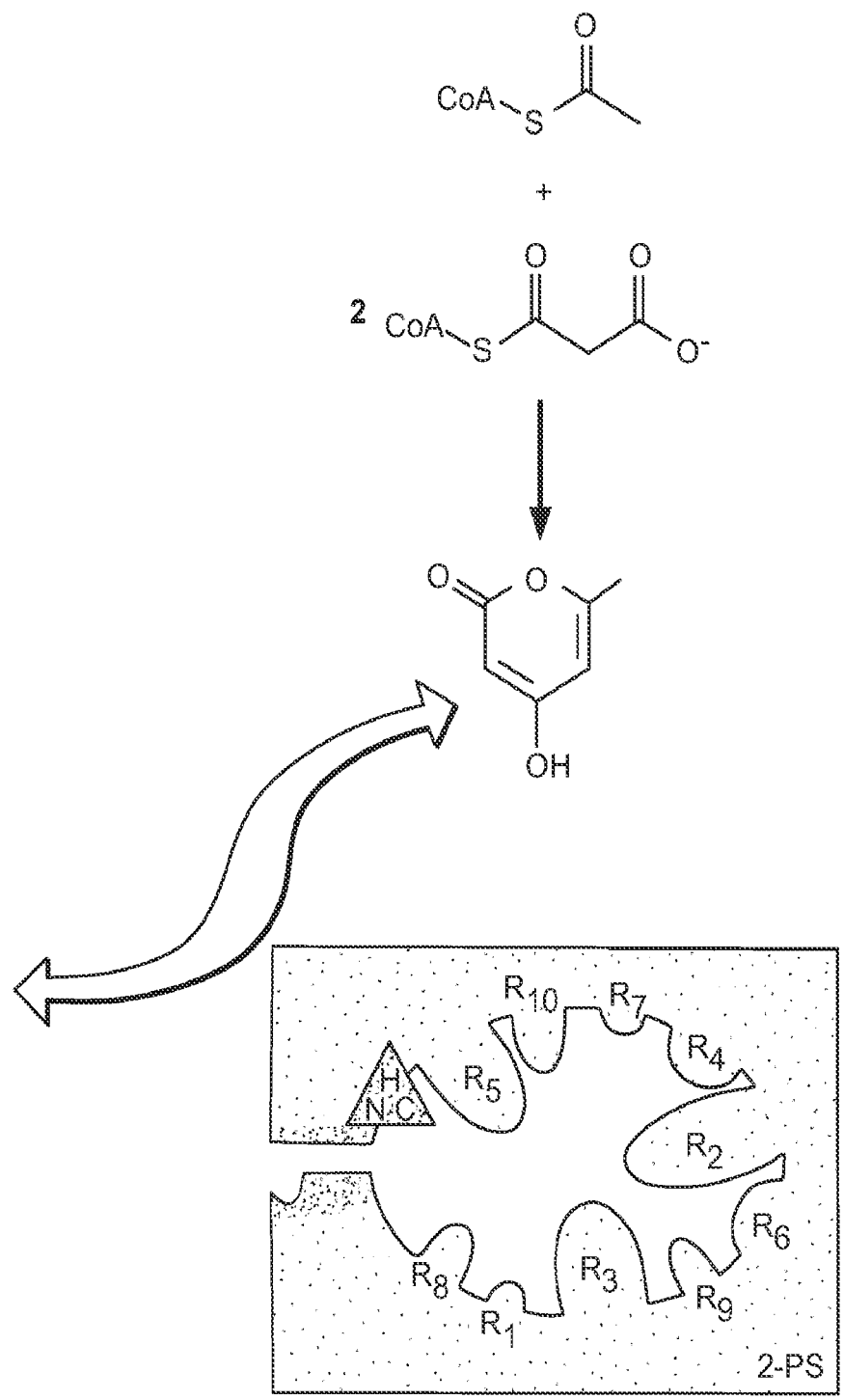
Figure 6:
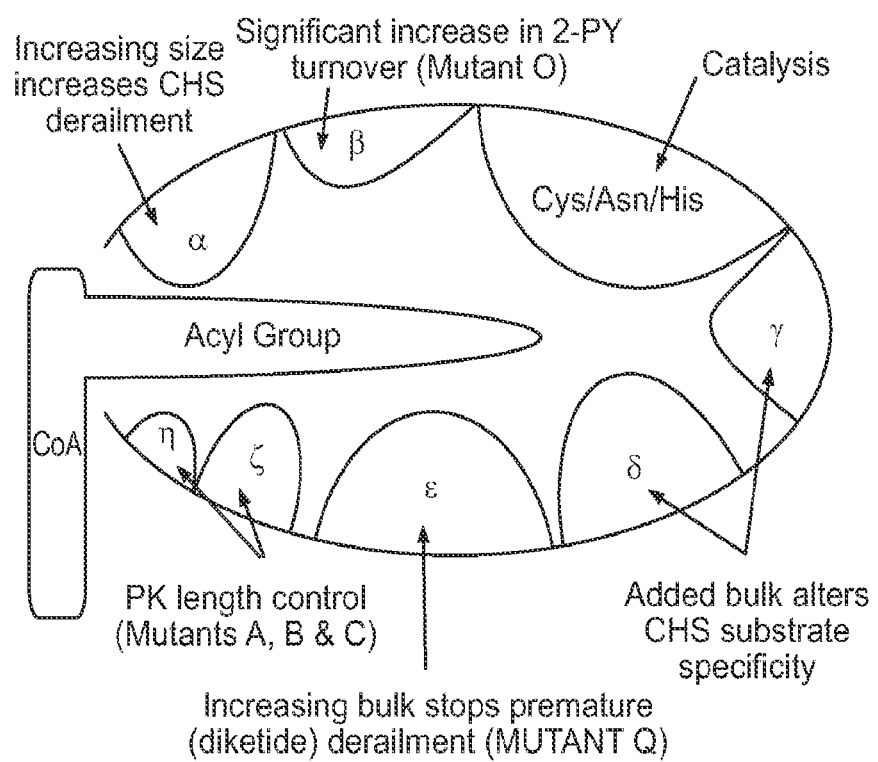
FIG. 6 provides a schematic representation of the 2-pyrone synthase active-site cavity. Highlighted are the constellation of amino-acid residue R-groups that sterically define the volume of the active-site cavity, and the observed alterations in enzyme properties resulting from the modification of these residues.

*G. hybrida* 2-Pyrone Synthase (2-PS) catalyses the iterative condensation of two malonyl-CoA derived acetyl-groups with one acetyl-CoA molecule to form 6-methyl-4-hydroxy-2-pyrone (a cyclic six-carbon product), via the intermediate, acetoacetyl CoA. The atomic-resolution crystal structure of the 2-Pyrone synthase has been determined. The structure has confirmed the substantially smaller (only one third the volume) active-site cavity of 2-Pyrone synthase in comparison to the closely related enzyme, chalcone synthase (also termed 2-CHS) (FIG. 4). Notably, CHS employs a larger starter molecule, coumaryl CoA, (as opposed to the smaller acetyl CoA preferred by 2-Pyrone synthase), and performs three iterations of the acetyl-group extension (as opposed to two by 2-Pyrone synthase) to generate chalcone, a bicyclic 15-carbon product. Alfalfa CHS and 2-Pyrone synthase share 74% sequence identity and thus differ at ~100 amino-acid positions, but remarkably, substitutions in CHS at only three active-site cavity residues by the corresponding residue in 2-Pyrone synthase is sufficient to render CHS functionally identical to 2-Pyrone synthase, in terms of both substrate/product specificity and enzyme kinetics. That the functional conversion of CHS to 2-Pyrone synthase can be effected through changes at a very small subset of residues supports an intuitively simple model for the steric modulation of enzyme activity of CHS/2-Pyrone synthase, and this model sets the stage for structure-based enzyme-engineering approaches (FIG. 5). The region of the 2-Pyrone synthase active site that accommodates the initial loading of the acetyl group from acetyl CoA appears to have sufficient volume to accommodate larger starter moieties, such as a benzoyl group (FIG. 6). Without being bound to a particular theory, steric restriction of this "starter loading pocket" may improve the efficiency of acetyl-group loading and subsequent extension with malonyl CoA.

Figure 1A:
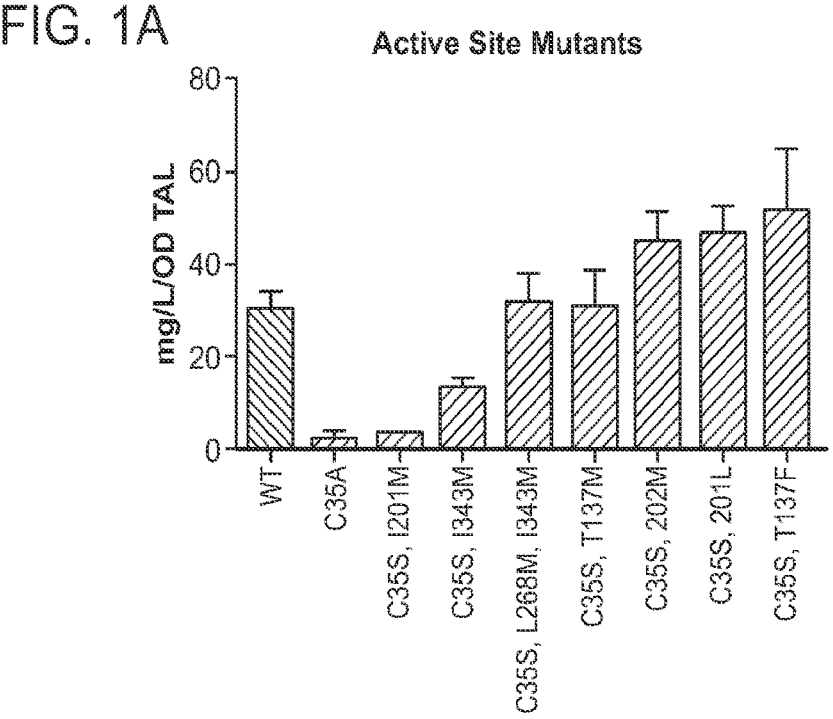
FIGS. 1A and 1B are graphs showing a comparison of triacetic lactone (TAL) production by various S. cerevisiae strains expressing wild-type or variant G. hybrida 2-pyrone synthase (2-PS).
Figure 1B:
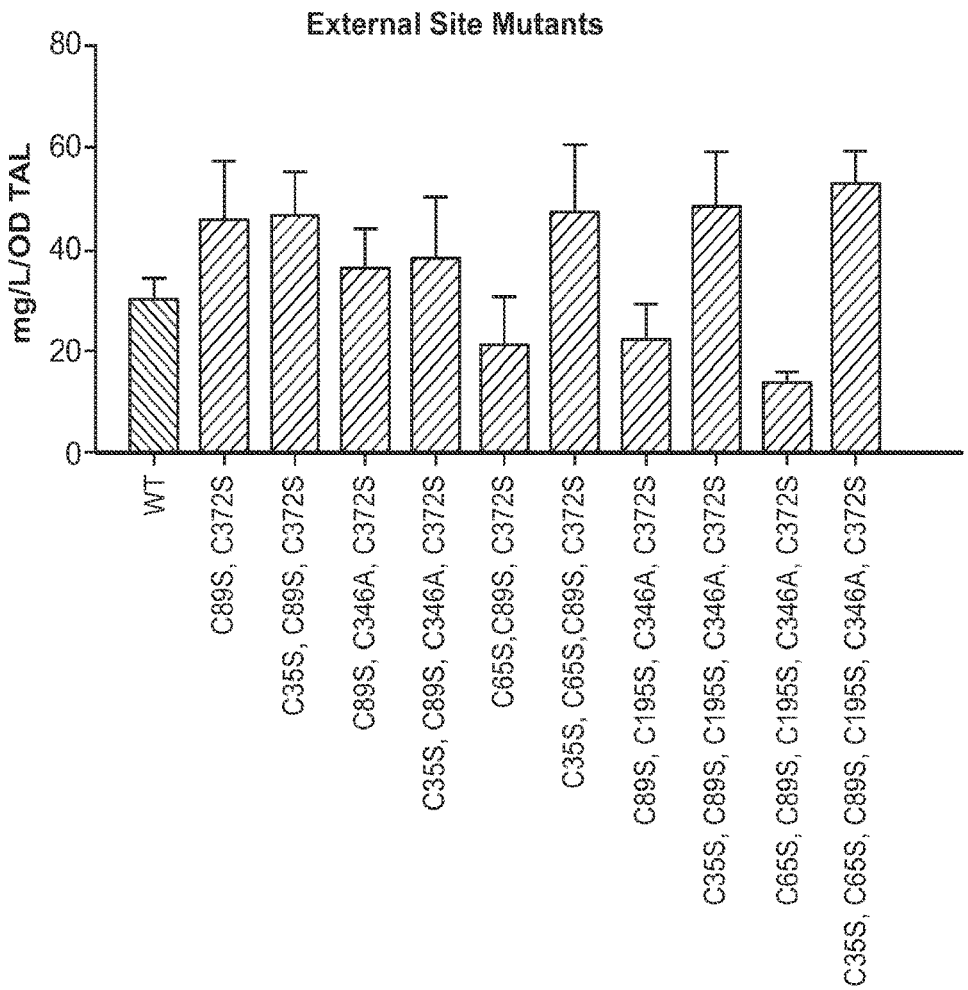

To this end, seven active-site residues were selected that demarcate the active-site cavity and systematically replaced with a residue possessing a longer and/or bulkier side chain (FIGS. 1A and 1B). Most of these substitutions proved to be deleterious for enzyme activity; however, substitutions at two positions (Leu202Phe and Leu268Met) have yielded positive results, with the mutant enzymes having an increased affinity for the reaction intermediate acetoacetyl CoA and a higher overall level of pyrone production. Active site modifications are summarized in Tables 1 and 2 below.

TABLE 1

2-Pyrone Synthase Active Site Variants with decreased activity compared to wild-type

C35S, I343F
C35S, I343M
C35S, I201M
C35S, L202F, L268M

TABLE 2

2-Pyrone Synthase Active Site Variants with increased activity compared to wild-type C35S, T137F
C35S, T137L
C35S, I201F
C35S, I201L
C35S, L202F
C35S, L202M
C35S, L268F
C35S, L268M Positions 137, 201, 202, and 268 responded positively to mutations, whereas substitution at position 343 consistently made the enzyme underperform.

Concurrent with enzyme-engineering approaches through active-site steric modulation, overall efficiency of pyrone production by 2-Pyrone synthase in a yeast (*Saccharomyces cerevisiae*) metabolic-engineering host was enhanced by creating variant forms of the enzyme that are more resilient and stable post expression. This component of the invention has focused on the replacement in 2-Pyrone synthase of cysteine residues with serine or alanine (FIG. 1B). Assessments of the overall production of pyrone by the mutant 2-Pyrone synthase enzymes expressed in a yeast host have demonstrated that replacements of Cys35 in particular and also Cys65, 89, 195, 346, and 372 have resulted in significant increases in pyrone yield. Without being bound to a particular theory, the C35S appears to be important for enhancing activity and/or stability. When the C35S modification is removed, the enzyme either reverts to WT levels or underperforms. In attempts to further improve pyrone production levels, individual beneficial cysteine substitutions have been combined with multi-site cysteine substitutions. External site modifications are summarized in Tables 3 and 4 below.

TABLE 3

2-Pyrone Synthase External Site Variants with decreased activity compared to wild-type

C35A
C35S, C65A
C35S, C346S
C35S, C135A
C65S, C89S, C372S

TABLE 3-continued

2-Pyrone Synthase External Site Variants with decreased activity compared to wild-type

C89S, C195S, C346A, C372S
C65S, C89S, C195S, C346A, C372S

TABLE 4

2-Pyrone Synthase External Site Variants with increased activity compared to wild-type C35S
C35S, C65S
C35S, C89S
C35S, C195S
C35S, C346A
C35S, C372A
C35S, C372S
C35S, C89S, C372S
C35S, C65S, C89S, C372S
C35S, C89S, C195S, C346A, C372S
C35S, C65S, C89S, C195S, C346A, C372S Regardless of how few cysteine substitutions are present, 2-pyrone synthase variants performed extremely well. Thus, an enzyme comprising C35S, C65S, C89S, C195S, C346A, C372S background might be useful for generating active site variants.

Figure 8:
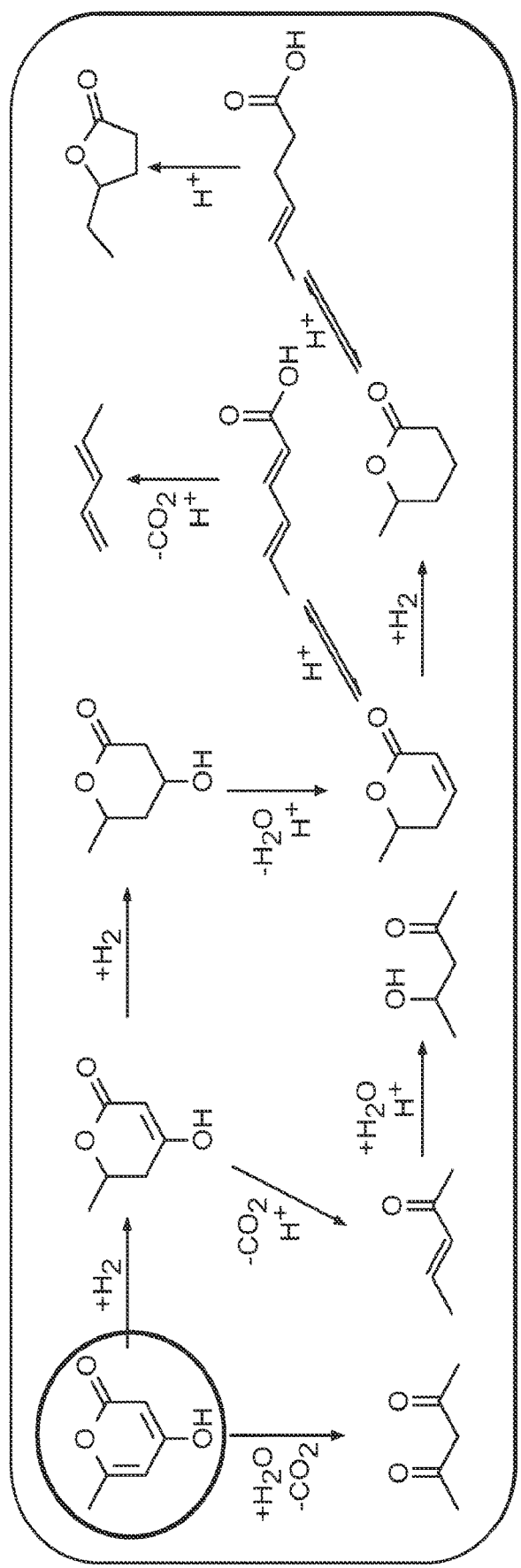
FIG. 8 depicts potential chemical intermediates and end-products identified and synthesized from triacetic acid lactone.

Measurement of the kinetic parameters ($k_{cat}$ and $K_m$) for the active-site 2-Pyrone synthase variants have shown increased levels of pyrone production (in comparison to native 2-Pyrone synthase) generated in double active-site variant (Leu202Phe and Leu268Met) when the variant 2-Pyrone synthase gene is integrated as a single copy gene in yeast. Measurements of kinetic parameters of 2-Pyrone synthase cysteine variants have also been performed. In yeast metabolic-engineering hosts, greater increases in pyrone production have been obtained with combinations of cysteine mutants than with the active-site mutants alone. The greatest increase thus far has been obtained with the Cys35Ser mutant expressed from multiply integrated copies of the 2-Pyrone synthase gene. Such exemplary engineered enzymes may be used to prepare commercially useful chemical compounds (FIG. 8).

Figure 14:
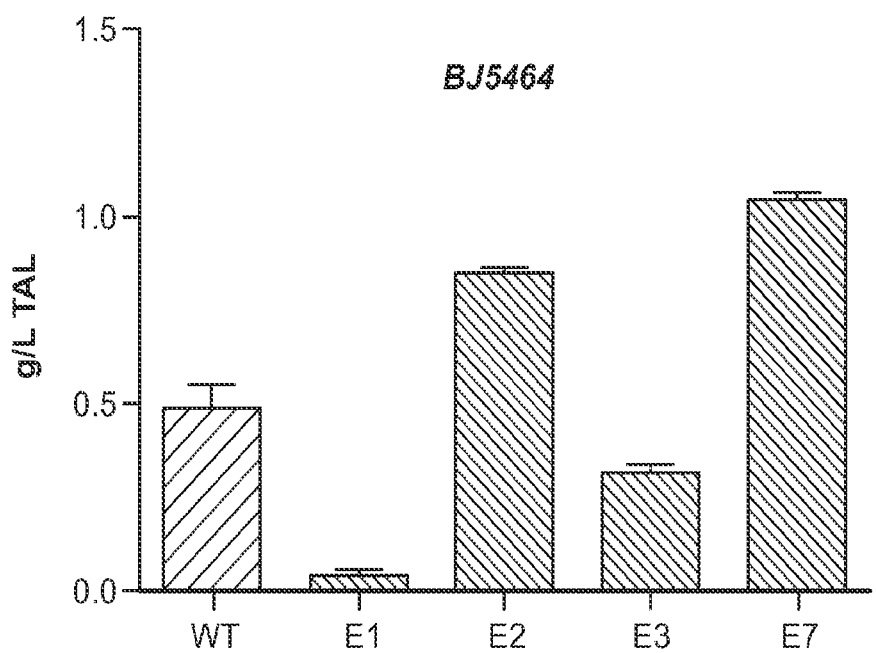

Example 4. 2-Pyrone Synthase C35S Variant Showed Increased Triacetic Lactone Synthesis In Vivo FIG. 14 shows the significance of 2-Pyrone synthase C35 and L268 modifications on the synthesis of triacetic lactone in vivo. Relative to the native *G. hybrida* 2-Pyrone synthase (WT), enzyme variants with modifications at C35 and/or L268 exhibited major changes to triacetic lactone production in vivo. While C35S increased titers, C35A rendered the enzyme nearly inactive, with poor synthesis. In combination with C35S, the L268F variant showed additional improvement suggesting there is active site enhancement using L268F. However, removal of C35S from the L268F variant caused triacetic lactone levels to revert to near wild-type levels. The results indicate that C35 is an important functional position outside of the catalytic cavity and that it may be important to obtain active site improvements.

Figure 15:
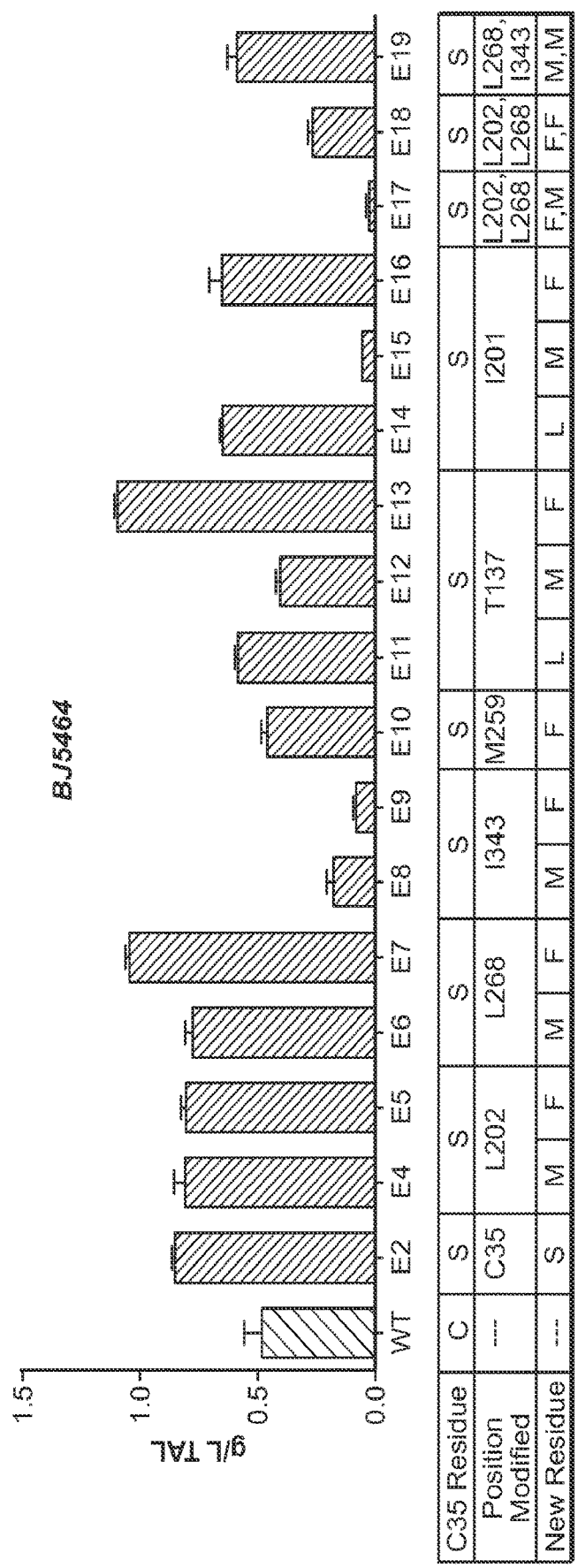
FIG. 15 includes a graph and a table. The graph compares triacetic lactone (TAL) titers (g/L) for -pyrone synthase (2-PS) variants with active site mutations at positions L202, L268, I343, M259, T137, and I201 in combination with the C35S mutation. Bars represent mean values±one standard deviation (n=6 independent experiments).

Example 5. 2-Pyrone Synthase Variants C35SL268F and C35ST137F Showed Increased Triacetic Lactone Synthesis 2-Pyrone synthase active site mutations coupled to the C35S mutation were screened (FIG. 15). Using steric hindrance as the motivation, various residues in the active site cavity were selected for replacement with bulkier residues (M, F). Following screening in vivo, variants C35SL268F and C35ST137F were found to result in higher triacetic lactone levels relative to the C35S variant. Several variants showed lower levels relative to C35S, and the deleterious effect of the I201M substitution suggests side chain chemistry using methionine is unfavorable at this position. Additional reduction in triacetic lactone levels when multiple residue changes are combined indicate that changes at one position alter the impact of other neighboring residues in the cavity.

Figure 16:
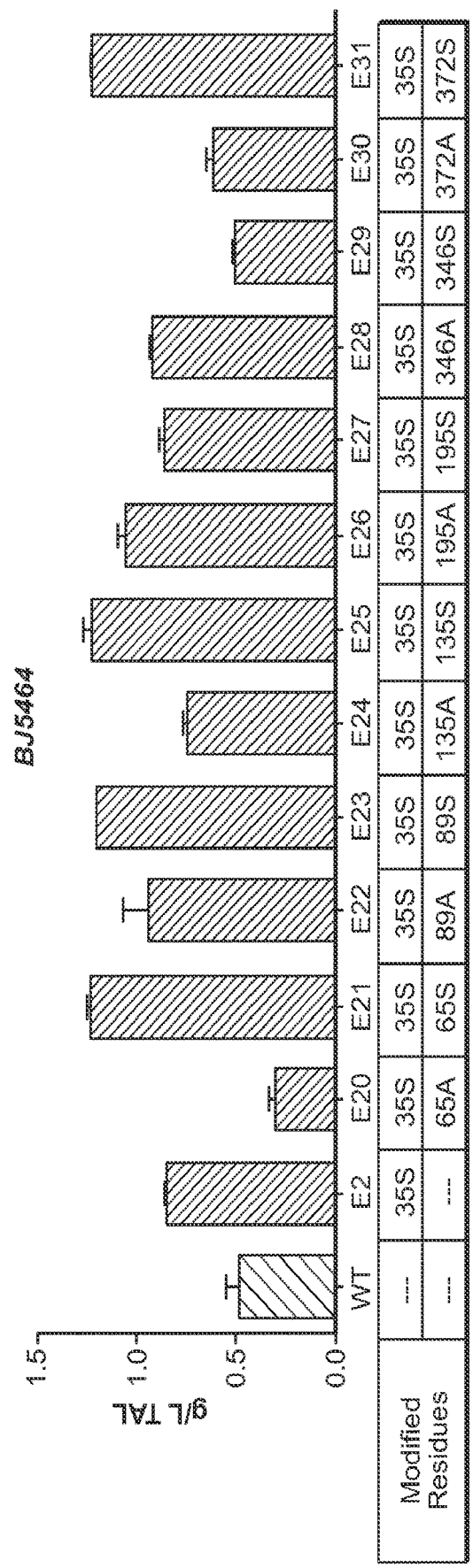
FIG. 16 provides a graph and a table. The graph compares triacetic lactone titers (g/L) for 2-Pyrone synthase variants with the C35S mutation and external cysteine mutations (to serine or alanine) at positions C65, C89, C135, C195, C346, and C372S. Bars represent mean values±one standard deviation (n=6 independent experiments).

Example 6. Variations in Residues Exposed to the Enzyme Surface Increased Triacetic Lactone Synthesis Individual cysteine residues, in addition to C35S, were modified to either an alanine or serine residue to mimic the size or chemistry of the thiol side chain. Significant changes in triacetic lactone titers were observed when using these cysteine variants, where residues highly exposed to the enzyme surface provided the largest improvements (FIG. 16). This screening process identified C65, C89, C135, C195, C346 and C372 as positions where substitution increases in vivo triacetic lactone levels.

Example 7. 2-Pyrone Synthase C36 is Important for Triacetic Lactone Synthesis

Figure 17:
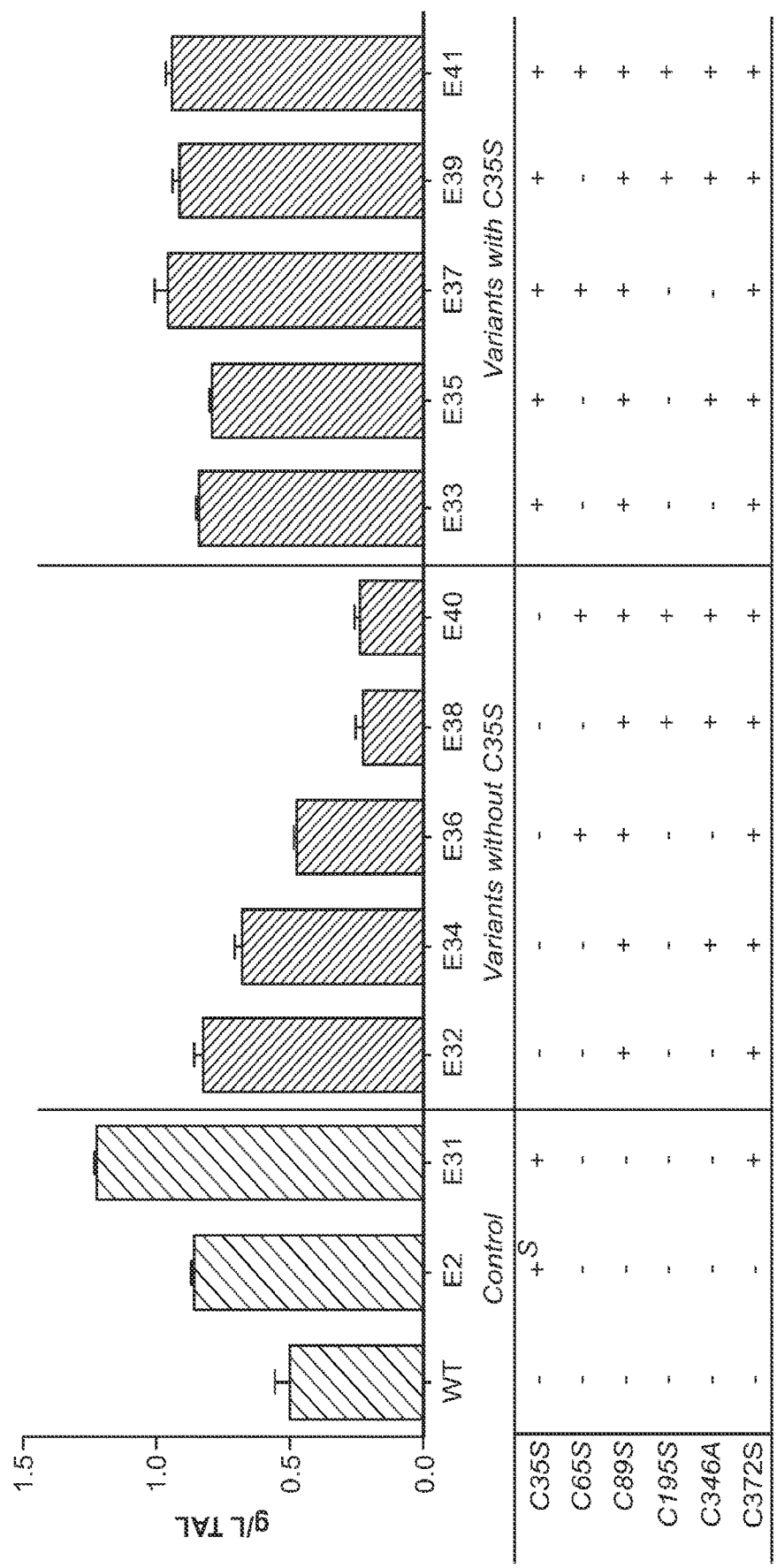
FIG. 17 provides a graph and a table. The graph compares triacetic lactone (TAL) titers (g/L) for 2-Pyrone synthase variants with either the native C35 or modified C35S, and incorporation of additional cysteine modifications. Bars represent mean values±one standard deviation (n=6 independent experiments).

Following evaluation of individual surface cysteine modifications (FIG. 16), different combinations of C65S, C89S, C195S, C346A, and C372S (with or without C35S) were evaluated (FIG. 17). In the absence of C35S, an increase in surface cysteine substitutions resulted in reduced triacetic lactone levels. In contrast, variants incorporating C35S showed comparable levels to the single C35S variant. However, no additional increase in in vivo TAL levels was observed beyond the C35SC372S double variant. These results further validate the importance of the C35 position, possibly in enzyme stability and protection from in vivo degradative processes.

Example 8. C35SC372S Protects 2-Pyrone Synthase from Proteolysis

Figure 7:
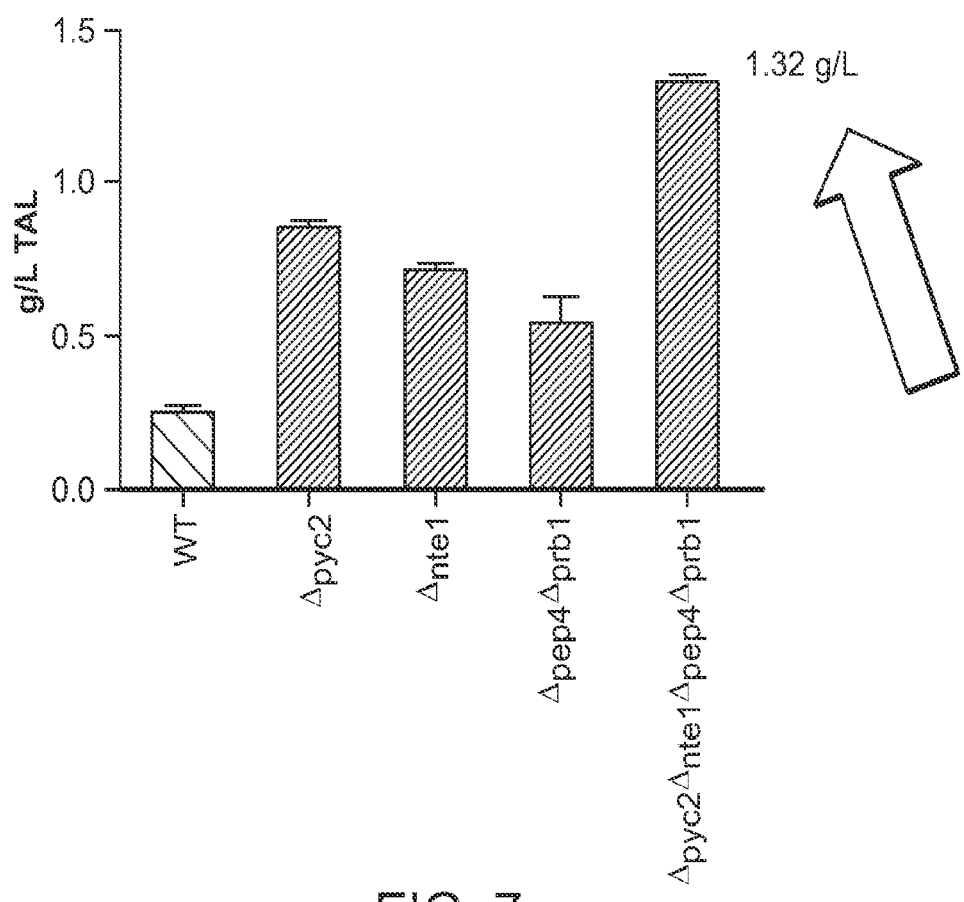
FIG. 7 is a graph showing increased triacetic lactone (TAL) production through 2-PS expression in S. cerevisiae strains with engineered disruption of the endogenous yeast genes encoding various proteases or metabolic enzymes. The knockouts affect genes involved in intracellular (vacuolar) protein degradation (PEP4, an aspartyl protease; and PRB, proteinase B); gluconeogenesis (PYC2, a pyruvate carboxylase); and regulation of lipid metabolism (NTE1, serine esterase). The maximal level of triacetic acid lactone production obtained was 1.32 g per liter of culture, with a yeast strain (Δpyc2 Δnte1 Δpep4 Δprb1) with four genes disrupted.

The C35S and C35SC372S 2-PS variants were evaluated in strains with protease knockouts. Knocking out PEP4 or PRB1 significantly improved triacetic lactone levels when the wild-type 2-Pyrone synthase was used (FIGS. 7 and 18). However, the increase was smaller with the C35S variant, and no improvement was seen with C35SC372S. These results suggest that C35SC372S is sufficient to protect the synthase from yeast proteolytic mechanisms targeting the enzyme.

The results described herein were obtained using the following materials and methods.

Strains and Plasmids

*Escherichia coli* strain XL1-Blue (Stratagene, Santa Clara, Calif.) was used for amplification of plasmids. *S. cerevisiae* strain BJ5464 (Jones, 1991) was used as the base strain for TAL production. The engineered strains BJΔpyc2Δnte1 and protease limited strains BYtΔpep4, BYtΔprb1, and BYtΔpep4Δprb1 (Cardenas and Da Silva, 2014) were used for the in vivo 2-PS evaluation studies. *S. cerevisiae* strain BY4741Δtrp1 (Open Biosystems, Huntsville, Ala.) was also used for comparison as a control.

The high copy 2-based pXP842 vector (Shen et al., 2012), harboring the glucose-repressed ADH2 promoter and the CYC1 terminator with a loxP-flanked URA3 selection marker, was used to express all 2-PS enzyme variants. Yeast cells were transformed as previously described (Gietz et al., 1992; Hill et al., 1991) using selective SDC-A plates. Cell colonies were allowed to grow for 3-5 days before generating inoculum cultures or glycerol stocks for long-term storage.

The *Gerbera hybrida* g2ps1 gene (encoding 2-PS) and all variant genes were PCR amplified from the pHIS8 cassette (Jez et al., 2000). Following SpeI and XhoI digestion, the gene was inserted into pXP842 (Shen et al., 2012) using the Rapid DNA Ligation Kit (Thermo Scientific, Waltham, Mass.). Plasmid recovery was performed using the GeneJet™ Plasmid Miniprep Kit (Thermo Scientific, Waltham, Mass.) and DNA sequence analysis confirmed the correct sequence of all PCR-amplified inserts (GeneWiz, South Plainfield, N.J.; Eton Biosciences, San Diego, Calif.).

The KOD Hot-start polymerase (EMD Chemicals, San Diego, Calif.) was used in PCR reactions for plasmid constructs. Restriction enzymes, T4 DNA ligase, Taq DNA polymerase, and deoxynucleotides were purchased from New England Biolabs. Oligonucleotide primers were purchased from IDT DNA (San Diego, Calif.).

Media and Cultivation

Luria-Bertani (LB) media was used for proliferation of XL1-Blue cells with 150 mg/L ampicillin for selection of plasmid-containing strains (Sambrook and Russell, 2001). For inoculum cultures, *S. cerevisiae* strains were grown for 16 h in 5 mL selective SDC(A) medium (1% dextrose, 0.67% yeast nitrogen base, 0.5% Bacto casamino acids, 0.5% ammonium sulfate and 100 mg/L adenine) in an air shaker (New Brunswick Scientific) at 250 rpm and 30° C. These were used to inoculate cultures in complex YPD media (1% dextrose; 1% Bacto yeast extract; 2% Bacto peptone) to an initial $OD_{600}$ of 0.3 (Shimadzu UV-2450 UV-VIS Spectrophotometer, Columbia, Md.). At 48 h, samples were taken and cell density determined. The samples were then centrifuged at 3,000 rpm (2,600 g) for 5 min at 4° C. (Beckman GS-6R Centrifuge, Brea, Calif.), and the supernatants stored at 4° C. for HPLC analysis of TAL levels in the culture broth.

HPLC Assay

The concentration of triacetic acid lactone was measured by HPLC using a Shimadzu HPLC system: LC-10AT pumps (Shimadzu), UV-VIS detector (SPD-10A VP, Shimadzu), Zorbax SB-C18 reversed-phase column (2.1×150 mm, Agilent Technologies). Acetonitrile buffered in 1% acetic acid was used as the mobile phase, while HPLC grade water buffered in 1% acetic acid was used as the aqueous phase. A gradient program using a 95-85% Pump B gradient ($H_2O$ with 1% acetic acid) provided an elution time of approximately 12 minutes (flow rate 0.25 mL/min, column temperature 25° C.).

Pyrone Synthase Assay

Activities of 2-Pyrone synthase and variants (0.5-2.5 g) were determined by monitoring product formation using a LC/MS assay. Standard assay conditions were 100 mM HEPES (pH 7.0), 30 M starter-CoA (usually acetyl-CoA), and 60 M malonyl-CoA in 2.0 ml at 25° C. Reactions were quenched with 5% acetic acid and extracted with ethyl acetate. Product formation was determined by analysis of extracts on a Hewlett-Packard HP1100 MSD single quadrupole mass spectrometer coupled to a Zorbax SB-C18 column (5 m, 2.1 mm×150 mm). High performance liquid chromatography conditions were as follows: gradient system from 0 to 100% methanol in water (each containing 0.2% acetic acid) over 20 min; flow rate 0.25 ml/min. LC/MS/MS data: 2PY (6-methyl-4-hydroxy-2-pyrone), Rt=9.62 min. Steady-state kinetic constants were determined from initial velocity measurements, in which product formation was linear over the time periods monitored, using standard assay conditions with a fixed malonyl-CoA concentration (120 M) and varying acetyl-CoA concentrations (0.5-50 M).

Thermal-Shift Binding Assay

The shifts in melting temperature of 2-Pyrone synthase proteins induced by a series of coenzyme-A ligands at varying concentrations were measured using a Thermofluor-type assay similar to one previously published (Niesen et al., 2007). Protein melting was monitored using a LightCycler480 System II (Roche), with the following temperature-ramping program: 30 seconds at 20° C., ramp up to 85° C. at 0.06° C./second, 30 seconds at 20° C. Using SYPRO Orange (Sigma; excitation wavelength 483 nm, emission wavelength 568 nm), an environmentally-sensitive fluorescent dye that can interact with hydrophobic amino-acid residues, the thermal melting of a protein can be monitored through the increased fluorescence signal accompanying exposure to the solvent medium of the hydrophobic core residues of a denatured protein. The maximum of the first-derivative curve of the fluorescence profile is typically used as a measure of the melting temperature ($T_m$).

REFERENCES

Adams, P. D., Afonine, P. V., Bunkóczi, G., Chen, V. B., Echols, N., Headd, J. J., Hung, L. W., Jain, S., Kapral, G. J., Grosse Kunstleve, R. W., McCoy, A. J., Moriarty, N. W., Oeffner, R. D., Read, R. J., Richardson, D. C., Richardson, J. S., Terwilliger, T. C., and Zwart, P. H. (2010). PHENIX: a comprehensive Python-based system for macromolecular structure solution. Acta Cryst. D Biol. Crystallogr. 66, 213-221.

Battye, T. G., Kontogiannis, L., Johnson, O., Powell, H. R., and Leslie, A. G. (2011). iMOSFLM: a new graphical interface for diffraction-image processing with MOSFLM. Acta Crystallogr. D Biol. Crystallogr. 67, 271-281.

Cardenas, J., Da Silva, N. A., 2014. Metabolic engineering of Saccharomyces cerevisiae for the production of triacetic acid lactone. Metabolic Engineering 25, 194-203.

Emsley, P., and Cowtan, K. (2004). Coot: model-building tools for molecular graphics. Acta Crystallogr. D Biol. Crystallogr. 60, 2126-2132.

Evans, P. R. (2006). Scaling and assessment of data quality. Acta Crystallogr. D Biol. Crystallogr. 62, 72-82.

Gietz, D., Jean, A. S., Woods, R. A., Schiestl, R. H., 1992. Improved method for high efficiency transformation of intact yeast cells. Nucl. Acids Res. 20, 1425-1425

Hill, J., Donald, K. A. I. G., Griffiths, D. E., 1991. DMSO-enhanced whole cell yeast transformation. Nucl. Acids Res. 19, 5791-5791

Jez, J. M., Bowman, M. E., Dixon, R. A., and Noel, J. P. (2000a). Structure and mechanism of the evolutionarily unique plant enzyme chalcone isomerase. Nat. Struct. Biol. 7, 786-791.

Jez, J. M., Austin, M. B., Ferrer, J., Bowman, M. E., Schroder, J., and Noel, J. P. (2000b). Structural control of polyketide formation in plant-specific polyketide synthases. Chem. Biol. 7, 919-930.

Niesen, F. H., Berglund, H. and Vedadi, M. (2007). The use of differential scanning fluorimetry to detect ligand interactions that promote protein stability. Nat. Protocols 9, 2212-2221.

Sambrook, J. J., Russell, D. D. W., 2001. Molecular cloning: a laboratory manual. Vol. 2. CSHL Press.

Shen, M. W. Y., Fang, F., Sandmeyer, S., Da Silva, N. A., 2012. Development and characterization of a vector set with regulated promoters for systematic metabolic engineering in Saccharomyces cerevisiae. Yeast 29, 495-503.

Vagin, A., and Teplyakov, A. (2010). Molecular replacement with MOLREP. Acta Crystallogr D Biol Crystallogr. 66, 22-25.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. An isolated nucleic acid molecule encoding a non-naturally occurring polyketide synthase variant of SEQ ID NO: 1 having polyketide synthase activity, wherein SEQ ID NO: 1 comprises an alteration at amino acid residue in SEQ ID NO: 1 selected from the group consisting of C35S, T137, I201, L268, C65, C195, C346, C372 and L202F, wherein the amino acid sequence of said polyketide synthase variant has 97% sequence identity to SEQ ID NO:1.

2. The isolated nucleic acid molecule of claim 1, wherein the non-naturally occurring polyketide synthase variant is a 2-pyrone synthase variant.

3. The isolated nucleic acid molecule of claim 1, wherein the altered amino acid residue is selected from the group consisting of C35S, C65S, C195S, C346A, C372S, L202F, and L268M.

4. An isolated nucleic acid molecule encoding SEQ ID NO: 1, wherein the altered amino acid residue is C35S.

5. The isolated nucleic acid molecule of claim 1, wherein the activity and/or stability of the non-naturally occurring polyketide synthase variant is increased relative to a wild-type polyketide synthase reference polypeptide which does not comprise said one or more altered amino acid residues.

6. A vector comprising the isolated nucleic acid molecule of claim 5.

7. A cell comprising the isolated nucleic acid molecule of claim 5.

8. The cell of claim 7, wherein the cell is a yeast, plant, algae, bacterial, mammalian, or insect cell.

9. The cell of claim 8, wherein the cell is in vitro or in vivo.

10. The isolated nucleic acid molecule of claim 5, wherein the increased polyketide synthase activity of the polyketide synthase variant results in production of a compound selected from the group consisting of a pyrone, a chromone, a lactone, a polyhydroxynaphthalene, a phloroglucinol, a resorcinol, a resorcinol acid, SEK 4, SEK4b, aloesone, and combinations thereof.

11. The isolated nucleic acid molecule of claim 10, wherein the lactone is triacetic acid lactone.

12. A kit comprising the isolated nucleic acid molecule of claim 1.

13. The kit of claim 12, further comprising instructions for production of polyketide, pyrone, lactone products, or combinations thereof.

14. An isolated nucleic acid molecule encoding SEQ ID NO: 1, having altered amino acid residues C35S and C372S.

* * * * *

SEQUENCE LISTING

```
<160> NUMBER OF SEQ ID NOS: 125

<210> SEQ ID NO 1
<211> LENGTH: 402
<212> TYPE: PRT
<213> ORGANISM: Gerbera hybrida

<400> SEQUENCE: 1

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Cys Val Ala Gln Ala Asp Tyr Ala Asp Tyr Tyr Phe Arg Val
        35                  40                  45
```

```
Thr Lys Ser Glu His Met Val Asp Leu Lys Glu Lys Phe Lys Arg Ile
 50                  55                  60
Cys Glu Lys Thr Ala Ile Lys Lys Arg Tyr Leu Ala Leu Thr Glu Asp
 65                  70                  75                  80
Tyr Leu Gln Glu Asn Pro Thr Met Cys Glu Phe Met Ala Pro Ser Leu
                 85                  90                  95
Asn Ala Arg Gln Asp Leu Val Val Thr Gly Val Pro Met Leu Gly Lys
                100                 105                 110
Glu Ala Ala Val Lys Ala Ile Asp Glu Trp Gly Leu Pro Lys Ser Lys
                115                 120                 125
Ile Thr His Leu Ile Phe Cys Thr Thr Ala Gly Val Asp Met Pro Gly
130                 135                 140
Ala Asp Tyr Gln Leu Val Lys Leu Leu Gly Leu Ser Pro Ser Val Lys
145                 150                 155                 160
Arg Tyr Met Leu Tyr Gln Gln Gly Cys Ala Ala Gly Gly Thr Val Leu
                165                 170                 175
Arg Leu Ala Lys Asp Leu Ala Glu Asn Asn Lys Gly Ser Arg Val Leu
                180                 185                 190
Ile Val Cys Ser Glu Ile Thr Ala Ile Leu Phe His Gly Pro Asn Glu
                195                 200                 205
Asn His Leu Asp Ser Leu Val Ala Gln Ala Leu Phe Gly Asp Gly Ala
210                 215                 220
Ala Ala Leu Ile Val Gly Ser Gly Pro His Leu Ala Val Glu Arg Pro
225                 230                 235                 240
Ile Phe Glu Ile Val Ser Thr Asp Gln Thr Ile Leu Pro Asp Thr Glu
                245                 250                 255
Lys Ala Met Lys Leu His Leu Arg Glu Gly Gly Leu Thr Phe Gln Leu
                260                 265                 270
His Arg Asp Val Pro Leu Met Val Ala Lys Asn Ile Glu Asn Ala Ala
                275                 280                 285
Glu Lys Ala Leu Ser Pro Leu Gly Ile Thr Asp Trp Asn Ser Val Phe
290                 295                 300
Trp Met Val His Pro Gly Gly Arg Ala Ile Leu Asp Gln Val Glu Arg
305                 310                 315                 320
Lys Leu Asn Leu Lys Glu Asp Lys Leu Arg Ala Ser Arg His Val Leu
                325                 330                 335
Ser Glu Tyr Gly Asn Leu Ile Ser Ala Cys Val Leu Phe Ile Ile Asp
                340                 345                 350
Glu Val Arg Lys Arg Ser Met Ala Glu Gly Lys Ser Thr Thr Gly Glu
                355                 360                 365
Gly Leu Asp Cys Gly Val Leu Phe Gly Phe Gly Pro Gly Met Thr Val
370                 375                 380
Glu Thr Val Val Leu Arg Ser Val Arg Val Thr Ala Ala Val Ala Asn
385                 390                 395                 400
Gly Asn

<210> SEQ ID NO 2
<211> LENGTH: 1555
<212> TYPE: DNA
<213> ORGANISM: Gerbera hybrida

<400> SEQUENCE: 2
aaaaggccta ctcaagcctt gaaattctct tttcttttct tttcattccc ttccctcaaa    60
ttataaactt acctttctgt ttcttcaaa gaatttagct gcctcaaacg aagatcttca   120
```

```
tatctcattt gttaggatat acaaacatca atctcgagta aaatgggatc ttactcatcc    180
gatgatgtgg aggtgattcg tgaggccgga cgggcacaag gtttagccac gattcttgcc    240
attggcactg ctactcctcc caattgcgtc gctcaagctg attatgcaga ctattatttt    300
cgtgtcacta agagcgaaca tatggttgat cttaaagaga aatttaaacg catttgtgag    360
aaaacagcga taagaaacg atacctagcc ctcaccgaag actatctgca agagaaccca    420
acaatgtgtg agttcatggc tccatcctta aacgctcgac aagacctagt ggtcaccggc    480
gtcccaatgc ttggcaaaga agccgcagtc aaggccattg atgaatgggg actaccaaaa    540
tccaagatca cccacctcat cttctgcacc accgctggcg ttgacatgcc cggtgctgac    600
tatcaactcg tcaaactcct tggtctctcc ccttcagtca aacgctatat gttgtaccaa    660
cagggatgtg ccgccggcgg cacagtcctc cggctagcca aggaccttgc tgaaaacaac    720
aagggctcac gagtccttat cgtctgctcc gagatcactg ctatcttatt ccatggaccc    780
aatgagaacc accttgactc actcgtcgct caagctttat tcggagacgg agctgcagca    840
ctcattgtgg gttcaggccc tcacttggcc gtagaacggc caatattcga gatcgtgtca    900
actgatcaaa caatcttgcc ggacactgag aaggcaatga agttacactt gagagaggga    960
gggttgacgt ttcagttgca tagagatgta cccttgatgg tcgcaaagaa catagagaac    1020
gcagcggaga aagcgttgtc tccactaggg ataactgatt ggaactcagt tttctggatg    1080
gtgcacccag gtggtcgagc catattggac caggtggagc gaaaactaaa ccttaaggaa    1140
gataagttaa gggctagcag gcatgtgctt agtgaatacg gaaacctgat tagcgcttgt    1200
gtgttgttca tcattgacga ggtgaggaag agatctatgg cggaagggaa gagtacaacc    1260
ggtgaaggtt tggattgcgg tgttttgttt ggatttggac cgggtatgac tgttgagact    1320
gttgttcttc gtagcgtccg cgttactgct gcggttgcca atggaaactg atcactgttg    1380
tttgcaaaat attacttttt actacggtat gtttccttgt ttatgagttt gtcattcacc    1440
tatgataata gggtctgtat ttttcttgtt tatgatttta ttttctcaaa gatgatgtaa    1500
gttggcaatt aaataaagat tgttttttcct atgaataata taagattaca ttttc         1555
```

<210> SEQ ID NO 3
<211> LENGTH: 402
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Met Gly Ser Tyr Ser Ser Asp Val Glu Val Ile Arg Glu Ala Gly
1               5                   10                  15

Arg Ala Gln Gly Leu Ala Thr Ile Leu Ala Ile Gly Thr Ala Thr Pro
                20                  25                  30

Pro Asn Cys Val Ala Gln Ala Asp Tyr Ala Asp Tyr Tyr Phe Arg Val
            35                  40                  45

Thr Lys Ser Glu His Met Val Asp Leu Lys Glu Lys Phe Lys Arg Ile
        50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
```

```
            100                 105                 110
Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
        130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Ala Ala Gly Gly Thr Val Leu
                165                 170                 175

Arg Leu Ala Lys Asp Leu Ala Glu Asn Asn Lys Gly Ser Arg Val Leu
                180                 185                 190

Ile Val Cys Ser Glu Ile Thr Ala Ile Leu Phe His Gly Pro Asn Glu
        195                 200                 205

Asn His Leu Asp Ser Leu Val Ala Gln Ala Leu Phe Gly Asp Gly Ala
        210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
                260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Cys Val Leu Phe Ile Ile Asp
                340                 345                 350

Glu Val Arg Lys Arg Ser Met Ala Glu Gly Lys Ser Thr Thr Gly Glu
        355                 360                 365

Gly Leu Asp Cys Gly Val Leu Phe Gly Phe Gly Pro Gly Met Thr Val
        370                 375                 380

Glu Thr Val Val Leu Arg Ser Val Arg Val Thr Ala Ala Val Ala Asn
385                 390                 395                 400

Gly Asn

<210> SEQ ID NO 4
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Gly Ser Tyr Ser Ser Asp Val Glu Val Ile Arg Glu Ala Gly
1               5                   10                  15

Arg Ala Gln Gly Leu Ala Thr Ile Leu Ala Ile Gly Thr Ala Thr Pro
                20                  25                  30

Pro Asn Ala Val Ala Gln Ala Asp Tyr Ala Asp Tyr Tyr Phe Arg Val
            35                  40                  45

Thr Lys Ser Glu His Met Val Asp Leu Lys Glu Lys Phe Lys Arg Ile
```

```
                50             55              60
Cys Glu Lys Thr Ala Ile Lys Lys Arg Tyr Leu Ala Leu Thr Glu Asp
 65                  70                  75                  80

Tyr Leu Gln Glu Asn Pro Thr Met Cys Glu Phe Met Ala Pro Ser Leu
                     85                  90                  95

Asn Ala Arg Gln Asp Leu Val Val Thr Gly Val Pro Met Leu Gly Lys
                100                 105                 110

Glu Ala Ala Val Lys Ala Ile Asp Glu Trp Gly Leu Pro Lys Ser Lys
                115                 120                 125

Ile Thr His Leu Ile Phe Cys Thr Thr Ala Gly Val Asp Met Pro Gly
                130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                    165                 170                 175

Arg Leu Ala Lys Asp Leu Ala Glu Asn Asn Lys Gly Ser Arg Val Leu
                180                 185                 190

Ile Val Cys Ser Glu Ile Thr Ala Ile Leu Phe His Gly Pro Asn Glu
                195                 200                 205

Asn His Leu Asp Ser Leu Val Ala Gln Ala Leu Phe Gly Asp Gly Ala
210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                    245                 250                 255

Lys Ala Met Lys Leu His Leu Arg Glu Gly Gly Leu Thr Phe Gln Leu
                    260                 265                 270

His Arg Asp Val Pro Leu Met Val Ala Lys Asn Ile Glu Asn Ala Ala
                275                 280                 285

Glu Lys Ala Leu Ser Pro Leu Gly Ile Thr Asp Trp Asn Ser Val Phe
                290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                    325                 330                 335

Ser Glu Tyr Gly Asn Leu Ile Ser Ala Cys Val Leu Phe Ile Ile Asp
                340                 345                 350

Glu Val Arg Lys Arg Ser Met Ala Glu Gly Lys Ser Thr Thr Gly Glu
                355                 360                 365

Gly Leu Asp Cys Gly Val Leu Phe Gly Phe Gly Pro Gly Met Thr Val
                370                 375                 380

Glu Thr Val Val Leu Arg Ser Val Arg Val Thr Ala Ala Val Ala Asn
385                 390                 395                 400

Gly Asn

<210> SEQ ID NO 5
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Gly Ser Tyr Ser Ser Asp Asp Val Glu Val Ile Arg Glu Ala Gly
```

```
  1               5                   10                  15
Arg Ala Gln Gly Leu Ala Thr Ile Leu Ala Ile Gly Thr Ala Thr Pro
                 20                  25                  30
Pro Asn Cys Val Ala Gln Ala Asp Tyr Ala Asp Tyr Tyr Phe Arg Val
                 35                  40                  45
Thr Lys Ser Glu His Met Val Asp Leu Lys Glu Lys Phe Lys Arg Ile
         50                  55                  60
Cys Glu Lys Thr Ala Ile Lys Lys Arg Tyr Leu Ala Leu Thr Glu Asp
65                   70                  75                  80
Tyr Leu Gln Glu Asn Pro Thr Met Cys Glu Phe Met Ala Pro Ser Leu
                 85                  90                  95
Asn Ala Arg Gln Asp Leu Val Val Thr Gly Val Pro Met Leu Gly Lys
                 100                 105                 110
Glu Ala Ala Val Lys Ala Ile Asp Glu Trp Gly Leu Pro Lys Ser Lys
                 115                 120                 125
Ile Thr His Leu Ile Phe Cys Thr Thr Ala Gly Val Asp Met Pro Gly
                 130                 135                 140
Ala Asp Tyr Gln Leu Val Lys Leu Leu Gly Leu Ser Pro Ser Val Lys
145                 150                 155                 160
Arg Tyr Met Leu Tyr Gln Gln Gly Cys Ala Ala Gly Gly Thr Val Leu
                 165                 170                 175
Arg Leu Ala Lys Asp Leu Ala Glu Asn Asn Lys Gly Ser Arg Val Leu
                 180                 185                 190
Ile Val Cys Ser Glu Ile Thr Ala Ile Phe Phe His Gly Pro Asn Glu
                 195                 200                 205
Asn His Leu Asp Ser Leu Val Ala Gln Ala Leu Phe Gly Asp Gly Ala
                 210                 215                 220
Ala Ala Leu Ile Val Gly Ser Gly Pro His Leu Ala Val Glu Arg Pro
225                 230                 235                 240
Ile Phe Glu Ile Val Ser Thr Asp Gln Thr Ile Leu Pro Asp Thr Glu
                 245                 250                 255
Lys Ala Met Lys Leu His Leu Arg Glu Gly Gly Leu Thr Phe Gln Leu
                 260                 265                 270
His Arg Asp Val Pro Leu Met Val Ala Lys Asn Ile Glu Asn Ala Ala
                 275                 280                 285
Glu Lys Ala Leu Ser Pro Leu Gly Ile Thr Asp Trp Asn Ser Val Phe
                 290                 295                 300
Trp Met Val His Pro Gly Gly Arg Ala Ile Leu Asp Gln Val Glu Arg
305                 310                 315                 320
Lys Leu Asn Leu Lys Glu Asp Lys Leu Arg Ala Ser Arg His Val Leu
                 325                 330                 335
Ser Glu Tyr Gly Asn Leu Ile Ser Ala Cys Val Leu Phe Ile Ile Asp
                 340                 345                 350
Glu Val Arg Lys Arg Ser Met Ala Glu Gly Lys Ser Thr Thr Gly Glu
                 355                 360                 365
Gly Leu Asp Cys Gly Val Leu Phe Gly Phe Gly Pro Gly Met Thr Val
                 370                 375                 380
Glu Thr Val Val Leu Arg Ser Val Arg Val Thr Ala Ala Val Ala Asn
385                 390                 395                 400
Gly Asn
```

<210> SEQ ID NO 6
<211> LENGTH: 402

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Cys Val Ala Gln Ala Asp Tyr Ala Asp Tyr Tyr Phe Arg Val
        35                  40                  45

Thr Lys Ser Glu His Met Val Asp Leu Lys Glu Lys Phe Lys Arg Ile
50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Ile Leu Phe His Gly Pro Asn Glu
        195                 200                 205

Asn His Leu Asp Ser Leu Val Ala Gln Ala Leu Phe Gly Asp Gly Ala
210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Phe Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Cys Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Cys Gly Val Leu Phe Gly Phe Gly Pro Gly Met Thr Val
370                 375                 380
```

Glu Thr Val Val Leu Arg Ser Val Arg Val Thr Ala Ala Val Ala Asn
385                 390                 395                 400

Gly Asn

<210> SEQ ID NO 7
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
                20                  25                  30

Pro Asn Cys Val Ala Gln Ala Asp Tyr Ala Asp Tyr Tyr Phe Arg Val
            35                  40                  45

Thr Lys Ser Glu His Met Val Asp Leu Lys Glu Lys Phe Lys Arg Ile
    50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
    130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Ile Leu Phe His Gly Pro Asn Glu
        195                 200                 205

Asn His Leu Asp Ser Leu Val Ala Gln Ala Leu Phe Gly Asp Gly Ala
    210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Met Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
    290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

```
Ser Glu Tyr Gly Asn Leu Ile Ser Ala Cys Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Cys Gly Val Leu Phe Gly Phe Gly Pro Gly Met Thr Val
    370                 375                 380

Glu Thr Val Val Leu Arg Ser Val Arg Val Thr Ala Ala Val Ala Asn
385                 390                 395                 400

Gly Asn

<210> SEQ ID NO 8
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
                20                  25                  30

Pro Asn Cys Val Ala Gln Ala Asp Tyr Ala Asp Tyr Tyr Phe Arg Val
            35                  40                  45

Thr Lys Ser Glu His Met Val Asp Leu Lys Glu Lys Phe Lys Arg Ile
    50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
    130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Ile Phe Phe His Gly Pro Asn Glu
        195                 200                 205

Asn His Leu Asp Ser Leu Val Ala Gln Ala Leu Phe Gly Asp Gly Ala
    210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Met Thr Phe Gln Leu
            260                 265                 270

His Arg Asp Val Pro Leu Met Val Ala Lys Asn Ile Glu Asn Ala Ala
        275                 280                 285
```

Glu Lys Ala Leu Ser Pro Leu Gly Ile Thr Asp Trp Asn Ser Val Phe
    290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Cys Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Cys Gly Val Leu Phe Gly Phe Gly Pro Gly Met Thr Val
    370                 375                 380

Glu Thr Val Val Leu Arg Ser Val Arg Val Thr Ala Ala Val Ala Asn
385                 390                 395                 400

Gly Asn

<210> SEQ ID NO 9
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Cys Val Ala Gln Ala Asp Tyr Ala Asp Tyr Tyr Phe Arg Val
        35                  40                  45

Thr Lys Ser Glu His Met Val Asp Leu Lys Glu Lys Phe Lys Arg Ile
    50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Ser Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
    130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Ile Leu Phe His Gly Pro Asn Glu
        195                 200                 205

Asn His Leu Asp Ser Leu Val Ala Gln Ala Leu Phe Gly Asp Gly Ala
    210                 215                 220

Ala Ala Leu Ile Val Gly Ser Gly Pro His Leu Ala Val Glu Arg Pro
225                 230                 235                 240

```
Ile Phe Glu Ile Val Ser Thr Asp Gln Thr Ile Leu Pro Asp Thr Glu
                245                 250                 255

Lys Ala Met Lys Leu His Leu Arg Glu Gly Leu Thr Phe Gln Leu
            260                 265                 270

His Arg Asp Val Pro Leu Met Val Ala Lys Asn Ile Glu Asn Ala Ala
            275                 280                 285

Glu Lys Ala Leu Ser Pro Leu Gly Ile Thr Asp Trp Asn Ser Val Phe
        290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Cys Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Ser Gly Val Leu Phe Gly Phe Gly Pro Gly Met Thr Val
    370                 375                 380

Glu Thr Val Val Leu Arg Ser Val Arg Val Thr Ala Ala Val Ala Asn
385                 390                 395                 400

Gly Asn

<210> SEQ ID NO 10
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Cys Val Ala Gln Ala Asp Tyr Ala Asp Tyr Tyr Phe Arg Val
        35                  40                  45

Thr Lys Ser Glu His Met Val Asp Leu Lys Glu Lys Phe Lys Arg Ile
    50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Ser Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
    130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190
```

```
Ile Val Cys Ser Glu Ile Thr Ala Ile Leu Phe His Gly Pro Asn Glu
            195                 200                 205

Asn His Leu Asp Ser Leu Val Ala Gln Ala Leu Phe Gly Asp Gly Ala
210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
            245                 250                 255

Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
            275                 280                 285

Glu Lys Ala Leu Ser Pro Leu Gly Ile Thr Asp Trp Asn Ser Val Phe
290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
            325                 330                 335

Ser Glu Tyr Gly Asn Leu Ile Ser Ala Ala Val Leu Phe Ile Ile Asp
            340                 345                 350

Glu Val Arg Lys Arg Ser Met Ala Glu Gly Lys Ser Thr Thr Gly Glu
            355                 360                 365

Gly Leu Asp Ser Gly Val Leu Phe Gly Phe Gly Pro Gly Met Thr Val
370                 375                 380

Glu Thr Val Val Leu Arg Ser Val Arg Val Thr Ala Ala Val Ala Asn
385                 390                 395                 400

Gly Asn

<210> SEQ ID NO 11
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Cys Val Ala Gln Ala Asp Tyr Ala Asp Tyr Tyr Phe Arg Val
            35                  40                  45

Thr Lys Ser Glu His Met Val Asp Leu Lys Glu Lys Phe Lys Arg Ile
    50                  55                  60

Ser Glu Lys Thr Ala Ile Lys Lys Arg Tyr Leu Ala Leu Thr Glu Asp
65                  70                  75                  80

Tyr Leu Gln Glu Asn Pro Thr Met Ser Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
            115                 120                 125

Ile Thr His Leu Ile Phe Cys Thr Thr Ala Gly Val Asp Met Pro Gly
130                 135                 140
```

```
Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
            165                 170                 175

Arg Leu Ala Lys Asp Leu Ala Glu Asn Asn Lys Gly Ser Arg Val Leu
        180                 185                 190

Ile Val Cys Ser Glu Ile Thr Ala Ile Leu Phe His Gly Pro Asn Glu
    195                 200                 205

Asn His Leu Asp Ser Leu Val Ala Gln Ala Leu Phe Gly Asp Gly Ala
        210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Cys Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Ser Gly Val Leu Phe Gly Phe Gly Pro Gly Met Thr Val
    370                 375                 380

Glu Thr Val Val Leu Arg Ser Val Arg Val Thr Ala Ala Val Ala Asn
385                 390                 395                 400

Gly Asn

<210> SEQ ID NO 12
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Cys Val Ala Gln Ala Asp Tyr Ala Asp Tyr Tyr Phe Arg Val
        35                  40                  45

Thr Lys Ser Glu His Met Val Asp Leu Lys Glu Lys Phe Lys Arg Ile
    50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Ser Glu Phe Met Ala Pro Ser Leu
                85                  90                  95
```

```
Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
    130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Ser Ser Glu Ile Thr Ala Ile Leu Phe His Gly Pro Asn Glu
        195                 200                 205

Asn His Leu Asp Ser Leu Val Ala Gln Ala Leu Phe Gly Asp Gly Ala
    210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
    290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Ala Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Ser Gly Val Leu Phe Gly Phe Gly Pro Gly Met Thr Val
    370                 375                 380

Glu Thr Val Val Leu Arg Ser Val Arg Val Thr Ala Ala Val Ala Asn
385                 390                 395                 400

Gly Asn

<210> SEQ ID NO 13
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Cys Val Ala Gln Ala Asp Tyr Ala Asp Tyr Tyr Phe Arg Val
        35                  40                  45
```

Thr Lys Ser Glu His Met Val Asp Leu Lys Glu Lys Phe Lys Arg Ile
 50                  55                  60

Ser Glu Lys Thr Ala Ile Lys Lys Arg Tyr Leu Ala Leu Thr Glu Asp
 65                  70                  75                  80

Tyr Leu Gln Glu Asn Pro Thr Met Ser Glu Phe Met Ala Pro Ser Leu
                 85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Ser Ser Glu Ile Thr Ala Ile Leu Phe His Gly Pro Asn Glu
        195                 200                 205

Asn His Leu Asp Ser Leu Val Ala Gln Ala Leu Phe Gly Asp Gly Ala
210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Ala Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Ser Gly Val Leu Phe Gly Phe Gly Pro Gly Met Thr Val
370                 375                 380

Glu Thr Val Val Leu Arg Ser Val Arg Val Thr Ala Ala Val Ala Asn
385                 390                 395                 400

Gly Asn

<210> SEQ ID NO 14
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Met Gly Ser Tyr Ser Ser Asp Asp Val Glu Val Ile Arg Glu Ala Gly
  1               5                  10                  15
Arg Ala Gln Gly Leu Ala Thr Ile Leu Ala Ile Gly Thr Ala Thr Pro
             20                  25                  30
Pro Asn Ser Val Ala Gln Ala Asp Tyr Ala Asp Tyr Tyr Phe Arg Val
         35                  40                  45
Thr Lys Ser Glu His Met Val Asp Leu Lys Glu Lys Phe Lys Arg Ile
     50                  55                  60
Ser Glu Lys Thr Ala Ile Lys Lys Arg Tyr Leu Ala Leu Thr Glu Asp
 65                  70                  75                  80
Tyr Leu Gln Glu Asn Pro Thr Met Ser Glu Phe Met Ala Pro Ser Leu
                 85                  90                  95
Asn Ala Arg Gln Asp Leu Val Val Thr Gly Val Pro Met Leu Gly Lys
             100                 105                 110
Glu Ala Ala Val Lys Ala Ile Asp Glu Trp Gly Leu Pro Lys Ser Lys
             115                 120                 125
Ile Thr His Leu Ile Phe Cys Thr Thr Ala Gly Val Asp Met Pro Gly
     130                 135                 140
Ala Asp Tyr Gln Leu Val Lys Leu Leu Gly Leu Ser Pro Ser Val Lys
145                 150                 155                 160
Arg Tyr Met Leu Tyr Gln Gln Gly Cys Ala Ala Gly Gly Thr Val Leu
                 165                 170                 175
Arg Leu Ala Lys Asp Leu Ala Glu Asn Asn Lys Gly Ser Arg Val Leu
             180                 185                 190
Ile Val Ser Ser Glu Ile Thr Ala Ile Leu Phe His Gly Pro Asn Glu
             195                 200                 205
Asn His Leu Asp Ser Leu Val Ala Gln Ala Leu Phe Gly Asp Gly Ala
     210                 215                 220
Ala Leu Ile Val Gly Ser Gly Pro His Leu Ala Val Glu Arg Pro
225                 230                 235                 240
Ile Phe Glu Ile Val Ser Thr Asp Gln Thr Ile Leu Pro Asp Thr Glu
                 245                 250                 255
Lys Ala Leu Lys Asn His Leu Arg Glu Gly Gly Leu Thr Phe Gln Leu
             260                 265                 270
His Arg Asp Val Pro Leu Met Val Ala Lys Asn Ile Glu Asn Ala Ala
             275                 280                 285
Glu Lys Ala Leu Ser Pro Leu Gly Ile Thr Asp Trp Asn Ser Val Phe
    290                 295                 300
Trp Met Val His Pro Gly Gly Arg Ala Ile Leu Asp Gln Val Glu Arg
305                 310                 315                 320
Lys Leu Asn Leu Lys Glu Asp Lys Leu Arg Ala Ser Arg His Val Leu
                325                 330                 335
Ser Glu Tyr Gly Asn Leu Ile Ser Ala Ala Val Leu Phe Ile Ile Asp
            340                 345                 350
Glu Val Arg Lys Arg Ser Met Ala Glu Gly Lys Ser Thr Thr Gly Glu
            355                 360                 365
Gly Leu Asp Ser Gly Val Leu Phe Gly Phe Pro Gly Met Thr Val
            370                 375                 380
Glu Thr Val Val Leu Arg Ser Val Arg Val Thr Ala Ala Val Ala Asn
385                 390                 395                 400
Gly Asn
```

<210> SEQ ID NO 15
<211> LENGTH: 402
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

```
Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
        35                  40                  45

Thr Lys Ser Glu His Met Val Asp Leu Lys Glu Lys Phe Lys Arg Ile
    50                  55                  60

Ser Glu Lys Thr Ala Ile Lys Lys Arg Tyr Leu Ala Leu Thr Glu Asp
65                  70                  75                  80

Tyr Leu Gln Glu Asn Pro Thr Met Ser Glu Phe Met Ala Pro Ser Leu
            85                  90                  95

Asn Ala Arg Gln Asp Leu Val Val Thr Gly Val Pro Met Leu Gly Lys
        100                 105                 110

Glu Ala Ala Val Lys Ala Ile Asp Glu Trp Gly Leu Pro Lys Ser Lys
    115                 120                 125

Ile Thr His Leu Ile Phe Cys Thr Phe Ala Gly Val Asp Met Pro Gly
130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
            165                 170                 175

Arg Leu Ala Lys Asp Leu Ala Glu Asn Asn Lys Gly Ser Arg Val Leu
        180                 185                 190

Ile Val Ser Ser Glu Ile Thr Ala Ile Gly Phe His Gly Pro Asn Glu
    195                 200                 205

Asn His Leu Asp Ser Leu Val Ala Gln Ala Leu Phe Gly Asp Gly Ala
210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
            245                 250                 255

Lys Ala Leu Lys Asn His Leu Arg Glu Gly Gly Leu Thr Phe Gln Leu
        260                 265                 270

His Arg Asp Val Pro Leu Met Val Ala Lys Asn Ile Glu Asn Ala Ala
    275                 280                 285

Glu Lys Ala Leu Ser Pro Leu Gly Ile Thr Asp Trp Asn Ser Val Phe
290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
            325                 330                 335

Ser Glu Tyr Gly Asn Leu Ile Ser Ala Ala Val Leu Phe Ile Ile Asp
        340                 345                 350

Glu Val Arg Lys Arg Ser Met Ala Glu Gly Lys Ser Thr Thr Gly Glu
    355                 360                 365
```

-continued

Gly Leu Asp Ser Gly Val Leu Phe Gly Phe Gly Pro Gly Met Thr Val
370                 375                 380

Glu Thr Val Val Leu Arg Ser Val Arg Val Thr Ala Ala Val Ala Asn
385                 390                 395                 400

Gly Asn

<210> SEQ ID NO 16
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
        35                  40                  45

Thr Lys Ser Glu His Met Val Asp Leu Lys Glu Lys Phe Lys Arg Ile
50                  55                  60

Ser Glu Lys Thr Ala Ile Lys Lys Arg Tyr Leu Ala Leu Thr Glu Asp
65                  70                  75                  80

Tyr Leu Gln Glu Asn Pro Thr Met Ser Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Ser Ser Glu Ile Thr Ala Phe Gly Phe His Gly Pro Asn Glu
        195                 200                 205

Asn His Leu Asp Ser Leu Val Ala Gln Ala Leu Phe Gly Asp Gly Ala
210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Leu Lys Asn His Leu Arg Glu Gly Gly Leu Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
290                 295                 300

Trp Met Val His Pro Gly Gly Arg Ala Ile Leu Asp Gln Val Glu Arg
305                 310                 315                 320

-continued

```
Lys Leu Asn Leu Lys Glu Asp Lys Leu Arg Ala Ser Arg His Val Leu
                325                 330                 335

Ser Glu Tyr Gly Asn Leu Ile Ser Ala Ala Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Ser Gly Val Leu Phe Gly Phe Gly Pro Gly Met Thr Val
370                 375                 380

Glu Thr Val Val Leu Arg Ser Val Arg Val Thr Ala Ala Val Ala Asn
385                 390                 395                 400

Gly Asn
```

<210> SEQ ID NO 17
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Met Gly Ser Tyr Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
        35                  40                  45

Thr Lys Ser Glu His Met Val Asp Leu Lys Glu Lys Phe Lys Arg Ile
50                  55                  60

Ser Glu Lys Thr Ala Ile Lys Lys Arg Tyr Leu Ala Leu Thr Glu Asp
65                  70                  75                  80

Tyr Leu Gln Glu Asn Pro Thr Met Ser Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Phe Ala Gly Val Asp Met Pro Gly
130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Ser Ser Glu Ile Thr Ala Ile Gly Phe His Gly Pro Asn Glu
        195                 200                 205

Asn His Leu Asp Ser Leu Val Ala Gln Ala Leu Phe Gly Asp Gly Ala
210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Leu Lys Asn His Leu Arg Glu Gly Gly Leu Thr Phe Gln Leu
            260                 265                 270
```

```
His Arg Asp Val Pro Leu Met Val Ala Lys Asn Ile Glu Asn Ala Ala
            275                 280                 285
Glu Lys Ala Leu Ser Pro Leu Gly Ile Thr Asp Trp Asn Ser Val Phe
        290                 295                 300
Trp Met Val His Pro Gly Gly Arg Ala Ile Leu Asp Gln Val Glu Arg
305                 310                 315                 320
Lys Leu Asn Leu Lys Glu Asp Lys Leu Arg Ala Ser Arg His Val Leu
                325                 330                 335
Ser Glu Tyr Gly Asn Leu Ile Ser Ala Ala Val Leu Phe Ile Ile Asp
            340                 345                 350
Glu Val Arg Lys Arg Ser Met Ala Glu Gly Lys Ser Thr Thr Gly Glu
        355                 360                 365
Gly Leu Asp Ser Gly Val Leu Phe Gly Phe Gly Pro Gly Met Thr Val
370                 375                 380
Glu Thr Val Val Leu Arg Ser Val Arg Val Thr Ala Ala Val Ala Asn
385                 390                 395                 400
Gly Asn

<210> SEQ ID NO 18
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Gly Ser Tyr Ser Ser Asp Asp Val Glu Val Ile Arg Glu Ala Gly
1               5                   10                  15
Arg Ala Gln Gly Leu Ala Thr Ile Leu Ala Ile Gly Thr Ala Thr Pro
            20                  25                  30
Pro Asn Ser Val Ala Gln Ala Asp Tyr Ala Asp Tyr Tyr Phe Arg Val
        35                  40                  45
Thr Lys Ser Glu His Met Val Asp Leu Lys Glu Lys Phe Lys Arg Ile
50                  55                  60
Ser Glu Lys Thr Ala Ile Lys Lys Arg Tyr Leu Ala Leu Thr Glu Asp
65                  70                  75                  80
Tyr Leu Gln Glu Asn Pro Thr Met Ser Glu Phe Met Ala Pro Ser Leu
                85                  90                  95
Asn Ala Arg Gln Asp Leu Val Val Thr Gly Val Pro Met Leu Gly Lys
            100                 105                 110
Glu Ala Ala Val Lys Ala Ile Asp Glu Trp Gly Leu Pro Lys Ser Lys
        115                 120                 125
Ile Thr His Leu Ile Phe Cys Thr Thr Ala Gly Val Asp Met Pro Gly
130                 135                 140
Ala Asp Tyr Gln Leu Val Lys Leu Leu Gly Leu Ser Pro Ser Val Lys
145                 150                 155                 160
Arg Tyr Met Leu Tyr Gln Gln Gly Cys Ala Ala Gly Gly Thr Val Leu
                165                 170                 175
Arg Leu Ala Lys Asp Leu Ala Glu Asn Asn Lys Gly Ser Arg Val Leu
            180                 185                 190
Ile Val Ser Ser Glu Ile Thr Ala Ile Gly Phe His Gly Pro Asn Glu
        195                 200                 205
Asn His Leu Asp Ser Leu Val Ala Gln Ala Leu Phe Gly Asp Gly Ala
210                 215                 220
```

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
            245                 250                 255

Lys Ala Leu Lys Asn His Leu Arg Glu Gly Gly Met Thr Phe Gln Leu
        260                 265                 270

His Arg Asp Val Pro Leu Met Val Ala Lys Asn Ile Glu Asn Ala Ala
    275                 280                 285

Glu Lys Ala Leu Ser Pro Leu Gly Ile Thr Asp Trp Asn Ser Val Phe
290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Ala Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Ser Gly Val Leu Phe Gly Phe Gly Pro Gly Met Thr Val
    370                 375                 380

Glu Thr Val Val Leu Arg Ser Val Arg Val Thr Ala Ala Val Ala Asn
385                 390                 395                 400

Gly Asn

<210> SEQ ID NO 19
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
        35                  40                  45

Thr Lys Ser Glu His Met Val Asp Leu Lys Glu Lys Phe Lys Arg Ile
    50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Ser Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
    130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

```
Arg Leu Ala Lys Asp Leu Ala Glu Asn Asn Lys Gly Ser Arg Val Leu
                180                 185                 190

Ile Val Cys Ser Glu Ile Thr Ala Ile Leu Phe His Gly Pro Asn Glu
            195                 200                 205

Asn His Leu Asp Ser Leu Val Ala Gln Ala Leu Phe Gly Asp Gly Ala
        210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
    290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Cys Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Ser Gly Val Leu Phe Gly Phe Gly Pro Gly Met Thr Val
    370                 375                 380

Glu Thr Val Val Leu Arg Ser Val Arg Val Thr Ala Ala Val Ala Asn
385                 390                 395                 400

Gly Asn

<210> SEQ ID NO 20
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
                20                  25                  30

Pro Asn Ser Val Ala Gln Ala Asp Tyr Ala Asp Tyr Tyr Phe Arg Val
            35                  40                  45

Thr Lys Ser Glu His Met Val Asp Leu Lys Glu Lys Phe Lys Arg Ile
        50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Ser Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125
```

```
Ile Thr His Leu Ile Phe Cys Thr Thr Ala Gly Val Asp Met Pro Gly
    130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Ile Leu Phe His Gly Pro Asn Glu
        195                 200                 205

Asn His Leu Asp Ser Leu Val Ala Gln Ala Leu Phe Gly Asp Gly Ala
    210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
    290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Ala Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Ser Gly Val Leu Phe Gly Phe Gly Pro Gly Met Thr Val
    370                 375                 380

Glu Thr Val Val Leu Arg Ser Val Arg Val Thr Ala Ala Val Ala Asn
385                 390                 395                 400

Gly Asn

<210> SEQ ID NO 21
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Gly Ser Tyr Ser Ser Asp Val Glu Val Ile Arg Glu Ala Gly
1               5                   10                  15

Arg Ala Gln Gly Leu Ala Thr Ile Leu Ala Ile Gly Thr Ala Thr Pro
                20                  25                  30

Pro Asn Ser Val Ala Gln Ala Asp Tyr Ala Asp Tyr Tyr Phe Arg Val
            35                  40                  45

Thr Lys Ser Glu His Met Val Asp Leu Lys Glu Lys Phe Lys Arg Ile
        50                  55                  60

Ser Glu Lys Thr Ala Ile Lys Lys Arg Tyr Leu Ala Leu Thr Glu Asp
65                  70                  75                  80
```

```
Tyr Leu Gln Glu Asn Pro Thr Met Ser Glu Phe Met Ala Pro Ser Leu
                 85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
            115                 120                 125

Ile Thr His Leu Ile Phe Cys Thr Thr Ala Gly Val Asp Met Pro Gly
            130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Ile Leu Phe His Gly Pro Asn Glu
            195                 200                 205

Asn His Leu Asp Ser Leu Val Ala Gln Ala Leu Phe Gly Asp Gly Ala
            210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
            275                 280                 285

Glu Lys Ala Leu Ser Pro Leu Gly Ile Thr Asp Trp Asn Ser Val Phe
290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Cys Val Leu Phe Ile Ile Asp
            340                 345                 350

Glu Val Arg Lys Arg Ser Met Ala Glu Gly Lys Ser Thr Thr Gly Glu
            355                 360                 365

Gly Leu Asp Ser Gly Val Leu Phe Gly Phe Gly Pro Gly Met Thr Val
            370                 375                 380

Glu Thr Val Val Leu Arg Ser Val Arg Val Thr Ala Ala Val Ala Asn
385                 390                 395                 400

Gly Asn

<210> SEQ ID NO 22
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30
```

Pro Asn Ser Val Ala Gln Ala Asp Tyr Ala Asp Tyr Phe Arg Val
            35                  40                  45

Thr Lys Ser Glu His Met Val Asp Leu Lys Glu Lys Phe Lys Arg Ile
 50                  55                  60

Cys Glu Lys Thr Ala Ile Lys Lys Arg Tyr Leu Ala Leu Thr Glu Asp
 65                  70                  75                  80

Tyr Leu Gln Glu Asn Pro Thr Met Ser Glu Phe Met Ala Pro Ser Leu
                 85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
            115                 120                 125

Ile Thr His Leu Ile Phe Cys Thr Thr Ala Gly Val Asp Met Pro Gly
130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Ser Ser Glu Ile Thr Ala Ile Leu Phe His Gly Pro Asn Glu
            195                 200                 205

Asn His Leu Asp Ser Leu Val Ala Gln Ala Leu Phe Gly Asp Gly Ala
            210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
            275                 280                 285

Glu Lys Ala Leu Ser Pro Leu Gly Ile Thr Asp Trp Asn Ser Val Phe
290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Ala Val Leu Phe Ile Ile Asp
            340                 345                 350

Glu Val Arg Lys Arg Ser Met Ala Glu Gly Lys Ser Thr Thr Gly Glu
            355                 360                 365

Gly Leu Asp Ser Gly Val Leu Phe Gly Phe Gly Pro Gly Met Thr Val
            370                 375                 380

Glu Thr Val Val Leu Arg Ser Val Arg Val Thr Ala Ala Val Ala Asn
385                 390                 395                 400

Gly Asn

<210> SEQ ID NO 23
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
        35                  40                  45

Thr Lys Ser Glu His Met Val Asp Leu Lys Glu Lys Phe Lys Arg Ile
    50                  55                  60

Ser Glu Lys Thr Ala Ile Lys Lys Arg Tyr Leu Ala Leu Thr Glu Asp
65                  70                  75                  80

Tyr Leu Gln Glu Asn Pro Thr Met Ser Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
    130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Ser Ser Glu Ile Thr Ala Ile Leu Phe His Gly Pro Asn Glu
        195                 200                 205

Asn His Leu Asp Ser Leu Val Ala Gln Ala Leu Phe Gly Asp Gly Ala
    210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
    290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Ala Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Ser Gly Val Leu Phe Gly Phe Gly Pro Gly Met Thr Val
    370                 375                 380

Glu Thr Val Val Leu Arg Ser Val Arg Val Thr Ala Ala Val Ala Asn
385                 390                 395                 400

Gly Asn
```

<210> SEQ ID NO 24
<211> LENGTH: 402
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
        35                  40                  45

Thr Lys Ser Glu His Met Val Asp Leu Lys Glu Lys Phe Lys Arg Ile
    50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Phe Ala Gly Val Asp Met Pro Gly
    130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Ile Leu Phe His Gly Pro Asn Glu
        195                 200                 205

Asn His Leu Asp Ser Leu Val Ala Gln Ala Leu Phe Gly Asp Gly Ala
    210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
    290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Cys Val Leu Phe Ile Ile Asp
            340                 345                 350

Glu Val Arg Lys Arg Ser Met Ala Glu Gly Lys Ser Thr Thr Gly Glu

-continued 355                 360                 365
Gly Leu Asp Cys Gly Val Leu Phe Gly Phe Gly Pro Gly Met Thr Val
        370                 375                 380
Glu Thr Val Val Leu Arg Ser Val Arg Val Thr Ala Ala Val Ala Asn
385                 390                 395                 400
Gly Asn <210> SEQ ID NO 25
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Gly Ser Tyr Ser Ser Asp Asp Val Glu Val Ile Arg Glu Ala Gly
1               5                   10                  15
Arg Ala Gln Gly Leu Ala Thr Ile Leu Ala Ile Gly Thr Ala Thr Pro
            20                  25                  30
Pro Asn Ser Val Ala Gln Ala Asp Tyr Ala Asp Tyr Tyr Phe Arg Val
        35                  40                  45
Thr Lys Ser Glu His Met Val Asp Leu Lys Glu Lys Phe Lys Arg Ile
    50                  55                  60
Cys Glu Lys Thr Ala Ile Lys Lys Arg Tyr Leu Ala Leu Thr Glu Asp
65                  70                  75                  80
Tyr Leu Gln Glu Asn Pro Thr Met Cys Glu Phe Met Ala Pro Ser Leu
                85                  90                  95
Asn Ala Arg Gln Asp Leu Val Val Thr Gly Val Pro Met Leu Gly Lys
            100                 105                 110
Glu Ala Ala Val Lys Ala Ile Asp Glu Trp Gly Leu Pro Lys Ser Lys
        115                 120                 125
Ile Thr His Leu Ile Phe Cys Thr Met Ala Gly Val Asp Met Pro Gly
    130                 135                 140
Ala Asp Tyr Gln Leu Val Lys Leu Leu Gly Leu Ser Pro Ser Val Lys
145                 150                 155                 160
Arg Tyr Met Leu Tyr Gln Gln Gly Cys Ala Ala Gly Gly Thr Val Leu
                165                 170                 175
Arg Leu Ala Lys Asp Leu Ala Glu Asn Asn Lys Gly Ser Arg Val Leu
            180                 185                 190
Ile Val Cys Ser Glu Ile Thr Ala Ile Leu Phe His Gly Pro Asn Glu
        195                 200                 205
Asn His Leu Asp Ser Leu Val Ala Gln Ala Leu Phe Gly Asp Gly Ala
    210                 215                 220
Ala Ala Leu Ile Val Gly Ser Gly Pro His Leu Ala Val Glu Arg Pro
225                 230                 235                 240
Ile Phe Glu Ile Val Ser Thr Asp Gln Thr Ile Leu Pro Asp Thr Glu
                245                 250                 255
Lys Ala Met Lys Leu His Leu Arg Glu Gly Gly Leu Thr Phe Gln Leu
            260                 265                 270
His Arg Asp Val Pro Leu Met Val Ala Lys Asn Ile Glu Asn Ala Ala
        275                 280                 285
Glu Lys Ala Leu Ser Pro Leu Gly Ile Thr Asp Trp Asn Ser Val Phe
    290                 295                 300
Trp Met Val His Pro Gly Gly Arg Ala Ile Leu Asp Gln Val Glu Arg

```
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Cys Val Leu Phe Ile Ile Asp
            340                 345                 350

Glu Val Arg Lys Arg Ser Met Ala Gly Lys Ser Thr Thr Gly Glu
            355                 360                 365

Gly Leu Asp Cys Gly Val Leu Phe Gly Phe Pro Gly Met Thr Val
        370                 375                 380

Glu Thr Val Val Leu Arg Ser Val Arg Val Thr Ala Ala Val Ala Asn
385                 390                 395                 400

Gly Asn

<210> SEQ ID NO 26
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
                20                  25                  30

Pro Asn Ser Val Ala Gln Ala Asp Tyr Ala Asp Tyr Tyr Phe Arg Val
            35                  40                  45

Thr Lys Ser Glu His Met Val Asp Leu Lys Glu Lys Phe Lys Arg Ile
        50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
        130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Ile Leu Phe His Gly Pro Asn Glu
        195                 200                 205

Asn His Leu Asp Ser Leu Val Ala Gln Ala Leu Phe Gly Asp Gly Ala
        210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Phe Lys Leu His Leu Arg Glu Gly Gly Leu Thr Phe Gln Leu
```

His Arg Asp Val Pro Leu Met Val Ala Lys Asn Ile Glu Asn Ala Ala
            275                 280                 285

Glu Lys Ala Leu Ser Pro Leu Gly Ile Thr Asp Trp Asn Ser Val Phe
        290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Cys Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Cys Gly Val Leu Phe Gly Phe Gly Pro Gly Met Thr Val
    370                 375                 380

Glu Thr Val Val Leu Arg Ser Val Arg Val Thr Ala Ala Val Ala Asn
385                 390                 395                 400

Gly Asn

<210> SEQ ID NO 27
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Gly Ser Tyr Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
        35                  40                  45

Thr Lys Ser Glu His Met Val Asp Leu Lys Glu Lys Phe Lys Arg Ile
    50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Leu Ala Gly Val Asp Met Pro Gly
130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Ile Leu Phe His Gly Pro Asn Glu
        195                 200                 205

Asn His Leu Asp Ser Leu Val Ala Gln Ala Leu Phe Gly Asp Gly Ala

```
                210                 215                 220
Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
                260                 265                 270

His Arg Asp Val Pro Leu Met Val Ala Lys Asn Ile Glu Asn Ala Ala
                275                 280                 285

Glu Lys Ala Leu Ser Pro Leu Gly Ile Thr Asp Trp Asn Ser Val Phe
290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Cys Val Leu Phe Ile Ile Asp
                340                 345                 350

Glu Val Arg Lys Arg Ser Met Ala Glu Gly Lys Ser Thr Thr Gly Glu
                355                 360                 365

Gly Leu Asp Cys Gly Val Leu Phe Gly Phe Gly Pro Gly Met Thr Val
                370                 375                 380

Glu Thr Val Val Leu Arg Ser Val Arg Val Thr Ala Ala Val Ala Asn
385                 390                 395                 400

Gly Asn

<210> SEQ ID NO 28
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
                20                  25                  30

Pro Asn Ser Val Ala Gln Ala Asp Tyr Ala Asp Tyr Tyr Phe Arg Val
                35                  40                  45

Thr Lys Ser Glu His Met Val Asp Leu Lys Glu Lys Phe Lys Arg Ile
                50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
                100                 105                 110

Glu Ala Ala Val Lys Ala Ile Asp Glu Trp Gly Leu Pro Lys Ser Lys
                115                 120                 125

Ile Thr His Leu Ile Phe Cys Thr Thr Ala Gly Val Asp Met Pro Gly
                130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
```

```
                165                 170                 175
Arg Leu Ala Lys Asp Leu Ala Glu Asn Asn Lys Gly Ser Arg Val Leu
            180                 185                 190

Ile Val Cys Ser Glu Ile Thr Ala Ile Leu Phe His Gly Pro Asn Glu
            195                 200                 205

Asn His Leu Asp Ser Leu Val Ala Gln Ala Leu Phe Gly Asp Gly Ala
            210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Leu Thr Phe Gln Leu
            260                 265                 270

His Arg Asp Val Pro Leu Met Val Ala Lys Asn Ile Glu Asn Ala Ala
            275                 280                 285

Glu Lys Ala Leu Ser Pro Leu Gly Ile Thr Asp Trp Asn Ser Val Phe
            290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Phe Ser Ala Cys Val Leu Phe Ile Ile Asp
            340                 345                 350

Glu Val Arg Lys Arg Ser Met Ala Glu Gly Lys Ser Thr Thr Gly Glu
            355                 360                 365

Gly Leu Asp Cys Gly Val Leu Phe Gly Phe Gly Pro Gly Met Thr Val
            370                 375                 380

Glu Thr Val Val Leu Arg Ser Val Arg Val Thr Ala Ala Val Ala Asn
385                 390                 395                 400

Gly Asn

<210> SEQ ID NO 29
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
            35                  40                  45

Thr Lys Ser Glu His Met Val Asp Leu Lys Glu Lys Phe Lys Arg Ile
        50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
```

```
                  115                 120                 125
Ile Thr His Leu Ile Phe Cys Thr Thr Ala Gly Val Asp Met Pro Gly
            130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Ile Leu Phe His Gly Pro Asn Glu
        195                 200                 205

Asn His Leu Asp Ser Leu Val Ala Gln Ala Leu Phe Gly Asp Gly Ala
    210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
    290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Met Ser Ala Cys Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Cys Gly Val Leu Phe Gly Phe Gly Pro Gly Met Thr Val
    370                 375                 380

Glu Thr Val Val Leu Arg Ser Val Arg Val Thr Ala Ala Val Ala Asn
385                 390                 395                 400

Gly Asn

<210> SEQ ID NO 30
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
        35                  40                  45

Thr Lys Ser Glu His Met Val Asp Leu Lys Glu Lys Phe Lys Arg Ile
50                  55                  60

Cys Glu Lys Thr Ala Ile Lys Lys Arg Tyr Leu Ala Leu Thr Glu Asp
```

```
            65                  70                  75                  80
Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
    130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Phe Leu Phe His Gly Pro Asn Glu
        195                 200                 205

Asn His Leu Asp Ser Leu Val Ala Gln Ala Leu Phe Gly Asp Gly Ala
    210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
    290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Cys Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Cys Gly Val Leu Phe Gly Phe Gly Pro Gly Met Thr Val
    370                 375                 380

Glu Thr Val Val Leu Arg Ser Val Arg Val Thr Ala Ala Val Ala Asn
385                 390                 395                 400

Gly Asn

<210> SEQ ID NO 31
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
```

```
                    20                  25                  30
Pro Asn Ser Val Ala Gln Ala Asp Tyr Ala Asp Tyr Tyr Phe Arg Val
                35                  40                  45

Thr Lys Ser Glu His Met Val Asp Leu Lys Glu Lys Phe Lys Arg Ile
 50                  55                  60

Cys Glu Lys Thr Ala Ile Lys Lys Arg Tyr Leu Ala Leu Thr Glu Asp
 65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
                100                 105                 110

Glu Ala Ala Val Lys Ala Ile Asp Glu Trp Gly Leu Pro Lys Ser Lys
                115                 120                 125

Ile Thr His Leu Ile Phe Cys Thr Thr Ala Gly Val Asp Met Pro Gly
                130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Ala Ala Gly Gly Thr Val Leu
                165                 170                 175

Arg Leu Ala Lys Asp Leu Ala Glu Asn Asn Lys Gly Ser Arg Val Leu
                180                 185                 190

Ile Val Cys Ser Glu Ile Thr Ala Ile Leu Phe His Gly Pro Asn Glu
                195                 200                 205

Asn His Leu Asp Ser Leu Val Ala Gln Ala Leu Phe Gly Asp Gly Ala
                210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
                260                 265                 270

His Arg Asp Val Pro Leu Met Val Ala Lys Asn Ile Glu Asn Ala Ala
                275                 280                 285

Glu Lys Ala Leu Ser Pro Leu Gly Ile Thr Asp Trp Asn Ser Val Phe
                290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Cys Val Leu Phe Ile Ile Asp
                340                 345                 350

Glu Val Arg Lys Arg Ser Met Ala Glu Gly Lys Ser Thr Thr Gly Glu
                355                 360                 365

Gly Leu Asp Cys Gly Val Leu Phe Gly Phe Gly Pro Gly Met Thr Val
                370                 375                 380

Glu Thr Val Val Leu Arg Ser Val Arg Val Thr Ala Ala Val Ala Asn
385                 390                 395                 400

Gly Asn

<210> SEQ ID NO 32
<211> LENGTH: 402
<212> TYPE: PRT
<213> ORGANISM: Artificial Sequence
<220> FEATURE:
```

<223> OTHER INFORMATION: Description of Artificial Sequence: Synthetic polypeptide

<400> SEQUENCE: 32

```
Met Gly Ser Tyr Ser Ser Asp Asp Val Glu Val Ile Arg Glu Ala Gly
1               5                   10                  15
Arg Ala Gln Gly Leu Ala Thr Ile Leu Ala Ile Gly Thr Ala Thr Pro
            20                  25                  30
Pro Asn Ser Val Ala Gln Ala Asp Tyr Ala Asp Tyr Tyr Phe Arg Val
        35                  40                  45
Thr Lys Ser Glu His Met Val Asp Leu Lys Glu Lys Phe Lys Arg Ile
50                  55                  60
Cys Glu Lys Thr Ala Ile Lys Lys Arg Tyr Leu Ala Leu Thr Glu Asp
65                  70                  75                  80
Tyr Leu Gln Glu Asn Pro Thr Met Cys Glu Phe Met Ala Pro Ser Leu
                85                  90                  95
Asn Ala Arg Gln Asp Leu Val Val Thr Gly Val Pro Met Leu Gly Lys
            100                 105                 110
Glu Ala Ala Val Lys Ala Ile Asp Glu Trp Gly Leu Pro Lys Ser Lys
        115                 120                 125
Ile Thr His Leu Ile Phe Cys Thr Thr Ala Gly Val Asp Met Pro Gly
130                 135                 140
Ala Asp Tyr Gln Leu Val Lys Leu Leu Gly Leu Ser Pro Ser Val Lys
145                 150                 155                 160
Arg Tyr Met Leu Tyr Gln Gln Gly Cys Ala Ala Gly Gly Thr Val Leu
                165                 170                 175
Arg Leu Ala Lys Asp Leu Ala Glu Asn Asn Lys Gly Ser Arg Val Leu
            180                 185                 190
Ile Val Cys Ser Glu Ile Thr Ala Ile Leu Phe His Gly Pro Asn Glu
        195                 200                 205
Asn His Leu Asp Ser Leu Val Ala Gln Ala Leu Phe Gly Asp Gly Ala
210                 215                 220
Ala Ala Leu Ile Val Gly Ser Gly Pro His Leu Ala Val Glu Arg Pro
225                 230                 235                 240
Ile Phe Glu Ile Val Ser Thr Asp Gln Thr Ile Leu Pro Asp Thr Glu
                245                 250                 255
Lys Ala Met Lys Leu His Leu Arg Glu Gly Gly Met Thr Phe Gln Leu
            260                 265                 270
His Arg Asp Val Pro Leu Met Val Ala Lys Asn Ile Glu Asn Ala Ala
        275                 280                 285
Glu Lys Ala Leu Ser Pro Leu Gly Ile Thr Asp Trp Asn Ser Val Phe
290                 295                 300
Trp Met Val His Pro Gly Gly Arg Ala Ile Leu Asp Gln Val Glu Arg
305                 310                 315                 320
Lys Leu Asn Leu Lys Glu Asp Lys Leu Arg Ala Ser Arg His Val Leu
                325                 330                 335
Ser Glu Tyr Gly Asn Leu Ile Ser Ala Cys Val Leu Phe Ile Ile Asp
            340                 345                 350
Glu Val Arg Lys Arg Ser Met Ala Glu Gly Lys Ser Thr Thr Gly Glu
        355                 360                 365
Gly Leu Asp Cys Gly Val Leu Phe Gly Phe Gly Pro Gly Met Thr Val
370                 375                 380
Glu Thr Val Val Leu Arg Ser Val Arg Val Thr Ala Ala Val Ala Asn
385                 390                 395                 400
```

Gly Asn

<210> SEQ ID NO 33
<211> LENGTH: 402
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

Met Gly Ser Tyr Ser Ser Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
            35                  40                  45

Thr Lys Ser Glu His Met Val Asp Leu Lys Glu Lys Phe Lys Arg Ile
        50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Ile Phe Phe His Gly Pro Asn Glu
        195                 200                 205

Asn His Leu Asp Ser Leu Val Ala Gln Ala Leu Phe Gly Asp Gly Ala
    210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
    290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Cys Val Leu Phe Ile Ile Asp
            340                 345                 350

Glu Val Arg Lys Arg Ser Met Ala Glu Gly Lys Ser Thr Thr Gly Glu
            355                 360                 365

Gly Leu Asp Cys Gly Val Leu Phe Gly Phe Gly Pro Gly Met Thr Val
370                 375                 380

Glu Thr Val Val Leu Arg Ser Val Arg Val Thr Ala Ala Val Ala Asn
385                 390                 395                 400

Gly Asn

<210> SEQ ID NO 34
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
        35                  40                  45

Thr Lys Ser Glu His Met Val Asp Leu Lys Lys Phe Lys Arg Ile
 50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Met Leu Phe His Gly Pro Asn Glu
        195                 200                 205

Asn His Leu Asp Ser Leu Val Ala Gln Ala Leu Phe Gly Asp Gly Ala
210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
290                 295                 300

```
Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
            325                 330                 335

Ser Glu Tyr Gly Asn Leu Ile Ser Ala Cys Val Leu Phe Ile Ile Asp
        340                 345                 350

Glu Val Arg Lys Arg Ser Met Ala Glu Gly Lys Ser Thr Thr Gly Glu
    355                 360                 365

Gly Leu Asp Cys Gly Val Leu Phe Gly Phe Gly Pro Gly Met Thr Val
370                 375                 380

Glu Thr Val Val Leu Arg Ser Val Arg Val Thr Ala Ala Val Ala Asn
385                 390                 395                 400

Gly Asn

<210> SEQ ID NO 35
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
        35                  40                  45

Thr Lys Ser Glu His Met Val Asp Leu Lys Glu Lys Phe Lys Arg Ile
    50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
    130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Leu Leu Phe His Gly Pro Asn Glu
        195                 200                 205

Asn His Leu Asp Ser Leu Val Ala Gln Ala Leu Phe Gly Asp Gly Ala
    210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255
```

```
Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
            275                 280                 285

Glu Lys Ala Leu Ser Pro Leu Gly Ile Thr Asp Trp Asn Ser Val Phe
            290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Cys Val Leu Phe Ile Ile Asp
            340                 345                 350

Glu Val Arg Lys Arg Ser Met Ala Glu Gly Lys Ser Thr Thr Gly Glu
            355                 360                 365

Gly Leu Asp Cys Gly Val Leu Phe Gly Phe Gly Pro Gly Met Thr Val
            370                 375                 380

Glu Thr Val Val Leu Arg Ser Val Arg Val Thr Ala Ala Val Ala Asn
385                 390                 395                 400

Gly Asn

<210> SEQ ID NO 36
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
            35                  40                  45

Thr Lys Ser Glu His Met Val Asp Leu Lys Glu Lys Phe Lys Arg Ile
        50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
            115                 120                 125

Ile Thr His Leu Ile Phe Cys Thr Thr Ala Gly Val Asp Met Pro Gly
            130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Ile Met Phe His Gly Pro Asn Glu
            195                 200                 205
```

Asn His Leu Asp Ser Leu Val Ala Gln Ala Leu Phe Gly Asp Gly Ala
            210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Cys Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Cys Gly Val Leu Phe Gly Phe Gly Pro Gly Met Thr Val
370                 375                 380

Glu Thr Val Val Leu Arg Ser Val Arg Val Thr Ala Ala Val Ala Asn
385                 390                 395                 400

Gly Asn

<210> SEQ ID NO 37
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
        35                  40                  45

Thr Lys Ser Glu His Met Val Asp Leu Lys Glu Lys Phe Lys Arg Ile
50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Ile Gly Phe His Gly Pro Asn Glu
        195                 200                 205

Asn His Leu Asp Ser Leu Val Ala Gln Ala Leu Phe Gly Asp Gly Ala
    210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Leu Lys Asn His Leu Arg Glu Gly Gly Leu Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
    290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Cys Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Cys Gly Val Leu Phe Gly Phe Gly Pro Gly Met Thr Val
    370                 375                 380

Glu Thr Val Val Leu Arg Ser Val Arg Val Thr Ala Ala Val Ala Asn
385                 390                 395                 400

Gly Asn

<210> SEQ ID NO 38
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
        35                  40                  45

Thr Lys Ser Glu His Met Val Asp Leu Lys Glu Lys Phe Lys Arg Ile
    50                  55                  60

Ser Glu Lys Thr Ala Ile Lys Lys Arg Tyr Leu Ala Leu Thr Glu Asp
65                  70                  75                  80

Tyr Leu Gln Glu Asn Pro Thr Met Ser Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
            115                 120                 125

Ile Thr His Leu Ile Phe Cys Thr Thr Ala Gly Val Asp Met Pro Gly
        130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Ser Ser Glu Ile Thr Ala Ile Gly Phe His Gly Pro Asn Glu
        195                 200                 205

Asn His Leu Asp Ser Leu Val Ala Gln Ala Leu Phe Gly Asp Gly Ala
    210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Leu Lys Asn His Leu Arg Glu Gly Gly Leu Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
    290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Ala Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Ser Gly Val Leu Phe Gly Phe Gly Pro Gly Met Thr Val
    370                 375                 380

Glu Thr Val Val Leu Arg Ser Val Arg Val Thr Ala Ala Val Ala Asn
385                 390                 395                 400

Gly Asn

<210> SEQ ID NO 39
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
        35                  40                  45

Thr Lys Ser Glu His Met Val Asp Leu Lys Glu Lys Phe Lys Arg Ile
    50                  55                  60

Cys Glu Lys Thr Ala Ile Lys Lys Arg Tyr Leu Ala Leu Thr Glu Asp
 65                  70                  75                  80

Tyr Leu Gln Glu Asn Pro Thr Met Cys Glu Phe Met Ala Pro Ser Leu
                 85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
    130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Ile Gly Phe His Gly Pro Asn Glu
        195                 200                 205

Asn His Leu Asp Ser Leu Val Ala Gln Ala Leu Phe Gly Asp Gly Ala
    210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
    290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Cys Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Cys Gly Val Leu Phe Gly Phe Gly Pro Gly Met Thr Val
    370                 375                 380

Glu Thr Val Val Leu Arg Ser Val Arg Val Thr Ala Ala Val Ala Asn
385                 390                 395                 400

Gly Asn

<210> SEQ ID NO 40
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
        20                  25                  30

Pro Asn Ser Val Ala Gln Ala Asp Tyr Ala Asp Tyr Tyr Phe Arg Val
            35                  40                  45

Thr Lys Ser Glu His Met Val Asp Leu Lys Lys Phe Lys Arg Ile
 50                  55                  60

Cys Glu Lys Thr Ala Ile Lys Lys Arg Tyr Leu Ala Leu Thr Glu Asp
 65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
            115                 120                 125

Ile Thr His Leu Ile Phe Cys Thr Thr Ala Gly Val Asp Met Pro Gly
 130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Ile Leu Phe His Gly Pro Asn Glu
            195                 200                 205

Asn His Leu Asp Ser Leu Val Ala Gln Ala Leu Phe Gly Asp Gly Ala
 210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Leu Lys Asn His Leu Arg Glu Gly Gly Leu Thr Phe Gln Leu
            260                 265                 270

His Arg Asp Val Pro Leu Met Val Ala Lys Asn Ile Glu Asn Ala Ala
            275                 280                 285

Glu Lys Ala Leu Ser Pro Leu Gly Ile Thr Asp Trp Asn Ser Val Phe
290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Cys Val Leu Phe Ile Ile Asp
            340                 345                 350

Glu Val Arg Lys Arg Ser Met Ala Glu Gly Lys Ser Thr Thr Gly Glu
            355                 360                 365

Gly Leu Asp Cys Gly Val Leu Phe Gly Phe Gly Pro Gly Met Thr Val
            370                 375                 380

Glu Thr Val Val Leu Arg Ser Val Arg Val Thr Ala Ala Val Ala Asn
385                 390                 395                 400

Gly Asn

<210> SEQ ID NO 41
<211> LENGTH: 402
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 41

```
Met Gly Ser Tyr Ser Ser Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
            35                  40                  45

Thr Lys Ser Glu His Met Val Asp Leu Lys Glu Lys Phe Lys Arg Ile
50                      55                      60

Ser Glu Lys Thr Ala Ile Lys Lys Arg Tyr Leu Ala Leu Thr Glu Asp
65                  70                  75                  80

Tyr Leu Gln Glu Asn Pro Thr Met Ser Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
            115                 120                 125

Ile Thr His Leu Ile Phe Cys Thr Thr Ala Gly Val Asp Met Pro Gly
130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Ser Ser Glu Ile Thr Ala Ile Gly Phe His Gly Pro Asn Glu
            195                 200                 205

Asn His Leu Asp Ser Leu Val Ala Gln Ala Leu Phe Gly Asp Gly Ala
210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
            275                 280                 285

Glu Lys Ala Leu Ser Pro Leu Gly Ile Thr Asp Trp Asn Ser Val Phe
290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Ala Val Leu Phe Ile Ile Asp
            340                 345                 350

Glu Val Arg Lys Arg Ser Met Ala Glu Gly Lys Ser Thr Thr Gly Glu
            355                 360                 365

Gly Leu Asp Ser Gly Val Leu Phe Gly Phe Gly Pro Gly Met Thr Val
370                 375                 380
```

Glu Thr Val Val Leu Arg Ser Val Arg Val Thr Ala Ala Val Ala Asn
385                 390                 395                 400

Gly Asn

<210> SEQ ID NO 42
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
        35                  40                  45

Thr Lys Ser Glu His Met Val Asp Leu Lys Glu Lys Phe Lys Arg Ile
    50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Ile Leu Phe His Gly Pro Asn Glu
        195                 200                 205

Asn His Leu Asp Ser Leu Val Ala Gln Ala Leu Phe Gly Asp Gly Ala
210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

```
Ser Glu Tyr Gly Asn Leu Ile Ser Ala Cys Val Leu Phe Ile Ile Asp
            340                 345                 350

Glu Val Arg Lys Arg Ser Met Ala Gly Lys Ser Thr Thr Gly Glu
        355                 360                 365

Gly Leu Asp Cys Gly Val Leu Phe Gly Phe Gly Pro Gly Met Thr Val
        370                 375                 380

Glu Thr Val Val Leu Arg Ser Val Arg Val Thr Ala Ala Val Ala Asn
385                 390                 395                 400

Gly Asn

<210> SEQ ID NO 43
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
        35                  40                  45

Thr Lys Ser Glu His Met Val Asp Leu Lys Glu Lys Phe Lys Arg Ile
    50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Leu Ala Gly Val Asp Met Pro Gly
    130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Ile Phe Phe His Gly Pro Asn Glu
        195                 200                 205

Asn His Leu Asp Ser Leu Val Ala Gln Ala Leu Phe Gly Asp Gly Ala
    210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Met Thr Phe Gln Leu
            260                 265                 270

His Arg Asp Val Pro Leu Met Val Ala Lys Asn Ile Glu Asn Ala Ala
        275                 280                 285
```

```
Glu Lys Ala Leu Ser Pro Leu Gly Ile Thr Asp Trp Asn Ser Val Phe
290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Cys Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Cys Gly Val Leu Phe Gly Phe Gly Pro Gly Met Thr Val
    370                 375                 380

Glu Thr Val Val Leu Arg Ser Val Arg Val Thr Ala Ala Val Ala Asn
385                 390                 395                 400

Gly Asn

<210> SEQ ID NO 44
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
        35                  40                  45

Thr Lys Ser Glu His Met Val Asp Leu Lys Glu Lys Phe Lys Arg Ile
    50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Met Ala Gly Val Asp Met Pro Gly
130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Ile Phe Phe His Gly Pro Asn Glu
        195                 200                 205

Asn His Leu Asp Ser Leu Val Ala Gln Ala Leu Phe Gly Asp Gly Ala
    210                 215                 220

Ala Ala Leu Ile Val Gly Ser Gly Pro His Leu Ala Val Glu Arg Pro
225                 230                 235                 240
```

```
Ile Phe Glu Ile Val Ser Thr Asp Gln Thr Ile Leu Pro Asp Thr Glu
                245                 250                 255

Lys Ala Met Lys Leu His Leu Arg Glu Gly Gly Met Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
    290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Phe Ser Ala Cys Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Cys Gly Val Leu Phe Gly Phe Gly Pro Gly Met Thr Val
    370                 375                 380

Glu Thr Val Val Leu Arg Ser Val Arg Val Thr Ala Ala Val Ala Asn
385                 390                 395                 400

Gly Asn

<210> SEQ ID NO 45
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
        35                  40                  45

Thr Lys Ser Glu His Met Val Asp Leu Lys Glu Lys Phe Lys Arg Ile
    50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
    130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190
```

-continued

Ile Val Cys Ser Glu Ile Thr Ala Ile Phe Phe His Gly Pro Asn Glu
            195                 200                 205

Asn His Leu Asp Ser Leu Val Ala Gln Ala Leu Phe Gly Asp Gly Ala
        210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Met Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Phe Ser Ala Cys Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Cys Gly Val Leu Phe Gly Phe Gly Pro Gly Met Thr Val
370                 375                 380

Glu Thr Val Val Leu Arg Ser Val Arg Val Thr Ala Ala Val Ala Asn
385                 390                 395                 400

Gly Asn

<210> SEQ ID NO 46
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
        35                  40                  45

Thr Lys Ser Glu His Met Val Asp Leu Lys Glu Lys Phe Lys Arg Ile
    50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
    130                 135                 140

```
Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Ile Leu Phe His Gly Pro Asn Glu
        195                 200                 205

Asn His Leu Asp Ser Leu Val Ala Gln Ala Leu Phe Gly Asp Gly Ala
    210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Cys Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Ser Gly Val Leu Phe Gly Phe Gly Pro Gly Met Thr Val
    370                 375                 380

Glu Thr Val Val Leu Arg Ser Val Arg Val Thr Ala Ala Val Ala Asn
385                 390                 395                 400

Gly Asn

<210> SEQ ID NO 47
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Gly Ser Tyr Ser Ser Asp Val Glu Val Ile Arg Glu Ala Gly
1               5                   10                  15

Arg Ala Gln Gly Leu Ala Thr Ile Leu Ala Ile Gly Thr Ala Thr Pro
                20                  25                  30

Pro Asn Ser Val Ala Gln Ala Asp Tyr Ala Asp Tyr Tyr Phe Arg Val
            35                  40                  45

Thr Lys Ser Glu His Met Val Asp Leu Lys Glu Lys Phe Lys Arg Ile
        50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
                85                  90                  95
```

```
Asn Ala Arg Gln Asp Leu Val Val Thr Gly Val Pro Met Leu Gly Lys
                100                 105                 110

Glu Ala Ala Val Lys Ala Ile Asp Glu Trp Gly Leu Pro Lys Ser Lys
            115                 120                 125

Ile Thr His Leu Ile Phe Cys Thr Thr Ala Gly Val Asp Met Pro Gly
        130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Ile Leu Phe His Gly Pro Asn Glu
        195                 200                 205

Asn His Leu Asp Ser Leu Val Ala Gln Ala Leu Phe Gly Asp Gly Ala
210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Cys Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Ala Gly Val Leu Phe Gly Phe Gly Pro Gly Met Thr Val
370                 375                 380

Glu Thr Val Val Leu Arg Ser Val Arg Val Thr Ala Ala Val Ala Asn
385                 390                 395                 400

Gly Asn

<210> SEQ ID NO 48
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
        35                  40                  45
```

```
Thr Lys Ser Glu His Met Val Asp Leu Lys Glu Lys Phe Lys Arg Ile
 50                  55                  60

Cys Glu Lys Thr Ala Ile Lys Lys Arg Tyr Leu Ala Leu Thr Glu Asp
 65                  70                  75                  80

Tyr Leu Gln Glu Asn Pro Thr Met Cys Glu Phe Met Ala Pro Ser Leu
                 85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
    130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Ile Leu Phe His Gly Pro Asn Glu
        195                 200                 205

Asn His Leu Asp Ser Leu Val Ala Gln Ala Leu Phe Gly Asp Gly Ala
    210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
    290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Ser Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Cys Gly Val Leu Phe Gly Phe Gly Pro Gly Met Thr Val
    370                 375                 380

Glu Thr Val Val Leu Arg Ser Val Arg Val Thr Ala Ala Val Ala Asn
385                 390                 395                 400

Gly Asn

<210> SEQ ID NO 49
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49
```

```
Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
                35                  40                  45

Thr Lys Ser Glu His Met Val Asp Leu Lys Glu Lys Phe Lys Arg Ile
    50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
            115                 120                 125

Ile Thr His Leu Ile Phe Cys Thr Thr Ala Gly Val Asp Met Pro Gly
    130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Ile Leu Phe His Gly Pro Asn Glu
    195                 200                 205

Asn His Leu Asp Ser Leu Val Ala Gln Ala Leu Phe Gly Asp Gly Ala
    210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
    275                 280                 285

Glu Lys Ala Leu Ser Pro Leu Gly Ile Thr Asp Trp Asn Ser Val Phe
            290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Ala Val Leu Phe Ile Ile Asp
            340                 345                 350

Glu Val Arg Lys Arg Ser Met Ala Glu Gly Lys Ser Thr Thr Gly Glu
    355                 360                 365

Gly Leu Asp Cys Gly Val Leu Phe Gly Phe Gly Pro Gly Met Thr Val
    370                 375                 380

Glu Thr Val Val Leu Arg Ser Val Arg Val Thr Ala Ala Val Ala Asn
385                 390                 395                 400

Gly Asn
```

<210> SEQ ID NO 50

```
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50
```

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
        35                  40                  45

Thr Lys Ser Glu His Met Val Asp Leu Lys Glu Lys Phe Lys Arg Ile
    50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
    130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Ser Ser Glu Ile Thr Ala Ile Leu Phe His Gly Pro Asn Glu
        195                 200                 205

Asn His Leu Asp Ser Leu Val Ala Gln Ala Leu Phe Gly Asp Gly Ala
    210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
    290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Cys Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Cys Gly Val Leu Phe Gly Phe Gly Pro Gly Met Thr Val

```
            370                 375                 380
Glu Thr Val Val Leu Arg Ser Val Arg Val Thr Ala Ala Val Ala Asn
385                 390                 395                 400

Gly Asn

<210> SEQ ID NO 51
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
                20                  25                  30

Pro Asn Ser Val Ala Gln Ala Asp Tyr Ala Asp Tyr Tyr Phe Arg Val
            35                  40                  45

Thr Lys Ser Glu His Met Val Asp Leu Lys Glu Lys Phe Lys Arg Ile
50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Ala Ser Glu Ile Thr Ala Ile Leu Phe His Gly Pro Asn Glu
        195                 200                 205

Asn His Leu Asp Ser Leu Val Ala Gln Ala Leu Phe Gly Asp Gly Ala
    210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
    290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
```

```
                          325                 330                 335
Ser Glu Tyr Gly Asn Leu Ile Ser Ala Cys Val Leu Phe Ile Ile Asp
                340                 345                 350
Glu Val Arg Lys Arg Ser Met Ala Glu Gly Lys Ser Thr Thr Gly Glu
            355                 360                 365
Gly Leu Asp Cys Gly Val Leu Phe Gly Phe Gly Pro Gly Met Thr Val
        370                 375                 380
Glu Thr Val Val Leu Arg Ser Val Arg Val Thr Ala Ala Val Ala Asn
385                 390                 395                 400

Gly Asn

<210> SEQ ID NO 52
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Gly Ser Tyr Ser Ser Asp Asp Val Glu Val Ile Arg Glu Ala Gly
1               5                   10                  15
Arg Ala Gln Gly Leu Ala Thr Ile Leu Ala Ile Gly Thr Ala Thr Pro
                20                  25                  30
Pro Asn Ser Val Ala Gln Ala Asp Tyr Ala Asp Tyr Tyr Phe Arg Val
            35                  40                  45
Thr Lys Ser Glu His Met Val Asp Leu Lys Glu Lys Phe Lys Arg Ile
        50                  55                  60
Cys Glu Lys Thr Ala Ile Lys Lys Arg Tyr Leu Ala Leu Thr Glu Asp
65                  70                  75                  80
Tyr Leu Gln Glu Asn Pro Thr Met Cys Glu Phe Met Ala Pro Ser Leu
                85                  90                  95
Asn Ala Arg Gln Asp Leu Val Val Thr Gly Val Pro Met Leu Gly Lys
            100                 105                 110
Glu Ala Ala Val Lys Ala Ile Asp Glu Trp Gly Leu Pro Lys Ser Lys
        115                 120                 125
Ile Thr His Leu Ile Phe Ser Thr Thr Ala Gly Val Asp Met Pro Gly
    130                 135                 140
Ala Asp Tyr Gln Leu Val Lys Leu Leu Gly Leu Ser Pro Ser Val Lys
145                 150                 155                 160
Arg Tyr Met Leu Tyr Gln Gln Gly Cys Ala Ala Gly Gly Thr Val Leu
                165                 170                 175
Arg Leu Ala Lys Asp Leu Ala Glu Asn Asn Lys Gly Ser Arg Val Leu
            180                 185                 190
Ile Val Cys Ser Glu Ile Thr Ala Ile Leu Phe His Gly Pro Asn Glu
        195                 200                 205
Asn His Leu Asp Ser Leu Val Ala Gln Ala Leu Phe Gly Asp Gly Ala
    210                 215                 220
Ala Ala Leu Ile Val Gly Ser Gly Pro His Leu Ala Val Glu Arg Pro
225                 230                 235                 240
Ile Phe Glu Ile Val Ser Thr Asp Gln Thr Ile Leu Pro Asp Thr Glu
                245                 250                 255
Lys Ala Met Lys Leu His Leu Arg Glu Gly Gly Leu Thr Phe Gln Leu
            260                 265                 270
His Arg Asp Val Pro Leu Met Val Ala Lys Asn Ile Glu Asn Ala Ala
```

```
                    275                 280                 285
Glu Lys Ala Leu Ser Pro Leu Gly Ile Thr Asp Trp Asn Ser Val Phe
290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Cys Val Leu Phe Ile Ile Asp
                340                 345                 350

Glu Val Arg Lys Arg Ser Met Ala Glu Gly Lys Ser Thr Thr Gly Glu
                355                 360                 365

Gly Leu Asp Cys Gly Val Leu Phe Gly Phe Gly Pro Gly Met Thr Val
                370                 375                 380

Glu Thr Val Val Leu Arg Ser Val Arg Val Thr Ala Ala Val Ala Asn
385                 390                 395                 400

Gly Asn

<210> SEQ ID NO 53
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
                20                  25                  30

Pro Asn Ser Val Ala Gln Ala Asp Tyr Ala Asp Tyr Tyr Phe Arg Val
            35                  40                  45

Thr Lys Ser Glu His Met Val Asp Leu Lys Glu Lys Phe Lys Arg Ile
        50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
                100                 105                 110

Glu Ala Ala Val Lys Ala Ile Asp Glu Trp Gly Leu Pro Lys Ser Lys
            115                 120                 125

Ile Thr His Leu Ile Phe Ala Thr Thr Ala Gly Val Asp Met Pro Gly
        130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Thr Val Leu
                165                 170                 175

Arg Leu Ala Lys Asp Leu Ala Glu Asn Asn Lys Gly Ser Arg Val Leu
                180                 185                 190

Ile Val Cys Ser Glu Ile Thr Ala Ile Leu Phe His Gly Pro Asn Glu
            195                 200                 205

Asn His Leu Asp Ser Leu Val Ala Gln Ala Leu Phe Gly Asp Gly Ala
        210                 215                 220

Ala Ala Leu Ile Val Gly Ser Gly Pro His Leu Ala Val Glu Arg Pro
```

```
              225                 230                 235                 240
    Ile Phe Glu Ile Val Ser Thr Asp Gln Thr Ile Leu Pro Asp Thr Glu
                    245                 250                 255

Lys Ala Met Lys Leu His Leu Arg Glu Gly Leu Thr Phe Gln Leu
                    260                 265                 270

His Arg Asp Val Pro Leu Met Val Ala Lys Asn Ile Glu Asn Ala Ala
                    275                 280                 285

Glu Lys Ala Leu Ser Pro Leu Gly Ile Thr Asp Trp Asn Ser Val Phe
                290                 295                 300

Trp Met Val His Pro Gly Gly Arg Ala Ile Leu Asp Gln Val Glu Arg
    305                 310                 315                 320

Lys Leu Asn Leu Lys Glu Asp Lys Leu Arg Ala Ser Arg His Val Leu
                    325                 330                 335

Ser Glu Tyr Gly Asn Leu Ile Ser Ala Cys Val Leu Phe Ile Ile Asp
                    340                 345                 350

Glu Val Arg Lys Arg Ser Met Ala Glu Gly Lys Ser Thr Thr Gly Glu
                    355                 360                 365

Gly Leu Asp Cys Gly Val Leu Phe Gly Phe Gly Pro Gly Met Thr Val
                370                 375                 380

Glu Thr Val Val Leu Arg Ser Val Arg Val Thr Ala Ala Val Ala Asn
    385                 390                 395                 400

Gly Asn

<210> SEQ ID NO 54
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Gly Ser Tyr Ser Ser Asp Asp Val Glu Val Ile Arg Glu Ala Gly
    1               5                   10                  15

Arg Ala Gln Gly Leu Ala Thr Ile Leu Ala Ile Gly Thr Ala Thr Pro
                    20                  25                  30

Pro Asn Ser Val Ala Gln Ala Asp Tyr Ala Asp Tyr Tyr Phe Arg Val
                    35                  40                  45

Thr Lys Ser Glu His Met Val Asp Leu Lys Glu Lys Phe Lys Arg Ile
                50                  55                  60

Cys Glu Lys Thr Ala Ile Lys Lys Arg Tyr Leu Ala Leu Thr Glu Asp
    65                  70                  75                  80

Tyr Leu Gln Glu Asn Pro Thr Met Ser Glu Phe Met Ala Pro Ser Leu
                    85                  90                  95

Asn Ala Arg Gln Asp Leu Val Val Thr Gly Val Pro Met Leu Gly Lys
                    100                 105                 110

Glu Ala Ala Val Lys Ala Ile Asp Glu Trp Gly Leu Pro Lys Ser Lys
                    115                 120                 125

Ile Thr His Leu Ile Phe Cys Thr Thr Ala Gly Val Asp Met Pro Gly
                130                 135                 140

Ala Asp Tyr Gln Leu Val Lys Leu Leu Gly Leu Ser Pro Ser Val Lys
    145                 150                 155                 160

Arg Tyr Met Leu Tyr Gln Gln Gly Cys Ala Ala Gly Gly Thr Val Leu
                    165                 170                 175

Arg Leu Ala Lys Asp Leu Ala Glu Asn Asn Lys Gly Ser Arg Val Leu
```

```
                    180                 185                 190
Ile Val Cys Ser Glu Ile Thr Ala Ile Leu Phe His Gly Pro Asn Glu
                195                 200                 205

Asn His Leu Asp Ser Leu Val Ala Gln Ala Leu Phe Gly Asp Gly Ala
            210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
        290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Cys Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Cys Gly Val Leu Phe Gly Phe Gly Pro Gly Met Thr Val
    370                 375                 380

Glu Thr Val Val Leu Arg Ser Val Arg Val Thr Ala Ala Val Ala Asn
385                 390                 395                 400

Gly Asn

<210> SEQ ID NO 55
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
        35                  40                  45

Thr Lys Ser Glu His Met Val Asp Leu Lys Glu Lys Phe Lys Arg Ile
    50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Ala Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
```

```
            130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
                180                 185                 190

Ile Val Cys Ser Glu Ile Thr Ala Ile Leu Phe His Gly Pro Asn Glu
            195                 200                 205

Asn His Leu Asp Ser Leu Val Ala Gln Ala Leu Phe Gly Asp Gly Ala
        210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
                260                 265                 270

His Arg Asp Val Pro Leu Met Val Ala Lys Asn Ile Glu Asn Ala Ala
            275                 280                 285

Glu Lys Ala Leu Ser Pro Leu Gly Ile Thr Asp Trp Asn Ser Val Phe
        290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Cys Val Leu Phe Ile Ile Asp
                340                 345                 350

Glu Val Arg Lys Arg Ser Met Ala Glu Gly Lys Ser Thr Thr Gly Glu
            355                 360                 365

Gly Leu Asp Cys Gly Val Leu Phe Gly Phe Gly Pro Gly Met Thr Val
        370                 375                 380

Glu Thr Val Val Leu Arg Ser Val Arg Val Thr Ala Ala Val Ala Asn
385                 390                 395                 400

Gly Asn

<210> SEQ ID NO 56
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
                20                  25                  30

Pro Asn Ser Val Ala Gln Ala Asp Tyr Ala Asp Tyr Tyr Phe Arg Val
            35                  40                  45

Thr Lys Ser Glu His Met Val Asp Leu Lys Glu Lys Phe Lys Arg Ile
        50                  55                  60

Ser Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
```

```
                    85                  90                  95
Asn Ala Arg Gln Asp Leu Val Val Thr Gly Val Pro Met Leu Gly Lys
                100                 105                 110

Glu Ala Ala Val Lys Ala Ile Asp Glu Trp Gly Leu Pro Lys Ser Lys
            115                 120                 125

Ile Thr His Leu Ile Phe Cys Thr Thr Ala Gly Val Asp Met Pro Gly
        130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Ile Leu Phe His Gly Pro Asn Glu
        195                 200                 205

Asn His Leu Asp Ser Leu Val Ala Gln Ala Leu Phe Gly Asp Gly Ala
    210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
    290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Cys Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Cys Gly Val Leu Phe Gly Phe Gly Pro Gly Met Thr Val
    370                 375                 380

Glu Thr Val Val Leu Arg Ser Val Arg Val Thr Ala Ala Val Ala Asn
385                 390                 395                 400

Gly Asn

<210> SEQ ID NO 57
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
```

```
            35                  40                  45
Thr Lys Ser Glu His Met Val Asp Leu Lys Glu Lys Phe Lys Arg Ile
 50                  55                  60
Ala Glu Lys Thr Ala Ile Lys Lys Arg Tyr Leu Ala Leu Thr Glu Asp
 65                  70                  75                  80
Tyr Leu Gln Glu Asn Pro Thr Met Cys Glu Phe Met Ala Pro Ser Leu
                 85                  90                  95
Asn Ala Arg Gln Asp Leu Val Val Thr Gly Val Pro Met Leu Gly Lys
            100                 105                 110
Glu Ala Ala Val Lys Ala Ile Asp Glu Trp Gly Leu Pro Lys Ser Lys
        115                 120                 125
Ile Thr His Leu Ile Phe Cys Thr Thr Ala Gly Val Asp Met Pro Gly
130                 135                 140
Ala Asp Tyr Gln Leu Val Lys Leu Leu Gly Leu Ser Pro Ser Val Lys
145                 150                 155                 160
Arg Tyr Met Leu Tyr Gln Gln Gly Cys Ala Ala Gly Gly Thr Val Leu
                165                 170                 175
Arg Leu Ala Lys Asp Leu Ala Glu Asn Asn Lys Gly Ser Arg Val Leu
            180                 185                 190
Ile Val Cys Ser Glu Ile Thr Ala Ile Leu Phe His Gly Pro Asn Glu
        195                 200                 205
Asn His Leu Asp Ser Leu Val Ala Gln Ala Leu Phe Gly Asp Gly Ala
210                 215                 220
Ala Ala Leu Ile Val Gly Ser Gly Pro His Leu Ala Val Glu Arg Pro
225                 230                 235                 240
Ile Phe Glu Ile Val Ser Thr Asp Gln Thr Ile Leu Pro Asp Thr Glu
                245                 250                 255
Lys Ala Met Lys Leu His Leu Arg Glu Gly Gly Leu Thr Phe Gln Leu
            260                 265                 270
His Arg Asp Val Pro Leu Met Val Ala Lys Asn Ile Glu Asn Ala Ala
        275                 280                 285
Glu Lys Ala Leu Ser Pro Leu Gly Ile Thr Asp Trp Asn Ser Val Phe
290                 295                 300
Trp Met Val His Pro Gly Gly Arg Ala Ile Leu Asp Gln Val Glu Arg
305                 310                 315                 320
Lys Leu Asn Leu Lys Glu Asp Lys Leu Arg Ala Ser Arg His Val Leu
                325                 330                 335
Ser Glu Tyr Gly Asn Leu Ile Ser Ala Cys Val Leu Phe Ile Ile Asp
            340                 345                 350
Glu Val Arg Lys Arg Ser Met Ala Glu Gly Lys Ser Thr Thr Gly Glu
        355                 360                 365
Gly Leu Asp Cys Gly Val Leu Phe Gly Phe Gly Pro Gly Met Thr Val
370                 375                 380
Glu Thr Val Val Leu Arg Ser Val Arg Val Thr Ala Ala Val Ala Asn
385                 390                 395                 400
Gly Asn

<210> SEQ ID NO 58
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 58

```
Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
        35                  40                  45

Thr Lys Ser Glu His Met Val Asp Leu Lys Lys Phe Lys Arg Ile
    50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
    130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Ser Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Ile Leu Phe His Gly Pro Asn Glu
        195                 200                 205

Asn His Leu Asp Ser Leu Val Ala Gln Ala Leu Phe Gly Asp Gly Ala
    210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
    290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Cys Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Cys Gly Val Leu Phe Gly Phe Gly Pro Gly Met Thr Val
    370                 375                 380

Glu Thr Val Val Leu Arg Ser Val Arg Val Thr Ala Ala Val Ala Asn
385                 390                 395                 400

Gly Asn
```

-continued

<210> SEQ ID NO 59
<211> LENGTH: 402
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 59

```
Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
        35                  40                  45

Thr Lys Ser Glu His Met Val Asp Leu Lys Glu Lys Phe Lys Arg Ile
    50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
    130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Ile Leu Phe His Gly Pro Asn Glu
        195                 200                 205

Asn His Leu Asp Ser Leu Val Ala Gln Ala Leu Phe Gly Asp Gly Ala
    210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
    290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly His Leu Ile Ser Ala Cys Val Leu Phe Ile Ile Asp
            340                 345                 350

Glu Val Arg Lys Arg Ser Met Ala Glu Gly Lys Ser Thr Thr Gly Glu
        355                 360                 365
```

```
Gly Leu Asp Cys Gly Val Leu Phe Gly Phe Gly Pro Gly Met Thr Val
        370                 375                 380

Glu Thr Val Val Leu Arg Ser Val Arg Val Thr Ala Ala Val Ala Asn
385                 390                 395                 400

Gly Asn

<210> SEQ ID NO 60
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
        35                  40                  45

Thr Lys Ser Glu His Met Val Asp Leu Lys Glu Lys Phe Lys Arg Ile
    50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
    130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Ile Leu Phe His Gly Pro Asn Glu
        195                 200                 205

Asn His Leu Asp Ser Leu Val Ala Gln Ala Leu Phe Gly Asp Gly Ala
    210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
    290                 295                 300

Trp Met Val Gln Pro Gly Gly Arg Ala Ile Leu Asp Gln Val Glu Arg
305                 310                 315                 320
```

```
Lys Leu Asn Leu Lys Glu Asp Lys Leu Arg Ala Ser Arg His Val Leu
            325                 330                 335

Ser Glu Tyr Gly Asn Leu Ile Ser Ala Cys Val Leu Phe Ile Ile Asp
            340                 345                 350

Glu Val Arg Lys Arg Ser Met Ala Glu Gly Lys Ser Thr Thr Gly Glu
            355                 360                 365

Gly Leu Asp Cys Gly Val Leu Phe Gly Phe Gly Pro Gly Met Thr Val
            370                 375                 380

Glu Thr Val Val Leu Arg Ser Val Arg Val Thr Ala Ala Val Ala Asn
385                 390                 395                 400

Gly Asn

<210> SEQ ID NO 61
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
            35                  40                  45

Thr Lys Ser Glu His Met Val Asp Leu Lys Glu Lys Phe Lys Arg Ile
50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
            85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
            115                 120                 125

Ile Thr His Leu Ile Phe Cys Thr Thr Ala Gly Val Asp Met Pro Gly
            130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
            165                 170                 175

Arg Leu Ala Lys Asp Leu Ala Glu Asn Asn Lys Gly Ser Arg Val Leu
            180                 185                 190

Ile Val Cys Ser Glu Ile Thr Ala Ile Phe Phe His Gly Pro Asn Glu
            195                 200                 205

Asn His Leu Asp Ser Leu Val Ala Gln Ala Leu Phe Gly Asp Gly Ala
            210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
            245                 250                 255

Lys Ala Met Lys Leu His Leu Arg Glu Gly Gly Phe Thr Phe Gln Leu
            260                 265                 270
```

His Arg Asp Val Pro Leu Met Val Ala Lys Asn Ile Glu Asn Ala Ala
            275                 280                 285

Glu Lys Ala Leu Ser Pro Leu Gly Ile Thr Asp Trp Asn Ser Val Phe
        290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Cys Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Cys Gly Val Leu Phe Gly Phe Gly Pro Gly Met Thr Val
370                 375                 380

Glu Thr Val Val Leu Arg Ser Val Arg Val Thr Ala Ala Val Ala Asn
385                 390                 395                 400

Gly Asn

<210> SEQ ID NO 62
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Ser Val Ala Gln Ala Asp Tyr Ala Asp Tyr Tyr Phe Arg Val
        35                  40                  45

Thr Lys Ser Glu His Met Val Asp Leu Lys Glu Lys Phe Lys Arg Ile
    50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Ile Leu Phe His Gly Pro Asn Glu
        195                 200                 205

Asn His Leu Asp Ser Leu Val Ala Gln Ala Leu Phe Gly Asp Gly Ala
210                 215                 220

```
Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Met Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
    290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Met Ser Ala Cys Val Leu Phe Ile Ile Asp
            340                 345                 350

Glu Val Arg Lys Arg Ser Met Ala Glu Gly Lys Ser Thr Thr Gly Glu
        355                 360                 365

Gly Leu Asp Cys Gly Val Leu Phe Gly Phe Gly Pro Gly Met Thr Val
    370                 375                 380

Glu Thr Val Val Leu Arg Ser Val Arg Val Thr Ala Ala Val Ala Asn
385                 390                 395                 400

Gly Asn

<210> SEQ ID NO 63
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
                20                  25                  30

Pro Asn Ser Val Ala Gln Ala Asp Tyr Ala Asp Tyr Tyr Phe Arg Val
            35                  40                  45

Thr Lys Ser Glu His Met Val Asp Leu Lys Glu Lys Phe Lys Arg Ile
        50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
    130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175
```

Arg Leu Ala Lys Asp Leu Ala Glu Asn Asn Lys Gly Ser Arg Val Leu
            180                 185                 190

Ile Val Cys Ser Glu Ile Thr Ala Ile Phe Phe His Gly Pro Asn Glu
            195                 200                 205

Asn His Leu Asp Ser Leu Val Ala Gln Ala Leu Phe Gly Asp Gly Ala
            210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Met Thr Phe Gln Leu
            260                 265                 270

His Arg Asp Val Pro Leu Met Val Ala Lys Asn Ile Glu Asn Ala Ala
            275                 280                 285

Glu Lys Ala Leu Ser Pro Leu Gly Ile Thr Asp Trp Asn Ser Val Phe
            290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
                325                 330                 335

Ser Glu Tyr Gly Asn Leu Ile Ser Ala Cys Val Leu Phe Ile Ile Asp
            340                 345                 350

Glu Val Arg Lys Arg Ser Met Ala Glu Gly Lys Ser Thr Thr Gly Glu
            355                 360                 365

Gly Leu Asp Cys Gly Val Leu Phe Gly Phe Gly Pro Gly Met Thr Val
            370                 375                 380

Glu Thr Val Val Leu Arg Ser Val Arg Val Thr Ala Ala Val Ala Asn
385                 390                 395                 400

Gly Asn

<210> SEQ ID NO 64
<211> LENGTH: 1209
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
atgggatctt actcatccga tgatgtggag gtgattcgtg aggccggacg ggcacaaggt    60
ttagccacga ttcttgccat tggcactgct actcctccca attgcgtcgc tcaagctgat   120
tatgcagact attattttcg tgtcactaag agcgaacata tggttgatct aaaagagaaa   180
tttaaacgca tttgtgagaa aacagcgata agaaacgat acctagccct caccgaagac   240
tatctgcaag agaacccaac aatgtgtgag ttcatggctc catccttaaa cgctcgacaa   300
gacctagtgg tcaccggcgt cccaatgctt ggcaaagaag ccgcagtcaa ggccattgat   360
gaatggggac taccaaaatc caagatcacc cacctcatct tctgcaccac cgctggcgtt   420
gacatgcccg tgctgactac tcaactcgtc aaactccttg tctctccccc ttcagtcaaa   480
cgctatatgt tgtaccaaca gggagctgcc gccggcggca cagtcctccg gctagccaag   540
gaccttgctg aaaacaacaa gggctcacga gtccttatcg tctgctccga gatcactgct   600
atcttattcc atggacccaa tgagaaccac cttgactcac tcgtcgctca agctttattc   660
ggagacggag ctgcagcact cattgtgggt tcaggccctc acttggccgt agaacggcca   720

```
atattcgaga tcgtgtcaac tgatcaaaca atcttgccgg acactgagaa ggcaatgaag    780
ttacacttga gagagggagg gttgacgttt cagttgcata gagatgtacc cttgatggtc    840
gcaaagaaca tagagaacgc agcggagaaa gcgttgtctc cactagggat aactgattgg    900
aactcagttt tctggatggt gcacccaggt ggtcgagcca tattggacca ggtggagcga    960
aaactaaacc ttaaggaaga taagttaagg gctagcaggc atgtgcttag tgaatacgga   1020
aacctgatta gcgcttgtgt gttgttcatc attgacgagg tgaggaagag atctatggcg   1080
gaagggaaga gtacaaccgg tgaaggtttg gattgcggtg ttttgtttgg atttggaccg   1140
ggtatgactg ttgagactgt tgttcttcgt agcgtccgcg ttactgctgc ggttgccaat   1200
ggaaactga                                                          1209
```

<210> SEQ ID NO 65
<211> LENGTH: 1209
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65

```
atgggatctt actcatccga tgatgtggag gtgattcgtg aggccggacg ggcacaaggt     60
ttagccacga ttcttgccat tggcactgct actcctccca atgccgtcgc tcaagctgat    120
tatgcagact attattttcg tgtcactaag agcgaacata tggttgatct taaagagaaa    180
tttaaacgca tttgtgagaa aacagcgata aagaaacgat acctagccct caccgaagac    240
tatctgcaag agaacccaac aatgtgtgag ttcatggctc catccttaaa cgctcgacaa    300
gacctagtgg tcaccggcgt cccaatgctt ggcaaagaag ccgcagtcaa ggccattgat    360
gaatggggac taccaaaatc caagatcacc cacctcatct tctgcaccac cgctggcgtt    420
gacatgcccg tgctgactga tcaactcgtc aaactccttg gtctctcccc ttcagtcaaa    480
cgctatatgt tgtaccaaca gggatgtgcc gccggcggca cagtcctccg gctagccaag    540
gaccttgctg aaaacaacaa gggctcacga gtccttatcg tctgctccga gatcactgct    600
atcttattcc atggacccaa tgagaaccac cttgactcac tcgtcgctca gctttattc    660 ggagacggag ctgcagcact cattgtgggt tcaggccctc acttggccgt agaacggcca    720
atattcgaga tcgtgtcaac tgatcaaaca atcttgccgg acactgagaa ggcaatgaag    780
ttacacttga gagagggagg gttgacgttt cagttgcata gagatgtacc cttgatggtc    840
gcaaagaaca tagagaacgc agcggagaaa gcgttgtctc cactagggat aactgattgg    900
aactcagttt tctggatggt gcacccaggt ggtcgagcca tattggacca ggtggagcga    960
aaactaaacc ttaaggaaga taagttaagg gctagcaggc atgtgcttag tgaatacgga   1020
aacctgatta gcgcttgtgt gttgttcatc attgacgagg tgaggaagag atctatggcg   1080
gaagggaaga gtacaaccgg tgaaggtttg gattgcggtg ttttgtttgg atttggaccg   1140
ggtatgactg ttgagactgt tgttcttcgt agcgtccgcg ttactgctgc ggttgccaat   1200
ggaaactga                                                          1209
```

<210> SEQ ID NO 66
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 66

| | | | | | |
|---|---|---|---|---|---|
| atgggatctt | actcatccga | tgatgtggag | gtgattcgtg | aggccggacg | ggcacaaggt | 60 |
| ttagccacga | ttcttgccat | tggcactgct | actcctccca | attgcgtcgc | tcaagctgat | 120 |
| tatgcagact | attattttcg | tgtcactaag | agcgaacata | tggttgatct | taaagagaaa | 180 |
| tttaaacgca | tttgtgagaa | aacagcgata | aagaaacgat | acctagccct | caccgaagac | 240 |
| tatctgcaag | agaacccaac | aatgtgtgag | ttcatggctc | catccttaaa | cgctcgacaa | 300 |
| gacctagtgg | tcaccggcgt | cccaatgctt | ggcaaagaag | ccgcagtcaa | ggccattgat | 360 |
| gaatggggac | taccaaaatc | caagatcacc | cacctcatct | tctgcaccac | cgctggcgtt | 420 |
| gacatgcccg | gtgctgacta | tcaactcgtc | aaactccttg | gtctctcccc | ttcagtcaaa | 480 |
| cgctatatgt | tgtaccaaca | gggatgtgcc | gccggcggca | cagtcctccg | gctagccaag | 540 |
| gaccttgctg | aaaacaacaa | gggctcacga | gtccttatcg | tctgctccga | gatcactgct | 600 |
| atcttcttcc | atggacccaa | tgagaaccac | cttgactcac | tcgtcgctca | agctttattc | 660 |
| ggagacggag | ctgcagcact | cattgtgggt | tcaggccctc | acttggccgt | agaacggcca | 720 |
| atattcgaga | tcgtgtcaac | tgatcaaaca | atcttgccgg | acactgagaa | ggcaatgaag | 780 |
| ttacacttga | gagggaggg | gttgacgttt | cagttgcata | gagatgtacc | cttgatggtc | 840 |
| gcaaagaaca | tagagaacgc | agcggagaaa | gcgttgtctc | cactagggat | aactgattgg | 900 |
| aactcagttt | tctggatggt | gcacccaggt | ggtcgagcca | tattggacca | ggtggagcga | 960 |
| aaactaaacc | ttaaggaaga | taagttaagg | gctagcaggc | atgtgcttag | tgaatacgga | 1020 |
| aacctgatta | gcgcttgtgt | gttgttcatc | attgacgagg | tgaggaagag | atctatggcg | 1080 |
| gaagggaaga | gtacaaccgg | tgaaggtttg | gattgcggtg | ttttgtttgg | atttggaccg | 1140 |
| ggtatgactg | ttgagactgt | tgttcttcgt | agcgtccgcg | ttactgctgc | ggttgccaat | 1200 |
| ggaaactga | | | | | 1209 |

<210> SEQ ID NO 67
<211> LENGTH: 1209
<212> TYPE: DNA
<213> ORGANISM: Artificial Sequence
<220> FEATURE:
<223> OTHER INFORMATION: Description of Artificial Sequence: Synthetic
   polynucleotide

<400> SEQUENCE: 67

| | | | | | |
|---|---|---|---|---|---|
| atgggatctt | actcatccga | tgatgtggag | gtgattcgtg | aggccggacg | ggcacaaggt | 60 |
| ttagccacga | ttcttgccat | tggcactgct | actcctccca | attgcgtcgc | tcaagctgat | 120 |
| tatgcagact | attattttcg | tgtcactaag | agcgaacata | tggttgatct | taaagagaaa | 180 |
| tttaaacgca | tttgtgagaa | aacagcgata | aagaaacgat | acctagccct | caccgaagac | 240 |
| tatctgcaag | agaacccaac | aatgtgtgag | ttcatggctc | catccttaaa | cgctcgacaa | 300 |
| gacctagtgg | tcaccggcgt | cccaatgctt | ggcaaagaag | ccgcagtcaa | ggccattgat | 360 |
| gaatggggac | taccaaaatc | caagatcacc | cacctcatct | tctgcaccac | cgctggcgtt | 420 |
| gacatgcccg | gtgctgacta | tcaactcgtc | aaactccttg | gtctctcccc | ttcagtcaaa | 480 |
| cgctatatgt | tgtaccaaca | gggatgtgcc | gccggcggca | cagtcctccg | gctagccaag | 540 |
| gaccttgctg | aaaacaacaa | gggctcacga | gtccttatcg | tctgctccga | gatcactgct | 600 |
| atcttattcc | atggacccaa | tgagaaccac | cttgactcac | tcgtcgctca | agctttattc | 660 |

```
ggagacggag ctgcagcact cattgtgggt tcaggccctc acttggccgt agaacggcca    720
atattcgaga tcgtgtcaac tgatcaaaca atcttgccgg acactgagaa ggcaatgaag    780
ttacacttga gagagggagg gttcacgttt cagttgcata gagatgtacc cttgatggtc    840
gcaaagaaca tagagaacgc agcggagaaa gcgttgtctc cactagggat aactgattgg    900
aactcagttt tctggatggt gcacccaggt ggtcgagcca tattggacca ggtggagcga    960
aaactaaacc ttaaggaaga taagttaagg gctagcaggc atgtgcttag tgaatacgga   1020
aacctgatta gcgcttgtgt gttgttcatc attgacgagg tgaggaagag atctatggcg   1080
gaagggaaga gtacaaccgg tgaaggtttg gattgcggtg ttttgtttgg atttggaccg   1140
ggtatgactg ttgagactgt tgttcttcgt agcgtccgcg ttactgctgc ggttgccaat   1200
ggaaactga                                                           1209

<210> SEQ ID NO 68
<211> LENGTH: 1209
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
atgggatctt actcatccga tgatgtggag gtgattcgtg aggccggacg ggcacaaggt     60
ttagccacga ttcttgccat tggcactgct actcctccca attgcgtcgc tcaagctgat    120
tatgcagact attattttcg tgtcactaag agcgaacata tggttgatct aaagagaaa    180 tttaaacgca tttgtgagaa acagcgata aagaaacgat acctagccct caccgaagac    240
tatctgcaag agaacccaac aatgtgtgag ttcatggctc catccttaaa cgctcgacaa    300
gacctagtgg tcaccggcgt cccaatgctt ggcaaagaag ccgcagtcaa ggccattgat    360
gaatggggac taccaaaatc caagatcacc cacctcatct tctgcaccac cgctggcgtt    420
gacatgcccg gtgctgacta tcaactcgtc aaactccttg gtctctcccc ttcagtcaaa    480
cgctatatgt tgtaccaaca gggatgtgcc gccggcggca cagtcctccg gctagccaag    540
gaccttgctg aaaacaacaa gggctcacga gtccttatcg tctgctccga gatcactgct    600
atcttattcc atggacccaa tgagaaccac cttgactcac tcgtcgctca agctttattc    660
ggagacggag ctgcagcact cattgtgggt tcaggccctc acttggccgt agaacggcca    720
atattcgaga tcgtgtcaac tgatcaaaca atcttgccgg acactgagaa ggcaatgaag    780
ttacacttga gagagggagg gatgacgttt cagttgcata gagatgtacc cttgatggtc    840
gcaaagaaca tagagaacgc agcggagaaa gcgttgtctc cactagggat aactgattgg    900
aactcagttt tctggatggt gcacccaggt ggtcgagcca tattggacca ggtggagcga    960
aaactaaacc ttaaggaaga taagttaagg gctagcaggc atgtgcttag tgaatacgga   1020
aacctgatta gcgcttgtgt gttgttcatc attgacgagg tgaggaagag atctatggcg   1080
gaagggaaga gtacaaccgg tgaaggtttg gattgcggtg ttttgtttgg atttggaccg   1140
ggtatgactg ttgagactgt tgttcttcgt agcgtccgcg ttactgctgc ggttgccaat   1200
ggaaactga                                                           1209

<210> SEQ ID NO 69
<211> LENGTH: 1209
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 69

```
atgggatctt actcatccga tgatgtggag gtgattcgtg aggccggacg ggcacaaggt      60
ttagccacga ttcttgccat tggcactgct actcctccca attgcgtcgc tcaagctgat     120
tatgcagact attattttcg tgtcactaag agcgaacata tggttgatct taaagagaaa     180
tttaaacgca tttgtgagaa aacagcgata aagaaacgat acctagccct caccgaagac     240
tatctgcaag agaacccaac aatgtgtgag ttcatggctc catccttaaa cgctcgacaa     300
gacctagtgg tcaccggcgt cccaatgctt ggcaaagaag ccgcagtcaa ggccattgat     360
gaatggggac taccaaaatc caagatcacc cacctcatct tctgcaccac cgctggcgtt     420
gacatgcccg tgctgactac tcaactcgtc aaactccttg gtctctcccc ttcagtcaaa     480
cgctatatgt tgtaccaaca gggatgtgcc gccggcggca cagtcctccg gctagccaag     540
gaccttgctg aaaacaacaa gggctcacga gtccttatcg tctgctccga gatcactgct     600
atcttcttcc atggacccaa tgagaaccac cttgactcac tcgtcgctca agctttattc     660
ggagacggag ctgcagcact cattgtgggt tcaggccctc acttggccgt agaacggcca     720
atattcgaga tcgtgtcaac tgatcaaaca atcttgccgg acactgagaa ggcaatgaag     780
ttacacttga gagagggagg gatgacgttt cagttgcata gagatgtacc cttgatggtc     840
gcaaagaaca tagagaacgc agcggagaaa gcgttgtctc cactagggat aactgattgg     900
aactcagttt tctggatggt gcacccaggt ggtcgagcca tattggacca ggtgagcga      960
aaactaaacc ttaaggaaga taagttaagg gctagcaggc atgtgcttag tgaatacgga    1020
aacctgatta gcgcttgtgt gttgttcatc attgacgagg tgaggaagag atctatggcg    1080
gaagggaaga gtacaaccgg tgaaggtttg gattgcggtg ttttgtttgg atttggaccg    1140
ggtatgactg ttgagactgt tgttcttcgt agcgtccgcg ttactgctgc ggttgccaat    1200
ggaaactga                                                             1209
```

<210> SEQ ID NO 70
<211> LENGTH: 1209
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70

```
atgggatctt actcatccga tgatgtggag gtgattcgtg aggccggacg ggcacaaggt      60
ttagccacga ttcttgccat tggcactgct actcctccca attgcgtcgc tcaagctgat     120
tatgcagact attattttcg tgtcactaag agcgaacata tggttgatct taaagagaaa     180
tttaaacgca tttgtgagaa aacagcgata aagaaacgat acctagccct caccgaagac     240
tatctgcaag agaacccaac aatgtctgag ttcatggctc catccttaaa cgctcgacaa     300
gacctagtgg tcaccggcgt cccaatgctt ggcaaagaag ccgcagtcaa ggccattgat     360
gaatggggac taccaaaatc caagatcacc cacctcatct tctgcaccac cgctggcgtt     420
gacatgcccg tgctgactac tcaactcgtc aaactccttg gtctctcccc ttcagtcaaa     480
cgctatatgt tgtaccaaca gggatgtgcc gccggcggca cagtcctccg gctagccaag     540
gaccttgctg aaaacaacaa gggctcacga gtccttatcg tctgctccga gatcactgct     600
atcttattcc atggacccaa tgagaaccac cttgactcac tcgtcgctca agctttattc     660
```

```
ggagacggag ctgcagcact cattgtgggt tcaggccctc acttggccgt agaacggcca    720
atattcgaga tcgtgtcaac tgatcaaaca atcttgccgg acactgagaa ggcaatgaag    780
ttacacttga gagagggagg gttgacgttt cagttgcata gagatgtacc cttgatggtc    840
gcaaagaaca tagagaacgc agcggagaaa gcgttgtctc cactagggat aactgattgg    900
aactcagttt tctggatggt gcacccaggt ggtcgagcca tattggacca ggtggagcga    960
aaactaaacc ttaaggaaga taagttaagg gctagcaggc atgtgcttag tgaatacgga   1020
aacctgatta gcgcttgtgt gttgttcatc attgacgagg tgaggaagag atctatggcg   1080
gaagggaaga gtacaaccgg tgaaggtttg gattccggtg ttttgtttgg atttggaccg   1140
ggtatgactg ttgagactgt tgttcttcgt agcgtccgcg ttactgctgc ggttgccaat   1200
ggaaactga                                                           1209
```

<210> SEQ ID NO 71
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 71

```
atgggatctt actcatccga tgatgtggag gtgattcgtg aggccggacg ggcacaaggt     60
ttagccacga ttcttgccat tggcactgct actcctccca attgcgtcgc tcaagctgat    120
tatgcagact attattttcg tgtcactaag agcgaacata tggttgatct taagagaaa     180 tttaaacgca tttgtgagaa aacagcgata aagaaacgat acctagccct caccgaagac    240
tatctgcaag agaacccaac aatgtctgag ttcatggctc catccttaaa cgctcgacaa    300
gacctagtgg tcaccggcgt cccaatgctt ggcaaagaag ccgcagtcaa ggccattgat    360
gaatggggac taccaaaatc caagatcacc cacctcatct tctgcaccac cgctggcgtt    420
gacatgcccg gtgctgacta tcaactcgtc aaactccttg gtctctcccc ttcagtcaaa    480
cgctatatgt tgtaccaaca gggatgtgcc gccggcggca cagtcctccg gctagccaag    540
gaccttgctg aaaacaacaa gggctcacga gtccttatcg tctgctccga gatcactgct    600
atcttattcc atggacccaa tgagaaccac cttgactcac tcgtcgctca agctttattc    660
ggagacggag ctgcagcact cattgtgggt tcaggccctc acttggccgt agaacggcca    720
atattcgaga tcgtgtcaac tgatcaaaca atcttgccgg acactgagaa ggcaatgaag    780
ttacacttga gagagggagg gttgacgttt cagttgcata gagatgtacc cttgatggtc    840
gcaaagaaca tagagaacgc agcggagaaa gcgttgtctc cactagggat aactgattgg    900
aactcagttt tctggatggt gcacccaggt ggtcgagcca tattggacca ggtggagcga    960
aaactaaacc ttaaggaaga taagttaagg gctagcaggc atgtgcttag tgaatacgga   1020
aacctgatta gcgctgctgt gttgttcatc attgacgagg tgaggaagag atctatggcg   1080
gaagggaaga gtacaaccgg tgaaggtttg gattccggtg ttttgtttgg atttggaccg   1140
ggtatgactg ttgagactgt tgttcttcgt agcgtccgcg ttactgctgc ggttgccaat   1200
ggaaactga                                                          1209
```

<210> SEQ ID NO 72
<211> LENGTH: 1209
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 72

```
atgggatctt actcatccga tgatgtggag gtgattcgtg aggccggacg ggcacaaggt    60
ttagccacga ttcttgccat tggcactgct actcctccca attgcgtcgc tcaagctgat   120
tatgcagact attattttcg tgtcactaag agcgaacata tggttgatct taaagagaaa   180
tttaaacgca tttctgagaa aacagcgata aagaaacgat acctagccct caccgaagac   240
tatctgcaag agaacccaac aatgtctgag ttcatggctc catccttaaa cgctcgacaa   300
gacctagtgg tcaccggcgt cccaatgctt ggcaaagaag ccgcagtcaa ggccattgat   360
gaatggggac taccaaaatc caagatcacc cacctcatct tctgcaccac cgctggcgtt   420
gacatgcccg gtgctgacta tcaactcgtc aaactccttg gtctctcccc ttcagtcaaa   480
cgctatatgt tgtaccaaca gggatgtgcc gccggcggca cagtcctccg gctagccaag   540
gaccttgctg aaaacaacaa gggctcacga gtccttatcg tctgctccga gatcactgct   600
atcttattcc atggacccaa tgagaaccac cttgactcac tcgtcgctca agctttattc   660
ggagacggag ctgcagcact cattgtgggt tcaggccctc acttggccgt agaacggcca   720
atattcgaga tcgtgtcaac tgatcaaaca atcttgccgg acactgagaa ggcaatgaag   780
ttacacttga gaggggagg gttgacgttt cagttgcata gagatgtacc cttgatggtc   840
gcaaagaaca tagagaacgc agcggagaaa gcgttgtctc cactagggat aactgattgg   900
aactcagttt tctggatggt gcacccaggt ggtcgagcca tattgaccag gtggagcga    960
aaactaaacc ttaaggaaga taagttaagg gctagcaggc atgtgcttag tgaatacgga  1020
aacctgatta gcgcttgtgt gttgttcatc attgacgagg tgaggaagag atctatggcg  1080
gaagggaaga gtacaaccgg tgaaggtttg gattccggtg ttttgtttgg atttggaccg  1140
ggtatgactg ttgagactgt tgttcttcgt agcgtccgcg ttactgctgc ggttgccaat  1200
ggaaactga                                                          1209
```

<210> SEQ ID NO 73
<211> LENGTH: 1209
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 73

```
atgggatctt actcatccga tgatgtggag gtgattcgtg aggccggacg ggcacaaggt    60
ttagccacga ttcttgccat tggcactgct actcctccca attgcgtcgc tcaagctgat   120
tatgcagact attattttcg tgtcactaag agcgaacata tggttgatct taaagagaaa   180
tttaaacgca tttgtgagaa aacagcgata aagaaacgat acctagccct caccgaagac   240
tatctgcaag agaacccaac aatgtctgag ttcatggctc catccttaaa cgctcgacaa   300
gacctagtgg tcaccggcgt cccaatgctt ggcaaagaag ccgcagtcaa ggccattgat   360
gaatggggac taccaaaatc caagatcacc cacctcatct tctgcaccac cgctggcgtt   420
gacatgcccg gtgctgacta tcaactcgtc aaactccttg gtctctcccc ttcagtcaaa   480
cgctatatgt tgtaccaaca gggatgtgcc gccggcggca cagtcctccg gctagccaag   540
gaccttgctg aaaacaacaa gggctcacga gtccttatcg tctcctccga gatcactgct   600
```

| | | |
|---|---|---|
| atcttattcc atggacccaa tgagaaccac cttgactcac tcgtcgctca agctttattc | 660 | |
| ggagacggag ctgcagcact cattgtgggt tcaggccctc acttggccgt agaacggcca | 720 | |
| atattcgaga tcgtgtcaac tgatcaaaca atcttgccgg acactgagaa ggcaatgaag | 780 | |
| ttacacttga gagagggagg gttgacgttt cagttgcata gagatgtacc cttgatggtc | 840 | |
| gcaaagaaca tagagaacgc agcggagaaa gcgttgtctc cactagggat aactgattgg | 900 | |
| aactcagttt tctggatggt gcacccaggt ggtcgagcca tattggacca ggtggagcga | 960 | |
| aaactaaacc ttaaggaaga taagttaagg gctagcaggc atgtgcttag tgaatacgga | 1020 | |
| aacctgatta gcgctgctgt gttgttcatc attgacgagg tgaggaagag atctatggcg | 1080 | |
| gaagggaaga gtacaaccgg tgaaggtttg gattccggtg ttttgtttgg atttggaccg | 1140 | |
| ggtatgactg ttgagactgt tgttcttcgt agcgtccgcg ttactgctgc ggttgccaat | 1200 | |
| ggaaactga | 1209 | |

<210> SEQ ID NO 74
<211> LENGTH: 1209
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 74

| | | |
|---|---|---|
| atgggatctt actcatccga tgatgtggag gtgattcgtg aggccggacg ggcacaaggt | 60 | |
| ttagccacga ttcttgccat tggcactgct actcctccca attgcgtcgc tcaagctgat | 120 | |
| tatgcagact attattttcg tgtcactaag agcgaacata tggttgatct taagagaaa | 180 | |
| tttaaacgca tttctgagaa aacagcgata aagaaacgat acctagccct caccgaagac | 240 | |
| tatctgcaag agaacccaac aatgtctgag ttcatggctc catccttaaa cgctcgacaa | 300 | |
| gacctagtgg tcaccggcgt cccaatgctt ggcaaagaag ccgcagtcaa ggccattgat | 360 | |
| gaatggggac taccaaaatc caagatcacc cacctcatct tctgcaccac cgctggcgtt | 420 | |
| gacatgcccg tgctgactta tcaactcgtc aaactccttg gtctctcccc ttcagtcaaa | 480 | |
| cgctatatgt tgtaccaaca gggatgtgcc gccggcggca cagtcctccg gctagccaag | 540 | |
| gaccttgctg aaaacaacaa gggctcacga gtccttatcg tctcctccga gatcactgct | 600 | |
| atcttattcc atggacccaa tgagaaccac cttgactcac tcgtcgctca agctttattc | 660 | |
| ggagacggag ctgcagcact cattgtgggt tcaggccctc acttggccgt agaacggcca | 720 | |
| atattcgaga tcgtgtcaac tgatcaaaca atcttgccgg acactgagaa ggcaatgaag | 780 | |
| ttacacttga gagagggagg gttgacgttt cagttgcata gagatgtacc cttgatggtc | 840 | |
| gcaaagaaca tagagaacgc agcggagaaa gcgttgtctc cactagggat aactgattgg | 900 | |
| aactcagttt tctggatggt gcacccaggt ggtcgagcca tattggacca ggtggagcga | 960 | |
| aaactaaacc ttaaggaaga taagttaagg gctagcaggc atgtgcttag tgaatacgga | 1020 | |
| aacctgatta gcgctgctgt gttgttcatc attgacgagg tgaggaagag atctatggcg | 1080 | |
| gaagggaaga gtacaaccgg tgaaggtttg gattccggtg ttttgtttgg atttggaccg | 1140 | |
| ggtatgactg ttgagactgt tgttcttcgt agcgtccgcg ttactgctgc ggttgccaat | 1200 | |
| ggaaactga | 1209 | |

<210> SEQ ID NO 75
<211> LENGTH: 1209
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 75

| | |
|---|---|
| atgggatctt actcatccga tgatgtggag gtgattcgtg aggccggacg ggcacaaggt | 60 |
| ttagccacga ttcttgccat tggcactgct actcctccca attccgtcgc tcaagctgat | 120 |
| tatgcagact attattttcg tgtcactaag agcgaacata tggttgatct taaagagaaa | 180 |
| tttaaacgca tttctgagaa aacagcgata agaaacgat acctagccct caccgaagac | 240 |
| tatctgcaag agaacccaac aatgtctgag ttcatggctc catccttaaa cgctcgacaa | 300 |
| gacctagtgg tcaccggcgt cccaatgctt ggcaagaag ccgcagtcaa ggccattgat | 360 |
| gaatggggac taccaaaatc caagatcacc cacctcatct tctgcaccac cgctggcgtt | 420 |
| gacatgcccg gtgctgacta tcaactcgtc aaactccttg gtctctcccc ttcagtcaaa | 480 |
| cgctatatgt tgtaccaaca gggatgtgcc gccggcggca cagtcctccg gctagccaag | 540 |
| gaccttgctg aaaacaacaa gggctcacga gtccttatcg tctcctccga gatcactgct | 600 |
| atcttattcc atggacccaa tgagaaccac cttgactcac tcgtcgctca agctttattc | 660 |
| ggagacggag ctgcagcact cattgtgggt tcaggccctc acttggccgt agaacggcca | 720 |
| atattcgaga tcgtgtcaac tgatcaaaca atcttgccgg acactgagaa ggcactgaag | 780 |
| aaccacttga gagggagg gttgacgttt cagttgcata gagatgtacc cttgatggtc | 840 |
| gcaaagaaca tagagaacgc agcggagaaa gcgttgtctc cactagggat aactgattgg | 900 |
| aactcagttt tctggatggt gcacccaggt ggtcgagcca tattggacca ggtggagcga | 960 |
| aaactaaacc ttaaggaaga taagttaagg gctagcaggc atgtgcttag tgaatacgga | 1020 |
| aacctgatta gcgctgctgt gttgttcatc attgacgagg tgaggaagag atctatggcg | 1080 |
| gaagggaaga gtacaaccgg tgaaggtttg gattccggtg ttttgtttgg atttggaccg | 1140 |
| ggtatgactg ttgagactgt tgttcttcgt agcgtccgcg ttactgctgc ggttgccaat | 1200 |
| ggaaactga | 1209 |

<210> SEQ ID NO 76
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 76

| | |
|---|---|
| atgggatctt actcatccga tgatgtggag gtgattcgtg aggccggacg ggcacaaggt | 60 |
| ttagccacga ttcttgccat tggcactgct actcctccca attccgtcgc tcaagctgat | 120 |
| tatgcagact attattttcg tgtcactaag agcgaacata tggttgatct taaagagaaa | 180 |
| tttaaacgca tttctgagaa aacagcgata agaaacgat acctagccct caccgaagac | 240 |
| tatctgcaag agaacccaac aatgtctgag ttcatggctc catccttaaa cgctcgacaa | 300 |
| gacctagtgg tcaccggcgt cccaatgctt ggcaagaag ccgcagtcaa ggccattgat | 360 |
| gaatggggac taccaaaatc caagatcacc cacctcatct tctgcacctt cgctggcgtt | 420 |
| gacatgcccg gtgctgacta tcaactcgtc aaactccttg gtctctcccc ttcagtcaaa | 480 |
| cgctatatgt tgtaccaaca gggatgtgcc gccggcggca cagtcctccg gctagccaag | 540 |
| gaccttgctg aaaacaacaa gggctcacga gtccttatcg tctcctccga gatcactgct | 600 |

```
atcggattcc atggacccaa tgagaaccac cttgactcac tcgtcgctca agctttattc    660
ggagacggag ctgcagcact cattgtgggt tcaggccctc acttggccgt agaacggcca    720
atattcgaga tcgtgtcaac tgatcaaaca atcttgccgg acactgagaa ggcactgaag    780
aaccacttga gagagggagg gttgacgttt cagttgcata gagatgtacc cttgatggtc    840
gcaaagaaca tagagaacgc agcggagaaa gcgttgtctc cactagggat aactgattgg    900
aactcagttt tctggatggt gcacccaggt ggtcgagcca tattgaccca ggtggagcga    960
aaactaaacc ttaaggaaga taagttaagg gctagcaggc atgtgcttag tgaatacgga   1020
aacctgatta gcgctgctgt gttgttcatc attgacgagg tgaggaagag atctatggcg   1080
gaagggaaga gtacaaccgg tgaaggtttg gattccggtg ttttgtttgg atttggaccg   1140
ggtatgactg ttgagactgt tgttcttcgt agcgtccgcg ttactgctgc ggttgccaat   1200
ggaaactga                                                           1209
```

```
<210> SEQ ID NO 77
<211> LENGTH: 1209
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
atgggatctt actcatccga tgatgtggag gtgattcgtg aggccggacg ggcacaaggt     60
ttagccacga ttcttgccat tggcactgct actcctccca attccgtcgc tcaagctgat    120
tatgcagact attattttcg tgtcactaag agcgaacata tggttgatct aaagagaaa    180 tttaaacgca tttctgagaa aacagcgata aagaaacgat acctagccct caccgaagac    240
tatctgcaag agaacccaac aatgtctgag ttcatggctc catccttaaa cgctcgacaa    300
gacctagtgg tcaccggcgt cccaatgctt ggcaaagaag ccgcagtcaa ggccattgat    360
gaatggggac taccaaaatc caagatcacc cacctcatct tctgcaccac cgctggcgtt    420
gacatgcccg tgctgactat caactcgtc aaactccttg gtctctcccc ttcagtcaaa    480
cgctatatgt tgtaccaaca gggatgtgcc gccggcggca cagtcctccg gctagccaag    540
gaccttgctg aaaacaacaa gggctcacga gtccttatcg tctcctccga gatcactgct    600
ttcggattcc atggacccaa tgagaaccac cttgactcac tcgtcgctca agctttattc    660
ggagacggag ctgcagcact cattgtgggt tcaggccctc acttggccgt agaacggcca    720
atattcgaga tcgtgtcaac tgatcaaaca atcttgccgg acactgagaa ggcactgaag    780
aaccacttga gagagggagg gttgacgttt cagttgcata gagatgtacc cttgatggtc    840
gcaaagaaca tagagaacgc agcggagaaa gcgttgtctc cactagggat aactgattgg    900
aactcagttt tctggatggt gcacccaggt ggtcgagcca tattgaccca ggtggagcga    960
aaactaaacc ttaaggaaga taagttaagg gctagcaggc atgtgcttag tgaatacgga   1020
aacctgatta gcgctgctgt gttgttcatc attgacgagg tgaggaagag atctatggcg   1080
gaagggaaga gtacaaccgg tgaaggtttg gattccggtg ttttgtttgg atttggaccg   1140
ggtatgactg ttgagactgt tgttcttcgt agcgtccgcg ttactgctgc ggttgccaat   1200
ggaaactga                                                           1209
```

```
<210> SEQ ID NO 78
<211> LENGTH: 1209
```

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
atgggatctt actcatccga tgatgtggag gtgattcgtg aggccggacg ggcacaaggt        60
ttagccacga ttcttgccat tggcactgct actcctccca attccgtcgc tcaagctgat       120
tatgcagact attattttcg tgtcactaag agcgaacata tggttgatct taaagagaaa       180
tttaaacgca tttctgagaa aacagcgata aagaaacgat acctagccct caccgaagac       240
tatctgcaag agaacccaac aatgtctgag ttcatggctc catccttaaa cgctcgacaa       300
gacctagtgg tcaccggcgt cccaatgctt ggcaaagaag ccgcagtcaa ggccattgat       360
gaatggggac taccaaaatc caagatcacc cacctcatct tctgcacctt cgctggcgtt       420
gacatgcccg tgctgactac tcaactcgtc aaactccttg gtctctcccc ttcagtcaaa       480
cgctatatgt tgtaccaaca gggatgtgcc gccggcggca cagtcctccg gctagccaag       540
gaccttgctg aaaacaacaa gggctcacga gtccttatcg tctcctccga gatcactgct       600
atcggattcc atgacccaa tgagaaccac cttgactcac tcgtcgctca agctttattc       660
ggagacggag ctgcagcact cattgtgggt tcaggccctc acttggccgt agaacggcca       720
atattcgaga tcgtgtcaac tgatcaaaca atcttgccgg acactgagaa ggcactgaag       780
aaccacttga gagggagg gttgacgttt cagttgcata gagatgtacc cttgatggtc       840
gcaaagaaca tagagaacgc agcggagaaa gcgttgtctc cactagggat aactgattgg       900
aactcagttt tctggatggt gcacccaggt ggtcgagcca tattggacca ggtggagcga       960
aaactaaacc ttaaggaaga taagttaagg gctagcaggc atgtgcttag tgaatacgga      1020
aacctgatta gcgctgctgt gttgttcatc attgacgagg tgaggaagag atctatggcg      1080
gaagggaaga gtacaaccgg tgaaggtttg gattccggtg ttttgtttgg atttggaccg      1140
ggtatgactg ttgagactgt tgttcttcgt agcgtccgcg ttactgctgc ggttgccaat      1200
ggaaactga                                                              1209

<210> SEQ ID NO 79
<211> LENGTH: 1209
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79
atgggatctt actcatccga tgatgtggag gtgattcgtg aggccggacg ggcacaaggt        60
ttagccacga ttcttgccat tggcactgct actcctccca attccgtcgc tcaagctgat       120
tatgcagact attattttcg tgtcactaag agcgaacata tggttgatct taaagagaaa       180
tttaaacgca tttctgagaa aacagcgata aagaaacgat acctagccct caccgaagac       240
tatctgcaag agaacccaac aatgtctgag ttcatggctc catccttaaa cgctcgacaa       300
gacctagtgg tcaccggcgt cccaatgctt ggcaaagaag ccgcagtcaa ggccattgat       360
gaatggggac taccaaaatc caagatcacc cacctcatct tctgcaccac cgctggcgtt       420
gacatgcccg tgctgactac tcaactcgtc aaactccttg gtctctcccc ttcagtcaaa       480
cgctatatgt tgtaccaaca gggatgtgcc gccggcggca cagtcctccg gctagccaag       540
```

```
gaccttgctg aaaacaacaa gggctcacga gtccttatcg tctcctccga gatcactgct    600
atcggattcc atggacccaa tgagaaccac cttgactcac tcgtcgctca agctttattc    660
ggagacggag ctgcagcact cattgtgggt tcaggccctc acttggccgt agaacggcca    720
atattcgaga tcgtgtcaac tgatcaaaca atcttgccgg acactgagaa ggcactgaag    780
aaccacttga gagggagg gatgacgttt cagttgcata gagatgtacc cttgatggtc       840
gcaaagaaca tagagaacgc agcggagaaa gcgttgtctc cactagggat aactgattgg    900
aactcagttt tctggatggt gcacccaggt ggtcgagcca tattggacca ggtggagcga    960
aaactaaacc ttaaggaaga taagttaagg gctagcaggc atgtgcttag tgaatacgga   1020
aacctgatta gcgctgctgt gttgttcatc attgacgagg tgaggaagag atctatggcg   1080
gaagggaaga gtacaaccgg tgaaggtttg gattccggtg ttttgtttgg atttggaccg   1140
ggtatgactg ttgagactgt tgttcttcgt agcgtccgcg ttactgctgc ggttgccaat   1200
ggaaactga                                                            1209
```

<210> SEQ ID NO 80
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 80

```
atgggatctt actcatccga tgatgtggag gtgattcgtg aggccggacg ggcacaaggt     60
ttagccacga ttcttgccat tggcactgct actcctccca attccgtcgc tcaagctgat    120
tatgcagact attattttcg tgtcactaag agcgaacata tggttgatct aaagagaaa    180
tttaaacgca tttgtgagaa aacagcgata agaaacgat acctagccct caccgaagac    240
tatctgcaag agaacccaac aatgtctgag ttcatggctc catccttaaa cgctcgacaa   300
gacctagtgg tcaccggcgt cccaatgctt ggcaaagaag ccgcagtcaa ggccattgat    360
gaatggggac taccaaaatc caagatcacc cacctcatct tctgcaccac cgctggcgtt    420
gacatgcccg gtgctgacta tcaactcgtc aaactccttg gtctctcccc ttcagtcaaa    480
cgctatatgt tgtaccaaca gggatgtgcc gccggcggca cagtcctccg gctagccaag    540
gaccttgctg aaaacaacaa gggctcacga gtccttatcg tctgctccga gatcactgct    600
atcttattcc atggacccaa tgagaaccac cttgactcac tcgtcgctca agctttattc    660
ggagacggag ctgcagcact cattgtgggt tcaggccctc acttggccgt agaacggcca    720
atattcgaga tcgtgtcaac tgatcaaaca atcttgccgg acactgagaa ggcaatgaag    780
ttacacttga gagggagg gttgacgttt cagttgcata gagatgtacc cttgatggtc       840
gcaaagaaca tagagaacgc agcggagaaa gcgttgtctc cactagggat aactgattgg    900
aactcagttt tctggatggt gcacccaggt ggtcgagcca tattggacca ggtggagcga    960
aaactaaacc ttaaggaaga taagttaagg gctagcaggc atgtgcttag tgaatacgga   1020
aacctgatta gcgcttgtgt gttgttcatc attgacgagg tgaggaagag atctatggcg   1080
gaagggaaga gtacaaccgg tgaaggtttg gattccggtg ttttgtttgg atttggaccg   1140
ggtatgactg ttgagactgt tgttcttcgt agcgtccgcg ttactgctgc ggttgccaat   1200
ggaaactga                                                            1209
```

<210> SEQ ID NO 81

<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 81

| | |
|---|---|
| atgggatctt actcatccga tgatgtggag gtgattcgtg aggccggacg ggcacaaggt | 60 |
| ttagccacga ttcttgccat tggcactgct actcctccca attccgtcgc tcaagctgat | 120 |
| tatgcagact attattttcg tgtcactaag agcgaacata tggttgatct taaagagaaa | 180 |
| tttaaacgca tttgtgagaa aacagcgata aagaaacgat acctagccct caccgaagac | 240 |
| tatctgcaag agaacccaac aatgtctgag ttcatggctc catccttaaa cgctcgacaa | 300 |
| gacctagtgg tcaccggcgt cccaatgctt ggcaaagaag ccgcagtcaa ggccattgat | 360 |
| gaatggggac taccaaaatc caagatcacc cacctcatct tctgcaccac cgctggcgtt | 420 |
| gacatgcccg tgctgactta tcaactcgtc aaactccttg gtctctcccc ttcagtcaaa | 480 |
| cgctatatgt tgtaccaaca gggatgtgcc gccggcggca cagtcctccg gctagccaag | 540 |
| gaccttgctg aaaacaacaa gggctcacga gtccttatcg tctgctccga gatcactgct | 600 |
| atcttattcc atggacccaa tgagaaccac cttgactcac tcgtcgctca gctttattc | 660 |
| ggagacggag ctgcagcact cattgtgggt tcaggccctc acttggccgt agaacggcca | 720 |
| atattcgaga tcgtgtcaac tgatcaaaca atcttgccgg acactgagaa ggcaatgaag | 780 |
| ttacacttga gagggagg gttgacgttt cagttgcata gagatgtacc cttgatggtc | 840 |
| gcaaagaaca tagagaacgc agcggagaaa gcgttgtctc cactagggat aactgattgg | 900 |
| aactcagttt tctggatggt gcacccaggt ggtcgagcca tattggacca ggtggagcga | 960 |
| aaactaaacc ttaaggaaga taagttaagg gctagcaggc atgtgcttag tgaatacgga | 1020 |
| aacctgatta gcgctgctgt gttgttcatc attgacgagg tgaggaagag atctatggcg | 1080 |
| gaagggaaga gtacaaccgg tgaaggtttg gattccggtg ttttgtttgg atttggaccg | 1140 |
| ggtatgactg ttgagactgt tgttcttcgt agcgtccgcg ttactgctgc ggttgccaat | 1200 |
| ggaaactga | 1209 |

<210> SEQ ID NO 82
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 82

| | |
|---|---|
| atgggatctt actcatccga tgatgtggag gtgattcgtg aggccggacg ggcacaaggt | 60 |
| ttagccacga ttcttgccat tggcactgct actcctccca attccgtcgc tcaagctgat | 120 |
| tatgcagact attattttcg tgtcactaag agcgaacata tggttgatct taaagagaaa | 180 |
| tttaaacgca tttctgagaa aacagcgata aagaaacgat acctagccct caccgaagac | 240 |
| tatctgcaag agaacccaac aatgtctgag ttcatggctc catccttaaa cgctcgacaa | 300 |
| gacctagtgg tcaccggcgt cccaatgctt ggcaaagaag ccgcagtcaa ggccattgat | 360 |
| gaatggggac taccaaaatc caagatcacc cacctcatct tctgcaccac cgctggcgtt | 420 |
| gacatgcccg tgctgactta tcaactcgtc aaactccttg gtctctcccc ttcagtcaaa | 480 |
| cgctatatgt tgtaccaaca gggatgtgcc gccggcggca cagtcctccg gctagccaag | 540 |

```
gaccttgctg aaaacaacaa gggctcacga gtccttatcg tctgctccga gatcactgct    600
atcttattcc atggacccaa tgagaaccac cttgactcac tcgtcgctca agctttattc    660
ggagacggag ctgcagcact cattgtgggt tcaggccctc acttggccgt agaacggcca    720
atattcgaga tcgtgtcaac tgatcaaaca atcttgccgg acactgagaa ggcaatgaag    780
ttacacttga gagagggagg gttgacgttt cagttgcata gagatgtacc cttgatggtc    840
gcaaagaaca tagagaacgc agcggagaaa gcgttgtctc cactagggat aactgattgg    900
aactcagttt tctggatggt gcacccaggt ggtcgagcca tattggacca ggtggagcga    960
aaactaaacc ttaaggaaga taagttaagg gctagcaggc atgtgcttag tgaatacgga   1020
aacctgatta gcgcttgtgt gttgttcatc attgacgagg tgaggaagag atctatggcg   1080
gaagggaaga gtacaaccgg tgaaggtttg gattccggtg ttttgtttgg atttggaccg   1140
ggtatgactg ttgagactgt tgttcttcgt agcgtccgcg ttactgctgc ggttgccaat   1200
ggaaactga                                                           1209
```

<210> SEQ ID NO 83
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 83

```
atgggatctt actcatccga tgatgtggag gtgattcgtg aggccggacg ggcacaaggt     60
ttagccacga ttcttgccat tggcactgct actcctccca attccgtcgc tcaagctgat    120
tatgcagact attattttcg tgtcactaag agcgaacata tggttgatct aaagagaaa    180 tttaaacgca tttgtgagaa aacagcgata agaaacgat acctagccct caccgaagac    240
tatctgcaag agaacccaac aatgtctgag ttcatggctc catccttaaa cgctcgacaa    300
gacctagtgg tcaccggcgt cccaatgctt ggcaaagaag ccgcagtcaa ggccattgat    360
gaatggggac taccaaaatc caagatcacc cacctcatct tctgcaccac cgctggcgtt    420
gacatgcccg gtgctgacta tcaactcgtc aaactccttg gtctctcccc ttcagtcaaa    480
cgctatatgt tgtaccaaca gggatgtgcc gccggcggca cagtcctccg gctagccaag    540
gaccttgctg aaaacaacaa gggctcacga gtccttatcg tctcctccga gatcactgct    600
atcttattcc atggacccaa tgagaaccac cttgactcac tcgtcgctca agctttattc    660
ggagacggag ctgcagcact cattgtgggt tcaggccctc acttggccgt agaacggcca    720
atattcgaga tcgtgtcaac tgatcaaaca atcttgccgg acactgagaa ggcaatgaag    780
ttacacttga gagagggagg gttgacgttt cagttgcata gagatgtacc cttgatggtc    840
gcaaagaaca tagagaacgc agcggagaaa gcgttgtctc cactagggat aactgattgg    900
aactcagttt tctggatggt gcacccaggt ggtcgagcca tattggacca ggtggagcga    960
aaactaaacc ttaaggaaga taagttaagg gctagcaggc atgtgcttag tgaatacgga   1020
aacctgatta gcgctgctgt gttgttcatc attgacgagg tgaggaagag atctatggcg   1080
gaagggaaga gtacaaccgg tgaaggtttg gattccggtg ttttgtttgg atttggaccg   1140
ggtatgactg ttgagactgt tgttcttcgt agcgtccgcg ttactgctgc ggttgccaat   1200
ggaaactga                                                           1209
```

<210> SEQ ID NO 84
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 84

| | | | | | |
|---|---|---|---|---|---|
| atgggatctt | actcatccga | tgatgtggag | gtgattcgtg | aggccggacg | ggcacaaggt | 60 |
| ttagccacga | ttcttgccat | tggcactgct | actcctccca | attccgtcgc | tcaagctgat | 120 |
| tatgcagact | attattttcg | tgtcactaag | agcgaacata | tggttgatct | aaagagaaa | 180 |
| tttaaacgca | tttctgagaa | aacagcgata | aagaaacgat | acctagccct | caccgaagac | 240 |
| tatctgcaag | agaacccaac | aatgtctgag | ttcatggctc | catccttaaa | cgctcgacaa | 300 |
| gacctagtgg | tcaccggcgt | cccaatgctt | ggcaaagaag | ccgcagtcaa | ggccattgat | 360 |
| gaatggggac | taccaaaatc | caagatcacc | cacctcatct | tctgcaccac | cgctggcgtt | 420 |
| gacatgcccg | gtgctgacta | tcaactcgtc | aaactccttg | gtctctcccc | ttcagtcaaa | 480 |
| cgctatatgt | tgtaccaaca | gggatgtgcc | gccggcggca | cagtcctccg | gctagccaag | 540 |
| gaccttgctg | aaaacaacaa | gggctcacga | gtccttatcg | tctcctccga | gatcactgct | 600 |
| atcttattcc | atggacccaa | tgagaaccac | cttgactcac | tcgtcgctca | agctttattc | 660 |
| ggagacggag | ctgcagcact | cattgtgggt | tcaggccctc | acttggccgt | agaacggcca | 720 |
| atattcgaga | tcgtgtcaac | tgatcaaaca | atcttgccgg | acactgagaa | ggcaatgaag | 780 |
| ttacacttga | gagagggagg | gttgacgttt | cagttgcata | gagatgtacc | cttgatggtc | 840 |
| gcaaagaaca | tagagaacgc | agcggagaaa | gcgttgtctc | cactagggat | aactgattgg | 900 |
| aactcagttt | tctggatggt | gcacccaggt | ggtcgagcca | tattggacca | ggtggagcga | 960 |
| aaactaaacc | ttaaggaaga | taagttaagg | gctagcaggc | atgtgcttag | tgaatacgga | 1020 |
| aacctgatta | gcgctgctgt | gttgttcatc | attgacgagg | tgaggaagag | atctatggcg | 1080 |
| gaagggaaga | gtacaaccgg | tgaaggtttg | gattccggtg | ttttgtttgg | atttggaccg | 1140 |
| ggtatgactg | ttgagactgt | tgttcttcgt | agcgtccgcg | ttactgctgc | ggttgccaat | 1200 |
| ggaaactga | | | | | 1209 |

<210> SEQ ID NO 85
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 85

| | | | | | |
|---|---|---|---|---|---|
| atgggatctt | actcatccga | tgatgtggag | gtgattcgtg | aggccggacg | ggcacaaggt | 60 |
| ttagccacga | ttcttgccat | tggcactgct | actcctccca | attccgtcgc | tcaagctgat | 120 |
| tatgcagact | attattttcg | tgtcactaag | agcgaacata | tggttgatct | aaagagaaaa | 180 |
| tttaaacgca | tttgtgagaa | aacagcgata | aagaaacgat | acctagccct | caccgaagac | 240 |
| tatctgcaag | agaacccaac | aatgtgtgag | ttcatggctc | catccttaaa | cgctcgacaa | 300 |
| gacctagtgg | tcaccggcgt | cccaatgctt | ggcaaagaag | ccgcagtcaa | ggccattgat | 360 |
| gaatggggac | taccaaaatc | caagatcacc | cacctcatct | tctgcacctt | cgctggcgtt | 420 |
| gacatgcccg | gtgctgacta | tcaactcgtc | aaactccttg | gtctctcccc | ttcagtcaaa | 480 |

| | |
|---|---|
| cgctatatgt tgtaccaaca gggatgtgcc gccggcggca cagtcctccg gctagccaag | 540 |
| gaccttgctg aaaacaacaa gggctcacga gtccttatcg tctgctccga gatcactgct | 600 |
| atcttattcc atggacccaa tgagaaccac cttgactcac tcgtcgctca agctttattc | 660 |
| ggagacggag ctgcagcact cattgtgggt tcaggccctc acttggccgt agaacggcca | 720 |
| atattcgaga tcgtgtcaac tgatcaaaca atcttgccgg acactgagaa ggcaatgaag | 780 |
| ttacacttga gagggagg gttgacgttt cagttgcata gagatgtacc cttgatggtc | 840 |
| gcaaagaaca tagagaacgc agcggagaaa gcgttgtctc cactagggat aactgattgg | 900 |
| aactcagttt tctggatggt gcacccaggt ggtcgagcca tattggacca ggtggagcga | 960 |
| aaactaaacc ttaaggaaga taagttaagg gctagcaggc atgtgcttag tgaatacgga | 1020 |
| aacctgatta gcgcttgtgt gttgttcatc attgacgagg tgaggaagag atctatggcg | 1080 |
| gaagggaaga gtacaaccgg tgaaggtttg gattgcggtg ttttgtttgg atttggaccg | 1140 |
| ggtatgactg ttgagactgt tgttcttcgt agcgtccgcg ttactgctgc ggttgccaat | 1200 |
| ggaaactga | 1209 |

<210> SEQ ID NO 86
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 86

| | |
|---|---|
| atgggatctt actcatccga tgatgtggag gtgattcgtg aggccggacg ggcacaaggt | 60 |
| ttagccacga ttcttgccat tggcactgct actcctccca attccgtcgc tcaagctgat | 120 |
| tatgcagact attattttcg tgtcactaag agcgaacata tggttgatct taagagaaa | 180 |
| tttaaacgca tttgtgagaa aacagcgata aagaaacgat acctagccct caccgaagac | 240 |
| tatctgcaag agaacccaac aatgtgtgag ttcatggctc catccttaaa cgctcgacaa | 300 |
| gacctagtgg tcaccggcgt cccaatgctt ggcaaagaag ccgcagtcaa ggccattgat | 360 |
| gaatggggac taccaaaatc caagatcacc cacctcatct tctgcaccat ggctggcgtt | 420 |
| gacatgcccg tgctgactac tcaactcgtc aaactccttg gtctctcccc ttcagtcaaa | 480 |
| cgctatatgt tgtaccaaca gggatgtgcc gccggcggca cagtcctccg gctagccaag | 540 |
| gaccttgctg aaaacaacaa gggctcacga gtccttatcg tctgctccga gatcactgct | 600 |
| atcttattcc atggacccaa tgagaaccac cttgactcac tcgtcgctca agctttattc | 660 |
| ggagacggag ctgcagcact cattgtgggt tcaggccctc acttggccgt agaacggcca | 720 |
| atattcgaga tcgtgtcaac tgatcaaaca atcttgccgg acactgagaa ggcaatgaag | 780 |
| ttacacttga gagggagg gttgacgttt cagttgcata gagatgtacc cttgatggtc | 840 |
| gcaaagaaca tagagaacgc agcggagaaa gcgttgtctc cactagggat aactgattgg | 900 |
| aactcagttt tctggatggt gcacccaggt ggtcgagcca tattggacca ggtggagcga | 960 |
| aaactaaacc ttaaggaaga taagttaagg gctagcaggc atgtgcttag tgaatacgga | 1020 |
| aacctgatta gcgcttgtgt gttgttcatc attgacgagg tgaggaagag atctatggcg | 1080 |
| gaagggaaga gtacaaccgg tgaaggtttg gattgcggtg ttttgtttgg atttggaccg | 1140 |
| ggtatgactg ttgagactgt tgttcttcgt agcgtccgcg ttactgctgc ggttgccaat | 1200 |
| ggaaactga | 1209 |

<210> SEQ ID NO 87
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 87

| | |
|---|---|
| atgggatctt actcatccga tgatgtggag gtgattcgtg aggccggacg ggcacaaggt | 60 |
| ttagccacga ttcttgccat tggcactgct actcctccca attccgtcgc tcaagctgat | 120 |
| tatgcagact attattttcg tgtcactaag agcgaacata tggttgatct aaagagaaa | 180 |
| tttaaacgca tttgtgagaa acagcgata aagaaacgat acctagccct caccgaagac | 240 |
| tatctgcaag agaacccaac aatgtgtgag ttcatggctc catccttaaa cgctcgacaa | 300 |
| gacctagtgg tcaccggcgt cccaatgctt ggcaagaag ccgcagtcaa ggccattgat | 360 |
| gaatggggac taccaaaatc caagatcacc cacctcatct tctgcaccac cgctggcgtt | 420 |
| gacatgcccg gtgctgacta tcaactcgtc aaactccttg gtctctcccc ttcagtcaaa | 480 |
| cgctatatgt tgtaccaaca gggatgtgcc gccggcggca cagtcctccg gctagccaag | 540 |
| gaccttgctg aaaacaacaa gggctcacga gtccttatcg tctgctccga gatcactgct | 600 |
| atcttattcc atggacccaa tgagaaccac cttgactcac tcgtcgctca agctttattc | 660 |
| ggagacggag ctgcagcact cattgtgggt tcaggccctc acttggccgt agaacggcca | 720 |
| atattcgaga tcgtgtcaac tgatcaaaca atcttgccgg acactgagaa ggcatttaag | 780 |
| ttacacttga gagagggagg gttgacgttt cagttgcata gagatgtacc cttgatggtc | 840 |
| gcaaagaaca tagagaacgc agcggagaaa gcgttgtctc cactagggat aactgattgg | 900 |
| aactcagttt tctggatggt gcacccaggt ggtcgagcca tattggacca ggtggagcga | 960 |
| aaactaaacc ttaaggaaga taagttaagg gctagcaggc atgtgcttag tgaatacgga | 1020 |
| aacctgatta gcgcttgtgt gttgttcatc attgacgagg tgaggaagag atctatggcg | 1080 |
| gaagggaaga gtacaaccgg tgaaggtttg gattgcggtg ttttgtttgg atttggaccg | 1140 |
| ggtatgactg ttgagactgt tgttcttcgt agcgtccgcg ttactgctgc ggttgccaat | 1200 |
| ggaaactga | 1209 |

<210> SEQ ID NO 88
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 88

| | |
|---|---|
| atgggatctt actcatccga tgatgtggag gtgattcgtg aggccggacg ggcacaaggt | 60 |
| ttagccacga ttcttgccat tggcactgct actcctccca attccgtcgc tcaagctgat | 120 |
| tatgcagact attattttcg tgtcactaag agcgaacata tggttgatct aaagagaaa | 180 |
| tttaaacgca tttgtgagaa acagcgata aagaaacgat acctagccct caccgaagac | 240 |
| tatctgcaag agaacccaac aatgtgtgag ttcatggctc catccttaaa cgctcgacaa | 300 |
| gacctagtgg tcaccggcgt cccaatgctt ggcaagaag ccgcagtcaa ggccattgat | 360 |
| gaatggggac taccaaaatc caagatcacc cacctcatct tctgcaccct cgctggcgtt | 420 |
| gacatgcccg gtgctgacta tcaactcgtc aaactccttg gtctctcccc ttcagtcaaa | 480 |

```
cgctatatgt tgtaccaaca gggatgtgcc gccggcggca cagtcctccg gctagccaag      540
gaccttgctg aaaacaacaa gggctcacga gtccttatcg tctgctccga gatcactgct      600
atcttattcc atggacccaa tgagaaccac cttgactcac tcgtcgctca agctttattc      660
ggagacggag ctgcagcact cattgtgggt tcaggccctc acttggccgt agaacggcca      720
atattcgaga tcgtgtcaac tgatcaaaca atcttgccgg acactgagaa ggcaatgaag      780
ttacacttga gagagggagg gttgacgttt cagttgcata gagatgtacc cttgatggtc      840
gcaaagaaca tagagaacgc agcggagaaa gcgttgtctc cactagggat aactgattgg      900
aactcagttt tctggatggt gcacccaggt ggtcgagcca tattggacca ggtggagcga      960
aaactaaacc ttaaggaaga taagttaagg gctagcaggc atgtgcttag tgaatacgga     1020
aacctgatta gcgcttgtgt gttgttcatc attgacgagg tgaggaagag atctatggcg     1080
gaagggaaga gtacaaccgg tgaaggtttg gattgcggtg ttttgtttgg atttggaccg     1140
ggtatgactg ttgagactgt tgttcttcgt agcgtccgcg ttactgctgc ggttgccaat     1200
ggaaactga                                                             1209
```

<210> SEQ ID NO 89
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 89

```
atgggatctt actcatccga tgatgtggag gtgattcgtg aggccggacg ggcacaaggt       60
ttagccacga ttcttgccat tggcactgct actcctccca attccgtcgc tcaagctgat      120
tatgcagact attattttcg tgtcactaag agcgaacata tggttgatct aaagagaaa      180 tttaaacgca tttgtgagaa aacagcgata aagaaacgat acctagccct caccgaagac      240
tatctgcaag agaacccaac aatgtgtgag ttcatggctc catccttaaa cgctcgacaa      300
gacctagtgg tcaccggcgt cccaatgctt ggcaaagaag ccgcagtcaa ggccattgat      360
gaatggggac taccaaaatc caagatcacc cacctcatct tctgcaccac cgctggcgtt      420
gacatgcccg gtgctgacta tcaactcgtc aaactccttg gtctctcccc ttcagtcaaa      480
cgctatatgt tgtaccaaca gggatgtgcc gccggcggca cagtcctccg gctagccaag      540
gaccttgctg aaaacaacaa gggctcacga gtccttatcg tctgctccga gatcactgct      600
atcttattcc atggacccaa tgagaaccac cttgactcac tcgtcgctca agctttattc      660
ggagacggag ctgcagcact cattgtgggt tcaggccctc acttggccgt agaacggcca      720
atattcgaga tcgtgtcaac tgatcaaaca atcttgccgg acactgagaa ggcaatgaag      780
ttacacttga gagagggagg gttgacgttt cagttgcata gagatgtacc cttgatggtc      840
gcaaagaaca tagagaacgc agcggagaaa gcgttgtctc cactagggat aactgattgg      900
aactcagttt tctggatggt gcacccaggt ggtcgagcca tattggacca ggtggagcga      960
aaactaaacc ttaaggaaga taagttaagg gctagcaggc atgtgcttag tgaatacgga     1020
aacctgttta gcgcttgtgt gttgttcatc attgacgagg tgaggaagag atctatggcg     1080
gaagggaaga gtacaaccgg tgaaggtttg gattgcggtg ttttgtttgg atttggaccg     1140
ggtatgactg ttgagactgt tgttcttcgt agcgtccgcg ttactgctgc ggttgccaat     1200
ggaaactga                                                             1209
```

<210> SEQ ID NO 90
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 90

| | |
|---|---|
| atgggatctt actcatccga tgatgtggag gtgattcgtg aggccggacg ggcacaaggt | 60 |
| ttagccacga ttcttgccat tggcactgct actcctccca attccgtcgc tcaagctgat | 120 |
| tatgcagact attattttcg tgtcactaag agcgaacata tggttgatct taaagagaaa | 180 |
| tttaaacgca tttgtgagaa aacagcgata aagaaacgat acctagccct caccgaagac | 240 |
| tatctgcaag agaacccaac aatgtgtgag ttcatggctc catccttaaa cgctcgacaa | 300 |
| gacctagtgg tcaccggcgt cccaatgctt ggcaaagaag ccgcagtcaa ggccattgat | 360 |
| gaatggggac taccaaaatc caagatcacc cacctcatct tctgcaccac cgctggcgtt | 420 |
| gacatgcccg tgctgactat caactcgtca aaactccttg gtctctcccc ttcagtcaaa | 480 |
| cgctatatgt tgtaccaaca gggatgtgcc gccggcggca cagtcctccg gctagccaag | 540 |
| gaccttgctg aaaacaacaa gggctcacga gtccttatcg tctgctccga atcactgct | 600 |
| atcttattcc atggacccaa tgagaaccac cttgactcac tcgtcgctca agctttattc | 660 |
| ggagacggag ctgcagcact cattgtgggt tcaggccctc acttggccgt agaacggcca | 720 |
| atattcgaga tcgtgtcaac tgatcaaaca atcttgccgg acactgagaa ggcaatgaag | 780 |
| ttacacttga gagagggagg gttgacgttt cagttgcata gagatgtacc cttgatggtc | 840 |
| gcaaagaaca tagagaacgc agcggagaaa gcgttgtctc cactagggat aactgattgg | 900 |
| aactcagttt tctggatggt gcacccaggt ggtcgagcca tattggacca ggtggagcga | 960 |
| aaactaaacc ttaaggaaga taagttaagg gctagcaggc atgtgcttag tgaatacgga | 1020 |
| aacctgatga gcgcttgtgt gttgttcatc attgacgagg tgaggaagag atctatggcg | 1080 |
| gaagggaaga gtacaaccgg tgaaggtttg gattgcggtg ttttgtttgg atttggaccg | 1140 |
| ggtatgactg ttgagactgt tgttcttcgt agcgtccgcg ttactgctgc ggttgccaat | 1200 |
| ggaaactga | 1209 |

<210> SEQ ID NO 91
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 91

| | |
|---|---|
| atgggatctt actcatccga tgatgtggag gtgattcgtg aggccggacg ggcacaaggt | 60 |
| ttagccacga ttcttgccat tggcactgct actcctccca attccgtcgc tcaagctgat | 120 |
| tatgcagact attattttcg tgtcactaag agcgaacata tggttgatct taaagagaaa | 180 |
| tttaaacgca tttgtgagaa aacagcgata aagaaacgat acctagccct caccgaagac | 240 |
| tatctgcaag agaacccaac aatgtgtgag ttcatggctc catccttaaa cgctcgacaa | 300 |
| gacctagtgg tcaccggcgt cccaatgctt ggcaaagaag ccgcagtcaa ggccattgat | 360 |
| gaatggggac taccaaaatc caagatcacc cacctcatct tctgcaccac cgctggcgtt | 420 |

```
gacatgcccg gtgctgacta tcaactcgtc aaactccttg gtctctcccc ttcagtcaaa    480
cgctatatgt tgtaccaaca gggatgtgcc gccggcggca cagtcctccg gctagccaag    540
gaccttgctg aaaacaacaa gggctcacga gtccttatcg tctgctccga gatcactgct    600
ttcttattcc atggacccaa tgagaaccac cttgactcac tcgtcgctca agctttattc    660
ggagacggag ctgcagcact cattgtgggt tcaggccctc acttggccgt agaacggcca    720
atattcgaga tcgtgtcaac tgatcaaaca atcttgccgg acactgagaa ggcaatgaag    780
ttacacttga gagaggagg gttgacgttt cagttgcata gagatgtacc cttgatggtc    840
gcaaagaaca tagagaacgc agcggagaaa gcgttgtctc cactagggat aactgattgg    900
aactcagttt tctggatggt gcacccaggt ggtcgagcca tattggacca ggtggagcga    960
aaactaaacc ttaaggaaga taagttaagg gctagcaggc atgtgcttag tgaatacgga   1020
aacctgatta gcgcttgtgt gttgttcatc attgacgagg tgaggaagag atctatggcg   1080
gaagggaaga gtacaaccgg tgaaggtttg gattgcggtg ttttgtttgg atttggaccg   1140
ggtatgactg ttgagactgt tgttcttcgt agcgtccgcg ttactgctgc ggttgccaat   1200
ggaaactga                                                           1209
```

<210> SEQ ID NO 92
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 92

```
atgggatctt actcatccga tgatgtggag gtgattcgtg aggccggacg ggcacaaggt     60
ttagccacga ttcttgccat tggcactgct actcctccca attccgtcgc tcaagctgat    120
tatgcagact attattttcg tgtcactaag agcgaacata tggttgatct aaagagaaa    180
tttaaacgca tttgtgagaa aacagcgata agaaacgat acctagccct caccgaagac    240
tatctgcaag agaacccaac aatgtgtgag ttcatggctc catccttaaa cgctcgacaa    300
gaccagtgg tcaccggcgt cccaatgctt ggcaaagaag ccgcagtcaa ggccattgat    360
gaatggggac taccaaaatc caagatcacc cacctcatct tctgcaccac cgctggcgtt    420
gacatgcccg gtgctgacta tcaactcgtc aaactccttg gtctctcccc ttcagtcaaa    480
cgctatatgt tgtaccaaca gggagctgcc gccggcggca cagtcctccg gctagccaag    540
gaccttgctg aaaacaacaa gggctcacga gtccttatcg tctgctccga gatcactgct    600
atcttattcc atggacccaa tgagaaccac cttgactcac tcgtcgctca agctttattc    660
ggagacggag ctgcagcact cattgtgggt tcaggccctc acttggccgt agaacggcca    720
atattcgaga tcgtgtcaac tgatcaaaca atcttgccgg acactgagaa ggcaatgaag    780
ttacacttga gagaggagg gttgacgttt cagttgcata gagatgtacc cttgatggtc    840
gcaaagaaca tagagaacgc agcggagaaa gcgttgtctc cactagggat aactgattgg    900
aactcagttt tctggatggt gcacccaggt ggtcgagcca tattggacca ggtggagcga    960
aaactaaacc ttaaggaaga taagttaagg gctagcaggc atgtgcttag tgaatacgga   1020
aacctgatta gcgcttgtgt gttgttcatc attgacgagg tgaggaagag atctatggcg   1080
gaagggaaga gtacaaccgg tgaaggtttg gattgcggtg ttttgtttgg atttggaccg   1140
ggtatgactg ttgagactgt tgttcttcgt agcgtccgcg ttactgctgc ggttgccaat   1200
```

```
ggaaactga                                                           1209

<210> SEQ ID NO 93
<211> LENGTH: 1209
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
atgggatctt actcatccga tgatgtggag gtgattcgtg aggccggacg ggcacaaggt      60
ttagccacga ttcttgccat tggcactgct actcctccca attccgtcgc tcaagctgat    120
tatgcagact attattttcg tgtcactaag agcgaacata tggttgatct aaagagaaa     180 tttaaacgca tttgtgagaa aacagcgata aagaaacgat acctagccct caccgaagac    240
tatctgcaag agaacccaac aatgtgtgag ttcatggctc catccttaaa cgctcgacaa    300
gacctagtgg tcaccggcgt cccaatgctt ggcaaagaag ccgcagtcaa ggccattgat    360
gaatggggac taccaaaatc caagatcacc cacctcatct tctgcaccac cgctggcgtt    420
gacatgcccg tgctgactaa tcaactcgtc aaactccttg gtctctcccc ttcagtcaaa    480
cgctatatgt tgtaccaaca gggatgtgcc gccggcggca cagtcctccg gctagccaag    540
gaccttgctg aaaacaacaa gggctcacga gtccttatcg tctgctccga gatcactgct    600
atcttattcc atggacccaa tgagaaccac cttgactcac tcgtcgctca gctttattc     660 ggagacggag ctgcagcact cattgtgggt tcaggccctc acttggccgt agaacggcca    720
atattcgaga tcgtgtcaac tgatcaaaca atcttgccgg acactgagaa ggcaatgaag    780
ttacacttga gagaggggagg gatgacgttt cagttgcata gagatgtacc cttgatggtc    840
gcaaagaaca tagagaacgc agcggagaaa gcgttgtctc cactagggat aactgattgg    900
aactcagttt tctggatggt gcacccaggt ggtcgagcca tattggacca ggtggagcga    960
aaactaaacc ttaaggaaga taagttaagg gctagcaggc atgtgcttag tgaatacgga   1020
aacctgatta gcgcttgtgt gttgttcatc attgacgagg tgaggaagag atctatggcg   1080
gaagggaaga gtacaaccgg tgaaggtttg gattgcggtg ttttgtttgg atttggaccg   1140
ggtatgactg ttgagactgt tgttcttcgt agcgtccgcg ttactgctgc ggttgccaat   1200
ggaaactga                                                           1209

<210> SEQ ID NO 94
<211> LENGTH: 1209
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94
atgggatctt actcatccga tgatgtggag gtgattcgtg aggccggacg ggcacaaggt      60
ttagccacga ttcttgccat tggcactgct actcctccca attccgtcgc tcaagctgat    120
tatgcagact attattttcg tgtcactaag agcgaacata tggttgatct aaagagaaa     180 tttaaacgca tttgtgagaa aacagcgata aagaaacgat acctagccct caccgaagac    240
tatctgcaag agaacccaac aatgtgtgag ttcatggctc catccttaaa cgctcgacaa    300
gacctagtgg tcaccggcgt cccaatgctt ggcaaagaag ccgcagtcaa ggccattgat    360
gaatggggac taccaaaatc caagatcacc cacctcatct tctgcaccac cgctggcgtt    420
```

```
gacatgcccg gtgctgacta tcaactcgtc aaactccttg gtctctcccc ttcagtcaaa    480
cgctatatgt tgtaccaaca gggatgtgcc gccggcggca cagtcctccg gctagccaag    540
gaccttgctg aaaacaacaa gggctcacga gtccttatcg tctgctccga gatcactgct    600
atcttcttcc atggacccaa tgagaaccac cttgactcac tcgtcgctca agctttattc    660
ggagacggag ctgcagcact cattgtgggt tcaggccctc acttggccgt agaacggcca    720
atattcgaga tcgtgtcaac tgatcaaaca atcttgccgg acactgagaa ggcaatgaag    780
ttacacttga gagagggagg gttgacgttt cagttgcata gagatgtacc cttgatggtc    840
gcaaagaaca tagagaacgc agcggagaaa gcgttgtctc cactagggat aactgattgg    900
aactcagttt tctggatggt gcacccaggt ggtcgagcca tattggacca ggtggagcga    960
aaactaaacc ttaaggaaga taagttaagg gctagcaggc atgtgcttag tgaatacgga   1020
aacctgatta gcgcttgtgt gttgttcatc attgacgagg tgaggaagag atctatggcg   1080
gaagggaaga gtacaaccgg tgaaggtttg gattgcggtg ttttgtttgg atttggaccg   1140
ggtatgactg ttgagactgt tgttcttcgt agcgtccgcg ttactgctgc ggttgccaat   1200
ggaaactga                                                           1209
```

<210> SEQ ID NO 95
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 95

```
atgggatctt actcatccga tgatgtggag gtgattcgtg aggccggacg ggcacaaggt     60
ttagccacga ttcttgccat tggcactgct actcctccca attccgtcgc tcaagctgat    120
tatgcagact attattttcg tgtcactaag agcgaacata tggttgatct taaagagaaa    180
tttaaacgca tttgtgagaa aacagcgata agaaacgat acctagccct caccgaagac    240
tatctgcaag agaacccaac aatgtgtgag ttcatggctc catccttaaa cgctcgacaa    300
gacctagtgg tcaccggcgt cccaatgctt ggcaaagaag ccgcagtcaa ggccattgat    360
gaatggggac taccaaaatc caagatcacc cacctcatct tctgcaccac cgctggcgtt    420
gacatgcccg gtgctgacta tcaactcgtc aaactccttg gtctctcccc ttcagtcaaa    480
cgctatatgt tgtaccaaca gggatgtgcc gccggcggca cagtcctccg gctagccaag    540
gaccttgctg aaaacaacaa gggctcacga gtccttatcg tctgctccga gatcactgct    600
atgttattcc atggacccaa tgagaaccac cttgactcac tcgtcgctca agctttattc    660
ggagacggag ctgcagcact cattgtgggt tcaggccctc acttggccgt agaacggcca    720
atattcgaga tcgtgtcaac tgatcaaaca atcttgccgg acactgagaa ggcaatgaag    780
ttacacttga gagagggagg gttgacgttt cagttgcata gagatgtacc cttgatggtc    840
gcaaagaaca tagagaacgc agcggagaaa gcgttgtctc cactagggat aactgattgg    900
aactcagttt tctggatggt gcacccaggt ggtcgagcca tattggacca ggtggagcga    960
aaactaaacc ttaaggaaga taagttaagg gctagcaggc atgtgcttag tgaatacgga   1020
aacctgatta gcgcttgtgt gttgttcatc attgacgagg tgaggaagag atctatggcg   1080
gaagggaaga gtacaaccgg tgaaggtttg gattgcggtg ttttgtttgg atttggaccg   1140
ggtatgactg ttgagactgt tgttcttcgt agcgtccgcg ttactgctgc ggttgccaat   1200
```

<210> SEQ ID NO 96
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 96

```
atgggatctt actcatccga tgatgtggag gtgattcgtg aggccggacg ggcacaaggt      60
ttagccacga ttcttgccat tggcactgct actcctccca attccgtcgc tcaagctgat     120
tatgcagact attattttcg tgtcactaag agcgaacata tggttgatct aaagagaaa     180
tttaaacgca tttgtgagaa aacagcgata aagaaacgat acctagccct caccgaagac     240
tatctgcaag agaacccaac aatgtgtgag ttcatggctc catccttaaa cgctcgacaa     300
gacctagtgg tcaccggcgt cccaatgctt ggcaaagaag ccgcagtcaa ggccattgat     360
gaatggggac taccaaaatc caagatcacc cacctcatct tctgcaccac cgctggcgtt     420
gacatgcccg tgctgactca tcaactcgtc aaactccttg gtctctcccc ttcagtcaaa     480
cgctatatgt tgtaccaaca gggatgtgcc gccggcggca cagtcctccg gctagccaag     540
gaccttgctg aaaacaacaa gggctcacga gtccttatcg tctgctccga gatcactgct     600
ttgttattcc atggacccaa tgagaaccac cttgactcac tcgtcgctca gctttattc     660
ggagacggag ctgcagcact cattgtgggt tcaggccctc acttggccgt agaacggcca     720
atattcgaga tcgtgtcaac tgatcaaaca atcttgccgg acactgagaa ggcaatgaag     780
ttacacttga gagagggagg gttgacgttt cagttgcata gagatgtacc cttgatggtc     840
gcaaagaaca tagagaacgc agcggagaaa gcgttgtctc cactagggat aactgattgg     900
aactcagttt tctggatggt gcacccaggt ggtcgagcca tattgaccta ggtggagcga     960
aaactaaacc ttaaggaaga taagttaagg gctagcaggc atgtgcttag tgaatacgga    1020
aacctgatta gcgcttgtgt gttgttcatc attgacgagg tgaggaagag atctatggcg    1080
gaagggaaga gtacaaccgg tgaaggtttg gattgcggtg ttttgtttgg atttggaccg    1140
ggtatgactg ttgagactgt tgttcttcgt agcgtccgcg ttactgctgc ggttgccaat    1200
ggaaactga                                                            1209
```

<210> SEQ ID NO 97
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 97

```
atgggatctt actcatccga tgatgtggag gtgattcgtg aggccggacg ggcacaaggt      60
ttagccacga ttcttgccat tggcactgct actcctccca attccgtcgc tcaagctgat     120
tatgcagact attattttcg tgtcactaag agcgaacata tggttgatct aaagagaaa     180
tttaaacgca tttgtgagaa aacagcgata aagaaacgat acctagccct caccgaagac     240
tatctgcaag agaacccaac aatgtgtgag ttcatggctc catccttaaa cgctcgacaa     300
gacctagtgg tcaccggcgt cccaatgctt ggcaaagaag ccgcagtcaa ggccattgat     360
```

```
gaatggggac taccaaaatc caagatcacc cacctcatct tctgcaccac cgctggcgtt    420
gacatgcccg gtgctgacta tcaactcgtc aaactccttg gtctctcccc ttcagtcaaa    480
cgctatatgt tgtaccaaca gggatgtgcc gccggcggca cagtcctccg gctagccaag    540
gaccttgctg aaaacaacaa gggctcacga gtccttatcg tctgctccga gatcactgct    600
atcatgttcc atggacccaa tgagaaccac cttgactcac tcgtcgctca agctttattc    660
ggagacggag ctgcagcact cattgtgggt tcaggccctc acttggccgt agaacggcca    720
atattcgaga tcgtgtcaac tgatcaaaca atcttgccgg acactgagaa ggcaatgaag    780
ttacacttga gagagggagg gttgacgttt cagttgcata gagatgtacc cttgatggtc    840
gcaaagaaca tagagaacgc agcggagaaa gcgttgtctc cactagggat aactgattgg    900
aactcagttt tctggatggt gcacccaggt ggtcgagcca tattggacca ggtggagcga    960
aaactaaacc ttaaggaaga taagttaagg gctagcaggc atgtgcttag tgaatacgga   1020
aacctgatta gcgcttgtgt gttgttcatc attgacgagg tgaggaagag atctatggcg   1080
gaagggaaga gtacaaccgg tgaaggtttg gattgcggtg ttttgtttgg atttggaccg   1140
ggtatgactg ttgagactgt tgttcttcgt agcgtccgcg ttactgctgc ggttgccaat   1200
ggaaactga                                                          1209
```

<210> SEQ ID NO 98
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 98

```
atgggatctt actcatccga tgatgtggag gtgattcgtg aggccggacg ggcacaaggt     60
ttagccacga ttcttgccat tggcactgct actcctccca attccgtcgc tcaagctgat    120
tatgcagact attattttcg tgtcactaag agcgaacata tggttgatct taaagagaaa    180
tttaaacgca tttgtgagaa aacagcgata aagaaacgat acctagccct caccgaagac    240
tatctgcaag agaacccaac aatgtgtgag ttcatggctc catccttaaa cgctcgacaa    300
gacctagtgg tcaccggcgt cccaatgctt ggcaaagaag ccgcagtcaa ggccattgat    360
gaatggggac taccaaaatc caagatcacc cacctcatct tctgcaccac cgctggcgtt    420
gacatgcccg gtgctgacta tcaactcgtc aaactccttg gtctctcccc ttcagtcaaa    480
cgctatatgt tgtaccaaca gggatgtgcc gccggcggca cagtcctccg gctagccaag    540
gaccttgctg aaaacaacaa gggctcacga gtccttatcg tctgctccga gatcactgct    600
atcggattcc atggacccaa tgagaaccac cttgactcac tcgtcgctca agctttattc    660
ggagacggag ctgcagcact cattgtgggt tcaggccctc acttggccgt agaacggcca    720
atattcgaga tcgtgtcaac tgatcaaaca atcttgccgg acactgagaa ggcactgaag    780
aaccacttga gagagggagg gttgacgttt cagttgcata gagatgtacc cttgatggtc    840
gcaaagaaca tagagaacgc agcggagaaa gcgttgtctc cactagggat aactgattgg    900
aactcagttt tctggatggt gcacccaggt ggtcgagcca tattggacca ggtggagcga    960
aaactaaacc ttaaggaaga taagttaagg gctagcaggc atgtgcttag tgaatacgga   1020
aacctgatta gcgcttgtgt gttgttcatc attgacgagg tgaggaagag atctatggcg   1080
gaagggaaga gtacaaccgg tgaaggtttg gattgcggtg ttttgtttgg atttggaccg   1140
```

<210> SEQ ID NO 99
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 99

```
atgggatctt actcatccga tgatgtggag gtgattcgtg aggccggacg ggcacaaggt      60
ttagccacga ttcttgccat tggcactgct actcctccca attccgtcgc tcaagctgat     120
tatgcagact attattttcg tgtcactaag agcgaacata tggttgatct aaagagaaa      180
tttaaacgca tttctgagaa aacagcgata agaaacgat acctagccct caccgaagac     240
tatctgcaag agaacccaac aatgtctgag ttcatggctc catccttaaa cgctcgacaa     300
gacctagtgg tcaccggcgt cccaatgctt ggcaaagaag ccgcagtcaa ggccattgat     360
gaatggggac taccaaaatc caagatcacc cacctcatct tctgcaccac cgctggcgtt     420
gacatgcccg gtgctgacta tcaactcgtc aaactccttg gtctctcccc ttcagtcaaa     480
cgctatatgt tgtaccaaca gggatgtgcc gccggcggca cagtcctccg gctagccaag     540
gaccttgctg aaaacaacaa gggctcacga gtccttatcg tctcctccga tcactgct     600
atcggattcc atggacccaa tgagaaccac cttgactcac tcgtcgctca agctttattc     660
ggagacggag ctgcagcact cattgtgggt tcaggccctc acttggccgt agaacggcca     720
atattcgaga tcgtgtcaac tgatcaaaca atcttgccgg acactgagaa ggcactgaag     780
aaccacttga gagggagg gttgacgttt cagttgcata gagatgtacc cttgatggtc     840
gcaaagaaca tagagaacgc agcggagaaa gcgttgtctc cactagggat aactgattgg     900
aactcagttt tctggatggt gcacccaggt ggtcgagcca tattggacca ggtggagcga     960
aaactaaacc ttaaggaaga taagttaagg gctagcaggc atgtgcttag tgaatacgga    1020
aacctgatta gcgctgctgt gttgttcatc attgacgagg tgaggaagag atctatggcg    1080
gaagggaaga gtacaaccgg tgaaggtttg gattccggtg ttttgtttgg atttggaccg    1140
ggtatgactg ttgagactgt tgttcttcgt agcgtccgcg ttactgctgc ggttgccaat    1200
ggaaactga                                                             1209
```

<210> SEQ ID NO 100
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 100

```
atgggatctt actcatccga tgatgtggag gtgattcgtg aggccggacg ggcacaaggt      60
ttagccacga ttcttgccat tggcactgct actcctccca attccgtcgc tcaagctgat     120
tatgcagact attattttcg tgtcactaag agcgaacata tggttgatct aaagagaaa      180
tttaaacgca tttgtgagaa aacagcgata agaaacgat acctagccct caccgaagac     240
tatctgcaag agaacccaac aatgtgtgag ttcatggctc catccttaaa cgctcgacaa     300
gacctagtgg tcaccggcgt cccaatgctt ggcaaagaag ccgcagtcaa ggccattgat     360
```

```
gaatggggac taccaaaatc caagatcacc cacctcatct tctgcaccac cgctggcgtt    420
gacatgcccg gtgctgacta tcaactcgtc aaactccttg gtctctcccc ttcagtcaaa    480
cgctatatgt tgtaccaaca gggatgtgcc gccggcggca cagtcctccg gctagccaag    540
gaccttgctg aaaacaacaa gggctcacga gtccttatcg tctgctccga gatcactgct    600
atcggattcc atggacccaa tgagaaccac cttgactcac tcgtcgctca agctttattc    660
ggagacggag ctgcagcact cattgtgggt tcaggccctc acttggccgt agaacggcca    720
atattcgaga tcgtgtcaac tgatcaaaca atcttgccgg acactgagaa ggcaatgaag    780
ttacacttga gagagggagg gttgacgttt cagttgcata gagatgtacc cttgatggtc    840
gcaaagaaca tagagaacgc agcggagaaa gcgttgtctc cactagggat aactgattgg    900
aactcagttt tctggatggt gcacccaggt ggtcgagcca tattggacca ggtggagcga    960
aaactaaacc ttaaggaaga taagttaagg gctagcaggc atgtgcttag tgaatacgga   1020
aacctgatta gcgcttgtgt gttgttcatc attgacgagg tgaggaagag atctatggcg   1080
gaagggaaga gtacaaccgg tgaaggtttg gattgcggtg ttttgtttgg atttggaccg   1140
ggtatgactg ttgagactgt tgttcttcgt agcgtccgcg ttactgctgc ggttgccaat   1200
ggaaactga                                                           1209

<210> SEQ ID NO 101
<211> LENGTH: 1209
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101
atgggatctt actcatccga tgatgtggag gtgattcgtg aggccggacg ggcacaaggt     60
ttagccacga ttcttgccat tggcactgct actcctccca attccgtcgc tcaagctgat    120
tatgcagact attattttcg tgtcactaag agcgaacata tggttgatct taaagagaaa    180
tttaaacgca tttgtgagaa aacagcgata aagaaacgat acctagccct caccgaagac    240
tatctgcaag agaacccaac aatgtgtgag ttcatggctc catccttaaa cgctcgacaa    300
gacctagtgg tcaccggcgt cccaatgctt ggcaaagaag ccgcagtcaa ggccattgat    360
gaatggggac taccaaaatc caagatcacc cacctcatct tctgcaccac cgctggcgtt    420
gacatgcccg gtgctgacta tcaactcgtc aaactccttg gtctctcccc ttcagtcaaa    480
cgctatatgt tgtaccaaca gggatgtgcc gccggcggca cagtcctccg gctagccaag    540
gaccttgctg aaaacaacaa gggctcacga gtccttatcg tctgctccga gatcactgct    600
atcttattcc atggacccaa tgagaaccac cttgactcac tcgtcgctca agctttattc    660
ggagacggag ctgcagcact cattgtgggt tcaggccctc acttggccgt agaacggcca    720
atattcgaga tcgtgtcaac tgatcaaaca atcttgccgg acactgagaa ggcactgaag    780
aaccacttga gagagggagg gttgacgttt cagttgcata gagatgtacc cttgatggtc    840
gcaaagaaca tagagaacgc agcggagaaa gcgttgtctc cactagggat aactgattgg    900
aactcagttt tctggatggt gcacccaggt ggtcgagcca tattggacca ggtggagcga    960
aaactaaacc ttaaggaaga taagttaagg gctagcaggc atgtgcttag tgaatacgga   1020
aacctgatta gcgcttgtgt gttgttcatc attgacgagg tgaggaagag atctatggcg   1080
gaagggaaga gtacaaccgg tgaaggtttg gattgcggtg ttttgtttgg atttggaccg   1140
```

```
ggtatgactg ttgagactgt tgttcttcgt agcgtccgcg ttactgctgc ggttgccaat    1200
ggaaactga                                                            1209

<210> SEQ ID NO 102
<211> LENGTH: 1209
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
atgggatctt actcatccga tgatgtggag gtgattcgtg aggccggacg ggcacaaggt      60
ttagccacga ttcttgccat tggcactgct actcctccca attccgtcgc tcaagctgat    120
tatgcagact attattttcg tgtcactaag agcgaacata tggttgatct taaagagaaa    180
tttaaacgca tttctgagaa aacagcgata aagaaacgat acctagccct caccgaagac    240
tatctgcaag agaacccaac aatgtctgag ttcatggctc catccttaaa cgctcgacaa    300
gacctagtgg tcaccggcgt cccaatgctt ggcaaagaag ccgcagtcaa ggccattgat    360
gaatggggac taccaaaatc caagatcacc cacctcatct tctgcaccac cgctggcgtt    420
gacatgcccg tgctgacta tcaactcgtc aaactccttg gtctctcccc ttcagtcaaa    480
cgctatatgt tgtaccaaca gggatgtgcc gccggcggca cagtcctccg gctagccaag    540
gaccttgctg aaaacaacaa gggctcacga gtccttatcg tctcctccga gatcactgct    600
atcggattcc atggacccaa tgagaaccac cttgactcac tcgtcgctca agctttattc    660
ggagacggag ctgcagcact cattgtgggt tcaggccctc acttggccgt agaacggcca    720
atattcgaga tcgtgtcaac tgatcaaaca atcttgccgg acactgagaa ggcaatgaag    780
ttacacttga gagggagg gttgacgttt cagttgcata gagatgtacc cttgatggtc    840
gcaaagaaca tagagaacgc agcggagaaa gcgttgtctc cactagggat aactgattgg    900
aactcagttt tctggatggt gcacccaggt ggtcgagcca tattggacca ggtggagcga    960
aaactaaacc ttaaggaaga taagttaagg gctagcaggc atgtgcttag tgaatacgga   1020
aacctgatta gcgctgctgt gttgttcatc attgacgagg tgaggaagag atctatggcg   1080
gaagggaaga gtacaaccgg tgaaggtttg gattccggtg ttttgtttgg atttggaccg   1140
ggtatgactg ttgagactgt tgttcttcgt agcgtccgcg ttactgctgc ggttgccaat   1200
ggaaactga                                                            1209

<210> SEQ ID NO 103
<211> LENGTH: 1209
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103
atgggatctt actcatccga tgatgtggag gtgattcgtg aggccggacg ggcacaaggt      60
ttagccacga ttcttgccat tggcactgct actcctccca attccgtcgc tcaagctgat    120
tatgcagact attattttcg tgtcactaag agcgaacata tggttgatct taaagagaaa    180
tttaaacgca tttgtgagaa aacagcgata aagaaacgat acctagccct caccgaagac    240
tatctgcaag agaacccaac aatgtgtgag ttcatggctc catccttaaa cgctcgacaa    300
```

| | |
|---|---|
| gacctagtgg tcaccggcgt cccaatgctt ggcaaagaag ccgcagtcaa ggccattgat | 360 |
| gaatggggac taccaaaatc caagatcacc cacctcatct tctgcaccac cgctggcgtt | 420 |
| gacatgcccg gtgctgacta tcaactcgtc aaactccttg gtctctcccc ttcagtcaaa | 480 |
| cgctatatgt tgtaccaaca gggatgtgcc gccggcggca cagtcctccg gctagccaag | 540 |
| gaccttgctg aaaacaacaa gggctcacga gtccttatcg tctgctccga gatcactgct | 600 |
| atcttattcc atggacccaa tgagaaccac cttgactcac tcgtcgctca agctttattc | 660 |
| ggagacggag ctgcagcact cattgtgggt tcaggccctc acttggccgt agaacggcca | 720 |
| atattcgaga tcgtgtcaac tgatcaaaca atcttgccgg acactgagaa ggcaatgaag | 780 |
| ttacacttga gagagggagg gttgacgttt cagttgcata gagatgtacc cttgatggtc | 840 |
| gcaaagaaca tagagaacgc agcggagaaa gcgttgtctc cactagggat aactgattgg | 900 |
| aactcagttt tctggatggt gcacccaggt ggtcgagcca tattggacca ggtggagcga | 960 |
| aaactaaacc ttaaggaaga taagttaagg gctagcaggc atgtgcttag tgaatacgga | 1020 |
| aacctgatta gcgcttgtgt gttgttcatc attgacgagg tgaggaagag atctatggcg | 1080 |
| gaagggaaga gtacaaccgg tgaaggtttg gattgcggtg ttttgtttgg atttggaccg | 1140 |
| ggtatgactg ttgagactgt tgttcttcgt agcgtccgcg ttactgctgc ggttgccaat | 1200 |
| ggaaactga | 1209 |

<210> SEQ ID NO 104
<211> LENGTH: 1209
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104

| | |
|---|---|
| atgggatctt actcatccga tgatgtggag gtgattcgtg aggccggacg ggcacaaggt | 60 |
| ttagccacga ttcttgccat tggcactgct actcctccca attccgtcgc tcaagctgat | 120 |
| tatgcagact attattttcg tgtcactaag agcgaacata tggttgatct taaagagaaa | 180 |
| tttaaacgca tttgtgagaa aacagcgata aagaaacgat acctagccct caccgaagac | 240 |
| tatctgcaag agaacccaac aatgtgtgag ttcatggctc catccttaaa cgctcgacaa | 300 |
| gacctagtgg tcaccggcgt cccaatgctt ggcaaagaag ccgcagtcaa ggccattgat | 360 |
| gaatggggac taccaaaatc caagatcacc cacctcatct tctgcaccct cgctggcgtt | 420 |
| gacatgcccg gtgctgacta tcaactcgtc aaactccttg gtctctcccc ttcagtcaaa | 480 |
| cgctatatgt tgtaccaaca gggatgtgcc gccggcggca cagtcctccg gctagccaag | 540 |
| gaccttgctg aaaacaacaa gggctcacga gtccttatcg tctgctccga gatcactgct | 600 |
| atcttcttcc atggacccaa tgagaaccac cttgactcac tcgtcgctca agctttattc | 660 |
| ggagacggag ctgcagcact cattgtgggt tcaggccctc acttggccgt agaacggcca | 720 |
| atattcgaga tcgtgtcaac tgatcaaaca atcttgccgg acactgagaa ggcaatgaag | 780 |
| ttacacttga gagagggagg gatgacgttt cagttgcata gagatgtacc cttgatggtc | 840 |
| gcaaagaaca tagagaacgc agcggagaaa gcgttgtctc cactagggat aactgattgg | 900 |
| aactcagttt tctggatggt gcacccaggt ggtcgagcca tattggacca ggtggagcga | 960 |
| aaactaaacc ttaaggaaga taagttaagg gctagcaggc atgtgcttag tgaatacgga | 1020 |
| aacctgatta gcgcttgtgt gttgttcatc attgacgagg tgaggaagag atctatggcg | 1080 |

| | |
|---|---|
| gaagggaaga gtacaaccgg tgaaggtttg gattgcggtg ttttgtttgg atttggaccg | 1140 |
| ggtatgactg ttgagactgt tgttcttcgt agcgtccgcg ttactgctgc ggttgccaat | 1200 |
| ggaaactga | 1209 |

<210> SEQ ID NO 105
<211> LENGTH: 1209
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105

| | |
|---|---|
| atgggatctt actcatccga tgatgtggag gtgattcgtg aggccggacg ggcacaaggt | 60 |
| ttagccacga ttcttgccat tggcactgct actcctccca attccgtcgc tcaagctgat | 120 |
| tatgcagact attattttcg tgtcactaag agcgaacata tggttgatct taaagagaaa | 180 |
| tttaaacgca tttgtgagaa aacagcgata aagaaacgat acctagccct caccgaagac | 240 |
| tatctgcaag agaacccaac aatgtgtgag ttcatggctc catccttaaa cgctcgacaa | 300 |
| gacctagtgg tcaccggcgt cccaatgctt ggcaaagaag ccgcagtcaa ggccattgat | 360 |
| gaatggggac taccaaaatc caagatcacc cacctcatct tctgcaccat ggctggcgtt | 420 |
| gacatgcccg tgctgactaa tcaactcgtc aaactccttg gtctctcccc ttcagtcaaa | 480 |
| cgctatatgt tgtaccaaca gggatgtgcc gccggcggca cagtcctccg gctagccaag | 540 |
| gaccttgctg aaaacaacaa gggctcacga gtccttatcg tctgctccga gatcactgct | 600 |
| atcttcttcc atggacccaa tgagaaccac cttgactcac tcgtcgctca gctttattc | 660 |
| ggagacggag ctgcagcact cattgtgggt tcaggccctc acttggccgt agaacggcca | 720 |
| atattcgaga tcgtgtcaac tgatcaaaca atcttgccgg acactgagaa ggcaatgaag | 780 |
| ttacacttga gagagggagg gatgacgttt cagttgcata gagatgtacc cttgatggtc | 840 |
| gcaaagaaca tagagaacgc agcggagaaa gcgttgtctc cactagggat aactgattgg | 900 |
| aactcagttt tctggatggt gcacccaggt ggtcgagcca tattggacca ggtggagcga | 960 |
| aaactaaacc ttaaggaaga taagttaagg ctagcaggc atgtgcttag tgaatacgga | 1020 |
| aacctgttta gcgcttgtgt gttgttcatc attgacgagg tgaggaagag atctatggcg | 1080 |
| gaagggaaga gtacaaccgg tgaaggtttg gattgcggtg ttttgtttgg atttggaccg | 1140 |
| ggtatgactg ttgagactgt tgttcttcgt agcgtccgcg ttactgctgc ggttgccaat | 1200 |
| ggaaactga | 1209 |

<210> SEQ ID NO 106
<211> LENGTH: 1209
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106

| | |
|---|---|
| atgggatctt actcatccga tgatgtggag gtgattcgtg aggccggacg ggcacaaggt | 60 |
| ttagccacga ttcttgccat tggcactgct actcctccca attccgtcgc tcaagctgat | 120 |
| tatgcagact attattttcg tgtcactaag agcgaacata tggttgatct taaagagaaa | 180 |
| tttaaacgca tttgtgagaa aacagcgata aagaaacgat acctagccct caccgaagac | 240 |
| tatctgcaag agaacccaac aatgtgtgag ttcatggctc catccttaaa cgctcgacaa | 300 |

```
gacctagtgg tcaccggcgt cccaatgctt ggcaaagaag ccgcagtcaa ggccattgat      360
gaatggggac taccaaaatc caagatcacc cacctcatct tctgcaccac cgctggcgtt      420
gacatgcccg gtgctgacta tcaactcgtc aaactccttg gtctctcccc ttcagtcaaa      480
cgctatatgt tgtaccaaca gggatgtgcc gccggcggca cagtcctccg gctagccaag      540
gaccttgctg aaaacaacaa gggctcacga gtccttatcg tctgctccga gatcactgct      600
atcttcttcc atggacccaa tgagaaccac cttgactcac tcgtcgctca agctttattc      660
ggagacggag ctgcagcact cattgtgggt tcaggccctc acttggccgt agaacggcca      720
atattcgaga tcgtgtcaac tgatcaaaca atcttgccgg acactgagaa ggcaatgaag      780
ttacacttga gagagggagg gatgacgttt cagttgcata gagatgtacc cttgatggtc      840
gcaaagaaca tagagaacgc agcggagaaa gcgttgtctc cactagggat aactgattgg      900
aactcagttt tctggatggt gcacccaggt ggtcgagcca tattggacca ggtggagcga      960
aaactaaacc ttaaggaaga taagttaagg gctagcaggc atgtgcttag tgaatacgga     1020
aacctgttta gcgcttgtgt gttgttcatc attgacgagg tgaggaagag atctatggcg     1080
gaagggaaga gtacaaccgg tgaaggtttg gattgcggtg ttttgtttgg atttggaccg     1140
ggtatgactg ttgagactgt tgttcttcgt agcgtccgcg ttactgctgc ggttgccaat     1200
ggaaactga                                                             1209

<210> SEQ ID NO 107
<211> LENGTH: 1209
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107
atgggatctt actcatccga tgatgtggag gtgattcgtg aggccggacg ggcacaaggt       60
ttagccacga ttcttgccat tggcactgct actcctccca attccgtcgc tcaagctgat      120
tatgcagact attattttcg tgtcactaag agcgaacata tggttgatct aaagagaaa       180 tttaaacgca tttgtgagaa aacagcgata agaaacgat acctagccct caccgaagac      240
tatctgcaag agaacccaac aatgtgtgag ttcatggctc catccttaaa cgctcgacaa      300
gacctagtgg tcaccggcgt cccaatgctt ggcaaagaag ccgcagtcaa ggccattgat      360
gaatggggac taccaaaatc caagatcacc cacctcatct tctgcaccac cgctggcgtt      420
gacatgcccg gtgctgacta tcaactcgtc aaactccttg gtctctcccc ttcagtcaaa      480
cgctatatgt tgtaccaaca gggatgtgcc gccggcggca cagtcctccg gctagccaag      540
gaccttgctg aaaacaacaa gggctcacga gtccttatcg tctgctccga gatcactgct      600
atcttattcc atggacccaa tgagaaccac cttgactcac tcgtcgctca agctttattc      660
ggagacggag ctgcagcact cattgtgggt tcaggccctc acttggccgt agaacggcca      720
atattcgaga tcgtgtcaac tgatcaaaca atcttgccgg acactgagaa ggcaatgaag      780
ttacacttga gagagggagg gttgacgttt cagttgcata gagatgtacc cttgatggtc      840
gcaaagaaca tagagaacgc agcggagaaa gcgttgtctc cactagggat aactgattgg      900
aactcagttt tctggatggt gcacccaggt ggtcgagcca tattggacca ggtggagcga      960
aaactaaacc ttaaggaaga taagttaagg gctagcaggc atgtgcttag tgaatacgga     1020
aacctgatta gcgcttgtgt gttgttcatc attgacgagg tgaggaagag atctatggcg     1080
```

```
gaagggaaga gtacaaccgg tgaaggtttg gattccggtg ttttgtttgg atttggaccg   1140
ggtatgactg ttgagactgt tgttcttcgt agcgtccgcg ttactgctgc ggttgccaat   1200
ggaaactga                                                           1209
```

<210> SEQ ID NO 108
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 108

```
atgggatctt actcatccga tgatgtggag gtgattcgtg aggccggacg ggcacaaggt    60
ttagccacga ttcttgccat tggcactgct actcctccca attccgtcgc tcaagctgat   120
tatgcagact attattttcg tgtcactaag agcgaacata tggttgatct aaagagaaa    180 tttaaacgca tttgtgagaa aacagcgata aagaaacgat acctagccct caccgaagac   240
tatctgcaag agaacccaac aatgtgtgag ttcatggctc catccttaaa cgctcgacaa   300
gacctagtgg tcaccggcgt cccaatgctt ggcaaagaag ccgcagtcaa ggccattgat   360
gaatggggac taccaaaatc caagatcacc cacctcatct tctgcaccac cgctggcgtt   420
gacatgcccg tgctgactta tcaactcgtc aaactccttg gtctctcccc ttcagtcaaa   480
cgctatatgt tgtaccaaca gggatgtgcc gccggcggca cagtcctccg gctagccaag   540
gaccttgctg aaaacaacaa gggctcacga gtccttatcg tctgctccga gatcactgct   600
atcttattcc atggacccaa tgagaaccac cttgactcac tcgtcgctca agctttattc   660
ggagacggag ctgcagcact cattgtgggt tcaggccctc acttggccgt agaacggcca   720
atattcgaga tcgtgtcaac tgatcaaaca atcttgccgg acactgagaa ggcaatgaag   780
ttacacttga gagagggagg gttgacgttt cagttgcata gagatgtacc cttgatggtc   840
gcaaagaaca tagagaacgc agcggagaaa gcgttgtctc cactagggat aactgattgg   900
aactcagttt tctggatggt gcacccaggt ggtcgagcca tattggacca ggtggagcga   960
aaactaaacc ttaaggaaga taagttaagg gctagcaggc atgtgcttag tgaatacgga  1020
aacctgatta gcgcttgtgt gttgttcatc attgacgagg tgaggaagag atctatggcg  1080
gaagggaaga gtacaaccgg tgaaggtttg gatgccggtg ttttgtttgg atttggaccg  1140
ggtatgactg ttgagactgt tgttcttcgt agcgtccgcg ttactgctgc ggttgccaat  1200
ggaaactga                                                          1209
```

<210> SEQ ID NO 109
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 109

```
atgggatctt actcatccga tgatgtggag gtgattcgtg aggccggacg ggcacaaggt    60
ttagccacga ttcttgccat tggcactgct actcctccca attccgtcgc tcaagctgat   120
tatgcagact attattttcg tgtcactaag agcgaacata tggttgatct aaagagaaa    180 tttaaacgca tttgtgagaa aacagcgata aagaaacgat acctagccct caccgaagac   240
```

| | |
|---|---|
| tatctgcaag agaacccaac aatgtgtgag ttcatggctc catccttaaa cgctcgacaa | 300 |
| gacctagtgg tcaccggcgt cccaatgctt ggcaaagaag ccgcagtcaa ggccattgat | 360 |
| gaatggggac taccaaaatc caagatcacc cacctcatct tctgcaccac cgctggcgtt | 420 |
| gacatgcccg gtgctgacta tcaactcgtc aaactccttg gtctctcccc ttcagtcaaa | 480 |
| cgctatatgt tgtaccaaca gggatgtgcc gccggcggca cagtcctccg gctagccaag | 540 |
| gaccttgctg aaaacaacaa gggctcacga gtccttatcg tctgctccga gatcactgct | 600 |
| atcttattcc atggacccaa tgagaaccac cttgactcac tcgtcgctca gctttattc | 660 |
| ggagacggag ctgcagcact cattgtgggt tcaggccctc acttggccgt agaacggcca | 720 |
| atattcgaga tcgtgtcaac tgatcaaaca atcttgccgg acactgagaa ggcaatgaag | 780 |
| ttacacttga gagagggagg gttgacgttt cagttgcata gagatgtacc cttgatggtc | 840 |
| gcaaagaaca tagagaacgc agcggagaaa gcgttgtctc cactagggat aactgattgg | 900 |
| aactcagttt tctggatggt gcacccaggt ggtcgagcca tattggacca ggtggagcga | 960 |
| aaactaaacc ttaaggaaga taagttaagg gctagcaggc atgtgcttag tgaatacgga | 1020 |
| aacctgatta gcgcttctgt gttgttcatc attgacgagg tgaggaagag atctatggcg | 1080 |
| gaagggaaga gtacaaccgg tgaaggtttg gattgcggtg ttttgtttgg atttggaccg | 1140 |
| ggtatgactg ttgagactgt tgttcttcgt agcgtccgcg ttactgctgc ggttgccaat | 1200 |
| ggaaactga | 1209 |

<210> SEQ ID NO 110
<211> LENGTH: 1209
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110

| | |
|---|---|
| atgggatctt actcatccga tgatgtggag gtgattcgtg aggccggacg ggcacaaggt | 60 |
| ttagccacga ttcttgccat tggcactgct actcctccca attccgtcgc tcaagctgat | 120 |
| tatgcagact attattttcg tgtcactaag agcgaacata tggttgatct taagagaaa | 180 |
| tttaaacgca tttgtgagaa aacagcgata aagaaacgat acctagccct caccgaagac | 240 |
| tatctgcaag agaacccaac aatgtgtgag ttcatggctc catccttaaa cgctcgacaa | 300 |
| gacctagtgg tcaccggcgt cccaatgctt ggcaaagaag ccgcagtcaa ggccattgat | 360 |
| gaatggggac taccaaaatc caagatcacc cacctcatct tctgcaccac cgctggcgtt | 420 |
| gacatgcccg gtgctgacta tcaactcgtc aaactccttg gtctctcccc ttcagtcaaa | 480 |
| cgctatatgt tgtaccaaca gggatgtgcc gccggcggca cagtcctccg gctagccaag | 540 |
| gaccttgctg aaaacaacaa gggctcacga gtccttatcg tctgctccga gatcactgct | 600 |
| atcttattcc atggacccaa tgagaaccac cttgactcac tcgtcgctca gctttattc | 660 |
| ggagacggag ctgcagcact cattgtgggt tcaggccctc acttggccgt agaacggcca | 720 |
| atattcgaga tcgtgtcaac tgatcaaaca atcttgccgg acactgagaa ggcaatgaag | 780 |
| ttacacttga gagagggagg gttgacgttt cagttgcata gagatgtacc cttgatggtc | 840 |
| gcaaagaaca tagagaacgc agcggagaaa gcgttgtctc cactagggat aactgattgg | 900 |
| aactcagttt tctggatggt gcacccaggt ggtcgagcca tattggacca ggtggagcga | 960 |
| aaactaaacc ttaaggaaga taagttaagg gctagcaggc atgtgcttag tgaatacgga | 1020 |

```
aacctgatta gcgctgctgt gttgttcatc attgacgagg tgaggaagag atctatggcg    1080
gaagggaaga gtacaaccgg tgaaggtttg gattgcggtg ttttgtttgg atttggaccg    1140
ggtatgactg ttgagactgt tgttcttcgt agcgtccgcg ttactgctgc ggttgccaat    1200
ggaaactga                                                             1209
```

<210> SEQ ID NO 111
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 111

```
atgggatctt actcatccga tgatgtggag gtgattcgtg aggccggacg ggcacaaggt    60
ttagccacga ttcttgccat tggcactgct actcctccca attccgtcgc tcaagctgat    120
tatgcagact attattttcg tgtcactaag agcgaacata tggttgatct taaagagaaa    180
tttaaacgca tttgtgagaa aacagcgata aagaaacgat acctagccct caccgaagac    240
tatctgcaag agaacccaac aatgtgtgag ttcatggctc catccttaaa cgctcgacaa    300
gacctagtgg tcaccggcgt cccaatgctt ggcaaagaag ccgcagtcaa ggccattgat    360
gaatggggac taccaaaatc caagatcacc cacctcatct tctgcaccac cgctggcgtt    420
gacatgcccg gtgctgacta tcaactcgtc aaactccttg gtctctcccc ttcagtcaaa    480
cgctatatgt tgtaccaaca gggatgtgcc gccggcggca cagtcctccg gctagccaag    540
gaccttgctg aaaacaacaa gggctcacga gtccttatcg tctcctccga gatcactgct    600
atcttattcc atggacccaa tgagaaccac cttgactcac tcgtcgctca agctttattc    660
ggagacggag ctgcagcact cattgtgggt tcaggccctc acttggccgt agaacggcca    720
atattcgaga tcgtgtcaac tgatcaaaca atcttgccgg acactgagaa ggcaatgaag    780
ttacacttga gagggaggg gttgacgttt cagttgcata gagatgtacc cttgatggtc    840
gcaaagaaca tagagaacgc agcggagaaa gcgttgtctc cactagggat aactgattgg    900
aactcagttt tctggatggt gcacccaggt ggtcgagcca tattggacca ggtggagcga    960
aaactaaacc ttaaggaaga taagttaagg gctagcaggc atgtgcttag tgaatacgga    1020
aacctgatta gcgcttgtgt gttgttcatc attgacgagg tgaggaagag atctatggcg    1080
gaagggaaga gtacaaccgg tgaaggtttg gattgcggtg ttttgtttgg atttggaccg    1140
ggtatgactg ttgagactgt tgttcttcgt agcgtccgcg ttactgctgc ggttgccaat    1200
ggaaactga                                                             1209
```

<210> SEQ ID NO 112
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 112

```
atgggatctt actcatccga tgatgtggag gtgattcgtg aggccggacg ggcacaaggt    60
ttagccacga ttcttgccat tggcactgct actcctccca attccgtcgc tcaagctgat    120
tatgcagact attattttcg tgtcactaag agcgaacata tggttgatct taaagagaaa    180
tttaaacgca tttgtgagaa aacagcgata aagaaacgat acctagccct caccgaagac    240
```

```
tatctgcaag agaacccaac aatgtgtgag ttcatggctc catccttaaa cgctcgacaa    300
gacctagtgg tcaccggcgt cccaatgctt ggcaaagaag ccgcagtcaa ggccattgat    360
gaatggggac taccaaaatc caagatcacc cacctcatct tctgcaccac cgctggcgtt    420
gacatgcccg gtgctgacta tcaactcgtc aaactccttg gtctctcccc ttcagtcaaa    480
cgctatatgt tgtaccaaca gggatgtgcc gccggcggca cagtcctccg gctagccaag    540
gaccttgctg aaaacaacaa gggctcacga gtccttatcg tctgcctccga gatcactgct    600 atcttattcc atggacccaa tgagaaccac cttgactcac tcgtcgctca agctttattc    660
ggagacggag ctgcagcact cattgtgggt tcaggccctc acttggccgt agaacggcca    720
atattcgaga tcgtgtcaac tgatcaaaca atcttgccgg acactgagaa ggcaatgaag    780
ttacacttga gagagggagg gttgacgttt cagttgcata gagatgtacc cttgatggtc    840
gcaaagaaca tagagaacgc agcggagaaa gcgttgtctc cactagggat aactgattgg    900
aactcagttt tctggatggt gcacccaggt ggtcgagcca tattgaccca ggtggagcga    960
aaactaaacc ttaaggaaga taagttaagg gctagcaggc atgtgcttag tgaatacgga   1020
aacctgatta gcgcttgtgt gttgttcatc attgacgagg tgaggaagag atctatggcg   1080
gaagggaaga gtacaaccgg tgaaggtttg gattgcggtg ttttgtttgg atttggaccg   1140
ggtatgactg ttgagactgt tgttcttcgt agcgtccgcg ttactgctgc ggttgccaat   1200
ggaaactga                                                           1209

<210> SEQ ID NO 113
<211> LENGTH: 1209
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113
atgggatctt actcatccga tgatgtggag gtgattcgtg aggccggacg ggcacaaggt     60
ttagccacga ttcttgccat tggcactgct actcctccca attccgtcgc tcaagctgat    120
tatgcagact attattttcg tgtcactaag agcgaacata tggttgatct taaagagaaa    180
tttaaacgca tttgtgagaa aacagcgata aagaaacgat acctagccct caccgaagac    240
tatctgcaag agaacccaac aatgtgtgag ttcatggctc catccttaaa cgctcgacaa    300
gacctagtgg tcaccggcgt cccaatgctt ggcaaagaag ccgcagtcaa ggccattgat    360
gaatggggac taccaaaatc caagatcacc cacctcatct tctccaccac cgctggcgtt    420
gacatgcccg gtgctgacta tcaactcgtc aaactccttg gtctctcccc ttcagtcaaa    480
cgctatatgt tgtaccaaca gggatgtgcc gccggcggca cagtcctccg gctagccaag    540
gaccttgctg aaaacaacaa gggctcacga gtccttatcg tctgcctcga gatcactgct    600
atcttattcc atggacccaa tgagaaccac cttgactcac tcgtcgctca agctttattc    660
ggagacggag ctgcagcact cattgtgggt tcaggccctc acttggccgt agaacggcca    720
atattcgaga tcgtgtcaac tgatcaaaca atcttgccgg acactgagaa ggcaatgaag    780
ttacacttga gagagggagg gttgacgttt cagttgcata gagatgtacc cttgatggtc    840
gcaaagaaca tagagaacgc agcggagaaa gcgttgtctc cactagggat aactgattgg    900
aactcagttt tctggatggt gcacccaggt ggtcgagcca tattgaccca ggtggagcga    960
aaactaaacc ttaaggaaga taagttaagg gctagcaggc atgtgcttag tgaatacgga   1020
```

```
aacctgatta gcgcttgtgt gttgttcatc attgacgagg tgaggaagag atctatggcg    1080
gaagggaaga gtacaaccgg tgaaggtttg gattgcggtg ttttgtttgg atttggaccg    1140
ggtatgactg ttgagactgt tgttcttcgt agcgtccgcg ttactgctgc ggttgccaat    1200
ggaaactga                                                             1209
```

<210> SEQ ID NO 114
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 114

```
atgggatctt actcatccga tgatgtggag gtgattcgtg aggccggacg ggcacaaggt      60
ttagccacga ttcttgccat tggcactgct actcctccca attccgtcgc tcaagctgat    120
tatgcagact attattttcg tgtcactaag agcgaacata tggttgatct aaagagaaa     180 tttaaacgca tttgtgagaa aacagcgata agaaacgat acctagccct caccgaagac    240
tatctgcaag agaacccaac aatgtgtgag ttcatggctc catccttaaa cgctcgacaa    300
gacctagtgg tcaccggcgt cccaatgctt ggcaaagaag ccgcagtcaa ggccattgat    360
gaatggggac taccaaaatc caagatcacc cacctcatct cgccaccac cgctggcgtt    420 gacatgcccg tgctgactat caactcgtc aaactccttg gtctctcccc ttcagtcaaa    480
cgctatatgt tgtaccaaca gggatgtgcc gccggcggca cagtcctccg gctagccaag    540
gaccttgctg aaaacaacaa gggctcacga gtccttatcg tctgctccga gatcactgct    600
atcttattcc atggacccaa tgagaaccac cttgactcac tcgtcgctca agctttattc    660
ggagacggag ctgcagcact cattgtgggt tcaggccctc acttggccgt agaacggcca    720
atattcgaga tcgtgtcaac tgatcaaaca atcttgccgg acactgagaa ggcaatgaag    780
ttacacttga gagggagg gttgacgttt cagttgcata gagatgtacc cttgatggtc    840
gcaaagaaca tagagaacgc agcggagaaa gcgttgtctc cactagggat aactgattgg    900
aactcagttt tctggatggt gcacccaggt ggtcgagcca tattggacca ggtggagcga    960 aaactaaaacc ttaaggaaga taagttaagg gctagcaggc atgtgcttag tgaatacgga    1020
aacctgatta gcgcttgtgt gttgttcatc attgacgagg tgaggaagag atctatggcg    1080
gaagggaaga gtacaaccgg tgaaggtttg gattgcggtg ttttgtttgg atttggaccg    1140
ggtatgactg ttgagactgt tgttcttcgt agcgtccgcg ttactgctgc ggttgccaat    1200
ggaaactga                                                             1209
```

<210> SEQ ID NO 115
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 115

```
atgggatctt actcatccga tgatgtggag gtgattcgtg aggccggacg ggcacaaggt      60
ttagccacga ttcttgccat tggcactgct actcctccca attccgtcgc tcaagctgat    120
tatgcagact attattttcg tgtcactaag agcgaacata tggttgatct aaagagaaaa    180
```

| | |
|---|---|
| tttaaacgca tttgtgagaa aacagcgata aagaaacgat acctagccct caccgaagac | 240 |
| tatctgcaag agaacccaac aatgtctgag ttcatggctc catccttaaa cgctcgacaa | 300 |
| gacctagtgg tcaccggcgt cccaatgctt ggcaaagaag ccgcagtcaa ggccattgat | 360 |
| gaatggggac taccaaaatc caagatcacc cacctcatct tctgcaccac cgctggcgtt | 420 |
| gacatgcccg gtgctgacta tcaactcgtc aaactccttg gtctctcccc ttcagtcaaa | 480 |
| cgctatatgt tgtaccaaca gggatgtgcc gccggcggca cagtcctccg gctagccaag | 540 |
| gaccttgctg aaaacaacaa gggctcacga gtccttatcg tctgctccga gatcactgct | 600 |
| atcttattcc atggacccaa tgagaaccac cttgactcac tcgtcgctca agctttattc | 660 |
| ggagacggag ctgcagcact cattgtgggt tcaggccctc acttggccgt agaacggcca | 720 |
| atattcgaga tcgtgtcaac tgatcaaaca atcttgccgg acactgagaa ggcaatgaag | 780 |
| ttacacttga gagagggagg gttgacgttt cagttgcata gagatgtacc cttgatggtc | 840 |
| gcaaagaaca tagagaacgc agcggagaaa gcgttgtctc cactagggat aactgattgg | 900 |
| aactcagttt tctggatggt gcacccaggt ggtcgagcca tattggacca ggtggagcga | 960 |
| aaactaaacc ttaaggaaga taagttaagg gctagcaggc atgtgcttag tgaatacgga | 1020 |
| aacctgatta gcgcttgtgt gttgttcatc attgacgagg tgaggaagag atctatggcg | 1080 |
| gaagggaaga gtacaaccgg tgaaggtttg gattgcggtg ttttgtttgg atttggaccg | 1140 |
| ggtatgactg ttgagactgt tgttcttcgt agcgtccgcg ttactgctgc ggttgccaat | 1200 |
| ggaaactga | 1209 |

<210> SEQ ID NO 116
<211> LENGTH: 1209
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 116

| | |
|---|---|
| atgggatctt actcatccga tgatgtggag gtgattcgtg aggccggacg ggcacaaggt | 60 |
| ttagccacga ttcttgccat ggcactgct actcctccca attccgtcgc tcaagctgat | 120 |
| tatgcagact attattttcg tgtcactaag agcgaacata tggttgatct taaagagaaa | 180 |
| tttaaacgca tttgtgagaa aacagcgata aagaaacgat acctagccct caccgaagac | 240 |
| tatctgcaag agaacccaac aatggctgag ttcatggctc catccttaaa cgctcgacaa | 300 |
| gacctagtgg tcaccggcgt cccaatgctt ggcaaagaag ccgcagtcaa ggccattgat | 360 |
| gaatggggac taccaaaatc caagatcacc cacctcatct tctgcaccac cgctggcgtt | 420 |
| gacatgcccg gtgctgacta tcaactcgtc aaactccttg gtctctcccc ttcagtcaaa | 480 |
| cgctatatgt tgtaccaaca gggatgtgcc gccggcggca cagtcctccg gctagccaag | 540 |
| gaccttgctg aaaacaacaa gggctcacga gtccttatcg tctgctccga gatcactgct | 600 |
| atcttattcc atggacccaa tgagaaccac cttgactcac tcgtcgctca agctttattc | 660 |
| ggagacggag ctgcagcact cattgtgggt tcaggccctc acttggccgt agaacggcca | 720 |
| atattcgaga tcgtgtcaac tgatcaaaca atcttgccgg acactgagaa ggcaatgaag | 780 |
| ttacacttga gagagggagg gttgacgttt cagttgcata gagatgtacc cttgatggtc | 840 |
| gcaaagaaca tagagaacgc agcggagaaa gcgttgtctc cactagggat aactgattgg | 900 |
| aactcagttt tctggatggt gcacccaggt ggtcgagcca tattggacca ggtggagcga | 960 |

```
aaactaaaacc ttaaggaaga taagttaagg gctagcaggc atgtgcttag tgaatacgga    1020
aacctgatta gcgcttgtgt gttgttcatc attgacgagg tgaggaagag atctatggcg    1080
gaagggaaga gtacaaccgg tgaaggtttg gattgcggtg ttttgtttgg atttggaccg    1140
ggtatgactg ttgagactgt tgttcttcgt agcgtccgcg ttactgctgc ggttgccaat    1200
ggaaactga                                                            1209
```

<210> SEQ ID NO 117
<211> LENGTH: 1209
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117

```
atgggatctt actcatccga tgatgtggag gtgattcgtg aggccggacg ggcacaaggt     60
ttagccacga ttcttgccat tggcactgct actcctccca attccgtcgc tcaagctgat    120
tatgcagact attattttcg tgtcactaag agcgaacata tggttgatct taagagaaa    180 tttaaacgca tttctgagaa acagcgata aagaaacgat acctagccct caccgaagac    240
tatctgcaag agaacccaac aatgtgtgag ttcatggctc catccttaaa cgctcgacaa    300
gacctagtgg tcaccggcgt cccaatgctt ggcaaagaag ccgcagtcaa ggccattgat    360
gaatggggac taccaaaatc caagatcacc cacctcatct tctgcaccac cgctggcgtt    420
gacatgcccg tgctgactac tcaactcgtc aaactccttg gtctctcccc ttcagtcaaa    480
cgctatatgt tgtaccaaca gggatgtgcc gccggcggca cagtcctccg gctagccaag    540
gaccttgctg aaaacaacaa gggctcacga gtccttatcg tctgctccga gatcactgct    600
atcttattcc atggacccaa tgagaaccac cttgactcac tcgtcgctca gctttattc    660 ggagacggag ctgcagcact cattgtgggt tcaggccctc acttggccgt agaacggcca    720
atattcgaga tcgtgtcaac tgatcaaaca atcttgccgg acactgagaa ggcaatgaag    780
ttacacttga gagggagg gttgacgttt cagttgcata gagatgtacc cttgatggtc    840
gcaaagaaca tagagaacgc agcggagaaa gcgttgtctc cactagggat aactgattgg    900
aactcagttt tctggatggt gcacccaggt ggtcgagcca tattggacca ggtggagcga    960 aaactaaaacc ttaaggaaga taagttaagg gctagcaggc atgtgcttag tgaatacgga   1020
aacctgatta gcgcttgtgt gttgttcatc attgacgagg tgaggaagag atctatggcg   1080
gaagggaaga gtacaaccgg tgaaggtttg gattgcggtg ttttgtttgg atttggaccg   1140
ggtatgactg ttgagactgt tgttcttcgt agcgtccgcg ttactgctgc ggttgccaat   1200
ggaaactga                                                           1209
```

<210> SEQ ID NO 118
<211> LENGTH: 1209
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118

```
atgggatctt actcatccga tgatgtggag gtgattcgtg aggccggacg ggcacaaggt     60
ttagccacga ttcttgccat tggcactgct actcctccca attccgtcgc tcaagctgat    120
tatgcagact attattttcg tgtcactaag agcgaacata tggttgatct taagagaaa    180
```

```
tttaaacgca ttgctgagaa aacagcgata agaaacgat  acctagccct caccgaagac    240
tatctgcaag agaacccaac aatgtgtgag ttcatggctc catccttaaa cgctcgacaa    300
gacctagtgg tcaccggcgt cccaatgctt ggcaaagaag ccgcagtcaa ggccattgat    360
gaatggggac taccaaaatc caagatcacc cacctcatct tctgcaccac cgctggcgtt    420
gacatgcccg gtgctgacta tcaactcgtc aaactccttg gtctctcccc ttcagtcaaa    480
cgctatatgt tgtaccaaca gggatgtgcc gccggcggca cagtcctccg gctagccaag    540
gaccttgctg aaaacaacaa gggctcacga gtccttatcg tctgctccga gatcactgct    600
atcttattcc atggacccaa tgagaaccac cttgactcac tcgtcgctca agctttattc    660
ggagacggag ctgcagcact cattgtgggt tcaggccctc acttggccgt agaacggcca    720
atattcgaga tcgtgtcaac tgatcaaaca atcttgccgg acactgagaa ggcaatgaag    780
ttacacttga gagagggagg gttgacgttt cagttgcata gagatgtacc cttgatggtc    840
gcaaagaaca tagagaacgc agcggagaaa gcgttgtctc cactagggat aactgattgg    900
aactcagttt tctggatggt gcacccaggt ggtcgagcca tattggacca ggtggagcga    960
aaactaaacc ttaaggaaga taagttaagg gctagcaggc atgtgcttag tgaatacgga   1020
aacctgatta gcgcttgtgt gttgttcatc attgacgagg tgaggaagag atctatggcg   1080
gaagggaaga gtacaaccgg tgaaggtttg gattgcggtg ttttgtttgg atttggaccg   1140
ggtatgactg ttgagactgt tgttcttcgt agcgtccgcg ttactgctgc ggttgccaat   1200
ggaaactga                                                          1209
```

<210> SEQ ID NO 119
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 119

```
atgggatctt actcatccga tgatgtggag gtgattcgtg aggccggacg ggcacaaggt     60
ttagccacga ttcttgccat tggcactgct actcctccca attccgtcgc tcaagctgat    120
tatgcagact attattttcg tgtcactaag agcgaacata tggttgatct taaagagaaa    180
tttaaacgca tttgtgagaa aacagcgata agaaacgat  acctagccct caccgaagac    240
tatctgcaag agaacccaac aatgtgtgag ttcatggctc catccttaaa cgctcgacaa    300
gacctagtgg tcaccggcgt cccaatgctt ggcaaagaag ccgcagtcaa ggccattgat    360
gaatggggac taccaaaatc caagatcacc cacctcatct tctgcaccac cgctggcgtt    420
gacatgcccg gtgctgacta tcaactcgtc aaactccttg gtctctcccc ttcagtcaaa    480
cgctatatgt tgtaccaaca gggatctgcc gccggcggca cagtcctccg gctagccaag    540
gaccttgctg aaaacaacaa gggctcacga gtccttatcg tctgctccga gatcactgct    600
atcttattcc atggacccaa tgagaaccac cttgactcac tcgtcgctca agctttattc    660
ggagacggag ctgcagcact cattgtgggt tcaggccctc acttggccgt agaacggcca    720
atattcgaga tcgtgtcaac tgatcaaaca atcttgccgg acactgagaa ggcaatgaag    780
ttacacttga gagagggagg gttgacgttt cagttgcata gagatgtacc cttgatggtc    840
gcaaagaaca tagagaacgc agcggagaaa gcgttgtctc cactagggat aactgattgg    900
aactcagttt tctggatggt gcacccaggt ggtcgagcca tattggacca ggtggagcga    960
```

| aaactaaacc ttaaggaaga taagttaagg gctagcaggc atgtgcttag tgaatacgga | 1020 |
| aacctgatta gcgcttgtgt gttgttcatc attgacgagg tgaggaagag atctatggcg | 1080 |
| gaagggaaga gtacaaccgg tgaaggtttg gattgcggtg ttttgtttgg atttggaccg | 1140 |
| ggtatgactg ttgagactgt tgttcttcgt agcgtccgcg ttactgctgc ggttgccaat | 1200 |
| ggaaactga | 1209 |

<210> SEQ ID NO 120
<211> LENGTH: 1209
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 120

| atgggatctt actcatccga tgatgtggag gtgattcgtg aggccggacg ggcacaaggt | 60 |
| ttagccacga ttcttgccat tggcactgct actcctccca attccgtcgc tcaagctgat | 120 |
| tatgcagact attattttcg tgtcactaag agcgaacata tggttgatct taaagagaaa | 180 |
| tttaaacgca tttgtgagaa aacagcgata aagaaacgat acctagccct caccgaagac | 240 |
| tatctgcaag agaacccaac aatgtgtgag ttcatggctc catccttaaa cgctcgacaa | 300 |
| gacctagtgg tcaccggcgt cccaatgctt ggcaaagaag ccgcagtcaa ggccattgat | 360 |
| gaatggggac taccaaaatc caagatcacc cacctcatct tctgcaccac cgctggcgtt | 420 |
| gacatgcccg tgctgactga tcaactcgtc aaactccttg gtctctcccc ttcagtcaaa | 480 |
| cgctatatgt tgtaccaaca gggatgtgcc gccggcggca cagtcctccg gctagccaag | 540 |
| gaccttgctg aaaacaacaa gggctcacga gtccttatcg tctgctccga gatcactgct | 600 |
| atcttattcc atggacccaa tgagaaccac cttgactcac tcgtcgctca gctttattc | 660 |
| ggagacggag ctgcagcact cattgtgggt tcaggccctc acttggccgt agaacggcca | 720 |
| atattcgaga tcgtgtcaac tgatcaaaca atcttgccgg acactgagaa ggcaatgaag | 780 |
| ttacacttga gagagggagg gttgacgttt cagttgcata gagatgtacc cttgatggtc | 840 |
| gcaaagaaca tagagaacgc agcggagaaa gcgttgtctc cactagggat aactgattgg | 900 |
| aactcagttt tctggatggt gcacccaggt ggtcgagcca tattggacca ggtggagcga | 960 |
| aaactaaacc ttaaggaaga taagttaagg gctagcaggc atgtgcttag tgaatacgga | 1020 |
| cacctgatta gcgcttgtgt gttgttcatc attgacgagg tgaggaagag atctatggcg | 1080 |
| gaagggaaga gtacaaccgg tgaaggtttg gattgcggtg ttttgtttgg atttggaccg | 1140 |
| ggtatgactg ttgagactgt tgttcttcgt agcgtccgcg ttactgctgc ggttgccaat | 1200 |
| ggaaactga | 1209 |

<210> SEQ ID NO 121
<211> LENGTH: 1209
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 121

| atgggatctt actcatccga tgatgtggag gtgattcgtg aggccggacg ggcacaaggt | 60 |
| ttagccacga ttcttgccat tggcactgct actcctccca attccgtcgc tcaagctgat | 120 |

| | |
|---|---|
| tatgcagact attattttcg tgtcactaag agcgaacata tggttgatct taaagagaaa | 180 |
| tttaaacgca tttgtgagaa aacagcgata agaaacgat acctagccct caccgaagac | 240 |
| tatctgcaag agaacccaac aatgtgtgag ttcatggctc catccttaaa cgctcgacaa | 300 |
| gacctagtgg tcaccggcgt cccaatgctt ggcaaagaag ccgcagtcaa ggccattgat | 360 |
| gaatggggac taccaaaatc caagatcacc cacctcatct tctgcaccac cgctggcgtt | 420 |
| gacatgcccg tgctgacta tcaactcgtc aaactccttg gtctctcccc ttcagtcaaa | 480 |
| cgctatatgt tgtaccaaca gggatgtgcc gccggcggca cagtcctccg gctagccaag | 540 |
| gaccttgctg aaaacaacaa gggctcacga gtccttatcg tctgctccga gatcactgct | 600 |
| atcttattcc atggacccaa tgagaaccac cttgactcac tcgtcgctca gctttattc | 660 |
| ggagacggag ctgcagcact cattgtgggt tcaggccctc acttggccgt agaacggcca | 720 |
| atattcgaga tcgtgtcaac tgatcaaaca atcttgccgg acactgagaa ggcaatgaag | 780 |
| ttacacttga gagagggagg gttgacgttt cagttgcata gagatgtacc cttgatggtc | 840 |
| gcaaagaaca tagagaacgc agcggagaaa gcgttgtctc cactagggat aactgattgg | 900 |
| aactcagttt tctggatggt gcagccaggt ggtcgagcca tattggacca ggtggagcga | 960 |
| aaactaaacc ttaaggaaga taagttaagg gctagcaggc atgtgcttag tgaatacgga | 1020 |
| aacctgatta gcgcttgtgt gttgttcatc attgacgagg tgaggaagag atctatggcg | 1080 |
| gaagggaaga gtacaaccgg tgaaggtttg gattgcggtg ttttgtttgg atttggaccg | 1140 |
| ggtatgactg ttgagactgt tgttcttcgt agcgtccgcg ttactgctgc ggttgccaat | 1200 |
| ggaaactga | 1209 |

<210> SEQ ID NO 122
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 122

| | |
|---|---|
| atgggatctt actcatccga tgatgtggag gtgattcgtg aggccggacg ggcacaaggt | 60 |
| ttagccacga ttcttgccat tggcactgct actcctccca attccgtcgc tcaagctgat | 120 |
| tatgcagact attattttcg tgtcactaag agcgaacata tggttgatct taaagagaaa | 180 |
| tttaaacgca tttgtgagaa aacagcgata agaaacgat acctagccct caccgaagac | 240 |
| tatctgcaag agaacccaac aatgtgtgag ttcatggctc catccttaaa cgctcgacaa | 300 |
| gacctagtgg tcaccggcgt cccaatgctt ggcaaagaag ccgcagtcaa ggccattgat | 360 |
| gaatggggac taccaaaatc caagatcacc cacctcatct tctgcaccac cgctggcgtt | 420 |
| gacatgcccg tgctgacta tcaactcgtc aaactccttg gtctctcccc ttcagtcaaa | 480 |
| cgctatatgt tgtaccaaca gggatgtgcc gccggcggca cagtcctccg gctagccaag | 540 |
| gaccttgctg aaaacaacaa gggctcacga gtccttatcg tctgctccga gatcactgct | 600 |
| atcttcttcc atggacccaa tgagaaccac cttgactcac tcgtcgctca gctttattc | 660 |
| ggagacggag ctgcagcact cattgtgggt tcaggccctc acttggccgt agaacggcca | 720 |
| atattcgaga tcgtgtcaac tgatcaaaca atcttgccgg acactgagaa ggcaatgaag | 780 |
| ttacacttga gagagggagg gttcacgttt cagttgcata gagatgtacc cttgatggtc | 840 |
| gcaaagaaca tagagaacgc agcggagaaa gcgttgtctc cactagggat aactgattgg | 900 |

```
aactcagttt tctggatggt gcacccaggt ggtcgagcca tattggacca ggtggagcga    960
aaactaaacc ttaaggaaga taagttaagg gctagcaggc atgtgcttag tgaatacgga   1020
aacctgatta gcgcttgtgt gttgttcatc attgacgagg tgaggaagag atctatggcg   1080
gaagggaaga gtacaaccgg tgaaggtttg gattgcggtg ttttgtttgg atttggaccg   1140
ggtatgactg ttgagactgt tgttcttcgt agcgtccgcg ttactgctgc ggttgccaat   1200
ggaaactga                                                           1209
```

<210> SEQ ID NO 123
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 123

```
atgggatctt actcatccga tgatgtggag gtgattcgtg aggccggacg ggcacaaggt     60
ttagccacga ttcttgccat tggcactgct actcctccca attccgtcgc tcaagctgat    120
tatgcagact attattttcg tgtcactaag agcgaacata tggttgatct aaagagaaa    180 tttaaacgca tttgtgagaa aacagcgata agaaacgat acctagccct caccgaagac    240
tatctgcaag agaacccaac aatgtgtgag ttcatggctc catccttaaa cgctcgacaa    300
gacctagtgg tcaccggcgt cccaatgctt ggcaaagaag ccgcagtcaa ggccattgat    360
gaatggggac taccaaaatc caagatcacc cacctcatct tctgcaccac cgctggcgtt    420
gacatgcccg gtgctgacta tcaactcgtc aaactccttg gtctctcccc ttcagtcaaa    480
cgctatatgt tgtaccaaca gggatgtgcc gccggcggca cagtcctccg gctagccaag    540
gaccttgctg aaaacaacaa gggctcacga gtccttatcg tctgctccga gatcactgct    600
atcttattcc atggacccaa tgagaaccac cttgactcac tcgtcgctca agctttattc    660
ggagacggag ctgcagcact cattgtgggt tcaggccctc acttggccgt agaacggcca    720
atattcgaga tcgtgtcaac tgatcaaaca atcttgccgg acactgagaa gcaatgaag    780 ttacacttga gagagggagg gatgacgttt cagttgcata gagatgtacc cttgatggtc    840
gcaaagaaca tagagaacgc agcggagaaa gcgttgtctc cactagggat aactgattgg    900
aactcagttt tctggatggt gcacccaggt ggtcgagcca tattggacca ggtggagcga    960
aaactaaacc ttaaggaaga taagttaagg gctagcaggc atgtgcttag tgaatacgga   1020
aacctgatga gcgcttgtgt gttgttcatc attgacgagg tgaggaagag atctatggcg   1080
gaagggaaga gtacaaccgg tgaaggtttg gattgcggtg ttttgtttgg atttggaccg   1140
ggtatgactg ttgagactgt tgttcttcgt agcgtccgcg ttactgctgc ggttgccaat   1200
ggaaactga                                                           1209
```

<210> SEQ ID NO 124
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 124

```
atgggatctt actcatccga tgatgtggag gtgattcgtg aggccggacg ggcacaaggt     60
ttagccacga ttcttgccat tggcactgct actcctccca attccgtcgc tcaagctgat    120
```

```
tatgcagact attattttcg tgtcactaag agcgaacata tggttgatct taaagagaaa    180
tttaaacgca tttgtgagaa aacagcgata aagaaacgat acctagccct caccgaagac    240
tatctgcaag agaacccaac aatgtgtgag ttcatggctc catccttaaa cgctcgacaa    300
gacctagtgg tcaccggcgt cccaatgctt ggcaaagaag ccgcagtcaa ggccattgat    360
gaatggggac taccaaaatc caagatcacc cacctcatct tctgcaccac cgctggcgtt    420
gacatgcccg tgctgactaa tcaactcgtc aaactccttg gtctctcccc ttcagtcaaa    480
cgctatatgt tgtaccaaca gggatgtgcc gccggcggca cagtcctccg gctagccaag    540
gaccttgctg aaaacaacaa gggctcacga gtccttatcg tctgctccga gatcactgct    600
atcttcttcc atggacccaa tgagaaccac cttgactcac tcgtcgctca agctttattc    660
ggagacggag ctgcagcact cattgtgggt tcaggccctc acttggccgt agaacggcca    720
atattcgaga tcgtgtcaac tgatcaaaca atcttgccgg acactgagaa ggcaatgaag    780
ttacacttga gagagggagg gatgacgttt cagttgcata gagatgtacc cttgatggtc    840
gcaaagaaca tagagaacgc agcggagaaa gcgttgtctc cactagggat aactgattgg    900
aactcagttt tctggatggt gcacccaggt ggtcgagcca tattggacca ggtggagcga    960
aaactaaacc ttaaggaaga taagttaagg gctagcaggc atgtgcttag tgaatacgga   1020
aacctgatta gcgcttgtgt gttgttcatc attgacgagg tgaggaagag atctatggcg   1080
gaagggaaga gtacaaccgg tgaaggtttg gattgcggtg ttttgtttgg atttggaccg   1140
ggtatgactg ttgagactgt tgttcttcgt agcgtccgcg ttactgctgc ggttgccaat   1200
ggaaactga                                                           1209
```

<210> SEQ ID NO 125
<211> LENGTH: 1209
<212> TYPE: DNA
<213> ORGANISM: Gerbera hybrida

<400> SEQUENCE: 125

```
atgggatctt actcatccga tgatgtggag gtgattcgtg aggccggacg ggcacaaggt     60
ttagccacga ttcttgccat ggcactgct actcctccca attgcgtcgc tcaagctgat    120
tatgcagact attattttcg tgtcactaag agcgaacata tggttgatct taaagagaaa    180
tttaaacgca tttgtgagaa aacagcgata aagaaacgat acctagccct caccgaagac    240
tatctgcaag agaacccaac aatgtgtgag ttcatggctc catccttaaa cgctcgacaa    300
gacctagtgg tcaccggcgt cccaatgctt ggcaaagaag ccgcagtcaa ggccattgat    360
gaatggggac taccaaaatc caagatcacc cacctcatct tctgcaccac cgctggcgtt    420
gacatgcccg tgctgactaa tcaactcgtc aaactccttg gtctctcccc ttcagtcaaa    480
cgctatatgt tgtaccaaca gggatgtgcc gccggcggca cagtcctccg gctagccaag    540
gaccttgctg aaaacaacaa gggctcacga gtccttatcg tctgctccga gatcactgct    600
atcttattcc atggacccaa tgagaaccac cttgactcac tcgtcgctca agctttattc    660
ggagacggag ctgcagcact cattgtgggt tcaggccctc acttggccgt agaacggcca    720
atattcgaga tcgtgtcaac tgatcaaaca atcttgccgg acactgagaa ggcaatgaag    780
ttacacttga gagagggagg gttgacgttt cagttgcata gagatgtacc cttgatggtc    840
gcaaagaaca tagagaacgc agcggagaaa gcgttgtctc cactagggat aactgattgg    900
aactcagttt tctggatggt gcacccaggt ggtcgagcca tattggacca ggtggagcga    960
```

```
aaactaaacc ttaaggaaga taagttaagg gctagcaggc atgtgcttag tgaatacgga    1020
aacctgatta gcgcttgtgt gttgttcatc attgacgagg tgaggaagag atctatggcg    1080
gaagggaaga gtacaaccgg tgaaggtttg gattgcggtg ttttgtttgg atttggaccg    1140
ggtatgactg ttgagactgt tgttcttcgt agcgtccgcg ttactgctgc ggttgccaat    1200
ggaaactga                                                            1209
```